United States Patent
Molloy et al.

(10) Patent No.: US 11,649,283 B2
(45) Date of Patent: May 16, 2023

(54) ANTI-HUMAN VISTA ANTIBODIES AND USE THEREOF

(71) Applicants: ImmuNext, Inc, Lebanon, NH (US); Janssen Pharmaceuticals, Inc., Raritan, NJ (US)

(72) Inventors: Michael Molloy, Enfield, NH (US); Jay Rothstein, Norwich, VT (US); Dov Pechenick, New Hampton, NH (US); Linda Snyder, Pottsdown, PA (US); Gordon Powers, Malvern, PA (US)

(73) Assignees: IMMUNEXT, INC., Lebanon, NH (US); JANSSEN PHARMACEUTICALS, INC., Raritan, NJ (US)

( * ) Notice: Subject to any disclaimer, the term of this patent is extended or adjusted under 35 U.S.C. 154(b) by 29 days.

(21) Appl. No.: 15/488,351

(22) Filed: Apr. 14, 2017

(65) Prior Publication Data
US 2018/0079811 A1    Mar. 22, 2018

Related U.S. Application Data

(63) Continuation of application No. PCT/US2017/027765, filed on Apr. 14, 2017.

(60) Provisional application No. 62/323,193, filed on Apr. 15, 2016, provisional application No. 62/343,355, filed on May 31, 2016, provisional application No. 62/372,362, filed on Aug. 9, 2016, provisional application No. 62/385,627, filed on Sep. 9, 2016, provisional application No. 62/425,184, filed on Nov. 22, 2016, provisional application No. 62/363,929, filed on Jul. 19, 2016, provisional application No. 62/365,085, filed on Jul. 21, 2016, provisional application No. 62/363,931, filed on Jul. 19, 2016, provisional application No. 62/365,102, filed on Jul. 21, 2016, provisional application No. 62/385,871, filed on Sep. 9, 2016, provisional application No. 62/363,917, filed on Jul. 19, 2016, provisional
(Continued)

(51) Int. Cl.
| | |
|---|---|
| C07K 16/28 | (2006.01) |
| A61K 39/395 | (2006.01) |
| A61P 17/06 | (2006.01) |
| A61P 1/16 | (2006.01) |
| A61P 37/06 | (2006.01) |
| A61P 19/02 | (2006.01) |
| A61P 13/12 | (2006.01) |
| A61P 1/00 | (2006.01) |
| A61K 45/06 | (2006.01) |
| A61K 38/17 | (2006.01) |
| A61K 39/00 | (2006.01) |

(52) U.S. Cl.
CPC .......... *C07K 16/2803* (2013.01); *A61K 38/17* (2013.01); *A61K 39/395* (2013.01); *A61K 39/3955* (2013.01); *A61K 45/06* (2013.01); *A61P 1/00* (2018.01); *A61P 1/16* (2018.01); *A61P 13/12* (2018.01); *A61P 17/06* (2018.01); *A61P 19/02* (2018.01); *A61P 37/06* (2018.01); *C07K 16/2827* (2013.01); *C07K 16/2896* (2013.01); *A61K 2039/505* (2013.01); *C07K 2317/21* (2013.01); *C07K 2317/24* (2013.01); *C07K 2317/31* (2013.01); *C07K 2317/33* (2013.01); *C07K 2317/34* (2013.01); *C07K 2317/52* (2013.01); *C07K 2317/522* (2013.01); *C07K 2317/53* (2013.01); *C07K 2317/565* (2013.01); *C07K 2317/73* (2013.01); *C07K 2317/74* (2013.01); *C07K 2317/75* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,366,241 | A | 12/1982 | Tom et al. |
| 4,376,110 | A | 3/1983 | David et al. |
| (Continued) | | | |

FOREIGN PATENT DOCUMENTS

| | | |
|---|---|---|
| CA | 2383456 | 3/2001 |
| CN | 1753912 | 3/2006 |
| (Continued) | | |

OTHER PUBLICATIONS

Dannschroder et al. Molecular Immunology (2004) 41: 985-1000.*
(Continued)

*Primary Examiner* — Ilia I Ouspenski
(74) *Attorney, Agent, or Firm* — Robin L. Teskin; Baker, Donelson, Bearman, Caldwell & Berkowitz, PC

(57) ABSTRACT

The invention provides antagonistic and agonistic anti-human VISTA antibodies and antibody fragments. These antagonist antibodies and antibody fragments may be used to inhibit or block VISTA's suppressive effects on T cell immunity and thereby promote T cell immunity. These agonist antibodies and antibody fragments may be used to potentiate or enhance or mimic VISTA's suppressive effects on T cell immunity and thereby suppress T cell immunity. These antagonist antibodies and antibody fragments are especially useful in the treatment of cancer and infectious conditions. These agonist antibodies and antibody fragments are especially useful in the treatment of autoimmunity, allergy, inflammatory conditions, GVHD, sepsis and transplant recipients. Screening assays for identifying these agonists are also provided.

24 Claims, 69 Drawing Sheets
Specification includes a Sequence Listing.

Related U.S. Application Data application No. 62/365,081, filed on Jul. 21, 2016, provisional application No. 62/385,888, filed on Sep. 9, 2016, provisional application No. 62/364,073, filed on Jul. 19, 2016, provisional application No. 62/365,166, filed on Jul. 21, 2016, provisional application No. 62/385,893, filed on Sep. 9, 2016, provisional application No. 62/363,925, filed on Jul. 19, 2016, provisional application No. 62/365,087, filed on Jul. 21, 2016, provisional application No. 62/385,785, filed on Sep. 9, 2016, provisional application No. 62/406,632, filed on Oct. 11, 2016, provisional application No. 62/385,805, filed on Sep. 9, 2016.

(56) References Cited

U.S. PATENT DOCUMENTS

| | | |
|---|---|---|
| 4,439,196 A | 3/1984 | Higuchi |
| 4,447,224 A | 5/1984 | DeCant, Jr. et al. |
| 4,447,233 A | 5/1984 | Mayfield |
| 4,475,196 A | 10/1984 | La Zor |
| 4,486,194 A | 12/1984 | Ferrara |
| 4,487,603 A | 12/1984 | Harris |
| 4,517,288 A | 5/1985 | Giegel et al. |
| 4,522,811 A | 6/1985 | Eppstein et al. |
| 4,596,556 A | 6/1986 | Morrow et al. |
| 4,676,980 A | 6/1987 | Segal et al. |
| 4,683,195 A | 7/1987 | Mullis et al. |
| 4,683,202 A | 7/1987 | Mullis |
| 4,699,880 A | 10/1987 | Goldstein |
| 4,736,866 A | 4/1988 | Leder et al. |
| 4,790,824 A | 12/1988 | Morrow et al. |
| 4,816,567 A | 3/1989 | Cabilly et al. |
| 4,837,168 A | 6/1989 | de Jaeger et al. |
| 4,870,009 A | 9/1989 | Evans et al. |
| 4,873,191 A | 10/1989 | Wagner et al. |
| 4,873,316 A | 10/1989 | Meade et al. |
| 4,881,175 A | 11/1989 | Ladner |
| 4,941,880 A | 7/1990 | Burns |
| 4,946,778 A | 8/1990 | Ladner et al. |
| 4,954,617 A | 9/1990 | Fanger et al. |
| 4,987,071 A | 1/1991 | Cech et al. |
| 5,013,653 A | 5/1991 | Huston et al. |
| 5,064,413 A | 11/1991 | McKinnon et al. |
| 5,091,513 A | 2/1992 | Huston et al. |
| 5,116,742 A | 5/1992 | Cech et al. |
| 5,116,964 A | 5/1992 | Capon et al. |
| 5,132,405 A | 7/1992 | Huston et al. |
| 5,139,941 A | 8/1992 | Muzyczka et al. |
| 5,190,878 A | 3/1993 | Wilhelm |
| 5,223,409 A | 6/1993 | Ladner et al. |
| 5,225,539 A | 7/1993 | Winter |
| 5,258,498 A | 11/1993 | Huston et al. |
| 5,260,203 A | 11/1993 | Ladner et al. |
| 5,272,071 A | 12/1993 | Chappel |
| 5,283,173 A | 2/1994 | Fields et al. |
| 5,283,317 A | 2/1994 | Saifer et al. |
| 5,288,641 A | 2/1994 | Roizman |
| 5,312,335 A | 5/1994 | McKinnon et al. |
| 5,328,470 A | 7/1994 | Nabel et al. |
| 5,374,548 A | 12/1994 | Caras |
| 5,383,851 A | 1/1995 | McKinnon, Jr. et al. |
| 5,399,163 A | 3/1995 | Peterson et al. |
| 5,399,331 A | 3/1995 | Loughrey et al. |
| 5,403,484 A | 4/1995 | Ladner et al. |
| 5,416,016 A | 5/1995 | Low et al. |
| 5,427,908 A | 6/1995 | Dower et al. |
| 5,455,030 A | 10/1995 | Ladner et al. |
| 5,476,786 A | 12/1995 | Huston |
| 5,476,996 A | 12/1995 | Wilson et al. |
| 5,478,925 A | 12/1995 | Wallach et al. |
| 5,482,858 A | 1/1996 | Huston et al. |
| 5,530,101 A | 6/1996 | Queen et al. |
| 5,545,806 A | 8/1996 | Lonberg et al. |
| 5,545,807 A | 8/1996 | Surani et al. |
| 5,547,853 A | 8/1996 | Wallner et al. |
| 5,569,825 A | 10/1996 | Lonberg et al. |
| 5,571,698 A | 11/1996 | Ladner et al. |
| 5,580,717 A | 12/1996 | Dower et al. |
| 5,580,756 A | 12/1996 | Linsley et al. |
| 5,585,089 A | 12/1996 | Queen et al. |
| 5,624,659 A | 4/1997 | Bigner et al. |
| 5,624,821 A | 4/1997 | Winter et al. |
| 5,625,126 A | 4/1997 | Lonberg et al. |
| 5,633,425 A | 5/1997 | Lonberg et al. |
| 5,648,260 A | 7/1997 | Winter et al. |
| 5,661,016 A | 8/1997 | Lonberg et al. |
| 5,677,425 A | 10/1997 | Bodmer et al. |
| 5,693,762 A | 12/1997 | Queen et al. |
| 5,698,767 A | 12/1997 | Wilson et al. |
| 5,714,350 A | 2/1998 | Co et al. |
| 5,723,125 A | 3/1998 | Chang et al. |
| 5,731,168 A | 3/1998 | Carter et al. |
| 5,770,429 A | 6/1998 | Lonberg et al. |
| 5,776,427 A | 7/1998 | Thorpe et al. |
| 5,789,650 A | 8/1998 | Lonberg et al. |
| 5,811,097 A | 9/1998 | Allison et al. |
| 5,814,318 A | 9/1998 | Lonberg et al. |
| 5,821,333 A | 10/1998 | Carter et al. |
| 5,837,243 A | 11/1998 | Deo et al. |
| 5,844,095 A | 12/1998 | Linsley et al. |
| 5,851,795 A | 12/1998 | Linsley et al. |
| 5,869,046 A | 2/1999 | Presta et al. |
| 5,874,299 A | 2/1999 | Lonberg et al. |
| 5,877,397 A | 3/1999 | Lonberg et al. |
| 5,885,793 A | 3/1999 | Griffiths et al. |
| 5,888,807 A | 3/1999 | Palsson et al. |
| 5,922,845 A | 7/1999 | Deo et al. |
| 5,932,448 A | 8/1999 | Tso et al. |
| 5,939,598 A | 8/1999 | Kucherlapati et al. |
| 5,969,108 A | 10/1999 | McCafferty et al. |
| 5,985,653 A | 11/1999 | Armstrong et al. |
| 6,054,297 A | 4/2000 | Carter et al. |
| 6,069,134 A | 5/2000 | Roth et al. |
| 6,075,181 A | 6/2000 | Kucherlapati et al. |
| 6,096,532 A | 8/2000 | Armstrong et al. |
| 6,114,598 A | 9/2000 | Kucherlapati et al. |
| 6,121,022 A | 9/2000 | Presta et al. |
| 6,150,584 A | 11/2000 | Kucherlapati et al. |
| 6,153,737 A | 11/2000 | Manoharan et al. |
| 6,162,963 A | 12/2000 | Kucherlapati et al. |
| 6,165,745 A | 12/2000 | Ward et al. |
| 6,172,197 B1 | 1/2001 | McCafferty et al. |
| 6,172,208 B1 | 1/2001 | Cook |
| 6,180,370 B1 | 1/2001 | Queen et al. |
| 6,187,287 B1 | 2/2001 | Leung et al. |
| 6,194,551 B1 | 2/2001 | Idusogie et al. |
| 6,277,375 B1 | 8/2001 | Ward |
| 6,300,319 B1 | 10/2001 | Manoharan |
| 6,335,434 B1 | 1/2002 | Guzaev et al. |
| 6,335,437 B1 | 1/2002 | Manoharan |
| 6,350,861 B1 | 2/2002 | Co et al. |
| 6,395,437 B1 | 5/2002 | Wollesen |
| 6,407,213 B1 | 6/2002 | Carter et al. |
| 6,444,806 B1 | 9/2002 | Veerapanani et al. |
| 6,486,308 B2 | 11/2002 | Kutyavin et al. |
| 6,492,123 B1 | 12/2002 | Holliger et al. |
| 6,521,404 B1 | 2/2003 | Griffiths et al. |
| 6,525,031 B2 | 2/2003 | Manoharan |
| 6,528,631 B1 | 3/2003 | Cook et al. |
| 6,544,731 B1 | 4/2003 | Griffiths et al. |
| 6,545,170 B2 | 4/2003 | Pitzele et al. |
| 6,548,640 B1 | 4/2003 | Winter |
| 6,555,313 B1 | 4/2003 | Griffiths et al. |
| 6,559,279 B1 | 5/2003 | Manoharan et al. |
| 6,562,576 B2 | 5/2003 | Manfredi |
| 6,582,915 B1 | 6/2003 | Griffiths et al. |
| 6,586,474 B2 | 7/2003 | Webber et al. |
| 6,591,889 B2 | 7/2003 | Bettio et al. |
| 6,593,081 B1 | 7/2003 | Griffiths et al. |
| 6,593,372 B2 | 7/2003 | Enikolopov et al. |
| 6,632,927 B2 | 10/2003 | Adair et al. |
| 6,639,055 B1 | 10/2003 | Carter et al. |
| 6,653,104 B2 | 11/2003 | Goldenberg |

(56) References Cited

U.S. PATENT DOCUMENTS

| | | |
|---|---|---|
| 6,696,686 B1 | 2/2004 | Wainer et al. |
| 6,790,624 B2 | 9/2004 | Mayer |
| 6,809,117 B2 | 10/2004 | Enikolopov et al. |
| 6,818,418 B1 | 11/2004 | Lipovsek et al. |
| 6,924,355 B2 | 8/2005 | Baker et al. |
| 6,936,436 B2 | 8/2005 | Baker et al. |
| 6,936,697 B2 | 8/2005 | Desnoyers et al. |
| 6,982,323 B1 | 1/2006 | Wang et al. |
| 7,026,448 B2 | 4/2006 | Baker et al. |
| 7,049,058 B2 | 5/2006 | Singh |
| 7,196,118 B2 | 3/2007 | Webber et al. |
| 7,226,759 B2 | 6/2007 | Sun |
| 7,250,297 B1 | 7/2007 | Beste et al. |
| 7,488,802 B2 | 2/2009 | Collins et al. |
| 7,595,048 B2 | 9/2009 | Honjo |
| 7,655,778 B2 | 2/2010 | Yang |
| 7,919,585 B2 | 4/2011 | Chen |
| 8,119,117 B2 | 2/2012 | Deisseroth et al. |
| 8,231,872 B2 | 7/2012 | Noelle et al. |
| 8,236,304 B2 | 8/2012 | Noelle et al. |
| 8,394,378 B2 * | 3/2013 | Kehoe .................. C07K 16/18 424/133.1 |
| 8,465,740 B2 | 6/2013 | Noelle et al. |
| 8,501,915 B2 | 8/2013 | Noelle et al. |
| 8,652,465 B2 | 2/2014 | Freeman |
| 9,217,035 B2 | 12/2015 | Noelle et al. |
| 9,381,244 B2 | 7/2016 | Noelle et al. |
| 9,631,018 B2 | 4/2017 | Noelle et al. |
| 9,879,092 B2 | 1/2018 | Laury-Kleintop et al. |
| 9,890,215 B2 | 2/2018 | Noelle et al. |
| 10,035,857 B2 | 7/2018 | Noelle et al. |
| 10,273,301 B2 | 4/2019 | Snyder et al. |
| 10,370,455 B2 | 8/2019 | Molloy et al. |
| 10,745,467 B2 | 8/2020 | Noelle et al. |
| 10,822,423 B2 | 11/2020 | Noelle |
| 10,899,836 B2 | 1/2021 | Snyder et al. |
| 11,180,557 B2 | 11/2021 | Noelle et al. |
| 2003/0031671 A1 | 2/2003 | Welt et al. |
| 2003/0054406 A1 | 3/2003 | Baker et al. |
| 2004/0110704 A1 | 6/2004 | Yamane et al. |
| 2004/0132028 A1 | 7/2004 | Stumpp et al. |
| 2004/0132101 A1 | 7/2004 | Lazar et al. |
| 2004/0259209 A1 | 12/2004 | Sun et al. |
| 2005/0043519 A1 | 2/2005 | Dooley et al. |
| 2005/0063948 A1 | 3/2005 | Dickerson et al. |
| 2006/0025576 A1 | 2/2006 | Miller et al. |
| 2006/0034852 A1 | 2/2006 | Rixon et al. |
| 2006/0084082 A1 | 4/2006 | Ruben et al. |
| 2007/0092512 A1 | 4/2007 | Daaka et al. |
| 2007/0122378 A1 | 5/2007 | Freeman et al. |
| 2007/0148167 A1 | 6/2007 | Stohl |
| 2007/0224633 A1 | 9/2007 | Skerra et al. |
| 2008/0069820 A1 | 3/2008 | Fuh et al. |
| 2008/0139791 A1 | 6/2008 | Lipovsek et al. |
| 2008/0166353 A1 | 7/2008 | Cherwinski |
| 2008/0248007 A1 | 10/2008 | Chen |
| 2008/0287358 A1 | 11/2008 | Noelle et al. |
| 2009/0215991 A1 | 8/2009 | Lazar et al. |
| 2010/0316639 A1 | 12/2010 | Lackner |
| 2010/0317834 A1 | 12/2010 | Lazar et al. |
| 2011/0027278 A1 | 2/2011 | Noelle et al. |
| 2011/0158995 A1 | 6/2011 | Tan et al. |
| 2011/0206699 A1 | 8/2011 | Hossain et al. |
| 2011/0223188 A1 | 9/2011 | Langermann |
| 2011/0243942 A1 | 10/2011 | Wang |
| 2012/0195894 A1 | 8/2012 | Noelle et al. |
| 2013/0177557 A1 | 7/2013 | Noelle et al. |
| 2014/0037634 A1 | 2/2014 | Noelle et al. |
| 2014/0056890 A1 | 2/2014 | Gurney et al. |
| 2014/0056892 A1 | 2/2014 | Noelle et al. |
| 2014/0105912 A1 | 4/2014 | Noelle et al. |
| 2014/0220012 A1 | 8/2014 | Noelle et al. |
| 2014/0227279 A1 | 8/2014 | Laury-Kleintop et al. |
| 2014/0341920 A1 | 11/2014 | Noelle et al. |
| 2015/0231215 A1 | 8/2015 | Noelle et al. |
| 2016/0008316 A1 | 1/2016 | Bacha et al. |
| 2016/0083472 A1 | 3/2016 | Noelle et al. |
| 2016/0096891 A1 | 4/2016 | Chen et al. |
| 2016/0159927 A1 | 6/2016 | Molloy et al. |
| 2016/0168248 A1 | 6/2016 | Noelle et al. |
| 2016/0318999 A9 | 11/2016 | Noelle et al. |
| 2016/0331803 A1 | 11/2016 | Noelle et al. |
| 2016/0369005 A1 | 12/2016 | Lippincott et al. |
| 2017/0051061 A1 | 2/2017 | Snyder et al. |
| 2017/0119877 A1 | 5/2017 | Green et al. |
| 2017/0233479 A1 | 8/2017 | Snyder et al. |
| 2017/0306019 A1 * | 10/2017 | Carriere ............ C07K 16/2896 |
| 2017/0306020 A1 * | 10/2017 | Noelle ............... C07K 16/2896 |
| 2017/0306021 A1 * | 10/2017 | Molloy ............. C07K 16/2896 |
| 2017/0306022 A1 * | 10/2017 | Molloy ............. C07K 16/2896 |
| 2017/0306023 A1 * | 10/2017 | Lemercier ......... C07K 16/2896 |
| 2017/0306024 A1 * | 10/2017 | Noelle ............... C07K 16/2896 |
| 2017/0320950 A1 | 11/2017 | Snyder et al. |
| 2017/0334990 A1 | 11/2017 | Noelle et al. |
| 2018/0051070 A1 | 2/2018 | Noelle et al. |
| 2018/0079811 A1 | 3/2018 | Molloy et al. |
| 2018/0215826 A1 | 8/2018 | Noelle et al. |
| 2019/0330349 A1 * | 10/2019 | Molloy .................... A61P 1/16 |
| 2020/0017589 A1 | 1/2020 | Snyder et al. |
| 2021/0017281 A1 * | 1/2021 | Molloy .................... A61P 9/10 |
| 2021/0317206 A1 * | 10/2021 | Molloy .................. A61P 37/02 |
| 2021/0317207 A1 * | 10/2021 | Noelle ................... A61P 37/08 |

FOREIGN PATENT DOCUMENTS

| | | |
|---|---|---|
| EP | 0 045 665 | 2/1982 |
| EP | 0 125 023 | 11/1984 |
| EP | 0 154 316 | 9/1985 |
| EP | 0 171 496 | 2/1986 |
| EP | 0 173 494 | 3/1986 |
| EP | 0 184 187 | 6/1986 |
| EP | 0 264 166 | 4/1988 |
| EP | 0 401 384 | 12/1990 |
| EP | 1 176 195 | 1/2002 |
| EP | 1 641 818 | 4/2006 |
| JP | 08-506635 | 3/2008 |
| WO | WO 00/045665 | 2/1982 |
| WO | WO 86/001533 | 3/1986 |
| WO | WO 87/002671 | 5/1987 |
| WO | WO 87/005330 | 9/1987 |
| WO | WO 88/000052 | 1/1988 |
| WO | WO 88/009810 | 12/1988 |
| WO | WO 89/010134 | 11/1989 |
| WO | WO 91/006667 | 5/1991 |
| WO | WO 92/003918 | 3/1992 |
| WO | WO 93/008829 | 5/1993 |
| WO | WO 93/012227 | 6/1993 |
| WO | WO 94/010300 | 5/1994 |
| WO | WO 94/010332 | 5/1994 |
| WO | WO 94/025585 | 11/1994 |
| WO | WO 94/029351 | 12/1994 |
| WO | WO 94/029436 | 12/1994 |
| WO | WO 97/007668 | 3/1997 |
| WO | WO 97/007669 | 3/1997 |
| WO | WO 97/013852 | 4/1997 |
| WO | WO 97/028267 | 8/1997 |
| WO | WO 98/024884 | 6/1998 |
| WO | WO 99/045962 | 9/1999 |
| WO | WO 99/054342 | 10/1999 |
| WO | WO 00/006593 | 2/2000 |
| WO | WO 00/029004 | 5/2000 |
| WO | WO 00/031113 | 6/2000 |
| WO | WO 00/042072 | 7/2000 |
| WO | WO 01/000814 | 1/2001 |
| WO | WO 01/003737 | 1/2001 |
| WO | WO 01/014424 | 3/2001 |
| WO | WO 02/029072 | 4/2002 |
| WO | WO 02/043478 | 6/2002 |
| WO | WO 02/079449 | 10/2002 |
| WO | WO 02/092780 | 11/2002 |
| WO | WO 03/035835 | 5/2003 |
| WO | WO 03/074679 | 9/2003 |
| WO | WO 04/018520 | 3/2004 |
| WO | WO 04/037999 | 5/2004 |

(56) References Cited

FOREIGN PATENT DOCUMENTS

| WO | WO 05/056764 | 6/2005 |
|---|---|---|
| WO | WO 05/112834 | 12/2005 |
| WO | WO 05/113606 | 12/2005 |
| WO | WO 06/012232 | 2/2006 |
| WO | WO 06/050247 | 5/2006 |
| WO | WO 06/050262 | 5/2006 |
| WO | WO 06/116181 | 11/2006 |
| WO | WO 07/030198 | 3/2007 |
| WO | WO 08/098796 | 8/2008 |
| WO | WO 09/089004 | 7/2009 |
| WO | WO 10/027827 | 3/2010 |
| WO | WO 11/120013 | 9/2011 |
| WO | WO 13/184912 | 12/2013 |
| WO | WO 13/192504 | 12/2013 |
| WO | WO 14/039983 | 3/2014 |
| WO | WO 14/190356 | 11/2014 |
| WO | WO 2014197849 | 12/2014 |
| WO | WO 15/097536 | 7/2015 |
| WO | WO 15/109340 | 7/2015 |
| WO | WO 15/191881 | 12/2015 |
| WO | WO 16/090347 | 6/2016 |
| WO | WO 2016207717 | 12/2016 |
| WO | WO 17/181109 | 10/2017 |
| WO | WO 17/181139 | 10/2017 |
| WO | WO 18/027042 | 2/2018 |

OTHER PUBLICATIONS

Khan et al. Sci. Rep. (2017) 7, 45163; doi: 10.1038/srep45163 (12 pages).*
Zhu et al. Cell (2015) 161: 1280-1292.*
Lee et al. Nature Medicine (2016) 22: 1456-1464.*
Abdiche et al. mAbs (2016) 8: 264-277.*
Konitzer et al. mAbs (2017) 9: 536-549.*
Ferrara et al. mAbs (2015) 7: 32-41.*
Parola et al. Immunology (2018) 153: 31-41.*
Boyd et al. Current Opinion in Immunology 2016, 40: 103-109.*
Van Regenmortel MHV. Front. Immunol. (2018) vol. 8, Article 2009 (11 pages).*
Conroy et al. Methods (2017) 116: 12-22.*
Sheehan et al. Microbiol. Spectr. (2015) 3(1): AID-0028-2014; 17 pages.*
Cadena et al. (2019) Front. Immunol. 10: 1638; p. 1-11.*
Xu et al. (2019) Cancer Immunol Res 7: 1497-1510.*
White et al. (2015) Conformation of the Human Immunoglobulin G2 Hinge Imparts Superagonistic Properties to Immunostimulatory Anticancer Antibodies. Cancer Cell 27(1): 138-148.*
Lightle et al. (2010) Mutations within a human IgG2 antibody form distinct and homogeneous disulfide isomers but do not affect Fc gamma receptor or C1q binding. Protein Science 19(4): 753-762.*
Allen et al. (2009) Interchain Disulfide Bonding in Human IgG2 Antibodies Probed by Site-Directed Mutagenesis. Biochemistry 48(17): 3755-3766.*
Beers SA, el al. "Influence of immunoglobulin isotype on therapeutic antibody function," Blood. Mar. 3, 2016; 127 (9):1097-101.
Burgers WA, et al. "The challenges of HIV vaccine development and testing," Best Pract Res Clin Obstet Gynaecol. Apr. 2005;19(2):277-91.
Chevalier MF, et al. "The split personality of regulatory T cells in HIV infection," Blood. Jan. 3, 2013;121(1):29-37.
Gupta S, et al. "Systemic Immunotherapy for Urothelial Cancer: Current Trends and Future Directions," Cancers (Basel). Jan. 27, 2017;9(2).
Konishi J, et al. "B7-H1 expression on non-small cell lung cancer cells and its relationship with tumor-infiltrating ymphocytes and their PD-1 expression," Clin Cancer Res. Aug. 1, 2004;10(15):5094-100.
Ladanyi A, et al. "Prognostic impact of B-cell density in cutaneous melanoma," Cancer Immunol Immunother. Dec. 2011;60(12):1729-38.

Ladjemi MZ, et al. "Anti-HER2 vaccines: new prospects for breast cancer therapy," Cancer Immunol Immunolher_2010 S,ep;59(9):1295-312.
Lapierre P, et al. "Regulatory T Cells in Autoimmune and Viral Chronic Hepatitis," J Immunol Res. 2015;2015:479703.
Lawrence MS, et al. "Mutational heterogeneity in cancer and the search for new cancer-associated genes," Nature. Jul. 11, 2013;499(7457):214-218.
Mor F, et al. "Identification of aldolase as a target antigen in Alzheimer's disease," J Immunol. Sep. 1, 2005 ; 175 (5):3439-45.
MS the Disease, National Multiple Sclerosis Society, https:/lwww.nationalmssociety.org/About-the-Society/Press-Room/MS-the-Disease, 2019. 5 pages.
Overdijk MB, et al. "Crosstalk between human IgG isotypes and murine effector cells," J Immunol. Oct. 1, 2012;189 (7):3430-8.
"Progress in Autoimmune Diseases Research," U.S. Department of Health and Human Services, National Institutes of Health, National Institute of Allergy and Infectious Diseases, Mar. 2005. 146 pages.
Quinn MA, et al. "How do you diagnose rheumatoid arthritis early?" Best Pract Res Clin Rheumatol. Mar. 2001;15(1):49-66.
Rizvi NA, et al. "Mutational landscape determines sensitivity to PD-1 blockade in non-small cell lung cancer," Science. Apr. 3, 2015;348(6230):124-8.
Topalian SL, et al. "Safety, activity, and immune correlates of anti-PD-1 antibody in cancer," N Engl J Med. Jun. 28, 2012;366(26):2443-54.
Wolff A, et al. "American Society of Clinical Oncology/College of American Pathologists guideline recommendations for human epidermal growth factor receptor 2 testing in breast cancer," Arch Pathol Lab Med. 2007;131(1):18-43.
Aalberse RC, et al. "IgG4 breaking the rules," Immunology. Jan. 2002;105(1):9-19.
Adriouch S, et al. "Improved Immunological Tolerance Following Combination Therapy with CTLA-4/Ig and AAV-Mediated PD-L1/2 Muscle Gene Transfer," Front Microbiol. Sep. 29, 2011;2:199.
Allen, T. M. "Ligand-targeted therapeutics in anticancer therapy," Nat Rev Cancer. Oct. 2002;2(10):750-63.
Almquist RG, et al. "Synthesis and biological activity of a ketomethylene analogue of a tripeptide inhibitor of angiotensin converting enzyme," J Med Chem. Dec. 1980;23(12):1392-8.
Al-Obeidi F, et al. "Peptide and peptidomimetic libraries. Molecular diversity and drug design," Mol Biotechnol. Jun. 1998;9(3):205-23.
Altman JD, et al. "Phenotypic analysis of antigen-specific T lymphocytes," Science. Oct. 4, 1996;274(5284):94-6.
Altschul SF, et al. "Basic local alignment search tool," J Mol Biol. Oct. 5, 1990;215(3):403-10.
Altschul SF, et al. "Gapped BLAST and PSI-BLAST: a new generation of protein database search programs," Nucleic Acids Res. Sep. 1, 1997;25(17):3389-402.
Amancha PK, et al. "In vivo blockade of the programmed cell death-1 pathway using soluble recombinant PD-1-Fc enhances CD4+ and CD8+ T cell responses but has limited clinical benefit," J Immunol. Dec. 15, 2013;191(12):6060-70.
Ansari MJ, et al. "The programmed death-1 (PD-1) pathway regulates autoimmune diabetes in nonobese diabetic (NOD) mice," J Exp Med. Jul. 7, 2003;198(1):63-9.
Arkin AP, et al. "An algorithm for protein engineering: simulations of recursive ensemble mutagenesis," Proc Natl Acad Sci U S A. Aug. 15, 1992;89(16):7811-5.
Attia, P., et al., Autoimmunity correlates with tumor regression in patients with metastatic melanoma treated with anti-cytotoxic T-lymphocyte antigen-4. J Clin Oncol, 2005. 23(25): p. 6043-53.
Auffray, C et al. "Blood monocytes: development, heterogeneity, and relationship with dendritic cells," Annu Rev Immunol, 2009. 27: p. 669-92.
Bagley RG, et al. "sFLT01: a novel fusion protein with antiangiogenic activity," Mol Cancer Ther. Mar. 2011;10(3):404-15.
Bak, S. P., et al., Murine ovarian cancer vascular leukocytes require arginase-1 activity for T cell suppression. Mol Immunol, 2008. 46(2): p. 258-68.
Baldari C, et al. "A novel leader peptide which allows efficient secretion of a fragment of human interleukin 1 beta in *Saccharomyces cerevisiae*," EMBO J. Jan. 1987;6(1):229-34.

(56) References Cited

OTHER PUBLICATIONS

Banerji J, et al. "A lymphocyte-specific cellular enhancer is located downstream of the joining region in immunoglobulin heavy chain genes," Cell. Jul. 1983;33(3):729-40.
Barringer KJ, et al. "Blunt-end and single-strand ligations by *Escherichia coli* ligase: influence on an in vitro amplification scheme," Gene. Apr. 30, 1990;89(1):117-22.
Bartel DP, et al. "Isolation of new ribozymes from a large pool of random sequences," Science. Sep. 10, 1993;261(5127):1411-8.
Baskar S, et al. "Constitutive expression of B7 restores immunogenicity of tumor cells expressing truncated major histocompatibility complex class II molecules," Proc Natl Acad Sci U S A. Jun. 15, 1993;90(12):5687-90.
Batzer MA, et al. "Enhanced evolutionary PCR using oligonucleotides with inosine at the 3'-terminus," Nucleic Acids Res. Sep. 25, 1991;19(18):5081.
Bauer S, et al. "Immunotherapy of human tumors with T-cell-activating bispecific antibodies: stimulation of cytotoxic pathways in vivo," Cancer Res. Apr. 15, 1999;59(8):1961-5.
Beidler CB, et al. "Cloning and high level expression of a chimeric antibody with specificity for human carcinoembryonic antigen," J Immunol. Dec. 1, 1988;141(11):4053-60.
Beilharz MW, et al. "Timed ablation of regulatory CD4+ T cells can prevent murine AIDS progression," J Immunol. Apr. 15, 2004;172(8):4917-25.
Belousov ES, et al. "Sequence-specific targeting and covalent modification of human genomic DNA," Nucleic Acids Res. Sep. 1, 1997;25(17):3440-4.
Béranger F, et al. "Getting more from the two-hybrid system: N-terminal fusions to LexA are efficient and sensitive baits for two-hybrid studies," Nucleic Acids Res. May 15, 1997;25(10):2035-6.
Berge SM, et al. "Pharmaceutical salts," J Pharm Sci. Jan. 1977;66(1):1-19.
Berney C, et al. "A member of the dendritic cell family that enters B cell follicles and stimulates primary antibody responses identified by a mannose receptor fusion protein," J Exp Med. Sep. 20, 1999;190(6):851-60.
Better M, et al. "*Escherichia coli* secretion of an active chimeric antibody fragment," Science. May 20, 1988;240(4855):1041-3.
Bird RE, et al. "Single-chain antigen-binding proteins," Science. Oct. 21, 1988;242(4877):423-6.
Blank C, et al. "Interaction of PD-L1 on tumor cells with PD-1 on tumor-specific T cells as a mechanism of immune evasion: implications for tumor immunotherapy," Cancer Immunol Immunother. Apr. 2005;54(4):307-14.
Blank, C., et al., "PD-L1/B7H-1 inhibits the effector phase of tumor rejection by T cell receptor (TCR) transgenic CD8+ T cells," Cancer Res, 2004. 64(3): p. 1140-5.
Blazer et al., "Infusion of anti-B7. 1 (CD80) and anti-B7. 2 (CD86) monoclonal antibodies inhibits murine graft-versus-host disease lethality in part via direct effects on CD4+ and CD8+ T cells." The Journal of Immunology 157.8 (1996): 3250-3259.
Bloemen PG, et al. "Adhesion molecules: a new target for immunoliposome-mediated drug delivery," FEBS Lett. Jan. 3, 1995;357(2):140-4.
Blommers MJ, et al. "Effects of the introduction of L-nucleotides into DNA. Solution structure of the heterochiral duplex d(G-C-G-(L)T-G-C-G).d(C-G-C-A-C-G-C) studied by NMR spectroscopy," Biochemistry. Jun. 28, 1994;33(25):7886-96.
Bluestone JA, et al. "Natural versus adaptive regulatory T cells," Nat Rev Immunol. Mar. 2003;3(3):253-7.
Bogdan C. "Nitric oxide and the immune response," Nat Immunol. Oct. 2001;2(10):907-16.
Bolhassani, A. et al., "Improvement of different vacine delivery systems for cancer therapy", Molecular Cancer, 2011, vol. 10, No. 1, Article No. 3.
Boon T, et al."Human T cell responses against melanoma," Annu. Rev. Immunol.. Apr. 23, 2006;24:175-208.

Borriello F, et al. "B7-1 and B7-2 have overlapping, critical roles in immunoglobulin class switching and germinal center formation," Immunity. Mar. 1997;6(3):303-13.
Borrok MJ, "pH-dependent Binding Engineering Reveals an FcRn Affinity Threshold That Governs IgG Recycling," The Journal of Biological Chemistry. 2015;290(7):4282-90.
Boulianne GL, et al. "Production of functional chimaeric mouse/human antibody," Nature. Dec. 13-19, 1984;312(5995):643-6.
Bowen JL, et al. "Innate immune CD11b+Gr-1+ cells, suppressor cells, affect the immune response during Theiler's virus-induced demyelinating disease," J Immunol. Dec. 1, 2009;183(11):6971-80.
Brahmer, J. R., et al., Phase I study of single-agent anti-programmed death-1 (MDX-1106) in refractory solid tumors: safety, clinical activity, pharmacodynamics, and immunologic correlates. J Clin Oncol, 2010. 28(19): p. 3167-75.
Brandt C, et al. "The B7 family member B7-H6 is a tumor cell ligand for the activating natural killer cell receptor NKp30 in humans," J Exp Med. Jul. 6, 2009;206(7):1495-503.
Brennan M, et al. "Preparation of bispecific antibodies by chemical recombination of monoclonal immunoglobulin G1 fragments," Science. Jul. 5, 1985;229(4708):81-3.
Briscoe P, et al. "Delivery of superoxide dismutase to pulmonary epithelium via pH-sensitive liposomes," Am J Physiol. Mar. 1995,268(3 Pt 1):L374-80.
Brisson, et al. "Expression of a bacterial gene in plants by using a viral vector," Nature vol. 310 Aug. 1984, 511-14.
Broglie R, et al. "Light-regulated expression of a pea ribulose-1,5-bisphosphate carboxylase small subunit gene in transformed plant cells," Science. May 25, 1984;224(4651):838-43.
Brown JP, et al. "Protein antigens of normal and malignant human cells identified by immunoprecipitation with monoclonal antibodies," J Biol Chem. Jun. 10, 1980;255(11):4980-3.
Brown JP, et al. "Structural characterization of human melanoma-associated antigen p97 with monoclonal antibodies," J Immunol. Aug. 1981;127(2):539-46.
Brys L, et al. "Reactive oxygen species and 12/15-lipoxygenase contribute to the antiproliferative capacity of alternatively activated myeloid cells elicited during helminth infection," J Immunol. May 15, 2005;174(10):6095-104.
Burg JL, et al. "Single molecule detection of RNA reporter probes by amplification with Q beta replicase," Mol Cell Probes. Aug. 1996;10(4):257-71.
Butte MJ, et al. "Programmed death-1 ligand 1 interacts specifically with the B7-1 costimulatory molecule to inhibit T cell responses," Immunity. Jul. 2007;27(1):111-22.
Byrne GW, et al. "Multiplex gene regulation: a two-tiered approach to transgene regulation in transgenic mice," Proc Natl Acad Sci U S A. Jul. 1989;86(14):5473-7.
Cabilly S, et al. "Generation of antibody activity from immunoglobulin polypeptide chains produced in *Escherichia coli*," Proc Natl Acad Sci U S A. Jun. 1984;81(11):3273-7.
Cabilly S, et al. "Immunoglobulin transcripts and molecular history of a hybridoma that produces antibody to carcinoembryonic antigen," Gene. 1985;40(1):157-61.
Calabro, L., et al., "Clinical studies with anti-CTLA-4 antibodies in non-melanoma indications," Semin Oncol, 2010. 37(5): p. 460-7.
Calame K, et al. "Transcriptional controlling elements in the immunoglobulin and T cell receptor loci," Adv Immunol. 1988;43:235-75.
Camper SA, et al. "Postnatal repression of the alpha-fetoprotein gene is enhancer independent," Genes Dev. Apr. 1989;3(4):537-46.
Cancer Prevention Overview (PDQ®), PDQ Cancer Information Summaries [Internet].2017, 14 pages.
Carell, et al. "A Solution-Phase Screening Procedure for the Isolation of Active Compounds from a Library of Molecules," Angew. Chem. Int. Ed. Engl. 1994, 33. No. 20, 2061-64.
Carter L, et al. "PD-1:PD-L inhibitory pathway affects both CD4(+) and CD8(+) T cells and is overcome by IL-2," Eur J Immunol. Mar. 2002;32(3):634-43.
Ceeraz S, et al. "VISTA Deficiency Accelerates the Development of Fatal Murine Lupus Nephritis," Arthritis Rheumatol. Apr. 2017;69(4):814-825.

(56) References Cited

OTHER PUBLICATIONS

Chambers CA, et al. "Lymphoproliferation in CTLA-4-deficient mice is mediated by costimulation-dependent activation of CD4+ T cells," Immunity. Dec. 1997;7(6):885-95.
Chan AC, et al. "Therapeutic antibodies for autoimmunity and inflammation," Nat Rev Immunol. May 2010;10(5):301-16.
Chen J, et al. "B cell development in mice that lack one or both immunoglobulin kappa light chain genes," EMBO J. Mar. 1993;12(3):821-30.
Chen J, et al. "Immunoglobulin gene rearrangement in B cell deficient mice generated by targeted deletion of the JH locus," Int Immunol. Jun. 1993;5(6):647-56.
Chen L, et al. "Costimulation of antitumor immunity by the B7 counterreceptor for the T lymphocyte molecules CD28 and CTLA-4," Cell. Dec. 24, 1992;71(7):1093-102.
Chen S, et al. "Immunosuppressive functions of hepatic myeloid-derived suppressor cells of normal mice and in a murine model of chronic hepatitis B virus," Clin Exp Immunol. Oct. 2011;166(1):134-42.
Chen SH, et al. "Gene therapy for brain tumors: regression of experimental gliomas by adenovirus-mediated gene transfer in vivo," Proc Natl Acad Sci U S A. Apr. 12, 1994;91(8):3054-7.
Chen, Y., "Development of a sandwich ELISA for evaluating soluble PD-LI (CD274) in human sera of different ages as well as supernatants of PD-L1(+) cell lines," Cytokine 2011.
Cho CY, et al. "An unnatural biopolymer," Science. Sep. 3, 1993;261(5126):1303-5.
Choi TK, et al. "Transgenic mice containing a human heavy chain immunoglobulin gene fragment cloned in a yeast artificial chromosome," Nat Genet. Jun. 1993;4(2):117-23.
Chothia C, et al. "Canonical structures for the hypervariable regions of immunoglobulins," J Mol Biol. Aug. 20, 1987;196(4):901-17.
Church GM, et al. "Genomic sequencing," Proc Natl Acad Sci U S A. Apr. 1984;81(7):1991-5.
Clark KL, et al. "Association of the *Arabidopsis* CTR1 Raf-like kinase with the ETR1 and ERS ethylene receptors," Proc Natl Acad Sci U S A. Apr. 28, 1998;95(9):5401-6.
Cohen AA, et al. "Structure design: an artificial intelligence-based method for the design of molecules under geometrical constraints," J Mol Graph. Sep. 1993;11(3):166-73.
Cole SP, et al. "Human monoclonal antibodies," Mol Cell Biochem. Jun. 1984;62(2):109-20.
Colman PM. "Effects of amino acid sequence changes on antibody-antigen interactions," Res Immunol. Jan. 1994;145(1):33-6.
Conejo-Garcia, J. R., et al., "Tumor-infiltrating dendritic cell precursors recruited by a beta-defensin contribute to vasculogenesis under the influence of Vegf-A," Nat Med, 2004. 10(9): p. 950-8.
Copin, R., et al., "MyD88-dependent activation of B220-CD11b+ LY-6C+ dendritic cells during *Brucella melitensis* infection," J Immunol, 2007. 178(8): p. 5182-91.
Coruzzi G, et al. "Tissue-specific and light-regulated expression of a pea nuclear gene encoding the small subunit of ribulose-1,5-bisphosphate carboxylase," EMBO J. Aug. 1984;3(8):1671-9.
Corzo, C. A., et al., "HIF-1alpha regulates function and differentiation of myeloid-derived suppressor cells in the tumor microenvironment," J Exp Med, 2010. 207(11): p. 2439-53.
Cote RJ, et al. "Generation of human monoclonal antibodies reactive with cellular antigens," Proc Natl Acad Sci U S A. Apr. 1983;80(7):2026-30.
Cox JP, et al. "A directory of human germ-line V kappa segments reveals a strong bias in their usage," Eur J Immunol. Apr. 1994;24(4):827-36.
Cubillos-Ruiz, J. R., et al., "Polyethylenimine-based siRNA nanocomplexes reprogram tumor-associated dendritic cells via TLR5 to elicit therapeutic antitumor immunity," J Clin Invest, 2009. 119(8): p. 2231-44.
Cull MG, et al. "Screening for receptor ligands using large libraries of peptides linked to the C terminus of the lac repressor," Proc Natl Acad Sci U S A. Mar. 1, 1992;89(5):1865-9.

Cunningham BC, et al. "High-resolution epitope mapping of hGH-receptor interactions by alanine-scanning mutagenesis," Science. Jun. 2, 1989;244(4908):1081-5.
Curiel, T. J., et al., "Blockade of B7-H1 improves myeloid dendritic cell-mediated antitumor immunity," Nat Med, 2003. 9(5): p. 562-7.
Curiel, T. J., et al., "Specific recruitment of regulatory T cells in ovarian carcinoma fosters immune privilege and predicts reduced survival," Nat Med, 2004. 10(9): p. 942-9.
Curis, Inc. "A Study of CA-170 (Oral PD-L1, PD-L2 and VISTA Checkpoint Antagonist) in Patients With Advanced Tumors and Lymphomas," U.S. National Library of Medicine, ClinicalTrials. gov; (https://clinicaltrials.gov) 2018. 8 pages.
Cwirla SE, et al. "Peptides on phage: a vast library of peptides for identifying ligands," Proc Natl Acad Sci U S A. Aug. 1990;87(16):6378-82.
Dal Porto J, et al. "A soluble divalent class I major histocompatibility complex molecule inhibits alloreactive T cells at nanomolar concentrations," Proc Natl Acad Sci U S A. Jul. 15, 1993;90(14):6671-5.
David GS, et al. "Protein iodination with solid state lactoperoxidase," Biochemistry. Feb. 26, 1974;13(5):1014-21.
De Vos AM, et al. "Human growth hormone and extracellular domain of its receptor: crystal structure of the complex," Science. Jan. 17, 1992;255(5042):306-12.
Dean PM. "Recent advances in drug design methods: where will they lead?" Bioessays. Sep. 1994;16(9):683-7.
Delagrave S, et al. "Recursive ensemble mutagenesis," Protein Eng. Apr. 1993;6(3):327-31.
Dellinger et al "International Guidelines for Management of Severe Sepsis and Septic Shock" (2013 Intensive Care Med 39: 165-228).
Deng J, et al. "A New VISTA on combination therapy for negative checkpoint regulator blockade," J Immunother Cancer. Dec. 20, 2016;4:86.
Deshayes S, et al. "Insight into the mechanism of internalization of the cell-penetrating carrier peptide Pep-1 through conformational analysis," Biochemistry. Feb. 17, 2004;43(6):1449-57.
D'Eustachio P, et al. "Somatic cell genetics and gene families," Science. May 27, 1983;220(4600):919-24.
Devlin JJ, et al. "Random peptide libraries: a source of specific protein binding molecules," Science. Jul. 27, 1990;249(4967):404-6.
DeWitt SH, et al. "'Diversomers': an approach to nonpeptide, nonoligomeric chemical diversity," Proc Natl Acad Sci U S A. Aug. 1, 1993;90(15):6909-13.
Di Maro, Antimo, et al. "Isolation and characterization of four type-1 ribosome-inactivating proteins, with polynucleotide: adenosine glycosidase activity, from leaves of *Phytolacca dioica* L." Planta 208.1 (1999): 125-131.
DiLillo DJ, et al. "Fc-Receptor Interactions Regulate Both Cytotoxic and Immunomodulatory Therapeutic Antibody Effector Functions," Cancer Immunology Research. 2015;3(7):704-13.
Dillon et al., "Optimization of a reversed-phase high-performance liquid chromatography/mass spectrometry method for characterizing recombinant antibody heterogeneity and stability," J Chromatogr A. Jul. 7, 2006;1120(1-2):112-20.
Dong C, et al. "ICOS co-stimulatory receptor is essential for T-cell activation and function," Nature. Jan. 4, 2001;409(6816):97-101.
Dong H, et al. "B7-H1 pathway and its role in the evasion of tumor immunity," J Mol Med (Berl). May 2003;81(5):281-7.
Dong H, et al. "Tumor-associated B7-H1 promotes T-cell apoptosis: a potential mechanism of immune evasion," Nat Med. Aug. 2002;8(8):793-800.
Dubey AK, et al. "Belimumab: First targeted biological treatment for systemic lupus erythematosus," J Pharmacol Pharmacother. 2011;2(4):317-9.
Duttagupta et al., "Costimulation signals for memory CD8+ T cells during viral infections." Critical Reviews™ in Immunology 29.6 (2009).
Edlund T, et al. "Cell-specific expression of the rat insulin gene: evidence for role of two distinct 5' flanking elements," Science. Nov. 22, 1985;230(4728):912-6.

(56) References Cited

OTHER PUBLICATIONS

Ehst BD, et al. "Development of a novel transgenic mouse for the study of interactions between CD4 and CD8 T cells during graft rejection," American Journal of Transplantation: 2003;3(11)1355-62.
Elbashir SM, et al. "Duplexes of 21-nucleotide RNAs mediate RNA interference in cultured mammalian cells," Nature. May 24, 2001;411(6836):494-8.
Ellenberger TE, et al. "The GCN4 basic region leucine zipper binds DNA as a dimer of uninterrupted alpha helices: crystal structure of the protein-DNA complex," Cell. Dec. 24, 1992;71(7):1223-37.
Erb E, et al. "Recursive deconvolution of combinatorial chemical libraries," Proc Natl Acad Sci U S A. Nov. 22, 1994;91(24):11422-6.
Evans BE, et al. "Design of nonpeptidal ligands for a peptide receptor: cholecystokinin antagonists," J Med Chem. Jul. 1987;30(7):1229-39.
Fallarino F, et al. "B7-1 engagement of cytotoxic T lymphocyte antigen 4 inhibits T cell activation in the absence of CD28," J Exp Med. Jul. 6, 1998;188(1):205-10.
Fan YS, et al. "Mapping small DNA sequences by fluorescence in situ hybridization directly on banded metaphase chromosomes," Proc Natl Acad Sci U S A. Aug. 1990;87(16):6223-7.
Felici F, et al. "Selection of antibody ligands from a large library of oligopeptides expressed on a multivalent exposition vector," J Mol Biol. Nov. 20, 1991;222(2):301-10.
Finn PJ, et al. "Synthesis and properties of DNA-PNA chimeric oligomers," Nucleic Acids Res. Sep. 1, 1996;24(17):3357-63.
Fishwild DM, et al. "High-avidity human IgG kappa monoclonal antibodies from a novel strain of minilocus transgenic mice," Nat Biotechnol. Jul. 1996;14(7):845-51.
Flicek P, et al. "Ensembl 2008," Nucleic Acids Res. Jan. 2008;36(Database issue):D707-14.
Flies DB, et al. "Coinhibitory receptor PD-1H preferentially suppresses CD4+ T cell-mediated immunity," J Clin Invest. May 2014;124(5):1966-75.
Flies DB, et al. "Cutting edge: A monoclonal antibody specific for the programmed death-1 homolog prevents graft-versus-host disease in mouse models," J Immunol. Aug. 15, 2011;187(4):1537-41.
Flies DB, et al. "Mechanistic Assessment of PD-1H Coinhibitory Receptor-Induced T Cell Tolerance to Allogeneic Antigens," J Immunol. Jun. 1, 2015;194(11):5294-304.
Fodor SP, et al. "Multiplexed biochemical assays with biological chips," Nature. Aug. 5, 1993;364(6437):555-6.
Fontenot JD, et al. "Regulatory T cell lineage specification by the forkhead transcription factor foxp3," Immunity. Mar. 2005;22(3):329-41.
Formstecher E, et al. "Protein interaction mapping: a *Drosophila* case study," Genome Res. Mar. 2005;15(3):376-84.
Franklin, et al. "Immunologic differences between the 19 S and 7 S components of normal human gamma-globulin," J Immunol. Jan. 1957;78(1):11-8.
Freeman GJ, et al. "Engagement of the PD-1 immunoinhibitory receptor by a novel B7 family member leads to negative regulation of lymphocyte activation," J Exp Med. Oct. 2, 2000;192(7):1027-34.
Freeman GJ, et al. "Uncovering of functional alternative CTLA-4 counter-receptor in B7-deficient mice," Science. Nov. 5, 1993;262(5135):907-9.
Freeman GJ. "Structures of PD-1 with its ligands: sideways and dancing cheek to cheek," Proc Natl Acad Sci U S A. Jul. 29, 2008;105(30):10275-6.
Freier SM, et al. "Improved free-energy parameters for predictions of RNA duplex stability," Proc Natl Acad Sci U S A. Dec. 1986;83(24):9373-7.
Frenkel K, et al. "7,12-dimethylbenz[a]anthracene induces oxidative DNA modification in vivo," Free Radic Biol Med. Sep. 1995;19(3):373-80.
Fromont-Racine M, et al. "Toward a functional analysis of the yeast genome through exhaustive two-hybrid screens," Nat Genet. Jul. 1997;16(3):277-82.
Futaki S. "Arginine-rich peptides: potential for intracellular delivery of macromolecules and the mystery of the translocation mechanisms," Int J Pharm. Oct. 1, 2002;245(1-2):1-7.
Gabrilovich D. "Mechanisms and functional significance of tumour-induced dendritic-cell defects," Nat Rev Immunol. Dec. 2004;4(12):941-52.
Gabrilovich DI, et al. "Myeloid-derived suppressor cells as regulators of the immune system," Nat Rev Immunol. Mar. 2009;9(3):162-74.
Galfre, G. et al. "Antibodies to major histocompatibility anitigens produced by hybrid cell lines," Nature, vol. 266, Apr. 1977, 550-52.
Gallop MA, et al. "Applications of combinatorial technologies to drug discovery. 1. Background and peptide combinatorial libraries," J Med Chem. Apr. 29, 1994;37(9):1233-51.
Gao J, et al. "VISTA is an inhibitory immune checkpoint that is increased after ipilimumab therapy in patients with prostate cancer," Nat Med. May 2017;23(5):551-555.
Gao, Q., et al., "Overexpression of PD-L1 significantly associates with tumor aggressiveness and postoperative recurrence in human hepatocellular carcinoma," Clin Cancer Res, 2009. 15(3): p. 971-9.
Garg A, et al. "HIV type 1 gp120-induced expansion of myeloid derived suppressor cells is dependent on interleukin 6 and suppresses immunity," J Infect Dis. Feb. 1, 2014;209(3):441-51.
Gautier C, et al. "Alpha-DNA. IV: Alpha-anomeric and beta-anomeric tetrathymidylates covalently linked to intercalating oxazolopyridocarbazole. Synthesis, physicochemical properties and poly (rA) binding," Nucleic Acids Res. Aug. 25, 1987;15(16):6625-41.
Gavin MA, et al. "Homeostasis and anergy of CD4(+)CD25(+) suppressor T cells in vivo," Nat Immunol. Jan. 2002;3(1):33-41.
Gefter ML, et al. "A simple method for polyethylene glycol-promoted hybridization of mouse myeloma cells," Somatic Cell Genet. Mar. 1977;3(2):231-6.
Geissmann, F., et al. "Blood monocytes consist of two principal subsets with distinct migratory properties," Immunity, 2003. 19(1): p. 71-82.
Geissmann, F., et al., "Blood monocytes: distinct subsets, how they relate to dendritic cells, and their possible roles in the regulation of T-cell responses," Immunol Cell Biol, 2008. 86(5): p. 398-408.
Geissmann, F., et al., "Development of monocytes, macrophages, and dendritic cells," Science, 2010. 327(5966): p. 656-61.
GenBank Accession No. NP.sub.—071436 (Sep. 3, 2009), platelet receptor Gi24 precursor [*Homo sapiens*].
GenBank Accession No. NP.sub.—083008 (Mar. 3, 3010) platelet receptor Gi24 isoform 1 precursor [Mus musculus].
Genbank entry EGW09616.1 (Mar. 14, 2015) [retrieved on Jun. 22, 2015 from http://www.ncbi.nlm.nih.gov/protein/EGW09616.1] 1 page.
Geng H, et al. "HSP70 vaccine in combination with gene therapy with plasmid DNA encoding sPD-1 overcomes immune resistance and suppresses the progression of pulmonary metastatic melanoma," Int J Cancer. Jun. 1, 2006;118(11):2657-64.
Ghiringhelli, F., et al., "Tumor cells convert immature myeloid dendritic cells into TGF-beta-secreting cells inducing CD4+CD25+ regulatory T cell proliferation," J Exp Med, 2005. 202(7): p. 919-29.
Gilliland DG, et al. "Antibody-directed cytotoxic agents: use of monoclonal antibody to direct the action of toxin A chains to colorectal carcinoma cells," Proc Natl Acad Sci U S A. Aug. 1980;77(8):4539-43.
Glennie MJ, et al. "Preparation and performance of bispecific F(ab' gamma)2 antibody containing thioether-linked Fab' gamma fragments," J Immunol. Oct. 1, 1987;139(7):2367-75.
Gluzman Y, et al. "SV40 early mutants that are defective for viral DNA synthesis but competent for transformation of cultured rat and simian cells," Virology. Nov. 1982;123(1):78-92.
Goeddel DV. "Systems for heterologous gene expression," Methods Enzymol. 1990;185:3-7.
Gorczynski RM, et al. "Checkpoint blockade in solid tumors and B-cell malignancies, with special consideration of the role of CD200," Cancer Manag Res. Nov. 13, 2017;9:601-609.
Grabie N, et al. "Endothelial programmed death-1 ligand 1 (PD-L1) regulates CD8+ T-cell mediated injury in the heart," Circulation. Oct. 30, 2007; 116(18):2062-71.

(56) References Cited

OTHER PUBLICATIONS

Graziano RF, et al. "Construction and characterization of a humanized anti-gamma-lg receptor type I (Fc gamma Rl) monoclonal antibody," J Immunol. Nov. 15, 1995;155(10):4996-5002.
Green KA, et al. "Antibody to the ligand for CD40 (gp39) inhibits murine AIDS-associated splenomegaly, hypergammaglobulinemia, and immunodeficiency in disease-susceptible C57BL/6 mice," J Virol. Apr. 1996;70(4):2569-75.
Green KA, et al. "Myeloid-derived suppressor cells in murine retrovirus-induced AIDS inhibit T- and B-cell responses in vitro that are used to define the immunodeficiency," J Virol. Feb. 2013;87(4):2058-71.
Greenwald RJ, et al. "The B7 family revisited," Annu Rev Immunol. 2005;23:515-48.
Groux H, et al. "A CD4+ T-cell subset inhibits antigen-specific T-cell responses and prevents colitis," Nature. Oct. 16, 1997;389(6652):737-42.
Gruber M, et al. "Efficient tumor cell lysis mediated by a bispecific single chain antibody expressed in *Escherichia coli*," J Immunol. Jun. 1, 1994;152(11):5368-74.
Guatelli JC, et al. "Isothermal, in vitro amplification of nucleic acids by a multienzyme reaction modeled after retroviral replication," Proc Natl Acad Sci U S A. Mar. 1990;87(5):1874-8.
Guindon S, et al. "A simple, fast, and accurate algorithm to estimate large phylogenies by maximum likelihood," Syst Biol. Oct. 2003;52(5):696-704.
Guleria I, et al. "A critical role for the programmed death ligand 1 in fetomaternal tolerance," J Exp Med. Jul. 18, 2005;202(2):231-7.
Gurley WB, et al. "Upstream sequences required for efficient expression of a soybean heat shock gene," Mol Cell Biol. Feb. 1986;6(2):559-65.
Hamilton AJ, et al. "A species of small antisense RNA in posttranscriptional gene silencing in plants," Science. Oct. 29, 1999;286(5441):950-2.
Hann M "On the Double Bond Isostere of the Peptide Bond: Preparation of an Enkephaline Analogue," Journal of the Chemical Society, Perkin Transactions 1982 (1), 307-14.
Hara M, et al. "IL-10 is required for regulatory T cells to mediate tolerance to alloantigens in vivo," J Immunol. Mar. 15, 2001;166(6):3789-96.
Harding FA, et al. "Class switching in human immunoglobulin transgenic mice," nn N Y Acad Sci. Sep. 29, 1995;764:536-46.
Haseloff J, et al. "Simple RNA enzymes with new and highly specific endoribonuclease activities," Nature. Aug. 18, 1988;334(6183):585-91.
Hashida H, et al. "Fusion of HIV-1 Tat protein transduction domain to poly-lysine as a new DNA delivery tool," Br J Cancer. Mar. 22, 2004;90(6):1252-8.
Haskins K, et al. "The major histocompatibility complex-restricted antigen receptor on T cells. I. Isolation with a monoclonal antibody," The Journal of Experimental Medicine. 1983;157(4):1149-69.
Hauser N, et al. "Interaction of cartilage matrix protein with aggrecan. Increased covalent cross-linking with tissue maturation," J Biol Chem. Dec. 13, 1996;271(50):32247-52.
Hauser N, et al. "Native cartilage matrix protein (CMP). A compact trimer of subunits assembled via a coiled-coil alpha-helix," J Biol Chem. Oct. 14, 1994;269(41):25747-53.
Haynes JR, et al. "Particle-mediated nucleic acid immunization," J Biotechnol. Jan. 26, 1996;44(1-3):37-42.
Hedbom E, et al. "Cartilage matrix proteins. An acidic oligomeric protein (COMP) detected only in cartilage," J Biol Chem. Mar. 25, 1992;267(9):6132-6.
Helene C, et al. "Control of gene expression by triple helix-forming oligonucleotides. The antigene strategy," Ann N Y Acad Sci. Oct. 28, 1992;660:27-36.
Hellstrom I, et al. "CD3-mediated activation of tumor-reactive lymphocytes from patients with advanced cancer," Proc Natl Acad Sci U S A. Jun. 5, 2001;98(12):6783-8.

Hinton PR, et al. "Engineered human IgG antibodies with longer serum half-lives in primates," J Biol Chem. Feb. 20, 2004;279(8):6213-6.
Hirano, F., et al., Blockade of B7-H1 and PD-1 by monoclonal antibodies potentiates cancer therapeutic immunity Cancer Res, 2005. 65(3): p. 1089-96.
Ho SN, et al. "Site-directed mutagenesis by overlap extension using the polymerase chain reaction," Gene. Apr. 15, 1989;77(1):51-9.
Ho VT, et al. "The history and future of T-cell depletion as graft-versus-host disease prophylaxis for allogeneic hematopoietic stem cell transplantation," Blood. Dec. 1, 2001;98(12):3192-204.
Hodi, F. S., Overcoming immunological tolerance to melanoma: Targeting CTLA-4. Asia Pac J Clin Oncol, 2010. 6 Suppl 1: p. S16-23.
Hogg N. "The structure and function of Fc receptors," Immunol Today. Jul.-Aug. 1988;9(7-8):185-7.
Holladay, M. W., et al. (1983). "Synthesis of hydroxyethylene and ketomethylene dipeptide isosteres," Tetrahedron Letters 1983 24(41), 4401-4404.
Hollenbaugh D, et al. "Cleavable CD40lg fusion proteins and the binding to sgp39," J Immunol Methods. Dec. 15, 1995;188(1):1-7.
Holliger P, et al. ""Diabodies": small bivalent and bispecific antibody fragments," Proc Natl Acad Sci U S A. Jul. 15, 1993;90(14):6444-8.
Holm L, et al. "DaliLite workbench for protein structure comparison," Bioinformatics. Jun. 2000;16(6):566-7.
Hoos, A., et al., "Development of ipilimumab: contribution to a new paradigm for cancer immunotherapy," Semin Oncol, 2010. 37(5): p. 533-46.
Hopp TP, et al. "Prediction of protein antigenic determinants from amino acid sequences," Proc Natl Acad Sci U S A. Jun. 1981;78(6):3824-8.
Horn JR, et al. "The role of protein dynamics in increasing binding affinity for an engineered protein-protein interaction established by H/D exchange mass spectrometry," Biochemistry. Jul. 18, 2006;45(28):8488-98.
Hotchkiss RS, et al. "Immunosuppression in sepsis: a novel understanding of the disorder and a new therapeutic approach," Lancet Infect Dis. Mar. 2013;13(3):260-8.
Houghten RA, et al. "The use of synthetic peptide combinatorial libraries for the identification of bioactive peptides," Bioorganic & Medicianl Chemistry Letters, vol. 3, No. 3, 1993. pp. 405-412.
Hruby VJ, et al. "Conformational and topographical considerations in the design of biologically active peptides," Biopolymers. Jul. 1993;33(7):1073-82.
Hruby VJ, et al. "Synthesis of oligopeptide and peptidomimetic libraries," Curr Opin Chem Biol. Jun. 1997;1(1):114-9.
Hruby VJ. "Conformational restrictions of biologically active peptides via amino acid side chain groups," Life Sci. Jul. 19, 1982;31(3):189-99.
Huarte, E., et al., "Depletion of dendritic cells delays ovarian cancer progression by boosting antitumor immunity," Cancer Res, 2008. 68(18): p. 7684-91.
Hudson D, et al. "Methionine enkephalin and isosteric analogues. I. Synthesis on a phenolic resin support," Int J Pept Protein Res. 1979;14(3):177-85.
Huston JS, et al. "Protein engineering of antibody binding sites: recovery of specific activity in an anti-digoxin single-chain Fv analogue produced in *Escherichia coli*," Proc Natl Acad Sci U S A. Aug. 1988;85(16):5879-83.
Hutloff A, et al. "ICOS is an inducible T-cell co-stimulator structurally and functionally related to CD28," Nature. Jan. 21, 1999;397(6716):263-6.
Hyrup B, e al. "Peptide nucleic acids (PNA): synthesis, properties and potential applications," Bioorg Med Chem. Jan. 1996;4(1):5-23.
Ike Y, et al. "Solid phase synthesis of polynucleotides. VIII. Synthesis of mixed oligodeoxyribonucleotides by the phosphotriester solid phase method," Nucleic Acids Res. Jan. 25, 1983;11(2):477-88.
Iliopoulos D, et al. "The negative costimulatory molecule PD-1 modulates the balance between immunity and tolerance via miR-21," Eur J Immunol. Jun. 2011;41(6):1754-63.

(56) References Cited

OTHER PUBLICATIONS

Inoue H, et al. "Sequence-dependent hydrolysis of RNA using modified oligonucleotide splints and RNase H," FEBS Lett. May 11, 1987;215(2):327-30.
Inoue H, et al. "Synthesis and hybridization studies on two complementary nona(2'-O-methyl)ribonucleotides," Nucleic Acids Res. Aug. 11, 1987;15(15):6131-48.
Invitrogen (2002) "Guide to Baculovirus Expression Vector Systems (BEVs) and Insect Culture Techniques" Instruction Manual. 30 pages.
Itakura K, et al. "Expression in *Escherichia coli* of a chemically synthesized gene for the hormone somatostatin," Science. Dec. 9, 1977;198(4321):1056-63.
Itakura K, et al. "Synthesis and use of synthetic oligonucleotides," Annu Rev Biochem. 1984;53:323-56.
Iwai, Y., et al., "Involvement of PD-L1 on tumor cells in the escape from host immune system and tumor immunotherapy by PD-L1 blockade," Proc Natl Acad Sci USA, 2002. 99(19): p. 12293-7.
Janssen Clinical Trials "A Study of Safety, Pharmacokinetics, Pharmacodynamics of JNJ-61610588 in Participants With Advanced Cancer," U.S. National Library of Medicine, ClinicalTrials.gov; (https://clinicaltrials.gov) 2017. 9 pages.
Jarvinen LZ, et al. "CD154 on the surface of CD4+CD25+ regulatory T cells contributes to skin transplant tolerance," Transplantation. Nov. 15, 2003;76(9):1375-9.
Jeisy-Scott V, et al. "Increased MDSC accumulation and Th2 biased response to influenza A virus infection in the absence of TLR7 in mice," PLoS One. 2011;6(9):e25242.
Jennings-White, C. et al. (1982). "Synthesis of ketomethylene analogs of dipeptides," Tetrahedron Letters 1982 23(25), 2533-2534.
Jones E, et al. "Depletion of CD25+ regulatory cells results in suppression of melanoma growth and induction of autoreactivity in mice," Cancer Immun. Feb. 22, 2002;2:1.
Jones PT, et al. "Replacing the complementarity-determining regions in a human antibody with those from a mouse," Nature. May 29-Jun. 4, 1986;321(6069):522-5.
Jones TD, et al. "The development of a modified human IFN-alpha2b linked to the Fc portion of human IgG1 as a novel potential therapeutic for the treatment of hepatitis C virus infection," J Interferon Cytokine Res. Sep. 2004;24(9):560-72.
Kaehler, K. C., et al., "Update on immunologic therapy with anti-CTLA-4 antibodies in melanoma: identification of clinical and biological response patterns, immune-related adverse events, and their management," Semin Oncol, 2010. 37(5): p. 485-98.
Kang SM, et al. "Transactivation by AP-1 is a molecular target of T cell clonal anergy," Science. Aug. 21, 1992;257(5073):1134-8.
Karpovsky B, et al. "Production of target-specific effector cells using hetero-cross-linked aggregates containing anti-target cell and anti-Fc gamma receptor antibodies," J Exp Med. Dec. 1, 1984;160(6):1686-701.
Kashmiri SV, et al. "SDR grafting—a new approach to antibody humanization," Methods. May 2005;36(1):25-34.
Kaufman RJ, et al. "Translational efficiency of polycistronic mRNAs and their utilization to express heterologous genes in mammalian cells," EMBO J. Jan. 1987;6(1):187-93.
Kay MA, et al. "Transient immunomodulation with anti-CD40 ligand antibody and CTLA4lg enhances persistence and secondary adenovirus-mediated gene transfer into mouse liver," Proc Natl Acad Sci U S A. Apr. 29, 1997;94(9):4686-91.
Keinänen K, et al. "Biosynthetic lipid-tagging of antibodies," FEBS Lett. Jun. 6, 1994;346(1):123-6.
Keir ME, et al. "PD-1 and its ligands in tolerance and immunity," Annu Rev Immunol. 2008;26:677-704.
Keir ME, et al. "PD-1 regulates self-reactive CD8+ T cell responses to antigen in lymph nodes and tissues," mmunol. Oct. 15, 2007;179(8):5064-70.
Kessel M, et al. "Murine developmental control genes," Science. Jul. 27, 1990;249(4967):374-9.

Killion JJ, et al. "Systemic targeting of liposome-encapsulated immunomodulators to macrophages for treatment of cancer metastasis," Immunomethods. Jun. 1994;4(3):273-9.
Kimmel AR, et al. "Preparation of cDNA and the generation of cDNA libraries: overview," Methods Enzymol. 1987;152:307-16.
Kipriyanov SM, et al. "Recombinant single-chain Fv fragments carrying C-terminal cysteine residues: production of bivalent and biotinylated miniantibodies," Mol Immunol. Oct. 1994;31(14):1047-58.
Kipriyanov SM, et al. "Single-chain antibody streptavidin fusions: tetrameric bifunctional scFv-complexes with biotin binding activity and enhanced affinity to antigen," Hum Antibodies Hybridomas. 1995;6(3):93-101.
Kiss I, et al. "Structure of the gene for cartilage matrix protein, a modular protein of the extracellular matrix. Exon/intron organization, unusual splice sites, and relation to alpha chains of beta 2 integrins, von Willebrand factor, complement factors B and C2, and epidermal growth factor," J Biol Chem. May 15, 1989;264(14):8126-34.
Klinken SP, et al. "Evolution of B cell lineage lymphomas in mice with a retrovirus-induced immunodeficiency syndrome, MAIDS," J Immunol. Feb. 15, 1988;140(4):1123-31.
Kohl S, et al. "Human antibody-dependent cellular cytotoxicity and natural killer cytotoxicity to herpes simplex virus-infected autologous and allogeneic cells," Immunology. Jan. 1983;48(1):187-93.
Köhler G, et al. "Continuous cultures of fused cells secreting antibody of predefined specificity," Nature. Aug. 7, 1975;256(5517):495-7.
Kolaskar AS, et al. "A semi-empirical method for prediction of antigenic determinants on protein antigens," FEBS Lett. Dec. 10, 1990;276(1-2):172-4.
Kostelny SA, et al. "Formation of a bispecific antibody by the use of leucine zippers," J Immunol. Mar. 1, 1992;148(5):1547-53.
Kozbor D, et al. "Specific immunoglobulin production and enhanced tumorigenicity following ascites growth of human hybridomas," J Immunol Methods. Jul. 16, 1985;81(1):31-42.
Kozbor D, et al. "The production of monoclonal antibodies from human lymphocytes," Immunol Today. Mar. 1983;4(3):72-9.
Krishnamurthy S, et al. "Molecular and biologic markers of premalignant lesions of human breast," Adv Anat Pathol. May 2002;9(3):185-97.
Krolick KA, et al. "Selective killing of normal or neoplastic B cells by antibodies coupled to the A chain of ricin," Proc Natl Acad Sci U S A. Sep. 1980;77(9):5419-23.
Kroll DJ, et al. "A multifunctional prokaryotic protein expression system: overproduction, affinity purification, and selective detection," DNA Cell Biol. Jun. 1993;12(5):441-53.
Krutzik, S. R., et al., "TLR activation triggers the rapid differentiation of monocytes into macrophages and dendritic cells," Nat Med, 2005. 11(6): p. 653-60.
Kryczek, I., et al., "B7-H4 expression identifies a novel suppressive macrophage population in human ovarian carcinoma," J Exp Med, 2006. 203(4): p. 871-81.
Kryczek, I., et al., "Cutting edge: induction of B7-H4 on APCs through IL-10: novel suppressive mode for regulatory T cells," J Immunol, 2006. 177(1): p. 40-4.
Kurjan J, et al. "Structure of a yeast pheromone gene (MF alpha): a putative alpha-factor precursor contains four tandem copies of mature alpha-factor," Cell. Oct. 1982;30(3):933-43.
Kuroiwa Y, et al. "Cloned transchromosomic calves producing human immunoglobulin," Nat Biotechnol. Sep. 2002;20(9):889-94.
Kwoh DY, et al. "Transcription-based amplification system and detection of amplified human immunodeficiency virus type 1 with a bead-based sandwich hybridization format," Proc Natl Acad Sci U S A. Feb. 1989;86(4):1173-7.
Labrijn AF, et al. "Efficient generation of stable bispecific IgG1 by controlled Fab-arm exchange," Proc Natl Acad Sci U S A. Mar. 26, 2013;110(13):5145-50.
LaFace D, et al. "Meeting report: regulatory myeloid cells," Int Immunopharmacol. Jul. 2011;11(7):780-2.
Lakso M, et al. "Targeted oncogene activation by site-specific recombination in transgenic mice," Proc Natl Acad Sci U S A. Jul. 15, 1992;89(14):6232-6.

(56) References Cited

OTHER PUBLICATIONS

Lam KS, et al. "A new type of synthetic peptide library for identifying ligand-binding activity," Nature. Nov. 7, 1991;354(6348):82-4.

Lam KS. "Application of combinatorial library methods in cancer research and drug discovery," Anticancer Drug Des. Apr. 1997;12(3):145-67. [Abstract Only].

Landegren U, et al. "A ligase-mediated gene detection technique," Science. Aug. 26, 1988;241(4869):1077-80.

Landt O, et al. "A general method for rapid site-directed mutagenesis using the polymerase chain reaction," Gene. Nov. 30, 1990;96(1):125-8.

Latchman Y, et al. "PD-L2 is a second ligand for PD-1 and inhibits T cell activation," Nat Immunol. Mar. 2001;2(3):261-8.

Latchman YE, et al. "PD-L1-deficient mice show that PD-L1 on T cells, antigen-presenting cells, and host tissues negatively regulates T cells," Proc Natl Acad Sci U S A. Jul. 20, 2004;101(29):10691-6.

Lathe R. "Synthetic oligonucleotide probes deduced from amino acid sequence data. Theoretical and practical considerations," J Mol Biol. May 5, 1985;183(1):1-12.

Laubach VE, et al. "Mice lacking inducible nitric oxide synthase are not resistant to lipopolysaccharide-induced death," Proc Natl Acad Sci U S A. Nov. 7, 1995;92(23):10688-92.

Lázár-Molnár E, et al. "Crystal structure of the complex between programmed death-1 (PD-1) and its ligand PD-L2," Proc Natl Acad Sci U S A. Jul. 29, 2008;105(30):10483-8.

Le Borgne, M., et al., "Dendritic cells rapidly recruited into epithelial tissues via CCR6/CCL20 are responsible for CD8+ T cell crosspriming in vivo," Immunity, 2006. 24(2): p. 191-201.

Le Mercier I, et al. "Beyond CTLA-4 and PD-1, the Generation Z of Negative Checkpoint Regulators," Front Immunol. Aug. 21, 2015;6:418.

Le Mercier I, et al. "VISTA Regulates the Development of Protective Antitumor Immunity," Cancer Res. Apr. 1, 2014;74(7):1933-44.

Lederman, Seth, et al. "A single amino acid substitution in a common African allele of the CD4 molecule ablates binding of the monoclonal antibody, OKT4." Molecular immunology 28.11 (1991): 1171-1181.

Lee et al., "Increased vaccine-specific T cell frequency after peptide-based vaccination correlates with increased susceptibility to in vitro stimulation but does not lead to tumor regression." The Journal of Immunology 163.11 (1999): 6292-6300.

Lemaitre M, et al. "Specific antiviral activity of a poly(L-lysine)-conjugated oligodeoxyribonucleotide sequence complementary to vesicular stomatitis virus N protein mRNA initiation site," Proc Natl Acad Sci U S A. Feb. 1987;84(3):648-52.

Leng et al., "Potential roles of IL-9 in the pathogenesis of systemic lupus erythematosus", American Journal of Clinical and Experimental Immunology 2012;I(I):28-32.

León B, et al. "Monocyte-derived dendritic cells formed at the infection site control the induction of protective T helper 1 responses against Leishmania," Immunity. Apr. 2007;26(4):519-31.

León B, et al. "Monocyte-derived dendritic cells in innate and adaptive immunity," Immunol Cell Biol. May-Jun. 2008;86(4):320-4.

Lerner EA. "How to make a hybridoma," Yale J Biol Med. Sep.-Oct. 1981;54(5):387-402.

Letsinger RL, et al. "Cholesteryl-conjugated oligonucleotides: synthesis, properties, and activity as inhibitors of replication of human immunodeficiency virus in cell culture," Proc Natl Acad Sci U S A. Sep. 1989;86(17):6553-6.

Li CH, et al. "beta-Endorphin omission analogs: dissociation of immunoreactivity from other biological activities," Proc Natl Acad Sci U S A. Jun. 1980;77(6):3211-4.

Li F, et al. "Inhibitory Fcγ receptor is required for the maintenance of tolerance through distinct mechanisms," J Immunol. Apr. 1, 2014;192(7):3021-8.

Li W, et al. "Immunotherapy of murine retrovirus-induced acquired immunodeficiency by CD4 T regulatory cell depletion and PD-1 blockade," J Virol. Dec. 2011;85(24):13342-53.

Li W, et al. "The role of CD4 T cells in the pathogenesis of murine AIDS," J Virol. Jun. 2006;80(12):5777-89.

Lin DY, et al. "The PD-1/PD-L1 complex resembles the antigen-binding Fv domains of antibodies and T cell receptors," Proc Natl Acad Sci U S A. Feb. 26, 2008;105(8):3011-6.

Lines JL, et al. "VISTA is a novel broad-spectrum negative checkpoint regulator for cancer immunotherapy," Cancer Immunol Res. Jun. 2014;2(6):510-7.

Lines JL, et al. "VISTA is an immune checkpoint molecule for human T cells," Cancer Res. Apr. 1, 2014;74(7):1924-32.

Liu AY, et al. "Chimeric mouse-human IgG1 antibody that can mediate lysis of cancer cells," Proc Natl Acad Sci U S A. May 1987;84(10):3439-43.

Liu J, et al. "Immune-checkpoint proteins VISTA and PD-1 nonredundantly regulate murine T-cell responses," Proc Natl Acad Sci U S A. May 26, 2015;112(21):6682-7.

Liu MA, et al. "Heteroantibody duplexes target cells for lysis by cytotoxic T lymphocytes," Proc Natl Acad Sci U S A. Dec. 1985;82(24):8648-52.

Lobley A, et al. "pGenTHREADER and pDomTHREADER: new methods for improved protein fold recognition and superfamily discrimination," Bioinformatics. Jul. 15, 2009;25(14):1761-7.

Lonberg N, et al. "Antigen-specific human antibodies from mice comprising four distinct genetic modifications," Nature. Apr. 28, 1994;368(6474):856-9.

Lonberg N, et al. "Human antibodies from transgenic mice," Int Rev Immunol. 1995;13(1):65-93.

Lopez-Pedrera et al., "Accelerated atherosclerosis in systemic lupus erythematosus: role of proinflammatory cytokines and therapeutic approaches", Journal of Biomedicine & Biotechnology, 2010 Article ID 607084.

Lorain S, et al. "Transient immunomodulation allows repeated injections of AAV1 and correction of muscular dystrophy in multiple muscles," Mol Ther. Mar. 2008;16(3):541-7.

Luckow VA, et al. "High level expression of nonfused foreign genes with Autographa californica nuclear polyhedrosis virus expression vectors," Virology. May 1989;170(1):31-9.

Lutz MB, et al. "An advanced culture method for generating large quantities of highly pure dendritic cells from mouse bone marrow," J Immunol Methods. Feb. 1, 1999;223(1):77-92.

Macatangay BJ, et al. "MDSC: a new player in HIV immunopathogenesis," AIDS. Jul. 31, 2012;26(12):1567-9.

Maher, LJ. "DNA triple-helix formation: an approach to artificial gene repressors?" Bioessays. Dec. 1992;14(12):807-15.

Mahnke K, et al. "The dendritic cell receptor for endocytosis, DEC-205, can recycle and enhance antigen presentation via major histocompatibility complex class II-positive lysosomal compartments," J Cell Biol. Oct. 30, 2000;151(3):673-84.

Malashkevich VN, et al. "The crystal structure of a five-stranded coiled coil in COMP: a prototype ion channel?" Science. Nov. 1, 1996;274(5288):761-5.

Marigo, I., et al. "Tumor-induced tolerance and immune suppression by myeloid derived suppressor cells," Immunol Rev, 2008. 222: p. 162-79.

Martinez T, et al. "Disulfide connectivity of human immunoglobulin G2 structural isoforms," Biochemistry. Jul. 15, 2008;47(28):7496-508.

McCafferty J, et al. "Phage antibodies: filamentous phage displaying antibody variable domains," Nature. Dec. 6, 1990,348(6301):552-4.

McConnell HM, et al. "The cytosensor microphysiometer: biological applications of silicon technology," Science. Sep. 25, 1992;257(5078):1906-12.

McHugh RS, et al. "CD4(+)CD25(+) immunoregulatory T cells: gene expression analysis reveals a functional role for the glucocorticoid-induced TNF receptor," Immunity. Feb. 2002;16(2):311-23.

McIvor RS, et al. "Isolation and characterization of a variant dihydrofolate reductase cDNA from methotrexate-resistant murine L5178Y cells," Nucleic Acids Res. Dec. 11, 1990;18(23):7025-32.

Medina D. "The preneoplastic phenotype in murine mammary tumorigenesis," J Mammary Gland Biol Neoplasia. Oct. 2000;5(4):393-407.

(56) References Cited

OTHER PUBLICATIONS

Melief CJ. "Cancer immunotherapy by dendritic cells," Immunity. Sep. 19, 2008;29(3):372-83.
Mencacci A, et al. "CD80+Gr-1+ myeloid cells inhibit development of antifungal Th1 immunity in mice with candidiasis," J Immunol. Sep. 15, 2002;169(6):3180-90.
Merrifield B. "Concept and early development of solid-phase peptide synthesis," Methods Enzymol. 1997;289:3-13.
Mezo AR, et al. "Atrial natriuretic peptide-Fc, ANP-Fc, fusion proteins: semisynthesis, in vitro activity and pharmacokinetics in rats," Bioconjug Chem. Mar. 21, 2012;23(3):518-26.
Milstein C, et al. "Hybrid hybridomas and their use in immunohistochemistry," Nature. Oct. 6-12, 1983;305(5934):537-40.
Mingozzi F, et al. "Immune responses to AAV vectors: overcoming barriers to successful gene therapy," Blood. Jul. 4, 2013;122(1):23-36.
Monteiro RC, et al. "Molecular heterogeneity of Fc alpha receptors detected by receptor-specific monoclonal antibodies," J Immunol. Mar. 15, 1992;148(6):1764-70.
Moore GJ. "Designing peptide mimetics," Trends Pharmacol Sci. Apr. 1994;15(4):124-9.
Morrison SL, et al. "Chimeric human antibody molecules: mouse antigen-binding domains with human constant region domains," Proc Natl Acad Sci U S A. Nov. 1984;81(21):6851-5.
Morrison SL. "Transfectomas provide novel chimeric antibodies," Science. Sep. 20, 1985;229(4719):1202-7.
Muller PY, et al. "Safety assessment and dose selection for first-in-human clinical trials with immunomodulatory monoclonal antibodies," Clin Pharmacol Ther. Mar. 2009;85(3):247-58.
Nakano H, et al. "Blood-derived inflammatory dendritic cells in lymph nodes stimulate acute T helper type 1 immune responses," Nat Immunol. Apr. 2009;10(4):394-402.
Nalbandian A, et al. "Interleukin-17 and systemic lupus erythematosus: current concepts," Clin Exp Immunol. Aug. 2009;157(2):209-15.
Nathwani AC, et al. "Adenovirus-associated virus vector-mediated gene transfer in hemophilia B," N Engl J Med. Dec. 22, 2011;365(25):2357-65.
NCBI Accession No. AAH89443 [gi:59807841] with Revision History—Feb. 16, 2005-Jun. 6, 2006.
NCBI Accession No. AK004116 [gi:12835174] with Revision History—Feb. 8, 2001-Sep. 2, 2005.
NCBI Accession No. BC089443 [gi:59807840] with Revision History—Feb. 15, 2005-Jun. 6, 2006.
NCBI Accession No. NM.sub.—022153 [gi:62339431] with Revision History—Apr. 7, 2005-Jun. 26, 2007.
NCBI Accession No. NM.sub.—026125 [gi:13385631] with Revision History—Mar. 20, 2001-May 7, 2006. 142365660 which replaced 13385631 is provided.
NCBI Accession No. NM.sub.—028732 [gi:31980769] with Revision History—Mar. 20, 2001-May 7, 2006. 143249860 which replaced 31980769 is provided.
NCBI Accession No. NM.sub.—138530 [gi:51491892] with Revision History—Apr. 4, 2002-Nov. 18, 2006.
NCBI Accession No. NP.sub.—071436 [gi:62339432] with Revision History—Apr. 7, 2005-Aug. 13, 2006.
NCBI Accession No. NP.sub.—080401 [gi:13385632] with Revision History—Mar. 20, 2001-May 7, 2006.
NCBI Accession No. XM.sub.—233720 [gi:109475938] with Revision History—Jan. 13, 2003-Jun. 22, 2006.
Nesbeth YC, et al. "CD4+ T cells elicit host immune responses to MHC class II-negative ovarian cancer through CCL5 secretion and CD40-mediated licensing of dendritic cells," J Immunol. May 15, 2010;184(10):5654-62.
Neuberger MS, et al. "A hapten-specific chimaeric IgE antibody with human physiological effector function," Nature. Mar. 21-27, 1985;314(6008):268-70.
Neuberger MS, et al. "Recombinant antibodies possessing novel effector functions," Nature. Dec. 13-19, 1984;312(5995):604-8.
Nielsen MB, et al. "Melanoma vaccines: the paradox of T cell activation without clinical response," Cancer Chemother Pharmacol. 2000;46 Suppl:S62-6.
Niklinski J, et al. "Molecular genetic abnormalities in premalignant lung lesions: biological and clinical implications," Eur J Cancer Prev. Jun. 2001;10(3):213-26.
Nishikawa H, et al. "Regulatory T cells in tumor immunity," Int J Cancer. Aug. 15, 2010;127(4):759-67.
Nishimura H, et al. "Autoimmune dilated cardiomyopathy in PD-1 receptor-deficient mice," Science. Jan. 12, 2001;291(5502):319-22.
Nishimura H, et al. "Development of lupus-like autoimmune diseases by disruption of the PD-1 gene encoding an ITIM motif-carrying immunoreceptor," Immunity. Aug. 1999;11(2):141-51.
Nomi, T. et al., Clinical significance and therapeutic potential of the programmed death-1 ligand/programmed death-1 pathway in human pancreatic cancer. Clin. Cancer Res. 2007, vol. 13, pp. 2152-2157.
Norde, W.J. et al., "Coinhibitory molecules in hematologic malignancies: targets for therapeutic intervention", Blood, Jul. 2012, vol. 120, No. 4, pp. 728-736.
Nowak EC, et al. "Immunoregulatory functions of VISTA," Immunol Rev. Mar. 2017;276(1):66-79.
Nygren H. "Conjugation of horseradish peroxidase to Fab fragments with different homobifunctional and heterobifunctional cross-linking reagents. A comparative study," J Histochem Cytochem. May 1982;30(5):407-12.
O'Gorman S, et al. "Recombinase-mediated gene activation and site-specific integration in mammalian cells," Science. Mar. 15, 1991;251(4999):1351-5.
Ohtsuka E, et al. "An alternative approach to deoxyoligonucleotides as hybridization probes by insertion of deoxyinosine at ambiguous codon positions," J Biol Chem. Mar. 10, 1985;260(5):2605-8.
Okazaki T, et al. "The PD-1-PD-L pathway in immunological tolerance," Trends Immunol. Apr. 2006;27(4):195-201.
Orlandi R, et al. "Cloning immunoglobulin variable domains for expression by the polymerase chain reaction," Proc Natl Acad Sci U S A. May 1989;86(10):3833-7.
Ortler S, et al. "B7-H1 restricts neuroantigen-specific T cell responses and confines inflammatory CNS damage: implications for the lesion pathogenesis of multiple sclerosis," Eur J Immunol. Jun. 2008;38(6):1734-44.
Ostergaard S, et al. "Peptomers: a versatile approach for the preparation of diverse combinatorial peptidomimetic bead libraries," Mol Divers. 1997;3(1):17-27.
Ostrand-Rosenberg S, et al. "Myeloid-derived suppressor cells: linking inflammation and cancer," J Immunol. Apr. 15, 2009;182(8):4499-506.
Ostrand-Rosenberg S. "Myeloid-derived suppressor cells: more mechanisms for inhibiting antitumor immunity," Cancer Immunol Immunother. Oct. 2010;59(10):1593-600.
Ostresh JM, et al. "Generation and use of nonsupport-bound peptide and peptidomimetic combinatorial libraries," Methods Enzymol. 1996;267:220-34.
Ottavi A, et al. "An improved method to obtain a single recombinant vasoactive intestinal peptide (VIP) analog," Biochimie. Apr. 1998;80(4):289-93.
Owais M, et al. "Chloroquine encapsulated in malaria-infected erythrocyte-specific antibody-bearing liposomes effectively controls chloroquine-resistant Plasmodium berghei infections in mice," Antimicrob Agents Chemother. Jan. 1995;39(1):180-4.
Oyarzun P, et al. "A bioinformatics tool for epitope-based vaccine design that accounts for human ethnic diversity: Application to emerging infectious diseases," Vaccine. 2015;33(10):1267-73.
Ozkaynak, E., et al. "Programmed death-1 targeting can promote allograft survival," J Immunol 2002. 169: 6546-6553.
Pain D, et al. "Preparation of protein A-peroxidase monoconjugate using a heterobifunctional reagent, and its use in enzyme immunoassays," J Immunol Methods. 1981;40(2):219-30.
Parisi, S., et al. "A regulatory loop involving Dies1 and miR-125a controls BMP4 signaling in mouse embryonic stem cells," FASEB J 2012. 26: 3957-3968.
Paulsson M, et al. "Purification and structural characterization of a cartilage matrix protein," Biochem J. Aug. 1, 1981;197(2):367-75.

(56) References Cited

OTHER PUBLICATIONS

Payne G. "Progress in immunoconjugate cancer therapeutics," Cancer Cell. Mar. 2003;3(3):207-12.
Peranzoni E, et al. "Myeloid-derived suppressor cell heterogeneity and subset definition," Curr Opin Immunol. Apr. 2010;22(2):238-44.
Perry-O'Keefe H, et al. "Peptide nucleic acid pre-gel hybridization: an alternative to southern hybridization," Proc Natl Acad Sci U S A. Dec. 10, 1996;93(25):14670-5.
Piccirillo CA, et al. "Naturally-occurring CD4+CD25+ immunoregulatory T cells: central players in the arena of peripheral tolerance," Semin Immunol. Apr. 2004;16(2):81-8.
Piccotti JR, et al. "T-cell-dependent antibody response: assay development in cynomolgus monkeys," J Immunotoxicol. Oct. 1, 2005;2(4):191-6.
Picha, Kristen M. et al., "Protein Engineering Strategies for Sustained Glucagon-Like Peptide-1 Receptor-Dependent Control of Glucose Homeostasis", Diabetes, 2008. vol. 57, pp. 1926-1934.
Pilat N, et al. "Costimulatory pathways in transplantation," Semin Immunol. Aug. 2011;23(4):293-303.
Pinkert CA, et al. "An albumin enhancer located 10 kb upstream functions along with its promoter to direct efficient, liver-specific expression in transgenic mice," Genes Dev. May 1987;1(3):268-76.
Platt et al., "Gene hunting in the genomic era: approaches to diagnostic dilemmas in patients with primary immunodeficiencies," J Allergy Clin Immunol 2014, 134: 262-268.
Podojil JR, et al. "B7-H4Ig inhibits mouse and human T-cell function and treats EAE via IL-10/Treg-dependent mechanisms," J Autoimmun. Aug. 2013;44:71-81.
Polyak SW, et al. "Introduction of spacer peptides N-terminal to a cleavage recognition motif in recombinant fusion proteins can improve site-specific cleavage," Protein Eng. Jun. 1997;10(6):615-9.
Pontén J. "Cell biology of precancer," Eur J Cancer. Oct. 2001;37 Suppl 8:S97-113.
Powell et al. "Peptide stability in drug development. II. Effect of single amino acid substitution and glycosylation on peptide reactivity in human serum," Pharm Res. Sep. 1993;10(9):1268-73.
Prasad, D. V., et al. "B7S1, a novel B7 family member that negatively regulates T cell activation," Immunity, 2003. 18(6): p. 863-73.
Prokunina, L., A regulatory polymorphism in PDCD1 is associated with susceptibility to systemic lupus erythematosus in humans. Nat Genet 2002. 32: 666-669.
Qin A, et al. "Expansion of monocytic myeloid-derived suppressor cells dampens T cell function in HIV-1-seropositive individuals," J Virol. Feb. 2013;87(3):1477-90.
Qin W, et al. "Fusion protein of CDR mimetic peptide with Fc inhibit TNF-alpha induced cytotoxicity," Mol Immunol. Feb. 2006;43(6):660-6.
Qu, C., et al., Role of CCR8 and other chemokine pathways in the migration of monocyte-derived dendritic cells to lymph nodes. J Exp Med, 2004. 200(10): p. 1231-41.
Queen C, et al. "Immunoglobulin gene transcription is activated by downstream sequence elements," Cell. Jul. 1983;33(3):741-8.
Queen, et al. "A humanized antibody that binds to the interleukin 2 receptor," Proc Natl Acad Sci U S A. Dec. 1989;86(24):10029-33.
Rabinovich, G. A., D. Gabrilovich, and E. M. Sotomayor, Immunosuppressive strategies that are mediated by tumor cells. Annu Rev Immunol, 2007. 25: p. 267-96.
Rai BK, et al. "MMM: a sequence-to-structure alignment protocol," Bioinformatics. Nov. 1, 2006;22(21):2691-2.
Rain J.C. et al. (2001) The protein-protein interaction map of Helicobacter pylori. Nature 409: 211-15.
Ranade VV. "Drug delivery systems. 1. site-specific drug delivery using liposomes as carriers," J Clin Pharmacol. Aug. 1989;29(8):685-94.
Randolph, G. J., et al. "Differentiation of phagocytic monocytes into lymph node dendritic cells in vivo," Immunity. 1999. 11(6): p. 753-61.

Rathore R, et al. "Current State of Tolerance: The Holy Grail," Arch Clin Nephrol 3(2): 057-063.
Rattan SI, et al. "Protein synthesis, posttranslational modifications, and aging," Ann N Y Acad Sci. Nov. 21, 1992;663:48-62.
Ravetch JV, et al. "IgG Fc receptors," Annu Rev Immunol. 2001;19:275-90.
Rice RH, et al. "Localization of hair shaft protein VSIG8 in the hair follicle, nail unit, and oral cavity," J Invest Dermatol. Sep. 2011;131(9):1936-8.
Rizo J, et al. "Constrained peptides: models of bioactive peptides and protein substructures," Annu Rev Biochem. 1992;61:387-418.
Robben, P. M., et al., Recruitment of Gr-1+ monocytes is essential for control of acute toxoplasmosis. J Exp Med, 2005. 201(11): p. 1761-9.
Roberge JY, et al. "A strategy for a convergent synthesis of N-linked glycopeptides on a solid support," Science. Jul. 14, 1995;269(5221):202-4.
Robertson JM, Jensen PE, Evavold BD. DO11.10 and OT-II T Cells Recognize a C-Terminal Ovalbumin 323-339 Epitope. The Journal of Immunology. 2000;164(9):4706-12. doi: 10.4049/jimmunol.164.9.4706.
Roda G, Jharap B, Neeraj N, Colombel J-F. Loss of Response to Anti-TNFs: Definition, Epidemiology, and Ma nagement. Clin Trans Gastroenterol. 2016;7:e135. doi: 10.1038/ctg.2015.63.
Rose TM, et al. "Consensus-degenerate hybrid oligonucleotide primers for amplification of distantly related sequences," Nucleic Acids Res. Apr. 1, 1998;26(7):1628-35.
Rossolini GM, et al. "Use of deoxyinosine-containing primers vs degenerate primers for polymerase chain reaction based on ambiguous sequence information," Mol Cell Probes. Apr. 1994;8(2):91-8.
Rowe WP, et al. "Plaque assay techniques for murine leukemia viruses," Virology. Dec. 1970;42(4):1136-9.
Saito G, et al. "Drug delivery strategy utilizing conjugation via reversible disulfide linkages: role and site of cellular reducing activities," Adv Drug Deliv Rev. Feb. 10, 2003;55(2):199-215.
Sakaguchi S, et al. "Immunologic self-tolerance maintained by activated T cells expressing IL-2 receptor alpha-chains (CD25). Breakdown of a single mechanism of self-tolerance causes various autoimmune diseases," J Immunol. Aug. 1, 1995;155(3):1151-64.
Sakaguchi S, et al. "Immunologic tolerance maintained by CD25+ CD4+ regulatory T cells: their common role in controlling autoimmunity, tumor immunity, and transplantation tolerance," Immunol Rev. Aug. 2001;182:18-32.
Sakaguchi S, et al. "Organ-specific autoimmune diseases induced in mice by elimination of T cell subset. I. Evidence for the active participation of T cells in natural self-tolerance; deficit of a T cell subset as a possible cause of autoimmune disease," J Exp Med. Jan. 1, 1985;161(1):72-87.
Sakaguchi S, et al. "Regulatory T cells: key controllers of immunologic self-tolerance," Cell. May 26, 2000;101(5):455-8.
Salama AD, et al. "Critical role of the programmed death-1 (PD-1) pathway in regulation of experimental autoimmune encephalomyelitis," J Exp Med. Jul. 7, 2003;198(1):71-8.
Sasikumar P, et al. "Abstact B006: Functional antagonism of VISG8-mediated immune suppression by oral VISTA agents," Abstacts AACR-NCI-EORTC International Conference: Molecular Targets and Cancer Therapeutics; Oct. 2017. 5 pages.
Scaria A, et al. "Antibody to CD40 ligand inhibits both humoral and cellular immune responses to adenoviral vectors and facilitates repeated administration to mouse airway," Gene Ther. Jun. 1997;4(6):611-7.
Scarlett, U. K., et al., In situ stimulation of CD40 and Toll-like receptor 3 transforms ovarian cancerinfiltrating dendritic cells from immunosuppressive to immunostimulatory cells. Cancer Res, 2009. 69(18): p. 7329-37.
Schreier et al. "Targeting of liposomes to cells expressing CD4 using glycosylphosphatidylinositol-anchored gp120. Influence of liposome composition on intracellular trafficking," J Biol Chem. Mar. 25, 1994;269(12):9090-8.
Schubbert R, et al. "Foreign (M13) DNA ingested by mice reaches peripheral leukocytes, spleen, and liver via the intestinal wall mucosa and can be covalently linked to mouse DNA," Proc Natl Acad Sci U S A. Feb. 4, 1997;94(3):961-6.

(56) References Cited

OTHER PUBLICATIONS

Schultz LD, et al. "Expression and secretion in yeast of a 400-kDa envelope glycoprotein derived from Epstein-Barr virus," Gene. 1987;54(1):113-23.
Scott JK, et al. "Searching for peptide ligands with an epitope library," Science. Jul. 27, 1990;249(4967):386-90.
Sedy, J. R., "B and T lymphocyte attenuator regulates T cell activation through interaction with herpesvirus entry mediator," Nat Immunol 2005. 6: 90-98.
Seed B. "An LFA-3 cDNA encodes a phospholipid-linked membrane protein homologous to its receptor CD2," Nature. Oct. 29-Nov. 4, 1987;329(6142):840-2.
Seifter S, et al. "Analysis for protein modifications and nonprotein cofactors," Methods Enzymol. 1990;182:626-46.
Senter PD, et al. "Selective activation of anticancer prodrugs by monoclonal antibody-enzyme conjugates," Adv Drug Deliv Rev. Dec. 31, 2001;53(3):247-64.
Sequence Alignment, 2010, 1 page. U.S. Pat. No. 8,236,304 (U.S. Appl. No. 11/912,397) on May 14, 2010.
Sequence Alignment, 2014, 2 pages. U.S. Pat. No. 9,631,018 (U.S. Appl. No. 13/637,381) on Oct. 29, 2014.
Sequence alignment, 2015, 3 pages. U.S. Appl. No. 13/925,034 on Oct. 16, 2015.
Serbina, N. V., et al., TNF/iNOS-producing dendritic cells mediate innate immune defense against bacterial infection. Immunity, 2003. 19(1): p. 59-70.
Seregin SS, et al. "Improving adenovirus based gene transfer: strategies to accomplish immune evasion,"Viruses. Sep. 2010;2(9):2013-36.
Sharma, M. D., et al., "Plasmacytoid dendritic cells from mouse tumor-draining lymph nodes directly activate mature Tregs via indoleamine 2,3-dioxygenase," J Clin Invest, 2007. 117(9): p. 2570-82.
Sharma, P. et al., "Novel cancer immunotherapy agents with survival benefit: recent successes and next steps", Nature Reviews Cancer, 2011, vol. 11, pp. 805-812.
Sharpe AH, et al. "The B7-CD28 superfamily," Nat Rev Immunol. Feb. 2002;2(2):116-26.
Shaw DR, et al. "Mouse/human chimeric antibodies to a tumor-associated antigen: biologic activity of the four human IgG subclasses," J Natl Cancer Inst. Dec. 7, 1988;80(19):1553-9.
Sheehan, K, et al. "The relationship between cyclooxygenase-2 expression and colorectal cancer," JAMA, 1999. 282: p. 1254-7.
Shevach EM. "Regulatory T cells in autoimmmunity," Annu Rev Immunol. 2000;18:423-49.
Shevach, E. M., CD4+ CD25+ suppressor T cells: more questions than answers. Nat Rev Immunol, 2002. 2(6): p. 389-400.
Shields RL, et al. "High resolution mapping of the binding site on human IgG1 for Fc gamma RI, Fc gamma RII, Fc gamma RIII, and FcRn and design of IgG1 variants with improved binding to the Fc gamma R," J Biol Chem. Mar. 2, 2001;276(9):6591-604.
Shields RL, et al. "Lack of fucose on human IgG1 N-linked oligosaccharide improves binding to human Fcgamma RIII and antibody-dependent cellular toxicity," J Biol Chem. Jul. 26, 2002;277(30):26733-40.
Shimizu J, et al. "Stimulation of CD25(+)CD4(+) regulatory T cells through GITR breaks immunological self-tolerance," Nat Immunol. Feb. 2002;3(2):135-42.
Shortman, K. et al. "Steady-state and inflammatory dendritic-cell development," Nat Rev Immunol, 2007. 7(1): p. 19-30.
Shulman M, et al. "A better cell line for making hybridomas secreting specific antibodies," Nature. Nov. 16, 1978;276(5685):269-70.
Sica GL, et al. "B7-H4, a molecule of the B7 family, negatively regulates T cell immunity," Immunity. Jun. 2003;18(6):849-61.
Simard C, et al. "Studies of the susceptibility of nude, CD4 knockout, and SCID mutant mice to the disease induced by the murine AIDS defective virus," J Virol. Apr. 1997;71(4):3013-22.

Sizemore DR, et al. "Attenuated Shigella as a DNA delivery vehicle for DNA-mediated immunization," Science. Oct. 13, 1995;270(5234):299-302.
Skehel JJ, et al. "Coiled coils in both intracellular vesicle and viral membrane fusion," Cell. Dec. 23, 1998;95(7):871-4.
Smith DB, et al. "Single-step purification of polypeptides expressed in *Escherichia coli* as fusions with glutathione S-transferase," Gene. Jul. 15, 1988;67(1):31-40.
Smith GE, et al. "Production of human beta interferon in insect cells infected with a baculovirus expression vector," Mol Cell Biol. Dec. 1983;3(12):2156-65.
Smith JH, et al. "Detection of Mycobacterium tuberculosis directly from sputum by using a prototype automated Q-beta replicase assay," J Clin Microbiol. Jun. 1997;35(6):1477-83.
Smith JH, et al. "Performance of an automated Q-beta replicase amplification assay for Mycobacterium tuberculosis in a clinical trial," J Clin Microbiol. Jun. 1997;35(6):1484-91.
Smith LJ, et al. "Human interleukin 4. The solution structure of a four-helix bundle protein," J Mol Biol. Apr. 20, 1992;224(4):899-904.
Son YI, et al. "A novel bulk-culture method for generating mature dendritic cells from mouse bone marrow cells," J Immunol Methods. Apr. 1, 2002;262(1-2):145-57.
Spatola AF, et al. "Structure-activity relationships of enkephalins containing serially replaced thiomethylene amide bond surrogates," Life Sci. Apr. 7, 1986;38(14):1243-9.
Steinman, R. M. et al. "Tolerogenic dendritic cells," Annu Rev Immunol, 2003. 21: p. 685-711.
Stewart MJ, et al. "Gene transfer in vivo with DNA-liposome complexes: safety and acute toxicity in mice," Hum Gene Ther. Jun. 1992;3(3):267-75.
Studier FW, et al. "Use of T7 RNA polymerase to direct expression of cloned genes," Methods Enzymol. 1990;185:60-89.
Su AI, et al. "Large-scale analysis of the human and mouse transcriptomes," Proc Natl Acad Sci U S A. Apr. 2, 2002;99(7):4465-70.
Suh, W. K., et al. "The B7 family member B7-H3 preferentially down-regulates T helper type 1-mediated immune responses," Nat Immunol 2003. 4:899-906.
Sun LK, et al. "Chimeric antibody with human constant regions and mouse variable regions directed against carcinoma-associated antigen 17-1A," Proc Natl Acad Sci U S A. Jan. 1987;84(1):214-8.
Sunderkotter, C., et al., "Subpopulations of mouse blood monocytes differ in maturation stage and inflammatory response," J Immunol, 2004. 172(7): p. 4410-7.
Tacke, F. et al. "Migratory fate and differentiation of blood monocyte subsets," Immunobiology, 2006. 211(6-8): p. 609-18.
Tafuri A, et al. "ICOS is essential for effective T-helper-cell responses," Nature. Jan. 4, 2001;409(6816):105-9.
Takamatsu N, et al. "Expression of bacterial chloramphenicol acetyltransferase gene in tobacco plants mediated by TMV-RNA," EMBO J. Feb. 1987;6(2):307-11.
Takamura S, et al. "Premature terminal exhaustion of Friend virus-specific effector CD8+ T cells by rapid induction of multiple inhibitory receptors," J Immunol. May 1, 2010;184(9):4696-707.
Takeda S, et al. "Construction of chimaeric processed immunoglobulin genes containing mouse variable and human constant region sequences," Nature. Apr. 4-10, 1985;314(6010):452-4.
Tarhini, A., E. Lo, and D. R. Minor, Releasing the brake on the immune system: ipilimumab in melanoma and other tumors. Cancer Biother Radiopharm, 2010. 25(6): p. 601-13.
Taylor LD, et al. "A transgenic mouse that expresses a diversity of human sequence heavy and light chain immunoglobulins," Nucleic Acids Res. Dec. 11, 1992;20(23):6287-95.
Taylor LD, et al. "Human immunoglobulin transgenes undergo rearrangement, somatic mutation and class switching in mice that lack endogenous IgM," Int Immunol. Apr. 1994;6(4):579-91.
Taylor WR. "The classification of amino acid conservation," J Theor Biol. Mar. 21, 1986;119(2):205-18.
Teft WA, et al. "A molecular perspective of CTLA-4 function," Annu Rev Immunol. 2006;24:65-97.

(56) References Cited

OTHER PUBLICATIONS

Terawaki, S., "Specific and high-affinity binding of tetramerized PD-LI extracellular domain to PD-I-expressing cells: possible application to enhance T cell function," Int Immunol 2007. 19: 881-890.
Thompson JA, et al. "A phase I trial of CD3/CD28-activated T cells (Xcellerated T cells) and interleukin-2 in patients with metastatic renal cell carcinoma," Clin Cancer Res. Sep. 1, 2003;9(10 Pt 1):3562-70.
Thompson JD, et al. "CLUSTAL W: improving the sensitivity of progressive multiple sequence alignment through sequence weighting, position-specific gap penalties and weight matrix choice," Nucleic Acids Res. Nov. 11, 1994;22(22):4673-80.
Thorpe et al., "The Preparation and Cytotoxic Properties of Antibody-Toxin Conjugates", Immunol. Rev., 62: 119-58 (1982).
Tivol EA, et al. "Loss of CTLA-4 leads to massive lymphoproliferation and fatal multiorgan tissue destruction, revealing a critical negative regulatory role of CTLA-4," Immunity. Nov. 1995;3(5):541-7.
Tomizuka K, et al. "Double trans-chromosomic mice: maintenance of two individual human chromosome fragments containing Ig heavy and kappa loci and expression of fully human antibodies," Proc Natl Acad Sci U S A. Jan. 18, 2000;97(2):722-7.
Tomlinson, et al. (1992) "The Repertoire of Human Germline VH Sequences Reveals about Fifty Groups of VH Segments with Different Hypervariable Loops" J. Mol. Biol. 227: 776-798.
Townsend SE, et al. "Tumor rejection after direct costimulation of CD8+ T cells by B7-transfected melanoma cells," Science. Jan. 15, 1993;259(5093):368-70.
Trail PA, et al. "Monoclonal antibody drug immunoconjugates for targeted treatment of cancer," Cancer Immunol Immunother. May 2003;52(5):328-37.
Transmembrane Region Prediction, "SACS MEMSAT2" 2018, 16 pages.
Traunecker A, et al. "Bispecific single chain molecules (Janusins) target cytotoxic lymphocytes on HIV infected cells," EMBO J. Dec. 1991;10(12):3655-9.
Tuaillon N, et al. "Human immunoglobulin heavy-chain minilocus recombination in transgenic mice: gene-segment use in mu and gamma transcripts," Proc Natl Acad Sci U S A. Apr. 15, 1993;90(8):3720-4.
Tuaillon N, et al. "Biased utilization of DHQ52 and JH4 gene segments in a human Ig transgenic minilocus is independent of antigenic selection," J Immunol. Mar. 15, 1994;152(6):2912-20.
Tuladhar et al., "Role of Co-stimulation in Leishmaniasis." Int J Biol Sci. 2011;7(9):1382-90.
Tutt A, et al. "Trispecific F(ab')3 derivatives that use cooperative signaling via the TCR/CD3 complex and CD2 to activate and redirect resting cytotoxic T cells," J Immunol. Jul. 1, 1991;147(1):60-9.
Umaña P, et al. "Engineered glycoforms of an antineuroblastoma IgG1 with optimized antibody-dependent cellular cytotoxic activity," Nat Biotechnol. Feb. 1999;17(2):176-80.
Umezawa F, et al. "Liposome targeting to mouse brain: mannose as a recognition marker," Biochem Biophys Res Commun. Jun. 30, 1988;153(3):1038-44.
Uy R, et al. "Posttranslational covalent modification of proteins," Science. Dec. 2, 1977;198(4320):890-6.
Vaccaro C, et al. "Engineering the Fc region of immunoglobulin G to modulate in vivo antibody levels," Nature Biotechnology. 2005;23(10):1283-8.
Van Elsas A, et al. "Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation," J Exp Med. Aug. 2, 1999;190(3):355-66.
Van Wauwe JP, et al. "OKT3: a monoclonal anti-human T lymphocyte antibody with potent mitogenic properties," The Journal of Immunology. 1980;124(6):2708-13.

Velu V, et al. "Enhancing SIV-specific immunity in vivo by PD-1 blockade," Nature. Mar. 12, 2009;458(7235):206-10.
Verhoeyen M, et al. "Reshaping human antibodies: grafting an antilysozyme activity," Science. Mar. 25, 1988;239(4847):1534-6.
Via CS. "Advances in lupus stemming from the parent-into-FI model". Trends Immunol., Jun. 31, 2010(6):236-45).
Wada K, et al. "Codon usage tabulated from the GenBank genetic sequence data," Nucleic Acids Res. May 11, 1992;20 Suppl:2111-8.
Wadia JS, et al. "Protein transduction technology," Curr Opin Biotechnol. Feb. 2002;13(1):52-6.
Walch A, et al. "Microdissection of tissue sections: application to the molecular genetic characterisation of premalignant lesions," Pathobiology. Jan.-Feb. 2000;68(1):9-17.
Walker JD, et al. "Oncolytic herpes simplex virus 1 encoding 15-prostaglandin dehydrogenase mitigates immune suppression and reduces ectopic primary and metastatic breast cancer in mice," J Virol. Jul. 2011;85(14):7363-71.
Wallace DJ, et al. "Long-Term Safety and Efficacy of Epratuzumab in the Treatment of Moderate-to-Severe Systemic Lupus Erythematosus: Results From an Open-Label Extension Study," Arthritis Care Res (Hoboken). Apr. 2016;68(4):534-43.
Wang et al. "Immune checkpoint protein VISTA regulate autoimmunity and anti-tumor immunity" J Immunol (May 2013) vol. 190 (Meeting Abstract Supplement) No. 53.35, abstract. 2 pages.
Wang G, et al. "The effects of PDL-Ig on collagen-induced arthritis," Rheumatol Int. Apr. 2011;31(4):513-9.
Wang HC, et al. "Maximum immunobioactivity of murine small intestinal intraepithelial lymphocytes resides in a subpopulation of CD43+ T cells," J Immunol. Nov. 15, 2004;173(10):6294-302.
Wang H-X, "Immune mechanisms of Concanavalin A model of autoimmune hepatitis," World Journal of Gastroenterology: WJG. 2012;18(2):119-25.
Wang L, et al. "Disruption of the immune-checkpoint VISTA gene imparts a proinflammatory phenotype with predisposition to the development of autoimmunity," Proc Natl Acad Sci U S A. Oct. 14, 2014;111(41):14846-51.
Wang, L., et al., "Programmed death 1 ligand signaling regulates the generation of adaptive Foxp3+CD4+ regulatory T cells," Proc Natl Acad Sci USA, 2008. 105(27): p. 9331-6.
Wang, X., "B7-H4 induces donor-specific tolerance in mouse islet allografts," Cell Transplant 2012. 21: 99-111.
Wang, X., "B7-H4 Treatment of T Cells Inhibits ERK, JN K, p38, and AKT Activation," PLoS One 2012. 7: e28232.
Ward ES, et al. "Binding activities of a repertoire of single immunoglobulin variable domains secreted from *Escherichia coli*," Nature. Oct. 12, 1989;341(6242):544-6.
Warrington et al. Allergy, Asthma & Clinical Immunology 2011, 7(Suppl 1):S1, 8 pages.
Waterhouse P, et al. "Lymphoproliferative disorders with early lethality in mice deficient in Ctla-4," Science. Nov. 10, 1995;270(5238):985-8.
Weber, J., "Immune checkpoint proteins: a new therapeutic paradigm for cancer—preclinical background: CTLA-4 and PD-1 blockade," Semin Oncol, 2010. 37(5): p. 430-9.
Weiner GJ. "Building better monoclonal antibody-based therapeutics," Nat Rev Cancer. 2015;15(6):361-70.
Weintraub H., et al. "Anti-sense RNA as a molecular tool for] genetic analysis," Trends in Genetics, 1985, pp. 22-25.
Weissmuller S, "TGN1412 Induces Lymphopenia and Human Cytokine Release in a Humanized Mouse Model," PloS One. 2016;II(3):e0149093.
Welling GW, et al. "Prediction of sequential antigenic regions in proteins," FEBS Lett. Sep. 2, 1985;188(2):215-8.
Wetmur JG. "DNA probes: applications of the principles of nucleic acid hybridization," Crit Rev Biochem Mol Biol. 1991;26(3-4):227-59.
Wilcox, R. A., "Cancer-associated myeloproliferation: old association, new therapeutic target," Mayo Clin Proc, 2010. 85(7): p. 656-63.
Wiley RA, et al. "Peptidomimetics derived from natural products," Med Res Rev. May 1993;13(3):327-84.
Williams G, et al. "Dissection of the extracellular human interferon gamma receptor alpha-chain into two immunoglobulin-like domains.

(56) References Cited

OTHER PUBLICATIONS

Production in an *Escherichia coli* thioredoxin gene fusion expression system and recognition by neutralizing antibodies," Biochemistry. Feb. 7, 1995;34(5):1787-97.
Willmon C, et al. "Vesicular stomatitis virus-induced immune suppressor cells generate antagonism between intratumoral oncolytic virus and cyclophosphamide," Mol Ther. Jan. 2011;19(1):140-9.
Wilmut I, et al. "Viable offspring derived from fetal and adult mammalian cells," Nature. Feb. 27, 1997;385(6619):810-3.
Wing, K., et al., "CTLA-4 control over Foxp3+ regulatory T cell function," Science, 2008. 322(5899): p. 271-5.
Winoto A, et al. "A novel, inducible and T cell-specific enhancer located at the 3' end of the T cell receptor alpha locus," EMBO J. Mar. 1989;8(3):729-33.
Winter G, et al. "Man-made antibodies," Nature. Jan. 24, 1991;349(6307):293-9.
Wojcik J, et al. "Prediction, assessment and validation of protein interaction maps in bacteria," J Mol Biol. Nov. 1, 2002;323(4):763-70.
Wolchok JD, et al. "Nivolumab plus ipilimumab in advanced melanoma," N Engl J Med. Jul. 11, 2013;369(2):122-33.
Wood CR, et al. "The synthesis and in vivo assembly of functional antibodies in yeast," Nature. Apr. 4, 1985;314(6010):446-9.
Wood KJ, et al. "Regulatory T cells in transplantation tolerance," Nat Rev Immunol. Mar. 2003;3(3):199-210.
Wu DY, et al. "The ligation amplification reaction (LAR)—amplification of specific DNA sequences using sequential rounds of template-dependent ligation," Genomics. May 1989;4(4):560-9.
Wu S, et al. "Development and application of 'phosphoflow' as a tool for immunomonitoring," Expert Rev Vaccines. 2010;9(6):631-43.
Xu X, et al. "The genomic sequence of the Chinese hamster ovary (CHO)-K1 cell line," Nat Biotechnol. Jul. 31, 2011;29(8):735-41.
Yamaguchi, T. et al. "Regulatory T cells in immune surveillance and treatment of cancer," Semin Cancer Biol, 2006. 16(2): p. 115-23.
Yamane-Ohnuki N, et al. "Establishment of FUT8 knockout Chinese hamster ovary cells: an ideal host cell line for producing completely defucosylated antibodies with enhanced antibody-dependent cellular cytotoxicity," Biotechnol Bioeng. Sep. 5, 2004;87(5):614-22.
Yamaura, K., "In vivo function of immune inhibitory molecule B7-H4 in alloimmune responses," Am J Transplant 2010. 10: 2355-2362.
Yeh MY, et al. "A cell-surface antigen which is present in the ganglioside fraction and shared by human melanomas," Int J Cancer. Mar. 15, 1982;29(3):269-75.
Yeh MY, et al. "Cell surface antigens of human melanoma identified by monoclonal antibody," Proc Natl Acad Sci U S A. Jun. 1979;76(6):2927-31.
Yetter RA, et al. "CD4+ T cells are required for development of a murine retrovirus-induced immunodeficiency syndrome (MAIDS)," J Exp Med. Aug. 1, 1988;168(2):623-35.
Yi, K. H., et al. "Fine tuning the immune response through B7-H3 and B7-H4," Immunol Rev, 2009. 229(1): p. 145-51.
Yoon KW, et al. "Control of signaling-mediated clearance of apoptotic cells by the tumor suppressor p53," Science. 2015;349(6247):1261669.
Yoshinaga SK, et al. "T-cell co-stimulation through B7RP-1 and ICOS," Nature. Dec. 16, 1999;402(6763):827-32.
Youle RJ, et al. "Anti-Thy 1.2 monoclonal antibody linked to ricin is a potent cell-type-specific toxin," Proc Natl Acad Sci U S A. Sep. 1980;77(9):5483-6.
Youn JI, et al. "The biology of myeloid-derived suppressor cells: the blessing and the curse of morphological and functional heterogeneity," Eur J Immunol. Nov. 2010;40(11):2969-75.
Youngnak, P., "Differential binding properties of B7-H1 and B7-DC to programmed death-1," Biochem Biophys Res Commun 2003. 307: 672-677.
Zelinskyy G, et al. "The regulatory T-cell response during acute retroviral infection is locally defined and controls the magnitude and duration of the virus-specific cytotoxic T-cell response," Blood. Oct. 8, 2009;114(15):3199-207.
Zenewicz, et al. "CD4 T-cell differentiation and inflammatory bowel disease," Trends Mol Med. May 2009;15(5):199-207.
Zervos AS, et al. "Mxi1, a protein that specifically interacts with Max to bind Myc-Max recognition sites," Cell. Jan. 29, 1993;72(2):223-32.
Zhang X, et al. "Bcr-Abl efficiently induces a myeloproliferative disease and production of excess interleukin-3 and granulocyte-macrophage colony-stimulating factor in mice: a novel model for chronic myelogenous leukemia," Blood. Nov. 15, 1998;92(10):3829-40.
Zhang, A., (2015), "Conformational difference in human IgG2 disulfide isoforms revealed by hydrogen/deuterium exchange mass spectrometry", Biochemistry, 54(10), 1956-1962.
Zheng, S. G., et al., "TGF-beta requires CTLA-4 early after T cell activation to induce FoxP3 and generate adaptive CD4+CD25+ regulatory cells," J Immunol, 2006. 176(6): p. 3321-9.
Zhu N, et al. "Systemic gene expression after intravenous DNA delivery into adult mice," Science. Jul. 9, 1993;261(5118):209-11.
Zhu Y, et al. "B7-H5 costimulates human T cells via CD28H," Nat Commun. 2013;4:2043.
Zhu Z, et al. "High level secretion of a humanized bispecific diabody from *Escherichia coli*," Biotechnology (N Y). Feb. 1996;14(2):192-6.
Zhu, G., "B7-H4-deficient mice display augmented neutrophil-mediated innate immunity," Blood 2009. 113: 1759-1767.
Zon G. "Oligonucleotide analogues as potential chemotherapeutic agents," Pharm Res. Sep. 1988;5(9):539-49.
Zou, W, et al. "Inhibitory B7-family molecules in the tumour microenvironment," Nat Rev Immunol, 2008. 8(6): p. 467-77.
Zou, W., "Regulatory T cells, tumour immunity and immunotherapy," Nat Rev Immunol, 2006. 6(4): p. 295-307.
Zuckermann RN, et al. "Discovery of nanomolar ligands for 7-transmembrane G-protein-coupled receptors from a diverse N-(substituted)glycine peptoid library," J Med Chem. Aug. 19, 1994;37(17):2678-85.
Antonarakis ES. "Combining active immunotherapy with immune checkpoint blockade for the treatment of advanced prostate cancer," Asian J Androl. Jul. 2012;14(4):520-1.
Brahmer JR, et al. "Safety and activity of anti-PD-L1 antibody in patients with advanced cancer," N Engl J Med. Jun. 28, 2012;366(26):2455-65.
Brahmer, et al. Supplementary Appendix, Jun. 28, 2012, 26 pages.
Brahmer, et al. Supplementary Protocol, Jun. 28, 2012, 700 pages.
Curran MA, et al. "PD-1 and CTLA-4 combination blockade expands infiltrating T cells and reduces regulatory T and myeloid cells within B16 melanoma tumors," Proc Natl Acad Sci USA. Mar. 2, 2010;107(9):4275-80.
Wang, Li PhD—Dartmouth Medical School Presentation at the SITC (Society for Immunotherapy of Cancer) 26th Annual Meeting Dec. 2011.
Martinez Forero I, et al. "Workshop on immunotherapy combinations. Society for Immunotherapy of Cancer annual meeting Bethesda, Nov. 3, 2011," J Transl Med. May 28, 2012;10:108.
Pilon-Thomas S, et al. "Blockade of programmed death ligand 1 enhances the therapeutic efficacy of combination mmunotherapy against melanoma," J Immunol. Apr. 1, 2010;184(7):3442-9.
Program of the SITC (Society for Immunotherapy of Cancer) 26th Annual Meeting Nov. 2011.
Quah BJ, et al. "The use of carboxyfluorescein diacetate succinimidyl ester (CFSE) to monitor lymphocyte proliferation," J Vis Exp. Oct. 12, 2010;(44). pii: 2259.
Topalian SL, et al. "Targeting the PD-1/B7-H1(PD-L1) pathway to activate anti-tumor immunity," Curr Opin Immunol. Apr. 2012;24(2):207-12.
Wang, L. et al. "Immune Checkpoint Protein Vista as a Novel Target for Cancer Immunotherapy," Abstracts for the 27th Annual Scientific Meeting of the Society for Immunotherapy of Cancer (SITC), J Immunother. Nov. 2012-Dec. 35 (9):721,781.

(56) References Cited

OTHER PUBLICATIONS

Yu P, et al. "Simultaneous blockade of multiple immune system inhibitory checkpoints enhances antitumor activity mediated by interleukin-15 in a murine metastatic colon carcinoma model," Clin Cancer Res. Dec. 15, 2010;16 (24):6019-28.

Yu P, et al. "Simultaneous inhibition of two regulatory T-cell subsets enhanced Interleukin-15 efficacy in a prostate tumor model," Proc Natl Acad Sci U S A. Apr. 17, 2012;109(16):6187-92.

Zitvogel L, et al. "Targeting PD-1/PD-L1 interactions for cancer immunotherapy," Oncoimmunology. Nov. 1, 2012;1(8):1223-1225.

Balducci, Lodovico. "Cancer Prevention in the Older Individual." Seminars in oncology nursing vol. 32,3 (2016): 314-24. doi:10.1016/j.soncn.2016.05.011.

Damschroder, Melissa M et al. "Analysis of human and primate CD2 molecules by protein sequence and epitope mapping with anti-human CD2 antibodies." Molecular immunology vol. 41,10 (2004): 985-1000. doi:10.1016/j.molimm.2004.05.004.

Kanyavuz, Alexia et al. "Breaking the law: unconventional strategies for antibody diversification." Nature reviews. Immunology vol. 19,6 (2019): 355-368. doi:10.1038/s41577-019-0126-7.

Khan, Lubina et al. "Cross-neutralizing anti-HIV-1 human single chain variable fragments(scFvs) against CD4 binding site and N332 glycan identified from a recombinant phage library." Scientific reports vol. 7 45163. Mar. 23, 2017, doi:10.1038/srep45163.

Lee, Jiwon et al. "Molecular-level analysis of the serum antibody repertoire in young adults before and after seasonal influenza vaccination." Nature medicine vol. 22,12 (2016): 1456-1464.doi:10.1038/nm.4224.

Linsley PS, et al. "The clinical utility of inhibiting CD28-mediated costimulation," Immunol Rev. May 2009;229(1):307-21.

Pettinello, Rita, and Helen Dooley. "The immunoglobulins of cold-blooded vertebrates." Biomolecules vol. 4,4 1045-69. Nov. 24, 2014, doi:10.3390/biom4041045.

Rizvi, N.A., et al., "Mutational landscape determines sensitivity to PD-1 blockade in non-small cell lung cancer," Science, vol. 348; No. 6230; 124-148 (2015).

Shashidharamurthy, Rangaiah et al. "Analysis of cross-species IgG binding to human and mouse Fcgamma receptors (FcγRs) (138.29)." Journal of Immunology 184 (2010): n. pag. Abstract only.

Shashidharamurthy, Rangaiah et al. "Dynamics of the interaction of human IgG subtype immune complexes with cells expressing R and H allelic forms of a low-affinity Fc gamma receptor CD32A." Journal of immunology (Baltimore, Md. : 1950) vol. 183,12 (2009): 8216-24. doi:10.4049/jimmunol.0902550.

UniProtKB/Swiss-Prot Q9H7M9.3 V-type immunoglobulin domain-containing suppressor of T-cell activation, 2019, 6 pages.

Vafa, Omid et al. "An engineered Fc variant of an IgG eliminates all immune effector functions via structural perturbations." Methods (San Diego, Calif.) vol. 65,1 (2014): 114-26. doi:10.1016/j.ymeth.2013.06.035.

Wang, L. et al., "Vista, a novel mouse Ig superfamily ligand that negatively regulates T cell response," J. Exp. Med. Mar. 7, 2011, vol. 208. No. 3, pp. 577-592.

Van Regenmortel, Marc H V. "Development of a Preventive HIV Vaccine Requires Solving Inverse Problems Which Is Unattainable by Rational Vaccine Design." Frontiers in immunology vol. 8 2009. Jan. 12, 2018, doi:10.3389/fimmu.2017.02009.

Wolff, A.C., et al., "American Society of Clinical Oncology/College of American Pathologists Guideline Recommendations for Human Epidermal Growth Factor Receptor 2 Testing in Breast Cancer," Arch Pathol Lab Med, vol. 131; 18-43 (2007).

Allen, Martin J et al. "Interchain disulfide bonding in human IgG2 antibodies probed by site-directed mutagenesis." Biochemistry vol. 48,17 (2009): 3755-66. doi:10.1021/bi8022174.

Lightle, Sandra et al. "Mutations within a human IgG2 antibody form distinct and homogeneous disulfide isomers but do not affect Fc gamma receptor or C1q binding." Protein science : a publication of the Protein Society vol. 19,4 (2w010): 753-62. doi:10.1002/pro.352.

Nowak, Elizabeth C et al. "Immunoregulatory functions of VISTA." Immunological reviews vol. 276,1 (2017): 66-79. doi:10.1111/imr.12525.

Papaconstantinou, Harry T, and J Scott Thomas. "Bacterial colitis." Clinics in colon and rectal surgery vol. 20,1 (2007): 18-27. doi:10.1055/s-2007-970196.

Tecklenborg, J et al. "The role of the immune system in kidney disease." Clinical and experimental immunology vol. 192,2 (2018): 142-150. doi:10.1111/cei.13119.

Wang, Xinhua et al. "IgG Fc engineering to modulate antibody effector functions." Protein & cell vol. 9,1 (2018): 63-73. doi:10.1007/s13238-017-0473-8.

White, Ann L et al. "Conformation of the human immunoglobulin G2 hinge imparts superagonistic properties to immunostimulatory anticancer antibodies." Cancer cell vol. 27,1 (2015): 138-48. doi:10.1016/j.ccell.2014.11.001.

Ben-Zvi, Lior et al. "Diagnosis and Management of Infectious Arthritis in Children." Current infectious disease reports vol. 21,7 23. May 29, 2019, doi:10.1007/s11908-019-0678-5.

\* cited by examiner

FIGURE 1
FIG. 1A
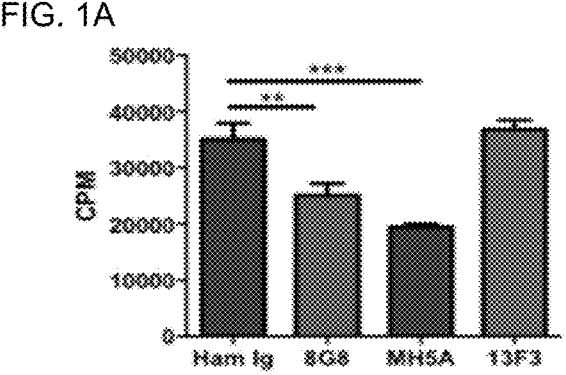
FIG. 1B
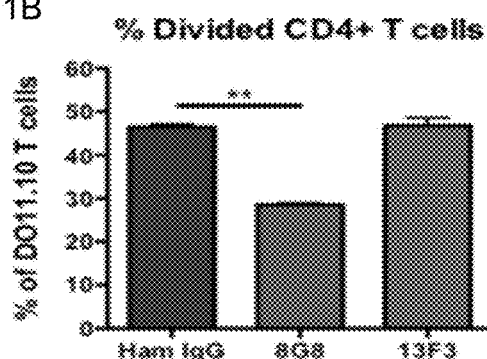
FIG. 1C
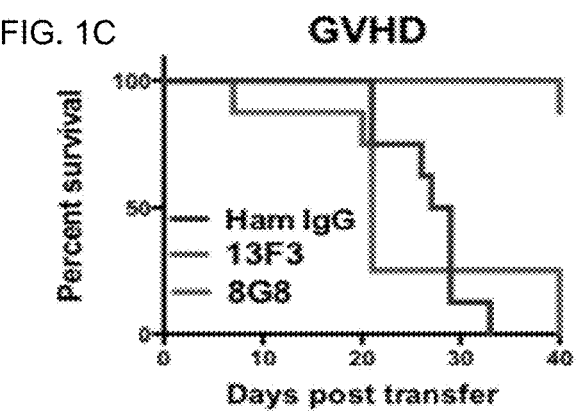
FIG. 1D
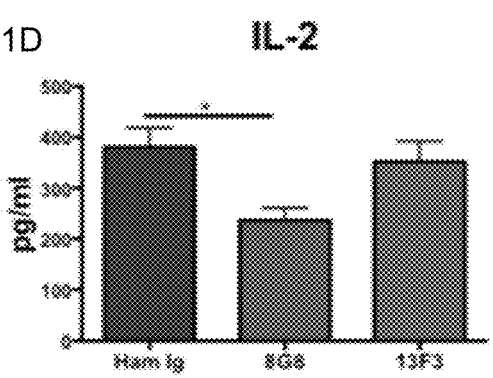
Figure 1. *In vitro* and *in vivo* screening assays can be used to identify suppressive VISTA mAb.

FIGURE 2
FIG. 2A
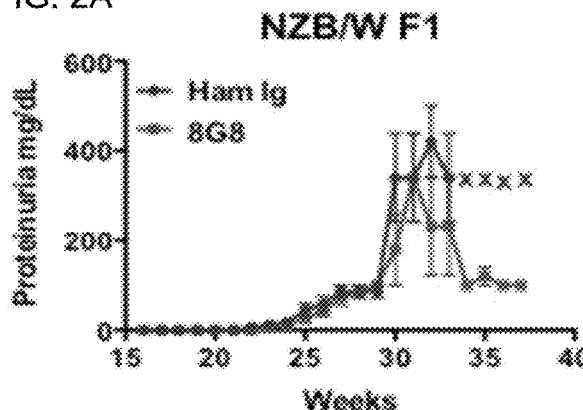
FIG. 2B
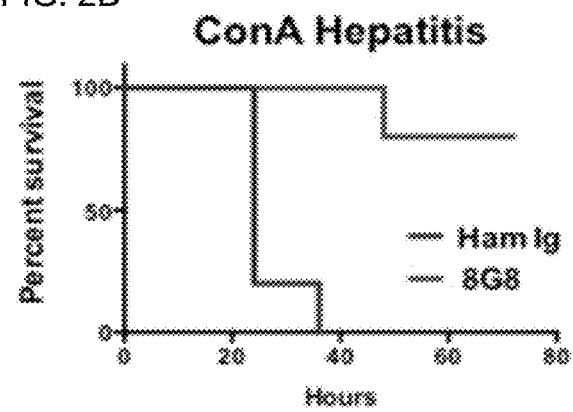
FIG. 2C
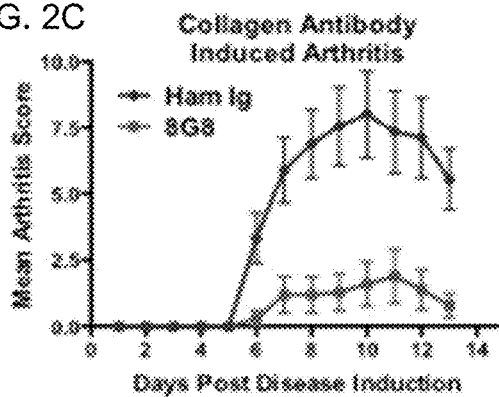
FIG. 2D
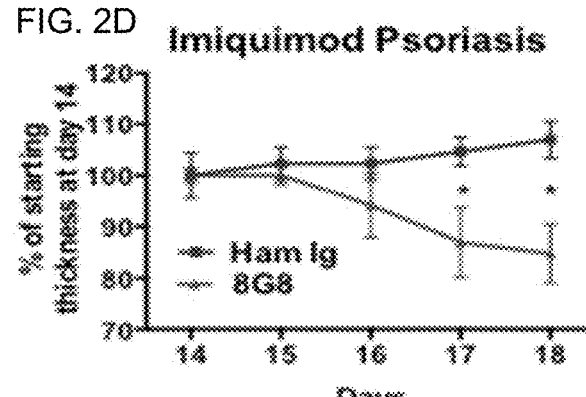
FIG. 2E
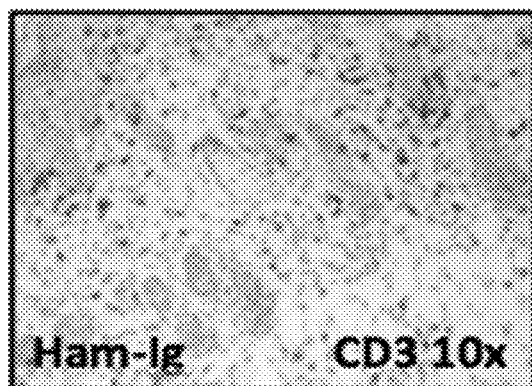
FIG. 2F
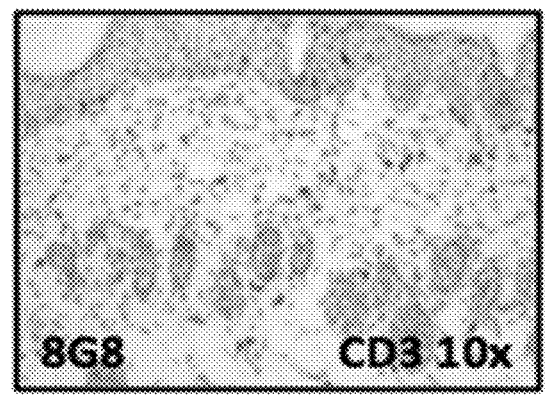
Figure 2. VISTA suppresses multiple models of autoimmune disease.

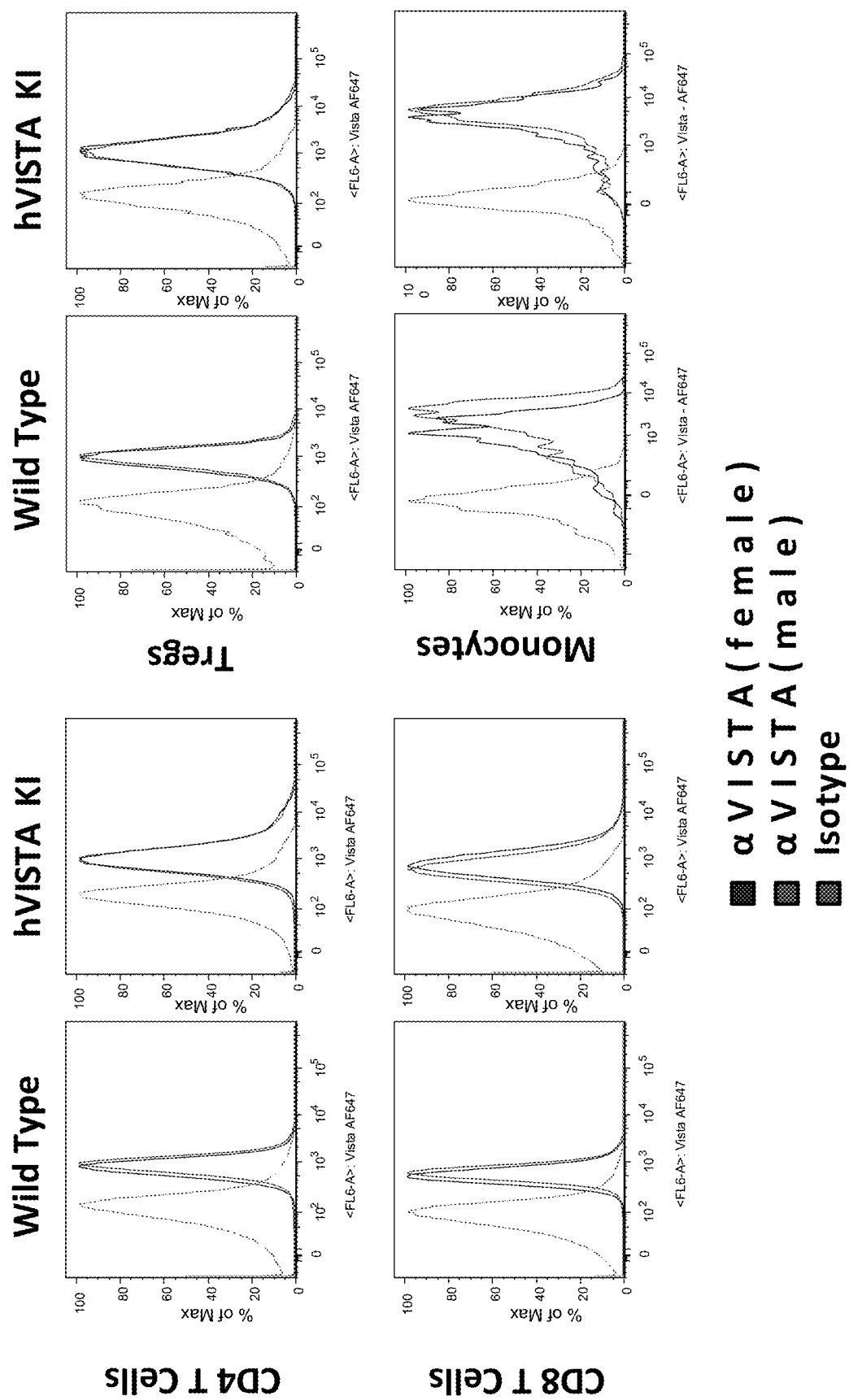
Figure 3. Expression of VISTA in WT and hV-KI mice.

FIGURE 4A

| mAb ID | Description | Epitope Sequence/ Epitope Group | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| GA1 | Mouse IgG1/kappa | LLDSGLYCC LVVEIRHHH SEHRVH | GYTLTDYN (SEQ ID NO:100) | INLNYAIT (SEQ ID NO:101) | ARGGYRYTY YAMDY (SEQ ID NO:102) | ENIYSN (SEQ ID NO:103) | AAT (SEQ ID NO:104) | QHFWGTP RT (SEQ ID NO:105) | EVQLQQFGAELVKPG ASVKISCKASGYTLTD YNMDWVKQSHGKSL EWIGHINLNYAITYN QKFKGKATLTVDKSS TAYMELRSLTSEDTAV YYCARGGYRYTYYAM DYWGQGTSVTVSS (SEQ ID NO:106) | AKTTPPSVYPLAPGSAAQT NSMVTLGCLVKGYFPEPVT VTMNSGSLSSGVHTFPAVL QSDLYTLSSSVVTVPSSTWPS ETVTCNVAHPASSTKVDKK IVPRDCGCKPCICTVPEVSS VFIFPPKPKDVLTITLTPKVT CVVVDISKDDPEVQFSWFV DDVEHTAQTQPREECQFN STFRSVSELPIMHQDWLN GKEFKCRVNSAAFPAPIEKT ISKTKLNPKS (SEQ ID NO:107) | DIQMTQSPASLSVS VGETVTITCRASENI YSNLAWYQQKQGK SPQLLVYAATNLAD GVPSRFSGSGSGTQ YSLKINSLQSEDFGS YYCQHFWGTPRTFG GGTKLEIK (SEQ ID NO:108) | RADAAPTVSI FPPSSEQLTSG GASVVCFLNN FYPKDINVKW KIDGSERQNG VLNSWTDQD SKDSTYSMSS TLTLTKDEYER HNSYTCEATH KTSTSPIVKSF NRNEC (SEQ ID NO:109) |
| GA1-IgG2 | Human IgG2 | LLDSGLYCC LVVEIRHHH SEHRVH | GYTLTDYN (SEQ ID NO:110) | INLNYAIT (SEQ ID NO:111) | ARGGYRYTY YAMDY (SEQ ID NO:112) | ENIYSN (SEQ ID NO:113) | AAT (SEQ ID NO:114) | QHFWGTP RT (SEQ ID NO:115) | EVQLQQFGAELVKPG ASVKISCKASGYTLTD YNMDWVKQSHGKSL EWIGHINLNYAITYN QKFKGKATLTVDKSS TAYMELRSLTSEDTAV YYCARGGYRYTYYAM DYWGQGTSVTVSS (SEQ ID NO:116) | ASTKGPSVFPLAPCSRSTSE STAALGCLVKDYFPEPVTVS WNSGALTSGVHTFPAVLQ SSGLYSLSSVVTVPSSNFGT QTYTCNVDHKPSNTKVDK TVERKCCVECPPCPAPPVA GPSVFLFPPKPKDTLMISRT PEVTCVVVDVSHEDPEVQF NWYVDGVEVHNAKTKPR EEQFNSTFRVVSVLTVVHQ DWLNGKEYKCKVSNKGLP APIEKTISKTKGQRPEPQVY TLPPSREEMTKNQVSLTCL VKGFYPSDIAVEWESNGQ PENNYKTTPPMLDSDGSFF LYSKLTVDKSRWQQGNVF SCSVMHEALHNHYTQKSLS LSPGK (SEQ ID NO:117) | DIQMTQSPASLSVS VGETVTITCRASENI YSNLAWYQQKQGK SPQLLVYAATNLAD GVPSRFSGSGSGTQ YSLKINSLQSEDFGS YYCQHFWGTPRTFG GGTKLEIK (SEQ ID NO:118) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:119) |
| GG8 | Mouse IgG1/? | LLDSGLYCC LVVEIRHHH SEHRVH; GHDVTFYK TWYRSSRG EVQTC | GYSFTGYT (SEQ ID NO:120) | INPYNGGI (SEQ ID NO:121) | ARRTLRPYF EDY (SEQ ID NO:122) | QSVSTSFSY (SEQ ID NO:123) | YAS (SEQ ID NO:124) | QHSWEIPY T (SEQ ID NO:125) | EVQLQQSGPELVKPG TSMKISCKASGYSFTG YTMNWVRQSHGKNL EWIGLINPYNGGINYN QKFKARATLTVDKSS TAYMELLSLTSEDSAV YYCARRTLRPYFFDY WGGGTTLTVSS (SEQ ID NO:126) | EVQLQQSGPELVKPGTSM KISCKASGYSFTGYTMNW VRQSHGKNLEWIGLINPYN GGINYNQKFKARATLTVDK SSTAYMELLSLTSEDSAVY YCARRTLRPYFFDYWGQG TTLTVSS (SEQ ID NO:127) | DIVLTQSPASLAVSL GQRATSCRASQSV STSFSYMHWYQQ KPGQPKLLIKYASN LESGVPARFSGSGS GTDFTLNIHPVEEED TATYYCQHSWEIPY TFGGGTKLEIK (SEQ ID NO:128) | DIVLTQSPAS LAVSLGQRATI SCRASQSVST STFSYMHWY QQKPGQPPK LLIKYASNLES GVPARFSGSG SGTDFTLNIHP VEEEDTATYY CQHSWEIPYT FGGGTKLEIK (SEQ ID NO:129) |

FIGURE 4B

| mAb ID | Description | Epitope Sequence/ Epitope Group | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| GG8-IgG2 | Human IgG2/kappa | LLDSGLYCC LVVEIRHHH SEHRVH; GHDVTFYK TWYRSSRG EVQTC | GYSFTGYT (SEQ ID NO:130) | INPYNGGI (SEQ ID NO:131) | ARRTLLRPYF FDY (SEQ ID NO:132) | QSVSTSTFSY (SEQ ID NO:133) | YAS (SEQ ID NO:134) | QHSWEIPY T (SEQ ID NO:135) | EVQLQQSGPELVKPG TSMKISCKASGYSFTG YTMNWVRQSHGKNL EWIGLINPYNGGINYN QKFKARATLTVDKSS TAYMELLSLTSEDSAV YYCARRTLLRPYFFDY WGQGTTLVSS (SEQ ID NO:136) | ASTKGPSVFPLAPCSRSTSE STAALGCLVKDYFPEPVTVS WNSGALTSGVHTFPAVLQ SSGLYSLSSVVTVPSSNFGT QTYTCNVDHKPSNTKVDK TVERKCCVECPPCPAPPVA GPSVFLFPPKPKDTLMISRT PEVTCVVVDVSHEDPEVQF NWYVDGVEVHNAKTKPR EEQFNSTFRVVSVLTVVHQ DWLNGKEYKCKVSNKGLP APIEKTISKTKGQPREPQVY TLPPSREEMTKNQVSLTCL VKGFYPSDIAVEWESNGQ PENNYKTTPPMLDSDGSFF LYSKLTVDKSRWQQGNVF SCSVMHEALHNHYTQKSLS LSPGK (SEQ ID NO:137) | DIVLTQSPASLAVSL GQRATSCRASQSV STSTFSYMHWYQQ KPGQPPKLLIKYASN LESGVPARFSGSGS GTDFTLNIHPVEEED TATYYCQHSWEIPY TFGGGTKLEIK (SEQ ID NO:138) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:139) |
| IE8 | Mouse IgG1/? | LLDSGLYCC LVVEIR | GFDFSRYW (SEQ ID NO:140) | VYPDSSTI (SEQ ID NO:141) | ARGRGDY (SEQ ID NO:142) | GNHNY (SEQ ID NO:143) | NAK (SEQ ID NO:144) | QNFWSTPF T (SEQ ID NO:145) | EVKLLESGGGLVQPG GSLKLSCAASGFDFSR YWMSWVRQAPGKG LEWIGEVYPDSSTINY TPSLKDKFIISRDNAK NTLYLQMIKVRSEDTA LYYCARGRGDYWGQ GTSVTVSS (SEQ ID NO:146) | ASTKGPSVFPLAPCSRSTSE STAALGCLVKDYFPEPVTVS WNSGALTSGVHTFPAVLQ SSGLYSLSSVVTVPSSNFGT QTYTCNVDHKPSNTKVDK TVERKCCVECPPCPAPPVA GPSVFLFPPKPKDTLMISRT PEVTCVVVDVSHEDPEVQF NWYVDGVEVHNAKTKPR EEQFNSTFRVVSVLTVVHQ DWLNGKEYKCKVSNKGLP APIEKTISKTKGQPREPQVY TLPPSREEMTKNQVSLTCL VKGFYPSDIAVEWESNGQ PENNYKTTPPMLDSDGSFF LYSKLTVDKSRWQQGNVF SCSVMHEALHNHYTQKSLS LSPGK (SEQ ID NO:147) | DIQMTQSPASLSAS VGETVTITCRASGNI HNYLSWYHQKQGK SPQLLVYNAKTLAD GVPSRFSGSGSGTQ YSLKINSLQPEDFGS YYCQNFWSTPFTFG SGTKLEIK (SEQ ID NO:148) | RTVAAPSVFI FPPSDEQLKS GTASVVCLLN NFYPREAKVQ WKVDNALQS GNSQESVTEQ DSKDSTYSLSS TLTLSKADYEK HKVYACEVTH QGLSSPVTKSF NRGEC (SEQ ID NO:149) |

FIGURE 4C

| mAb ID | Description | Epitope Sequence/ Epitope Group | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| IE8-IgG2 | Human IgG2/kappa | LLDSGLYCC LVVEIR | GFDFSRYW (SEQ ID NO:150) | VYPDSSTI (SEQ ID NO:151) | ARGRGDY (SEQ ID NO:152) | GNIHNY (SEQ ID NO:153) | NAK (SEQ ID NO:154) | QNFWSTPF T (SEQ ID NO:155) | EVKLLESGGGLVQPG GSLKLSCAASGFDFSR YWMSWVRQAPGKG LEWIGEVYPDSSTINY TPSLKDKFIISRDNAK NTLYLQMIKVRSEDTA LYYCARGRGDYWGQ GTSVTVSS (SEQ ID NO:156) | ASTKGPSVFPLAPCSRSTSE STAALGCLVKDYFPEPVTVS WNSGALTSGVHTFPAVLQ SSGLYSLSSVVTVPSSNFGT QTYTCNVDHKPSNTKVDK TVERKCCVECPPCPAPPVA GPSVFLFPPKPKDTLMISRT PEVTCVVVDVSHEDPEVQF NWYVDGVEVHNAKTKPR EEQFNSTFRVVSVLTVVHQ DWLNGKEYKCKVSNKGLP APIEKTISKTKGQPREPQVY TLPPSREEMTKNQVSLTCL VKGFYPSDIAVEWESNGQ PENNYKTTPPMLDSDGSFF LYSKLTVDKSRWQQGNVF SCSVMHEALHNHYTQKSLS LSPGK (SEQ ID NO:157) | DIQMTQSPASLSAS VGETVTITCRASGNI HNYLSWYHQKCQK SPQLLVYNAKTLAD GVPSRFSGSGSGTQ YSLKINSLQPEDFGS YYCQNFWSTPFTFG SGTKLEIK (SEQ ID NO:158) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:159) |
| IE8-IgG2-C127S | Human mutated IgG2/kappa | LLDSGLYCC LVVEIR | GFDFSRYW (SEQ ID NO:160) | VYPDSSTI (SEQ ID NO:161) | ARGRGDY (SEQ ID NO:162) | GNIHNY (SEQ ID NO:163) | NAK (SEQ ID NO:164) | QNFWSTPF T (SEQ ID NO:165) | EVKLLESGGGLVQPG GSLKLSCAASGFDFSR YWMSWVRQAPGKG LEWIGEVYPDSSTINY TPSLKDKFIISRDNAK NTLYLQMIKVRSEDTA LYYCARGRGDYWGQ GTSVTVSS (SEQ ID NO:166) | ASTKGPSVFPLAPSSRSTSE STAALGCLVKDYFPEPVTVS WNSGALTSGVHTFPAVLQ SSGLYSLSSVVTVPSSNFGT QTYTCNVDHKPSNTKVDK TVERKCCVECPPCPAPPVA GPSVFLFPPKPKDTLMISRT PEVTCVVVDVSHEDPEVQF NWYVDGVEVHNAKTKPR EEQFNSTFRVVSVLTVVHQ DWLNGKEYKCKVSNKGLP APIEKTISKTKGQPREPQVY TLPPSREEMTKNQVSLTCL VKGFYPSDIAVEWESNGQ PENNYKTTPPMLDSDGSFF LYSKLTVDKSRWQQGNVF SCSVMHEALHNHYTQKSLS LSPGK (SEQ ID NO:167) | DIQMTQSPASLSAS VGETVTITCRASGNI HNYLSWYHQKCQK SPQLLVYNAKTLAD GVPSRFSGSGSGTQ YSLKINSLQPEDFGS YYCQNFWSTPFTFG SGTKLEIK (SEQ ID NO:168) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:169) |

FIGURE 4D

| mAb ID | Description | Epitope Sequence/ Epitope Group | Heavy-chain cdr1 (imgt) | Heavy-chain cdr2 (imgt) | Heavy-chain cdr3 (imgt) | Light-chain cdr1 (imgt) | Light-chain cdr2 (imgt) | Light-chain cdr3 (imgt) | Heavy-chain Variable | Heavy-chain Constant | Light-chain Variable | Light-chain Constant |
|---|---|---|---|---|---|---|---|---|---|---|---|---|
| VSTB100 | Human IgG1/kappa | Group 1 | GYSFTSYW (SEQ ID NO:170) | IYPGDSDT (SEQ ID NO:171) | ARDVSSFYGY SPMFDY (SEQ ID NO:172) | QSVSSY (SEQ ID NO:173) | DAS (SEQ ID NO:174) | QQRSNWP LT (SEQ ID NO:175) | EVQLVQSGAEVKKPG ESLKISCKGSGYSFTSY WIGWVRQMPGKGLE WMGIIYPGDSDTRYS PSFQGQVTISADKSIS TAYLQWSSLKASDTA MYYCARDVSSFYGYS PMFDYWGQGTLVTV SS (SEQ ID NO:176) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:177) | EIVLTQSPATLSLSPG ERATLSCRASQSVSS YLAWYQQKPGQAP RLLIYDASNRATGIP ARFSGSGSGTDFTLT ISSLEPEDFAVYYCQ QRSNWPLTFGQGT KVEIK (SEQ ID NO:178) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:179) |
| VSTB101 | Human IgG1/Kappa | VSTB101 Group 1 | GYSFTSYW (SEQ ID NO:180) | IYPGDSDT (SEQ ID NO:181) | ARDAHSFYG YSALLDY (SEQ ID NO:182) | QSVSSSY (SEQ ID NO:183) | GAS (SEQ ID NO:184) | QQYGSSPL T (SEQ ID NO:185) | EVQLVQSGAEVKKPG ESLKISCKGSGYSFTSY WIGWVRQMPGKGLE WMGIIYPGDSDTRYS PSFQGQVTISADKSIS TAYLQWSSLKASDTA MYYCARDAHSFYGYS ALLDYWGQGTLVTVS (SEQ ID NO:186) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:187) | EIVLTQSPGTLSLSPG ERATLSCRASQSVSS SYLAWYQQKPGQA PRLLIYGASSRATGIP DRFSGSGSGTDFTLT ISRLEPEDFAVYYCQ QYGSSPLTFGQGTK VEIK (SEQ ID NO:188) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:189) |

FIGURE 4E

| mAb ID | Description | Epitope Sequence/ Epitope Group | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB102 | Human IgG1/kappa | Group 1 | GYSFTSYW (SEQ ID NO:190) | IYPGDSDT (SEQ ID NO:191) | ARDSYFYGH TPVLDY (SEQ ID NO:192) | QSVSSSY (SEQ ID NO:193) | GAS (SEQ ID NO:194) | QQYGSSPL T (SEQ ID NO:195) | EVQLVQSGAEVKKPG ESLKISCKGSGYSFTSY WIGWVRQMPGKGLE WMGIIYPGDSDTRYS PSFQGQVTISADKSIS TAYLQWSSLKASDTA MYYCARDSYSFYGHT PVLDYWGQGTLVTVS S (SEQ ID NO:196) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:197) | EIVLTQSPGTLSLSPG ERATLSCRASQSVSS SYLAWYQQKPGQA PRLLIYGASSRATGIP DRFSGSGSGTDFTLT ISRLEPEDFAVYYCQ QYGSSPLTFGQGTK VEIK (SEQ ID NO:198) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:199) |
| VSTB103 INX904 | Human IgG1/kappa | VSTB101 Group 1 | GYSFTSYW (SEQ ID NO:200) | IYPGDSDT (SEQ ID NO:201) | ARDDALYGG YYLDY (SEQ ID NO:202) | QSVLYSSNNK NY (SEQ ID NO:203) | WAS (SEQ ID NO:204) | QQYYSTPLT (SEQ ID NO:205) | EVQLVQSGAEVKKPG ESLKISCKGSGYSFTSY WIGWVRQMPGKGLE WMGIIYPGDSDTRYS PSFQGQVTISADKSIS TAYLQWSSLKASDTA MYYCARDDALYGGYY LDYWGQGTLVTVSS (SEQ ID NO:206) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:207) | DIVMTQSPDSLAVS LGERATINCKSSQSV LYSSNNKNYLAWYQ QKPGQPPKLLIYWA STRESGVPDRFSGS GSGTDFTLTISSLQA EDVAVYYCQQYYST PLTFGQGTKVEIK ((SEQ ID NO:208) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:209) |

FIGURE 4F

| mAb ID | Description | Epitope Sequence/ Epitope Group | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB104 | Human IgG1/kappa | Group 1 | GYSFTSYW (SEQ ID NO:210) | IYPGDSDT (SEQ ID NO:211) | ARDANSFYS AASIFDY (SEQ ID NO:212) | QSVLYSSNNK NY (SEQ ID NO:213) | WAS (SEQ ID NO:214) | QQYYSTPLT (SEQ ID NO:215) | EVQLVQSGAEVKKPG ESLKISCKGSGYSFTSY WHGWVRQMPGKGLE WMGIIYPGDSDTRYS PSFQGQVTISADKSIS TAYLQWSSLKASDTA MYYCARDANSFYSAA SIFDYWGQGTLVTVS S (SEQ ID NO:216) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:217) | DIVMTQSPDSLAVS LGERATINCKSSQSV LYSSNNKNYLAWYQ QKPGQPPKLLIYWA STRESGVPDRFSGS GSGTDFTLTISSLQA EDVAVYYCQQYYST PLTFGQGTKVEIK (SEQ ID NO:218) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:219) |
| VSTB105 | Human IgG1/kappa | Group 1 | GGTFSSYA (SEQ ID NO:220) | IIPIFGTA (SEQ ID NO:221) | ARSSYGWSY EFDY (SEQ ID NO:222) | QSIATN (SEQ ID NO:223) | AAS (SEQ ID NO:224) | QQNDDRPI T (SEQ ID NO:225) | QVQLVQSGAEVKKPG SSVKVSCKASGGTFSS YAISWVRQAPGQGLE WMGGIIPIFGTANYA QKFQGRVTITADESTS TAYMELSSLRSEDTAV YYCARSSYGWSYEFD YWGQGTLVTVSS (SEQ ID NO:226) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK ((SEQ ID NO:227) | DIQMTQSPSSLSAS VGDRVTITCRASQSI ATNLNWYQQKPGK APKLLIYAASSLQSG VPSRFSGSGSGTDFT LTISSLQPEDFATYYC QQNDDRPITFGQGT KVEIK (SEQ ID NO:228) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:229) |

FIGURE 4G

| mAb ID | Description | Epitope Sequence/ Epitope Group | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB106 INX915 | Human IgG1/kappa | Group 1 | GGTFSSYA (SEQ ID NO:230) | IIPIFGTA (SEQ ID NO:231) | ARSSYGWSY EFDY (SEQ ID NO:232) | QSIRTD (SEQ ID NO:233) | SAS (SEQ ID NO:234) | QQNERTPIT (SEQ ID NO:235) | QVQLVQSGAEVKKPG SSVKVSCKASGGTFSS YAISWVRQAPGQGLE WMGGIIPIFGTANYA QKFQGRVTITADESTS TAYMELSLRSEDTAV YYCARSSYGWSYEFD YWGQGTLVTVSS (SEQ ID NO:236) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:237) | DIQMTQSPSSLSAS VGDRVTITCRASQSI RTDLNWYQQKPGK APKLLIYSASSLQSG VPSRFSGSGSGTDFT LTISSLQPEDFATYYC QQNERTPITFGQGT KVEIK (SEQ ID NO:238) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:239) |
| VSTB107 INX916 | Human IgG1/kappa | Group 1 | GGTFSSYA (SEQ ID NO:240) | IIPIFGTA (SEQ ID NO:241) | ARSSYGWSY EFDY (SEQ ID NO:242) | QSINND (SEQ ID NO:243) | AAS (SEQ ID NO:244) | QQNRATPI T (SEQ ID NO:245) | QVQLVQSGAEVKKPG SSVKVSCKASGGTFSS YAISWVRQAPGQGLE WMGGIIPIFGTANYA QKFQGRVTITADESTS TAYMELSLRSEDTAV YYCARSSYGWSYEFD YWGQGTLVTVSS (SEQ ID NO:246) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:247) | DIQMTQSPSSLSAS VGDRVTITCRASQSI NNDLNWYQQKPGK APKLLIYAASSLQSG VPSRFSGSGSGTDFT LTISSLQPEDFATYYC QQNRATPITFGQGT KVEIK (SEQ ID NO:248) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:249) |

FIGURE 4H

| mAb ID | Description | Epitope Sequence/ Epitope Group | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB108 | Human IgG1/kappa | Group 1 | GGTFSSYA (SEQ ID NO:250) | IIPIFGTA (SEQ ID NO:251) | ARNTFGWSG ELDY (SEQ ID NO:252) | QSISNR (SEQ ID NO:253) | SAS (SEQ ID NO:254) | QQNHDNPI T (SEQ ID NO:255) | QVQLVQSGAEVKKPG SSVKVSCKASGGTFSS YAISWVRQAPGQGLE WMGGIIPIFGTANYA QKFQGRVTITADESTS TAYMELSLRSEDTAV YYCARNTFGWSGELD YWGQGTLVTVSS (SEQ ID NO:256) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:257) | DIQMTQSPSSLSAS VGDRVTITCRASQSI SNRLNWYQQKPGK APKLLIYSASSLQSG VPSRFSGSGSGTDFT LTISSLQPEDFATYYC QQNHDNPITFGQG TKVEIK (SEQ ID NO:258) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:259) |
| VSTB109 | Human IgG1/kappa | Group 1 | GGTFSSYA (SEQ ID NO:260) | IIPIFGTA (SEQ ID NO:261) | ARSSYGWSY EFDY (SEQ ID NO:262) | QSIATY (SEQ ID NO:263) | AAS (SEQ ID NO:264) | QQNHNRPI T (SEQ ID NO:265) | QVQLVQSGAEVKKPG SSVKVSCKASGGTFSS YAISWVRQAPGQGLE WMGGIIPIFGTANYA QKFQGRVTITADESTS TAYMELSLRSEDTAV YYCARSSYGWSYEFD YWGQGTLVTVSS (SEQ ID NO:266) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:267) | DIQMTQSPSSLSAS VGDRVTITCRASQSI ATYLNWYQQKPGK APKLLIYAASSLQSG VPSRFSGSGSGTDFT LTISSLQPEDFATYYC QQNHNRPITFGQGT KVEIK (SEQ ID NO:268) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:269) |

FIGURE 4I

| mAb ID | Description | Epitope Sequence/ Epitope Group | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB110 INX917 | Human IgG1/kappa | Group 1 | GGTFSSYA (SEQ ID NO:270) | IIPIFGTA (SEQ ID NO:271) | ARHSIGWVA ELDY (SEQ ID NO:272) | QSINTD (SEQ ID NO:273) | AAS (SEQ ID NO:274) | QQGASDPIT (SEQ ID NO:275) | QVQLVQSGAEVKKPG SSVKVSCKASGGTFSS YAISWVRQAPGQGLE WMGGIIPIFGTANYA QKFQGRVTITADESTS TAYMELSSLRSEDTAV YYCARHSIGWVAELD YWGQGTLVTVSS (SEQ ID NO:276) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:277) | DIQMTQSPSSLSAS VGDRVTITCRASQSI NTDLNWYQQKPGK APKLLIYAASSLQSG VPSRFSGSGSGTDFT LTISSLQPEDFATYYC QQGASDPITFGQGT KVEIK (SEQ ID NO:278) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:279) |
| VSTB111 | Human IgG1/kappa | Group 1 | GGTFSSYA (SEQ ID NO:280) | IIPIFGTA (SEQ ID NO:281) | ARSSYGWSY EFDY (SEQ ID NO:282) | QSINTD (SEQ ID NO:283) | AAS (SEQ ID NO:284) | QQNRGSPI T (SEQ ID NO:285) | QVQLVQSGAEVKKPG SSVKVSCKASGGTFSS YAISWVRQAPGQGLE WMGGIIPIFGTANYA QKFQGRVTITADESTS TAYMELSSLRSEDTAV YYCARSSYGWSYEFD YWGQGTLVTVSS (SEQ ID NO:286) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:287) | DIQMTQSPSSLSAS VGDRVTITCRASQSI NTDLNWYQQKPGK APKLLIYAASSLQSG VPSRFSGSGSGTDFT LTISSLQPEDFATYYC QQNRGSPITFGQGT KVEIK (SEQ ID NO:288) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:289) |

FIGURE 4J

| mAb ID | Description | Epitope Sequence/ Epitope Group | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB113 INX918 | Human IgG1/kappa | Group 1 | GGTFSSYA (SEQ ID NO:290) | IIPIFGTA (SEQ ID NO:291) | ARHSIGWVA ELDY (SEQ ID NO:292) | QSIATD (SEQ ID NO:293) | AAS (SEQ ID NO:294) | QQAHWYP LT (SEQ ID NO:295) | QVQLVQSGAEVKKPG SSVKVSCKASGGTFSS YAISWVRQAPGQGLE WMGGIIPIFGTANYA QKFQGRVTITADESTS TAYMELSSLRSEDTAV YYCARHSIGWVAELD YWGQGTLVTVSS (SEQ ID NO:296) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:297) | DIQMTQSPSSLSAS VGDRVTITCRASQSI ATDLNWYQQKPGK APKLLIYAASSLQSG VPSRFSGSGSGTDFT LTISSLQPEDFATYYC QQAHWYPLTFGQG TKVEIK (SEQ ID NO:298) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:299) |
| VSTB114 | Human IgG1/kappa | Group 1 | GGTFSSYA (SEQ ID NO:300) | IIPIFGTA (SEQ ID NO:301) | ARHSIGWVA ELDY (SEQ ID NO:302) | QSIATS (SEQ ID NO:303) | YAS (SEQ ID NO:304) | QQGAYYPL T (SEQ ID NO:305) | QVQLVQSGAEVKKPG SSVKVSCKASGGTFSS YAISWVRQAPGQGLE WMGGIIPIFGTANYA QKFQGRVTITADESTS TAYMELSSLRSEDTAV YYCARHSIGWVAELD YWGQGTLVTVSS (SEQ ID NO:306) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:307) | DIQMTQSPSSLSAS VGDRVTITCRASQSI ATSLNWYQQKPGK APKLLIYYASSLQSG VPSRFSGSGSGTDFT LTISSLQPEDFATYYC QQGAYYPLTFGQGT KVEIK (SEQ ID NO:308) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:309) |

FIGURE 4K

| mAb ID | Description | Epitope Sequence/ Epitope Group | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB115 INX919 | Human IgG1/kappa | Group 1 | GGTFSSYA (SEQ ID NO:310) | IIPIFGTA (SEQ ID NO:311) | ARSSYGWSY EFDY (SEQ ID NO:312) | QSIRTY (SEQ ID NO:313) | AAS (SEQ ID NO:314) | QQAYSNPI T (SEQ ID NO:315) | QVQLVQSGAEVKKPG SSVKVSCKASGGTFSS YAISWVRQAPGQGLE WMGGIIPIFGTANYA QKFQGRVTITADESTS TAYMELSSLRSEDTAV YYCARSSYGWSYEFD YWGQGTLVTVSS (SEQ ID NO:316) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:317) | DIQMTQSPSSLSAS VGDRVTITCRASQSI RTYLNWYQQKPGK APKLLIYAASSLQSG VPSRFSGSGSGTDFT LTISSLQPEDFATYYC QQAYSNPITFGQGT KVEIK (SEQ ID NO:318) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:319) |
| VSTB116 | Human IgG1/kappa | Group 1 | GGTFSSYA (SEQ ID NO:320) | IIPIFGTA (SEQ ID NO:321) | ARSSYGWSY EFDY (SEQ ID NO:322) | QSINTN (SEQ ID NO:323) | AAS (SEQ ID NO:324) | QQARDTPI T (SEQ ID NO:325) | QVQLVQSGAEVKKPG SSVKVSCKASGGTFSS YAISWVRQAPGQGLE WMGGIIPIFGTANYA QKFQGRVTITADESTS TAYMELSSLRSEDTAV YYCARSSYGWSYEFD YWGQGTLVTVSS (SEQ ID NO:326) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:327) | DIQMTQSPSSLSAS VGDRVTITCRASQSI NTNLNWYQQKPGK APKLLIYAASSLQSG VPSRFSGSGSGTDFT LTISSLQPEDFATYYC QQARDTPITFGQGT KVEIK (SEQ ID NO:328) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:329) |

FIGURE 4L

| mAb ID | Description | Epitope Sequence/Epitope Group | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB49 | Human IgG1/kappa | Group 1 | GYTFPSHT (SEQ ID NO:330) | INPFIDST (SEQ ID NO:331) | ARGIRGYTMDY (SEQ ID NO:332) | ESVDNYGLSF (SEQ ID NO:333) | GAS (SEQ ID NO:334) | QQSKEVPYT (SEQ ID NO:335) | QVQLVQSGAEVKKPG ASVKVSCKASGYTFPS HTIHWVRQAPGQRLE WMGSIYPFIDSTYNQ KFKDRVTITRDTSAST AYMELSLRSEDTAVY YCARGIRGYTMDYW GQGTLVTVSS (SEQ ID NO:336) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:337) | DVVMTQSPLSLPVT LGQPASISCRASESV DNYGLSFMNWFQQ RPGQSPRRLIYGAS NQGSGVPDRFSGSG SGTDFTLKISRVEAE DVGVYYCQQSKEVP YTFGQGTKLEIK (SEQ ID NO:338) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:339) |
| VSTB50 INX500 | Human IgG1/kappa | NLTLLDSGL and VQTGKDAP SNC Group 2 | GYTFTNYG (SEQ ID NO:340) | INPYTGEP (SEQ ID NO:341) | AREGYGNYIFPY (SEQ ID NO:342) | ESVDTYANSL (SEQ ID NO:343) | RAS (SEQ ID NO:344) | QQTNEDPRT (SEQ ID NO:345) | QVQLVQSGSELKKPG ASVKVSCKASGYTFTN YGLNWVRQAPGQGL EWMGWINPYTGEPT YADDFKGRFVFSLDTS VSTAYLQICSLKAEDT AVYYCAREGYGNYIFP YWGQGTLVTVSS (SEQ ID NO:346) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:347) | DIVMTQTPLSLSVTP GQPASSCRASESVD TYANSLMHWYLQK PGQPPQLLIYRASNL ESGVPDRFSGSGSG TDFTLKISRVEAEDV GVYYCQQTNEDPRT FGQGTKLEIK (SEQ ID NO:348) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:349) |

FIGURE 4M

| mAb ID | Description | Epitope Sequence/ Epitope Group | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB51 | Human IgG1/kappa | Group 1 | GFTFSSYT (SEQ ID NO:350) | ISNGGSYT (SEQ ID NO:351) | ARDTVLSPFDY (SEQ ID NO:352) | SSISY (SEQ ID NO:353) | DTS (SEQ ID NO:354) | HQRSSFT (SEQ ID NO:355) | EVQLVESGGGLVQPG GSLRLSCAASGFTFSSY TMSWVRQAPGKGLE WVATISNSGSYTYYLD SVKGRFTISRDNAKNS LYLQMNSLRAEDTAV YYCARDTVLSPFDYW GQGTTVTVSS (SEQ ID NO:356) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:357) | EIVLTQSPDFQSVTP KEKVTITCSATSSISY MHWYQQKPDQSP KLLIKDTSELASGVPS RFSGSGSGTDFTLTI NSLEAEDAATYYCH QRSSFTGQGTKLEI K (SEQ ID NO:358) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:359) |
| VSTB52 | Human IgG1/kappa | | GGTFSNYW (SEQ ID NO:360) | IYPGGGFT (SEQ ID NO:361) | ARYVRSDEDY SMDF (SEQ ID NO:362) | QSLLYSNGKT Y (SEQ ID NO:363) | LVS (SEQ ID NO:364) | VQATHFPQ T (SEQ ID NO:365) | QVQLVQSGAEVKKPG SSVKVSCKASGGTFSN YWIGWVRQAPGQGL EWMGEIYPGGGFTHY NEKFKGRVTITADEST STAYMELSSLRSEDTA VYYCARYVRSDEDYS MDFWGQGTLVTVSS (SEQ ID NO:366) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:367) | DVVMTQSPLSLPVT LGQPASISCKSSQSL LYSNGKTYLNWFCQQ RPGQSPRRLIYLVSK LDSGVPDRF5GSGS GTDFTLKISRVEAED VGVYYCVQATHFPQ TFGQGTKLEIK (SEQ ID NO:368) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:369) |

FIGURE 4N

| mAb ID | Description | Epitope Sequence/ Epitope Group | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB53 INX905 | Human IgG1/kappa | Group 1 | GYTFTHYT (SEQ ID NO:370) | IIPSSGYS (SEQ ID NO:371) | ARGAYDDYY DYYAMDY (SEQ ID NO:372) | QTVHSNGN TY (SEQ ID NO:373) | KVS (SEQ ID NO:374) | FQASHVPW T (SEQ ID NO:375) | QVQLVQSGAEVKKPG ASVKVSCKASGYTFTH YTHWVRQAPGQGLE WMGYIIPSSGYSEYN QKFKDRVTMTRDTST STVYMELSLRSEDTA VYYCARGAYDDYYDY YAMDYWGQGTLVTV SS (SEQ ID NO:376) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:377) | DIVMTQSPLSLPVTP GEPASISCRSSQTIV HSNGNTYLEWYLQK PGQSPQLLIYKVSNR FSGVPDRFSGSGSG TDFTLKISRVEAEDV GVYYCFQASHVPW TFGQGTKLEIK (SEQ ID NO:378) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:379) |
| VSTB54 INX906 | Human IgG1/kappa | Group 2 | GYNIKDTY (SEQ ID NO:380) | IDPTHGYV (SEQ ID NO:381) | ARDRFDPYW FLDV (SEQ ID NO:382) | ESVEYYGTSL (SEQ ID NO:383) | DAF (SEQ ID NO:384) | QQSRKVP WT (SEQ ID NO:385) | QVQLVQSGAEVKKPG ASVKVSCKASGYNIKD TYNMWVRQAPGQG LEWMGRIDPTHGYVI YDPKFQGRVTMTRDT STSTVYMELSSLRSED TAVYYCARDRFDPYW FLDVWGQGTLVTVSS (SEQ ID NO:386) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:387) | DIVMTQTPLSLSVTP GQPASISCRASESVE YYGTSLMQWYLQK PGQSPQLLIYDAFN VESGVPDRFSGSGS GTDFTLKISRVEAED VGVYYCQQSRKVP WTFGQGTKLEIK (SEQ ID NO:388) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:389) |

FIGURE 40

| mAb ID | Description | Epitope Sequence/ Epitope Group | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB55 | Human IgG1/kappa | | GYSIASDYV (SEQ ID NO:390) | ISYSGST (SEQ ID NO:391) | ARITTVVPTG SYYGVDF (SEQ ID NO:392) | SSVNF (SEQ ID NO:393) | DTS (SEQ ID NO:394) | QQWSNYPY FT (SEQ ID NO:395) | QVQLQESGPGLVKPS ETLSLTCAVSGYSIASD YVWNWIRQPPGKGL EWIGYISYSGSTSNNP SLNSRVTISVDTSKNQ FSLKLSSVTAADTAVY YCARITTVVPTGSYYG VDFWGQGTTVTVSS (SEQ ID NO:396) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:397) | EIVLTQSPDFQSVTP KEKVTITCSGSSSVN FMYWYQQKPDQSP KLLIKDTSNLASGVP SRFSGSGSGTDFTLTI NSLEAEDAATYYCQ QWSNYPFTFGQGT KLEIK (SEQ ID NO:398) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:399) |
| VSTB56 INX901 | Human IgG1/kappa | Group 2 | GYTFTSYW (SEQ ID NO:400) | IIPNTLHT (SEQ ID NO:401) | ARLDGDYD ALDY (SEQ ID NO:402) | ESVEYYGTSF (SEQ ID NO:403) | TAS (SEQ ID NO:404) | QQSRKVPY T (SEQ ID NO:405) | QVQLVQSGAEVKKPG ASVKVSCKASGYTFTS YWLHWVRQAPGQG LEMMGYIIPNTLHTD YNQKFKDRVTMTRD TSTSTVMELSSLRSE DTAVYYCARLDGDYD YALDYWGQGTLVTVS S (SEQ ID NO:406) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:407) | DIVMTQTPLSLVTP GQPASSCRASESVE YYGTSFMQWYLQK PGQPPQLLIYTASNV ESGVPDRFSGSGSG TDFTLKISRVEAEDV GVYYCQQSRKVPYT FGQGTKLEIK (SEQ ID NO:408) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:409) |

FIGURE 4P

| mAb ID | Description | Epitope Sequence/ Epitope Group | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB57 | Human IgG1/kappa | | GFTFSTYA (SEQ ID NO:410) | ISSGGSDT (SEQ ID NO:411) | ARPTYYGIFS VFDY (SEQ ID NO:412) | SSVSY (SEQ ID NO:413) | STS (SEQ ID NO:414) | HQWRTYPT (SEQ ID NO:415) | EVQLVESGGGLVQPG GSLRLSCAASGFTFSTY AMSWVRQAPGKGLE WVATISSGGSDTYYP DTVKGRFTISRDNAK NSLYLQMNSLRAEDT AVYYCARPTYYGIFSY FDYWGQGTLVTVSS (SEQ ID NO:416) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:417) | DIQLTQSPSFLSASV GDRVTITCSASSSVS YMHWYQQKPGKA PKLLIYSTSNLASGVP SRFSGSGSGTEFTLTI SSLQPEDFATYYCH QWRTYPTFGQGTKL EIK (SEQ ID NO:418) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:419) |
| VSTB58 | Human IgG1/kappa | | GFSLT NYG (SEQ ID NO:420) | IWRGG NT (SEQ ID NO:421) | ARSMV SYTVDY (SEQ ID NO:422) | SSVSY (SEQ ID NO:423) | DTS (SEQ ID NO:424) | QQWS SYPPT (SEQ ID NO:425) | QVQLQESGPGLVKPS ETLSLTCTVSGFSLTNV GVHWIRQPPGKGLE WIGVIWRGGNTDYN AAFMSRVTISVDTSK NQFSLKLSSVTAADTA VYYCARSMVSYTVDY WGQGTLVTVSS (SEQ ID NO:426) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:427) | EIVLTQSPDFQSVTP KEKVTITCSASSSVS MHWYQQKPDQSP KLLKDTSNLASGVP SRFSGSGSGTDFTLTI NSLEAEDAATYYCQ QWSSYPPTFGQGTK LEIK (SEQ ID NO:428) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:429) |

FIGURE 4Q

| mAb ID | Description | Epitope Sequence/ Epitope Group | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB59 | Human IgG1/kappa | Group 1 | GYTFTDVW (SEQ ID NO:430) | IETSLNYP (SEQ ID NO:431) | ARWGIYGNP WFAY (SEQ ID NO:432) | ESVDSYVNSF (SEQ ID NO:433) | RAS (SEQ ID NO:434) | QQSNEDPY T (SEQ ID NO:435) | QVQLVQSSGAEVKKPG ASVKVSCKASGYTFTD YWMHWVRQAPGQ GLEWMGAIETSLNYP SYNQKFKGRVTMTRD TSTSTVYMELSSLRSE DTAVYYCARWGIYGN PWFAYWGRGTLVTV SS (SEQ ID NO:436) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:437) | DIVMTQTPLSLSVTP GQPASISCRASESVD SYVNSFVHWYLQKP GQPPQLLIYRASNLE SGVPDRFSGSGSGT DFTLKISRVEAEDVG VYYCQQSNEDPYTF GQGTKLEIK (SEQ ID NO:438) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:439) |
| VSTB60 Group 2 | Human IgG1/kappa | NITLLDSGL and VQTGKDAP SNC Group 2 | GYTFTNYG (SEQ ID NO:440) | INTYTGES (SEQ ID NO:441) | ARDYGIYVS AY (SEQ ID NO:442) | ESVDNYANS F (SEQ ID NO:443) | RAS (SEQ ID NO:444) | QQSHEDPY T (SEQ ID NO:445) | QVQLVQSGSELKKPG ASVKVSCKASGYTFTN YGMTWVRQAPGQG LEWMGWINTYTGES TYADDFKGRPVFSLDT SVSTAVLQICSLKAEDT AVYYCARDYGIYVSA YWGQGTLVTVSS (SEQ ID NO:446) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:447) | DIVMTQTPLSLSVTP GQPASISCRASESVD NYANSFMHWYLQK PGQSPQLLIYRASNL ESGVPDRFSGSGSG TDFTLKISRVEAEDV GVYYCQQSHEDPYT FGQGTKLEIK (SEQ ID NO:448) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:449) |

FIGURE 4R

| mAb ID | Description | Epitope Sequence/ Epitope Group | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB61 | Human IgG1/kappa | | GYTFTSHW (SEQ ID NO:450) | INPRDGRT (SEQ ID NO:451) | ARGDFHYGD YFWYFDV (SEQ ID NO:452) | QNVHGA (SEQ ID NO:453) | MAS (SEQ ID NO:454) | LQHWNYLT (SEQ ID NO:455) | QVQLVQSGAEVKKPG ASVKVSCKASGYTFTS HWMHWVRQAPGQ GLEWMGEINPRDGR TNYNEKFKTRVTMTR DTSTSTVYMELSSLRS EDTAVYYCARGDFHY GDYFWYFDVWGQGT LVTVSS (SEQ ID NO:456) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:457) | DIQMTQSPSSLSAS VGDRVTITCKASQN VHGAVAWYQQKP GKVPKLLIYMASNR PTGVPSRFSGSGSG TDFTLTISSLQPEDV ATYYCLQHWNYLTF GQGTKLEIK (SEQ ID NO:458) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:459) |
| VSTB62 | Human IgG1/kappa | | GYTFTHYW (SEQ ID NO:460) | IYPGDGDT (SEQ ID NO:461) | ARRDYDYGD Y (SEQ ID NO:462) | SSVSH (SEQ ID NO:463) | LTS (SEQ ID NO:464) | QQYQTYPP T (SEQ ID NO:465) | QVQLVQSGAEVKKPG ASVKVSCKASGYTFTH YWIQWVRQAPGQGL EWMGAIYPGDGDTR YTQKFKGRVTMTRDT STSTVYMELSSLRSED TAVYYCARRDYDYGD YWGQGTTVTVSS (SEQ ID NO:466) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:467) | EIVLTQSPDFQSVTP KEKVTITCSASSSVS HMYWYQQKPDQS PKLLIKLTSNLASGVP SRFSGSGSGTDFTLT NSLEAEDAATYYCQ QYQTYPPTFGQGTR LEIK (SEQ ID NO:468) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:469) |

FIGURE 4S

| mAb ID | Description | Epitope Sequence/ Epitope Group | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB63 INX902 | Human IgG1/kappa | Group 2 | GFSITSDFA (SEQ ID NO:470) | ITYSGFT (SEQ ID NO:471) | ARQEYGNYV WYFDV (SEQ ID NO:472) | ESVEYYGTSL (SEQ ID NO:473) | AAS (SEQ ID NO:474) | QQSRKVP WT (SEQ ID NO:475) | QVQLQESGPGLVKPS ETLSLTCAVSGFSITSD FAWNWIRQPPGKGL EWIGYITYSGFTNYNP SLESRVTISVDTSKNQ FSLKLSSVTAADTAVY YCARQEYGNYVWYF DVWGQGTLVTVSS (SEQ ID NO:476) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:477) | DIVMTQTPLSLSVTP GQPASISCRASESVE YYGTSLLQWYLQKP GQPPQLLIYAASNV ESGVPDRFSGSGSG TDFTLKISRVEAEDV GVYYCQQSRKVPW TFGQGTKLEIK (SEQ ID NO:478) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:479) |
| VSTB64 | Human IgG1/kappa | | GYSITSGYF (SEQ ID NO:480) | MGYDGRI (SEQ ID NO:481) | AREGDYYGS GFAYW (SEQ ID NO:482) | QNVNTN (SEQ ID NO:483) | SAS (SEQ ID NO:484) | QQYNNYPL T (SEQ ID NO:485) | QVQLQESGPGLVKPS ETLSLTCAVSGYSITSG YFWNWIRQPPGKGL EWIGYMGYDGRIFYS PSLKNRVTISVDTSKN QFSLKLSSVTAADTAV YYCAREGDYYGSGFA YWGQGTLVTVSS (SEQ ID NO:486) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:487) | DIQMTQSPSSLSAS VGDRVTITCKASQN VNTNLAWYQQKPG KVPKLLIYASYRYS GVPSRFSGSGSGTD FTLTISSLQPEDVATY YCQQYNNYPLTFGQ GTKLEIK (SEQ ID NO:488) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:489) |

FIGURE 4T

| mAb ID | Description | Epitope Sequence/ Epitope Group | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB65 | Human IgG1/kappa | Group 1 | GYTFTSYW (SEQ ID NO:490) | INPSNGLT (SEQ ID NO:491) | ARSYDYDGD YYAMDY (SEQ ID NO:492) | QSIVHSNGN TY (SEQ ID NO:493) | KVS (SEQ ID NO:494) | FQASHVPW T (SEQ ID NO:495) | QVQLVQSGAEVKKPG ASVKVSCKASGYTFTS YWIHWVRQAPGQGL EWMGEINPSNGLTNY NEKFRNRVTMTRDTS TSTVYMELSSLRSEDT AVYYCARSYDYDGDY YAMDYWGQGTLVTV SS (SEQ ID NO:496) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:497) | DIVMTQSPLSLPVTP GEPASISCRSTQSIV HSNGNTYLEWYLQK PGQSPQLLIYKVSNR FSGVPDRFSGSGSG TDFTLKISRVEAEDV GVYYCFQASHVPW TFGQGTKLEIK (SEQ ID NO:498) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:499) |
| VSTB66 INX907 | Human IgG1/kappa | Group 2 | GYPFTGYF (SEQ ID NO:500) | INPYNGGT (SEQ ID NO:501) | ARWTFDGLF MDY (SEQ ID NO:502) | ENVDKYGISF (SEQ ID NO:503) | ATS (SEQ ID NO:504) | QQSKEDPY T (SEQ ID NO:505) | QVQLVQSGAEVKKPG ASVKVSCKASGYPFTG YFMHWVRQAPGQG LEWMMGRINPYNGGT VYNQNFNDRVTMTR DTSTSTVYMELSSLRS EDTAVYYCARWTFDG LFMDYWGQGTTVTV SS (SEQ ID NO:506) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:507) | DVVMTQSPLSLPVT LGQPASISCRASENV DKYGISFMNWFQQ RPGQSPRRLIYATSN GTDFTLKISRVEAED VGVYYCQQSKEDPY TFGQGTKLEIK (SEQ ID NO:508) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:509) |

FIGURE 4U

| mAb ID | Description | Epitope Sequence/ Epitope Group | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB67 INX909 | Human IgG1/kappa | Group 1 | DYIFSSYW (SEQ ID NO:510) | IFPGSGGT (SEQ ID NO:511) | ARAIYDYD MYFDS (SEQ ID NO:512) | QDISSY (SEQ ID NO:513) | YTS (SEQ ID NO:514) | QHVNTLP WT (SEQ ID NO:515) | QVQLVQSGAEVKKPG ASVKVSCKASDYIFSS YWIQWVRQAPGQGL EWMGEIFPGSGGTNY NEKFKGRVTMTRDTS TSTVYMELSSLRSEDT AVYYCARAIYDYDM YFDSWGQGTTVTVS S (SEQ ID NO:516) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:517) | DIQMTQSPSSLSAS VGDRVTITCRASQDI SSYLNWYQQKPGK VPKLLIYYTSRLHSG VPSRFSGSGSGTDFT LTISSLQPEDVATYY CQHVNTLPWTFGQ GTKLEIK (SEQ ID NO:518) | RTVAAPSVFIF PPSDEQLKSGT ASVVCLLNNFY PREAKVQWK VDNALQSGNS QESVTEQDSK DSTYSLSSTLTL SKADYEKHKV YACEVTHQGL SSPVTKSFNRG EC (SEQ ID NO:519) |
| VSTB68 | Human IgG1/kappa | | GYTFTDYT (SEQ ID NO:520) | INPYNGG T (SEQ ID NO:521) | ARHYGNYN WYFDV (SEQ ID NO:522) | QYVNTA (SEQ ID NO:523) | SAS (SEQ ID NO:524) | QQHFTTPI T (SEQ ID NO:525) | QVQLVQSGAEVKKPG ASVKVSCKASGYTFTD YTMNWVRQAPGQRL EWMGLINPYNGGTT YNQKFKGRVTITRDTS ASTAYMELSSLRSEDT AVYYCARHYGNYNW YFDVWGQGTTVTVSS (SEQ ID NO:526) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:527) | DIQLTQSPSFLSASV GDRVTTCKASQYV NTAVAWYQQKPGK APKLLIYSASYRYTG VPSRFSGSGSGTEFT LTISSLQPEDFATYYC QQHFTTPITFGQGT KLEIK (SEQ ID NO:528) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:529) |

FIGURE 4V

| mAb ID | Description | Epitope Sequence/ Epitope Group | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB69 | Human IgG1/kappa | | GYTFTNYG (SEQ ID NO:530) | INTYTGEP (SEQ ID NO:531) | ARNYGNYV AY (SEQ ID NO:532) | QDINSY (SEQ ID NO:533) | RAN (SEQ ID NO:534) | LQYDEFPL T (SEQ ID NO:535) | QVQLVQSGSELKKPG ASVKVSCKASGYTFTN YGMNWVRQAPGQG LEWMGWINTYTGEP TYADDFKGRFVFSLDT SVSTAVLQICSLKAEDT AVYYCARNYGNYVAY WGQGTTVTVSS (SEQ ID NO:536) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:537) | DIQMTQSPSSLSAS VGDRVTITCKASQDI NSYLSWFQQKPGK APKSLIYRANRLVDG VPSRFSGSGSGTDFT LTISSLQPEDFATYYC LQYDEFPLTFGQGT RLEIK (SEQ ID NO:538) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:539) |
| VSTB70 | Human IgG1/kappa | Group 1 | GYTFSNVW (SEQ ID NO:540) | ILPGSGNV (SEQ ID NO:541) | ATPPHYYGY DYYDVNY (SEQ ID NO:542) | QSLLDSDGKT Y (SEQ ID NO:543) | LVS (SEQ ID NO:544) | WQGTHFP QT (SEQ ID NO:545) | EVQLVQSGAEVKKPG ATVKISCKCVSGYTFSN YWIEWVQQAPGKGL EWMGEILPGSGNVH YNEKFKGRVTITADTS TDTAYMELSSLRSEDT AVYYCATPPHYYGYD YDVNYWGQGTLVT VSS (SEQ ID NO:546) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:547) | DVVMTQSPLSLPVT LGQPASISCKSSQSL LDSDGKTYLNWFQ QRPGQSPRRLIYLVS ELDSGVPDRFSGSG SGTDFTLKISRVEAE DVGVYCWQGTHF PQTFGQGTKLEIK (SEQ ID NO:548) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:549) |

FIGURE 4W

| mAb ID | Description | Epitope Sequence/ Epitope Group | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB71 | Human IgG1/kappa | | GYVFSRSW (SEQ ID NO:550) | IYPGDGDT (SEQ ID NO:551) | ARRWFL (SEQ ID NO:552) | QSLLNSGDQKSY (SEQ ID NO:553) | GAS (SEQ ID NO:554) | QNDHSYPLT (SEQ ID NO:555) | QVQLVQSGAEVKKPG SSVKVSCKASGYVFSR SWINWVRQAPGQGL EWMGRIYPGDGDTN YNGKFKGRVTITADES TSTAYMELSLRSEDT AVYYCARRWFLWGQ GTLVTVSS (SEQ ID NO:556) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:557) | DIVMTQSPDSLAVS LGERATINCKSSQSL LNSGDQKSYLAWY QQKPGQPPKLLIYG ASTRESGVPDRFSGS GSGTDFTLTISSLQA EDVAVYYCQNDHSY PLTFGQGTKLEIK (SEQ ID NO:558) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:559) |
| VSTB72 | Human IgG1/kappa | | GFTFSSYA (SEQ ID NO:560) | ISSGGSHT (SEQ ID NO:561) | ARRGNLYDGPY (SEQ ID NO:562) | SSVSH (SEQ ID NO:563) | DTS (SEQ ID NO:564) | QQWNFPFT (SEQ ID NO:565) | EVQLVESGGGLVQPG GSLRLSCAASGFTFSSY AMSWVRQAPGKGLE WVAEISSGGSHTYYP DTVTGRFTISRDNAK NSLYLQMNSLRAEDT AVYYCARRGNLYDGP YWGQGTLVTVSS (SEQ ID NO:566) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:567) | EIVLTQSPATLSLPG ERATLSCASSSVSH MYWYQQKPGQAP RLLIYDTSKLASGIPA RFSGSGSGTDFTLTIS SLEPEDFAVYYCQQ WNFYPTFGQGTKL EIK (SEQ ID NO:568) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:569) |

FIGURE 4X

| mAb ID | Description | Epitope Sequence/ Epitope Group | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB73 INX910 | Human IgG1/kappa | Group 2 | GYTFTDYV (SEQ ID NO:570) | IYPGSGNT (SEQ ID NO:571) | ARVLVSVMDY (SEQ ID NO:572) | SSINY (SEQ ID NO:573) | DTS (SEQ ID NO:574) | HQRSSYPWT (SEQ ID NO:575) | QVQLVQSGAEVKKPG ASVKVSCKASGYTFTD YVISWVRQAPGQGLE WMGEIYPGSGNTYYY EKFKGRVTMTRDTST STVYMELSSLRSEDTA VYYCARVLVSVMDY WGQGTLVTVSS (SEQ ID NO:576) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:577) | EIVLTQSPDFQSVTP KEKVTITCSASSSINY ITWYQQKPDQSPKL LIKDTSKLASGVPSR FSGSGSGTDFTLTIN SLEAEDAATYCHQ RSSYPWTFGQGTRL EIK (SEQ ID NO:578) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:579) |
| VSTB74 | Human IgG1/kappa Group 4 | Group 4 | GYIFTDYN (SEQ ID NO:580) | INPKYDST (SEQ ID NO:581) | AADGSSAM DY (SEQ ID NO:582) | QSLLNSGHQ KNY (SEQ ID NO:583) | GAS (SEQ ID NO:584) | QNDHRYPL T (SEQ ID NO:585) | QMQLVQSGPEVKKP GTSVKVSCKASGYIFT DYNIDWVRQARGQR LEWIGDINPKYDSTRY NQKFKGRVTITRDMS TSTAYMELSSLRSEDT AVYYCAADGSSAMD YWGQGTTVTVSS (SEQ ID NO:586) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:587) | DIVMTQSPDSLAVS LGERATINCKSSQSL LNSGHQKNYLAWY QQKPGQPPKLLIYG ASTRESGVPDRFSGS GSGTDFTLTISSLQA EDVAVYYCQNDHR YPLTFGQGTKLEIK (SEQ ID NO:588) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:589) |

FIGURE 4Y

| mAb ID | Description | Epitope Sequence/ Epitope Group | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB75 | Human IgG1/kappa | | GFNIKDYY (SEQ ID NO:590) | IDPENGNT (SEQ ID NO:591) | ARDYGYFDY W (SEQ ID NO:592) | SSVIY (SEQ ID NO:593) | STS (SEQ ID NO:594) | QQRSSYPH T (SEQ ID NO:595) | QVQLVQSGAEVKKPG SSVKVSCKASGFNIKD YYIHWVRQAPGQGLE WMGWIDPENGNTIY DPKFQGRVTITADEST STAYMELSSLRSEDTA VYYCARDYGYFDYW GQGTLVTVSS (SEQ ID NO:596) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:597) | DVVMTQSPAFLSVT PGEKVTITCSAGSSV IYMYWYQQKPDQA PKLLIKSTSNLASGVP SRFSGSGSGTDFTFT ISSLEAEDAATYYCQ QRSSYPHTFGQGTK LEIK (SEQ ID NO:598) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:599) |
| VSTB76 INX911 | Human IgG1/kappa | Group 2 | GYTFTDVW (SEQ ID NO:600) | IYPSHSYT (SEQ ID NO:601) | ARGGYRYPY YAMDY (SEQ ID NO:602) | ENIYGA (SEQ ID NO:603) | GAT (SEQ ID NO:604) | QNVLSTPYT (SEQ ID NO:605) | QVQLVQSGAEVKKPG ASVKVSCKASGYTFTD YWINWVRQAPGQGL EWMGNIYPSHSYTNY NQEFKDRVTMTRDTS TSTVYMELSSLRSEDT AVYYCARGGYRYPY AMDYWGQGTTVTVS S (SEQ ID NO:606) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:607) | AIQLTQSPSSLSASV GDRVTITCGASENIY GALNWYQQKPGKA PKLLIYGATNLADGV PSRFSGSGSGTDFTL TISSLQPEDFATYYC QNVLSTPYTFGQGT KLEIK (SEQ ID NO:608) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:609) |

FIGURE 4Z

| mAb ID | Description | Epitope Sequence/ Epitope Group | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB78 | Human IgG1/kappa | Group 2 | GYTFTNVW (SEQ ID NO:610) | INPSSGYT (SEQ ID NO:611) | ARDGGSVLF GY (SEQ ID NO:612) | QSLLNSGIRK NY (SEQ ID NO:613) | SAS (SEQ ID NO:614) | KQSYNLYT (SEQ ID NO:615) | QVQLVQSGAEVKKPG ASVKVSCKASGYTFTN YWMHWVRQAPGQ GLEWMGYINPSSGYT EYNQKFKDRVTMTR DTSTSTVMELSSLRS EDTAVYYCARDGGSV LFGYWGQGTTVTVSS (SEQ ID NO:616) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:617) | DIVMTQSPDSLAVS LGERATINCKSSQSL LNSGIRKNYLAWYQ QKPGQPPKLLIYSAS TRESGVPDRFSGSG SGTDFTLTISSLQAE DVAVYYCKQSYNLY TFGQGTKLEIK (SEQ ID NO:618) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:619) |
| VSTB79 | Human IgG1/kappa | | AVSITSDY A (SEQ ID NO:620) | ITYSGST (SEQ ID NO:621) | ARSFGY (SEQ ID NO:622) | QSIGTS (SEQ ID NO:623) | YAS (SEQ ID NO:624) | QQINSWP TT (SEQ ID NO:625) | QVQLQESGPGLVKPS ETLSLTCAVSAYSITSD YAMNWIRQPPGKGL EWIGYITYSGSTRYNP SLKSRVTISVDTSKNQ FSLKLSSVTAADTAVY YCARSFGYWGQGTT VTVSS (SEQ ID NO:626) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:627) | EIVMTQSPATLSVSP GERATLSCRASQSIG TSIHWYQQKPGQA PRLLIYYASESSGIPA RFSGSGSGTEFTLTIS SLQSEDFAVYYCQQI NSWPTTFGQGTKLE IK (SEQ ID NO:628) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:629) |

FIGURE 4AA

| mAb ID | Description | Epitope Sequence/ Epitope Group | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB80 | Human IgG1/kappa | | GFNIKDYY (SEQ ID NO:630) | IDPENGDT (SEQ ID NO:631) | ARDMGSSYVY (SEQ ID NO:632) | SSVIY (SEQ ID NO:633) | STS (SEQ ID NO:634) | QQRSSYPFT (SEQ ID NO:635) | QVQLVQSGAEVKKPG ASVKVSCKASGFNIKD YYMHWVRQAPGQG LEWMGWIDPENGDT EYAPKFQDRVTMTRD TSTSTVMELSLSRSE DTAVYYCARDMGSSY VYWGRGTLVTVSS (SEQ ID NO:636) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:637) | DVVMTQSPAFLSVT PGEKVTITCSASSSVI YMHWYQQKPDQA PKLLIKSTSNLASGVP SRFSGSGSGTDFFT ISSLEAEDAATYYCQ QRSSYPFTFGQGTKL EIK (SEQ ID NO:638) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:639) |
| VSTB81 | Human IgG1/kappa | Group 1 | GFSLSTSG MG (SEQ ID NO:640) | IYWDDDK (SEQ ID NO:641) | ARRPDYFGSS YVD (SEQ ID NO:642) | ESVDTYGNSF (SEQ ID NO:643) | LAS (SEQ ID NO:644) | QQNNEDP WT (SEQ ID NO:645) | QVTLKESGPALVKPT QTLTLTCTFSGFSLSTS GMGVSWIRQPPGKA LEWLAHYWDDDKRY NPSLKSRLTISKDTSKN QVVLTMTNMDPVDT ATYYCARRPDYFGSSY VDWGQGTTVTVSS (SEQ ID NO:646) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:647) | DIVMTQTPLSLSVTP GQPASISCRASESVD TYGNSFMHWYLQK PGQPPQLLIYLASNL DFGVPDRFSGSGSG TDFTLKISRVEAEDV GVYYCQQNNEDPW TFGQGTKLEIK (SEQ ID NO:648) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:649) |

FIGURE 4BB

| mAb ID | Description | Epitope Sequence/ Epitope Group | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB82 | Human IgG1/kappa | | GYSITSDYA (SEQ ID NO:650) | ITYSGST (SEQ ID NO:651) | ARSHYGSTY WYFDV (SEQ ID NO:652) | ESVEYYGTSL (SEQ ID NO:653) | AAS (SEQ ID NO:654) | QQTRKVP WT (SEQ ID NO:655) | QVQLQESGPGLVKPS ETLSLTCAVSGYSITSD YAWNWIRQPPGKGL EWIGFITYSGSTNYNP SLKSRVTISVDTSKNQ FSLKLSSVTAADTAVY YCARSHYGSTYWYFD VWGQGTTVTVSS (SEQ ID NO:656) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:657) | DIVMTQTPLSLSVTP GQPASISCRASESVE YYGTSLMQWYLQK PGQSPQLLIYAASN VESGVPDRFSGSGS GTDFTLKISRVEAED VGVYYCQQTRKVP WTFGQGTRLEIK (SEQ ID NO:658) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:659) |
| VSTB83 | Human IgG1/kappa | | GYTFTSYD (SEQ ID NO:660) | IYPGDGYT (SEQ ID NO:661) | ARWGYGSYA MDY (SEQ ID NO:662) | QSLVHSNGN TY (SEQ ID NO:663) | KVS (SEQ ID NO:664) | SQSTHVPP T (SEQ ID NO:665) | QVQLVQSGAEVKKPG ASVKVSCKASGYTFTS YDINWVRQAPGQGL EWMGWIYPGDGYTE YNEKFRGRVTMTRDT STSTVYMELSSLRSED TAVYYCARWGYGSYA MDYWGQGTLVTVSS (SEQ ID NO:666) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:667) | DIVMTQSPLSLPVTP GEPASISCRSSQSLV HSNGNTYLHWYLQ KPGQSPQLLIYKVSN RFSGVPDRFSGSGS GTDFTLKISRVEAED VGVYYCSQSTHVPP TFGQGTKLEIK (SEQ ID NO:668) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:669) |

FIGURE 4CC

| mAb ID | Description | Epitope Sequence/ Epitope Group | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB84 INX912 | Human IgG1/kappa | Group 2 | GYTFTSYW (SEQ ID NO:670) | INPSTGYP (SEQ ID NO:671) | ARSYDYDG GAWFAY (SEQ ID NO:672) | ESVEYYGTSL (SEQ ID NO:673) | AAS (SEQ ID NO:674) | QQSRKVPS T (SEQ ID NO:675) | QVQLVQSGAEVKKPG ASVKVSCKASGYTFTS YWMHWVRQAPGQ GLEWMGYINPSTGYP GYNQKFKDRVTMTR DTSTSTVYMELSSLRS EDTAVYYCARSYYDY DGGAWFAYWGQGT TVTVSS (SEQ ID NO:676) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:677) | DIVMTQTPLSLSVTP GQPASBCRASESVE YYGTSLMQWYLQK PGQPPQLLIYAASN VESGVPDRFSGSGS GTDFTLKISRVEAED VGVYYCQQSRKVPS TFGQGTKLEIK (SEQ ID NO:678) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:679) |
| VSTB85 INX913 | Human IgG1/kappa | Group 1 | GYTFTDYA (SEQ ID NO:680) | IDTYYGNT (SEQ ID NO:681) | ARGGGDALD Y (SEQ ID NO:682) | QSVSND (SEQ ID NO:683) | YAS (SEQ ID NO:684) | QQGYTSLR T (SEQ ID NO:685) | QVQLVQSGAEVKKPG ASVKVSCKASGYTFTD YAMHWVRQAPGQG LEWMGVIDTYYGNT NYNQKFKGRVTMTR DTSISTAYMELSSLRS DDTAVYYCARGGGD ALDYWGQGTTVTVSS (SEQ ID NO:686) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:687) | DIQMTQSPSSLSAS VGDRVTITCKASQS VSNDVVWYQQKPG KAPKLLIYASNRYI GVPSRFSGSGSGTD FTFTISSLQPEDIATY YCQQGYTSLRTFGQ GTKLEIK (SEQ ID NO:688) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:689) |

FIGURE 4DD

| mAb ID | Description | Epitope Sequence/ Epitope Group | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB87 | Human IgG1/kappa | | GYSITSGYS (SEQ ID NO:690) | IHYIGIT (SEQ ID NO:691) | AREDYDYDG VFAY (SEQ ID NO:692) | QSISNN (SEQ ID NO:693) | YAS (SEQ ID NO:694) | QQSNSWP HT (SEQ ID NO:695) | QVQLQESGPGLVKPS ETLSLTCAVSGYSITSG YSWHWIRQPPGKGL EWIGYIHYIGITNNNP SLKSRVTISVDTSKNQ FSLKLSSVTAADTAVY YCAREDYDYDGVFAY WGQGTLVTVSS (SEQ ID NO:696) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:697) | EIVLTQSPATLSLSPG ERATLSCRASQSISN NLHWYQQKPGQAP RLLIYYASQSISGIPA RFSGSGSGTDFTLTIS SLEPEDFAVYYCQQ SNSWPHTFGQGTKL EIK (SEQ ID NO:698) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:699) |
| VSTB88 | Human IgG1/kappa | | GFSLTNYD (SEQ ID NO:700) | IWTGGGT (SEQ ID NO:701) | AREGLLLPLY (SEQ ID NO:702) | QNVGTN (SEQ ID NO:703) | SAS (SEQ ID NO:704) | QQYNSYPL T (SEQ ID NO:705) | QVQLQESGPGLVRPS ETLSLTCTVSGFSLTNY DISWIRQPPGKGLEW IGVIWTGGGTNYNSA FMSRVTISVDTSKNQF SLKLSSVTAADTAVVY CAREGLLLPLYWGQG TLVTVSS (SEQ ID NO:706) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:707) | DIQMTQSPSSLSAS VGDRVTITCKASQN VGTNVAWYQQKPG KVPKLLIYSASYRYS GVPSRFSGSGSGTD FTLTISSLQPEDVATY YCQQYNSYPLTFGQ GTKLEIK (SEQ ID NO:708) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:709) |

FIGURE 4EE

| mAb ID | Description | Epitope Sequence/ Epitope Group | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB89 | Human IgG1/kappa | | GYTFTNFG (SEQ ID NO:710) | INTYTGEP (SEQ ID NO:711) | ARGAYYYGS RVWFAY (SEQ ID NO:712) | QNLVHSNGNTY (SEQ ID NO:713) | KVS (SEQ ID NO:714) | SQSSHVPYT (SEQ ID NO:715) | QVQLVQSGSELKKPG ASVKVSCKASGYTFTN FGMNWVRQAPGQG LEWMGWINTYTGEP TYADDFKGRFVFSLDT SVSTAYLQICSLKAEDT AVYYCARGAYYYGSR VWFAYWGQGTLVTV SS (SEQ ID NO:716) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:717) | DIVMTQSPLSLPVTP GEPASISCTSSQNLV HSNGNTYLHWYLQ KPGQSPQLLIYKVSN RFSGVPDRFSGSGS GTDFTLKISRVEAED VGVYYCSQSSHVPY TFGQGTKLEIK (SEQ ID NO:718) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:719) |
| VSTB90 | Human IgG1/kappa | | GFSLTSSG (SEQ ID NO:720) | IWSGGNT (SEQ ID NO:721) | AREDYDYDW YFDV (SEQ ID NO:722) | ESVEYYGTSL (SEQ ID NO:723) | AAS (SEQ ID NO:724) | QQSRKVP WT (SEQ ID NO:725) | QVQLQESGPGLVKPS ETLSLTCTVSGFSLTSS GVHWIRQPPGKGLE WIGVIWSGGNTDYN AAFISRVTISVDTSKN QFSLKLSSVTAADTAV YYCAREDYDYDWYFD VWGQGTTVTVSS (SEQ ID NO:726) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:727) | DIVMTQTPLSLSVTP GQPASSCRASESVE YYGTSLMQWYLQK PGQPPQLLIYAASN VKSGVPDRFSGSGS GTDFTLKISRVEAED VGVYYCQQSRKVP WTFGQGTKLEIK (SEQ ID NO:728) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:729) |

FIGURE 4FF

| mAb ID | Description | Epitope Sequence/ Epitope Group | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB91 | Human IgG1/kappa | | GYTFA NFW (SEQ ID NO:730) | IFPGNS DT (SEQ ID NO:731) | ARELTG TYYFDY (SEQ ID NO:732) | SSVSY (SEQ ID NO:733) | SSS (SEQ ID NO:734) | HQWS GMFT (SEQ ID NO:735) | QVQLVQSGAEVKKPG ASVKVSCKASGYTFA NFWMHWVRQAPGQ GLEWMGAIFPGNSDT GYNQKFKGRVTMTR DTSTSTVMELSSLRS EDTAVYYCARELTGTY YFDYWGQGTLVTVSS (SEQ ID NO:736) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:737) | EIVLTQSPATLSLSPG ERATLSCSATSSVSY MHWYQQKPGQAP RLLYSSSNLASGIPA RFSGSGSGTDFTLTIS SLEPEDFAVYYCHQ WSGHFTFGQGTKLE IK (SEQ ID NO:738) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:739) |
| VSTB92 INX908 | Human IgG1/kappa | Group 1 | GYTFANYL (SEQ ID NO:740) | IYPGGGFI (SEQ ID NO:741) | ARRFDYGGY FFDY (SEQ ID NO:742) | QSIVHSNGNI Y (SEQ ID NO:743) | KVS (SEQ ID NO:744) | FQGSHVP WT (SEQ ID NO:745) | QVQLVQSGAEVKKPG ASVKVSCKASGYTFA NYLIGWVRQAPGQRL EWMGDIYPGGGFISY NEKFKGRVTITRDTSA STAYMELSSLRSEDTA VYYCARRFDYGGYFF DYWGQGTLVTVSS (SEQ ID NO:746) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:747) | DIVMTQSPLSLPVTP GEPASISCRSSQSIV HSNGNIYLEWYLQK PGQSPQLLIYKVSNR FSGVPDRFSGSGSG TDFTLKISRVEAEDV GVYYCFQGSHVPW TFGQGTKLEIK (SEQ ID NO:748) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:749) |

FIGURE 4GG

| mAb ID | Description | Epitope Sequence/ Epitope Group | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB93 | Human IgG1/kappa | | GFSITNYD (SEQ ID NO:750) | IWTGGGT (SEQ ID NO:751) | ARDRSPYFGY DY (SEQ ID NO:752) | QSLVHSNGN TY (SEQ ID NO:753) | KVS (SEQ ID NO:754) | SQSTHVPW T (SEQ ID NO:755) | QVQLQESGPGLVKPS ETLSLTCTVSGFSITNY DISWIRQPPGKGLEW IGVIWTGGGTNYNSA FMSRVTISVDTSKNQF SLKLSSVTAADTAVVY CARDRSPYFGYDYWG QGTTVTVSS (SEQ ID NO:756) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:757) | DIVMTQTPLSLSVTP GQPASBCRSSQSLV HSNGNTYLHWYLQ KPGQSPQLLIYKVSN RFSGVPDRFSGSGS GTDFTLKISRVEAED VGVYYCSQSTHVP WTFGQGTKLEIK (SEQ ID NO:758) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:759) |
| VSTB94 | Human IgG1/kappa | | GYSITSDYA (SEQ ID NO:760) | MMYSGSA (SEQ ID NO:761) | ARFDHYYGR FDY (SEQ ID NO:762) | SSVSY (SEQ ID NO:763) | EIS (SEQ ID NO:764) | QQWNYPLF T (SEQ ID NO:765) | QVQLQESGPGLVKPS ETLSLTCAVSGYSITSD YAWTWIRQPPGKGL EWIGYMMYSGSASY NPSLKGRVTISVDTSK NQFSLKLSSVTAADTA VYYCARFDHYYGRFD YWGQGTTVTVSS (SEQ ID NO:766) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:767) | AIQLTQSPSSLSASV GDRVTTCSASSSVS YIHWYQQKPGKAP KLLIYEISKLASGVPS RFSGSGSGTDFTLTIS SLQPEDFATYYCQQ WNYPLFTFGQGTKL EIK (SEQ ID NO:768) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:769) |

FIGURE 4HH

| mAb ID | Description | Epitope Sequence/ Epitope Group | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB95 INX903 | Human IgG1/kappa | PVDKGHDVTF and RRPIRDLTFQDL Group 1 | GFTFRNYG (SEQ ID NO:770) | IISGGSYT (SEQ ID NO:771) | ARIYDHDGDYYAMDY (SEQ ID NO:772) | QSIVHSNGNTY (SEQ ID NO:773) | KVS (SEQ ID NO:774) | FQGSHVPWT (SEQ ID NO:775) | EVQLVESGGGLVQPGGSLRLSCAASGFTFRNYGMSWVRQAPGKGLEWVASIISGGSYTYYPDSVKGRFTISRDNAKNSLYLQMNSLRAEDTAVYYCARIYDHDGDYYAMDYWGQGTTVTVSS (SEQ ID NO:776) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO:777) | DIVMTQSPLSLPVTPGEPASISCRSSQSIVHSNGNTYLEWYLQKPGQSPQLLIYKVSNRFSGVPDRFSGSGSGTDFTLKISRVEAEDVGVYYCFQGSHVPWTFGQGTKLEIK (SEQ ID NO:778) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO:779) |
| VSTB96 | Human IgG1/kappa | | (SEQ ID NO:780) | (SEQ ID NO:781) | (SEQ ID NO:782) | (SEQ ID NO:783) | (SEQ ID NO:784) | (SEQ ID NO:785) | QVQLVQSGAEVKKPGSSVKVSCKASGYTFTSYDINWVRQAPGQGLEWMGRIYPGDGSTKYNEKFKGRVTITADKSTSTAYMELSSLRSEDTAVYYCAREGITPFAYWGQGTTVTVSS (SEQ ID NO:786) | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO:787) | AIQLTQSPSSLSASVGDRVTITCRASKSISKYLAWYQQKPGKAPKLLIYSGSTLQSGVPSRFSGSGSGTDFTLTISSLQPEDFATYYCQQHNEYPWTFGQGTKLEIK (SEQ ID NO:788) | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO:789) |

FIGURE 4II

| mAb ID | Description | Epitope Sequence/ Epitope Group | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB97 INX914 | Human IgG1/kappa | Group 1 | GGTFSSYA (SEQ ID NO:790) | IIPIFGTA (SEQ ID NO:791) | ARSSYGWSY EFDY (SEQ ID NO:792) | QSISSY (SEQ ID NO:793) | AAS (SEQ ID NO:794) | QQSYSTPLT (SEQ ID NO:795) | QVQLVQSGAEVKKPG SSVKVSCKASGGTFSS YAISWVRQAPGQGLE WMGGIIPIFGTANYA QKFQGRVTITADESTS TAYMELSSLRSEDTAV YYCARSSYGWSYEFD YWGQGTLVTVSS (SEQ ID NO:796) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:797) | DIQMTQSPSSLSAS VGDRVTITCRASQSI SSYLNWYQQKPGK APKLLIYAASSLQSG VPSRFSGSGSGTDFT LTISSLQPEDFATYYC QQSYSTPLTFGQGT KVEIK (SEQ ID NO:798) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:799) |
| VSTB98 | Human IgG1/kappa | Group 1 | GGTFSSYA (SEQ ID NO:800) | IIPIFGTA (SEQ ID NO:801) | ARSTVGWSY EFDY (SEQ ID NO:802) | QSISSY (SEQ ID NO:803) | AAS (SEQ ID NO:804) | QQSYSTPLT (SEQ ID NO:805) | QVQLVQSGAEVKKPG SSVKVSCKASGGTFSS YAISWVRQAPGQGLE WMGGIIPIFGTANYA QKFQGRVTITADESTS TAYMELSSLRSEDTAV YYCARSTVGWSYEFD YWGQGTLVTVSS (SEQ ID NO:806) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:807) | DIQMTQSPSSLSAS VGDRVTITCRASQSI SSYLNWYQQKPGK APKLLIYAASSLQSG VPSRFSGSGSGTDFT LTISSLQPEDFATYYC QQSYSTPLTFGQGT KVEIK (SEQ ID NO:808) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:809) |

FIGURE 4JJ

| mAb ID | Description | Epitope Sequence/ Epitope Group | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB99 | Human IgG1/kappa | Group 1 | GGTFSSYA (SEQ ID NO:810) | IIPIFGTA (SEQ ID NO:811) | ARHVLGWVL ELDY (SEQ ID NO:812) | QSISSY (SEQ ID NO:813) | AAS (SEQ ID NO:814) | QQSYSTPLT (SEQ ID NO:815) | QVQLVQSGAEVKKPG SSVKVSCKASGGTFSS YAISWVRQAPGQGLE WMGGIIPIFGTANYA QKFQGRVTITADESTS TAYMELSSLRSEDTAV YYCARHVLGWVLELD YWGQGTLVTVSS (SEQ ID NO:816) | ASTKGPSVFPLAPSSKSTSG GTAALGCLVKDYFPEPVTV SWNSGALTSGVHTFPAVL QSSGLYSLSSVVTVPSSSLG TQTYICNVNHKPSNTKVDK KVEPKSCDKTHTCPPCPAP ELLGGPSVFLFPPKPKDTLM ISRTPEVTCVVVDVSHEDPE VKFNWYVDGVEVHNAKT KPREEQYNSTYRVVSVLTV LHQDWLNGKEYKCKVSNK ALPAPIEKTISKAKGQPREP QVYTLPPSRDELTKNQVSL TCLVKGFYPSDIAVEWESN GQPENNYKTTPPVLDSDGS FFLYSKLTVDKSRWQQGN VFSCSVMHEALHNHYTQK SLSLSPGK (SEQ ID NO:817) | DIQMTQSPSSLSAS VGDRVTITCRASQSI SSYLNWYQQKPGK APKLLIYAASSLQSG VPSRFSGSGSGTDFT LTISSLQPEDFATYC QQSYSTPLTFGQGT KVEIK (SEQ ID NO:818) | RTVAAPSVFIF PPSDEQLKSG TASVVCLLNN FYPREAKVQ WKVDNALQS GNSQESVTEQ DSKDSTYSLSS TLTLSKADYEK HKVYACEVTH QGLSSPVTKSF NRGEC (SEQ ID NO:819) |

FIGURE 4KK

| mAb ID | Description | Epitope Sequence | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| GA1 | Mouse IgG1/kappa | LLDSGLYCCLVVE IRHHHSEHRVH | GYTLTDYN | INLNYAIT | ARGGYRYTYYA MDY | ENIYSN | AAT | QHFWGT PRT | EVQLQQFGAELVKPGASVKISCKASGY TLTDYNMDWVKQSHGKSLEWIGHIN LNYAITTYNQKFKGKATLTVDKSSSTA YMELRSLTSEDTAVYYCARGGYRYTYY AMDYWGQGTSVTVSS | AKTTPPSVYPLAPGSSAAQTNSMVTLGCLVKGYFPE PVTVTWNSGSLSSGVHTFPAVLQSDLYTLSSSVTVP SSTWPSETVTCNVAHPASSTKVDKKIVPRDCGCKP CICTVPEVSSVFIFPPKPKDVLTITLTPKVTCVVVDIS KDDPEVQFSWFVDDVEVHTAQTQPREEQFNSTFR SVSELPIMHQDWLNGKEFKCRVNSAAFPAPIEKTIS KTKLNPKS | DIQMTQSPASLSVSVGETVTITCRA SENIYSNLAWYQQKQGKSPQLLVY AATNLADGVPSRFSGSGSGTQYSLK INSLQSEDFGSYYCCQHFWGTPRTFG GGTKLEIK | RADAAPTVSIFPPSSEQLTS GGASVVCFLNNFYPKDIN VKWKIDGSERQNGVLNS WTDQDSKDSTYSMSSTLT LTKDEVERHNSYTCEATHK TSTSPIVKSFNRNEC |
| GA1-IgG2 | Human IgG2/kappa | LLDSGLYCCLVVE IRHHHSEHRVH | GYTLTDYN | INLNYAIT | ARGGYRYTYYA MDY | ENIYSN | AAT | QHFWGT PRT | EVQLQQFGAELVKPGASVKISCKASGY TLTDYNMDWVKQSHGKSLEWIGHIN LNYAITTYNQKFKGKATLTVDKSSSTA YMELRSLTSEDTAVYYCARGGYRYTYY AMDYWGQGTSVTVSS | ASTKGPSVFPLAPCSRSTSESTAALGCLVKDYFPEPV TVSWNSGALTSGVHTFPAVLQSSGLYSLSSVVTVPS SNFGTQTYTCNVDHKPSNTKVDKTVERKCCVECPP CPAPPVAGPSVFLFPPKPKDTLMISRTPEVTCVVVD VSHEDPEVQFNWYVDGVEVHNAKTKPREEQFNST FRVVSVLTVVHQDWLNGKEYKCKVSNKGLPAPIEK TISKTKGQPREPQVYTLPPSREEMTKNQVSLTCLVK GFYPSDIAVEWESNGQPENNYKTTPPMLDSDGSF FLYSKLTVDKSRWQQGNVFSCSVMHEALHNHYTQ KSLSLSPGK | DIQMTQSPASLSVSVGETVTITCRA SENIYSNLAWYQQKQGKSPQLLVY AATNLADGVPSRFSGSGSGTQYSLK INSLQSEDFGSYYCCQHFWGTPRTFG GGTKLEIK | RTVAAPSVFIFPPSDEQLKS GTASVVCLLNNFYPREAKV QWKVDNALQSGNSQESV TEQDSKDSTYSLSSTLTSK ADYEKHKVYACEVTHQGL SSPVTKSFNRGEC |
| GG8 | Mouse IgG1 | LLDSGLYCCLVVE IRHHHSEHRVH; GHDVTFYKTWY RSSRGEVQTC | GYSFTGYT | INPYNGGI | ARRTLLRPYFFD Y | QSVSTSTFS Y | YAS | QHSWEIP YT | EVQLQQSGPELVKPGTSMKISCKASGY SFTGYTMNWVRQSHGKNLEWIGLIN PYNGGINYNQKFKARATLTVDKSSSTA YMELLSLTSEDSAVYYCARRTLLRPYFF DYWGQGTTLTVSS | | DIVLTQSPASLAVSLGQRATISCRAS QSVSTSTFSYMHWYQQKPGQPPKL LIKYASNLESGVPARFSGSGSGTDFT LNIHPVEEEDTATYYCQHSWEIPYTF GGGTKLEIK | |
| GG8-IgG2 | Human IgG2/kappa | LLDSGLYCCLVVE IRHHHSEHRVH; GHDVTFYKTWY RSSRGEVQTC | GYSFTGYT | INPYNGGI | ARRTLLRPYFFD Y | QSVSTSTFS Y | YAS | QHSWEIP YT | EVQLQQSGPELVKPGTSMKISCKASGY SFTGYTMNWVRQSHGKNLEWIGLIN PYNGGINYNQKFKARATLTVDKSSSTA YMELLSLTSEDSAVYYCARRTLLRPYFF DYWGQGTTLTVSS | ASTKGPSVFPLAPCSRSTSESTAALGCLVKDYFPEPV TVSWNSGALTSGVHTFPAVLQSSGLYSLSSVVTVPS SNFGTQTYTCNVDHKPSNTKVDKTVERKCCVECPP CPAPPVAGPSVFLFPPKPKDTLMISRTPEVTCVVVD VSHEDPEVQFNWYVDGVEVHNAKTKPREEQFNST FRVVSVLTVVHQDWLNGKEYKCKVSNKGLPAPIEK TISKTKGQPREPQVYTLPPSREEMTKNQVSLTCLVK GFYPSDIAVEWESNGQPENNYKTTPPMLDSDGSF FLYSKLTVDKSRWQQGNVFSCSVMHEALHNHYTQ KSLSLSPGK | DIVLTQSPASLAVSLGQRATISCRAS QSVSTSTFSYMHWYQQKPGQPPKL LIKYASNLESGVPARFSGSGSGTDFT LNIHPVEEEDTATYYCQHSWEIPYTF GGGTKLEIK | RTVAAPSVFIFPPSDEQLKS GTASVVCLLNNFYPREAKV QWKVDNALQSGNSQESV TEQDSKDSTYSLSSTLTSK ADYEKHKVYACEVTHQGL SSPVTKSFNRGEC |

FIGURE 4LL

| mAb ID | Description | Epitope Sequence | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| IE8 | Mouse IgG1/? | LLDSGLYCCLVVEIR | GFDFSRYW | VYPDSSTI | ARGRGDY | GNIHNY | NAK | QNFWSTPFT | EVKLLESGGGLVQPGGSLKLSCAASGFDFSRYWMSWVRQAPGKGLEWIGEVYPDSSTINYTPSLKDKFIISRDNAKNTLYLQMIKVRSEDTALYYCARGRGDYWGQGTSVTVSS | | DIQMTQSPASLSASVGETVTITCRASGNIHNYLSWYHQKQGKSPQLLVYNAKTLADGVPSRFSGSGSGTQYSLKINSLQPEDFGSYYCQNFWSTPFTFGSGTKLEIK | |
| IE8-IgG2 | Human IgG2/kappa | LLDSGLYCCLVVEIR | GFDFSRYW | VYPDSSTI | ARGRGDY | GNIHNY | NAK | QNFWSTPFT | EVKLLESGGGLVQPGGSLKLSCAASGFDFSRYWMSWVRQAPGKGLEWIGEVYPDSSTINYTPSLKDKFIISRDNAKNTLYLQMIKVRSEDTALYYCARGRGDYWGQGTSVTVSS | ASTKGPSVFPLAPCSRSTSESTAALGCLVKDYFPEPVTVSWNSGALTSGVHTFPAVLQSSGLYSLSSVVTVPSSNFGTQTYTCNVDHKPSNTKVDKTVERKCCVECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPGK | DIQMTQSPASLSASVGETVTITCRASGMIHNYLSWYHQKQKSPQLLVYNAKTLADGVPSRFSGSGSGTQYSLKINSLQPEDFGSYYCQNFWSTPFTFGSGTKLEIK | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| IE8-IgG2-C127S | Human mutated IgG2/kappa | LLDSGLYCCLVVEIR | GFDFSRYW | VYPDSSTI | ARGRGDY | GNIHNY | NAK | QNFWSTPFT | EVKLLESGGGLVQPGGSLKLSCAASGFDFSRYWMSWVRQAPGKGLEWIGEVYPDSSTINYTPSLKDKFIISRDNAKNTLYLQMIKVRSEDTALYYCARGRGDYWGQGTSVTVSS | ASTKGPSVFPLAPSSRSTSESTAALGCLVKDYFPEPVTVSWNSGALTSGVHTFPAVLQSSGLYSLSSVVTVPSSNFGTQTYTCNVDHKPSNTKVDKTVERKCCVECPPCPAPPVAGPSVFLFPPKPKDTLMISRTPEVTCVVVDVSHEDPEVQFNWYVDGVEVHNAKTKPREEQFNSTFRVVSVLTVVHQDWLNGKEYKCKVSNKGLPAPIEKTISKTKGQPREPQVYTLPPSREEMTKNQVSLTCLVKGFYPSDIAVEWESNGQPENNYKTTPPMLDSDGSFFLYSKLTVDKSRWQQGNVFSCSVMHEALHNHYTQKSLSLSPGK | DIQMTQSPASLSASVGETVTITCRASGMIHNYLSWYHQKQKSPQLLVYNAKTLADGVPSRFSGSGSGTQYSLKINSLQPEDFGSYYCQNFWSTPFTFGSGTKLEIK | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| VSTB100 | Human IgG1/kappa | | GYSFTSYW | IYPGDSDT | ARDVSSFYGYSPMFDY | QSVSSY | DAS | QQRSNWPLT | EVQLVQSGAEVKKPGESLKISCKGSGYSFTSYWIGWVRQMPGKGLEWMGIIYPGDSDTRYSPSFQGQVTISADKSISTAYLQWSSLKASDTAMYYCARDVSSFYGYSPMFDYWGQGTLVTVSS | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | EIVLTQSPATLSLSPGERATLSCRASQSVSSYLAWYQQKPGQAPRLLIYDASNRATGIPARFSGSGSGTDFTLTISSLEPEDFAVYYCQQRSNWPLTFGQGTKVEIK | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| VSTB101 | Human IgG1/kappa | | GYSFTSYW | IYPGDSDT | ARDAHSFYGYSALLDY | QSVSSSY | GAS | QQYGSSPLT | EVQLVQSGAEVKKPGESLKISCKGSGYSFTSYWIGWVRQMPGKGLEWMGIIYPGDSDTRYSPSFQGQVTISADKSISTAYLQWSSLKASDTAMYYCARDAHSFYGYSALLDYWGQGTLVTVSS | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | EIVLTQSPGTLSLSPGERATLSCRASQSVSSYLAWYQQKPGQAPRLLIYGASSRATGIPDRFSGSGSGTDFTLTISRLEPEDFAVYYCQQYGSSPLTFGQGTKVEIK | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

FIGURE 4MM

| mAb ID | Description | Epitope Sequence | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB102 | Human IgG1/kappa | | GYSFTSYW | IYPGDSDT | ARDSYSFPYGHTP VLDY | QSVSSSY | GAS | QQYGSSP LT | EVQLVQSGAEVKKPGESLKISCKGSGY SFTSYWIGWVRQMPGKGLEWMGIIY PGDSDTRYSPSFQGQVTISADKSISTAY LQWSSLKASDTAMYYCARDSYSFYGH TPVLDYWGQGTLVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | EIVLTQSPGTLSLSPGERATLSCRAS QSVSSSYLAWYQQKPGQAPRLIY GASSRATGIPDRFSGSGSGTDFTLTI SRLEPEDFAVYYCQQYGSSPLTFGQ GTKVEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |
| VSTB103 | Human IgG1/kappa | | GYSFTSYW | IYPGDSDT | ARDDALYGGYVL DY | QSVLYSSN NKNY | WAS | QQYVSTP LT | EVQLVQSGAEVKKPGESLKISCKGSGY SFTSYWIGWVRQMPGKGLEWMGIIY PGDSDTRYSPSFQGQVTISADKSISTAY LQWSSLKASDTAMYYCARDDALYGG YYLDYWGQGTLVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | DIVMTQSPDSLAVSLGERATINCKS SQSVLYSSNNKNYLAWYQQKPGQ PPKLLIYWASTRESGVPDRFSGSGS GTDFTLTISSLQAEDVAVYYCQQYV STPLTFGQGTKVEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |
| VSTB104 | Human IgG1/kappa | | GYSFTSYW | IYPGDSDT | ARDANSFYSAAS IFDY | QSVLYSSN NKNY | WAS | QQYVSTP LT | EVQLVQSGAEVKKPGESLKISCKGSGY SFTSYWIGWVRQMPGKGLEWMGIIY PGDSDTRYSPSFQGQVTISADKSISTAY LQWSSLKASDTAMYYCARDANSFYSA ASIFDYWGQGTLVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | DIVMTQSPDSLAVSLGERATINCKS SQSVLYSSNNKNYLAWYQQKPGQ PPKLLIYWASTRESGVPDRFSGSGS GTDFTLTISSLQAEDVAVYYCQQYV STPLTFGQGTKVEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |
| VSTB105 | Human IgG1/kappa | | GGTFSSYA | IIPIFGTA | ARSSYGWSYEFD Y | QSIATN | AAS | QQNDDR PIT | QVQLVQSGAEVKKPGSSVKVSCKASG GTFSSYAISWVRQAPGQGLEWMGGII PIFGTANYAQKFQGRVTITADESTSTA YMELSSLRSEDTAVYYCARSSYGWSYE FDYWGQGTLVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | DIQMTQSPSSLSASVGDRVTITCRA SQSIATNLNWYQQKPGKAPKLLIYA ASSLQSGVPSRFSGSGSGTDFTLTIS SLQPEDFATYYCQQNDDRPITFGQ GTKVEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |
| VSTB106 | Human IgG1/kappa | | GGTFSSYA | IIPIFGTA | ARSSYGWSYEFD Y | QSIRTD | SAS | QQNERTP IT | QVQLVQSGAEVKKPGSSVKVSCKASG GTFSSYAISWVRQAPGQGLEWMGGII PIFGTANYAQKFQGRVTITADESTSTA YMELSSLRSEDTAVYYCARSSYGWSYE FDYWGQGTLVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | DIQMTQSPSSLSASVGDRVTITCRA SQSIRTDLNWYQQKPGKAPKLLIYS ASSLQSGVPSRFSGSGSGTDFTLTIS SLQPEDFATYYCQQNERTPITFGQG TKVEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |

FIGURE 4NN

| mAb ID | Description | Epitope Sequence | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB107 | Human IgG1/kappa | | GGTFSSYA | IIPIFGTA | ARSSYGWSYEFDY | QSINND | AAS | QQNRATPIT | QVQLVQSGAEVKKPGSSVKVSCKASGGTFSSYAISWVRQAPGQGLEWMGGIIPIFGTANYAQKFQGRVTITADESTSTAYMELSSLRSEDTAVYYCARSSYGWSYEFDYWGQGTLVTVSS | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | DIQMTQSPSSLSASVGDRVTITCRASQSINNDLNWYQQKPGKAPKLLIYAASSLQSGVPSRFSGSGSGTDFTLTISSLQPEDFATYYCQQNRATPITFGQGTKVEIK | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| VSTB108 | Human IgG1/kappa | | GGTFSSYA | IIPIFGTA | ARNTFGWSGELDY | QSISNR | SAS | QQNHDNPIT | QVQLVQSGAEVKKPGSSVKVSCKASGGTFSSYAISWVRQAPGQGLEWMGGIIPIFGTANYAQKFQGRVTITADESTSTAYMELSSLRSEDTAVYYCARNTFGWSGELDYWGQGTLVTVSS | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | DIQMTQSPSSLSASVGDRVTITCRASQSINRLNWYQQKPGKAPKLLIYSASSLQSGVPSRFSGSGSGTDFTLTISSLQPEDFATYYCQQNHDNPITFGQGTKVEIK | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| VSTB109 | Human IgG1/kappa | | GGTFSSYA | IIPIFGTA | ARSSYGWSYEFDY | QSIATY | AAS | QQNHNRPIT | QVQLVQSGAEVKKPGSSVKVSCKASGGTFSSYAISWVRQAPGQGLEWMGGIIPIFGTANYAQKFQGRVTITADESTSTAYMELSSLRSEDTAVYYCARSSYGWSYEFDYWGQGTLVTVSS | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | DIQMTQSPSSLSASVGDRVTITCRASQSIATYLNWYQQKPGKAPKLLIYAASSLQSGVPSRFSGSGSGTDFTLTISSLQPEDFATYYCQQNHNRPITFGQGTKVEIK | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| VSTB110 | Human IgG1/kappa | | GGTFSSYA | IIPIFGTA | ARHSIGWVAELDY | QSINTD | AAS | QQGASDPIT | QVQLVQSGAEVKKPGSSVKVSCKASGGTFSSYAISWVRQAPGQGLEWMGGIIPIFGTANYAQKFQGRVTITADESTSTAYMELSSLRSEDTAVYYCARHSIGWVAELDYWGQGTLVTVSS | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | DIQMTQSPSSLSASVGDRVTITCRASQSINTDLNWYQQKPGKAPKLLIYAASSLQSGVPSRFSGSGSGTDFTLTISSLQPEDFATYYCQQGASDPITFGQGTKVEIK | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| VSTB111 | Human IgG1/kappa | | GGTFSSYA | IIPIFGTA | ARSSYGWSYEFDY | QSINTD | AAS | QQNRGSPIT | QVQLVQSGAEVKKPGSSVKVSCKASGGTFSSYAISWVRQAPGQGLEWMGGIIPIFGTANYAQKFQGRVTITADESTSTAYMELSSLRSEDTAVYYCARSSYGWSYEFDYWGQGTLVTVSS | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | DIQMTQSPSSLSASVGDRVTITCRASQSINTDLNWYQQKPGKAPKLLIYAASSLQSGVPSRFSGSGSGTDFTLTISSLQPEDFATYYCQQNRGSPITFGQGTKVEIK | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

FIGURE 40O

| mAb ID | Descriptio n | Epitope Sequence | Heavy-chain cdr1 (imgt) | Heavy-chain cdr2 (imgt) | Heavy-chain cdr3 (imgt) | Light-chain cdr1 (imgt) | Light-chain cdr2 (imgt) | Light-chain cdr3 (imgt) | Heavy-chain Variable | Heavy-chain Constant | Light-chain Variable | Light-chain Constant |
|---|---|---|---|---|---|---|---|---|---|---|---|---|
| VSTB113 | Human IgG1/kappa | | GGTFSSYA | IIPIFGTA | ARHSIGWVAEL DY | QSIATD | AAS | QQAHWY PLT | QVQLVQSGAEVKKPGSSVKVSCKASG GTFSSYAISWVRQAPGQGLEWMGGII PIFGTANYAQKFQGRVTITADESTSTA YMELSSLRSEDTAVYYCARHSIGWVAE LDYWGQGTLVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | DIQMTQSPSSLSASVGDRVTITCRA SQSIATDLNWYQQKPGKAPKLLIYA ASSLQSGVPSRFSGSGSGTDFTLTIS SLQPEDFATYYCQQAHWYPLTFGQ GTKVEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |
| VSTB114 | Human IgG1/kappa | | GGTFSSYA | IIPIFGTA | ARHSIGWVAEL DY | QSIATS | YAS | QQGAYYP LT | QVQLVQSGAEVKKPGSSVKVSCKASG GTFSSYAISWVRQAPGQGLEWMGGII PIFGTANYAQKFQGRVTITADESTSTA YMELSSLRSEDTAVYYCARHSIGWVAE LDYWGQGTLVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | DIQMTQSPSSLSASVGDRVTITCRA SQSIATSLNWYQQKPGKAPKLLIYY ASSLQSGVPSRFSGSGSGTDFTLTIS SLQPEDFATYYCQQGAYYPLTFGQ GTKVEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |
| VSTB115 | Human IgG1/kappa | | GGTFSSYA | IIPIFGTA | ARSSYGWSYEFD Y | QSIRTY | AAS | QQARDTP IT | QVQLVQSGAEVKKPGSSVKVSCKASG GTFSSYAISWVRQAPGQGLEWMGGII PIFGTANYAQKFQGRVTITADESTSTA YMELSSLRSEDTAVYYCARSSYGWSYE FDYWGQGTLVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | DIQMTQSPSSLSASVGDRVTITCRA SQSIRTYLNWYQQKPGKAPKLLIYA ASSLQSGVPSRFSGSGSGTDFTLTIS SLQPEDFATYYCQQAYSNPITFGQG TKVEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |
| VSTB116 | Human IgG1/kappa | | GGTFSSYA | IIPIFGTA | ARSSYGWSYEFD Y | QSINTN | AAS | QQSKEVP YT | QVQLVQSGAEVKKPGASVKVSCKASG GTFSSYAISWVRQAPGQRLEWMGSYI YTPSHTHWVRQAPGQRLEWMGSYI PFIDSTIYNQKFKDRVTITRDTSASTAY MELSSLRSEDTAVYYCARGIRGYTMDY WGQGTLVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | DIQMTQSPSSLSASVGDRVTITCRA SQSINTNLNWYQQKPGKAPKLLIYA ASSLQSGVPSRFSGSGSGTDFTLTIS SLQPEDFATYYCQQSKEVPYTFGQG TKVEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |
| VSTB49 | Human IgG1/kappa | | GYTFPSHT | IYPFIDST | ARGIRGYTMDY | ESVDNYGL SF | GAS | QQSKEVP YT | QVQLVQSGAEVKKPGASVKVSCKASG YTFPSHTHWVRQAPGQRLEWMGSYI PFIDSTIYNQKFKDRVTITRDTSASTAY MELSSLRSEDTAVYYCARGIRGYTMDY WGQGTLVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | DVVMTQSPLSLPVTLGQPASISCRA SESVDNYGLSFMNWFQQRPGQSP RRLIYGASNQGSGVPDRFSGSGSGT DFTLKISRVEAEDVGVYYCQQSKEV PYTFGQGTKLEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |

FIGURE 4PP

| mAb ID | Description | Epitope Sequence | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB50 | Human IgG1/kappa | NLTYLLDSGL and VQTGKDAPSNC | GYTFTNYG | INPYTGEP | AREGVGNYIFPY | ESVDTYAN SL | RAS | QQTNEDP RT | QVQLVQSGSEELKKPGASVKVSCKASG YTFTNYGINWVRQAPGQGLEWMG WINPYTGEPTYADDFKGRFVFSLDTSV STAYLQICSLKAEDTAVYYCAAREGVGN YIFPVWGQGTLVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | DIVMTQTPLSLSVTPGQPASISCRAS ESVDTYANSLMHWYLQKPGQPPQ LLIYRASNLESGVPDRFSGSGSGTDF STAYLQICSLKAEDVGVYYCQQTNEDPR TFGQGTKLEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |
| VSTB51 | Human IgG1/kappa | | GFTFSSYT | ISNSGSYT | ARDTVLSPFDY | SSISY | DTS | HQRSSFT | EVQLVESGGGLVQPGGSLRLSCAASGF TFSSYTMSWVRQAPGKGLEWVATISN SGSYTYYLDSVKGRFTISRDNAKNSLYL QMNSLRAEDTAVYYCARDTVLSPFDY WGQGTTVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | EIVLTQSPDFQSVTPKEKVTITCSATS SISYMHWYQQKPDQSPKLLIKDTSE LASGVPSRFSGSGSGTDFTLTINSLE AEDAATYYCHQRSSFTFGQGTKLEI K | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |
| VSTB52 | Human IgG1/kappa | | GGTFSNYW | IYPGGGFT | ARYRSDEDYS MDF | QSLLYSNG KTY | LVS | VQATHFP QT | QVQLVQSGAEVKKPGSSVKVSCKASG GTFSNYWIGWVRQAPGQGLEWMGE IYPGGGFTHYNEKFKGRVTITADESTST AYMELSSLRSEDTAVYYCARYRSDED YSMDFWGQGTLVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | DVVMTQSPLSLPVTLGQPASICKS SQSLLYSNGKTYLNWFQQRPGQSP RRLIYLVSKLDSGVPDRFSGSGSGTD FTLKISRVEAEDVGVYCVQATHFP QTFGQGGTKLEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |
| VSTB53 | Human IgG1/kappa | | GYTFTHYT | IIPSSGYS | ARGAYDVYDY YAMDY | QTIVHSNG NTY | KVS | FQASHFP WT | QVQLVQSGAEVKKPGASVKVSCKASG YTFTHYTIHWVRQAPGQGLENMGYII PSSGYSEYNQKFKDRVTMTRDTSTSTV YMELSSLRSEDTAVYYCARGAYDVYDY DYYAMDYWGQGTLVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | DIVMTQSPLSLPVTPGEPASISCRSS QTIVHSNGNTYLEWYLQKPGQSPQ LLIYKVSNRFSGVPDRFSGSGSGTDF TLKISRVEAEDVGVYCFQASHVPW TFGQGTKLEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |
| VSTB54 | Human IgG1/kappa | | GYNIKDTY | IDPTHGYV | ARDRFDPYWFL DV | ESVEYYGT SL | DAF | QQSRKVP WT | QVQLVQSGAEVKKPGASVKVSCKASG YNIKDTYMHWVRQAPGQGLEWMG RIDPTHGYVYDPKFQGRVTMTRDTST STVVMELSSLRSEDTAVYYCARDRFDP YWFLDVWGQGTLVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | DIVMTQTPLSLSVTPGQPASICRAS ESVEYYGTSLMQWYLQKPGQSPQL LIYDAFNVESGVPDRFSGSGSGTDF TLKISRVEAEDVGVYCCQQSRKVP WTFGQGTKLEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |

FIGURE 4QQ

| mAb ID | Descriptio n | Epitope Sequence | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB55 | Human IgG1/kapp a | | GYSIASDYV | ISYSGST | ARITTVVPTGSY YGVDF | SSVNF | DTS | QQWSNY PFT | QVQLQESGPGLVKPSETLSLTCAVSGY SIASDYVWNWIRQPPGKGLEWIGVIS YSGSTSNNPSLNSRVTISVDTSKNQFSL KLSSVTAADTAVYYCARITTVVPTGSY YGVDFWGQGTLVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | EIVLTQSPDFQSVTPKEKVTITCSGSS SVNFMYVWYQQKPDQSPKLLIKDTS NLASGVPSRFSGSGSGTDFTLTINSL EAEDAATYYCQQWSNYPFTFGQGT KLEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |
| VSTB56 | Human IgG1/kapp a | | GYTFTSYW | IHPNTLHT | ARLDGDYDVAL DY | ESVEYYGT SF | TAS | QQSRKVP YT | QVQLVQSGAEVKKPGASVKVSCKASG YTFTSYWLHWVRQAPGQGLEWMGY IHPNTLHTDYNQKFKDRVTMTRDTSTS TVYMELSSLRSEDTAVYYCARLDGDYD VALDYWGQGTLVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | DIVMTQTPLSLSVTPGQPASISCRAS ESVEYYGTSFMQWYLQKPGQPPQL LIYTASNVESGVPDRFSGSGSGTDFT LKISRVEAEDVGVYYCQQSRKVPYT FGQGTKLEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |
| VSTB57 | Human IgG1/kapp a | | GFTFSTVA | ISSGGSDT | ARPTYYGIFSYFD Y | SSVSY | STS | HQWRTY PT | EVQLVESGGGLVQPGGSLRLSCAASGF TFSTYAMSWVRQAPGKGLEWVATISS GGSDTYYPDTVKGRFTISRDNAKNSLY LQMNSLRAEDTAVYYCARPTYYGIFSY FDYWGQGTLVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | DIQLTQSPDFLSASVGDRVTITCSAS SSVSYMHWYQQKPGKAPKLLIYSTS NLASGVPSRFSGSGSGTEFTLTISSL QPEDFATYYCHQWRTYPTFGQGTK LEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |
| VSTB58 | Human IgG1/kapp a | | GFSLTNYG | IWRGGNT | ARSMVSYTVDY | SSVSY | DTS | QQWSSY PPT | QVQLQESGPGLVKPSETLTCVSGFS LTNYGVHWVRQPPGKGLEWVGVIWR GGNTDYNAAFMSRVTISVDTSKNQFS LKLSSVTAADTAVYYCARSMVSYTVDY WGQGTLVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | EIVLTQSPDFQSVTPKEKVTITCSASS SVSYMHWYQQKPDQSPKLLIKDTS NLASGVPSRFSGSGSGTDFTLTINSL EAEDAATYYCQQWSSYPPTFGQGT KLEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |
| VSTB59 | Human IgG1/kapp a | | GYTFTDYW | IETSLNVP | ARWGIYGNPWF AY | ESVDSYVN SF | RAS | QQSNEDP YT | QVQLVQSGAEVKKPGASVKVSCKASG YTFTDYWMHWVRQAPGQGLEWMMG IETSLNVPSNVQKFKGRVTMTRDTST AIETSLNVPSNVQKFKGRVTMTRDTST STVVMELSSLRSEDTAVYYCARWGIYG NPWFAYWGRGTLVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | DIVMTQTPLSLSVTPGQPASISCRAS ESVDSYVNSFVHWYLQKPGQPPQL LIYRASNLESGVPDRFSGSGSGTDFT LKISRVEAEDVGVYYCQQSNEDPYT FGQGTKLEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |

FIGURE 4RR

| mAb ID | Description | Epitope Sequence | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB60 | Human IgG1/kappa | NLTLLDSGL and VQTGKDAPSNC | GYTFTNYG | INTYTGES | ARDYYGHYVSAY | ESVDNYAN SF | RAS | QQSHEDP YT | QVQLVQSGSELKKPGASVKVSCKASG YTFTNYGMTWVRQAPGQGLEWMG WINTYTGESTYADDFKGRFVSLDTSV STAYLQCSLKAEDTAVYYCARDYYGH YVSAVWGQGTLVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | DIVMTQTPLSLSVTPGQPASISCRAS ESVDNYANSFNHWYLQKPGQSPQ LLIYRASNLESGVPDRFSGSGSGTDF TLKISRVEAEDVGVYYCQQSHEDPY TFGQGTKLEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |
| VSTB61 | Human IgG1/kappa | | GYTFTSHW | INPRDGRT | ARGDFHYGDYF WYFDV | QNVHGA | MAS | LQHWNY LT | QVQLVQSGAEVKKPGASVKVSCKASG YTFTSHWMHWVRQAPGQGLEWMG EINPRDGRTNYNEKFKTRVTMTRDTS TSTVYMELSSLRSEDTAVYYCARGDFH YGDFWYFDVWGQGTLVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | DIQMTQSPSSLSASVGDRVTITCKA SQNVHGAVAWYQQKPGKVPKLLIY MASNRPTGVPSRFSGSGSGTDFTLT ISSLQPEDVATYYCLQHWNYLTFGQ GTKLEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |
| VSTB62 | Human IgG1/kappa | | GYTFTHVW | IYPGDGDT | ARRDYDYGDY | SSVSH | LTS | QQYQTYP PT | QVQLVQSGAEVKKPGASVKVSCKASG YTFTHYWIQWVRQAPGQGLEWMGA LPAPIEKTISKAKGQPREPQVYTLPPSRDELTKNQV NPGDGDTRYTQKFKGRVTMTRDTST STVVMELSSLRSEDTAVYYCARRDYDY GDYWGQGTTVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | EIVLTQSPDFQSVTPKEKVTITCSASS SVSHRWYWYQQKPDQSPKLLIKLTS NLASGVPSRFSGSGSGTDFTLTINSL EAEDAATYYCQQYQTYPPTFGQGT RLEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |
| VSTB63 | Human IgG1/kappa | | GFSITSDFA | ITYSGFT | ARQEYGNYVMY FDV | ESVEYYGT SL | AAS | QQSRKVP WT | QVQLQESGPGLVKPSETLSLTCAVSGF SITSDFAWNWIRQPPGKGLEWIGYTI SGFTNYNPSLESRVTISVDTSKNQFSLK LSSVTAADTAVYYCARQEYGNYVMYF DVWGQGTLVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | DIVMTQTPLSLSVTPGQPASISCRAS ESVEYYGTSLLQWYLQKPGQPPQLL IYAASNVESGVPDRFSGSGSGTDFT LKISRVEAEDVGVYYCQQSRKVPW TFGQGTKLEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |
| VSTB64 | Human IgG1/kappa | | GYSITSGYF | MGVDGRI | AREGDYYGSGFA YW | QNVNTN | SAS | QQYNNY PLT | QVQLQESGPGLVKPSETLSLTCAVSGY SITSGYFWNWIRQPPGKGLEWIGYM GYDGRIFYPSLKNRVTISVDTSKNQFS LKLSSVTAADTAVYYCAREGDYYGSGF AYWGQGTLVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | DIQMTQSPSSLSASVGDRVTITCKA SQNVNTNLAWYQQKPGKVPKLLIY SASYRYSGVPSRFSGSGSGTDFTLT SSLQPEDVATYYCQQYNNYPLTFG QGTKLEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |

FIGURE 4SS

| mAb ID | Description | Epitope Sequence | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB65 | Human IgG1/kappa | | GYTFTSYW | INPSNGLT | ARSYDVDGDYYAMDY | QSIVHSNGNTY | KVS | FQASHVPWT | QVQLVQSGAEVKKPGASVKVSCKASGYTFTSYWIHWVRQAPGQGLEWMGEINPSNGLTNYNEKFRNRVTMTRDTSTSTVYMELSSLRSEDTAVYYCARSYDVDGDYYAMDYWGQGTLVTVSS | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | DIVMTQSPLSLPVTPGEPASISCRSTQSIVHSNGNTYLEWYLQKPGQSPQLLIYKVSNRFSGVPDRFSGSGSGTDFTLKISRVEAEDVGVYYCFQASHVPWTFGQGTKLEIK | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| VSTB66 | Human IgG1/kappa | | GYPETGYF | INPYNGGT | ARWTFDGLFMDY | ENVDKYGISF | ATS | QQSKEDPYT | QVQLVQSGAEVKKPGASVKVSCKASGYPETGYFMHWVRQAPGQGLEWMGRINPYNGGTVYNQNFNDRVTMTRDTSTSTVYMELSSLRSEDTAVYYCARWTFDGLFMDYWGQGTTVTVSS | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | DVVMTQSPLSLPVTLGQPASISCRASENVDKYGISFMNWFQQRPGQSPRRLIYATSNQGSGVPDRFSGSGSGTDFTLKISRVEAEDVGVYYCQQSKEDPYTFGQGTKLEIK | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| VSTB67 | Human IgG1/kappa | | DYIFSSYW | IPGSGGT | ARAIYDYDMYYFDS | QDISSY | YTS | QHVNTLPWT | QVQLVQSGAEVKKPGASVKVSCKASDYIFSSYWIQWVRQAPGQGLEWMGLIPGSGGTTNYNEKFKGRVTMTRDTSTSTVYMELSSLRSEDTAVYYCARAIYDYDMYYFDSWGQGTTVTVSS | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | DIQMTQSPSSLSASVGDRVTITCRASQDISSYLNWVQQKPGKVPKLLIYYTSRLHSGVPSRFSGSGSGTDFTLTISSLQPEDVATYYCQHVNTLPWTFGQGTKLEIK | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| VSTB68 | Human IgG1/kappa | | GYTFTDYT | INPYNGGT | ARHYGNYNWVFDV | QYVNTA | SAS | QQHFFTPIT | QVQLVQSGAEVKKPGASVKVSCKASGYTFTDYTMNWVRQAPGQGLEWMGLINPYNGGTTYNQKFKGRVTITRDTSASTAYMELSSLRSEDTAVYYCARHYGNYNWVFDVWGQGTTVTVSS | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | DIQLTQSPSFLSASVGDRVTITCKASQYVNTAVAWYQQKPGKAPKLLIYSASYRYTGVPSRFSGSGSGTEFTLTISSLQPEDFATYYCQQHFFTPITFGQGTKLEIK | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| VSTB69 | Human IgG1/kappa | | GYTFTNVG | INTYTGEP | ARNYGNYVAY | QDINSY | RAN | LQYDEFPLT | QVQLVQSSELKKPGASVKVSCKASGYTFTNVGMNWVRQAPGQGLEWMGWINTYTGEPTYADDFKGRFVFSLDTSVSTAYLQICSLKAEDTAVYYCARNYGNYVAYWGQGTTVTVSS | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | DIQMTQSPSSLSASVGDRVTITCKASQDINSYLSWFQQKPGKAPKSLIYRANRLHDGVPSRFSGSGSGTDFTLTISSLQPEDFATYYCLQYDEFPLTFGQGTRLEIK | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

FIGURE 4TT

| mAb ID | Description | Epitope Sequence | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB70 | Human IgG1/kappa | | GYTFSNYW | ILPGSGNV | ATPPHYGYGYDY DVNY | QSLLDSDG KTY | LVS | WQGTHF PQT | EVQLVQSGAEVKKPGATVKISCKVSGY TFSNYWIEMVVQQAPGKGLEWMGEIL PGSGNVHNEKFKGRVFTTADTSTDTA SLTCLVKGFYPSDIAVEWESNGQPENNYKTTPPVL DSDGSFFLYSKLTVDKSRWQQGNVFSCSVMHEAL HNHYTQKSLSLSPGK | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | DVIMTQSPLSLPVTLGQPASISCKS SQSLLDSDGKTYLNWFQQRPGQSP RRLLVLSELDSGVPDRFSGSGSGTD FTLKISRVEAEDVGVYYCWQGTHFP QTFGQGTKLEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |
| VSTB71 | Human IgG1/kappa | | GYVFSRSW | IYPGDGDT | ARRWFL | QSLLNSGD QKSY | GAS | QNDHSYP LT | QVQLVQSGAEVKKPGSSVKVSCKASG YVFSRSWINWVRQAPGQGLEWMGR IYPGDGDTNYNGKFKGRVTTTADESTS TAYMELSSLRSEDTAVYYCARRWFLW GQGTLVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | DIVMTQSPDSLAVSLGERATINCKS SQSLLNSGDQKSYLANWYQQKPGQP PKLLIYGASTRESGVPDRFSGSGSGT DFTLTISSLQAEDVAVYYCQNDHSY PLTFGQGTKLEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |
| VSTB72 | Human IgG1/kappa | | GFTFSSYA | ISSGGSHT | ARRGNLYDGPY | SSVSH | DTS | QQWNFY PFT | EVQLVESGGGLVQPGGSLRLSCAASGF TFSSYAMSWVRQAPGKGLEWVAEISS GSHYTYPDTVTGRFTISRDNAKNSLY LQMNSLRAEDTAVYYCARRGNLYDGP YWGQGTLVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | EIVLTQSPATLSLSPGERATLSCSASS SVSHMYWYQQKPGQAPRLLIYDTS KLASGIPARFSGSGSGTDFTLTISSLE PEDFAVYYCQQWNFYPFTFGQGTK LEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |
| VSTB73 | Human IgG1/kappa | | GYTFTDYV | IYPGSGNT | ARVLVSMDY | SSINY | DTS | HQRSSYP WT | QVQLVQSGAEVKKPGASVKVSCKASG YTFTDYVISWVRQAPGQGLEWMGEI YPGSGNTYYEKFKGRVTMTRDTSTST VYMELSSLRSEDTAVYYCARVLVSVM DYWGQGTLVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | EIVLTQSPDFQSVTPKEKVTITCSASS SINYITWYQQKPDQSPKLLIKDTSKL ASGVPSRFSGSGSGTDFTLTINSLEA EDAATYCHQRSSYPWTFGQGTRL EIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |
| VSTB74 | Human IgG1/kappa | | GVIFTDYN | INPKYDST | AADGSSAAMDY | QSLLNSGH QKNV | GAS | QNDHRYP LT | QMQLVQSGPEVKKPGTSVKVSCKASG VIFTDYNIDWVRQARGQRLEWIGDIN PKYDSTRYNQDFKGRVTITRDMSTSTA YMELSSLRSEDTAVYYCAADGSSAAMD YWGGGTTVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | DIVMTQSPDSLAVSLGERATINCKS SQSLLNSGHQKNVLAWVYQQKPGQ PKLLIYGASTRESGVPDRFSGSGSGG TDFTLTISSLQAEDVAVYYCQNDHR YPLTFGQGTKLEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |

FIGURE 4UU

| mAb ID | Description | Epitope Sequence | Heavy-chain cdr1 (imgt) | Heavy-chain cdr2 (imgt) | Heavy-chain cdr3 (imgt) | Light-chain cdr1 (imgt) | Light-chain cdr2 (imgt) | Light-chain cdr3 (imgt) | Heavy-chain Variable | Heavy-chain Constant | Light-chain Variable | Light-chain Constant |
|---|---|---|---|---|---|---|---|---|---|---|---|---|
| VSTB75 | Human IgG1/kappa | | GFNIKDYY | IDPENGNT | ARDYGYFDYW | SSVIY | STS | QQRSSYPHT | QVQLVQSGAEVKKPGSSVKVSCKASGFNIKDYYIHWVRQAPGQGLEWMGWIDPENGNTIYDPKFQGRVTITADESTSTAYMELSSLRSEDTAVYYCARDYGYFDYWGQGTLVTVSS | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | DVVMTQSPAFLSVTPGEKVTITCSADSSVHYMWYQQKPDQAPKLLIKSTSNLASGVPSRFSGSGSGTDFTFTISSLEAEDAATYYCQQRSSYPHTFGQGTKLEIK | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| VSTB76 | Human IgG1/kappa | | GYTFTDYW | IYPSHSYT | ARGGYRYPYYAMDY | ENIYGA | GAT | QNVLSTPYT | QVQLVQSGAEVKKPGASVKVSCKASGYTFTDYWINWVRQAPGQGLEWMGNIYPSHSYTNYNQEFKDRVTMTRDTSTSTVYMELSSLRSEDTAVYYCARGGYRYPYYAMDYWGQGTTVTVSS | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | AIQLTQSPSSLSASVGDRVTITCGASENIYGALNWYQQAKPGKAPKLLIYGATNLADGVPSRFSGSGSGTDFTLTISSLQPEDFATYYCQNVLSTPYTFGQGTKLEIK | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| VSTB78 | Human IgG1/kappa | | GYTFTNYW | INPSSGYT | ARDGGSVLFGY | QSLLNSGIRKNY | SAS | KQSYNLYT | QVQLVQSGAEVKKPGASVKVSCKASGYTFTNYWMHWVRQAPGQGLEWMMGYINPSSGYTEYNQKFKDRVTMTRDTSTSTVYMELSSLRSEDTAVYYCARDGGSVLFGYWGQGTLVTVSS | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | DIVMTQSPDSLAVSLGERATINCKSSQSLLNSGIRKNYLAWYQQKPGQPPKLLIYSASTRESGVPDRFSGSGSGTDFTLTISSLQAEDVAVYYCKQSYNLYTFGQGTKLEIK | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| VSTB79 | Human IgG1/kappa | | AYSITSDYA | ITYSGST | ARSFGY | QSIGTS | YAS | QQINSWPTT | QVQLQESGPGLVKPSETLSLTCAVSAYSITSDYAWNWIRQPPGKGLEWIGYITYSGSTRVNPSLKSRVTISVDTSKNQFSLKLSSVTAADTAVYYCARSFGYWGQGTTVTVSS | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | EIVMTQSPATLSVSPGERATLSCRASQSIGTSIHWYQQKPGQAPRLLIYYASESISGIPARFSGSGSGTEFTLTISSLQSEDFAVYYCQQINSWPTTFGQGTKLEIK | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| VSTB80 | Human IgG1/kappa | | GFNIKDYY | IDPENGDT | ARDMGSSYVY | SSVIY | STS | QQRSSYPFT | QVQLVQSGAEVKKPGASVKVSCKASGFNIKDYYMHWVRQAPGQGLEWMGWIDPENGDTEYAPKFQDRVTMTRDTSTSTVYMELSSLRSEDTAVYYCARDMGSSYVWGRGTLVTVSS | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | DVVMTQSPAFLSVTPGEKVTITCSASSVYMHWYQQKPDQAPKLLIKSTSNLASGVPSRFSGSGSGTDFTFTISSLEAEDAATYYCQQRSSYPFTFGQGTKLEIK | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

FIGURE 4VV

| mAb ID | Description | Epitope Sequence | Heavy-chain cdr1 (imgt) | Heavy-chain cdr2 (imgt) | Heavy-chain cdr3 (imgt) | Light-chain cdr1 (imgt) | Light-chain cdr2 (imgt) | Light-chain cdr3 (imgt) | Heavy-chain Variable | Heavy-chain Constant | Light-chain Variable | Light-chain Constant |
|---|---|---|---|---|---|---|---|---|---|---|---|---|
| VSTB81 | Human IgG1/kappa | | GFSLSTSGMG | IYWDDDK | ARRPDYFGSSYY D | ESVDTYGN SF | LAS | QQNNED PWT | QVTLKESGPALVKPTQTLTLTCFSGFS LSTSGMGVSWIRQPPGKALEWLAHIY WDDDKRYNPSLKSRLTSKDTSKNQV VLTMTNMDPVDTATYYCARRPDYFG SSYVDWGQGTTVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | DIVMTQTPLSLSVTPGQPASISCRAS ESVDTYGNSFMHWYLQKPGQPPQ LLYLASMLDFGVPDRFSGSGSGTDF TLKISRVEAEDVGVYYCCQQNNEDP WTFGQGTKLEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |
| VSTB82 | Human IgG1/kappa | | GYSITSDYA | ITYSGST | ARSHYGSTYWY FDV | ESVEYYGT SL | AAS | QQTRKVP WT | QVQLQESGPGLVKPSETLSLTCAVSGY SITSDYAWNWIRQPPGKGLEWIGFITY SGSTNYMPSLKSRVTISVDTSKNQFSLK LSSVTAADTAVYYCARSHYGSTYWYF DVWGQGTTVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | DIVMTQTPLSLSVTPGQPASISCRAS ESVEYYGTSLMQWYLQKPGQSPQL LIYAASNVESGVPDRFSGSGSGTDF TLKISRVEAEDVGVYYCCQQTRKVP WTFGQGTRLEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |
| VSTB83 | Human IgG1/kappa | | GYTFTSYD | IYPGDGYT | ARWGYGSYAM DY | QSLVHSNG NTY | KVS | SQSTHVP PT | QVQLVQSGAEVKKPGASVKVSCKASG YTFTSYDINWVRQAPGQGLEWMGWI YPGDGYTEYNEKFRGRVTMTRDTSTS TVYMELSSLRSEDTAVYYCARWGYGS YAMDYWGQGTLVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | DIVMTQSPLSLPVTPGEPASISCRSS QSLVHSNGNTYLHWYLQKPGQSP QLLIYKVSNRFSGVPDRFSGSGSGT DFTLKISRVEAEDVGVYYCSQSTHV PPTFGQGTKLEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |
| VSTB84 | Human IgG1/kappa | | GYTFTSYW | INPSTGYP | ARSYDYDGGA WFAY | ESVEYYGT SL | AAS | QQSRKVP ST | QVQLVQSGAEVKKPGASVKVSCKASG YTFTSYWMHWVRQAPGQGLEWMG YINPSTGYPGYNQKFKDRVTMTRDTS ISTVYMELSSLRSEDTAVYYCARSYO YDGGAWFAYWGQGTTVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | DIVMTQTPLSLSVTPGQPASISCRAS ESVEYYGTSLMQWYLQKPGQSPQL LIYAASNVESGVPDRFSGSGSGTDF TLKISRVEAEDVGVYYCCQQSRKVPS TFGQGTKLEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |
| VSTB85 | Human IgG1/kappa | | GYTFTDYA | IDTYYGNT | ARGGGDALDY | QSVSMD | YAS | QQGYTSL RT | QVQLVQSGAEVKKPGASVKVSCKASG YTFTDYAMHWVRQAPGQGLEWMG VIDTYYGNTNYNQKFKGRVTMTRDTS ISTAYMELSRLRSDDTAVYYCARGGGD ALDYWGQGTTVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | DIQMTQSPSSLSASVGDRVTITCKA SQSVSMDVVWYQQKPGKAPKLLIY YASNRYIGVPSRFSGSGSGTDFTFTI SSLQPEDIATYYCQQGYTSLRTFGQ GTKLEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |

FIGURE 4WW

| mAb ID | Description | Epitope Sequence | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB87 | Human IgG1/kappa | | GYSITSGYS | IHYIGT | AREDYDYDGVFAY | QSISNN | YAS | QQSNSWPHT | QVQLQESGPGLVKPSETLSLTCAVSGYSITSGYSWHWIRQPPGKGLEWIGYHYIGITNNNPSLKSRVTISVDTSKNQFSLKLSSVTAADTAVYYCAREDYDYDGVFAYWGQGTLVTVSS | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | EIVLTQSPATLSLSPGERATLSCRASQSISNNLHWYQQKPGQAPRLLIYASQSIGIPARFSGSGSGTDFTLTISSLEPEDFAVYYCQQSNSWPHTFGQGTKLEIK | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| VSTB88 | Human IgG1/kappa | | GFSLTMYD | IWTGGGT | AREGLLLPLY | QNVGTN | SAS | QQYNSYPLT | QVQLQESGPGLVKPSETLSLTCTVSGFSLTNYDISWIRQPPGKGLEWMGVIWTGGGTNYNSAFMSRVTISVDTSKNQFSLKLSSVTAADTAVYYCAREGLLLPLYWGQGTLVTVSS | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | DIQMTQSPSSLSASVGDRVTITCKASQNVGTNVAWYQQKPGKVPKLLIYSASYRYSGVPSRFSGSGSGTDFTLTISASYRVPSGYYCQQYNSYPLTFGQGTKLEIK | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| VSTB89 | Human IgG1/kappa | | GYTFTNFG | INTYTGEP | ARGAYYYGSRVWFAY | QNLVHSNGNTY | KVS | SQSSHVPYT | QVQLVQSGSELKKPGASVKVSCKASGYTFTNFGMNWVRQAPGQGLEWMGWINTYTGEPTYADDFKGRFVFSLDTSVSTAYLQICSLKAEDTAVYYCARGAYYYGSRVWFAYWGQGTLVTVSS | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | DIVMTQSPLSLPVTPGEPASISCTSSQNLVHSNGNTYLHWYLQKPGQSPQLLIYKVSNRFSGVPDRFSGSGSGTDFTLKISRVEAEDVGVYYCSQSSHVPYTFGQGTKLEIK | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| VSTB90 | Human IgG1/kappa | | GRSLTSSG | IWSGGNT | AREDYDYDWYFDV | ESVEYYGTSL | AAS | QQSRKVPWT | QVQLQESGAEVKKPGASVKVSCKASGGTFSSSGISWVRQAPGQGLEWMGGIWSGGNTDYNAAFSRVTISVDTSKNQFSLKLSSVTAADTAVYYCAREDYDYDWYFDVWGQGTTVTVSS | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | DIVMTQTPLSLSVTPGQPASISCRASESVEYYGTSLMQWYLQKPGQSPQLLIYAASNWKSGVPDRFSGSGSGTDFTLKISRVEAEDVGVYYCQQSRKVPWTFGQGTKLEIK | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| VSTB91 | Human IgG1/kappa | | GYTFANFW | IFPGNSDT | ARELTGTYYFDY | SSVSY | SSS | HQWSGHFT | QVQLVQSGAEVKKPGASVKVSCKASGYTFANFWMHWVRQAPGQGLEWMGVTFANWFWMHWVRQAPGQGLEWMGVIFPGNSDTGYNQKFKGRVTMTRDTSTSTVYMELSSLRSEDTAVYYCARELTGTYYFDYWGQGTLVTVSS | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK | EIVLTQSPATLSLSPGERATLSCSATSSVSMHWYQQKPGQAPRLLIYSSNLASGIPARFSGSGSGTDFTLTISSLEPEDFAVYYCHQWSGHFTFGQGTKLEIK | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

FIGURE 4XX

| mAb ID | Description | Epitope Sequence | Heavy-chain cdr1 (imgt) | Heavy-chain cdr2 (imgt) | Heavy-chain cdr3 (imgt) | Light-chain cdr1 (imgt) | Light-chain cdr2 (imgt) | Light-chain cdr3 (imgt) | Heavy-chain Variable | Heavy-chain Constant | Light-chain Variable | Light-chain Constant |
|---|---|---|---|---|---|---|---|---|---|---|---|---|
| VSTB92 | Human IgG1/kappa | | GYTFANYL | IYPGGGFI | ARRFDYGGYFFDY | QSIVHSNG NTY | KVS | FQGSHVP WT | QVQLVQSGAEVKKPGASVKVSCKASG YTFANYLIGWVRQAPGQRLEWMGDI VPGGGFISYNEKFKGRVTITRDTSASTA YMELSSLRSEDTAVYYCARRFDYGGYF FDYWGQGTLVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | DIVMTQSPLSLPVTPGEPASISCRSS QSIVHSNGNIYLEWYLQKPGQSPQL LIYKVSNRFSGVPDRFSGSGSGTDFT LKISRVEAEDVGVYYCFQGSHVPW TFGQGTKLEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |
| VSTB93 | Human IgG1/kappa | | GFSITNYD | IWTGGGT | ARDRSPYFGYDV | QSLVHSNG NTY | KVS | SQSTHVP WT | QVQLQESGPGLVKPSETLSLTCTVSGFS ITNYDISWIRQPPGKGLEWIGVINWTG GGTMYNSAFMSRVTISVDTSKNQFSLK LSSVTAADTAVYYCARDRSPYFGYDY WGQGTTVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | DIVMTQTPLSLSVTPGQPASISCRSS QSLVHSNGNTYLHWYLQKPGQSP QLLIYKVSNRFSGVPDRFSGSGSGT DFTLKISRVEAEDVGVYYCSQSTHV PWTFGQGTKLEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |
| VSTB94 | Human IgG1/kappa | | GYSITSDYA | MMYSGSA | ARFDHYYGRFDY | SSVSY | EIS | QQWNYP LFT | QVQLQESGPGLVKPSETLSLTCAVSGY SITSDYAWTWIRQPPGKGLEWIGYM MYSGSASYNPSLKGRVTISVDTSKNQF SLKLSSVTAADTAVYYCARFDHYYGRF DYWGQGTTVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | AIQLTQSPSSLSASVGDRVTITCSAS SSVSIVHWYQQKPGKAPKLLIYEISK LASGVPSRFSGSGSGTDFTLTISSLQ PEDFATYYCQQWNYPLFTFGQGTK LEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |
| VSTB95 | Human IgG1/kappa | | GFTFRNYG | IISGGSYT | ARYDHDGDYA MDY | QSIVHSNG NTY | KVS | FQGSHVP WT | EVQLVESGGGLVQPGGSLRLSCAASGF TFRNYGMSWVRQAPGKGLEWVASII SGGSYTYYPDSVKGRFTISRDNAKNSL VLQMNSLRAEDTAVYYCARIYDHDGD YYAMDYWGQGTTVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | DIVMTQSPLSLPVTPGEPASISCRSS QSIVHSNGNTYLEWYLQKPGQSPQ LLIYKVSNRFSGVPDRFSGSGSGTDF TLKISRVEAEDVGVYYCFQGSHVP WTFGQGTKLEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |
| VSTB96 | Human IgG1/kappa | PVDKGHDVTF and RRPIRDLTFQDL | GYTFTSYD | IYPGDGST | AREGITPFAY | KSISKY | SGS | QQHNEYP WT | QVQLVQSGAEVKKPGSSVKVSCKASG YTFTSYDINWVRQAPGQGLEWMGRI YPGDGSTKYNEKFKGRVTITADKSTST AYMELSSLRSEDTAVYYCAREGITPFAY WGQGTTVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | AIQLTQSPSSLSASVGDRVTITCRAS KSISKYLAWYQQKPGKAPKLLIYSGS TLQSGVPSRFSGSGSGTDFTLTISSL QPEDFATYYCQQHNEYPWTFGQG TKLEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |

FIGURE 4YY

| mAb ID | Descriptio n | Epitope Sequence | Heavy-chain cdr1 (Imgt) | Heavy-chain cdr2 (Imgt) | Heavy-chain cdr3 (Imgt) | Light-chain cdr1 (Imgt) | Light-chain cdr2 (Imgt) | Light-chain cdr3 (Imgt) | Heavy-chain Variable | Heavy-chain Constant | Light-chain Variable | Light-chain Constant |
|---|---|---|---|---|---|---|---|---|---|---|---|---|
| VSTB97 | Human IgG1/kapp a | | GGTFSSYA | IIPIFGTA | ARSSYGWSYEFD Y | QSISSY | AAS | QQSYSTP LT | QVQLVQSGAEVKKPGSSVKVSCKASG GTFSSYAISWVRQAPGQGLEWMGGII PIFGTANYAQKFQGRVTITADESTSTA YMELSSLRSEDTAVYYCARSSYGWSYE FDYWGQGTLVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | DIQMTQSPSSLSASVGDRVTITCRA SQSISSYLNWYQQKPGKAPKLLIYA ASSLQSGVPSRFSGSGSGTDFTLTIS SLQPEDFATYYCQQSYSTPLTFGQG TKVEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |
| VSTB98 | Human IgG1/kapp a | | GGTFSSYA | IIPIFGTA | ARSTVGWSYEF DY | QSISSY | AAS | QQSYSTP LT | QVQLVQSGAEVKKPGSSVKVSCKASG GTFSSYAISWVRQAPGQGLEWMGGII PIFGTANYAQKFQGRVTITADESTSTA YMELSSLRSEDTAVYYCARSTVGWSYE FDYWGQGTLVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | DIQMTQSPSSLSASVGDRVTITCRA SQSISSYLNWYQQKPGKAPKLLIYA ASSLQSGVPSRFSGSGSGTDFTLTIS SLQPEDFATYYCQQSYSTPLTFGQG TKVEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |
| VSTB99 | Human IgG1/kapp a | | GGTFSSYA | IIPIFGTA | ARHVLGWVLEL DY | QSISSY | AAS | QQSYSTP LT | QVQLVQSGAEVKKPGSSVKVSCKASG GTFSSYAISWVRQAPGQGLEWMGGII PIFGTANYAQKFQGRVTITADESTSTA YMELSSLRSEDTAVYYCARHVLGWVL ELDYWGQGTLVTVSS | ASTKGPSVFPLAPSSKSTSGGTAALGCLVKDYFPEP VTVSWNSGALTSGVHTFPAVLQSSGLYSLSSVVTV PSSSLGTQTYICNVNHKPSNTKVDKKVEPKSCDKT HTCPPCPAPELLGGPSVFLFPPKPKDTLMISRTPEV TCVVVDVSHEDPEVKFNWYVDGVEVHNAKTKPRE EQYNSTYRVVSVLTVLHQDWLNGKEYKCKVSNKA LPAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK | DIQMTQSPSSLSASVGDRVTITCRA SQSISSYLNWYQQKPGKAPKLLIYA ASSLQSGVPSRFSGSGSGTDFTLTIS SLQPEDFATYYCQQSYSTPLTFGQG TKVEIK | RTVAAPSVFIFPPSDEQLKS GTASVVCLLNNFYPREAKV QWKVDNALQSGNSQESV TEQDSKDSTYSLSSTLTLSK ADYEKHKVYACEVTHQGL SSPVTKSFNRGEC |

Effects Of Agonist Anti-Human VISTA Abs In A GVHD Animal Model.

Agonist VISTA Antibodies Suppress CD3 driven T cell response

FIGURE 9: Effects of VISTA Abs in ConA Assay and on Select Proinflammatory Cytokines and Markers

FIGURE 10
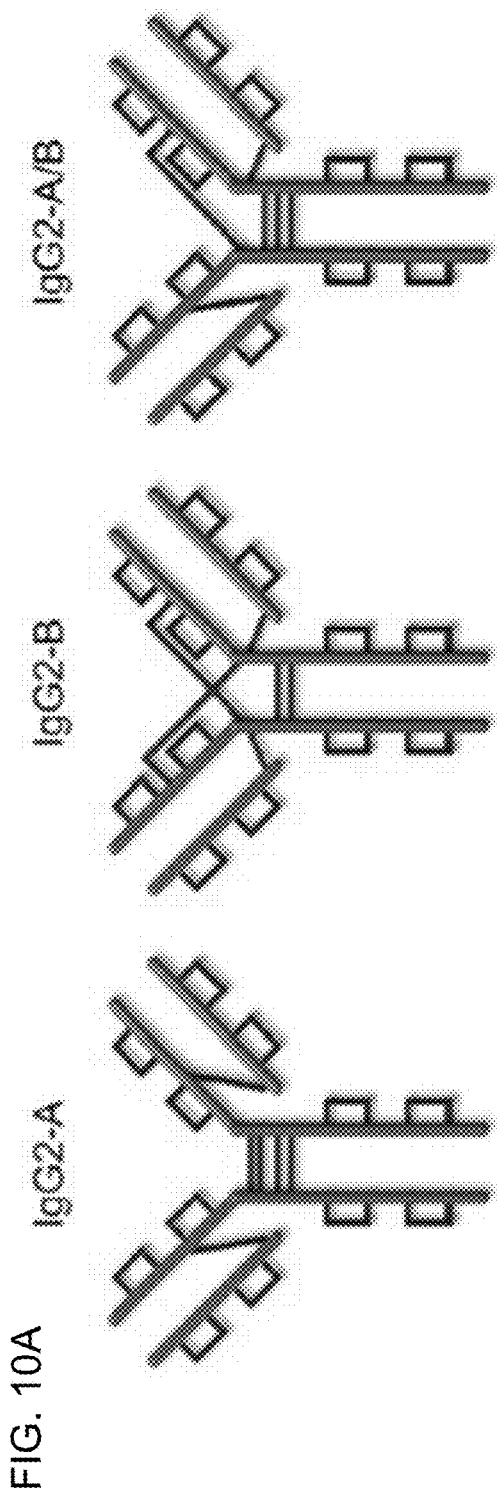
FIG. 10A
FIG. 10B
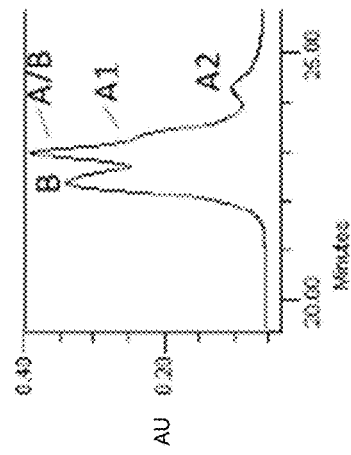
FIG. 10C
Figure 10: IgG2 Isoforms.

Figure 11: Chemical enrichment of IgG2 A or B isoforms.

Figure 12: Comparison of INX901 Fc-silent variants with respect to disulfide shuffling.

Figure 13. Biochemically skewed INX901 forms can still reduce cytokine production in the MLR.

Figure 14. Genetically locked INX901 forms can still reduce cytokine production in the MLR, but Fc silent variants cannot.

Figure 15. Genetically locked INX908 forms can still reduce cytokine production in the MLR, but Fc silent variants cannot Pepscan uses peptide arrays to determine both linear and discontinuous epitopes

FIG 17 All suppressive INX abs bind same core seq

HDX/Crystal Results (Above ECD Sequence)
Bold indicates crystal support

VSTB112/95 (INX903¹)          LLGPVDKGHDVTFY TWYRSSR  QTCSERR RQLTFQDLHLH                    TMR       LVVEIRHHSEHRVHGAMEL
VSTB50/60 (INX900²) HDX only
VISTA ECD
FNVATPYSLYVCVEGQNVTLTCRLLGPVDKGHHVTFYKTWYRSSR EVQTCSERR RQLTFQDLHLH LRKKGHGAANTSHDLAQRHGLESASDHHGNFSITMRNLTLLDSGLYCCLVVELRHHSEHRVHGAMELQVTGKDAPSNCVVYPSSSQESEHIT AA INX800¹     TCRLLGPVDKG                                              HGGHQAA     SASDHHGNFS                           HHHSEHRVHGAM

INX803¹     LTCRLLGPV                                                HLHHGGHQAA  SDHRGNFS                             HHHSEHRVHGAM
INX804²

INX900²     LLGPVDKGHDVTFYK              EVQTCSERRPIR                            LAQRHGLESASDHHG                      HHHSEHRVHGAM

INX901² INX904¹ INX907²   NVTLTCRLLGPV
INX902² INX906² INX908¹    (6/7/8)   EVQTCSERR**                             SDHRGNFS                             HHHSEH

INX903¹                                  EVQTCSERR   TPQDLHLHHGGHQAA                              CLVVEIRHHHEHH

INX905¹   TCRLLGPVDKG                    EVQTCSERR                SDHHG                                           HHHSEHRVHGAM

Green = Potent Agonist
Red = Stability Issues (not potent)
1/2 = Competitive Binding Bin Pepscan Results (Below ECD Sequence)
Bold indicates dominantly recognized core sequences
<u>Underlined</u> indicates strong linear epitope recognition
*Important residues

FIG 18: Epitope Mapping Summary

| | mGVHD | NSG | MLR | CAIA | Epitope EQVT? |
|---|---|---|---|---|---|
| INX800 | +/- | - | - | - | no |
| INX803 | + | | | | yes |
| INX804 | + | | | | yes |
| INX900 | - | | | | yes |
| INX901 | + | + | + | + | yes |
| INX902 | + | + | + | + | yes |
| INX903 | + | + | + | + | yes |
| INX904 | - | - | | | yes |
| INX905 | + | + | + | | yes |
| INX906 | + | + | + | + | yes |
| INX907 | | | | | yes |
| INX908 | + | + | + | + | yes |

FIG 19: VISTA Epitopes

HDX/Crystal Results
Bold indicates crystal support

```
VSTB112/95 (INX903¹)      LLGPVDKGHDVTFY   TWYRSR---QTCSERPIRQLTFQDLHLH                    TMR   LVYEIRHHSEHRVHGAMEL
VSTB50/60 (INX900²) HDX only                                                    NLTLLDSGL                             VQTGKDAPSMC VISTA ECD
     FKVATPYSLYVCPEGQNVTLTCRLLGPVDKGHDVTFYKTWYRSSRGEVQTCSERRPIRNLTFQDLHLHHGGHQAAKTSHDLAQRGLESASDHHGNFSIMPRNLTLLDSGLYCCLVYEIRHHSEHRVHGAMELQVQTGKDAPSNCVVYPSSSQESE INX800¹                TCRLLGPVDKG                           HGGRQAA         SASDHHGNFS                              HHHSEHRVHGAM INX803¹                LTCRLLGPV                             HLHHGGRQAA       SDHHGNFS                               HHHSEHRVHGAM
INX804²

INX900²                         LLGPVDKGHDVTFYK                              LAQRGLESASDHHG                           HHHSEHRVHGAM

INX901² INX904¹ INX907²  **(6/7/8)
INX902² INX906² INX908¹  EVQTCSERRPIR
                         NVTLTCRLLGPV                                         SDHHGNFS                                HHHSER

INX903¹                TCRLLGPVDKG          EVQTCSERR         TFQDLHLHHGGHQAA                                         CLVYEIRHHHSEH
                                            **
INX905¹                                    EVQTCSERRPIR                       SDHHG                                   HHHSEHRVHGAM
```

Green = Potent Agonist
Red = Stability Issues (not potent)
1/2 = Competitive Binding Bin

Pepscan Results
Bold indicates dominantly recognized core sequences
<u>Underlined</u> indicates strong linear epitope recognition
*Important residues

ANTI-HUMAN VISTA ANTIBODIES AND USE THEREOF

RELATED APPLICATIONS

This application claims priority to U.S. Provisional Application Nos. 62/323,193 filed Apr. 15, 2016, 62/343,355 filed May 31, 2016, 62/372,362 filed Aug. 9, 2016, 62/385,627 filed Sep. 9, 2016, 62/425,184 filed Nov. 22, 2016, 62/363,929 filed Jul. 19, 2016, 62/365,085 filed Jul. 21, 2016, 62/385,805 filed Sep. 9, 2016, 62/363,931 filed Jul. 19, 2016, 62/365,102 filed Jul. 21, 2016, 62/385,871 filed Sep. 9, 2016, 62/363,917 filed Jul. 19, 2016, 62/365,081 filed Jul. 21, 2016, 62/385,888 filed Sep. 9, 2016, 62/364,073 filed Jul. 19, 2016, 62/365,166 filed Jul. 21, 2016, 62/385,893 filed Sep. 9, 2016, 62/363,925 filed Jul. 19, 2016, 62/365,087 filed Jul. 21, 2016, 62/385,785 filed Sep. 9, 2016, 62/406,632 filed Oct. 11, 2016, each and all of which are incorporated herein by reference. This application relates to PCT application PCT/US17/27765 filed Apr. 14, 2017 "ANTI-HUMAN VISTA ANTIBODIES AND USE THEREOF" which is being incorporated by reference and to which priority is also claimed.

FIELD

The invention relates to the identification of novel anti-human VISTA antibodies and antibody fragments, i.e., anti-human VISTA (V-region Immunoglobulin-containing Suppressor of T cell Activation(1)), ("VISTA") antibodies and antibody fragments. More specifically, the present application provides novel human VISTA agonists, i.e., anti-human VISTA antibodies and antibody fragments which agonize or promote the suppressive effects of human VISTA on immunity, particularly T cell immunity. Also, the invention relates to the use of such agonists to enhance or mimic the suppressive effects of VISTA on immunity such as its suppressive effects on CD4+ or CD8+ T cell proliferation, CD4+ or CD8+ T cell activation and its suppressive effect on the production of immune cytokines, particularly proinflammatory cytokines. Also the invention relates to the specific use of these agonistic antibodies and antibody fragments as prophylactics or therapeutics, especially in treating conditions wherein the prevention or inhibition of T cell immunity and the expression of proinflammatory cytokines is therapeutically beneficial such as autoimmunity, inflammation, allergic disorders, sepsis, GVHD or in alleviating the inflammatory side effects of some conditions such as cancer.

The present application also provides novel antagonists, i.e., anti-human VISTA antibodies and antibody fragments which antagonize or inhibit the suppressive effects of human VISTA on immunity, particularly VISTA's effects on T cell immunity. Also, the invention relates to the use of such novel antagonists to block or inhibit the suppressive effects of VISA on immunity, i.e., its suppressive effects on CD4+ or CD8+ T cell proliferation, CD4+ or CD8+ T cell activation and the production of immune cytokines. Also the invention also relates to the specific use of these antagonistic antibodies and antibody fragments as prophylactics or therapeutics, especially in treating conditions wherein promoting T cell immunity is therapeutically beneficial such as in the treatment of cancer and infectious diseases.

SEQUENCE LISTING

This application includes as part of its disclosure a biological sequence listing text file named "4326002206.txt" having a size of 536,197 bytes that was created Jul. 3, 2017, which is incorporated by reference in its entirety.

BACKGROUND

Immune negative checkpoint regulator (NCR) pathways have proven to be extraordinary clinical targets in the treatment of human immune-related diseases. Blockade of two NCRs, CTLA-4 and PD-1, using monoclonal antibodies (mAbs) to enhance tumor immunity is revolutionizing the treatment of cancer and has established these pathways as clinically validated targets in human disease. Also soluble versions of NCR ligands that trigger NCR pathways have entered the clinic as immunosuppressive drugs to treat autoimmunity (i.e., AMP-110/B7-H4-Ig for Rheumatoid arthritis).

VISTA (see Ref 1), is an NCR ligand, whose closest phylogenetic relative is PD-L1. VISTA bears homology to PD-L1 but displays a unique expression pattern that is restricted to the hematopoietic compartment. Specifically, VISTA is constitutively and highly expressed on $CD11b^{high}$ myeloid cells, and expressed at lower levels on CD4+ and CD8+ T cells. Like PD-L1, VISTA is a ligand that profoundly suppresses immunity (Ref 1), and like PD-L1, blocking VISTA allows for the development of therapeutic immunity to cancer in pre-clinical oncology models (see Ref 2). Whereas blocking VISTA enhances immunity, especially CD8+ and CD4+ mediated T cell immunity, treatment with a soluble Ig fusion protein of the extracellular domain of VISTA (VISTA-Ig) suppresses immunity and has been shown to arrest the progression of multiple murine models of autoimmune disease.

Clear scientific evidence has shown that VISTA is a ligand that induces profound T cell suppression. Numerous antagonistic anti-human VISTA antibodies have been reported by different groups including Dartmouth College and Jannsen. These antibodies are useful in the treatment of conditions wherein the suppression of the immunosuppressive effects of VISTA on T cell immunity is desired such as cancer and infection. However, to the best of the inventors' knowledge no anti-human VISTA antibody or antibody fragment has been previously identified which agonizes the effects of human VISTA. Such agonistic anti-human VISTA antibodies and antibody fragments would be desirable in treating conditions wherein the suppression of immunity, particularly T cell immunity is desired and/or conditions wherein VISTA expression is aberrantly downregulated.

SUMMARY

It is an object of the invention to provide novel antibodies and antibody fragments which specifically bind to human VISTA and variants thereof, e.g., chimeric, human, humanized or multispecific anti-human VISTA antibodies which specifically bind to human VISTA and which promote or mimic the effects of human VISTA on immunity.

It is a specific object of the invention to provide agonistic antibody or antibody fragment thereof comprising an antigen binding region that specifically binds to human VISTA wherein the agonistic antibody or antibody fragment binds to the same or overlapping epitope as any one of the anti-human VISTA antibodies having the CDR and variable heavy and light polypeptides shown in FIG. 4.

It is a specific object of the invention to provide an isolated antibody or antibody fragment thereof comprising an antigen binding region that specifically binds to human V-domain Ig Suppressor of T cell Activation (human VISTA), wherein the antibody or antibody fragment agonizes or promotes one or more of the effects of VISTA on immunity, e.g., comprising a human IgG2 constant or human IgG2 Fc region optionally wherein the human IgG2 constant or Fc region binds to Fc gamma receptors including human CD32A and/or containing a human IgG2 constant or Fc region which comprises the native human IgG2 binding to Fc gamma receptors and/or an IgG2 which binds to FcγRs including one or more of hFcγRI(CD64), FcγRIIA or hFcγRIIB, (CD32 or CD32A) and FcγRIIIA (CD16A) or FcγRIIIB (CD16B).

It is a specific object of the invention to provide agonistic antibody or antibody fragment thereof comprising an antigen binding region that specifically binds to human VISTA wherein the agonistic antibody or antibody fragment binds to a VISTA epitope which includes or overlaps with the epitope bound by any of the anti-human VISTA antibodies having the sequences of FIG. 4.

It is a specific object of the invention to provide agonistic antibody or antibody fragment thereof comprising an antigen binding region that specifically binds to human VISTA wherein the agonistic antibody or antibody fragment binds or interacts with one of more residues of an epitope comprising residues of LLDSGLYCCLVVEIRHHSEHRVH.

It is a specific object of the invention to provide agonistic antibody or antibody fragment thereof comprising an antigen binding region that specifically binds to human VISTA wherein the agonistic antibody or antibody fragment binds or interacts with one of more residues of an epitope comprising one or more residues of 79EVQTCSERRPIR90, 48NVTLTCRLLGPV60, 153HHHSEHRVHGAM164, 52LTCRLLGPV60, 56LLGPVDKGHDVTFYK70, 113LAQRHGLESASDHHG127, 153HHHSEHRVHGAM164, 93TFQDLHLHHGGHQAA107, 146CLVVEIRHHSEH158, 53TCRLLGPVDKG63, 123SDHHG127 and/or 153HHHSEHRVHGAM164.

It is a specific object of the invention to provide agonistic antibody or antibody fragment thereof comprising an antigen binding region that specifically binds to human VISTA wherein the agonistic antibody or antibody fragment binds or interacts with one of more residues of an epitope comprising one or more residues of 79EVQTCSERRPIR90.

It is a specific object of the invention to provide agonistic antibody or antibody fragment thereof comprising an antigen binding region that specifically binds to human VISTA wherein the agonistic antibody or antibody fragment promotes or enhances at least one effect of human VISTA on immunity, e.g. its suppressive effect on any one or more of T cell immunity, activation of monocytes, induction of T-cell proliferation; induction or suppression of cytokine expression, increased survival of monocytes, induction of antibody-dependent cell-mediated cytotoxicity (ADCC) in cells-expressing VISTA; and induction of antibody-dependent cellular phagocytosis (ADCP) in cells-expressing VISTA.

It is a specific object of the invention to provide agonistic antibody or antibody fragment thereof comprising an antigen binding region that specifically binds to human VISTA wherein the agonistic antibody or antibody fragment comprising an antigen binding region that specifically binds to human VISTA, wherein the antibody or antibody fragment which comprises variable heavy and light sequences having the identical CDR polypeptides as any one of the anti-human VISTA antibodies having the CDR and variable heavy and light polypeptides shown in FIG. 4, with the proviso that if said antibody or fragment comprises an antagonist anti-human VISTA antibody or antibody fragment then the antibody or antibody fragment does not comprise the same CDRs as any one of VSTB112, VSTB116, VSTB95, VSTB50, VSTB53 or VSTB60.

It is a specific object of the invention to provide agonistic antibody or antibody fragment thereof comprising an antigen binding region that specifically binds to human VISTA wherein the agonistic antibody or antibody which comprises an antagonist anti-human VISTA antibody or fragment then the antibody or antibody fragment does not comprise the same CDRs as any one of VSTB112, VSTB116, VSTB95, VSTB50, VSTB53 or VSTB60.

It is a specific object of the invention to provide agonistic antibody or antibody fragment thereof comprising an antigen binding region that specifically binds to human VISTA wherein the agonistic antibody or antibody fragment comprises a variable heavy and/or variable light polypeptide having at least 90% sequence identity to those of an anti-human VISTA antibody selected from any one of VSTB49-VSTB116, wherein the variable heavy and light polypeptide sequences thereof are shown in FIG. 4, with the proviso that if said antibody or fragment comprises an antagonist anti-human VISTA antibody or fragment then the antibody or antibody fragment does not comprise the same CDRs as any one of VSTB112, VSTB116, VSTB95, VSTB50, VSTB53 or VSTB60.

It is a specific object of the invention to provide agonistic antibody or antibody fragment thereof comprising an antigen binding region that specifically binds to human VISTA wherein the agonistic antibody or antibody comprises an antigen binding region that specifically binds to human VISTA wherein the agonistic antibody or antibody fragment comprises a variable heavy and/or variable light polypeptide having at least 95% sequence identity to those of an anti-human VISTA antibody selected from any one of VSTB49-VSTB116, wherein the variable heavy and light polypeptide sequences thereof are shown in FIG. 4, with the proviso that if said antibody or fragment comprises an antagonist anti-human VISTA antibody or antibody fragment then the antibody or antibody fragment does not comprise the same CDRs as any one of VSTB112, VSTB116, VSTB95, VSTB50, VSTB53 or VSTB60.

It is a specific object of the invention to provide agonistic antibody or antibody fragment thereof comprising an antigen binding region that specifically binds to human VISTA wherein the agonistic antibody or antibody fragment comprises a variable heavy and/or variable light polypeptide having at least 96-99% sequence identity to those of an anti-human VISTA antibody selected from any one of VSTB49-VSTB116, wherein the variable heavy and light polypeptide sequences thereof are shown in FIG. 4, with the proviso that if said antibody or fragment comprises an antagonist anti-human VISTA antibody or antibody fragment then the antibody or antibody fragment does not comprise the same CDRs as any one of VSTB112, VSTB116, VSTB95, VSTB50, VSTB53 or VSTB60.

It is a specific object of the invention to provide agonistic antibody or antibody fragment thereof comprising an antigen binding region that specifically binds to human VISTA wherein the agonistic antibody or antibody fragment which comprises a variable heavy and/or variable light polypeptide identical to those of an anti-human VISTA antibody selected from one of VSTB49-VSTB116, wherein the variable heavy and light polypeptide sequences thereof are shown in FIG. 4, with the proviso that if said antibody or fragment comprises an antagonist anti-human VISTA antibody or antibody fragment then the antibody or antibody fragment does not comprise the same CDRs as any one of VSTB112, VSTB116, VSTB95, VSTB50, VSTB53 or VSTB60.

It is a specific object of the invention to provide an antagonistic antibody or antibody fragment thereof comprising an antigen binding region that specifically binds to human VISTA according to any of the foregoing which antagonizes or blocks at least one effect of human VISTA on immunity.

It is a specific object of the invention to provide an agonistic antibody or antibody fragment thereof comprising an antigen binding region that specifically binds to human VISTA according to any of the foregoing which agonizes or promotes at least one effect of human VISTA on immunity.

It is a specific object of the invention to provide an agonistic antibody or antibody fragment thereof comprising an antigen binding region that specifically binds to human VISTA according to any of the foregoing which comprises a human constant domain.

It is a specific object of the invention to provide agonistic antibody or antibody fragment thereof comprising an antigen binding region that specifically binds to human VISTA according to any of the foregoing which comprises a human constant domain selected from IgG1, IgG2, IgG3 and IgG4, which optionally is modified, e.g., by deletion, substitution or addition mutations or any combination of the foregoing.

It is a specific object of the invention to provide agonistic antibody or antibody fragment thereof comprising an antigen binding region that specifically binds to human VISTA according to any of the foregoing wherein the antibody fragment comprises or is a Fab, F(ab')2, or scFv antibody fragment.

It is a specific object of the invention to provide an antagonistic antibody or antibody fragment thereof comprising an antigen binding region that specifically binds to human VISTA according to any of the foregoing which blocks or suppresses at least one of the effects of human VISTA on immunity, e.g., selected from its suppressive effect on T cell immunity, activation of monocytes, or T-cell proliferation; induction or suppression of cytokine expression, increased survival of monocytes, suppression of antibody-dependent cell-mediated cytotoxicity (ADCC) of cells-expressing VISTA; and suppression of antibody-dependent cellular phagocytosis (ADCP) of cells-expressing VISTA.

It is a specific object of the invention to provide agonistic antibody or antibody fragment thereof comprising an antigen binding region that specifically binds to human VISTA according to any of the foregoing which promotes or enhances at least one of the effects of human VISTA on immunity, e.g., selected from its suppressive effect T cell immunity, activation of monocytes, suppression of T-cell proliferation; induction or suppression of cytokine expression, increased survival of monocytes, suppression of antibody-dependent cell-mediated cytotoxicity (ADCC) in cells-expressing VISTA; and suppression of antibody-dependent cellular phagocytosis (ADCP) of cells-expressing VISTA.

It is a specific object of the invention to provide agonistic antibody or antibody fragment thereof comprising an antigen binding region that specifically binds to human VISTA according to any of the foregoing which comprises a human IgG2 constant or Fc region.

It is a specific object of the invention to provide agonistic antibody or antibody fragment thereof comprising an antigen binding region that specifically binds to human VISTA according to any of the foregoing that promotes or enhances the suppressive effect of human VISTA on immunity, e.g. its effect on any one or more of T cell immunity, activation of monocytes, T-cell proliferation; cytokine expression, survival of monocytes, antibody-dependent cell-mediated cytotoxicity (ADCC) in cells-expressing VISTA; and antibody-dependent cellular phagocytosis (ADCP) in cells-expressing VISTA.

It is a specific object of the invention to provide an agonistic antibody or antibody fragment thereof comprising an antigen binding region that specifically binds to human VISTA according to any of the foregoing which inhibits T cell immunity and/or proinflammatory cytokine expression.

It is a specific object of the invention to provide an agonistic antibody or antibody fragment thereof comprising an antigen binding region that specifically binds to human VISTA according to any of the foregoing which is a human, humanized or chimeric antibody that comprises a human Fc region, e.g., human IgG1, IgG2, IgG3 and IgG4 or a chimera of any of the foregoing.

It is a specific object of the invention to provide an agonistic antibody or antibody fragment thereof comprising an antigen binding region that specifically binds to human VISTA according to any of the foregoing which is chimeric, human or humanized.

It is a specific object of the invention to provide agonistic antibody or antibody fragment thereof comprising an antigen binding region that specifically binds to human VISTA according to any of the foregoing which comprises a human IgG2 constant domain or Fc region which potentially may be mutated.

It is a specific object of the invention to provide an agonistic antibody or antibody fragment thereof comprising an antigen binding region that specifically binds to human VISTA according to any of the foregoing which comprises a human IgG2 constant domain or fragment thereof or an hIgG1, hIgG3, hIgG4, IgA, IgD, IgE, or IgM, wherein the entire or substantially the entire hinge and CH1 domains of said antibody and optionally the entire or substantially the entire light chain constant region have been replaced with the corresponding entire or substantially the entire light chain, and the hinge and CH1 domains ("H2 regions" or "H2 domains") of hIgG2.

It is a specific object of the invention to provide agonistic antibody or antibody fragment thereof comprising an antigen binding region that specifically binds to human VISTA according to any of the foregoing which (i) comprises an IgG2 Fc region wherein either or both of the heavy chain cysteine residue at position 127 and the light chain cysteine residue at position 214 (wherein numbering is according to Kabat) are deleted or changed to a different amino acid residue, resulting in an increase in the agonistic properties of the resultant modified antibody relative to an antibody wherein these residues are unchanged, (ii) the cysteine residue at position 214 in the H2 region of said antibody is mutated or substituted with another amino acid and/or one or more of the cysteine residues at positions 127, 232 or 233 of the heavy chain are deleted or substituted with another amino acid, (iii) it comprises a human IgG2 constant domain wherein at least one cysteine residue is deleted or changed to another amino acid, (iv) it competes with or binds to the same epitope on human VISTA as VSTB95 (variable heavy and light sequences shown in FIG. 4).

It is a specific object of the invention to provide agonistic antibody or antibody fragment thereof comprising an antigen binding region that specifically binds to human VISTA according to any of the foregoing which:
(i) comprises the $V_H$ CDRs of SEQ ID NO:100, 101 and 102 and the $V_L$ CDRs of SEQ ID NO:103, 104 and 105;

(ii) comprises the $V_H$ CDRs of SEQ ID NO:110, 111 and 112 and the $V_L$ CDRs of SEQ ID NO:113, 114 and 115;
(iii) comprises the $V_H$ CDRs of SEQ ID NO:120, 121 and 122 and the VL CDRs of SEQ ID NO:123, 124 and 125;
(iv) comprises the $V_H$ CDRs of SEQ ID NO:130, 131 and 132 and the $V_L$ CDRs of SEQ ID NO:133, 134 and 135;
(v) comprises the $V_H$ CDRs of SEQ ID NO:140, 141 and 142 and the $V_L$ CDRs of SEQ ID NO:143, 144 and 145;
(vi) comprises the $V_H$ CDRs of SEQ ID NO:150, 151 and 152 and the VL CDRs of SEQ ID NO:153, 154 and 155;
(vii) comprises the $V_H$ CDRs of SEQ ID NO:160, 161 and 162 and the VL CDRs of SEQ ID NO:163, 164 and 165;
(viii) comprises the $V_H$ CDRs of SEQ ID NO:170, 171 and 172 and the VL CDRs of SEQ ID NO:173, 174 and 175;
(ix) comprises the $V_H$ CDRs of SEQ ID NO:180, 181 and 182 and the $V_L$ CDRs of SEQ ID NO:183, 184 and 185;
(x) comprises the $V_H$ CDRs of SEQ ID NO:190, 191 and 192 and the $V_L$ CDRs of SEQ ID NO:193, 194 and 195;
(xi) comprises the $V_H$ CDRs of SEQ ID NO:200, 201 and 202 and the $V_L$ CDRs of SEQ ID NO:203, 204 and 205;
(xii) comprises the $V_H$ CDRs of SEQ ID NO:210, 211 and 212 and the $V_L$ CDRs of SEQ ID NO:213, 214 and 215;
(xiii) comprises the $V_H$ CDRs of SEQ ID NO:220, 221 and 222 and the $V_L$ CDRs of SEQ ID NO:223, 224 and 225;
(xiv) comprises the $V_H$ CDRs of SEQ ID NO:230, 231 and 232 and the $V_L$ CDRs of SEQ ID NO:233, 234 and 235;
(xv) comprises the $V_H$ CDRs of SEQ ID NO:240, 241 and 242 and the $V_L$ CDRs of SEQ ID NO:243, 244 and 245;
(xvi) comprises the $V_H$ CDRs of SEQ ID NO:250, 251 and 252 and the $V_L$ CDRs of SEQ ID NO:253, 254 and 255;
(xvii) comprises the $V_H$ CDRs of SEQ ID NO:260, 261 and 262 and the $V_L$ CDRs of SEQ ID NO:263, 264 and 265;
(xviii) comprises the $V_H$ CDRs of SEQ ID NO:270, 271 and 272 and the $V_L$ CDRs of SEQ ID NO:273, 274 and 275;
(xix) comprises the $V_H$ CDRs of SEQ ID NO:280, 281 and 282 and the $V_L$ CDRs of SEQ ID NO:283, 284 and 285;
(xx) comprises the $V_H$ CDRs of SEQ ID NO:290, 291 and 292 and the $V_L$ CDRs of SEQ ID NO:293, 294 and 295;
(xxi) comprises the $V_H$ CDRs of SEQ ID NO:300, 301 and 302 and the $V_L$ CDRs of SEQ ID NO:303, 304 and 305;
(xxii) comprises the $V_H$ CDRs of SEQ ID NO:310, 311 and 312 and the $V_L$ CDRs of SEQ ID NO:313, 314 and 315;
(xxiii) comprises the $V_H$ CDRs of SEQ ID NO:320, 321 and 322 and the $V_L$ CDRs of SEQ ID NO:323, 324 and 325;
(xxiv) comprises the $V_H$ CDRs of SEQ ID NO:330, 331 and 332 and the $V_L$ CDRs of SEQ ID NO:333, 334 and 335;
(xxv) comprises the $V_H$ CDRs of SEQ ID NO:340, 341 and 342 and the $V_L$ CDRs of SEQ ID NO:343, 344 and 345;
(xxvi) comprises the $V_H$ CDRs of SEQ ID NO:350, 351 and 352 and the $V_L$ CDRs of SEQ ID NO:353, 354 and 355;
(xxvii) comprises the $V_H$ CDRs of SEQ ID NO:360, 361 and 362 and the $V_L$ CDRs of SEQ ID NO:363, 364 and 365;
(xxviii) comprises the $V_H$ CDRs of SEQ ID NO:370, 371 and 372 and the $V_L$ CDRs of SEQ ID NO:373, 374 and 375;
(xxix) comprises the $V_H$ CDRs of SEQ ID NO:380, 381 and 382 and the $V_L$ CDRs of SEQ ID NO:383, 384 and 385;
(xxx) comprises the $V_H$ CDRs of SEQ ID NO:390, 391 and 392 and the $V_L$ CDRs of SEQ ID NO:393, 394 and 395;
(xxxi) comprises the $V_H$ CDRs of SEQ ID NO:400, 401 and 402 and the $V_L$ CDRs of SEQ ID NO:403, 404 and 405;
(xxxii) comprises the $V_H$ CDRs of SEQ ID NO:410, 411 and 412 and the $V_L$ CDRs of SEQ ID NO:413, 414 and 415;
(xxxiii) comprises the $V_H$ CDRs of SEQ ID NO:420, 421 and 422 and the $V_L$ CDRs of SEQ ID NO:423, 424 and 425;
(xxxiv) comprises the $V_H$ CDRs of SEQ ID NO:430, 431 and 432 and the $V_L$ CDRs of SEQ ID NO:433, 434 and 435;
(xxxv) comprises the $V_H$ CDRs of SEQ ID NO:440, 441 and 442 and the $V_L$ CDRs of SEQ ID NO:443, 444 and 445;
(xxxvi) comprises the $V_H$ CDRs of SEQ ID NO:450, 451 and 452 and the $V_L$ CDRs of SEQ ID NO:453, 454 and 455;
(xxxvii) comprises the $V_H$ CDRs of SEQ ID NO:460, 461 and 462 and the $V_L$ CDRs of SEQ ID NO:463, 464 and 465;
(xxxviii) comprises the $V_H$ CDRs of SEQ ID NO:470, 471 and 472 and the $V_L$ CDRs of SEQ ID NO:473, 474 and 475;
(xxxix) comprises the $V_H$ CDRs of SEQ ID NO:480, 481 and 482 and the $V_L$ CDRs of SEQ ID NO:483, 484 and 485;
(xl) comprises the $V_H$ CDRs of SEQ ID NO:490, 491 and 492 and the VL CDR polypeptides of SEQ ID NO:493, 494 and 495;
(xli) comprises the $V_H$ CDRs of SEQ ID NO:500, 501 and 502 and the VL CDR polypeptides of SEQ ID NO:503, 504 and 505;
(xlii) comprises the $V_H$ CDRs of SEQ ID NO:510, 511 and 512 and the VL CDR polypeptides of SEQ ID NO:513, 514 and 515;
(xliii) comprises the $V_H$ CDRs of SEQ ID NO:520, 521 and 522 and the VL CDR polypeptides of SEQ ID NO:523, 524 and 525;
(xliv) comprises the $V_H$ CDRs of SEQ ID NO:530, 531 and 532 and the VL CDR polypeptides of SEQ ID NO:533, 534 and 535;
(xlv) comprises the $V_H$ CDRs of SEQ ID NO:540, 541 and 542 and the VL CDR polypeptides of SEQ ID NO:543, 544 and 545;
(xlvi) comprises the $V_H$ CDRs of SEQ ID NO:550, 551 and 552 and the VL CDR polypeptides of SEQ ID NO:553, 554 and 555;
(xlvii) comprises the $V_H$ CDRs of SEQ ID NO:560, 561 and 562 and the $V_L$ CDRs of SEQ ID NO:563, 564 and 565;
(xlviii) comprises the $V_H$ CDRs of SEQ ID NO:570, 571 and 572 and the $V_L$ CDRs of SEQ ID NO:573, 574 and 575;

(xlix) comprises the V<sub>H</sub> CDRs of SEQ ID NO:580, 581 and 582 and the V<sub>L</sub> CDRs of SEQ ID NO:583, 584 and 585;
(l) comprises the V<sub>H</sub> CDRs of SEQ ID NO:590, 591 and 592 and the V<sub>L</sub> CDRs of SEQ ID NO:593, 594 and 595;
(li) comprises the V<sub>H</sub> CDRs of SEQ ID NO:600, 601 and 602 and the V<sub>L</sub> CDRs of SEQ ID NO:603, 604 and 605;
(lii) comprises the V<sub>H</sub> CDRs of SEQ ID NO:610, 611 and 612 and the V<sub>L</sub> CDRs of SEQ ID NO:613, 614 and 615;
(liii) comprises the V<sub>H</sub> CDRs of SEQ ID NO:620, 621 and 622 and the V<sub>L</sub> CDRs of SEQ ID NO:623, 624 and 625;
(liv) comprises the V<sub>H</sub> CDRs of SEQ ID NO:630, 631 and 632 and the V<sub>L</sub> CDRs of SEQ ID NO:633, 634 and 635;
(lv) comprises the V<sub>H</sub> CDRs of SEQ ID NO:640, 641 and 642 and the V<sub>L</sub> CDRs of SEQ ID NO:643, 644 and 645;
(lvi) comprises the V<sub>H</sub> CDRs of SEQ ID NO:650, 651 and 652 and the V<sub>L</sub> CDRs of SEQ ID NO:653, 654 and 655;
(lvii) comprises the V<sub>H</sub> CDRs of SEQ ID NO:660, 661 and 662 and the V<sub>L</sub> CDRs of SEQ ID NO:663, 664 and 665;
(lviii) comprises the V<sub>H</sub> CDRs of SEQ ID NO:670, 671 and 672 and the V<sub>L</sub> CDRs of SEQ ID NO:673, 674 and 675;
(lix) comprises the V<sub>H</sub> CDRs of SEQ ID NO:680, 681 and 682 and the V<sub>L</sub> CDRs of SEQ ID NO:683, 684 and 685;
(lx) comprises the V<sub>H</sub> CDRs of SEQ ID NO:690, 691 and 692 and the V<sub>L</sub> CDRs of SEQ ID NO:693, 694 and 695;
(lxi) comprises the V<sub>H</sub> CDRs of SEQ ID NO:700, 701 and 702 and the V<sub>L</sub> CDRs of SEQ ID NO:703, 704 and 705;
(lxii) comprises the V<sub>H</sub> CDRs of SEQ ID NO:710, 711 and 712 and the V<sub>L</sub> CDRs of SEQ ID NO:713, 714 and 715;
(lxiii) comprises the V<sub>H</sub> CDRs of SEQ ID NO:720, 721 and 722 and the V<sub>L</sub> CDRs of SEQ ID NO:723, 724 and 725;
(lxiv) comprises the V<sub>H</sub> CDRs of SEQ ID NO:730, 731 and 732 and the V<sub>L</sub> CDRs of SEQ ID NO:733, 734 and 735;
(lxv) comprises the V<sub>H</sub> CDRs of SEQ ID NO:740, 741 and 742 and the V<sub>L</sub> CDRs of SEQ ID NO:743, 744 and 745;
(lxvi) comprises the V<sub>H</sub> CDRs of SEQ ID NO:750, 751 and 752 and the V<sub>L</sub> CDRs of SEQ ID NO:753, 754 and 755;
(lxvii) comprises the V<sub>H</sub> CDRs of SEQ ID NO:760, 761 and 762 and the V<sub>L</sub> CDRs of SEQ ID NO:763, 764 and 765;
(lxviii) comprises the V<sub>H</sub> CDRs of SEQ ID NO:770, 771 and 772 and the V<sub>L</sub> CDRs of SEQ ID NO:773, 774 and 775;
(lxix) comprises the V<sub>H</sub> CDRs of SEQ ID NO:780, 781 and 782 and the V<sub>L</sub> CDRs of SEQ ID NO:783, 784 and 785;
(lxx) comprises the V<sub>H</sub> CDRs of SEQ ID NO:790, 791 and 792 and the V<sub>L</sub> CDRs of SEQ ID NO:793, 794 and 795;
(lxxi) comprises the V<sub>H</sub> CDRs of SEQ ID NO:800, 801 and 802 and the V<sub>L</sub> CDRs of SEQ ID NO:803, 804 and 805;
(lxxii) comprises the V<sub>H</sub> CDRs of SEQ ID NO:810, 811 and 812 and the V<sub>L</sub> CDRs of SEQ ID NO: 813, 814 and 815.

It is an object of the invention to provide a VISTA agonist according to any of the foregoing which:
(i) comprises the V<sub>H</sub> polypeptide of SEQ ID NO:106 and the V<sub>L</sub> polypeptide of SEQ ID NO:108;
(ii) comprises the V<sub>H</sub> polypeptide of SEQ ID NO:116 and the V<sub>L</sub> polypeptide of SEQ ID NO:118;
(iii) comprises the V<sub>H</sub> polypeptide of SEQ ID NO:126 and the V<sub>L</sub> polypeptide of SEQ ID NO:128;
(iv) comprises the V<sub>H</sub> polypeptide of SEQ ID NO:136 and the V<sub>L</sub> polypeptide f SEQ ID NO:138;
(v) comprises the V<sub>H</sub> polypeptide of SEQ ID NO:146 and the V<sub>L</sub> polypeptide of SEQ ID NO:148;
(vi) comprises the V<sub>H</sub> polypeptide of SEQ ID NO:156 and the V<sub>L</sub> polypeptide of SEQ ID NO:158;
(vii) comprises the V<sub>H</sub> polypeptide of SEQ ID NO:166 and the V<sub>L</sub> polypeptide of SEQ ID NO:168;
(viii) comprises the V<sub>H</sub> polypeptide of SEQ ID NO:176 and the V<sub>L</sub> polypeptide of SEQ ID NO:178;
(ix) comprises the V<sub>H</sub> polypeptide of SEQ ID NO:186 and the V<sub>L</sub> polypeptide of SEQ ID NO:188;
(x) comprises the V<sub>H</sub> polypeptide of SEQ ID NO:196 and the V<sub>L</sub> polypeptide of SEQ ID NO:198;
(xi) comprises the V<sub>H</sub> polypeptide of SEQ ID NO:206 and the V<sub>L</sub> polypeptide of SEQ ID NO:208;
(xii) comprises the V<sub>H</sub> polypeptide of SEQ ID NO:216 and the V<sub>L</sub> polypeptide of SEQ ID NO:218;
(xiii) comprises the V<sub>H</sub> polypeptide of SEQ ID NO:226 and the V<sub>L</sub> polypeptide of SEQ ID NO:228;
(xiv) comprises the V<sub>H</sub> polypeptide of SEQ ID NO:236 and the V<sub>L</sub> polypeptide of SEQ ID NO:238;
(xv) comprises the V<sub>H</sub> polypeptide of SEQ ID NO:246 and the V<sub>L</sub> polypeptide of SEQ ID NO:248;
(xvi) comprises the V<sub>H</sub> polypeptide of SEQ ID NO:256 and the V<sub>L</sub> polypeptide of SEQ ID NO:258;
(xvii) comprises the V<sub>H</sub> polypeptide of SEQ ID NO:266 and the V<sub>L</sub> polypeptide of SEQ ID NO:268;
(xviii) comprises the V<sub>H</sub> polypeptide of SEQ ID NO:276 and the VL polypeptide of SEQ ID NO:278;
(xix) comprises the V<sub>H</sub> polypeptide of SEQ ID NO:286 and the V<sub>L</sub> polypeptide of SEQ ID NO:288;
(xx) comprises the V<sub>H</sub> polypeptide of SEQ ID NO:296 and the V<sub>L</sub> polypeptide of SEQ ID NO:298;
(xxi) comprises the V<sub>H</sub> polypeptide of SEQ ID NO:306 and the V<sub>L</sub> polypeptide of SEQ ID NO:308;
(xxii) comprises the V<sub>H</sub> polypeptide of SEQ ID NO:316 and the V<sub>L</sub> polypeptide of SEQ ID NO:318;
(xxiii) comprises the V<sub>H</sub> polypeptide of SEQ ID NO:326 and the V<sub>L</sub> polypeptide of SEQ ID NO:328;
(xxiv) comprises the V<sub>H</sub> polypeptide of SEQ ID NO:336 and the V<sub>L</sub> polypeptide of SEQ ID NO:338;
(xxv) comprises the V<sub>H</sub> polypeptide of SEQ ID NO:346 and the V<sub>L</sub> polypeptide of SEQ ID NO:348;
(xxvi) comprises the V<sub>H</sub> polypeptide of SEQ ID NO:356 and the V<sub>L</sub> polypeptide of SEQ ID NO:358;
(xxvii) comprises the V<sub>H</sub> polypeptide of SEQ ID NO:366 and the V<sub>L</sub> polypeptide of SEQ ID NO:368;
(xxviii) comprises the V<sub>H</sub> polypeptide of SEQ ID NO:376 and the V<sub>L</sub> polypeptide of SEQ ID NO:378;
(xxix) comprises the V<sub>H</sub> polypeptide of SEQ ID NO:386 and the V<sub>L</sub> polypeptide of SEQ ID NO:388;
(xxx) comprises the V<sub>H</sub> polypeptide of SEQ ID NO:396 and the V<sub>L</sub> polypeptide of SEQ ID NO:398;
(xxxi) comprises the V<sub>H</sub> polypeptide of SEQ ID NO:406 and the V<sub>L</sub> polypeptide of SEQ ID NO:408;
(xxxii) comprises the V<sub>H</sub> polypeptide of SEQ ID NO:416 and the V<sub>L</sub> polypeptide of SEQ ID NO:418;
(xxxiii) comprises the V<sub>H</sub> polypeptide of SEQ ID NO:426 and the V<sub>L</sub> polypeptide of SEQ ID NO:428;
(xxxiv) comprises the V<sub>H</sub> polypeptide of SEQ ID NO:436 and the V<sub>L</sub> polypeptide of SEQ ID NO:438;

(xxxv) comprises the V$_H$ polypeptide of SEQ ID NO:446 and the V$_L$ polypeptide of SEQ ID NO:448;
(xxxvi) comprises the V$_H$ polypeptide of SEQ ID NO:456 and the V$_L$ polypeptide of SEQ ID NO:458;
(xxxvii) comprises the V$_H$ polypeptide of SEQ ID NO:466 and the V$_L$ polypeptide of SEQ ID NO:468;
(xxxviii) comprises the V$_H$ polypeptide of SEQ ID NO:476 and the V$_L$ polypeptide of SEQ ID NO:478;
(xxxix) comprises the V$_H$ polypeptide of SEQ ID NO:486 and the V$_L$ polypeptide of SEQ ID NO:488;
(xl) comprises the V$_H$ polypeptide of SEQ ID NO:496 and the V$_L$ polypeptide of SEQ ID NO:498;
(xli) comprises the V$_H$ polypeptide of SEQ ID NO:506 and the V$_L$ polypeptide of SEQ ID NO:508;
(xlii) comprises the V$_H$ polypeptide of SEQ ID NO:516 and the V$_L$ polypeptide of SEQ ID NO:518;
(xliii) comprises the V$_H$ polypeptide of SEQ ID NO:526 and the V$_L$ polypeptide of SEQ ID NO:528;
(xliv) comprises the V$_H$ polypeptide of SEQ ID NO:536 and the V$_L$ polypeptide of SEQ ID NO:533, 534 and 535;
(xlv) comprises the V$_H$ polypeptide of SEQ ID NO:546 and the V$_L$ polypeptide of SEQ ID NO:548;
(xlvi) comprises the V$_H$ polypeptide of SEQ ID NO:556 and the V$_L$ polypeptide of SEQ ID NO:558;
(xlvii) comprises the V$_H$ polypeptide of SEQ ID NO:566 and the V$_L$ polypeptide of SEQ ID NO:568;
(xlviii) comprises the V$_H$ polypeptide of SEQ ID NO:576 and the V$_L$ polypeptide of SEQ ID NO:578;
(xlix) comprises the V$_H$ polypeptide of SEQ ID NO:586 and the V$_L$ polypeptide of SEQ ID NO:588;
(l) comprises the V$_H$ polypeptide of SEQ ID NO:596 and the V$_L$ polypeptide of SEQ ID NO:598;
(li) comprises the V$_H$ polypeptide of SEQ ID NO:606 and the V$_L$ polypeptide of SEQ ID NO:608;
(lii) comprises the V$_H$ polypeptide of SEQ ID NO:616 and the V$_L$ polypeptide of SEQ ID NO:618;
(liii) comprises the V$_H$ polypeptide of SEQ ID NO:626 and the V$_L$ polypeptide of SEQ ID NO:628;
(liv) comprises the V$_H$ polypeptide of SEQ ID NO:636 and the V$_L$ polypeptide of SEQ ID NO:638;
(lv) comprises the V$_H$ polypeptide of SEQ ID NO:646 and the V$_L$ polypeptide of SEQ ID NO:648;
(lvi) comprises the V$_H$ polypeptide of SEQ ID NO:656 and the V$_L$ polypeptide of SEQ ID NO:658;
(lvii) comprises the V$_H$ polypeptide of SEQ ID NO:666 and the V$_L$ polypeptide of SEQ ID NO:668;
(lviii) comprises the V$_H$ polypeptide of SEQ ID NO:676 and the V$_L$ polypeptide of SEQ ID NO:678;
(lix) comprises the V$_H$ polypeptide of SEQ ID NO:686 and the V$_L$ polypeptide of SEQ ID NO:688;
(lx) comprises the V$_H$ polypeptide of SEQ ID NO:696 and the V$_L$ polypeptide of SEQ ID NO:698;
(lxi) comprises the V$_H$ polypeptide of SEQ ID NO:706 and the V$_L$ polypeptide of SEQ ID NO:708;
(lxii) comprises the V$_H$ polypeptide of SEQ ID NO:716 and the V$_L$ polypeptide of SEQ ID NO:718;
(lxiii) comprises the V$_H$ polypeptide of SEQ ID NO:726 and the V$_L$ polypeptide of SEQ ID NO:728;
(lxiv) comprises the V$_H$ polypeptide of SEQ ID NO:736 and the V$_L$ polypeptide of SEQ ID NO:738;
(lxv) comprises the V$_H$ polypeptide of SEQ ID NO:746 and the V$_L$ polypeptide of SEQ ID NO:748;
(lxvi) comprises the V$_H$ polypeptide of SEQ ID NO:756 and the V$_L$ polypeptide of SEQ ID NO:758;
(lxvii) comprises the V$_H$ polypeptide of SEQ ID NO:766 and the V$_L$ polypeptide of SEQ ID NO:768;
(lxviii) comprises the V$_H$ polypeptide of SEQ ID NO:776 and the V$_L$ polypeptide of SEQ ID NO:778;
(lxix) comprises the V$_H$ polypeptide of SEQ ID NO:786 and the V$_L$ polypeptide of SEQ ID NO:788;
(lxx) comprises the V$_H$ polypeptide of SEQ ID NO:796 and the V$_L$ polypeptide of SEQ ID NO:798;
(lxxi) comprises the V$_H$ polypeptide of SEQ ID NO:806 and the V$_L$ polypeptide of SEQ ID NO:808; and
(lxxii) comprises the V$_H$ polypeptide of SEQ ID NO:816 and the V$_L$ polypeptide of SEQ ID NO: 818.

It is a specific object of the invention to provide an agonistic antibody or antibody fragment thereof comprising an antigen binding region that specifically binds to human VISTA according to any of the foregoing which comprises a human IgG2 constant domain wherein optionally at least one cysteine residue is deleted or changed to another amino acid.

It is a specific object of the invention to provide an agonistic antibody or antibody fragment thereof comprising an antigen binding region that specifically binds to human VISTA according to any of the foregoing which mediates any one or combination of at least one of the following immmunoinhibitory effects: (i) decreases immune response, (ii) decreases T cell activation, (iii) decreases cytotoxic T cell activity, (iv) decreases natural killer (NK) cell activity, (v) decreases T-cell activity, (vi) decreases pro-inflammatory cytokine secretion, (vii) decreases IL-2 secretion; (viii) decreases interferon-γ production, (ix) decreases Th1 response, (x) decreases Th2 response, (xi) increases cell number and/or activity of regulatory T cells, (xii) increases regulatory cell activity and/or one or more of myeloid derived suppressor cells (MDSCs), iMCs, mesenchymal stromal cells, TIE2-expressing monocytes, (xiii) increases regulatory cell activity and/or the activity of one or more of myeloid derived suppressor cells (MDSCs), iMCs, mesenchymal stromal cells, TIE2-expressing monocytes, (xiii) increases M2 macrophages, (xiv) increases M2 macrophage activity, (xv) increases N2 neutrophils, (xvi) increases N2 neutrophils activity, (xvii) increases inhibition of T cell activation, (xviii) increases inhibition of CTL activation, (xix) increases inhibition of NK cell activation, (xx) increases T cell exhaustion, (xxi) decreases T cell response, (xxii) decreases activity of cytotoxic cells, (xxiii) reduces antigen-specific memory responses, (xxiv) inhibits apoptosis or lysis of cells, (xxv) decreases cytotoxic or cytostatic effect on cells, (xxvi) reduces direct killing of cells, (xxvii) decreases Th17 activity, and/or (xxviii) reduces complement dependent cytotoxicity and/or antibody dependent cell-mediated cytotoxicity, with the proviso that said anti-VISTA antibody or antigen-binding fragment may elicit an opposite effect to one or more of (i)-(xxviii) and optionally is used to treat autoimmunity, allergy, inflammation, transplant or sepsis.

It is a specific object of the invention to provide a pharmaceutical or diagnostic composition comprising an agonistic antibody or antibody fragment thereof comprising an antigen binding region that specifically binds to human VISTA according to any of the foregoing.

It is a specific object of the invention to provide a method of treatment and/or diagnosis, or use of a composition containing at least one antagonistic antibody or antibody fragment according to any of the foregoing claims for diagnostic or therapeutic use, which method or use comprises the administration to a subject in need thereof at least one dosage or composition comprising a therapeutically or diagnostically effective amount of at least one at least one antagonistic antibody or antibody fragment according to any of the foregoing, e.g., cancer or an infectious disorder, optionally wherein the cancer is a blood cancer or solid tumor, e.g., one surrounded by a tumor stroma comprising myeloid cells, T-cells, or a combination of myeloid cells and T-cells or a cancer selected from leukemia, lymphoma, myelodysplastic syndrome or myeloma, lung cancer or a combination thereof or a leukemia which comprises acute lymphoblastic leukemia (ALL), chronic lymphocytic leukemia (CLL), acute myeloid (myelogenous) leukemia (AML), chronic myelogenous leukemia (CML); hairy cell leukemia, T-cell prolymphocytic leukemia, large granular lymphocytic leukemia, or adult T-cell leukemia.

It is a specific object of the invention to provide a method of treatment and/or diagnosis, or use of a composition containing at least one agonistic antibody or antibody fragment according to any of the foregoing claims for diagnostic or therapeutic use, which method or use comprises the administration to a subject in need thereof at least one dosage or composition comprising a therapeutically or diagnostically effective amount of at least one at least one agonistic antibody or antibody fragment according to any of the foregoing or composition containing according to any of the foregoing.

It is a specific object of the invention to provide a method or use of any agonistic antibody or antibody fragment according to any of the foregoing for effecting in vitro and/or in vivo any one or combination of at least one of the following immmunoinhibitory effects: (i) decreases immune response, (ii) decreases T cell activation, (iii) decreases cytotoxic T cell activity, (iv) decreases natural killer (NK) cell activity, (v) decreases T-cell activity, (vi) decreases pro-inflammatory cytokine secretion, (vii) decreases IL-2 secretion; (viii) decreases interferon-γ production, (ix) decreases Th1 response, (x) decreases Th2 response, (xi) increases cell number and/or activity of regulatory T cells, (xii) increases regulatory cell activity and/or one or more of myeloid derived suppressor cells (MDSCs), iMCs, mesenchymal stromal cells, TIE2-expressing monocytes, (xiii) increases regulatory cell activity and/or the activity of one or more of myeloid derived suppressor cells (MDSCs), iMCs, mesenchymal stromal cells, TIE2-expressing monocytes, (xiii) increases M2 macrophages, (xiv) increases M2 macrophage activity, (xv) increases N2 neutrophils, (xvi) increases N2 neutrophils activity, (xvii) increases inhibition of T cell activation, (xviii) increases inhibition of CTL activation, (xix) increases inhibition of NK cell activation, (xx) increases T cell exhaustion, (xxi) decreases T cell response, (xxii) decreases activity of cytotoxic cells, (xxiii) reduces antigen-specific memory responses, (xxiv) inhibits apoptosis or lysis of cells, (xxv) decreases cytotoxic or cytostatic effect on cells, (xxvi) reduces direct killing of cells, (xxvii) decreases Th17 activity, and/or (xxviii) reduces complement dependent cytotoxicity and/or antibody dependent cell-mediated cytotoxicity, with the proviso that said anti-VISTA antibody or antigen-binding fragment may elicit an opposite effect to one or more of (i)-(xxviii) and optionally is used to treat autoimmunity, allergy, inflammation, transplant or sepsis.

It is a specific object of the invention to provide a method or use of any agonistic antibody or antibody fragment according to any of the foregoing for use in the treatment or prevention of allergy, autoimmunity, transplant, gene therapy, inflammation, cancer, GVHD or sepsis, or to treat or prevent inflammatory, autoimmune, or allergic side effects associated with any of the foregoing therewith in a human subject.

An anti-VISTA antibody or antigen-binding fragment or composition, or method or use according to any of the foregoing, further comprising another immunomodulatory antibody or fusion protein which is selected from immmunoinhibitory antibodies or fusion proteins targeting one or more of CTLA4, PD-1, PDL-1, LAG-3, TIM-3, BTLA, B7-H4, B7-H3, VISTA, and/or agonistic antibodies or fusion protein targeting one or more of CD40, CD137, OX40, GITR, CD27, CD28 or ICOS.

A method or use of any of the foregoing which includes assaying VISTA protein by the individual's cells or in bodily fluids prior, concurrent and/or after treatment.

A method or use of any of the foregoing which includes assaying VISTA levels on hematopoietic cells.

A method or use of any of the foregoing which includes assaying VISTA levels on hematopoietic cells selected from any one or more of myeloid lineage cells and/or a lymphocytes, monocyte or a neutrophils, T cells, B cells, a natural killer (NK) cells or a natural killer T (NKT) cells.

A method or use of any of the foregoing wherein the agonist anti-human VISTA antibody or fragment comprises the same CDRs as an antibody selected from VSTB49-VSTB116 and a human IgG2 Fc region which optionally may be mutated or wherein the IgG2 constant or Fc region retains native FcR binding and/or the ability to bind CD32A.

The antibody, composition, method or use of any of the foregoing wherein the anti-human VISTA antibody or fragment comprises an affinity or KD for human VISTA which is 50M or less as determined by surface plasmon resonance at 37° C.

The antibody, composition, method or use of any of the foregoing wherein the anti-human VISTA antibody or fragment comprises an affinity or KD for human VISTA which is 1 nM or less as determined by surface plasmon resonance at 37° C.

It is a specific object of the invention to provide isolated antagonistic and agonistic anti-human VISTA antibodies and agonistic antibody fragments comprising an antigen binding region that specifically binds to human VISTA wherein the antibodies or antibody fragments comprise variable heavy and light sequences having the CDR polypeptides of any one of the anti-human VISTA antibodies having the sequences shown in FIG. 4, with the proviso that if said antibody or fragment comprises an antagonist anti-human VISTA antibody or antibody fragment then the antibody or antibody fragment does not comprise the same CDRs as any one of VSTB112, VSTB116, VSTB95, VSTB50, VSTB53 or VSTB60.

It is a specific object of the invention to provide isolated antagonistic and agonistic anti-human VISTA antibodies and agonistic antibody fragments comprising an antigen binding region that specifically binds to human VISTA wherein the antibodies or antibody fragments comprise variable heavy and light sequences having the CDR polypeptides of an anti-human VISTA antibody selected from VSTB49-VSTB116, with the proviso that if said antibody or fragment comprises an antagonistic anti-human VISTA antibody or anti-human VISTA antibody fragment then the anti-human VISTA antibody or antibody fragment does not comprise the same CDRs as any one of VSTB112, VSTB116, VSTB95, VSTB50, VSTB53 or VSTB60.

It is another specific object of the invention to provide isolated antagonistic and agonistic antibodies and antibody fragments comprising the CDRs of an anti-human VISTA antibody selected from VSTB49-VSTB116, which comprise a variable heavy and/or variable light polypeptide having at least 90%, 95%, or 96-99% sequence identity to the variable heavy and light polypeptide sequences of VSTB49-VSTB116, with the proviso that if said antibody or fragment comprises an antagonistic anti-human VISTA antibody or fragment then the antibody or antibody fragment does not comprise the same CDRs as any one of VSTB112, VSTB116, VSTB95, VSTB50, VSTB53 or VSTB60.

It is another specific object of the invention to provide isolated antagonistic and agonistic antibodies or antibody fragments comprising the same CDRs any one of VSTB49-VSTB116, which comprise a variable heavy and/or variable light polypeptide which is/are identical to the variable heavy and light polypeptide sequences of VSTB49-VSTB116, with the proviso that if said antibody or fragment comprises an antagonistic anti-human VISTA antibody or fragment then the antibody or antibody fragment does not comprise the same CDRs as any one of VSTB112, VSTB116, VSTB95, VSTB50, VSTB53 or VSTB60.

It is another specific object of the invention to provide isolated antagonistic or agonistic chimeric, human, humanized, multispecific (e.g., bispecific) anti-human VISTA antibodies or antibody fragments comprising an antigen binding region that specifically binds to human VISTA which comprise variable heavy and light sequences having the CDR polypeptides as any one of the anti-human VISTA antibodies comprising the CDR and variable heavy and light polypeptides disclosed in FIG. 4, with the proviso that if said antibody or fragment comprises an antagonistic anti-human VISTA antibody or antibody fragment then the antibody or antibody fragment does not comprise the same CDRs as any one of VSTB112, VSTB116, VSTB95, VSTB50, VSTB53 or VSTB60.

It is another specific object of the invention to provide novel immunosuppressants, i.e., anti-human VISTA antibodies and antibody fragments, e.g., those containing human IgG2 constant domains or IgG2 Fc regions, optionally wherein the FcR binding capability of the human IgG2 constant domains or IgG2 Fc regions are maintained or are enhanced compared to the wild-type human IgG2 constant domains or IgG2 Fc regions, which agonize, elicit or mimic the effects of human VISTA on immunity, e.g., its suppressive effects on T cell activity, differentiation and proliferation and its suppressive effects on the expression of proinflammatory cytokines.

It is another specific object of the invention to provide novel antagonists, i.e., novel anti-human VISTA antibodies and antibody fragments which antagonize or block the effects of human VISTA on immunity, particularly its suppressive effects on T cell activity, differentiation and proliferation and its suppressive effects on the expression of proinflammatory cytokines.

It is another specific object of the invention to provide novel immunosuppressive antibodies and antibody fragments which enhance or mimic the suppressive effects of VISTA on T cell immunity, i.e., which suppress CD4$^+$ or CD8$^+$ T cell proliferation, CD4$^+$ or CD8$^+$ T cell activation and its suppression of the production of immune cytokines, particularly proinflammatory cytokines such as IL-2, IL-4, IL-6, IL-17, TNF-α, and/or GM-CSF (granulocyte-macrophage colony-stimulating factor), and its promoting effects on the expression of chemokines or chemoattractants such as KC (keratinocyte chemoattractant) or MIP-2 (Macrophage inflammatory protein 2).

It is another specific object of the invention to provide novel antibodies and antibody fragments which block or reduce the suppressive effects of VISTA on T cell immunity, i.e., which enhance CD4$^+$ or CD8$^+$ T cell proliferation, CD4$^+$ or CD8$^+$ T cell activation, and its suppressive effects on the production of proinflammatory immune cytokines, particularly proinflammatory cytokines such as IL-2, IL-4, IL-6, IL-17, TNF-α, and/or GM-CSF (granulocyte-macrophage colony-stimulating factor), and its promoting effects on the expression of chemokines or chemoattractants such as KC (keratinocyte chemoattractant) or MIP-2 (Macrophage inflammatory protein 2).

It is another specific object of the invention to provide novel immunosuppressive or agonistic anti-human VISTA antibodies and antibody fragments of specific epitopic specificity or which compete for binding to human VISTA with specific anti-human VISTA antibodies.

It is another specific object of the invention to provide novel immunosuppressive or agonistic anti-human VISTA antibodies and antibody fragments of specific epitopic specificity or which compete for binding to human VISTA with specific anti-human VISTA antibodies which agonize (enhance, elicit or mimic) the suppressive effects of VISTA on immunity, e.g., its suppressive effects on T cell immunity, i.e., CD4$^+$ or CD8$^+$ T cell proliferation, CD4$^+$ or CD8$^+$ T cell activation, and/or which suppress the production of proinflammatory immune cytokines such as IL-2, IL-4, IL-6, IL-17, TNF-α, and/or GM-CSF (granulocyte-macrophage colony-stimulating factor), and its promoting effects on the expression of chemokines or chemoattractants such as KC (keratinocyte chemoattractant) or MIP-2 (Macrophage inflammatory protein 2).

Also the invention also relates to the specific use of these agonistic anti-human VISTA antibodies and antibody fragments as prophylactics or therapeutics, especially in treating conditions wherein preventing or inhibiting or reducing immune reactions is therapeutically desirable, and more particularly wherein the preventing or inhibiting or reducing T cell immunity, or more specifically CD4$^+$ or CD8$^+$ mediated T cell immunity is therapeutically beneficial such as autoimmunity, inflammation, allergic disorders, sepsis, GVHD, and/or in treating transplant or cell therapy recipients, e.g., CAR-T recipients, or in alleviating the inflammatory side effects of some conditions such as cancer.

Also the invention relates to the use of novel antagonistic anti-human VISTA antibodies and antibody fragments as prophylactics or therapeutics, especially in treating conditions wherein promoting immunity is desired, e.g., T cell immunity or CD4$^+$ or CD8$^+$-mediated T cell immunity is therapeutically beneficial such as cancer and infectious disease.

It is another specific object of the invention to provide an agonist or antagonist anti-human VISTA antibody according to the invention which is attached to a detectable label, linker or a therapeutic moiety.

It is another specific object of the invention to provide a diagnostic or therapeutic composition comprising a diagnostically or therapeutically effective amount of an agonist or antagonist anti-human VISTA antibody according to the invention, e.g., one containing the same CDRs as any of the antibodies having the sequences shown in FIG. 4 which is suitable for use in human therapy, such as an intravenous, subcutaneous or intramuscular administrable composition.

It is another specific object of the invention to provide a diagnostic or therapeutic methods which use an agonist antibody according to the invention in association with another immune agonist, e.g., a PD-1 or PD-L1 agonist, e.g., wherein the PD-1 or PD-L1 agonist is selected from an anti-PD-1 antibody or antibody fragment, an anti-PD-L1 antibody or antibody fragment, a PD-L1 polypeptide or fragment thereof which may be monovalent or multimeric, a PD-1 polypeptide or fragment thereof which may be monovalent or multimeric, or a complex or fusion protein comprising any of the foregoing.

It is another specific object of the invention to provide diagnostic or therapeutic methods which use an antagonist antibody according to the invention in association with another immune antagonist, e.g., a PD-1 or PD-L1 antagonist, e.g., wherein the PD-1 or PD-L1 agonist is selected from an antagonist anti-PD-1 antibody or antibody fragment, an antagonist anti-PD-L1 antibody or antibody fragment.

It is another specific object of the invention to provide methods of contacting immune cells in vitro or in vivo with an antagonist or agonist antibody according to the invention, e.g., human immune cells, e.g., wherein the contacted cells are infused into a human subject such as a subject who has cancer or an infectious disease or one who has an inflammatory, allergic or autoimmune condition.

BRIEF DESCRIPTION OF THE FIGURES

FIG. 1A-D. This figure shows in vitro and in vivo screening assays which can be used to identify suppressive VISTA mAbs. A) Purified T cells were plated on top of anti-CD3 in the presence of the indicated mAb for 72 hours. Proliferation was measured by H3 incorporation. B) Purified DO11.10 T cells were stimulated by ISQ pulsed APCs for 6 days in the presence of the indicated antibody. Proliferation was measured through use of CTV dilution dye. C) GVHD was induced by transfer of C57BL/6 cells into irradiated BALB/c recipients. Mice were injected I.P. with 200 μg of antibody on day 0, 2 and 4 post transfer and survival was analyzed. D) Mice were treated with 10 mpk of the indicated antibody 3 hours prior to administration of ConA (15 mpk) and IL-2 was analyzed in plasma at 6 by Luminex.

FIG. 2A-F. This figure shows that agonist VISTA antibodies are immunosuppressive in multiple models of autoimmune disease. A) NZB/W F1 mice were treated 3×/week with either 8G8 or Ham Ig (200 μg) starting at 25 weeks until the end of the experiment. "X" denotes time points where the control treated group had all been sacrificed. B) Mice were treated with 200 μg of antibody 3 hours prior to administration of 15 mg/kg (mpk) of ConA and survival was followed for 80 hours. C) Mice were treated sequentially with Collagen II mAb followed by LPS and arthritis was measured by measuring for paw swelling. 8G8 and Ham-Ig were administered (200 μg) 3× every other day. D) Imiquimod was applied to the ear of mice daily. At day 14, 8G8 or Ham-Ig (200 μg) were administered every other day and ear thickness was measured with calipers. E, F) Imiquimod applied to the backs of mice daily. At day 9, mice were euthanized and skin was sectioned & stained for CD3 expression by IHC.

FIG. 3. This figure shows the expression of VISTA in WT and hV-KI mice. CD4+ T cells, CD8+ T cells, Tregs (CD4+ FoxP3+), and monocytes, CD11b+, Ly6C+, Ly6G were isolated from the lymph nodes of WT and VISTA KI mice, and stained with αVISTA antibodies against mouse or human protein respectively.

FIG. 4 contains the sequences of different anti-human VISTA antibodies including those of INX800, INX801, and INX900-INX919.

FIG. 10A-C: shows different IgG2 Isoforms. (A) Disulfide shuffling leads to isoforms A and B, along with the transition for A/B (figure from Zhang, A. et al., 2015). (B) Isoforms are distinguishable by RP-HPLC. (C) Observed RP-HPLC chromatogram for INX901.

FIG. 17: This figure shows that agonist anti-human VISTA antibodies bind to the same core sequence.

FIG. 18: This figure summarizes the epitope analysis for different anti-human VISTA antibodies according to the invention.

FIG. 19: This figure shows the epitopes bound by agonist anti-human VISTA antibodies and further identifies important residues involved in binding.

DETAILED DESCRIPTION

Figure 5:
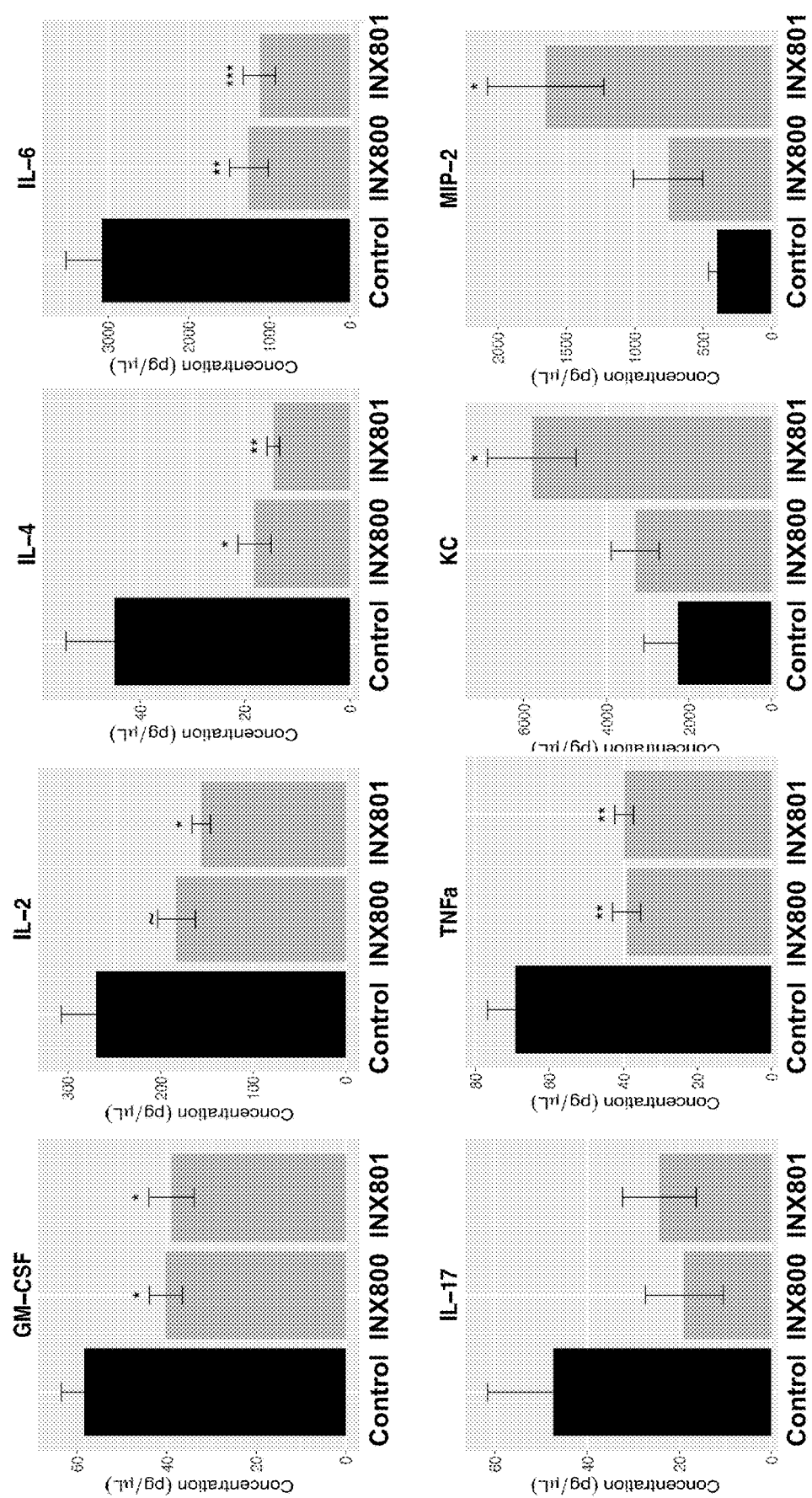
FIG. 5 shows the effects of exemplary anti-human VISTA antibodies, i.e., INX800 and INX801 in a ConA hepatitis model which assesses the effects thereof on the expression of different cytokines, chemokines and chemoattractants.

Unless defined otherwise, all technical and scientific terms used herein have the same meaning as those commonly understood by one of ordinary skill in the art to which this invention belongs. Although methods and materials similar or equivalent to those described herein may be used in the invention or testing of the present invention, suitable methods and materials are described herein. The materials, methods and examples are illustrative only, and are not intended to be limiting. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques may be used for chemical syntheses, chemical analyses, pharmaceutical preparation, formulation, and delivery, and treatment of patients.

As used in the description herein and throughout the claims that follow, the meaning of "a," "an," and "the" includes plural reference unless the context clearly dictates otherwise.

"Activating receptor," as used herein, refers broadly to immune cell receptors that bind antigen, complexed antigen (e.g., in the context of MHC molecules), Ig-fusion proteins, ligands, or antibodies. Activating receptors but are not limited to T cell receptors (TCRs), B cell receptors (BCRs), cytokine receptors, LPS receptors, complement receptors, and Fc receptors. For example, T cell receptors are present on T cells and are associated with CD3 molecules. T cell receptors are stimulated by antigen in the context of MHC molecules (as well as by polyclonal T cell activating reagents). T cell activation via the TCR results in numerous changes, e.g., protein phosphorylation, membrane lipid changes, ion fluxes, cyclic nucleotide alterations, RNA transcription changes, protein synthesis changes, and cell volume changes. For example, T cell receptors are present on T cells and are associated with CD3 molecules. T cell receptors are stimulated by antigen in the context of MHC molecules (as well as by polyclonal T cell activating reagents). T cell activation via the TCR results in numerous changes, e.g., protein phosphorylation, membrane lipid changes, ion fluxes, cyclic nucleotide alterations, RNA transcription changes, protein synthesis changes, and cell volume changes.

"Adjuvant" as used herein, refers to an agent used to stimulate the immune system and increase the response to a vaccine, without having any specific antigenic effect in itself.

"Agonist" herein refers to a molecule, generally an antibody or fusion proteins which enhances or mimics the effects of a specific molecule on immunity. Generally in the present application this will refer to anti-human VISTA agonist antibodies and antibody fragments which enhance or mimic the effects of human VISTA on immunity, particularly VISTA's suppressive effects on T cell immunity (CD4+ and/or CD8+ T cell immunity), the expression of proinflammatory cytokines and its effects of the expression of specific chemokines and chemoattractants.

"Aids in the diagnosis" or "aids in the detection" of a disease herein means that the expression level of a particular marker polypeptide or expressed RNA is detected alone or in association with one or more other markers in order to assess whether a subject has cells characteristic of a particular disease condition or the onset of a particular disease condition or comprises immune dysfunction such as immunosuppression characterized by VISTA expression or abnormal immune upregulation characterized by cells having reduced VISTA levels, such as during autoimmunity, inflammation or allergic responses, e.g., in individuals with chronic and non-chronic diseases.

"Allergic disease," as used herein, refers broadly to a disease involving allergic reactions. More specifically, an "allergic disease" is defined as a disease for which an allergen is identified, where there is a strong correlation between exposure to that allergen and the onset of pathological change, and where that pathological change has been proven to have an immunological mechanism. Herein, an immunological mechanism means that leukocytes show an immune response to allergen stimulation.

"Amino acid," as used herein refers broadly to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified (e.g., hydroxyproline, γ-carboxyglutamate, and O-phosphoserine.) Amino acid analogs refers to compounds that have the same basic chemical structure as a naturally occurring amino acid (i.e., a carbon that is bound to a hydrogen, a carboxyl group, an amino group), and an R group (e.g., homoserine, norleucine, methionine sulfoxide, methionine methyl sulfonium.) Analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

"Anergy" or "tolerance," or "prolonged antigen-specific T cell suppression" or "prolonged immunosuppression" as used herein refers broadly to refractivity to activating receptor-mediated stimulation. Refractivity is generally antigen-specific and persists after exposure to the tolerizing antigen has ceased. For example, anergy in T cells (as opposed to unresponsiveness) is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory molecule) results in failure to produce cytokines and, thus, failure to proliferate. Anergic T cells can, however, mount responses to unrelated antigens and can proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the API sequence that can be found within the enhancer (Kang et al. (1992) Science 257: 1134). Modulation of a costimulatory signal results in modulation of effector function of an immune cell.

"Antagonist" herein refers to a molecule, generally an antibody or fusion proteins which blocks or reduces the effects of a specific molecule on immunity. Generally in the present application this will refer to anti-human VISTA antagonist antibodies and antibody fragments which block or reduce the effects of human VISTA on immunity, particularly VISTA's suppressive effects on T cell immunity (CD4$^+$ and/or CD8+ T cell immunity), the expression of proinflammatory cytokines and VISTA's effects of the expression of specific chemokines and chemoattractants.

"Antibody", as used herein, refers broadly to an "antigen-binding portion" of an antibody (also used interchangeably with "antibody portion," "antigen-binding fragment," "antibody fragment"), as well as whole antibody molecules. The term "antigen-binding portion", as used herein, refers to one or more fragments of an antibody that retain the ability to specifically bind to an antigen (e.g., VISTA or specific portions thereof)). The term "antibody" as referred to herein includes whole polyclonal and monoclonal antibodies and any antigen-binding fragment (i.e., "antigen-binding portion") or single chains thereof as well as bispecific and multispecific antibodies, e.g., those that bind to multiple antigens or multiple antigen epitopes. An "antibody" refers to a glycoprotein comprising at least two heavy (H) chains and two light (L) chains interconnected by disulfide bonds, or an antigen-binding portion thereof. Each heavy chain is comprised of at least one heavy chain variable region (abbreviated herein as VH) and a heavy chain constant region. The heavy chain constant region is comprised of three domains, $C_{H1}$, Cm and Cm—Each light chain is comprised of at least one light chain variable region (abbreviated herein as $V_L$) and a light chain constant region. The light chain constant region is comprised of one domain, CL—The $V_H$ and $V_L$ regions can be further subdivided into regions of hypervariability, termed complementarity determining regions (CDRs), interspersed with regions that are more conserved, termed framework regions (FRs). Each VH and VL is composed of three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. More generally, the term "antibody" is intended to include any polypeptide chain-containing molecular structure with a specific shape that fits to and recognizes an epitope, where one or more non-covalent binding interactions stabilize the complex between the molecular structure and the epitope. The archetypal antibody molecule is the immunoglobulin, and all types of immunoglobulins, IgG, IgM, IgA, IgE, IgD, etc., from all sources, e.g. human, rodent, rabbit, cow, sheep, pig, dog, other mammals, chicken, other avians, etc., are considered to be "antibodies."

The antigen-binding function of an antibody can be performed by fragments of a full-length antibody. Non-limiting examples of antigen-binding fragments encompassed within the term "antigen-binding portion" of an antibody include (a) a Fab fragment, a monovalent fragment consisting of the $V_L$, $V_H$, $C_L$, and $C_{H1}$ domains; (b) a F(ab')$_2$ fragment, a bivalent fragment comprising two Fab fragments linked by a disulfide bridge at the hinge region; (c) a Fd fragment consisting of the $V_H$ and $C_{H1}$ domains; (d) a Fv fragment consisting of the VL and VH domains of a single arm of an antibody; (e) a dAb fragment (Ward, et al. (1989) *Nature* 341: 544-546), which consists of a $V_H$ domain; and (f) an isolated complementarily determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv). See e.g., Bird, et al. (1988) *Science* 242: 423-426; Huston, et al. (1988) *Proc Natl. Acad. Sci. USA* 85: 5879-5883; and Osbourn, et al. (1998) *Nat. Biotechnol.* 16: 778. Single chain antibodies are also intended to be encompassed within the term "antigen-binding portion" of an antibody. Any $V_H$ and $V_L$ sequences of specific scFv can be linked to human immunoglobulin constant region cDNA or genomic sequences, in order to generate expression vectors encoding complete IgG molecules or other isotypes. VH and $V_L$ can also be used in the generation of Fab, Fv, or other fragments of immunoglobulins using either protein chemistry or recombinant DNA technology. Other forms of single chain antibodies, such as diabodies are also encompassed. Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen-binding sites. See e.g. Holliger, et al. (1993) *Proc Natl. Acad. Sci. USA* 90: 6444-6448; Poljak, et al. (1994) *Structure* 2: 1121-1123. Still further, an antibody or antigen-binding portion thereof (antigen-binding fragment, antibody fragment, antibody portion) may be part of a larger immunoadhesion molecules, formed by covalent or noncovalent association of the antibody or antibody portion with one or more other proteins or peptides. Examples of immunoadhesion molecules include use of the streptavidin core region to make a tetrameric scFv molecule (Kipriyanov, et al. (1995) *Hum. Antibodies Hybridomas* 6: 93-101) and use of a cysteine residue, a marker peptide and a C-terminal polyhistidine tag to make bivalent and biotinylated scFv molecules. Kipriyanov, et al. (1994) *Mol. Immunol.* 31: 1047-1058. Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein. Antibodies may be polyclonal, monoclonal, xenogeneic, allogeneic, syngeneic, or modified forms thereof, e.g., humanized, chimeric, bispecific or multispecific antibodies.

"Antibody recognizing an antigen" and "an antibody specific for an antigen" is used interchangeably herein with the term "an antibody which binds specifically to an antigen" and refers to an immunoglobulin or fragment thereof that specifically binds an antigen.

"Antigen," as used herein, refers broadly to a molecule or a portion of a molecule capable of being bound by an antibody which is additionally capable of inducing an animal to produce an antibody capable of binding to an epitope of that antigen. An antigen may have one epitope, or have more than one epitope. The specific reaction referred to herein indicates that the antigen will react, in a highly selective manner, with its corresponding antibody and not with the multitude of other antibodies which may be evoked by other antigens. In the case of a desired enhanced immune response to particular antigens of interest, antigens include, but are not limited to; infectious disease antigens for which a protective immune response may be elicited are exemplary.

"Antigen presenting cell," as used herein, refers broadly to professional antigen presenting cells (e.g., B lymphocytes, monocytes, dendritic cells, and Langerhans cells) as well as other antigen presenting cells (e.g., keratinocytes, endothelial cells, astrocytes, fibroblasts, and oligodendrocytes).

"Antisense nucleic acid molecule," as used herein, refers broadly to a nucleotide sequence which is complementary to a "sense" nucleic ac*id encoding a protein (e.g., complementary to the coding strand of a double-stranded cDNA molecule) complementary to an mRNA sequence or complementary to the coding strand of a gene. Accordingly, antisense nucleic acid molecules can hydrogen bond to sense nucleic acid molecules.

"Apoptosis," as used herein, refers broadly to programmed cell death which can be characterized using techniques which are known in the art. Apoptotic cell death can be characterized by cell shrinkage, membrane blebbing, and chromatin condensation culminating in cell fragmentation. Cells undergoing apoptosis also display a characteristic pattern of internucleosomal DNA cleavage.

"Autoimmunity" or "autoimmune disease or condition," as used herein, refers broadly to a disease or disorder arising from and directed against an individual's own tissues or a co-segregate or manifestation thereof or resulting condition therefrom, and includes. Herein autoimmune conditions include inflammatory or allergic conditions, e.g., chronic diseases characterized by a host immune reaction against self-antigens potentially associated with tissue destruction such as rheumatoid arthritis.

"B cell receptor" (BCR)," as used herein, refers broadly to the complex between membrane Ig (mIg) and other transmembrane polypeptides (e.g., IgA. and Ig) found on B cells. The signal transduction function of mIg is triggered by crosslinking of receptor molecules by oligomeric or multimeric antigens. B cells can also be activated by anti-immunoglobulin antibodies. Upon BCR activation, numerous changes occur in B cells, including tyrosine phosphorylation.

"Cancer," as used herein, refers broadly to any neoplastic disease (whether invasive or metastatic) characterized by abnormal and uncontrolled cell division causing malignant growth or tumor (e.g., unregulated cell growth.) The term "cancer" or "cancerous" as used herein should be understood to encompass any neoplastic disease (whether invasive, non-invasive or metastatic) which is characterized by abnormal and uncontrolled cell division causing malignant growth or tumor, non-limiting examples of which are described herein. This includes any physiological condition in mammals that is typically characterized by unregulated cell growth. Examples of cancer are exemplified in the working examples. Further cancers include but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenström's Macroglobulinemia); chronic lymphocytic leukemia (CLL); acute lymphoblastic leukemia (ALL); Hairy cell leukemia; chronic myeloblasts leukemia; multiple myeloma and post-transplant lymphoproliferative disorder (PTLD). Other cancers amenable for treatment by the present invention include, but are not limited to, carcinoma, lymphoma, blastoma, sarcoma, and leukemia or lymphoid malignancies. More particular examples of such cancers include colorectal, bladder, ovarian, melanoma, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenström's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome. Preferably, the cancer is selected from the group consisting of colorectal cancer, breast cancer, colorectal cancer, rectal cancer, non-small cell lung cancer, non-Hodgkin's lymphoma (NHL), renal cell cancer, prostate cancer, liver cancer, pancreatic cancer, soft-tissue sarcoma, Kaposi's sarcoma, carcinoid carcinoma, head and neck cancer, melanoma, ovarian cancer, mesothelioma, and multiple myeloma. In an exemplary embodiment the cancer is an early or advanced (including metastatic) bladder, ovarian or melanoma. In another embodiment the cancer is colorectal cancer. The cancerous conditions amenable for treatment of the invention include cancers that express or do not express VISTA and further include non-metastatic or non-invasive as well as invasive or metastatic cancers wherein VISTA expression by immune, stromal or diseased cells suppress antitumor responses and anti-invasive immune responses. The method of the present invention is particularly suitable for the treatment of vascularized tumors. Cancers according to the invention include cancers that express or do not express VISTA and further include non-metastatic or non-invasive as well as invasive or metastatic cancers wherein VISTA expression by immune, stromal or diseased cells suppress antitumor responses and anti-invasive immune responses, and those characterized by vascularized tumors.

"Chimeric antibody," as used herein, refers broadly to an antibody molecule in which the constant region, or a portion thereof, is altered, replaced or exchanged so that the antigen-binding site (variable region) is linked to a constant region of a different or altered class, effector function and/or species, or an entirely different molecule which confers new properties to the chimeric antibody, e.g., an enzyme, toxin, hormone, growth factor, drug, the variable region or a portion thereof, is altered, replaced or exchanged with a variable region having a different or altered antigen specificity.

"Coding region," as used herein, refers broadly to regions of a nucleotide sequence comprising codons which are translated into amino acid residues, whereas the term "non-coding region" refers to regions of a nucleotide sequence that are not translated into amino acids (e.g., 5' and 3' untranslated regions).

"Conservatively modified variants," as used herein, applies to both amino acid and nucleic acid sequences, and with respect to particular nucleic acid sequences, refers broadly to conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. "Silent variations" are one species of conservatively modified nucleic acid variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) may be modified to yield a functionally identical molecule.

"Complementarity determining region," "hypervariable region," or "CDR," as used herein, refers broadly to one or more of the hyper-variable or complementarily determining regions (CDRs) found in the variable regions of light or heavy chains of an antibody. See Kabat, et al. (1987) Sequences of Proteins of Immunological Interest National Institutes of Health, Bethesda, Md. These expressions include the hypervariable regions as defined by Kabat, et al. (1983) *Sequences of Proteins of Immunological Interest*, U.S. Dept. of Health and Human Services or the hypervariable loops in 3-dimensional structures of antibodies. Chothia and Lesk (1987) *J. Mol. Biol.* 196: 901-917. The CDRs in each chain are held in close proximity by framework regions and, with the CDRs from the other chain, contribute to the formation of the antigen-binding site. Within the CDRs there are select amino acids that have been described as the selectivity determining regions (SDRs) which represent the critical contact residues used by the CDR in the antibody-antigen interaction. (Kashmiri *Methods* 36: 25-34 (2005)).

"Control amount," as used herein, refers broadly to a marker can be any amount or a range of amounts to be compared against a test amount of a marker. For example, a control amount of a marker may be the amount of a marker in a patient with a particular disease or condition or a person without such a disease or condition. A control amount can be either in absolute amount (e.g., microgram/ml) or a relative amount (e.g., relative intensity of signals).

"Costimulatory receptor," as used herein, refers broadly to receptors which transmit a costimulatory signal to an immune cell, e.g., CD28 or ICOS. As used herein, the term "inhibitory receptors" includes receptors which transmit a negative signal to an immune cell, e.g., a T cell or an NK cell.

"Costimulate," as used herein, refers broadly to the ability of a costimulatory molecule to provide a second, non-activating, receptor-mediated signal (a "costimulatory signal") that induces proliferation or effector function. For example, a costimulatory signal can result in cytokine secretion (e.g., in a T cell that has received a T cell-receptor-mediated signal) Immune cells that have received a cell receptor-mediated signal (e.g., via an activating receptor) may be referred to herein as "activated immune cells." With respect to T cells, transmission of a costimulatory signal to a T cell involves a signaling pathway that is not inhibited by cyclosporin A. In addition, a costimulatory signal can induce cytokine secretion (e.g., IL-2 and/or IL-10) in a T cell and/or can prevent the induction of unresponsiveness to antigen, the induction of anergy, or the induction of cell death in the T cell.

"Costimulatory polypeptide" or "costimulatory molecule" herein refers to a polypeptide that, upon interaction with a cell-surface molecule on T cells, modulates T cell responses.

"Costimulatory signaling" as used herein is the signaling activity resulting from the interaction between costimulatory polypeptides on antigen presenting cells and their receptors on T cells during antigen-specific T cell responses. Without wishing to be limited by a single hypothesis, the antigen-specific T cell response is believed to be mediated by two signals: 1) engagement of the T cell Receptor (TCR) with antigenic peptide presented in the context of MHC (signal 1), and 2) a second antigen-independent signal delivered by contact between different costimulatory receptor/ligand pairs (signal 2). Without wishing to be limited by a single hypothesis, this "second signal" is critical in determining the type of T cell response (activation vs inhibition) as well as the strength and duration of that response, and is regulated by both positive and negative signals from costimulatory molecules, such as the B7 family of proteins.

"B7" polypeptide herein means a member of the B7 family of proteins that costimulate T cells including, but not limited to B7-1, B7-2, B7-DC, B7-H5, B7-HI, B7-H2, B7-H3, B7-H4, B7-H6, B7-S3 and biologically active fragments and/or variants thereof. Representative biologically active fragments include the extracellular domain or fragments of the extracellular domain that costimulate T cells.

"Cytoplasmic domain," as used herein, refers broadly to the portion of a protein which extends into the cytoplasm of a cell.

"Diagnostic," as used herein, refers broadly to identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

"Diagnosing," or "aiding in the diagnosis" as used herein refers broadly to classifying a disease or a symptom, and/or determining the likelihood that an individual has a disease condition (e.g., based on absence or presence of VISTA expression, and/or increased or decreased expression by immune, stromal and/or putative diseased cells); determining a severity of the disease, monitoring disease progression, forecasting an outcome of a disease and/or prospects of recovery. The term "detecting" may also optionally encompass any of the foregoing. Diagnosis of a disease according to the present invention may, in some embodiments, be affected by determining a level of a polynucleotide or a polypeptide of the present invention in a biological sample obtained from the subject, wherein the level determined can be correlated with predisposition to, or presence or absence of the disease. It should be noted that a "biological sample obtained from the subject" may also optionally comprise a sample that has not been physically removed from the subject.

"Effective amount," as used herein, refers broadly to the amount of a compound, antibody, antigen, or cells that, when administered to a patient for treating a disease, is sufficient to effect such treatment for the disease. The effective amount may be an amount effective for prophylaxis, and/or an amount effective for prevention. The effective amount may be an amount effective to reduce, an amount effective to prevent the incidence of signs/symptoms, to reduce the severity of the incidence of signs/symptoms, to eliminate the incidence of signs/symptoms, to slow the development of the incidence of signs/symptoms, to prevent the development of the incidence of signs/symptoms, and/or effect prophylaxis of the incidence of signs/symptoms. The "effective amount" may vary depending on the disease and its severity and the age, weight, medical history, susceptibility, and pre-existing conditions, of the patient to be treated. The term "effective amount" is synonymous with "therapeutically effective amount" for purposes of this invention.

"Extracellular domain" or "ECD" as used herein refers broadly to the portion of a protein that extends from the surface of a cell.

"Expression vector," as used herein, refers broadly to any recombinant expression system for the purpose of expressing a nucleic acid sequence of the invention in vitro or in vivo, constitutively or inducibly, in any cell, including prokaryotic, yeast, fungal, plant, insect or mammalian cell. The term includes linear or circular expression systems. The term includes expression systems that remain episomal or integrate into the host cell genome. The expression systems can have the ability to self-replicate or not, i.e., drive only transient expression in a cell. The term includes recombinant expression cassettes which contain only the minimum elements needed for transcription of the recombinant nucleic acid.

"Family," as used herein, refers broadly to the polypeptide and nucleic acid molecules of the invention is intended to mean two or more polypeptide or nucleic acid molecules having a common structural domain or motif and having sufficient amino acid or nucleotide sequence homology as defined herein. Family members can be naturally or non-naturally occurring and can be from either the same or different species. For example, a family can contain a first polypeptide of human origin, as well as other, distinct polypeptides of human origin or alternatively, can contain homologues of non-human origin (e.g., monkey polypeptides.) Members of a family may also have common functional characteristics.

"Fc receptor" (FcRs) as used herein, refers broadly to cell surface receptors for the Fc portion of immunoglobulin molecules (Igs). Fc receptors are found on many cells which participate in immune responses. Among the human FcRs that have been identified so far are those which recognize IgG (designated FcγR), IgE (FceRI), IgA (FcaR), and polymerized IgM/A (FcεμR). FcRs are found in the following cell types: FceRI (mast cells), FceRII (many leukocytes), FcaR (neutrophils), and FcμR (glandular epithelium, hepatocytes). (Hogg Immunol. Today 9: 185-86 (1988)). The widely studied FcγRs are central in cellular immune defenses, and are responsible for stimulating the release of mediators of inflammation and hydrolytic enzymes involved in the pathogenesis of autoimmune disease. (Unkeless, Annu. Rev. Immunol. 6: 251-87 (1988)). The FcγRs provide a crucial link between effector cells and the lymphocytes that secrete Ig, since the macrophage/monocyte, polymorphonuclear leukocyte, and natural killer (NK) cell FcγRs confer an element of specific recognition mediated by IgG. Human leukocytes have at least three different types of FcγRs for IgG: hFcγRI(CD64) (found on monocytes/macrophages), hFcγRIIA or hFcγRIIB, (CD32 or CD32A) (found on monocytes, neutrophils, eosinophils, platelets, possibly B cells, and the K562 cell line) and FcγRIIIA (CD16A) or FcγRIIIB (CD16B) (found on NK cells, neutrophils, eosinophils, and macrophages).

"Framework region" or "FR," as used herein refers broadly to one or more of the framework regions within the variable regions of the light and heavy chains of an antibody. See Kabat, et al. *Sequences of Proteins of Immunological Interest* National Institutes of Health, Bethesda, Md. (1987). These expressions include those amino acid sequence regions interposed between the CDRs within the variable regions of the light and heavy chains of an antibody.

"Heterologous," as used herein, refers broadly to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid (e.g., a promoter from one source and a coding region from another source.) Similarly, a heterologous protein indicates that the protein comprises two or more subsequences that are not found in the same relationship to each other in nature (e.g., a fusion protein).

"High affinity," as used herein, refers broadly to an antibody or fusion protein having a KD of at least $10^6$ M, more preferably $10^7$ M, even more preferably at least $10^8$ M and even more preferably at least $10^9$ M, $10^{10}$ M, $10^{11}$ M, or $10^{12}$ M for a target antigen or receptor. "High affinity" for an IgG antibody or fusion protein herein refers to an antibody having a KD of $10^6$ M or less, more preferably $10^7$ M or less, preferably $10^8$ M or less, more preferably $10^9$ M or less and even more preferably $10^{10}$ M, $10^{11}$ M, or $10^{12}$ M or less for a target antigen or receptor. With particular respect to antibodies, "high affinity" binding can vary for different antibody isotypes. For example, "high affinity" binding for an IgM isotype refers to an antibody having a $K_D$ of $10^{-7}$ M or less, more preferably $10^{-8}$ M or less.

"Homology," as used herein, refers broadly to a degree of similarity between a nucleic acid sequence and a reference nucleic acid sequence or between a polypeptide sequence and a reference polypeptide sequence. Homology may be partial or complete. Complete homology indicates that the nucleic acid or amino acid sequences are identical. A partially homologous nucleic acid or amino acid sequence is one that is not identical to the reference nucleic acid or amino acid sequence. The degree of homology can be determined by sequence comparison, for example using BlastP software of the National Center of Biotechnology Information (NCBI) using default parameters. The term "sequence identity" may be used interchangeably with "homology."

"Host cell," as used herein, refers broadly to refer to a cell into which a nucleic acid molecule of the invention, such as a recombinant expression vector of the invention, has been introduced. Host cells may be prokaryotic cells (e.g., *E. coli*), or eukaryotic cells such as yeast, insect (e.g., SF9), amphibian, or mammalian cells such as CHO, HeLa, HEK-293, e.g., cultured cells, explants, and cells in vivo. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, progeny may not, in fact, be identical to the parent cell, but are still included within the scope of the term as used herein.

"Human monoclonal antibody" refers to antibodies displaying a single binding specificity which have variable regions in which both the framework and CDR regions are derived from human germline immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell. This includes fully human monoclonal antibodies and conjugates and variants thereof, e.g., which are bound to effector agents such as therapeutics or diagnostic agents.

"Humanized antibody," as used herein, refers broadly to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

"Hybridization," as used herein, refers broadly to the physical interaction of complementary (including partially complementary) polynucleotide strands by the formation of hydrogen bonds between complementary nucleotides when the strands are arranged antiparallel to each other.

"IgV domain" and "IgC domain" as used herein, refer broadly to Ig superfamily member domains. These domains correspond to structural units that have distinct folding patterns called Ig folds. Ig folds are comprised of a sandwich of two P sheets, each consisting of antiparallel P strands of 5-10 amino acids with a conserved disulfide bond between the two sheets in most, but not all, domains. IgC domains of Ig, TCR, and MHC molecules share the same types of sequence patterns and are called the Cl set within the Ig superfamily. Other IgC domains fall within other sets. IgV domains also share sequence patter and are called V set domains. IgV domains are longer than C-domains and form an additional pair of β strands.

"Immune cell," as used herein, refers broadly to cells that are of hematopoietic origin and that play a role in the immune response. Immune cells include but are not limited to lymphocytes, such as B cells and T cells; natural killer cells; dendritic cells, and myeloid cells, such as monocytes, macrophages, eosinophils, mast cells, basophils, and granulocytes.

"Immunoassay," as used herein, refers broadly to an assay that uses an antibody to specifically bind an antigen. The immunoassay may be characterized by the use of specific binding properties of a particular antibody to isolate, target, and/or quantify the antigen.

"Immune related disease (or disorder or condition)" as used herein should be understood to encompass any disease disorder or condition selected from the group including but not limited to autoimmune diseases, inflammatory disorders and immune disorders associated with graft transplantation rejection, such as acute and chronic rejection of organ transplantation, allogenic stem cell transplantation, autologous stem cell transplantation, bone marrow transplantation, and graft versus host disease.

"Immune response," as used herein, refers broadly to T cell-mediated and/or B cell-mediated immune responses that are influenced by modulation of T cell costimulation. Exemplary immune responses include B cell responses (e.g., antibody production) T cell responses (e.g., cytokine production, and cellular cytotoxicity) and activation of cytokine responsive cells, e.g., macrophages. As used herein, the term "downmodulation" with reference to the immune response includes a diminution in any one or more immune responses, while the term "upmodulation" with reference to the immune response includes an increase in any one or more immune responses. It will be understood that upmodulation of one type of immune response may lead to a corresponding downmodulation in another type of immune response. For example, upmodulation of the production of certain cytokines (e.g., IL-10) can lead to downmodulation of cellular immune responses.

"Immunologic", "immunological" or "immune" response herein refer to the development of a humoral (antibody mediated) and/or a cellular (mediated by antigen-specific T cells or their secretion products) response directed against a peptide in a recipient patient. Such a response can be an active response induced by administration of immunogen or a passive response induced by administration of antibody or primed T-cells. Without wishing to be limited by a single hypothesis, a cellular immune response is elicited by the presentation of polypeptide epitopes in association with Class II or Class I MHC molecules to activate antigen-specific $CD4^+$ T helper cells and/or $CD8_+$ cytotoxic T cells, respectively. The response may also involve activation of monocytes, macrophages, NK cells, basophils, dendritic cells, astrocytes, microglia cells, eosinophils, activation or recruitment of neutrophils or other components of innate immunity. The presence of a cell-mediated immunological response can be determined by proliferation assays ($CD4^+$ T cells) or CTL (cytotoxic T lymphocyte) assays. The relative contributions of humoral and cellular responses to the protective or therapeutic effect of an immunogen can be distinguished by separately isolating antibodies and T cells from an immunized syngeneic animal and measuring protective or therapeutic effect in a second subject.

"Immunogenic agent" or "immunogen" is a moiety capable of inducing an immunological response against itself on administration to a mammal, optionally in conjunction with an adjuvant.

"Inflammatory disorders", "inflammatory conditions" and/or "inflammation", used interchangeably herein, refers broadly to chronic or acute inflammatory diseases, and expressly includes inflammatory autoimmune diseases and inflammatory allergic conditions. These conditions include by way of example inflammatory abnormalities characterized by dysregulated immune response to harmful stimuli, such as pathogens, damaged cells, or irritants. Inflammatory disorders underlie a vast variety of human diseases. Non-immune diseases with etiological origins in inflammatory processes include cancer, atherosclerosis, and ischemic heart disease. Examples of disorders associated with inflammation include: Chronic prostatitis, Glomerulonephritis, Hypersensitivities, Pelvic inflammatory disease, Reperfusion injury, Sarcoidosis, Vasculitis, Interstitial cystitis, normocomplementemic urticarial vasculitis, pericarditis, myositis, antisynthetase syndrome, scleritis, macrophage activation syndrome, Behçet's Syndrome, PAPA Syndrome, Blau's Syndrome, gout, adult and juvenile Still's disease, cryropyrinopathy, Muckle-Wells syndrome, familial cold-induced auto-inflammatory syndrome, neonatal onset multisystemic inflammatory disease, familial Mediterranean fever, chronic infantile neurologic, cutaneous and articular syndrome, systemic juvenile idiopathic arthritis, Hyper IgD syndrome, Schnitzler's syndrome, TNF receptor-associated periodic syndrome (TRAPSP), gingivitis, periodontitis, hepatitis, cirrhosis, pancreatitis, myocarditis, vasculitis, gastritis, gout, gouty arthritis, and inflammatory skin disorders, selected from the group consisting of psoriasis, atopic dermatitis, eczema, rosacea, urticaria, and acne.

"Inhibitory signal," as used herein, refers broadly to a signal transmitted via an inhibitory receptor molecule on an immune cell. A signal antagonizes a signal via an activating receptor (e.g., via a TCR, CD3, BCR, or Fc molecule) and can result, e.g., in inhibition of: second messenger generation; proliferation; or effector function in the immune cell, e.g., reduced phagocytosis, antibody production, or cellular cytotoxicity, or the failure of the immune cell to produce mediators (e.g., cytokines (e.g., IL-2) and/or mediators of allergic responses); or the development of anergy.

"Isolated," as used herein, refers broadly to material removed from its original environment in which it naturally occurs, and thus is altered by the hand of man from its natural environment and includes "recombinant" polypeptides. Isolated material may be, for example, exogenous nucleic acid included in a vector system, exogenous nucleic acid contained within a host cell, or any material which has been removed from its original environment and thus altered by the hand of man (e.g., "isolated antibody"). For example, "isolated" or "purified," as used herein, refers broadly to a protein, DNA, antibody, RNA, or biologically active portion thereof, that is substantially free of cellular material or other contaminating proteins from the cell or tissue source from which the biological substance is derived, or substantially free from chemical precursors or other chemicals when chemically synthesized. As used herein the term "isolated" refers to a compound of interest (for example a polynucleotide or a polypeptide) that is in an environment different from that in which the compound naturally occurs e.g., separated from its natural milieu such as by concentrating a peptide to a concentration at which it is not found in nature. "Isolated" includes compounds that are within samples that are substantially enriched for the compound of interest and/or in which the compound of interest is partially or substantially purified.

"Isolated antibody", as used herein, is intended to refer to an antibody that is substantially free of other antibodies having different antigenic specificities (e.g., an isolated antibody that specifically binds VISTA) is substantially free of antibodies that specifically bind antigens other than VISTA). Moreover, an isolated antibody may be substantially free of other cellular material and/or chemicals.

"Isotype" herein refers to the antibody class (e.g., IgM or IgG1) that is encoded by the heavy chain constant region genes.

"K-assoc" or "Ka", as used herein, refers broadly to the association rate of a particular antibody-antigen interaction, whereas the term "Kdiss" or "Kd," as used herein, refers to the dissociation rate of a particular antibody-antigen interaction.

The term "$K_D$", as used herein, is intended to refer to the dissociation constant, which is obtained from the ratio of Kd to Ka (i.e., Kd/Ka) and is expressed as a molar concentration (M). $K_D$ values for antibodies can be determined using methods well established in the art such as plasmon resonance (BIAcore®), ELISA and KINEXA. A preferred method for determining the $K_D$ of an antibody is by using surface Plasmon resonance, preferably using a biosensor system such as a BIAcore® system or by ELISA. Typically these methods are effected at 25° or 37° C. Antibodies for therapeutic usage generally will possess a $K_D$ when determined by surface Plasmon resonance of 50 nM or less or more typically 1 nM or less at 25° or 37° C.

"Label" or a "detectable moiety" as used herein, refers broadly to a composition detectable by spectroscopic, photochemical, biochemical, immunochemical, chemical, or other physical means.

"Low stringency," "medium stringency," "high stringency," or "very high stringency conditions," as used herein, refers broadly to conditions for nucleic acid hybridization and washing. Guidance for performing hybridization reactions can be found in Ausubel, et al., *Short Protocols in Molecular Biology* (5th Ed.) John Wiley & Sons, NY (2002). Exemplary specific hybridization conditions include but are not limited to: (1) low stringency hybridization conditions in 6× sodium chloride/sodium citrate (SSC) at about 45° C., followed by two washes in 0.2×SSC, 0.1% SDS at least at 50° C. (the temperature of the washes can be increased to 55° C. for low stringency conditions); (2) medium stringency hybridization conditions in 6×SSC at about 45° C., followed by one or more washes in 0.2×SSC, 0.1% SDS at 60° C.; (3) high stringency hybridization conditions in 6×SSC at about 45° C. followed by one or more washes in 0.2×SSC, 0.1% SDS at 65° C.; and (4) very high stringency hybridization conditions are 0.5M sodium phosphate, 7% SDS at 65° C., followed by one or more washes at 0.2×SSC, and 1% SDS at 65° C.

"Mammal," as used herein, refers broadly to any and all warm-blooded vertebrate animals of the class Mammalia, including humans, characterized by a covering of hair on the skin and, in the female, milk-producing mammary glands for nourishing the young. Examples of mammals include but are not limited to alpacas, armadillos, capybaras, cats, camels, chimpanzees, chinchillas, cattle, dogs, goats, gorillas, hamsters, horses, humans, lemurs, llamas, mice, non-human primates, pigs, rats, sheep, shrews, squirrels, tapirs, and voles. Mammals include but are not limited to bovine, canine, equine, feline, murine, ovine, porcine, primate, and rodent species. Mammal also includes any and all those listed on the Mammal Species of the World maintained by the National Museum of Natural History, Smithsonian Institution in Washington D.C.

"Multispecific antibody" refers to an antibody with 2 or more antigen binding regions. This includes bispecific antibodies. These antigen binding regions may bind to different antigens or to different epitopes of the same antigen.

"Naturally-occurring nucleic acid molecule," as used herein, refers broadly refers to an RNA or DNA molecule having a nucleotide sequence that occurs in nature (e.g., encodes a natural protein).

"Nucleic acid" or "nucleic acid sequence," as used herein, refers broadly to a deoxy-ribonucleotide or ribonucleotide oligonucleotide in either single- or double-stranded form. The term encompasses nucleic acids, i.e., oligonucleotides, containing known analogs of natural nucleotides. The term also encompasses nucleic-acid-like structures with synthetic backbones. Unless otherwise indicated, a particular nucleic acid sequence also implicitly encompasses conservatively modified variants thereof (e.g., degenerate codon substitutions) and complementary sequences, as well as the sequence explicitly indicated. The term nucleic acid is used interchangeably with gene, cDNA, mRNA, oligonucleotide, and polynucleotide.

"Operatively linked", as used herein, refers broadly to when two DNA fragments are joined such that the amino acid sequences encoded by the two DNA fragments remain in-frame.

"Paratope," as used herein, refers broadly to the part of an antibody which recognizes an antigen (e.g., the antigen-binding site of an antibody.) Paratopes may be a small region (e.g., 15-22 amino acids) of the antibody's Fv region and may contain parts of the antibody's heavy and light chains. See Goldsby, et al. Antigens (Chapter 3) Immunology (5th Ed.) New York: W. H. Freeman and Company, pages 57-75.

"Patient," or "subject" or "recipient", "individual", or "treated individual" are used interchangeably herein, and refers broadly to any animal that is in need of treatment either to alleviate a disease state or to prevent the occurrence or reoccurrence of a disease state. Also, "Patient" as used herein, refers broadly to any animal that has risk factors, a history of disease, susceptibility, symptoms, and signs, was previously diagnosed, is at risk for, or is a member of a patient population for a disease. The patient may be a clinical patient such as a human or a veterinary patient such as a companion, domesticated, livestock, exotic, or zoo animal.

"Polypeptide," "peptide" and "protein," are used interchangeably and refer broadly to a polymer of amino acid residues s of any length, regardless of modification (e.g., phosphorylation or glycosylation). The terms apply to amino acid polymers in which one or more amino acid residue is an analog or mimetic of a corresponding naturally occurring amino acid, as well as to naturally occurring amino acid polymers. The terms apply to amino acid polymers in which one or more amino acid residue is an artificial chemical mimetic of a corresponding naturally occurring amino acid, as well as to naturally occurring amino acid polymers and non-naturally occurring amino acid polymer. Polypeptides can be modified, e.g., by the addition of carbohydrate residues to form glycoproteins. The terms "polypeptide," "peptide" and "protein" expressly include glycoproteins, as well as non-glycoproteins.

"Promoter," as used herein, refers broadly to an array of nucleic acid sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A constitutive" promoter is a promoter that is active under most environmental and developmental conditions. An "inducible" promoter is a promoter that is active under environmental or developmental regulation.

"Prophylactically effective amount," as used herein, refers broadly to the amount of a compound that, when administered to a patient for prophylaxis of a disease or prevention of the reoccurrence of a disease, is sufficient to effect such prophylaxis for the disease or reoccurrence. The prophylactically effective amount may be an amount effective to prevent the incidence of signs and/or symptoms. The "prophylactically effective amount" may vary depending on the disease and its severity and the age, weight, medical history, predisposition to conditions, preexisting conditions, of the patient to be treated.

"Prophylactic vaccine" and/or "Prophylactic vaccination" refers to a vaccine used to prevent a disease or symptoms associated with a disease such as cancer or an infectious condition.

"Prophylaxis," as used herein, refers broadly to a course of therapy where signs and/or symptoms are not present in the patient, are in remission, or were previously present in a patient. Prophylaxis includes preventing disease occurring subsequent to treatment of a disease in a patient. Further, prevention includes treating patients who may potentially develop the disease, especially patients who are susceptible to the disease (e.g., members of a patent population, those with risk factors, or at risk for developing the disease).

"Recombinant" as used herein, refers broadly with reference to a product, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline VH and VL sequences, may not naturally exist within the human antibody germline repertoire in vivo.

"Signal sequence" or "signal peptide," as used herein, refers broadly to a peptide containing about 15 or more amino acids which occurs at the N-terminus of secretory and membrane bound polypeptides and which contains a large number of hydrophobic amino acid residues. For example, a signal sequence contains at least about 10-30 amino acid residues, preferably about 15-25 amino acid residues, more preferably about 18-20 amino acid residues, and even more preferably about 19 amino acid residues, and has at least about 35-65%, preferably about 38-50%, and more preferably about 40-45% hydrophobic amino acid residues (e.g., Valine, Leucine, Isoleucine or Phenylalanine). A "signal sequence," also referred to in the art as a "signal peptide," serves to direct a polypeptide containing such a sequence to a lipid bilayer, and is cleaved in secreted.

"Specifically (or selectively) binds" to an antibody or "specifically (or selectively) immunoreactive with," or "specifically interacts or binds," as used herein, refers broadly to a protein or peptide (or other epitope), refers, in some embodiments, to a binding reaction that is determinative of the presence of the protein in a heterogeneous population of proteins and other biologies. For example, under designated immunoassay conditions, the specified antibodies bind to a particular protein at least two times greater than the background (non-specific signal) and do not substantially bind in a significant amount to other proteins present in the sample. Typically a specific or selective reaction will be at least twice background signal or noise and more typically more than about 10 to 100 times background.

"Specifically hybridizable" and "complementary" as used herein, refer broadly to a nucleic acid can form hydrogen bond(s) with another nucleic acid sequence by either traditional Watson-Crick or other non-traditional types. The binding free energy for a nucleic acid molecule with its complementary sequence is sufficient to allow the relevant function of the nucleic acid to proceed, e.g., RNAi activity. Determination of binding free energies for nucleic acid molecules is well known in the art. (See, e.g., Turner, et al. *CSH Symp. Quant. Biol. LII:* 123-33 (1987); Frier, et al. *PNAS* 83: 9373-77 1986); Turner, et al. *J. Am. Chem. Soc.* 109:3783-85 (1987)). A percent complementarity indicates the percentage of contiguous residues in a nucleic acid molecule that can form hydrogen bonds (e.g., Watson-Crick base pairing) with a second nucleic acid sequence (e.g., about at least 5, 6, 7, 8, 9, 10 out of 10 being about at least 50%, 60%, 70%, 80%, 90%, and 100% complementary, inclusive). "Perfectly complementary" or 100% complementarity refers broadly all of the contiguous residues of a nucleic acid sequence hydrogen bonding with the same number of contiguous residues in a second nucleic acid sequence.

"Substantial complementarity" refers to polynucleotide strands exhibiting about at least 90% complementarity, excluding regions of the polynucleotide strands, such as overhangs, that are selected so as to be noncomplementary. Specific binding requires a sufficient degree of complementarity to avoid non-specific binding of the oligomeric compound to non-target sequences under conditions in which specific binding is desired, i.e., under physiological conditions in the case of in vivo assays or therapeutic treatment, or in the case of in vitro assays, under conditions in which the assays are performed. The non-target sequences typically may differ by at least 5 nucleotides.

"Signs" of disease, as used herein, refers broadly to any abnormality indicative of disease, discoverable on examination of the patient; an objective indication of disease, in contrast to a symptom, which is a subjective indication of disease.

"Solid support," "support," and "substrate," as used herein, refers broadly to any material that provides a solid or semi-solid structure with which another material can be attached including but not limited to smooth supports (e.g., metal, glass, plastic, silicon, and ceramic surfaces) as well as textured and porous materials.

"Soluble ectodomain (ECD)" or "ectodomain" or "soluble VISTA protein(s)/molecule(s)" of VISTA as used herein means non-cell-surface-bound VISTA molecules or any portion thereof, including, but not limited to: VISTA fusion proteins or VISTA ECD-Ig fusion proteins, wherein the extracellular domain of VISTA or fragment thereof is fused to an immunoglobulin (Ig) moiety rendering the fusion molecule soluble, or fragments and derivatives thereof, proteins with the extracellular domain of VISTA fused or joined with a portion of a biologically active or chemically active protein such as the papillomavirus E7 gene product, melanoma-associated antigen p97 or HIV env protein, or fragments and derivatives thereof; hybrid (chimeric) fusion proteins such as VISTA-Ig, or fragments and derivatives thereof. Such fusion proteins are described in greater detail below.

"Soluble VISTA protein(s)/molecule(s)" herein also include VISTA molecules with the transmembrane domain removed to render the protein soluble, or fragments and derivatives thereof; fragments, portions or derivatives thereof, and soluble VISTA mutant molecules. The soluble VISTA molecules used in the methods according to at least some embodiments of the invention may or may not include a signal (leader) peptide sequence.

"Subject" or "patient" or "individual" in the context of therapy or diagnosis herein includes any human or nonhuman animal. The term "nonhuman animal" includes all vertebrates, e.g., mammals and non-mammals, such as non-human primates, sheep, dogs, cats, horses, cows, chickens, amphibians, reptiles, etc., i.e., anyone suitable to be treated according to the present invention include, but are not limited to, avian and mammalian subjects, and are preferably mammalian. Any mammalian subject in need of being treated according to the present invention is suitable. Human subjects of both genders and at any stage of development (i.e., neonate, infant, juvenile, adolescent, and adult) can be treated according to the present invention. The present invention may also be carried out on animal subjects, particularly mammalian subjects such as mice, rats, dogs, cats, cattle, goats, sheep, and horses for veterinary purposes, and for drug screening and drug development purposes. "Subjects" is used interchangeably with "individuals" and "patients."

"Substantially free of chemical precursors or other chemicals," as used herein, refers broadly to preparations of VISTA protein in which the protein is separated from chemical precursors or other chemicals which are involved in the synthesis of the protein. In one embodiment, the language "substantially free of chemical precursors or other chemicals" includes preparations of VISTA protein having less than about 30% (by dry weight) of chemical precursors or non-VISTA chemicals, more preferably less than about 20% chemical precursors or non-VISTA chemicals, still more preferably less than about 10% chemical precursors or non-VISTA chemicals, and most preferably less than about 5% chemical precursors or non-VISTA chemicals.

"Symptoms" of disease as used herein, refers broadly to any morbid phenomenon or departure from the normal in structure, function, or sensation, experienced by the patient and indicative of disease.

"T cell," as used herein, refers broadly to CD4+ T cells and CD8+ T cells. The term T cell also includes both T helper 1 type T cells and T helper 2 type T cells.

"Therapy," "therapeutic," "treating," or "treatment", as used herein, refers broadly to treating a disease, arresting, or reducing the development of the disease or its clinical symptoms, and/or relieving the disease, causing regression of the disease or its clinical symptoms. Therapy encompasses prophylaxis, treatment, remedy, reduction, alleviation, and/or providing relief from a disease, signs, and/or symptoms of a disease. Therapy encompasses an alleviation of signs and/or symptoms in patients with ongoing disease signs and/or symptoms (e.g., inflammation, pain). Therapy also encompasses "prophylaxis". The term "reduced", for purpose of therapy, refers broadly to the clinical significant reduction in signs and/or symptoms. Therapy includes treating relapses or recurrent signs and/or symptoms (e.g., inflammation, pain). Therapy encompasses but is not limited to precluding the appearance of signs and/or symptoms anytime as well as reducing existing signs and/or symptoms and eliminating existing signs and/or symptoms. Therapy includes treating chronic disease ("maintenance") and acute disease. For example, treatment includes treating or preventing relapses or the recurrence of signs and/or symptoms (e.g., inflammation, pain).

"Treg cell" (sometimes also referred to as suppressor T cells or inducible Treg cells or iTregs) as used herein refers to a subpopulation of T cells which modulate the immune system and maintain tolerance to self-antigens and can abrogate autoimmune diseases. Foxp3$^+$CD4$^+$CD25$^+$ regulatory T cells (Tregs) are critical in maintaining peripheral tolerance under normal conditions.

"Transmembrane domain," as used herein, refers broadly to an amino acid sequence of about 15 amino acid residues in length which spans the plasma membrane. More preferably, a transmembrane domain includes about at least 20, 25, 30, 35, 40, or 45 amino acid residues and spans the plasma membrane. Transmembrane domains are rich in hydrophobic residues, and typically have an a-helical structure. In an embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta, et al. *Annu. Rev. Neurosci.* 19:235-263 (1996).

"Transgenic animal," as used herein, refers broadly to a non-human animal, preferably a mammal, more preferably a mouse, in which one or more of the cells of the animal includes a "transgene". The term "transgene" refers to exogenous DNA which is integrated into the genome of a cell from which a transgenic animal develops and which remains in the genome of the mature animal, for example directing the expression of an encoded gene product in one or more cell types or tissues of the transgenic animal.

"Unresponsiveness," as used herein, refers broadly to refractivity of immune cells to stimulation, e.g., and stimulation via an activating receptor or a cytokine. Unresponsiveness can occur, e.g., because of exposure to immunosuppressants or high doses of antigen.

"Variable region" or "VR," as used herein, refers broadly to the domains within each pair of light and heavy chains in an antibody that are involved directly in binding the antibody to the antigen. Each heavy chain has at one end a variable domain ($V_H$) followed by a number of constant domains. Each light chain has a variable domain ($V_L$) at one end and a constant domain at its other end; the constant domain of the light chain is aligned with the first constant domain of the heavy chain, and the light chain variable domain is aligned with the variable domain of the heavy chain.

"Vector," as used herein, refers broadly to a nucleic acid molecule capable of transporting another nucleic acid molecule to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. The techniques and procedures are generally performed according to conventional methods well known in the art and as described in various general and more specific references that are cited and discussed throughout the present specification. See, e.g., Sambrook, et al. *Molec. Cloning: Lab. Manual* [3rd Ed] Cold Spring Harbor Laboratory Press (2001). Standard techniques may be used for recombinant DNA, oligonucleotide synthesis, and tissue culture, and transformation (e.g., electroporation, lipofection). Enzymatic reactions and purification techniques may be performed according to manufacturer's specifications or as commonly accomplished in the art or as described herein.

Having defined certain terms and phrases used in the present application, the anti-VISTA antibodies and antigen binding antibody fragments and methods for the production and use thereof which are embraced by the invention are further described below.

The present invention relates to antibodies and antibody fragments comprising an antigen binding region that binds to a V-domain Ig Suppressor of T cell Activation (VISTA). VISTA is a checkpoint regulator that negatively suppresses immune responses. See Wang et al., "VISTA, a novel mouse Ig superfamily ligand that negatively regulates T cell responses," *J. Exp. Med.*, 208(3) 577-92 (2011). This protein is expressed on normal human neutrophils, monocytes and T cells subsets. In addition, cynomolgus monkey cells express VISTA in a similar pattern to normal human cells. VISTA is also expressed in the peripheral blood cells e.g., of cancer patients.

The binding of an antagonist anti-VISTA antibody or antibody fragment to VISTA according to the invention will antagonize at least one of the effects of VISTA on immunity thereby suppressing the suppressive effects of VISTA on immunity, e.g., T cell immunity and/or cytokine expression. By contrast, the binding of an agonist anti-VISTA antibody or antibody fragment to VISTA according to the invention will agonize, elicit or mimic at least one of the effects of VISTA on immunity thereby promoting at least one of the suppressive effects of VISTA on immunity, e.g., the suppression of T cell immunity or the suppression of the expression of specific proinflammatory cytokines or its promoting effect on the expression of certain chemoattractants and chemokines.

Such antibody fragments include by way of example Fab, F(ab')$_2$, and scFv antibody fragments. These antibody or antibody fragments can comprise an antibody constant region or fragment or variant thereof. Such antibodies and antibody fragments include those which bind to VISTA proteins expressed on hematopoietic and other cells, for example, myeloid cells and/or lymphocytes, monocytes, neutrophils, T cells, natural killer (NK) cells, natural killer T (NKT) cells, a tumor cell, and/or in the tumor microenvironment (TME). The tumor microenvironment is the cellular environment of the tumor. It can include surrounding immune cells, fibroblasts, blood vessels, other cells, signaling molecules, and the extracellular matrix.

Antibodies that block or inhibit the effects of VISTA may be used to enhance human immune responses, in particular immune responses to malignancies and infection. By contrast molecules that agonize VISTA such as soluble VISTA, e.g., VISTA-Ig and the subject agonist anti-human VISTA antibodies and fragments may be used to suppress undesired human immune responses such as autoimmune, allergic, GVHD, sepsis or undesirable inflammatory immune responses.

The subject application provides novel antagonist and agonist anti-human VISTA antibodies including those comprising the same CDR5 as any of the anti-human VISTA antibodies having the sequences shown in FIG. 4. While prior to the present invention a number of antagonist anti-human VISTA antibodies have been reported in the literature, no agonistic anti-human VISTA antibodies or antibody fragments have been reported.

As disclosed in the experimental examples which follow the inventors initially produced 2 chimeric anti-human VISTA antibodies derived from a murine anti-human VISTA antibody (1E8 having sequences in FIG. 4) which respectively contain unmodified IgG2 human constant regions or IgG2 constant regions wherein the cysteine residue at position 127 of the kappa chain was changed to a serine residue. As shown in the Examples and the Figures referenced therein, both antibodies were found to agonize or mimic the suppressive effects of VISTA on immunity at least based on (i) their ability to decrease the expression of certain proinflammatory cytokines such as IL-2, IL-4, IL-6, IL-17, granulocyte macrophage colony stimulating factor (GM-CSF) and tumor necrosis factor-alpha (TNF-α) as well as reducing the expression of certain chemokines or chemoattractants such as KC (keratinocyte derived chemokine) or MIP-2 (Macrophage Inflammatory Protein-2); (ii) suppress T cell activity in GVHD model; and to (iii) suppress CD3-driven T cell responses.

Additionally after isolation of these 2 agonist antibodies another 10 chimeric agonist anti-human VISTA antibodies containing human IgG2 constant or Fc regions have been obtained using analogous methods. These antibodies were derived from the antibodies referred to herein as GG8, VSTB95 (INX903), VSTB103 (INX904), VSTB53 (INX905), VSTB92 (INX908), VSTB50 (INX900), VSTB56 (INX901), VSTB63 (INX902), VSTB54 (INX906) and VSTB66 (INX907) (having the sequences in FIG. 4).

Particularly, these chimeric anti-human VISTA antibodies have the variable sequences shown in FIG. 4 and human IgG2 constant regions. As reported in the Summary Tables 1 and 2 infra these anti-human VISTA antibodies when assessed by use of antibody binning were found to bind to 2 different epitope groups designated Group 1 and Group 2. As noted in FIG. 4 the epitope corresponding to Group 2 includes residues in 2 different peptides present in human VISTA, i.e., NLTLLDSGL and VQTGKDAPSNC.

As is indicated in the Tables 1 and 2 infra these 12 different anti-human VISTA antibodies were found to be immunosuppressive in at least one model of immunosuppression and many in several immunosuppression models. Particularly INX905, INX908, INX901, INX902 and INX906 were shown to be immunosuppressive in 2 different assay formats. While all of these antibodies were immunosuppressive and appear to elicit, promote or agonize the immunosuppressive effects of VISTA, INX901, INX902 and INX906 and INX908 appear to be the most immunosuppressive.

Also, other chimeric anti-human VISTA antibodies comprising human IgG2 constant domains containing the variable sequences of other anti-VISTA antibodies shown in FIG. 4 are to be screened for their immunosuppressive properties and their ability to agonize or mimic the immunosuppressive and other effects of human VISTA. Based on the results obtained to date this screening should identify other agonist anti-human VISTA antibodies, particularly those which bind the same epitope. Additionally agonist anti-human VISTA antibodies according to the invention have been shown to be effective (immunosuppressive) in numerous autoimmune and inflammatory animal disease models including arthritis, lupus or SLE, GVHD, inflammatory bowel disease (IBD) or colitis, chronic and acute infectious disease or hepatotoxicity and psoriasis animal models. Based thereon the subject anti-human VISTA agonist antibodies should be well suited for use in therapeutic and prophylactic treatment of autoimmune, allergic and inflammatory conditions.

As noted chimeric IgG2 anti-human VISTA antibodies having the sequences shown in FIG. 4 were shown to be immunosuppressive in different models of immunosuppression. These antibodies moreover elicit these immunosuppressive effects in a specific immunomodulatory manner rather than by effecting the depletion of specific types of T cells or by depleting T cells in general.

As further shown in the examples chimeric IgG2 agonistic anti-human VISTA antibodies containing a mutation in the hinge region elicited substantially the same suppressive effects on immunity, i.e., the mutation within in IgG2 constant region appeared to elicit no enhancement in suppression under the tested experimental conditions. Rather both the IgG2A and IgG2 B forms and mixtures thereof elicited the same immunosuppressive effects. Additionally, based on experiments disclosed in the examples it would appear that FcγR binding may contribute to the agonist properties of the subject anti-human VISTA antibodies. In particular it was found that the inclusion of silent IgG2 constant regions ablated the immunosuppressive properties of the tested agonist antibodies. Based on these results it is hypothesized that one or more FcγRs may affect the agonistic properties of these antibodies and in particular it is hypothesized that FcγRIIA (CD32 or CD32A) or FcγRIIB (CD32B) binding may be involved in the agonist properties of the subject agonist antibodies.

Using these same methods it is expected that other agonist anti-human VISTA IgG2 antibodies may be obtained, e.g., others derived from anti-human VISTA antibodies having the sequences shown in FIG. 4. As mentioned 12 agonist anti-human VISTA antibodies have been obtained to date including those having the sequences contained in FIG. 4. Based on these results it is anticipated that other agonistic anti-human VISTA antibodies may be generated and shown to be immunosuppressive. Also it is anticipated that other agonistic anti-human VISTA antibodies may be generated which bind to the same or overlapping epitope and/or compete with any of the antibodies containing the sequences shown in FIG. 4. In exemplary embodiments these antibodies will bind to the epitope corresponding to Group 1 or Group 2 antibodies or will compete for binding to human VISTA with such antibodies.

Methods for identifying the specific epitope(s) bound by an antibody are known in the art. In the working examples Applicants disclose the elucidation of the epitope bound by a number of anti-VISTA antibodies according to the invention. Thus, in exemplary embodiments agonist anti-human VISTA antibodies according to the invention will comprise IgG2 constant regions or fragments thereof, of the A form, B form or a mixture of the foregoing. In exemplary embodiments these antibodies will bind to one or more FcγRs, e.g., they will bind to the same FcγRs as an intact or wild-type human IgG2 Fc region. In other exemplary embodiments the antibody will bind to CD32 (CD32A and/or CD32B). This may be accomplished by the use of wild-type or modified IgG2 constant regions which bind to CD32 (CD32A and/or CD32B). Further, the agonist antibody may be modified to incorporate another polypeptide such as another Fc polypeptide or antigen binding region which binds to FcγRs such as CD32A and/or CD32B.

The IgG2 Fc or constant regions contained in the inventive agonist anti-human VISTA antibodies optionally may be modified, e.g., in order to alter effector function, e.g., to alter FcR binding, FcRN binding, complement binding, glycosylation and the like. In particular, the IgG2 Fc or constant regions contained in the inventive agonist anti-human VISTA antibodies optionally may be modified by the conversion of the cysteine at position 27 or further optionally by the conversion of another cysteine residue or other residues, e.g., in the hinge region to another amino acid, e.g., a serine. Other potential Fc modifications are disclosed infra.

These VISTA agonist antibodies may be used in treating or preventing diseases conditions or for treating or reducing, ameliorating the pathological effects associated therewith, e.g., inflammation, in treating or preventing conditions wherein the suppression of T cell immunity or the expression of proinflammatory cytokines and or increased expression of chemokines and chemoattractants is therapeutically or prophylactically beneficial. These conditions include in particular autoimmunity, allergy, inflammatory disorders, sepsis, GVHD and for inhibiting unwanted T cell immune responses against transplanted cells, tissues or organs such as CAR-T cell or gene therapy constructs or cells containing.

As mentioned exemplary conditions which may be treated therapeutically or prophylactically using an agonist anti-human VISTA antibody according to the invention include autoimmune conditions, allergy conditions, inflammatory conditions, GVHD, transplant and sepsis. As mentioned, agonist anti-human VISTA antibodies according to the invention have been shown to be therapeutically effective and to be immunosuppressive in numerous animal disease models including arthritis, inflammatory bowel disease (IBD), lupus, GVHD, chronic acute infection/hepatotoxicity and psoriasis disease models. Therefore the inventive antibodies should be well suited for use in treating conditions wherein the suppression of immunity, especially T cell immunity is therapeutically desired.

A. Use of Agonistic or Antagonistic Anti-Human Vista Antibodies and Fragments in Therapy and Diagnosis Compositions containing agonists according to the invention may be used to inhibit T cell immunity and to treat conditions where this is therapeutically desirable such as autoimmunity, allergy or inflammatory conditions. These compositions will comprise an amount of an agonist antibody or antibody fragment according to the invention effective to suppress T cell activation or proliferation or cytokine expression or other effects of VISTA in a subject in need thereof. Such autoimmune, inflammatory and allergic conditions include for example arthritic conditions such as RA, psoriatic arthritis, psoriasis, scleroderma, multiple sclerosis, lupus, IBD, ITP, diabetes, GVHD, sarcoidosis, allergic asthma, hepatitis associated hepatotoxicity and for inhibiting unwanted T cell immune responses against transplanted cells, tissues or organs such as CAR-T cell or gene therapy constructs or cells containing and the like.

Specific conditions wherein the inventive antibodies may be used alone or in association with other therapeutics, especially other immunosuppressant molecules include acquired immune deficiency syndrome (AIDS), acquired splenic atrophy, acute anterior uveitis, Acute Disseminated Encephalomyelitis (ADEM), acute gouty arthritis, acute necrotizing hemorrhagic leukoencephalitis, acute or chronic sinusitis, acute purulent meningitis (or other central nervous system inflammatory disorders), acute serious inflammation, Addison's disease, adrenalitis, adult onset diabetes mellitus (Type II diabetes), adult-onset idiopathic hypoparathyroidism (AOIH), Agammaglobulinemia, agranulocytosis, vasculitides, including vasculitis, optionally, large vessel vasculitis, optionally, polymyalgia rheumatica and giant cell (Takayasu's) arthritis, allergic conditions, allergic contact dermatitis, allergic dermatitis, allergic granulomatous angiitis, allergic hypersensitivity disorders, allergic neuritis, allergic reaction, alopecia areata, alopecia totalis, Alport's syndrome, alveolitis, optionally allergic alveolitis or fibrosing alveolitis, Alzheimer's disease, amyloidosis, amylotrophic lateral sclerosis (ALS; Lou Gehrig's disease), an eosinophil-related disorder, optionally eosinophilia, anaphylaxis, ankylosing spondylitis, angiectasis, antibody-mediated nephritis, Anti-GBM/Anti-TBM nephritis, antigen-antibody complex-mediated diseases, antiglomerular basement membrane disease, antiphospholipid antibody syndrome, antiphospholipid syndrome (APS), aphthae, aphthous stomatitis, aplastic anemia, arrhythmia, arteriosclerosis, arteriosclerotic disorders, arthritis, optionally rheumatoid arthritis such as acute arthritis, or chronic rheumatoid arthritis, arthritis chronica progrediente, arthritis deformans, ascariasis, aspergilloma, granulomas containing eosinophils, aspergillosis, aspermiogenese, asthma, optionally asthma bronchiale, bronchial asthma, or auto-immune asthma, ataxia telangiectasia, ataxic sclerosis, atherosclerosis, autism, autoimmune angioedema, autoimmune aplastic anemia, autoimmune atrophic gastritis, autoimmune diabetes, autoimmune disease of the testis and ovary including autoimmune orchitis and oophoritis, autoimmune disorders associated with collagen disease, autoimmune dysautonomia, autoimmune ear disease, optionally autoimmune inner ear disease (AGED), autoimmune endocrine diseases including thyroiditis such as autoimmune thyroiditis, autoimmune enteropathy syndrome, autoimmune gonadal failure, autoimmune hearing loss, autoimmune hemolysis, Autoimmune hepatitis, autoimmune hepatological disorder, autoimmune hyperlipidemia, autoimmune immunodeficiency, autoimmune inner ear disease (AIED), autoimmune myocarditis, autoimmune neutropenia, autoimmune pancreatitis, autoimmune polyendocrinopathies, autoimmune polyglandular syndrome type I, autoimmune retinopathy, autoimmune thrombocytopenic purpura (ATP), autoimmune thyroid disease, autoimmune urticaria, autoimmune-mediated gastrointestinal diseases, Axonal & neuronal neuropathies, Balo disease, Behçet's disease, benign familial and ischemia-reperfusion injury, benign lymphocytic angiitis, Berger's disease (IgA nephropathy), bird-fancier's lung, blindness, Boeck's disease, bronchiolitis obliterans (non-transplant) vs NSIP, bronchitis, bronchopneumonic aspergillosis, Bruton's syndrome, bullous pemphigoid, Caplan's syndrome, Cardiomyopathy, cardiovascular ischemia, Castleman's syndrome, Celiac disease, celiac sprue (gluten enteropathy), cerebellar degeneration, cerebral ischemia, and disease accompanying vascularization, Chagas disease, channelopathies, optionally epilepsy, channelopathies of the CNS, chorioretinitis, choroiditis, an autoimmune hematological disorder, chronic active hepatitis or autoimmune chronic active hepatitis, chronic contact dermatitis, chronic eosinophilic pneumonia, chronic fatigue syndrome, chronic hepatitis, chronic hypersensitivity pneumonitis, chronic inflammatory arthritis, Chronic inflammatory demyelinating polyneuropathy (CIDP), chronic intractable inflammation, chronic mucocutaneous candidiasis, chronic neuropathy, optionally IgM polyneuropathies or IgM-mediated neuropathy, chronic obstructive airway disease, chronic pulmonary inflammatory disease, Chronic recurrent multifocal osteomyelitis (CRMO), chronic thyroiditis (Hashimoto's thyroiditis) or subacute thyroiditis, Churg-Strauss syndrome, cicatricial pemphigoid/benign mucosal pemphigoid, CNS inflammatory disorders, CNS vasculitis, Coeliac disease, Cogan's syndrome, cold agglutinin disease, colitis polyposa, colitis such as ulcerative colitis, colitis ulcerosa, collagenous colitis, conditions involving infiltration of T cells and chronic inflammatory responses, congenital heart block, congenital rubella infection, Coombs positive anemia, coronary artery disease, Coxsackie myocarditis, CREST syndrome (calcinosis, Raynaud's phenomenon), Crohn's disease, cryoglobulinemia, Cushing's syndrome, cyclitis, optionally chronic cyclitis, heterochronic cyclitis, iridocyclitis, or Fuch's cyclitis, cystic fibrosis, cytokine-induced toxicity, deafness, degenerative arthritis, demyelinating diseases, optionally autoimmune demyelinating diseases, demyelinating neuropathies, dengue, dermatitis herpetiformis and atopic dermatitis, dermatitis including contact dermatitis, dermatomyositis, dermatoses with acute inflammatory components, Devic's disease (neuromyelitis optica), diabetic large-artery disorder, diabetic nephropathy, diabetic retinopathy, Diamond Blackfan anemia, diffuse interstitial pulmonary fibrosis, dilated cardiomyopathy, discoid lupus, diseases involving leukocyte diapedesis, Dressler's syndrome, Dupuytren's contracture, echovirus infection, eczema including allergic or atopic eczema, encephalitis such as Rasmussen's encephalitis and limbic and/or brainstem encephalitis, encephalomyelitis, optionally allergic encephalomyelitis or encephalomyelitis allergica and experimental allergic encephalomyelitis (EAE), endarterial hyperplasia, endocarditis, endocrine ophthalmopathy, endometriosis, endomyocardial fibrosis, endophthalmia phacoanaphylactica, endophthalmitis, enteritis allergica, eosinophilia-myalgia syndrome, eosinophilic fascitis, epidemic keratoconjunctivitis, epidermolysis bullosa acquisita (EBA), episclera, episcleritis, Epstein-Barr virus infection, erythema elevatum et diutinum, erythema multiforme, erythema nodosum leprosum, erythema nodosum, erythroblastosis fetalis, esophageal dysmotility, Essential mixed cryoglobulinemia, ethmoid, Evan's syndrome, Experimental Allergic Encephalomyelitis (EAE), Factor VIII deficiency, farmer's lung, febris rheumatica, Felty's syndrome, fibromyalgia, fibrosing alveolitis, filariasis, focal segmental glomerulosclerosis (FSGS), food poisoning, frontal, gastric atrophy, giant cell arthritis (temporal arthritis), giant cell hepatitis, giant cell polymyalgia, glomerulonephritides, glomerulonephritis (GN) with and without nephrotic syndrome such as chronic or acute glomerulonephritis (e.g., primary GN), Goodpasture's syndrome, gouty arthritis, granulocyte transfusion-associated syndromes, granulomatosis including lymphomatoid granulomatosis, granulomatosis with polyangiitis (GPA), granulomatous uveitis, Grave's disease, Guillain-Barre syndrome, gutatte psoriasis, hemoglobinuria paroxysmatica, Hamman-Rich's disease, Hashimoto's disease, Hashimoto's encephalitis, Hashimoto's thyroiditis, hemochromatosis, hemolytic anemia or immune hemolytic anemia including autoimmune hemolytic anemia (AIHA), hemolytic anemia, hemophilia A, Henoch-Schönlein purpura, Herpes gestationis, human immunodeficiency virus (HIV) infection, hyperalgesia, hypogammaglobulinemia, hypogonadism, hypoparathyroidism, idiopathic diabetes insipidus, idiopathic facial paralysis, idiopathic hypothyroidism, idiopathic IgA nephropathy, idiopathic membranous GN or idiopathic membranous nephropathy, idiopathic nephritic syndrome, idiopathic pulmonary fibrosis, idiopathic sprue, Idiopathic thrombocytopenic purpura (ITP), IgA nephropathy, IgE-mediated diseases, optionally anaphylaxis and allergic or atopic rhinitis, IgG4-related sclerosing disease, ileitis regionalis, immune complex nephritis, immune responses associated with acute and delayed hypersensitivity mediated by cytokines and T-lymphocytes, immune-mediated GN, immunoregulatory lipoproteins, including adult or acute respiratory distress syndrome (ARDS), Inclusion body myositis, infectious arthritis, infertility due to antispermatozoan antibodies, inflammation of all or part of the uvea, inflammatory bowel disease (IBD) inflammatory hyperproliferative skin diseases, inflammatory myopathy, insulin-dependent diabetes (type 1), insulitis, Interstitial cystitis, interstitial lung disease, interstitial lung fibrosis, iritis, ischemic reperfusion disorder, joint inflammation, Juvenile arthritis, juvenile dermatomyositis, juvenile diabetes, juvenile onset (Type I) diabetes mellitus, including pediatric insulin-dependent diabetes mellitus (IDDM), juvenile-onset rheumatoid arthritis, Kawasaki syndrome, keratoconjunctivitis sicca, kypanosomiasis, Lambert-Eaton syndrome, leishmaniasis, leprosy, leucopenia, leukocyte adhesion deficiency, Leukocytoclastic vasculitis, leukopenia, lichen planus, lichen sclerosus, ligneous conjunctivitis, linear IgA dermatosis, Linear IgA disease (LAD), Loffler's syndrome, lupoid hepatitis, lupus (including nephritis, cerebritis, pediatric, non-renal, extrarenal, discoid, alopecia), Lupus (SLE), lupus erythematosus disseminatus, Lyme arthritis, Lyme disease, lymphoid interstitial pneumonitis, malaria, male and female autoimmune infertility, maxillary, medium vessel vasculitis (including Kawasaki's disease and polyarteritis nodosa), membrano- or membranous proliferative GN (MPGN), including Type I and Type II, and rapidly progressive GN, membranous GN (membranous nephropathy), Meniere's disease, meningitis, microscopic colitis, microscopic polyangiitis, migraine, minimal change nephropathy, Mixed connective tissue disease (MCTD), mononucleosis infectiosa, Mooren's ulcer, Mucha-Habermann disease, multifocal motor neuropathy, multiple endocrine failure, multiple organ injury syndrome such as those secondary to septicemia, trauma or hemorrhage, multiple organ injury syndrome, multiple sclerosis (MS) such as spino-optical MS, multiple sclerosis, mumps, muscular disorders, myasthenia gravis such as thymoma-associated myasthenia gravis, myasthenia gravis, myocarditis, myositis, narcolepsy, necrotizing enterocolitis, and transmural colitis, and autoimmune inflammatory bowel disease, necrotizing, cutaneous, or hypersensitivity vasculitis, neonatal lupus syndrome (NLE), nephrosis, nephrotic syndrome, neurological disease, neuromyelitis optica (Devic's), neuromyelitis optica, neuromyotonia, neutropenia, non-cancerous lymphocytosis, nongranulomatous uveitis, non-malignant thymoma, ocular and orbital inflammatory disorders, ocular cicatricial pemphigoid, oophoritis, ophthalmia symphatica, opsoclonus myoclonus syndrome (OMS), opsoclonus or opsoclonus myoclonus syndrome (OMS), and sensory neuropathy, optic neuritis, orchitis granulomatosa, osteoarthritis, palindromic rheumatism, pancreatitis, pancytopenia, PANDAS (Pediatric Autoimmune Neuropsychiatric Disorders Associated with *Streptococcus*), paraneoplastic cerebellar degeneration, paraneoplastic syndrome, paraneoplastic syndromes, including neurologic paraneoplastic syndromes, optionally Lambert-Eaton myasthenic syndrome or Eaton-Lambert syndrome, parasitic diseases such as *Leishmania*, paroxysmal nocturnal hemoglobinuria (PNH), Parry Romberg syndrome, pars planitis (peripheral uveitis), Parsonnage-Turner syndrome, parvovirus infection, pemphigoid such as pemphigoid bullous and skin pemphigoid, pemphigus (including pemphigus vulgaris), pemphigus erythematosus, pemphigus foliaceus, pemphigus mucus-membrane pemphigoid, pemphigus, peptic ulcer, periodic paralysis, peripheral neuropathy, perivenous encephalomyelitis, pernicious anemia (anemia perniciosa), pernicious anemia, phacoantigenic uveitis, pneumonocirrhosis, POEMS syndrome, polyarteritis nodosa, Type I, II, & III, polyarthritis chronica primaria, polychondritis (e.g., refractory or relapsed polychondritis), polyendocrine autoimmune disease, polyendocrine failure, polyglandular syndromes, optionally autoimmune polyglandular syndromes (or polyglandular endocrinopathy syndromes), polymyalgia rheumatica, polymyositis, polymyositis/dermatomyositis, polyneuropathies, polyradiculitis acuta, post-cardiotomy syndrome, posterior uveitis, or autoimmune uveitis, postmyocardial infarction syndrome, postpericardiotomy syndrome, post-streptococcal nephritis, post-vaccination syndromes, presenile dementia, primary biliary cirrhosis, primary hypothyroidism, primary idiopathic myxedema, primary lymphocytosis, which includes monoclonal B cell lymphocytosis, optionally benign monoclonal gammopathy and monoclonal garnmopathy of undetermined significance, MGUS, primary myxedema, primary progressive MS (PPMS), and relapsing remitting MS (RRMS), primary sclerosing cholangitis, progesterone dermatitis, progressive systemic sclerosis, proliferative arthritis, psoriasis such as plaque psoriasis, psoriasis, psoriatic arthritis, pulmonary alveolar proteinosis, pulmonary infiltration eosinophilia, pure red cell anemia or aplasia (PRCA), pure red cell aplasia, purulent or nonpurulent sinusitis, pustular psoriasis and psoriasis of the nails, pyelitis, pyoderma gangrenosum, Quervain's thyroiditis, Raynaud's phenomenon, reactive arthritis, recurrent abortion, reduction in blood pressure response, reflex sympathetic dystrophy, refractory sprue, Reiter's disease or syndrome, relapsing polychondritis, reperfusion injury of myocardial or other tissues, reperfusion injury, respiratory distress syndrome, restless legs syndrome, retinal autoimmunity, retroperitoneal fibrosis, Reynaud's syndrome, rheumatic diseases, rheumatic fever, rheumatism, rheumatoid arthritis, rheumatoid spondylitis, rubella virus infection, Sampter's syndrome, sarcoidosis, schistosomiasis, Schmidt syndrome, SCID and Epstein-Barr virus-associated diseases, sclera, scleritis, sclerodactyl, scleroderma, optionally systemic scleroderma, sclerosing cholangitis, sclerosis disseminata, sclerosis such as systemic sclerosis, sensoneural hearing loss, seronegative spondyloarthritides, Sheehan's syndrome, Shulman's syndrome, silicosis, Sjögren's syndrome, sperm & testicular autoimmunity, sphenoid sinusitis, Stevens-Johnson syndrome, stiffman (or stiff-person) syndrome, subacute bacterial endocarditis (SBE), subacute cutaneous lupus erythematosus, sudden hearing loss, Susac's syndrome, Sydenham's chorea, sympathetic ophthalmia, systemic lupus erythematosus (SLE) or systemic lupus erythematodes, cutaneous SLE, systemic necrotizing vasculitis, ANCA-associated vasculitis, optionally Churg-Strauss vasculitis or syndrome (CSS), tabes dorsalis, Takayasu's arteritis, telangiectasia, temporal arteritis/Giant cell arteritis, thromboangiitis ubiterans, thrombocytopenia, including thrombotic thrombocytopenic purpura (TTP) and autoimmune or immune-mediated thrombocytopenia such as idiopathic thrombocytopenic purpura (ITP) including chronic or acute ITP, thrombocytopenic purpura (TTP), thyrotoxicosis, tissue injury, Tolosa-Hunt syndrome, toxic epidermal necrolysis, toxic-shock syndrome, transfusion reaction, transient hypogammaglobulinemia of infancy, transverse myelitis, traverse myelitis, tropical pulmonary eosinophilia, tuberculosis, ulcerative colitis, undifferentiated connective tissue disease (UCTD), urticaria, optionally chronic allergic urticaria and chronic idiopathic urticaria, including chronic autoimmune urticaria, uveitis, anterior uveitis, uveoretinitis, valvulitis, vascular dysfunction, vasculitis, vertebral arthritis, vesiculobullous dermatosis, vitiligo, Wegener's granulomatosis (Granulomatosis with Polyangiitis (GPA)), Wiskott-Aldrich syndrome, or x-linked hyper IgM syndrome.

By contrast compositions containing VISTA antagonist antibodies according to the invention may be used to promote T cell immunity and to treat conditions where this is therapeutically desirable such as cancer and infectious conditions such as viral, bacterial, yeast, fungal, protozoal and parasite infections. These compositions will comprise an amount of an antagonist according to the invention effective to promote T cell activation or proliferation or cytokine expression or other effects of VISTA in a subject in need thereof. Such cancer conditions include for example blood cancers, and solid tumors such as leukemias, lymphomas, myelodysplastic syndrome, myeloma, lung cancer, and other cancers identified herein.

It should be understood that the disease conditions identified herein are intended to be exemplary and not exhaustive.

The subject agonists and antagonists may be combined with other therapeutics which may be administered in the same or different compositions, at the same or different time. For example, the subject agonists may be administered in a therapeutic regimen that includes the administration of a PD-1 or PD-L1 agonist, CTLA4-Ig, a cytokine, a cytokine agonist or antagonist, or another receptor agonist or antagonist.

Downregulation of Immune Responses

Upregulating or enhancing the inhibitory function of a VISTA polypeptide may be used to downregulate immune responses. Downregulation can be in the form of inhibiting or blocking an immune response already in progress, or may involve preventing the induction of an immune response. The functions of activated immune cells can be inhibited by downregulating immune cell responses or by inducing specific anergy in immune cells, or both. For example, VISTA agonist antibodies may bind to the VISTA polypeptide which is expressed on various immune cells and thereby down modulate the immune response. This agonist antibody may be monospecific or multispecific, e.g., it may comprise a bispecific antibody such as a BiTE. For example, such an antibody can comprise a VISTA antigen binding moiety and another antigen binding moiety, e.g., which targets a cell surface receptor on an immune cell, e.g., a T cell, a B cell, or a myeloid cell. Such an antibody, in addition to comprising a VISTA antigen binding site, may comprise a binding site which binds to a B cell antigen receptor, a T cell antigen receptor, or an Fc or other receptor, in order to target the molecule to a specific cell population. Selection of this second antigen for the bispecific antibody provides flexibility in selection of cell population to be targeted. VISTA agonist antibodies that promote or mimic VISTA activity may enhance the interaction of VISTA with its natural binding partners. As disclosed herein other human VISTA activating or agonist antibodies can be identified by their ability to inhibit T cell activity or proliferation and/or based on their immunosuppressive effects in vitro or inflammatory, allergic or autoimmune disease models.

A number of art-recognized readouts of cell activation can be employed to measure, e.g., cell proliferation or effector function (e.g., antibody production, cytokine production, phagocytosis) in the presence of the activating agent. The ability of a test antibody to agonize or promote the effects of human VISTA and thereby block this activation can be readily determined by measuring the ability of the agent to affect a decrease in proliferation or effector function being measured. Accordingly, the ability of a test antibody to be immunosuppressive and to block immune activation can be determined by measuring cytokine production and/or proliferation at different concentrations of antigen.

Tolerance may be induced against specific antigens by co-administering an antigen with a VISTA agonist antibody according to the invention. For example, tolerance may be induced to specific polypeptides Immune responses to allergens or foreign polypeptides to which an immune response is undesirable can be inhibited. For example, patients that receive Factor VIII frequently generate antibodies against this clotting factor. Co-administration of a VISTA agonist antibody according to the invention that stimulates or mimics VISTA activity or interaction with its natural binding partner, with recombinant factor VIII may suppress this undesired immune response.

A VISTA agonist antibody according to the invention may be used in combination with another agent that blocks the activity of costimulatory receptors on an immune cell or which agonizes the activity of another immunosuppressive receptor or ligand expressed on immune cells in order to downmodulate immune responses. Exemplary molecules include: PD-1, PDL-1 agonists, soluble forms of CTLA-4, anti-B7-1 antibodies, anti-B7-2 antibodies, antagonistic antibodies targeting one or more of LAG-3, TIM-3, BTLA, B7-H4, B7H3, et al. and/or agonistic antibodies targeting one or more of CD40, CD137, OX40, GITR, CD27, CD28 or ICOS or combinations thereof. These moieties can be combined in a single composition or compound, e.g., a bispecific antibody containing a VISTA agonist antibody according to the invention and further comprising another immune agonist antibody or it may comprise a fusion polypeptide containing a VISTA agonist antibody according to the invention which is fused to another immunosuppressive polypeptide or other active agent. Alternatively these moieties may be administered as separate or discrete entities (simultaneously or sequentially) in the same or different compositions to down regulate immune cell mediated immune responses in a subject.

Examples of specific immmunoinhibitory molecules that may be combined with VISTA agonist antibodies according to the invention include antibodies that block a costimulatory signal (e.g., against CD28 or ICOS), antibodies that activate an inhibitory signal via CTLA4, and/or antibodies against other immune cell markers (e.g., against CD40, CD40 ligand, or cytokines), fusion proteins (e.g., CTLA4-Fc or PD-1-Fc), and immunosuppressive drugs (e.g., rapamycin, cyclosporine A, or FK506).

In a further embodiment, bispecific antibodies containing VISTA agonist antibodies according to the invention are useful for targeting a specific cell population, e.g., using a marker found only on a certain type of cell, e.g., B lymphocytes, monocytes, dendritic cells, or Langerhans cells. Down regulating immune responses by activating VISTA activity or VISTA-immune cell interactions (and thus stimulating the negative signaling function of VISTA) is useful in downmodulating the immune response, e.g., in situations of tissue, skin and organ transplantation, in graft-versus-host disease (GVHD), or allergies, or in autoimmune and inflammatory diseases such as systemic lupus erythematosus, IBD, RA, psoriasis and multiple sclerosis. For example, blockage of immune cell function results in reduced tissue destruction in tissue transplantation. Typically, in tissue transplants, rejection of the transplant is initiated through its recognition as foreign by immune cells, followed by an immune reaction that destroys the transplant. The administration of a molecule which promotes the activity of VISTA or the interaction of VISTA with its natural binding partner(s), on immune cells alone or in conjunction with another downmodulatory agent prior to or at the time of transplantation can inhibit the generation of a costimulatory signal. Moreover, promotion of VISTA activity may also be sufficient to anergize the immune cells, thereby inducing tolerance in a subject.

To achieve sufficient immunosuppression or tolerance in some diseases or in some subjects, it may necessary to block the costimulatory function of other molecules. For example, it may be desirable to block the function of B7-1 and B7-2 by administering a soluble form of a combination of peptides having an activity of each of these antigens or blocking antibodies against these antigens (separately or together in a single composition) prior to or at the time of transplantation. Alternatively, it may be desirable to promote inhibitory activity of VISTA and to further inhibit a costimulatory activity of B7-1 and/or B7-2.

The subject anti-human VISTA agonist antibodies are especially useful in treating autoimmune disease. Many autoimmune disorders are the result of inappropriate activation of immune cells that are reactive against self-tissue and which promote the production of cytokines and autoantibodies involved in the pathology of the diseases. Preventing the activation of autoreactive immune cells may reduce or eliminate disease symptoms. Administration of the subject anti-human VISTA agonist antibodies that promote activity of VISTA or VISTA interaction with its natural binding partner(s), may induce antigen-specific tolerance of autoreactive immune cells which could lead to long-term relief from the disease. Additionally, co-administration of agents which block costimulation of immune cells by disrupting receptor-ligand interactions of B7 molecules with costimulatory receptors may be useful in inhibiting immune cell activation to prevent production of autoantibodies or cytokines which may be involved in the disease process.

Down regulation of an immune response via stimulation of VISTA activity or VISTA interaction with its natural binding partner(s) using the subject anti-human VISTA agonist antibodies may also be useful in treating an autoimmune attack of autologous tissues. Thus, conditions that are caused or exacerbated by autoimmune attack (e.g., heart disease, myocardial infarction or atherosclerosis) may be ameliorated or improved by increasing VISTA activity or VISTA binding to its natural binding partner. It is therefore within the scope of the invention to modulate conditions exacerbated by autoimmune attack, such as autoimmune disorders (as well as conditions such as heart disease, myocardial infarction, and atherosclerosis) by stimulating VISTA activity or VISTA interaction with its counter receptor using the subject anti-human VISTA agonist antibodies.

As mentioned previously the efficacy of agonist anti-human VISTA antibodies according to the invention for preventing or alleviating autoimmune and inflammatory disorders can be determined using a number of well-characterized animal models of human autoimmune and inflammatory diseases. Examples include murine experimental autoimmune encephalitis, systemic lupus erythematosus in MRL/Ipr/Ipr mice or NZB hybrid mice, murine autoimmune collagen arthritis, diabetes mellitus in NOD mice and BB rats, and murine experimental myasthenia gravis. See Paul ed., *Fundamental Immunology*, Raven Press, New York, 1989, pages 840-856.

Inhibition of immune cell activation is further useful therapeutically in the treatment of allergies and allergic reactions, e.g., by inhibiting IgE production. The subject anti-human VISTA agonist antibodies which promote or mimic VISTA activity or VISTA interaction with its natural binding partner(s) can be administered to an allergic subject to inhibit immune cell-mediated allergic responses in the subject. Stimulation of VISTA activity or interaction with its natural binding partner(s), can be accompanied by exposure to allergen in conjunction with appropriate MHC molecules. Allergic reactions can be systemic or local in nature, depending on the route of entry of the allergen and the pattern of deposition of IgE on mast cells or basophils. Thus, immune cell-mediated allergic responses can be inhibited locally or systemically by administration of the subject anti-human VISTA agonist antibodies.

Selection of Anti-VISTA Antibodies that Bind to the Same Epitope

In certain embodiments, an agonistic anti-VISTA antibody according to the invention possesses desired functional properties such as modulation of immune stimulation and related functions. As shown in FIG. 4 and disclosed in the working examples, the epitopic specificity of a number of anti-human VISTA agonist antibodies according to the invention has been elucidated. As a number of antibodies which have been shown to bind to the same epitope have been found to be immunosuppressive it is expected that other VISTA agonist antibodies may be identified which bind to the same or overlapping epitope, i.e., they will interact with one or more of the amino acid residues of human VISTA polypeptide with which the exemplary VISTA agonist antibodies bind. Other antibodies with the same epitopic specificity may be selected and/or those which have the ability to cross-compete for binding to VISTA antigen with the desired antibodies. For example, the epitopic specificity of a desired antibody may be determined using a library of overlapping peptides comprising the entire VISTA polypeptide, e.g., 15-mers or an overlapping peptide library constituting a portion containing a desired epitope of VISTA and antibodies which bind to the same peptides or one or more residues thereof in the library are determined to bind the same linear or conformational epitope. In the examples the epitopic specificity was determined using Pepscan® methods which may be used to identify linear and conformational epitopes.

Modification of Agonist Antibodies According to the Invention

In addition or as an alternative to modifications made within the framework or CDR regions, antibodies according to at least some embodiments of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody according to at least some embodiments of the invention may be chemically modified (e.g., one or more chemical moieties can be attached to the antibody) or be modified to alter its glycosylation, again to alter one or more functional properties of the antibody. Such embodiments are described further below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CHI is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcal protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, one or more of the following mutations can be introduced: T252L, T254S, and T256F, as described in U.S. Pat. No. 6,277,375 to Ward. Alternatively, to increase the biological half-life, the antibody can be altered within the CHI or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the Cl component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et al.

In yet another example, the Fc region is modified to increase the affinity of the antibody for an Fγ receptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta. Moreover, the binding sites on human IgGI for FcγRI, FcγRII, FcγRIII and FcRn have been mapped and variants with improved binding have been described (see Shields, R. L. et al. (2001) *J. Biol. Chem.* 276:6591-6604). Specific mutations at positions 256, 290, 298, 333, 334 and 339 are shown to improve binding to FcγRIII. Additionally, the following combination mutants are shown to improve FcγRIII binding: T256A/S298A, S298A/E333A, S298A/

K224A and S298A/E333A/K334A. Furthermore, mutations such as M252Y/S254T/T256E or M428L/N434S improve binding to FcRn and increase antibody circulation half-life (see Chan C A and Carter P J (2010) *Nature Rev Immunol* 10:301-316).

In still another embodiment, the antibody can be modified to abrogate in vivo Fab arm exchange. Specifically, this process involves the exchange of IgG4 half-molecules (one heavy chain plus one light chain) between other IgG4 antibodies that effectively results in b specific antibodies which are functionally monovalent. Mutations to the hinge region and constant domains of the heavy chain can abrogate this exchange (see Aalberse, R C, Schuurman J., 2002, *Immunology* 105:9-19).

In still another embodiment, the glycosylation of an antibody is modified. For example, an aglycosylated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglyclosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies according to at least some embodiments of the invention to thereby produce an antibody with altered glycosylation. For example, the cell lines Ms704, Ms705, and Ms709 lack the fucosyltransferase gene, FUT8 (a (1,6) fucosyltransferase), such that antibodies expressed in the Ms704, Ms705, and Ms709 cell lines lack fucose on their carbohydrates. The Ms704, Ms705, and Ms709 FUT8 cell lines are created by the targeted disruption of the FUT8 gene in CHO/DG44 cells using two replacement vectors (see U.S. Patent Publication No. 20040110704 by Yamane et al. and Yamane-Ohnuki et al. (2004) *Biotechnol Bioeng* 87:614-22). As another example, EP 1,176,195 by Hanai et al. describes a cell line with a functionally disrupted FUT8 gene, which encodes a fucosyl transferase, such that antibodies expressed in such a cell line exhibit hypofucosylation by reducing or eliminating the a 1,6 bond-related enzyme. Hanai et al. also describe cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al. (2002) *J. Biol. Chem.* 277:26733-26740). PCT Publication WO 99/54342 by Umana et al. describes cell lines engineered to express glycoprotein-modifying glycosyl transferases (e.g., P(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) *Nat. Biotech.* 17: 176-180). Alternatively, the fucose residues of the antibody may be cleaved off using a fucosidase enzyme. For example, the fucosidase α-L-fucosidase removes fucosyl residues from antibodies (Tarentino, A. L. et al. (1975) *Biochem.* 14:5516-23).

Another modification of the antibodies herein that is contemplated by the invention is pegylation or the addition of other water soluble moieties, typically polymers, e.g., in order to enhance half-life. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (Ci-Cio) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies according to at least some embodiments of the invention. See for example, EP 0 154 316 by Nishimura et al. and EP 0 401 384 by Ishikawa et al.

Methods of Engineering Antibodies

In certain embodiments, an agonist anti-VISTA antibody according to the invention having $V_H$ and $V_I$ sequences can be used to create new anti-VISTA antibodies, respectively, by modifying the $V_H$ and/or $V_I$ sequences, or the constant regions attached thereto. Thus, in another aspect according to at least some embodiments of the invention, the structural features of an anti-VISTA antibody according to at least some embodiments of the invention, are used to create structurally related anti-VISTA antibodies that retain at least one functional property of the antibodies according to at least some embodiments of the invention, such as binding to human VISTA. For example, one or more CDR regions of one VISTA antibody or mutations thereof can be combined recombinantly with known framework regions and/or other CDRs to create additional, recombinantly-engineered, anti-VISTA antibodies according to at least some embodiments of the invention, as discussed above. Other types of modifications include those described in the previous section. The starting material for the engineering method is one or more of the $V_H$ and/or $V_I$ sequences provided herein, or one or more CDR regions thereof. To create the engineered antibody, it is not necessary to actually prepare (i.e., express as a protein) an antibody having one or more of the $V_H$ and/or VL sequences provided herein, or one or more CDR regions thereof. Rather, the information contained in the sequences is used as the starting material to create a "second generation" sequences derived from the original sequences and then the "second generation" sequences is prepared and expressed as a protein.

Standard molecular biology techniques can be used to prepare and express altered antibody sequence. Preferably, the anti-VISTA antibody encoded by the altered antibody sequences is one that retains one, some or all of the functional properties of the anti-VISTA antibodies, respectively, produced by methods and with sequences provided herein, which functional properties include binding to VISTA antigen with a specific $K_D$ level or less and/or modulating immune responses and/or selectively binding to desired target cells such as for example, that express VISTA antigen.

The functional properties of the altered antibodies can be assessed using standard assays available in the art and/or described herein. In certain embodiments of the methods of engineering antibodies according to at least some embodiments of the invention, mutations can be introduced randomly or selectively along all or part of an anti-VISTA antibody coding sequence and the resulting modified anti-VISTA antibodies can be screened for binding activity and/or other desired functional properties.

Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Nucleic Acid Molecules Encoding Antibodies

The invention further provides nucleic acids which encode an anti-VISTA antibody according to the invention, or a fragment or conjugate thereof. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. (1987) *Current Protocols in Molecular Biology*, Greene Publishing and Wiley Interscience, New York. A nucleic acid according to at least some embodiments of the invention can be, for example, DNA or RNA and may or may not contain intronic sequences. In a preferred embodiment, the nucleic acid is a cDNA molecule.

Nucleic acids according to at least some embodiments of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$ or $V_H$-encoding DNA fragment is operatively linked to another DNA fragment encoding another protein, such as an antibody constant region or a flexible linker. As previously defined, "operatively linked" means that that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions (CH1, CH2 and CH3). The sequences of human heavy chain constant region genes are known in the art (see e.g., Kabat, E. A., el al. (1991) *Sequences of Proteins of Immunological Interest*, Fifth Edition, U.S. Department of Health and Human Services, NIH Publication No. 91-3242) and DNA fragments encompassing these regions can be obtained by standard PCR amplification. The heavy chain constant region can be an IgGI, IgG2, IgG3, IgG4, IgA, IgE, IgM or IgD constant region, but most preferably is an IgGI, IgG2 or IgG4 constant region. For a Fab fragment heavy chain gene, the VH-encoding DNA can be operatively linked to another DNA molecule encoding only the heavy chain $C_{H1}$ constant region.

The isolated DNA encoding the $V_L$ region can be converted to a full-length light chain gene (as well as a Fab light chain gene) by operatively linking the $V_L$-encoding DNA to another DNA molecule encoding the light chain constant region, $C_L$—The sequences of human light chain constant region genes are known in the art (see e.g., Kabat, E. A., et al. (1991) *Sequences of Proteins of Immunological Interest*, Fifth Edition, U.S. Department of Health and Human Services, NIH Publication No. 91-3242) and DNA fragments encompassing these regions can be obtained by standard PCR amplification. The light chain constant region can be a kappa (κ) or lambda (λ) constant region, but most preferably is a K constant region.

To create a scFv gene, the $V_H$- and $V_L$-encoding DNA fragments are operatively linked to another fragment encoding a flexible linker, e.g., encoding the amino acid sequence (Gly4-Ser)3, such that the $V_H$ and $V_I$ sequences can be expressed as a contiguous single-chain protein, with the $V_I$ and $V_H$ regions joined by the flexible linker (see e.g., Bird et al. (1988) *Science* 242:423-426; Huston et al. (1988) *Proc. Natl. Acad. Sci., USA* 85:5879-5883; McCafferty et al., (1990) *Nature* 348:552-554).

Production of Anti-VISTA Monoclonal Antibodies

Anti-VISTA monoclonal antibodies (mAbs) and antigen-binding fragments according to the present invention can be produced by a variety of techniques, including conventional monoclonal antibody methodology e.g., the standard somatic cell hybridization technique of Kohler and Milstein (1975) *Nature* 256:495. Although somatic cell hybridization procedures are preferred, in principle, other techniques for producing monoclonal antibody can be employed e.g., viral or oncogenic transformation of B lymphocytes.

A preferred animal system for preparing hybridomas is the murine system. Hybridoma production in the mouse is a very well-established procedure. Immunization protocols and techniques for isolation of immunized splenocytes for fusion are known in the art. Fusion partners (e.g., murine myeloma cells) and fusion procedures are also known. Chimeric or humanized antibodies of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter and U.S. Pat. Nos. 5,530,101; 5,585,089; 5,693, 762 and 6,180,370 to Queen et al.).

According to at least some embodiments of the invention, the antibodies are human monoclonal antibodies. Such human monoclonal antibodies directed against VISTA can be generated using transgenic or transchromosomic mice carrying parts of the human immune system rather than the mouse system. These transgenic and transchromosomic mice include mice referred to herein as the HuMAb Mouse™ and KM Mouse™ respectively, and are collectively referred to herein as "human Ig mice." The HuMAb Mouse™ (Medarex Inc.) contains human immunoglobulin gene miniloci that encode unrearranged human heavy μ and γ and κ light chain immunoglobulin sequences, together with targeted mutations that inactivate the endogenous μ and κ chain loci (see e.g., Lonberg, et al. (1994) *Nature* 368 (6474): 856-859). Accordingly, the mice exhibit reduced expression of mouse IgM or κ and in response to immunization, the introduced human heavy and light chain transgenes undergo class switching and somatic mutation to generate high affinity human IgG κ monoclonal (Lonberg, N. et al. (1994), supra; reviewed in Lonberg, N. (1994) *Handbook of Experimental Pharmacology* 113:49-101; Lonberg, N. and Huszar, D. (1995) Intern. Rev. Immunol. 13: 65-93, and Harding, F. and Lonberg, N. (1995) *Ann. N.Y. Acad. Sci.* 764:536-546). The preparation and use of the HuMab Mouse®, and the genomic modifications carried by such mice, is further described in Taylor, L. et al. (1992) *Nucleic Acids Research* 20:6287-6295; Chen, J. et al. (1993) International Immunology 5:647-656; Tuaillon et al. (1993) *Proc. Natl. Acad. Sci. USA* 90:3720-3724; Choi et al. (1993) *Nature Genetics* 4: 117-123; Chen, J. et al. (1993) EMBO J. 12: 821-830; Tuaillon et al. (1994) *J. Immunol.* 152:2912-2920; Taylor, L. et al. (1994) *International Immunology* 6:579-591; and Fishwild, D. et al. (1996) *Nature Biotechnology* 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In another embodiment, human antibodies according to at least some embodiments of the invention can be raised using a mouse that carries human immunoglobulin sequences on both transgenes and transchomosomes, such as a mouse that carries a human heavy chain transgene and a human light chain transchromosome. Such mice, referred to herein as "KM Mice™", are described in detail in PCT Publication WO 02/43478 to Ishida et al.

Still further, alternative transgenic animal systems expressing human immunoglobulin genes are available in the art and can be used to raise anti-VISTA antibodies according to at least some embodiments of the invention. For example, an alternative transgenic system referred to as the Xenomouse (Abgenix, Inc.) can be used; such mice are described in, for example, U.S. Pat. Nos. 5,939,598; 6,075,181; 6,114,598; 6, 150,584 and 6,162,963 to Kucherlapati et al.

Moreover, alternative transchromosomic animal systems expressing human immunoglobulin genes are available in the art and can be used to raise anti-VISTA antibodies according to at least some embodiments of the invention. For example, mice carrying both a human heavy chain transchromosome and a human light chain transchromosome, referred to as "TC mice" can be used; such mice are described in Tomizuka et al. (2000) *Proc. Natl. Acad Sci. USA* 97:722-727. Furthermore, cows carrying human heavy and light chain transchromosomes have been described in the art (Kuroiwa et al. (2002) *Nature Biotechnology* 20:889-894) and can be used to raise anti-VISTA antibodies according to at least some embodiments of the invention.

Human monoclonal antibodies according to at least some embodiments of the invention can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies according to at least some embodiments of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Immunization of Human Ig Mice

In some embodiments human Ig mice are used to raise human anti-VISTA antibodies according to the invention, e.g., by immunizing such mice with a purified or enriched preparation of VISTA antigen and/or recombinant VISTA, or VISTA fusion protein, as described by Lonberg, N. et al. (1994) *Nature* 368(6474): 856-859; Fishwild, D. et al. (1996) *Nature Biotechnology* 14: 845-851; and PCT Publication WO 98/24884 and WO 01/14424. Preferably, the mice will be 6-16 weeks of age upon the first infusion. For example, a purified or recombinant preparation (dose ranging from 0.5-500 μg) of VISTA antigen can be used to immunize the human Ig mice intraperitoneally.

In general transgenic mice respond when initially immunized intraperitoneally (IP) with antigen in complete Freund's adjuvant, followed by every other week IP immunizations (up to a total of 6) with antigen in incomplete Freund's adjuvant. However, adjuvants other than Freund's are also found to be effective. In addition, whole cells in the absence of adjuvant are found to be highly immunogenic. The immune response can be monitored over the course of the immunization protocol with plasma samples being obtained by retroorbital bleeds. The plasma can be screened by ELISA (as described below), and mice with sufficient titers of anti-VISTA human immunoglobulin can be used for fusions. Mice can be boosted intravenously with antigen 3 days before sacrifice and removal of the spleen. It is expected that 2-3 fusions for each immunization may need to be performed. Between 6 and 24 mice are typically immunized for each antigen. Usually both HCo7 and HCo12 strains are used. In addition, both HCo7 and HCo12 transgene can be bred together into a single mouse having two different human heavy chain transgenes (HCo7/HCo 12). Alternatively or additionally, the KM Mouse™ strain can be used. In an exemplary embodiment these mice will be engineered to selectively produce human IgG2 antibodies.

Generation of Hybridomas Producing Human Monoclonal Antibodies

In certain embodiments, hybridomas producing a human monoclonal anti-VISTA antibody according to the invention may be generated using splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the numbers of P3X63-Ag8.653 nonsecreting mouse myeloma cells (ATCC, CRL 1580) with 50% PEG. Cells are plated at approximately 2×105 in flat bottom microtiter plate, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and IX HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-Sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

Generation of Transfectomas Producing Monoclonal Antibodies

In certain embodiments, an anti-VISTA antibody according to the invention can be produced in a host cell transfectoma using, for example, a combination of recombinant DNA techniques and gene transfection methods as is well known in the art (e.g., Morrison, S. (1985) *Science* 229: 1202). For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the $C_H$ segments within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

Characterization of Antibody Binding to Antigen

In certain embodiments, the binding specificity of an agonistic anti-VISTA antibody according to the invention is determined by known antibody binding assay techniques such as ELISA. In an exemplary ELISA, microtiter plates are coated with a purified antigen, herein VISTA at 0.25 μg/ml in PBS, and then blocked with 5% bovine serum albumin in PBS. Dilutions of antibody (e.g., dilutions of plasma from-immunized mice) are added to each well and incubated for 1-2 hours at 37° C. The plates are washed with PBS/Tween and then incubated with secondary reagent (e.g., for human antibodies, a goat-anti-human IgG Fc-specific polyclonal reagent) conjugated to alkaline phosphatase for 1 hour at 37° C. After washing, the plates are developed with pNPP substrate (1 mg/ml), and analyzed at OD of 405-650. Preferably, mice which develop the highest titers will be used for fusions.

An ELISA assay as described above can also be used to screen for hybridomas that show positive reactivity with VISTA immunogen. Hybridomas that bind with high avidity to VISTA are subcloned and further characterized. One clone from each hybridoma, which retains the reactivity of the parent cells (by ELISA), can be chosen for making a 5-10 vial cell bank stored at −140° C., and for antibody purification.

To purify anti-VISTA antibodies, selected hybridomas can be grown in two-liter spinner-flasks for monoclonal antibody purification. Supernatants can be filtered and concentrated before affinity chromatography with protein A-Sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

To determine if the selected anti-VISTA monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using VISTA coated-ELISA plates as described above. Biotinylated mAb binding can be detected with a strep-avidin-alkaline phosphatase probe.

To determine the isotype of purified antibodies, isotype ELISAs can be performed using reagents specific for antibodies of a particular isotype, e.g., IgG2's. For example, to determine the isotype of a human monoclonal antibody, wells of microtiter plates can be coated with ˆg/ml of anti-human immunoglobulin overnight at 4° C. After blocking with 1% BSA, the plates are reacted with 1 mug/ml or less of test monoclonal antibodies or purified isotype controls, at ambient temperature for one to two hours. The wells can then be reacted with either human IgG1 or human IgM-specific alkaline phosphatase-conjugated probes. Plates are developed and analyzed as described above.

Anti-VISTA human IgGs can be further tested for reactivity with VISTA antigen, respectively, by Western blotting. Briefly, VISTA antigen can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

In another aspect, the present invention features antibody-drug conjugates (ADCs), consisting of an antibody (or antibody fragment such as a single-chain variable fragment (scFv) linked to a payload drug (often cytotoxic). The antibody causes the ADC to bind to the target cancer cells. Often the ADC is then internalized by the cell and the drug is released into the cell. Because of the targeting, the side effects are lower and give a wider therapeutic window. Hydrophilic linkers (e.g., PEG4Mal) help prevent the drug being pumped out of resistant cancer cells through MDR (multiple drug resistance) transporters.

In another aspect, the present invention features immunoconjugates comprising an anti-VISTA antibody, or a fragment thereof, conjugated to a therapeutic agent, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include Taxol, cytochalasin B, gramicidin D, ethidium bromide, emetine, mitomycin, etoposide, teniposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thiotepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other examples of therapeutic cytotoxins that can be conjugated to an antibody according to at least some embodiments of the invention include duocarmycins, calicheamicin, maytansines and auristatins, and derivatives thereof. An example of a calicheamicin antibody conjugate is commercially available (Mylotarg™ Wyeth).

Cytotoxins can be conjugated to antibodies according to at least some embodiments of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D). For further discussion of types of cytotoxins, linkers and methods for conjugating therapeutic agents to antibodies, see also Saito, G. et al. (2003) *Adv. Drug Deliv. Rev.* 55: 199-215; Trail, P. A. et al. (2003) *Cancer Immunol. Immunother.* 52:328-337; Payne, G. (2003) *Cancer Cell* 3:207-212; Allen, T. M. (2002) *Nat. Rev. Cancer* 2:750-763; Pastan, I. and Kreitman, R. J. (2002) *Curr. Opin. Investig. Drugs* 3: 1089-1091; Senter, P. D. and Springer, C. J. (2001) *Adv. Drug Deliv. Rev.* 53:247-264.

Antibodies of the present invention also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine 131, indium 111, yttrium 90 and lutetium 177. Methods for preparing radioimmunoconjugates are established in the art. Radioimmunoconjugates are commercially available, including Zevalin® (BiogenIDEC) and Bexxar®. (Corixa Pharmaceuticals), and similar methods can be used to prepare radioimmunoconjugates using the antibodies according to at least some embodiments of the invention.

The agonist anti-human VISTA antibodies and conjugates containing according to at least some embodiments of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, *pseudomonas* exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in *Monoclonal Antibodies And Cancer Therapy*, Reisfeld et al. (eds.), pp. 243-56 (Alan R. Liss, Inc. 1985); Hellstrom et al., "Antibodies For Drug Delivery", in *Controlled Drug Delivery* (2nd Ed.), Robinson et al. (eds.), pp. 623-53 (Marcel Dekker, Inc. 1987); Thorpe, "Carriers Of Cytotoxic Agents In Cancer Therapy: A Review", in *Monoclonal Antibodies '84: Biological And Clinical Applications*, Pinchera et al. (eds.), pp. 475-506 (1985); "Analysis, Results, And Future Prospective Of The Therapeutic Use Of Radiolabeled Antibody In Cancer Therapy", in *Monoclonal Antibodies For Cancer Detection And Therapy*, Baldwin et al. (eds.), pp. 303-16 (Academic Press 1985), and Thorpe et al., "The Preparation And Cytotoxic Properties Of Antibody-Toxin Conjugates", *Immunol. Rev.,* 62: 119-58 (1982).

Bispecific Molecules

According to at least some embodiments the invention also encompasses multispecific anti-VISTA agonist antibodies. Multispecific antibodies are monoclonal antibodies that have binding specificities for at least two different sites. In another aspect, the present invention features bispecific molecules comprising an anti-VISTA antibody, or a fragment thereof, according to at least some embodiments of the invention. An antibody according to at least some embodiments of the invention, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody according to at least some embodiments of the invention may in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule according to at least some embodiments of the invention, an antibody can be functionally linked (e.g., by chemical coupling, genetic fusion, noncovalent association or otherwise) to one or more other binding molecules, such as another antibody, antibody fragment, peptide or binding mimetic, such that a bispecific molecule results. In certain embodiments, one of the binding specificities of the bispecific antibodies is for VISTA and the other is for any other antigen. In certain embodiments, bispecific antibodies may bind to two different epitopes of VISTA. Bispecific antibodies may also be used to localize cytotoxic agents to cells which express VISTA. Bispecific antibodies can be prepared as full length antibodies or antibody fragments.

A bispecific antibody according to at least some embodiments of the invention is an antibody which can bind simultaneously to two targets which are of different structure. Bispecific antibodies (bsAb) and bispecific antibody fragments (bsFab) according to at least some embodiments of the invention have at least one arm that specifically binds to a B-cell antigen or epitope and at least one other arm that specifically binds a targetable conjugate.

According to at least some embodiments the invention encompasses also a fusion antibody protein, which is a recombinantly produced antigen-binding molecule in which two or more different single-chain antibody or antibody fragment segments with the same or different specificities are linked. A variety of bispecific fusion antibody proteins can be produced using molecular engineering. In one form, the bispecific fusion antibody protein is monovalent, consisting of, for example, a sent with a single binding site for one antigen and a Fab fragment with a single binding site for a second antigen. In another form, the bispecific fusion antibody protein is divalent, consisting of, for example, an IgG with two binding sites for one antigen and two scFv with two binding sites for a second antigen.

The invention further encompasses engineered antibodies with three or more functional antigen-binding sites, including "Octopus antibodies" (see, e.g. US 2006/0025576A1), and "Dual Acting FAb" or "DAF" antibodies comprising an antigen-binding site that binds to VISTA as well as another, different antigen (see e.g. US 2008/0069820). Accordingly, the present invention includes bispecific molecules comprising at least one first binding specificity for VISTA and a second binding specificity for a second target epitope. According to at least some embodiments of the invention, the second target epitope is an Fc receptor, e.g., human FcγRI (CD64) or a human FcαR receptor (CD89). Therefore, the invention includes bispecific molecules capable of binding both to FcγR, FcαR or FcsR expressing effector cells (e.g., monocytes, macrophages or polymorphonuclear cells (PMNs)), and to target cells expressing VISTA, respectively. These bispecific molecules target VISTA expressing cells to effector cell and trigger Fc receptor-mediated effector cell activities, such as phagocytosis of an VISTA expressing cells, antibody dependent cell-mediated cytotoxicity (ADCC), cytokine release, or generation of superoxide anion.

According to at least some embodiments of the invention in which the bispecific molecule is multispecific, the molecule can further include a third binding specificity, in addition to an anti-Fc binding specificity. In one embodiment, the third binding specificity is an anti-enhancement factor (EF) portion, e.g., a molecule which binds to a surface protein involved in cytotoxic activity and thereby increases the immune response against the target cell.

The "anti-enhancement factor portion" can be an antibody, functional antibody fragment or a ligand that binds to a given molecule, e.g., an antigen or a receptor, and thereby results in an enhancement of the effect of the binding determinants for the Fc receptor or target cell antigen. The "anti-enhancement factor portion" can bind an Fc receptor or a target cell antigen. Alternatively, the anti-enhancement factor portion can bind to an entity that is different from the entity to which the first and second binding specificities bind. For example, the anti-enhancement factor portion can bind a cytotoxic T-cell (e.g., via CD2, CD3, CD8, CD28, CD4, CD40, ICAM-1 or other immune cell that results in an increased immune response against the target cell).

According to at least some embodiments of the invention, the bispecific molecules comprise as a binding specificity at least one antibody, or an antibody fragment thereof, including, e.g., an Fab, Fab', F(ab')2, Fv, or a single chain Fv. The antibody may also be a light chain or heavy chain dimer, or any minimal fragment thereof such as a Fv or a single chain construct as described in Ladner et al. U.S. Pat. No. 4,946,778, the contents of which are expressly incorporated by reference.

In one embodiment, the binding specificity for an Fcγ receptor is provided by a monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fcγ receptor classes: FcγRI (CD64), FcγRII(CD32), and FcγRIII (CD16). In one preferred embodiment, the Fcγ receptor is a human high affinity FcγRI. The human FcγRI is a 72 kDa molecule, which shows high affinity for monomeric IgG. The production and characterization of certain preferred anti-Fcγ monoclonal antibodies are described by Fanger et al. in PCT Publication WO 88/00052 and in U.S. Pat. No. 4,954,617, the teachings of which are fully incorporated by reference herein. These antibodies bind to an epitope of FcγRI, FcγRII or FcγRIII at a site which is distinct from the Fcy binding site of the receptor and, thus, their binding is not blocked substantially by physiological levels of IgG. Known anti-FcγRI antibodies include mAb 22, mAb 32, mAb 44, mAb 62 and mAb 197. The hybridoma producing mAb 32 is available from the American Type Culture Collection, ATCC Accession No. HB9469. In other embodiments, the anti-Fcγ receptor antibody is a humanized form of monoclonal antibody 22 (H22). The production and characterization of the H22 antibody is described in Graziano, R. F. et al. (1995) *J. Immunol.* 155 (10): 4996-5002 and PCT Publication WO 94/10332. The H22 antibody producing cell line is deposited at the American Type Culture Collection under the designation HA022CLI and has the accession no. CRL 11177.

In still other embodiments, the binding specificity for an Fc receptor is provided by an antibody that binds to a human IgA receptor, e.g., an Fc-α receptor (Fc αRI(CD89)), the binding of which is preferably not blocked by human immunoglobulin A (IgA). The term "IgA receptor" is intended to include the gene product of one a-gene (FcαRI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcαRI has medium affinity (Approximately $5\times10^{-7}$ $M^{-1}$) for both IgA1 and IgA2, which is increased upon exposure to cytokines such as G-CSF or GM-CSF (Morton, H. C. et al. (1996) *Critical Reviews in Immunology* 16:423-440). Four FcαRI-specific monoclonal antibodies, identified as A3, A59, A62 and A77, which bind FcαRI outside the IgA ligand binding domain, have been described (Monteiro, R. C. et al. (1992) *J. Immunol.* 148: 1764).

While human monoclonal antibodies are preferred, other antibodies which can be employed in the bispecific molecules according to at least some embodiments of the invention are murine, chimeric and humanized monoclonal antibodies. The bispecific molecules of the present invention can be prepared by conjugating the constituent binding specificities, e.g., the anti-FcR and anti-VISTA binding specificities, using methods known in the art. For example, the binding specificity of each bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyld-dithio propionate (SPDP), and sulfosuccinimidyl 4-(N-maleimidomethyl) cyclohexane-I-carboxylate (sulfo-SMCC) (see e.g., Karpovsky et al. (1984) *J. Exp. Med.* 160: 1686; Liu, M A et al. (1985) *Proc. Natl. Acad. Sci. USA* 82:8648). Other methods include those described in Paulus (1985) Behring Ins. Mitt. No. 78, 118-132; Brennan et al. (1985) *Science* 229:81-83), and Glennie et al. (1987) *J. Immunol.* 139: 2367-2375). Preferred conjugating agents are SATA and sulfo-SMCC, both available from Pierce Chemical Co. (Rockford, Ill.). When the binding moieties are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAbXmAb, mAbXFab, FabXF(ab')2 or ligandXFab fusion protein. A bispecific molecule according to at least some embodiments of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); controlled Fab-arm exchange (see Labrijn et al., *Proc. Natl. Acad. Sci. USA* 110(13):5145-50 (2013)); cross-linking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., J. Immunol., 148(5): 1547-1553 (1992)); using "diabody" technology for making bispecific antibody fragments (see, e.g., Hollinger et al., *Proc. Natl. Acad. Sci. USA* 90:6444-6448 (1993)); and using single-chain Fv (sFv) dimers (see, e.g. Gruber et al., *J. Immunol.*, 152:5368 (1994)); and preparing trispecific antibodies as described, e.g., in Tutt et al. *J. Immunol.* 147: 60 (1991).

Binding of the bispecific molecules to their specific targets can be confirmed by, for example, enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., *Principles of Radioimmunoassays*, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

Uses of Antagonist Antibodies and Pharmaceutical Compositions Containing

Cancer Immunotherapy

Unlike tumor-targeted therapies, which are aimed at inhibiting molecular pathways that are crucial for tumor growth and development, and/or depleting tumor cells, cancer immunotherapy is aimed to stimulate the patient's own immune system to eliminate cancer cells, providing long-lived tumor destruction. Various approaches can be used in cancer immunotherapy, among them are therapeutic cancer vaccines to induce tumor-specific T cell responses, and immunostimulatory antibodies (i.e. antagonists of inhibitory receptors=immune checkpoints) to remove immunosuppressive pathways.

Clinical responses with targeted therapy or conventional anti-cancer therapies tend to be transient as cancer cells develop resistance, and tumor recurrence takes place. However, the clinical use of cancer immunotherapy in the past few years has shown that this type of therapy can have durable clinical responses, showing dramatic impact on long term survival. However, although responses are long term, only a small number of patients respond (as opposed to conventional or targeted therapy, where a large number of patients respond, but responses are transient).

By the time a tumor is detected clinically, it has already evaded the immune-defense system by acquiring immunoresistant and immunosuppressive properties and creating an immunosuppressive tumor microenvironment through various mechanisms and a variety of immune cells. Thus, in cancer immunotherapy it is becoming increasingly clear that a combination of therapies is be required for clinical efficacy.

Combination approaches are needed and expected to increase the number of patients benefiting from immunotherapy and expand the number and types of cancers that are responsive, expanding the potential cancer indications for checkpoint agents well beyond the initial indications currently showing efficacy of immune checkpoint blockade as monotherapy. The combination of immunomodulatory approaches is meant to maximize the outcomes and overcome the resistance mechanisms of most tumors to a single approach. Thus, tumors traditionally thought of as non-immunogenic can likely become immunogenic and respond to immunotherapy though co-administration of pro-immunogenic therapies designed to increase the patient's anti-tumor immune responses. Potential priming agents are detailed herein below.

The underlying scientific rationale for the dramatic increased efficacy of combination therapy claims that immune checkpoint blockade as a monotherapy will induce tumor regressions only when there is pre-existing strong anti-tumor immune response to be 'unleashed' when the pathway is blocked. According to at least some embodiments of the present invention, VISTA-specific antibodies, antibody fragments, conjugates and compositions comprising same, are used for treatment of all types of cancer in cancer immunotherapy in combination therapy.

The term "treatment" as used herein, refers to both therapeutic treatment and prophylactic or preventative measures, which in this Example relates to treatment inflammatory side effects of cancer; however, also as described below, uses of antibodies and pharmaceutical compositions are also provided for treatment of infectious disease, sepsis, and/or autoimmune conditions, and/or for inhibiting an undesirable immune activation that follows gene therapy. Those in need of treatment include those already with cancer as well as those in which the cancer is to be prevented. Hence, the mammal to be treated herein may have been diagnosed as having the cancer or may be predisposed or susceptible to the cancer. As used herein the term "treating" refers to preventing, delaying the onset of, curing, reversing, attenuating, alleviating, minimizing, suppressing, halting the deleterious effects or stabilizing of discernible symptoms of the above-described cancerous diseases, disorders or conditions. It also includes managing the cancer as described above. By "manage" it is meant reducing the severity of the disease, reducing the frequency of episodes of the disease, reducing the duration of such episodes, reducing the severity of such episodes, slowing/reducing cancer cell growth or proliferation, slowing progression of at least one symptom, amelioration of at least one measurable physical parameter and the like. For example, immunostimulatory anti-VISTA antibodies should promote T cell or NK or cytokine immunity against target cells, e.g., cancer, infected or pathogen cells and thereby treat cancer or infectious diseases by depleting the cells involved in the disease condition. Agonistic anti-VISTA antibodies should reduce T cell or NK activity and/or or the secretion of proinflammatory cytokines which are involved in the disease pathology of some immune disease such as autoimmune, inflammatory or allergic conditions and thereby treat or ameliorate the disease pathology and tissue destruction that may be associated with such conditions (e.g., joint destruction associated with rheumatoid arthritis conditions).

"Mammal" for purposes of treatment refers to any animal classified as a mammal, including humans, domestic and farm animals, and zoo, sports, or pet animals, such as dogs, horses, cats, cows, etc. Preferably, the mammal is human. Preferably the mammal is a human which is diagnosed with one of the disease, disorder or conditions described hereinabove, or alternatively one who is predisposed to at least one type of cancer.

A "therapeutically effective amount" refers to an amount of agent according to the present invention that is effective to treat a disease or disorder in a mammal. The therapeutic agents of the present invention can be provided to the subject alone, or as part of a pharmaceutical composition where they are mixed with a pharmaceutically acceptable carrier.

An anti-VISTA antibody, a fragment, a conjugate thereof as herein described and/or a pharmaceutical composition comprising same, according to at least some embodiments of the present invention also can be administered in combination therapy, i.e., combined with other potentiating agents and/or other therapies. According to at least some embodiments, the anti-VISTA antibody could be used in combination with any of the known in the art standard of care cancer treatment (as can be found, for example, in http://www.cancer.gov/cancertopics).

For example, the combination therapy can include an anti-VISTA antibody, a fragment, a conjugate thereof and/or a pharmaceutical composition comprising same, combined with at least one other therapeutic or immune modulatory agent, other compounds or immunotherapies, or immuno stimulatory strategy as described herein.

Antagonistic anti-VISTA antibodies may be used in combination with agonistic antibodies targeting immune checkpoints including anti-CTLA4 mAbs, such as ipilimumab, tremelimumab; anti-PD-1 such as nivolumab BMS-936558/MDX-1106/ONO-4538, AMP224, CT-011, MK-3475, anti-PDL-1 antagonists such as BMS-936559/MDX-1105, MED14736, RG-7446/MPDL3280A; Anti-LAG-3 such as IMP-321), anti-TIM-3, anti-BTLA, anti-B7-H4, anti-B7-H3; Agonistic antibodies targeting immunostimulatory proteins, including anti-CD40 mAbs such as CP-870,893, lucatumumab, dacetuzumab; anti-CD137 mAbs such as BMS-663513 urelumab, PF-05082566; anti-OX40 mAbs, such as anti-OX40; anti-GITR mAbs such as TRX518; anti-CD27 mAbs, such as CDX-1127; and anti-ICOS mAbs.

Cytokines are molecular messengers that allow the cells of the immune system to communicate with one another to generate a coordinated, robust, but self-limited response to a target antigen. Cytokine-based therapies embody a direct attempt to stimulate the patient's own immune system to reject cancer. The growing interest over the past two decades in harnessing the immune system to eradicate cancer has been accompanied by heightened efforts to characterize cytokines and exploit their vast signaling networks to develop cancer treatments. Cytokines directly stimulate immune effector cells and stromal cells at the tumor site and enhance tumor cell recognition by cytotoxic effector cells. Numerous animal tumor model studies have demonstrated that cytokines have broad anti-tumor activity and this has been translated into a number of cytokine-based approaches for cancer therapy (Lee and Margolin 2011, *Cancers* 3(4): 3856-93). A number of cytokines are in preclinical or clinical development as agents potentiating anti-tumor immune responses for cancer immunotherapy, including among others: IL-2, IL-7, IL-12, IL-15, IL-17, IL-18 and IL-21, IL-23, IL-27, GM-CSF, IFNα (interferon α), IFNβ, and IFNγ.

Antagonist anti-VISTA antibodies and pharmaceutical compositions containing may also be administered in conjunction with other compounds or immunotherapies. For example, the combination therapy can include a compound of the present invention combined with at least one other therapeutic or immune modulatory agent, or immuno stimulatory strategy, including, but not limited to, tumor vaccines, adoptive T cell therapy, Treg depletion, antibodies (e.g. bevacizumab, Erbitux), peptides, peptibodies, small molecules, chemotherapeutic agents such as cytotoxic and cytostatic agents (e.g. paclitaxel, cisplatin, vinorelbine, docetaxel, gemcitabine, temozolomide, irinotecan, 5FU, carboplatin), immunological modifiers such as interferons and interleukins, immuno stimulatory antibodies, growth hormones or other cytokines, folic acid, vitamins, minerals, aromatase inhibitors, RNAi, Histone Deacetylase Inhibitors, proteasome inhibitors, and so forth.

According to at least some embodiments, immune cells, preferably T cells can be contacted in vivo or ex vivo with the subject therapeutic agents to modulate immune responses. The T cells contacted with the therapeutic agents can be any cell which expresses the T cell receptor, including α/β and γ/δ T cell receptors. T-cells include all cells which express CD3, including T-cell subsets which also express CD4 and CDS. T-cells include both naive and memory cells and effector cells such as CTL. T-cells also include cells such as Th1, Tel, Th2, Th2, Th3, Thl7, Th22, Treg, and Trl cells. T-cells also include NKT-cells and similar unique classes of the T-cell lineage.

Use of Agonistic Anti-Vista Antibodies and Pharmaceutical Compositions Containing for Treatment of Autoimmune Disease According to at least some embodiments, anti-VISTA antibodies, fragments, conjugates thereof or a pharmaceutical composition comprising same, as described herein, which function as VISTA stimulating therapeutic agents, may be used for treating an immune system related disease.

Optionally, the immune system related condition comprises an immune related condition, autoimmune diseases as recited herein, transplant rejection and graft versus host disease and/or for blocking or promoting immune stimulation mediated by VISTA, immune related diseases as recited herein and/or for immunotherapy (promoting or inhibiting immune stimulation).

Optionally the immune condition is selected from autoimmune disease, transplant rejection, inflammatory disease, allergic condition or graft versus host disease. Optionally the treatment is combined with another moiety useful for treating immune related condition.

Thus, treatment of multiple sclerosis using the agents according to at least some embodiments of the present invention may be combined with, for example, any known therapeutic agent or method for treating multiple sclerosis, optionally as described herein.

Thus, treatment of rheumatoid arthritis or other arthritic condition, using the subject agonist antibodies may be combined with, for example, any known therapeutic agent or method for treating rheumatoid arthritis, optionally as described herein.

Thus, treatment of IBD, using the using the subject agonist antibodies may be combined with, for example, any known therapeutic agent or method for treating IBD, optionally as described herein.

Thus, treatment of psoriasis, using the subject agonist antibodies may be combined with, for example, any known therapeutic agent or method for treating psoriasis, optionally as described herein.

Thus, treatment of type 1 diabetes using the subject agonist antibodies may be combined with, for example, any known therapeutic agent or method for treating type 1 diabetes, optionally as described herein.

Thus, treatment of uveitis, using the subject agonist antibodies may be combined with, for example, any known therapeutic agent or method for treating uveitis, optionally as described herein.

Thus, treatment of psoriasis using the subject agonist antibodies may be combined with, for example, any known therapeutic agent or method for treating psoriasis, optionally as described herein.

Thus, treatment of Sjögren's syndrome, using the subject agonist antibodies may be combined with, for example, any known therapeutic agent or method for treating for Sjögren's syndrome, optionally as described herein.

Thus, treatment of systemic lupus erythematosus, using the subject agonist antibodies may be combined with, for example, any known therapeutic agent or method for treating for systemic lupus erythematosus, optionally as described herein.

Thus, treatment of GVHD, using the subject agonist antibodies may be combined with, for example, any known therapeutic agent or method for treating GVHD, optionally as described herein.

Thus, treatment of chronic or acute infection and/or hepatotoxicity associated therewith, e.g., hepatitis, using the subject agonist antibodies may be combined with, for example, any known therapeutic agent or method for treating for chronic or acute infection and/or hepatotoxicity associated therewith, optionally as described herein.

In the above-described therapies preferably a subject with one of the aforementioned or other autoimmune or inflammatory conditions will be administered an immmunoinhibitory anti-VISTA antibody disclosed herein or antigen-binding fragment according to the invention, which antibody mimics or agonizes at least one VISTA-mediated effect on immunity, e.g., it suppresses cytotoxic T cells, or NK activity and/or the production of proinflammatory cytokines which are involved in the disease pathology, thereby preventing or ameliorating the disease symptoms and potentially resulting in prolonged disease remission, e.g., because of the induction of Tregs which elicit T cell tolerance or prolonged immunosuppression.

The therapeutic agents and/or a pharmaceutical composition comprising same, as recited herein, according to at least some embodiments of the invention, may be administered as the sole active ingredient or together with other drugs in immunomodulating regimens or other anti-inflammatory agents e.g. for the treatment or prevention of allo- or xenograft acute or chronic rejection or inflammatory or autoimmune disorders, or to induce tolerance.

Use of Agonistic Anti-Vista Antibodies and Pharmaceutical Compositions Containing for Treatment of Sepsis According to at least some embodiments, VISTA antibodies, fragments, conjugates thereof and/or pharmaceutical compositions as described herein, may be used for treating sepsis. Sepsis is a potentially life-threatening complication of an infection. Sepsis represents a complex clinical syndrome that develops when the initial host response against an infection becomes inappropriately amplified and dysregulated, becoming harmful to the host. The initial hyperinflammatory phase ('cytokine storm') in sepsis is followed by a state of immunosuppression (Hotchkiss et al 2013 *Lancet Infect. Dis.* 13:260-268). This latter phase of impaired immunity, also referred to as 'immunoparalysis', is manifested in failure to clear the primary infection, reactivation of viruses such as HSV and cytomegalovirus, and development of new, secondary infections, often with organisms that are not particularly virulent to the immunocompetent patient. The vast majority of septic patients today survive their initial hyperinflammatory insult only to end up in the intensive care unit with sepsis-induced multiorgan dysfunction over the ensuing days to weeks. Sepsis-induced immunosuppression is increasingly recognized as the overriding immune dysfunction in these vulnerable patients. The impaired pathogen clearance after primary infection and/or susceptibility to secondary infections contribute to the high rates of morbidity and mortality associated with sepsis.

According to at least some embodiments of the present invention, there is provided use of a combination of the therapeutic agents and/or a pharmaceutical composition comprising same, as recited herein, and a known therapeutic agent effective for treating sepsis.

According to at least some embodiments of the present invention, there is provided use of a combination of the therapeutic agents and/or a pharmaceutical composition comprising same, as recited herein, can be combined with standard of care or novel treatments for sepsis, with therapies that block the cytokine storm in the initial hyperinflammatory phase of sepsis, and/or with therapies that have immunostimulatory effect in order to overcome the sepsis-induced immunosuppression phase.

Combination with standard of care treatments for sepsis, as recommended by the "International Guidelines for Management of Severe Sepsis and Septic Shock" (Dellinger et al 2013 Intensive Care Med 39: 165-228), some of which are described below.
1. Broad spectrum antibiotics having activity against all likely pathogens (bacterial and/or fungal—treatment starts when sepsis is diagnosed, but specific pathogen is not identified)—example Cefotaxime (Claforan®), Ticarcillin and clavulanate (Timentin®), Piperacillin and tazobactam (Zosyn®), Imipenem and cilastatin (Primaxin®), Meropenem (Merrem®), Clindamycin (Cleocin), Metronidazole (Flagyl®), Ceftriaxone (Rocephin®), Ciprofloxacin (Cipro®), Cefepime (Maxipime®), Levofloxacin (Levaquin®), Vancomycin or any combination of the listed drugs.
2. Vasopressors: example Norepinephrine, Dopamine, Epinephrine, vasopressin
3. Steroids: example: Hydrocortisone, Dexamethasone, or Fludrocortisone, intravenous or otherwise Inotropic therapy: example Dobutamine for sepsis patients with myocardial dysfunction
4. Recombinant human activated protein C (rhAPC), such as drotrecogin alfa (activated) (DrotAA).
5. 3-blockers additionally reduce local and systemic inflammation.
6. Metabolic interventions such as pyruvate, succinate or high dose insulin substitutions.

Use of Anti-Vista Antibodies and Pharmaceutical Compositions Containing for Reducing the Undesirable Immune Activation that Follows Gene or Cell Therapy or Transplant As used herein the term "gene therapy" encompasses any type of gene therapy, vector-mediated gene therapy, gene transfer, virus-mediated gene transfer and further encompasses certain cell therapies, e.g., CAR T and CAR NK cell therapies. According to at least some embodiments of the present invention, agonist VISTA antibodies, a fragment, a conjugate thereof and/or a pharmaceutical compositions as described herein, which target VISTA and have inhibitory activity on immune responses, could be used as therapeutic agents for reducing the undesirable immune activation that follows gene or cell therapy used for treatment of various genetic diseases. Without wishing to be limited by a single hypothesis, such antibodies have VISTA-like inhibitory activity on immune responses and/or enhance VISTA immune inhibitory activity, optionally by inhibition of pathogenic T cells and/or NK cells.

Many gene therapy products for the treatment of genetic diseases are currently in clinical trials. Recent studies document therapeutic success for several genetic diseases using gene therapy vectors. Gene therapy strategies are characterized by 3 critical elements, the gene to be transferred, the target tissue into which the gene will be introduced, and the vector (gene delivery vehicle) used to facilitate entry of the gene to the target tissue. The vast majority of gene therapy clinical trials have exploited viral vectors as very efficient delivery vehicles, including retroviruses, lentiviruses, adenoviruses, adeno-associated viruses, pseudotype viruses and herpes simplex viruses. However, the interactions between the human immune system and all the components of gene therapy vectors seem to represent one of the major limitations to long-lasting therapeutic efficacy. Human studies have shown that the likelihood of a host immune response to the viral vector is high. Such immune responses to the virus or the transgene product itself, resulting in formation of neutralizing antibodies and/or destruction of transduced cells by cytotoxic cells, can greatly interfere with therapeutic efficacy (Seregin and Amalfitano 2010 Viruses 2:2013; Mingozzi and High 2013 Blood 122:23; Masat et al 2013 Discov Med. 15:379). Therefore, developing strategies to circumvent immune responses and facilitate long-term expression of transgenic therapeutic proteins is one of the main challenges for the success of gene therapy in the clinic.

Factors influencing the immune response against transgenic proteins encoded by viral vectors include route of administration, vector dose, immunogenicity of the transgenic protein, inflammatory status of the host and capsid serotype. These factors are thought to influence immunogenicity by triggering innate immunity, cytokine production, APC maturation, antigen presentation and, ultimately, priming of naive T lymphocytes to functional effectors (Mingozzi and High 2013 Blood 122:23). Therefore, the idea to dampen immune activation by interfering with these very mechanisms has logically emerged with the aim to induce a short-term immunosuppression, avoid the early immune priming that follows vector administration and promote long-term tolerance.

As a strategy to inhibit the undesirable immune activation that follows gene therapy, particularly after multiple injections, immunomodulation treatment by targeting of two non-redundant checkpoints of the immune response at the time of vector delivery was tested in animal models. Studies of vector-mediated immune responses upon adenoviral vector instilled into the lung in mice or monkeys showed that transient treatment with an anti-CD40L antibody lead to suppression of adenovirus-induced immune responses; consequently, the animals could be re-administered with adenovirus vectors. Short treatment with this Ab resulted in long-term effects on immune functions and prolonged inhibition of the adenovirus-specific humoral response well beyond the time when the Ab effects were no longer significant, pointing to the therapeutic potential in blockade of this costimulatory pathway as an immunomodulatory regimen to enable administration of gene transfer vectors (Scaria et al. 1997 Gene Ther. 4: 611; Chirmule et al 2000 J. Virol. 74: 3345). Other studies showed that co-administration of CTLA4-Ig and an anti-CD40L Ab around the time of primary vector administration decreased immune responses to the vector, prolonged long term adenovirus-mediated gene expression and enabled secondary adenovirus-mediated gene transfer even after the immunosuppressive effects of these agents were no longer present, indicating that it may be possible to obtain persistence as well as secondary adenoviral-mediated gene transfer with transient immunosuppressive therapies (Kay et al 1997 Proc. Natl. Acad. Sci. U.S.A. 94:4686). In another study, similar administration of CTLA4-Ig and an anti-CD40L Ab abrogated the formation of neutralizing Abs against the vector, and enabled gene transfer expression, provided the treatment was administered during each gene transfer injection (Lorain et al 2008

*Molecular Therapy* 16:541). Furthermore, administration of CTLA4-Ig to mice, even as single administration, resulted in suppression of immune responses and prolonged transgene expression at early time points (Adriouch et al 2011 *Front. Microbiol.* 2: 199). However, CTLA4-Ig alone was not sufficient to permanently wipe out the immune responses against the transgene product. Combined treatment targeting two immune checkpoints with CTLA4-Ig and PD-L1 or PDL-2 resulted in synergistic improvement of transgene tolerance at later time points, by probably targeting two non-redundant mechanisms of immunomodulation, resulting in long term transgene persistence and expression (Adriouch et al 2011 *Front. Microbiol.* 2: 199).

According to at least some embodiments of the present invention, the subject agonists may be used to overcome the limitation of immune responses to gene therapy, could be used for reducing the undesirable immune activation that follows gene therapy alone or with other actives. Current approaches include exclusion of patients with antibodies to the delivery vector, administration of high vector doses, use of empty capsids to adsorb anti-vector antibodies allowing for subsequent vector transduction, repeated plasma exchange (plasmapheresis) cycles to adsorb immunoglobulins and reduce the anti-vector antibody titer.

Novel approaches attempting to overcome these limitations can be divided into two broad categories: selective modification of the Ad vector itself and pre-emptive immune modulation of the host (Seregin and Amalfitano 2010 *Viruses* 2:2013). The first category comprises several innovative strategies including: (1) Ad-capsid-display of specific inhibitors or ligands; (2) covalent modifications of the entire Ad vector capsid moiety; (3) the use of tissue specific promoters and local administration routes; (4) the use of genome modified Ads; and (5) the development of chimeric or alternative serotype Ads.

The second category of methods includes the use of immunosuppressive drugs or specific compounds to block important immune pathways, which are known to be induced by viral vectors. Immunosuppressive agents have been tested in preclinical studies and shown efficacy in prevention or eradication of immune responses to the transfer vector and transgene product. These include general immunosuppressive agents such as cyclosporine A; cyclophosphamide; FK506; glucocorticoids or steroids such as dexamethasone; TLR9 blockade such as the TLR9 antagonist oligonucleotide ODN-2088; TNF-α blockade with anti-TNF-α antibodies or TNFR-Ig antibody, Erk and other signaling inhibitors such as U0126. In the clinical setting, administration of glucocorticoids has been successfully used to blunt T cell responses directed against the viral capsid upon liver gene transfer of adenovirus-associated virus (AAV) vector expressing human factor IX transgene to severe hemophilia B patients (Nathwani et al 2011 *N. Engl. J. Med.* 365:2357).

In contrast to the previous approaches that utilize drugs that tend to "globally" and non-specifically immunosuppress the host, more selective immunosuppressive approaches have been developed. These include the use of agents which provide blockade of positive co-stimulatory interactions, such as between CD40 and CD154, ICOS and ICOSL, CD28 and CD80 or CD86 (including CTLA4-Ig), NKG2D and NKG2D ligands, LFA-1 and ICAM, LFA-3 and CD2, 4-1BB and 4-1BBL, OX40 and OX40L, GITR and GITRL and agents that stimulate negative costimulatory receptors such as CTLA-4, PD-1, BTLA, LAG-3, TIM-1, TEVI-3, KIRs, and the receptors for B7-H4 and B7-H3. Some of these have been utilized in preclinical or clinical transplantation studies (Pilat et al 2011 *Sem. Immunol.* 23:293).

In the above-described gene or cell therapies or in treating transplant indications preferably a subject who has or is to receive cell or gene therapy or a transplanted tissue or organ will be administered an immmunoinhibitory anti-VISTA antibody disclosed herein or antigen-binding fragment according to the invention, which antibody enhances, agonizes or mimics at least one VISTA-mediated effect on immunity, e.g., its inhibitory effect on cytotoxic T cells or NK activity and/or its inhibitory effect on the production of proinflammatory cytokines, or its stimulatory effect on Tregs thereby preventing or reducing host immune responses against the cell or gene used in therapy or an undesired immune response against the transplanted cells, organ or tissue. Preferably the treatment will elicit prolonged immune tolerance against the transplanted or infused cells, tissue or organ. In some instances, e.g., in the case of transplanted cells, tissues or organs containing immune cells, the immmunoinhibitory anti-VISTA antibody disclosed herein or antigen-binding fragment may be contacted with the cells, tissue or organ prior to infusion or transplant, and/or potentially immune cells of the transplant recipient in order to tolerize the immune cells and potentially prevent an undesired immune response or GVHD immune reaction.

Pharmaceutical Compositions

In another aspect, the present invention provides a composition, e.g., a pharmaceutical composition, containing one or a combination of anti-human VISTA antibodies according to the invention and optionally another immunosuppressive or other active agent. Thus, the present invention features a pharmaceutical composition comprising a therapeutically effective amount of anti-human VISTA antibodies according to at least some embodiments of the present invention. In particular the present invention features a pharmaceutical composition comprising a therapeutically effective [immunosuppressive] amount of at least one agonist anti-human VISTA antibody or antibody fragment according to the present invention A pharmaceutical composition according to at least some embodiments of the present invention [i.e., in the case of VISTA antagonist antibodies disclosed herein] may be used for the treatment of cancer, wherein the cancer is non-metastatic, invasive or metastatic, and/or for treatment of immune related disorders, autoimmunity, allergy, GVHD, inflammation or hepatotoxicity associated with infectious disorder and/or sepsis [i.e., in the case of VISTA agonist antibodies disclosed herein]. "Treatment" refers to both therapeutic treatment and prophylactic or preventative measures. Those in need of treatment include those already with the disorder as well as those in which the disorder is to be prevented. Hence, the mammal to be treated herein may have been diagnosed as having the disorder or may be predisposed or susceptible to the disorder. "Mammal" for purposes of treatment refers to any animal classified as a mammal, including humans, domestic and farm animals, and zoo, sports, or pet animals, such as dogs, horses, cats, cows, etc. Preferably, the mammal is human.

The term "therapeutically effective amount" refers to an amount of agent according to the present invention that is effective to treat a disease or disorder in a mammal. The therapeutic agents of the present invention can be provided to the subject alone or as part of a pharmaceutical composition where they are mixed with a pharmaceutically acceptable carrier. In many instances agonist or antagonist anti-VISTA antibodies according to the invention will be used in combination with other immunotherapeutics or other therapeutic agents useful in treating a specific condition.

A composition is said to be a "pharmaceutically acceptable carrier" if its administration can be tolerated by a recipient patient. As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion).

Such compositions include sterile water, buffered saline (e.g., Tris-HCl, acetate, phosphate), pH and ionic strength and optionally additives such as detergents and solubilizing agents (e.g., Polysorbate 20, Polysorbate 80), antioxidants (e.g., ascorbic acid, sodium metabisulfite), preservatives (e.g., Thimersol, benzyl alcohol) and bulking substances (e.g., lactose, mannitol). Non-aqueous solvents or vehicles may also be used as detailed below.

Examples of suitable aqueous and nonaqueous carriers that may be employed in the pharmaceutical compositions according to at least some embodiments of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. Depending on the route of administration, the active compound, i.e., monoclonal or polyclonal antibodies and antigen-binding fragments and conjugates containing same, and/or alternative scaffolds, that specifically bind any one of VISTA proteins, or bispecific molecule, may be coated in a material to protect the compound from the action of acids and other natural conditions that may inactivate the compound. The pharmaceutical compounds according to at least some embodiments of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66: 1-19). Examples of such salts include acid addition salts and base addition salts. Acid addition salts include those derived from nontoxic inorganic acids, such as hydrochloric, nitric, phosphoric, sulfuric, hydrobromic, hydriodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition according to at least some embodiments of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, a-tocopherol, and the like; and (3) metal chelating agents, such as citric acid, ethylenediamine tetraacetic acid (EDTA), sorbitol, tartaric acid, phosphoric acid, and the like.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions according to at least some embodiments of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin. Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

A composition of the present invention can be administered via one or more routes of administration using one or more of a variety of methods known in the art. As will be appreciated by the skilled artisan, the route and/or mode of administration will vary depending upon the desired results. Preferred routes of administration for therapeutic agents according to at least some embodiments of the invention include intravascular delivery (e.g. injection or infusion), intravenous, intramuscular, intradermal, intraperitoneal, subcutaneous, spinal, oral, enteral, rectal, pulmonary (e.g. inhalation), nasal, topical (including transdermal, buccal and sublingual), intravesical, intravitreal, intraperitoneal, vaginal, brain delivery (e.g. intra-cerebroventricular, intracerebral, and convection enhanced diffusion), CNS delivery (e.g. intrathecal, perispinal, and intra-spinal) or parenteral (including subcutaneous, intramuscular, intravenous and intradermal), transmucosal (e.g., sublingual administration), administration or administration via an implant, or other parenteral routes of administration, for example by injection or infusion, or other delivery routes and/or forms of administration known in the art. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. In a specific embodiment, a protein, a therapeutic agent or a pharmaceutical composition according to at least some embodiments of the present invention can be administered intraperitoneally or intravenously.

Alternatively, an VISTA specific antibody according to the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in a preferred embodiment, a therapeutic composition according to at least some embodiments of the invention can be administered with a needles hypodermic injection device, such as the devices disclosed in U.S. Pat. No. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the anti-VISTA antibodies can be formulated to ensure proper distribution in vivo. For example, the blood-brain barrier (BBB) excludes many highly hydrophilic compounds. To ensure that the therapeutic compounds according to at least some embodiments of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153: 1038); antibodies (P. G. Bloeman et al. (1995) *FEBS Lett.* 357: 140; M. Owais et al. (1995) *Antimicrob. Agents Chemother.* 39: 180); surfactant protein A receptor (Briscoe et al. (1995) *Am. J Physiol.* 1233: 134); p 120 (Schreier et al. (1994) *J. Biol. Chem.* 269:9090); see also K. Keinanen; M. L. Laukkanen (1994) *FEBS Lett.* 346: 123; J. J. Killion; and I. J. Fidler (1994) *Immunomethods* 4:273.

In yet another embodiment, immunoconjugates of the invention can be used to target compounds (e.g., therapeutic agents, labels, cytotoxins, radiotoxins immunosuppressants, etc.) to cells which have VISTA cell surface receptors by linking such compounds to the antibody disclosed herein. Thus, the invention also provides methods for localizing ex vivo or in vivo cells expressing VISTA (e.g., with a detectable label, such as a radioisotope, a fluorescent compound, an enzyme, or an enzyme co-factor). Alternatively, the immunoconjugates can be used to kill cells which have VISTA cell surface receptors by targeting cytotoxins or radiotoxins to VISTA antigen.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., soluble polypeptide conjugate containing the ectodomain of the VISTA antigen, antibody, immunoconjugate, alternative scaffolds, and/or bispecific molecule, may be coated in a material to protect the compound from the action of acids and other natural conditions that may inactivate the compound. The pharmaceutical compounds according to at least some embodiments of the present invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66: 1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition according to at least some embodiments of the present invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, a-tocopherol, and the like; and (3) metal chelating agents, such as citric acid, ethylenediamine tetraacetic acid (EDTA), sorbitol, tartaric acid, phosphoric acid, and the like. Examples of suitable aqueous and nonaqueous carriers that may be employed in the pharmaceutical compositions according to at least some embodiments of the present invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions according to at least some embodiments of the present invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin. Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about I percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms according to at least some embodiments of the present invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the VISTA antibody disclosed herein, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an antibody disclosed herein according to at least some embodiments of the present invention include 1 mg/kg body weight or 3 mg/kg body weight via intravenous administration, with the antibody disclosed herein being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously in which case the dosage of each antibody disclosed herein administered falls within the ranges indicated. Antibody disclosed herein is usually administered on multiple occasions. Intervals between single dosages can be, for example, daily, weekly, monthly, every three months or yearly. Intervals can also be irregular as indicated by measuring blood levels of antibody to the target antigen in the patient. In some methods, dosage is adjusted to achieve a plasma antibody concentration of about 1-1000 mug/ml and in some methods about 25-300 microgram/ml.

Alternatively, therapeutic agent can be administered as a sustained release formulation, in which case less frequent administration is required. Dosage and frequency vary depending on the half-life of the therapeutic agent in the patient. In general, human antibodies show the longest half-life, followed by humanized antibodies, chimeric antibodies, and nonhuman antibodies. The half-life for fusion proteins may vary widely. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

Having described the invention the following examples are provided to further illustrate the invention and its inherent advantages.

EXAMPLES

Example 1: Use of Assays to Screen for Immunosuppressive Anti-Mouse VISTA Abs The present inventors developed various assays to screen for putative agonistic anti-mouse VISTA antibodies. As shown in FIG. 1 in vitro and in vivo screening assays were used to identify immunosuppressive anti-VISTA mAbs. In the experiments in FIG. 1A purified T cells were plated on top of anti-CD3 in the presence of the indicated mAb for 72 hours. Proliferation was measured by H3 incorporation. In the experiments in FIG. 1B purified DO11.10 T cells were stimulated by ISQ pulsed APCs for 6 days in the presence of the indicated antibody. Proliferation was measured through use of CTV dilution dye. In the experiments in FIG. 1C GVHD was induced by transfer of C57BL/6 cells into irradiated BALB/c recipients. Mice were injected I.P. with 200 μg of antibody on day 0, 2 and 4 post transfer and survival was analyzed. In the experiments in FIG. 1D mice were treated with 10 mpk of the indicated antibody 3 hours prior to administration of ConA (15 mpk) and IL-2 was analyzed in plasma at 6 by Luminex.

More particularly, in the first assay, $CD4^+$ T cells were isolated and incubated with Ab1, Ab2 or Ab3 before being added to anti-CD3 coated plates. After 3 days in culture, the T cells were pulsed with tritiated thymidine, which is incorporated by proliferating cells. Notably, both Ab1 and Ab2 induced a significant reduction in the proliferative rate of the T cells, while Ab3 had no effect (FIG. 1) In a similar assay where transgenic T cells were stimulated with antigen pulsed APCs instead, T cell activation was measured by proliferative dye dilution. Similar to the anti-CD3 assay, Ab1 suppressed antigen-specific T cell proliferation by 50% (FIG. 1B). These data indicate that the Ab3 mAb blocks mVISTA function (i.e., enhances immune responses) whereas Ab1 and Ab3 stimulate mVISTA function and down regulate key immune responses.

We also determined whether Ab3 and Ab1 could be distinguished using in vivo animal models, particularly in GVHD and ConA hepatitis models. Mice with GVHD which were treated with a control antibody (Ham Ig) had progressive disease and needed to be euthanized by 4 weeks post graft as expected (FIG. 1C). Ab3 treated mice were also susceptible to GVHD, and in fact most mice died prior to the control treated group, indicating Ab3 may exacerbate disease. Conversely, all of the Ab1 treated mice showed no obvious symptoms of GVHD and almost all were healthy for at least 40 days. Specifically in these experiments mice with GVHD treated with a control antibody (Ham Ig) had progressive disease and needed to be euthanized by 4 weeks post graft as expected (FIG. 1C). Ab3 treated mice were also susceptible to GVHD, and in fact most mice died prior to the control treated group, indicating Ab3 may exacerbate disease. Conversely, all of the Ab1 treated mice showed no obvious symptoms of GVHD and almost all were healthy for at least 40 days.

In the ConA model, the inventors tested whether each VISTA antibody would impact the well-characterized T cell cytokine response to ConA. Notably Ab1, but not Ab3, induced decreased plasma cytokine levels of IL-2 (FIG. 1D). Specifically, in the ConA model, the inventors further tested whether each VISTA antibody would impact the well-characterized T cell cytokine response to ConA. Notably Ab1, but not Ab3, induced decreased plasma cytokine levels of IL-2 (FIG. 1D).

Accordingly these results demonstrate that both anti-VISTA mAbs (Ab1 and Ab2) are immunosuppressive and it has also been shown that such immunosuppressive anti-mouse VISTA antibodies can be distinguished from inflammatory immunosuppressive anti-mouse VISTA antibodies (Ab3). As shown in FIG. 1 Ab1 is efficacious (immunosuppressive) in multiple inflammatory models including GVHD, NZB/W F1 lupus-like glomerulonephritis, concanavalin A (ConA)-induced hepatitis, collagen antibody induced arthritis (CAIA), and Imiquimod induced psoriasis. In each of these diseases, administration of Ab1 during the progression of disease greatly diminished pathology and/or mortality. Each model listed has a unique requirement on T cells for disease progression. GVHD and ConA are both driven by Th1 T cell responses.

Example 2: Identification of Anti-VISTA Abs which Suppresses Autoimmunity in Different Autoimmune Disease Models In the experiments in FIG. 2A-F the effects of different anti-mouse VISTA Abs were again compared in different disease models. In the experiments in FIG. 2A NZB/W F1 mice were treated 3×/week with either Ab1 or Ham Ig (200 µg) starting at 25 weeks until the end of the experiment. "X" denotes time points where the control treated group had all been sacrificed. In the experiment in FIG. 2B mice were treated with 200 µg of antibody 3 hours prior to administration of 15 mg/kg (mpk) of ConA and survival was followed for 80 hours. In the experiment in FIG. 2C mice were treated sequentially with Collagen II mAb followed by LPS and arthritis was measured by measuring for paw swelling. In the experiments Ab1 and Ham-Ig were administered (200 µg) 3× every other day. In the experiment in FIG. 2D Imiquimod was applied to the ear of mice daily. At day 14, Ab1 or Ham-Ig (200 µg) were administered every other day and ear thickness was measured with calipers. In the experiment in the same FIG. 2E-F imiquimod was applied to the backs of mice daily. At day 9, mice were euthanized and skin was sectioned & stained for CD3 expression by IHC.

As shown in FIG. 2A-F, in each of these experimental models, administration of Ab1 during the progression of the particular disease greatly diminished pathology and/or mortality. Each model listed has a unique requirement on T cells for disease progression. GVHD and ConA are both driven by Th1 T cell responses.

Imiquimod induced psoriasis is an IL-17/23 driven disease where T cells are recruited into the dermal layer of the skin. Ab1 drastically reduced the number of CD3$^+$ cells in the dermis (FIGS. 2E and F), but had no impact on splenic T cell populations (data not shown), indicating that this anti-mouse VISTA Ab preferentially suppressed immunity at the inflammatory lesion.

NZB/W F1 lupus is a multifactorial disease with contributions from B cells, T cells and myeloid cells. In this model, therapeutic administration of Ab1 reduced proteinuria levels indicating decreased damage to the kidneys. Finally, CAIA does not involve adaptive immunity, instead being driven by macrophages and granulocytes. Suppression by anti-VISTA in this model indicates that the antibody may also impact upon the myeloid compartment. As such, suppressive VISTA mAb appear to mediate effects on both the T cell and innate immune compartments.

Therefore, as shown in FIG. 1 and FIG. 2 both monoclonal hamster anti-mouse VISTA Abs Ab1 and AB2 induced a significant reduction in the proliferative rate of the T cells, while Ab3 had no effect (FIG. 1). In a similar assay where transgenic T cells were stimulated with antigen pulsed APCs, T cell activation was measured by proliferative dye dilution. Similar to the anti-CD3 assay, Ab1 suppressed antigen-specific T cell proliferation by ~50% (FIG. 1B). These data suggest that Ab1 and Ab2 stimulate VISTA function and thereby down regulate key immune responses.

Particularly, Ab1, a hamster anti-mouse VISTA antibody was efficacious in multiple inflammatory models including GVHD, NZB/W F1 lupus-like glomerulonephritis, concanavalin A (ConA)-induced hepatitis, collagen antibody induced arthritis (CAIA), and Imiquimod induced psoriasis (FIGS. 1 and 2). In each of these diseases, administration of Ab1 during the progression of disease greatly diminished pathology and/or mortality. Each model listed has a unique requirement on T cells for disease progression. GVHD and ConA are both driven by Th1 T cell responses. As noted above, Imiquimod induced psoriasis is an IL-17/23 driven disease where T cells are recruited into the dermal layer of the skin. Therefore, suppression by Ab1 in this particular autoimmune model indicates that this antibody may also be affecting the myeloid compartment. Therefore, these immunosuppressive anti-mouse VISTA mAb's appear to mediate effects on both the T cell and innate immune compartments.

Example 3: Development of Human VISTA Knock-in Mice for Use in Screening for Agonistic Anti-Human VISTA Abs The previous examples relate to the isolation and characterization of agonistic anti-mouse VISTA Abs. Heretofore an agonistic anti-human VISTA Ab has never been reported in the literature. This is despite the fact that very many antagonistic anti-human VISTA antibodies have been identified by the present Assignee and other groups. Accordingly, prior to this invention it was uncertain whether agonistic anti-human VISTA antibodies would be identified.

Such antibodies would be highly beneficial as currently there is no approved human therapeutics that exploit the natural function of NCR's to suppress the immune response. Although Orencia (CTLA4-Ig) is effective, it only acts by blocking the CD28-B7 interaction and pathway and does not work by stimulating a downregulatory pathway. As illustrated by the potent immunosuppressive effects of 2 different agonistic anti-VISTA mAbs as shown in the examples which follow, the engagement of this pathway may prove to be a revolution in the management of different human autoimmune diseases. Moreover, the immunosuppressive impact of anti-VISTA on both adaptive and innate autoimmune effector mechanisms sets it apart from many other anti-inflammatory agents.

With respect to the foregoing, it was hypothesized that a desirable and necessary reagent in screening for agonistic anti-human VISTA Abs is a human VISTA knock-in mouse. A human VISTA knock-in mouse has been created by the present Assignee ("hV-KI Mouse"). These hV-KI mice express human VISTA in replacement of mouse VISTA. Particularly, as shown in FIG. 3 CD4$^+$ T cells, CD8$^+$ T cells, Tregs (CD4$^+$FoxP3$^+$), and monocytes, CD11b$^+$, Ly6C$^+$, Ly6G were isolated from the lymph nodes of WT and VISTA KI mice, and stained with αVISTA antibodies against mouse or human protein respectively. The expression pattern of the hV-KI is identical to what is seen in WT mice as CD4$^+$ and CD8$^+$ T cells, regulatory T cells and monocytes all express consistent amounts of surface protein between the two strains (see FIG. 3).

Additionally, hV-KI mice do not develop any signs of inflammatory disease that are observed in VISTA KO mice, indicating that hVISTA is fully functional within the mouse immune system (data not shown). Accordingly, this mouse model may be used in different assays to screen for immunosuppressive mAbs.

Example 4: Synthesis of Putative Agonistic Anti-Human VISTA Antibodies

The sequences of different anti-human VISTA antibodies is contained in FIG. 4. These antibodies specifically bind to human VISTA, e.g., VSTB49-VSTB116, and possess VISTA antagonist properties, i.e., these antibodies inhibit the suppressive effects of VISTA on immunity when in the IgG1 format, e.g., when the antibody comprises an IgG1 Fc region which is wild-type, i.e., unmodified.

Among the antibodies identified in FIG. 4 is 1E8. This murine anti-human VISTA antibody comprises the variable heavy and light chain polypeptides set forth below and was converted by the inventors into two human chimeric forms. The first chimeric antibody referred to herein as INX800 was obtained by the attachment of human IgG2 heavy and light constant region polypeptides to the 1E8 variable heavy and light chain polypeptides. In this first chimeric antibody none of the amino acid residues within the IgG2 constant regions were modified.

The second chimeric antibody referred to herein as INX801 was similarly obtained by the attachment of human IgG2 heavy and light constant region polypeptides to the 1E8 variable heavy and light chain polypeptides. In this second chimeric antibody the cysteine residue at position 127 within the human IgG2 kappa chain was converted into a serine. Otherwise none of the amino acid residues within the IgG2 constant regions were modified.

```
IE8 V_H Polypeptide
                              (SEQ ID NO: 57)
EVKLLESGGGLVQPGGSLKLSCAASGFDFSRYWMSWVRQAPGKGLEWIGE

VYPDSSTINYTPSLKDKFIISRDNAKNTLYLQMIKVRSEDTALYYCARGR

GDYWGQGTSVTVSS

IE8 V_L Polypeptide
                              (SEQ ID NO: 58)
DIQMTQSPASLSASVGETVTITCRASGNIHNYLSWYHQKQGKSPQLLVYN

AKTLADGVPSRFSGSGSGTQYSLKINSLQPEDFGSYYCQNFWSTPFTFGS

GTKLEIKR.
```

Example 5: Evaluation of Putative Agonistic Anti-Human VISTA Antibodies in ConA Animal Model The effects of both chimeric IgG2 antibodies and control antibodies were compared in a Concavalin A Hepatitis model. In this in vivo model different animals were predosed with 10 mg/kg of either chimeric IgG2 antibody (INX800 or INX801) or with a control antibody 3 hours prior to Concavalin A administration. 3 hours after antibody administration the mice were then dosed with ConA at 12 mg/kg. These animals and the controls were then bled by cardiac puncture 6 hours after ConA dosing. All of the mice appeared fine, no obvious morbidity or mortality.

The blood was then analyzed for cytokine expression. Particularly, a 32-plex was run using plasma obtained from the collected blood samples using conventional methods and cytokine test kit conventionally used for cytokine analysis. As shown in FIG. 5 the expression of several proinflammatory cytokines was significantly suppressed in the animals administered INX800 or INX801 antibodies compared to the control animals. Particularly, GM-CSF, IL-2, IL-4, IL-6, IL-17 and TNF-α levels were all significantly lower in the INX800 or INX801 treated animals compared to the controls. [Reduced] expression of these cytokines was substantially identical in the INX800 or INX801 treated animals.

Also, the expression of certain chemokines (keratinocyte derived chemokine or "KC") and macrophage inflammatory protein 2 (MIP-2) were substantially increased in the INX800 or INX801 treated animals compared to the controls. Again, the [increased] expression of these proteins was substantially identical in the INX800 or INX801 treated animals. Based on these results both INX800 and INX801 appear to be potent VISTA agonists as they appear to elicit the analogous immunosuppressive effects that VISTA elicits ion the expression of various inflammatory cytokines.

Figure 6:
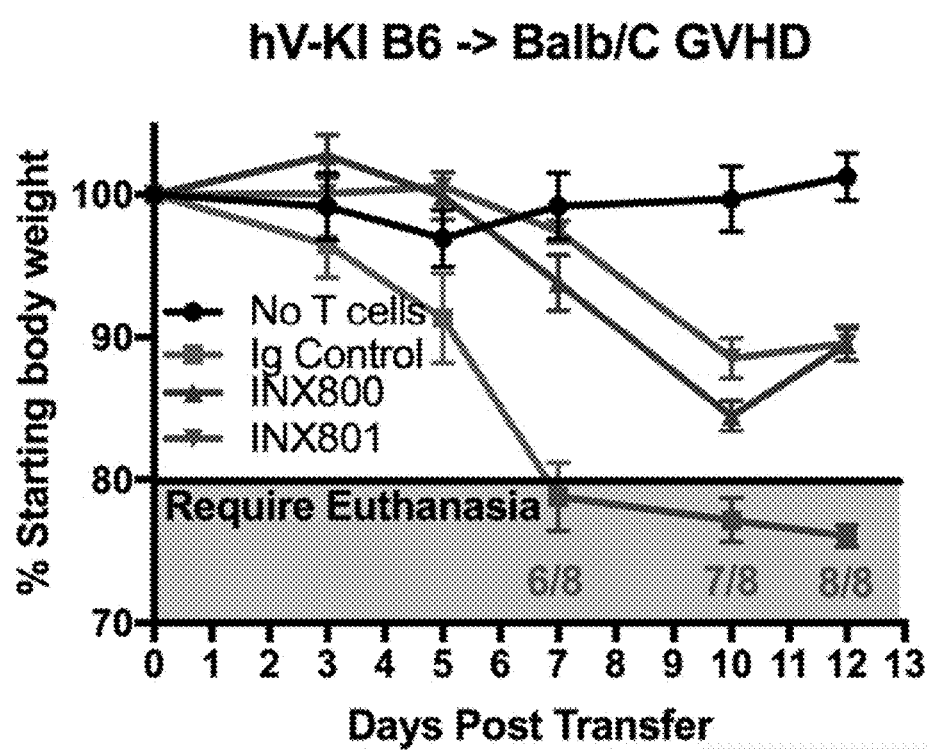
FIG. 6 shows the effects of exemplary anti-human VISTA antibodies, i.e., INX800 and INX801 in an in vivo graft versus host disease (GVHD) animal model.

Example 6: Evaluation Of Putative Agonistic Anti-Human VISTA Antibodies In Graft Versus Host Disease (GVHD) Animal Model The effects of the same putative agonistic anti-human VISTA antibodies, INX800 and INX801 were also compared in a graft versus host disease (GVHD) animal model compared to untreated animals or controls treated with irrelevant antibody. In this animal model T cells were adoptively transferred into irradiated hosts and body-weight was measured as a read out of disease. Based on GVHD disease progression all of the Control mice (8/8) had to be euthanized. The results of these animal studies are shown in FIG. 6. As shown none of the INX800 or INX801 [0/8] treated mice needed to be euthanized as GVHD was considerably depressed as a result of treatment with INX800 or INX801 antibody. Based on these results both INX800 and INX801 appear to be potent VISTA agonists as they appear to potently suppress GVHD immune responses.

Figure 7:
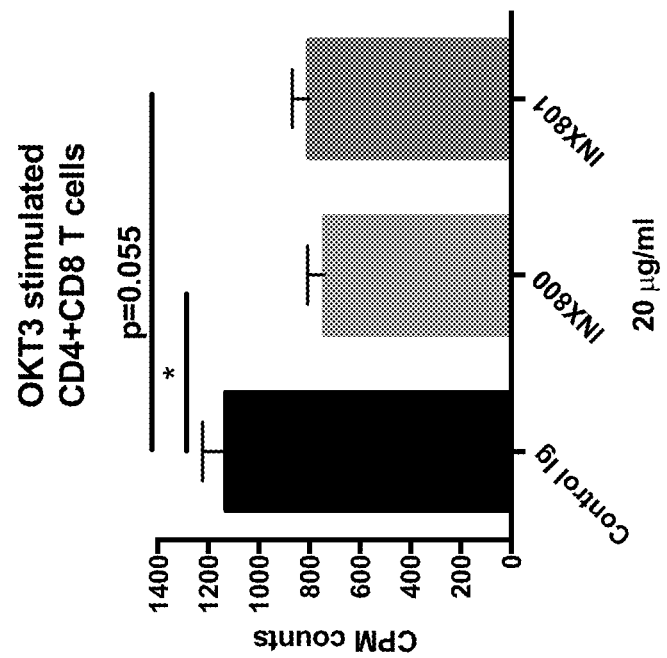
FIG. 7 shows the effects of exemplary agonistic anti-human VISTA antibodies, i.e., INX800 or INX801 on CD3-driven T cell immune responses.

Example 7: Effects Of Putative Agonistic Anti-Human VISTA Antibodies On CD3-Driven T Cell Immune Responses The effects of the same agonistic anti-human VISTA antibodies, INX800 and INX801 were also compared as to their potential to suppress CD3-driven T cell immune response. In these experiments plates were coated with OKT3 (2.5 μg/ml). T cells were the preincubated with antibody for 30 minutes. The antibody treated T cells were then added to the OKT3 coated plates and the T cells cultured on these plates for 72 hours. As a readout of the possible effects of the antibodies on CD3-driven T cell immune responses T cell proliferation was determined using Tritium incorporation methods, a well-accepted method for detecting T cell proliferation. As shown in FIG. 7, T cell proliferation was considerably reduced in the cultured T cells which were treated with INX800 or INX801 antibodies compared to the control T cell cultures.

Example 8: Effects of Putative Agonistic Anti-Human VISTA Antibodies on Specific T Cell Populations and Total T Cell Numbers Experiments were also affected in order to compare the possible effects of the same anti-human VISTA antibodies, INX800 and INX801, on the numbers of specific T cells as well as on the total number of T cells. These experiments were conducted in order to assess whether the observed effects of the subject anti-human VISTA antibodies on cytokines and T cells could have been attributable to cell depletion (a non-specific effect) rather than the antibodies eliciting an immunosuppressive effect based on their promoting specific VISTA-mediated immunosuppressive effects on immunity.

Figure 8:
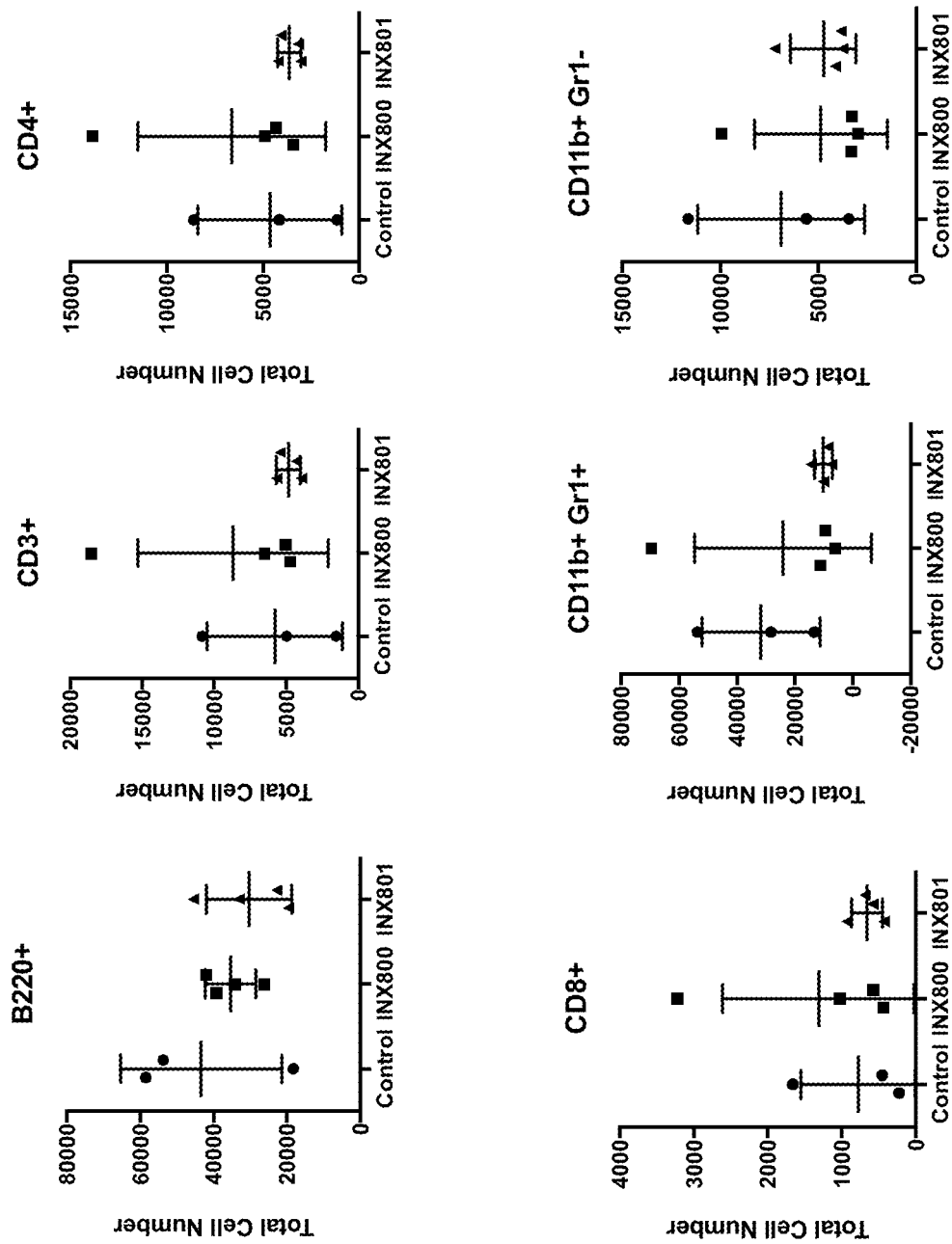
FIG. 8 shows the effects of exemplary agonistic anti-human VISTA antibodies, i.e., INX800 or INX801 on the number of specific T cell populations or on total T cell numbers.

Both agonistic anti-human VISTA antibodies, INX800 and INX801, had no significant effect on the number of specific T cell populations, or on the total number of T cells. Moreover, the results with both the INX800 and INX801 antibodies were substantially the same. The results of exemplary experiments are in FIG. 8.

Based thereon, the observed agonistic effects of INX800 and INX801 do not appear to be attributable to cell depletion. Rather, both of these antibodies appear to elicit an immunosuppressive effect on T cell activation/proliferation, GVHD immune responses and the expression of proinflammatory cytokines based on their promoting specific VISTA-mediated immunosuppressive effects on immunity.

Example 9: Summary of Effects of Different Agonistic Anti-Human VISTA Abs in Different Immune Models As shown in Table 1 and 2 below the agonistic or immunosuppressive effects of different anti-human VISTA antibodies was evaluated having the sequences are in FIG. 4. To date 12 different chimeric anti-human VISTA antibodies have been demonstrated to be immunosuppressive. Some of the results obtained to date are summarized in the Tables. Antibodies in Bin 1 all compete for binding to human VISTA but do not compete for VISTA binding with antibodies in Bin 2. Conversely, the anti-human VISTA antibodies in Bin 2 all compete for binding to human VISTA with each other but not with antibodies in Bin 1.

The antibody in Table 2 which is marked "inconclusive" elicited different effects, including immunosuppressive effects in the same assay or elicited ambiguous results for other reasons. As shown in Table 1 and 2 a total of 12 anti-human VISTA antibodies have been isolated which are immunosuppressive in MLR assays or ConA assays and/or other in vitro and in vivo assays or autoimmune, inflammatory or GVHD disease models and which mimic or agonize the immunosuppressive effects of human VISTA. Based on these results it is expected that other anti-human VISTA antibodies may be obtained by analogous methods including those having the same or different VISTA epitopic specificity.

Figure 9:
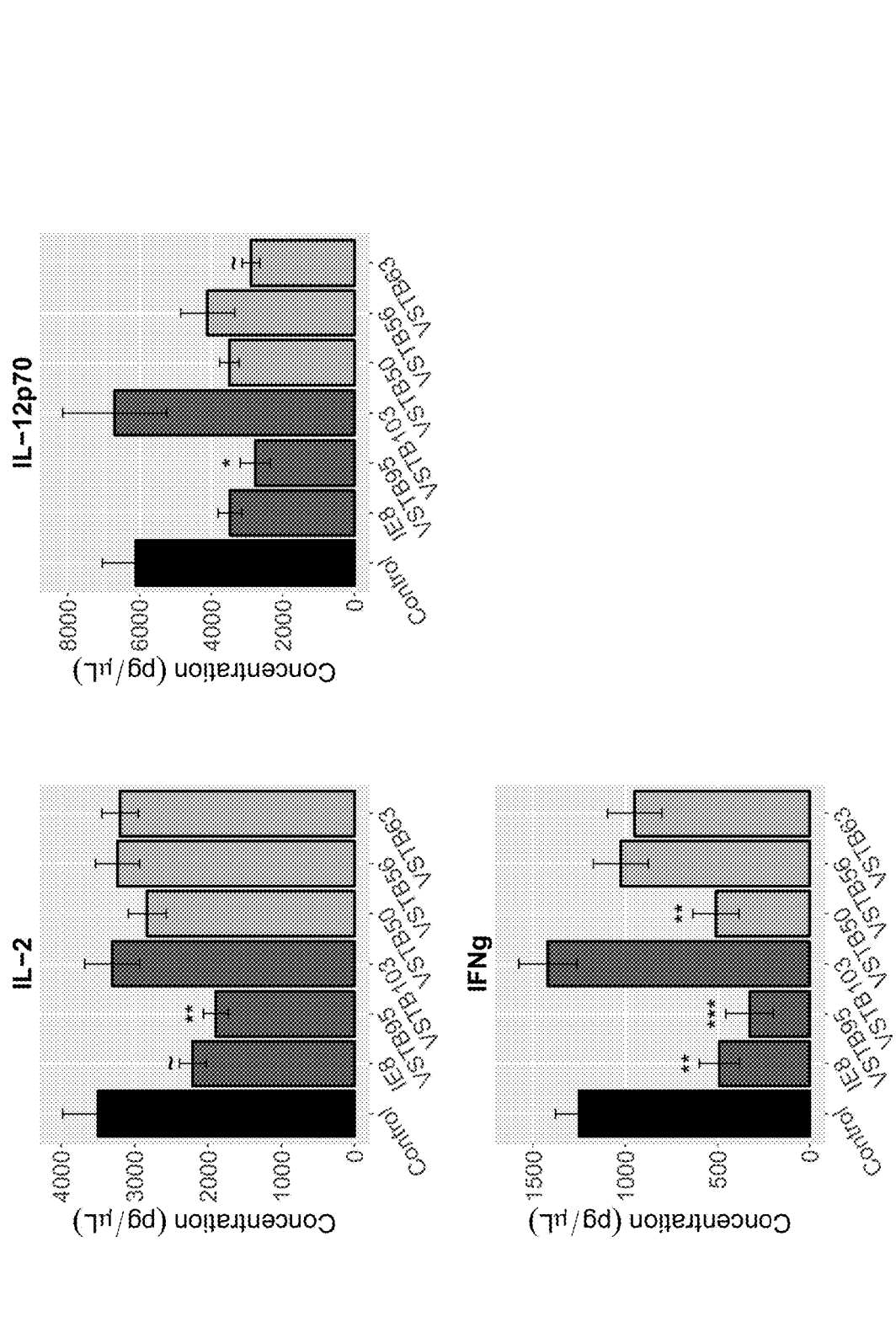
FIG. 9 compares the effects of exemplary anti-human VISTA antibodies in ConA assays and on the expression of select proinflammatory cytokines and inflammation markers, i.e., IL-2, γ interferon and IL-12p70.

Also, the experiments in FIG. 9 compare the effects of different anti-human VISTA antibodies in ConA assays and on the expression of select proinflammatory cytokines and inflammation markers, i.e., IL-2, γ interferon and IL-12p70.

TABLE 1

(HUMAN OR HUMANIZED ANTI-HUMAN VISTA ANTIBODIES)

| mAb ID | Epitope Group | Origin | 1st Assay MLR Prolif as IgG1 | Kd, M | Status | Suppression as IgG2 In MLR and/or ConA Hep Assay | 2nd Assay MLR Prolif. as IgG1) |
|---|---|---|---|---|---|---|---|
| INX903\|VSTB95 | 1 | HFA Hybr (His) | ++ | 1.26E−10 | Tested For immuno suppression | + | |
| INX904\|VSTB103 | 1 | Phage, original | − | 6.36E−10 | Tested For immuno suppression | +/− | yes |
| INX905\|VSTB53 | 1 | HFA Hybr (Fc) | ++ | 2.64E−11 | Tested For immuno suppression | ++ | |
| INX908\|VSTB92 | 1 | HFA Hybr (Fc) | ++ | 9.34E−11 | **Tested For immuno suppression | ++ | |
| INX900\|VSTB50 | 2 | HFA Hybr (Fc) | ++ | 6.32E−10 | Tested For immuno suppression | +/− | |
| INX901\|VSTB56 | 2 | HFA Hybr (Fc) | +/− | 2.35E−11 | Tested For immuno suppression | ++ | yes |
| INX902\|VSTB63 | 2 | HFA Hybr (Fc) | +/− | 8.30E−10 | Tested For immuno suppression | ++ | yes |
| INX906\|VSTB54 | 2 | HFA Hybr (Fc) | +/− | 2.53E−11 | Tested For immuno suppression | ++ | |
| INX907\|VSTB66 | 2 | HFA Hybr (Fc) | +/− | 8.06E−11 | Tested For immuno suppression | + | yes |

TABLE 1-continued (HUMAN OR HUMANIZED ANTI-HUMAN VISTA ANTIBODIES)

| mAb ID | Epitope Group | Origin | 1st Assay MLR Prolif as IgG1 | Kd, M | Status | Suppression as IgG2 In MLR and/or ConA Hep Assay | 2nd Assay MLR Prolif. as IgG1) |
|---|---|---|---|---|---|---|---|
| INX909|VSTB67 | 1 | HFA Hybr (Fc) | +/− | 6.29E−11 | To be tested | | |
| INX913|VSTB85 | 1 | HFA Hybr (InterFAD) | ++ | 3.78E−11 | To be tested | | |
| INX914|VSTB97 | 1 | Phage, original | +/− | 7.68E−10 | To be tested | | |
| INX915|VSTB106 | 1 | Phage, ILM | +/− | 1.67E−10 | To be tested | | |
| INX916|VSTB107 | 1 | Phage, ILM | ++ | 8.90E−11 | To be tested | | |
| INX917|VSTB110 | 1 | Phage, ILM | +/− | 2.02E−10 | To be tested | | |
| INX918|VSTB113 | 1 | Phage, ILM | ++ | 4.33E−11 | To be tested | | |
| INX919|VSTB115 | 1 | Phage, ILM | +/− | 1.45E−10 | To be tested | | yes |
| INX910|VSTB73 | 2 | HFA Hybr (His) | +/− | 2.26E−09 | To be tested | | yes |
| INX911|VSTB76 | 2 | HFA Hybr (His) | +/− | 1.31E−09 | To be tested | | |
| INX912|VSTB84 | 2 | HFA Hybr (InterFAD) | + | 2.03E−09 | To be tested | | |
| VSTB100 | 1 | Phage, original | +/− | 1.48E−09 | | | |
| VSTB101 | 1 | Phage, original | +/− | 3.18E−09 | | | |
| VSTB102 | 1 | Phage, original | +/− | 2.98E−09 | | | |
| VSTB104 | 1 | Phage, original | + | 6.75E−10 | | | |
| VSTB105 | 1 | Phage, ILM | + | 1.15E−10 | | | |
| VSTB108 | 1 | Phage, ILM | + | 4.94E−10 | | | |
| VSTB109 | 1 | Phage, ILM | +/− | 1.02E−10 | | | |
| VSTB111 | 1 | Phage, ILM | ++ | 1.71E−10 | | | |
| VSTB112 | 1 | Phage, ILM | ++ | 1.56E−10 | | | |
| VSTB114 | 1 | Phage, ILM | ++ | 1.52E−10 | | | |
| VSTB116 | 1 | Phage, ILM | ++ | 2.13E−10 | | | |
| VSTB49 | 1 | HFA Hybr (Fc) | + | 5.07E−10 | | | |
| VSTB51 | 1 | HFA Hybr (Fc) | ++ | 1.04E−10 | | | |
| VSTB59 | 1 | HFA Hybr (Fc) | + | 1.06E−10 | | | |
| VSTB65 | 1 | HFA Hybr (Fc) | ++ | 1.08E−09 | | | |
| VSTB70 | 1 | HFA Hybr (His) | +/− | 2.23E−09 | | | |
| VSTB81 | 1 | HFA Hybr (InterFAD) | +/− | 3.12E−10 | | | |
| VSTB98 | 1 | Phage, original | + | 2.28E−09 | | | |
| VSTB99 | 1 | Phage, original | +/− | 1.54E−09 | | | |
| VSTB60 | 2 | HFA Hybr (Fc) | + | 3.56E−10 | | | |

TABLE 1-continued (HUMAN OR HUMANIZED ANTI-HUMAN VISTA ANTIBODIES)

| mAb ID | Epitope Group | Origin | 1st Assay MLR Prolif as IgG1 | Kd, M | Status | Suppression as IgG2 In MLR and/or ConA Hep Assay | 2nd Assay MLR Prolif. as IgG1) |
|---|---|---|---|---|---|---|---|
| VSTB78 | 2 | HFA Hybr (InterFAD) | ++ | 1.13E−09 | | | |
| VSTB74 | 4 | HFA Hybr (His) | − | 5.62E−10 | | | |

TABLE 2

(MURINE ANTI-HUMAN VISTA ANTIBODIES)

| Antibody | Bin | Suppressive? | MLR Prolif. | Kd, M |
|---|---|---|---|---|
| 1E8* | 1 | Yes | ++ | NT |
| GG8 | 1 | Yes | ++ | NT |
| GA1 | 2 | Inconclusive | − | NT |

*Shown to be immunosuppressive in 2 different IgG2 forms.

Example 10: Determination of Epitopes of Anti-Human VISTA Antibodies by B Cell Epitope Mapping The epitopic specificity of some putative agonistic anti-human VISTA antibodies was determined using custom peptide arrays using fragments of human VISTA, using proprietary methods [ProArray Ultra™ ] Essentially, the determination of peptide-antibody binding was performed by incubation of a3ntibody samples with a ProArray Ultra™ peptide microarray, followed by incubation with a fluorescently labeled secondary antibody. After several washing steps the ProArray Ultra™ arrays were dried and scanned using a high-resolution fluorescence microarray scanning.

All peptides (listed below) are synthesized separately, and then bound to the ProArray Ultra™ slide surface using ProImmune's proprietary technology. This optimized process ensures that peptides are presented on the array in such a manner as to closely mimic the properties of the corresponding protein region, circumventing the inherent physiochemical variation of the free peptides themselves and making a compatible, combined peptide and protein array platform. The test analytes (peptides and proteins) are dispensed onto the ProArray Ultra™ slide in discrete spots and appropriate gal-files enable exact alignment of the resulting array features back to the analyte deposited.

Peptide-antibody binding is determined by incubation of antibody samples (provided by the customer) with the ProArray Ultra™ slides, followed by incubation with a fluorescently labeled secondary antibody. After the final incubation and washing steps the microarrays are dried and scanned in a high-resolution microarray scanning system.

After scanning the fluorescently labeled ProArray Ultra™ slides, the scanner records an image which is evaluated using image analysis software—enabling interpretation and quantification of the levels of fluorescent intensities associated with each fluorescent spot on the scanned microarray slide. The peptide microarray was based on an overlapping peptide library synthesized from the human VISTA polypeptide sequence. Based on the sequence 15-mer microarray peptides, overlapping by 12 amino acids, were generated using ProImmune's ProArray Ultra™ technology. Details of the peptides synthesized are listed in TABLE 3 (below). 'Position' refers to the start and end amino acid within the polypeptide sequence from which the peptide was derived. Synthesized peptides were immobilised onto ProArray Ultra™ slides in 24 identical sub-arrays, each comprising test-peptides and control features in sextuplicate spots. The peptides are shown in Table 3 below.

TABLE 3

ProArray Ultra Peptide Details

| Peptide ID | Position | Sequence |
|---|---|---|
| 1 | 1-15 | FKVATPYSLYVCPEG (SEQ ID NO: 7) |
| 2 | 4-18 | ATPYSLYVCPEGQNV (SEQ ID NO: 8) |
| 3 | 7-21 | YSLYVCPEGQNVTLT (SEQ ID NO: 9) |
| 4 | 10-24 | YVCPEGQNVTLTCRL (SEQ ID NO: 10) |
| 5 | 13-27 | PEGQNVTLTCRLLGP (SEQ ID NO: 11) |
| 6 | 16-30 | QNVTLTCRLLGPVDK (SEQ ID NO: 12) |
| 7 | 19-33 | TLTCRLLGPVDKGHD (SEQ ID NO: 13) |
| 8 | 22-36 | CRLLGPVDKGHDVTF (SEQ ID NO: 14) |
| 9 | 25-39 | LGPVDKGHDVTFYKT (SEQ ID NO: 15) |
| 10 | 28-42 | VDKGHDVTFYKTWYR (SEQ ID NO: 16) |
| 11 | 31-45 | GHDVTFYKTWYRSSR (SEQ ID NO: 17) |
| 12 | 34-48 | VTFYKTWYRSSRGEV (SEQ ID NO: 18) |
| 13 | 37-51 | YKTWYRSSRGEVQTC (SEQ ID NO: 19) |
| 14 | 40-54 | WYRSSRGEVQTCSER (SEQ ID NO: 20) |

TABLE 3-continued

ProArray Ultra Peptide Details

| Peptide ID | Position | Sequence |
|---|---|---|
| 15 | 43-57 | SSRGEVQTCSERRPI (SEQ ID NO: 21) |
| 16 | 46-60 | GEVQTCSERRPIRNL (SEQ ID NO: 22) |
| 17 | 49-63 | QTCSERRPIRNLTFQ (SEQ ID NO: 23) |
| 18 | 52-66 | SERRPIRNLTFQDLH (SEQ ID NO: 24) |
| 19 | 55-69 | RPIRNLTFQDLHLHH (SEQ ID NO: 25) |
| 20 | 58-72 | RNLTFQDLHLHHGGH (SEQ ID NO: 26) |
| 21 | 61-75 | TFQDLHLHHGGHQAA (SEQ ID NO: 27) |
| 22 | 64-78 | DLHLHHGGHQAANTS (SEQ ID NO: 28) |
| 23 | 67-81 | LHHGGHQAANTSHLD (SEQ ID NO: 29) |
| 24 | 70-84 | GGHQAANTSHDLAQR (SEQ ID NO: 30) |
| 25 | 73-87 | QAANTSHDLQARHGL (SEQ ID NO: 31) |
| 26 | 76-90 | NTSHDLAQRHGLESA (SEQ ID NO: 32) |
| 27 | 79-93 | HDLAQRHGLESASDH (SEQ ID NO: 33) |
| 28 | 82-96 | AQRHGLESASDHHGN (SEQ ID NO: 34) |
| 29 | 85-99 | HGLESASDHHGNFSI (SEQ ID NO: 35) |
| 30 | 88-102 | ESASDHHGNFSITMR (SEQ ID NO: 36) |
| 31 | 91-105 | SDHHGNFSITMRNLT (SEQ ID NO: 37) |
| 32 | 94-108 | HGNFSITMRNLTLLD (SEQ ID NO: 38) |
| 33 | 97-111 | FSITMRNLTLLDSGL (SEQ ID NO: 39) |
| 34 | 100-114 | TMRNLTLLDSGLYCC (SEQ ID NO: 40) |
| 35 | 103-117 | NLTLLDSGLYCCLVV (SEQ ID NO: 41) |
| 36 | 106-120 | LLDSGLYCCLVVEIR (SEQ ID NO: 42) |
| 37 | 109-123 | SGLYCCLVVEIRHHH (SEQ ID NO: 43) |
| 38 | 112-126 | YCCLVVEIRHHHSEH (SEQ ID NO: 44) |
| 39 | 115-129 | LVVEIRHHHSEHRVH (SEQ ID NO: 45) |
| 40 | 118-132 | EIRHHHSEHLVHGAM (SEQ ID NO: 46) |
| 41 | 121-135 | HHHSEHRVHGAMELQ (SEQ ID NO: 47) |
| 42 | 124-138 | SEHRVHGAMELQVQT (SEQ ID NO: 48) |
| 43 | 127-141 | RVHGAMELQVQTGKD (SEQ ID NO: 49) |
| 44 | 130-144 | GAMELQVQTGKDAPS (SEQ ID NO: 50) |
| 45 | 133-147 | ELQVQTGKDAPSNCV (SEQ ID NO: 51) |
| 46 | 136-150 | VQTGKDAPSNCVVYP (SEQ ID NO: 52) |
| 47 | 139-153 | GKDAPSNCVVYPSSS (SEQ ID NO: 53) |
| 48 | 142-156 | APSNCVVYPSSSQDS (SEQ ID NO: 54) |
| 49 | 145-159 | NCVVYPSSSQDSENI (SEQ ID NO: 55) |
| 50 | 148-162 | VYPSSSQDSENITAA (SEQ ID NO: 56) |

The results of this epitope analysis with particular anti-human VISTA antibodies are summarized in FIG. 4.

Example 11: Epitope Binning Assay

Additionally the epitopic binding properties of some anti-human VISTA antibodies having sequences shown in FIG. 4 were characterized by placing these antibodies into different epitope "bins" based on their binding characteristics as described below.

Methods: ProteOn XPR36 system (BioRad) was used to perform epitope binning. ProteOn GLC chips (BioRad, Cat #176-5011) were coated with two sets of 6 monoclonal antibodies (mAbs) using the manufacturer instructions for amine-coupling chemistry (BioRad, cat #176-2410). Competing mAbs were pre-incubated in excess (250 nM final concentration) with human VISTA (25 nM final concentration) for 4 hours at room temperature and 6 at a time were run over the chip coated with the panels of coated mAbs with an association time of 4 minutes followed by dissociation for 5 minutes. Following each run, the chips were regenerated with 100 nM phosphoric acid.

The data analysis involved grouping all sensorgrams by ligand and applying an alignment wizard, which automatically performs an X and Y axis alignment, and artifact removal. An Interspot correction was then applied to the data.

A non-competing mAb was defined as having a binding signal the same or >Al signal (binding to human VISTA only). A competing mAb was defined as having binding signal <<Al signal (i.e., binding to human VISTA only). For example VSTB49 and VSTB51 complexed with VISTA did not bind to the VSTB85 coated on the chip and therefore were classified as competing for the same binding site on VISTA as VSTB85. The results of this binning analysis with particular anti-human VISTA antibodies are summarized in FIG. 4.

Example 12: Epitope Mapping of Anti-VISTA Antibodies Using Hydrogen/Deuterium (H D) Exchange Studies Antibody epitopes of anti-VISTA antibodies may be identified by various methods such as alanine scanning and Hydrogen/Deuterium (H D) Exchange and overlapping peptide arrays as described in the previous Example. Another exemplary means for identifying epitopes of putative agonistic anti-human VISTA antibodies is described below.

To identify the epitopes for VSTB50, 60, 95 and 112 on human VISTA, solution hydrogen/deuterium exchange-mass spectrometry (HDX-MS) was performed using the corresponding Fabs. For H/D exchange, the procedures used to analyze the Fab perturbation were similar to that described previously (Hamuro et al, J. Biomol. Techniques 14:171-182, 2003; Horn et al, Biochemistry 45:8488-8498, 2006) with some modifications. Fabs were prepared from the IgGs with papain digestion and Protein A capture using Pierce Fab Preparation Kit (Thermo Scientific, Cat #44985). The human VISTA protein sequence contains six N-linked glycosylation sites. To improve the sequence coverage, the protein was deglycosylated with PNGase F. The deglycosylated VISTA protein was incubated in a deuterated water solution for predetermined times resulting in deuterium incorporation at exchangeable hydrogen atoms. The deuterated VISTA protein was in complex with a Fab of VSTB50, VSTB60, VSTB95 or VSTB112 in 46 deuterium oxide (D20) at 4° C. for 30 sec, 2 min, 10 min and 60 min. The exchange reaction was quenched by low pH and the proteins were digested with pepsin. The deuterium levels at the identified peptides were monitored from the mass shift on LC-MS. As a reference control, VISTA protein was processed similarly except that it was not in complex with the Fab molecules. Regions bound to the Fab were inferred to be those sites relatively protected from exchange and, thus, containing a higher fraction of deuterium than the reference VISTA protein. About 94% of the protein could be mapped to specific peptides.

The solution HDX-MS perturbation maps of VISTA with VSTB50/VSTB60, and VSTB95/VSTB112 were mapped and two epitope groups were identified. Anti-VISTA VSTB50 recognizes the same epitope as VSTB60 does; VSTB95 binds to another epitope region as VSTB112 does on VISTA. Anti-VISTA VSTB50 and 60 share the same epitope which comprises segments, 103 NLTLLDSGL111 (SEQ ID NO:59), and 136VQTGKDAPSNC146 (SEQ ID NO:60) Anti-VISTA VSTB95 and VSTB112 appear to target similar epitopes, comprising segments 27PVDKGHDVTF36 (SEQ ID NO:61), and 54RRPIRDLTFQDL65 (SEQ ID NO:62). These HDX-MS results provide the peptide level epitopes for exemplary anti-VISTA antibodies having the sequences identified in FIG. 4. There were no overlapping epitope regions for these two epitope groups. These results are in agreement with the previous competition binning data in that they do not compete with each other. Again the epitope analysis results for various anti-human VISTA antibodies analyzed as described herein is summarized in FIG. 4.

Example 13: Assays for Identifying Agonist Anti-Human VISTA Antibodies

As disclosed herein, we have identified a dozen agonistic anti-human VISTA antibodies and should be in possession of others once further corroborative experiments in the aforedescribed immune models are conducted or repeated with other antibodies. The antibodies identified in FIG. 4 by "VSTB" designations are fully-human, high-affinity cynomolgus monkey cross-reactive anti-VISTA antibodies (library affinity range 298-24 pM for human and 443-26 pM for cynomolgus monkey) which, based on the successful isolation of numerous agonistic anti-human antibodies as described herein should give rise to the identification of other agonistic anti-human VISTA antibodies, especially others which bind to epitope group 1 or 2. These methods are described below.

Functional Screening In Vitro

Direct CD4 Mediated:

In this approach $CD4^+$ T cells are isolated by negative selection from hV-KI splenocytes. $1 \times 10^5$ T cells will then be incubated with each of the 50 VISTA mAb (20 µg/ml) or an isotype control for 30 minutes on ice. The T cells and antibody will then be placed on anti-CD3 coated 96-well flat-bottom plates and cultured for 72 hours. At the 72-hour time point, tritiated thymidine will be added to the culture for 8 hours to measure proliferation by H3 incorporation. Using this assay, we can screen all 50 mAb in a single experiment in technical triplicates. Each antibody will be tested in three independent experiments to confirm activity. MAb that decrease proliferation to a statistically significant extent in comparison to the isotype control will be identified as "suppressive." All suppressive mAb identified in the initial screen will then be retested in the same assay, to generate a dose-response curve. Each antibody will be tested at half-log dilutions (30 µg/ml→0.01 g/ml) and IC50 values will be calculated for proliferation. All antibodies that are identified as suppressive in the hV-KI assay will be confirmed on primary human T cells, and ranked by IC50 scores for proliferation.

NHP Cross-Reactivity Assay:

In this assay we will screen for functional activity in a relevant tox species, Macaca fascicularis (hereafter referred to as nonhuman primates or "NHPs"), through the identical CD3 mediated proliferation assays described for mouse and human, through use of the CD3 clone SP34 which drives potent T cell proliferation. Whole blood from NHPs will be obtained from World Wide Primates (Florida, USA), and T cells will be isolated through magnetic separation. The T cells will be incubated with antibody and cultured on CD3 coated plates for 72 hours. Proliferation will be measured by tritium incorporation and IC50 scores will be generated for each antibody.

Functional Screening Using In Vivo Animal Models

1. Testing of Vista Agonist Antibodies According to the Invention in Concanavalin A-Induced Hepatitis Animal Model.

Autoimmune hepatitis (AIH) is a chronic inflammatory disease of the liver, characterized by the loss of self-tolerance leading to B and T cell responses against the liver. The ConA model represents the best-characterized system for understanding the pathogenesis of AIH. ConA is a lectin that binds to specific sugar moieties, which are enriched in the liver. The modification of these sugar residues by ConA results in rapid CD4; T cell activation through interaction with modified MHC structures expressed by liver macrophages. An intense, but transient, cytokine production occurs with most canonical T cell cytokines (IL-2, IL-3, IFNγ and TNFα) reaching peak plasma levels within 4-6 hours. Notably, ConA induced inflammation can be blocked by depleting CD4+ T cells. The ConA model with hV-KI mice may be used to confirm suppressive activity of agonistic anti-VISTA mAbs according to the invention. Mice are weighed and treated with 10 mpk of anti-VISTA antibody or the appropriate isotype control 3 hours prior to injection with 15 mpk of ConA. The anti-VISTA mAbs are administered I.P. while ConA is injected via the tail-vein in these mice. At the 6-hour time-point post ConA administration, the mice are euthanized and blood is collected. The plasma fraction is then be analyzed for plasma cytokines by a multiplex assay for 32 cytokines. Each antibody is tested two times in independent experiments to confirm activity. For each cytokine in the 32-plex, a one-way ANOVA will be performed, with a Dunnett's post-test to compare each anti-VISTA antibody to the isotype control. The tested anti-VISTA mAb is ranked based upon efficacy of cytokine suppression (how much was the cytokine suppressed) and variability (how consistent is the suppression within each experiment and between experiments). Additional emphasis is placed on mAb that suppress cytokines that are canonically associated with T cell activation.

As disclosed in a related PCT application filed on even date and supra, several anti-human VISTA antibodies according to the invention were screened in the ConA model and were efficacious (immunosuppressive) therein, i.e., they suppressed ConA-induced cytokine production and promoted survival and in particular suppressed the expression of cytokines involved in T cell activation including IL-2. Particularly, the inventors tested INX800, INX801, and INX903 and INX904 as well as agonist anti-murine VISTA antibodies and all were efficacious (immunosuppressive) in the ConA hepatitis model. Therefore, agonist anti-human VISTA antibodies according to the invention should be useful in treating/preventing inflammation and hepatotoxicity associated with some chronic and acute infectious conditions such as hepatitis.

2. Testing of Vista Agonist Antibodies According to the Invention in Graft Versus Host Disease Animal Models GVHD is a systemic disease mediated by adoptive transfer of allogeneic T cells into an irradiated host. There are five major steps that are critical in the pathogenesis of GVHD; 1) Damage to the host, most commonly in the form of the irradiation event that precedes the T cell transfer; 2) Activation of the allogeneic T cells by both host and donor APCs; 3) Expansion of the T cells in the lymph nodes and spleen; 4) Trafficking into peripheral sites such as the skin, gut, liver and lung; and 5) Damage to the host driven by T cells and also recruited myeloid cells. In certain models, such as F1→Parental strain, a chronic GVHD occurs that is a suitable model for lupus as the mice develop anti-nuclear mAb and immune complex mediated glomerular nephritis. Of note, genetic deletion of VISTA from the donor T cells results in a more aggressive form of GHVD than seen in mice receiving WT T cells.

This assay may be used to identify and rank agonism of agonistic anti-human VISTA candidates. Also this assay may be used to confirm that agonist antibodies according to the invention may be used to treat or prevent GVHD. In this model BALB/c mice are lethally irradiated and given allogeneic bone marrow and splenic T cells from hV-KI mice to induce GVHD; with one group not receiving T cells as a negative control. Mice receiving the allogeneic T cells are split into the control Ig group and the treatment groups. Up to four unique VISTA mAb will be used in a single experiment, with eight mice per group, and two replicate experiments will be conducted. 10 mpk or another dose of antibody is administered at the time of T cell transfer, as well as at days 2 and 4 post transfer. The body weight of each mouse will be tracked, and any mouse that loses more than 20% of its initial starting bodyweight will be sacrificed. Kaplan Meier curves are generated for each experiment with a log-rank statistical test comparing each anti-VISTA antibody to the control. Should all four VISTA mAb fully protect against GVHD, then dose response assays will be run in the GVHD model with groups being treated with 10, 3, 1 and 0.3 mpk of antibody. LD50 values will be calculated for each antibody.

As disclosed in a related application filed on even date and supra a number of agonist anti-human VISTA antibodies according to the invention were evaluated in this animal model. These tested antibodies all were efficacious (immunosuppressive) in this model, i.e., they reduced the symptoms of the disease, slowed disease progression, reduced disease-associated weight loss and promoted survival. Particularly, each of INX800, INX801, INX901, INX902, INX903 and INX904 were evaluated and were demonstrated to alleviate or prevent disease symptoms in this animal model. Also, it was determined using the A and B forms of INX901 that either the A or B form were equally effective in the GVHD animal model.

3. Testing of Vista Agonist Antibodies According to the Invention in an Animal Model of Inflammatory Bowel Disease.

Inflammatory bowel diseases (IBD), Crohn's disease and ulcerative colitis result from incompletely defined and complex interactions between host immune responses, genetic susceptibility, environmental factors, and the enteric luminal contents. Recent genome-wide association studies report associations between immune cell regulatory genes and IBD susceptibility. Both innate and adaptive immune cell intrinsic genes are represented in these studies, indicating a central role for these cell populations in IBD pathogenesis. There currently exist more than 50 animal models of human IBD. While no one model perfectly phenocopies human IBD, many are useful for studying various aspects of human disease, including disease onset and progression and the wound-healing response.

In one well established IBD model intestinal inflammation is initiated with syngeneic splenic $CD4^+CD45RB^-$ cell adoptive transfer into T and B cell deficient recipient mice. The CD4+CD45RBhi T cell population contains mainly naive T cells primed for activation that are capable of inducing chronic small bowel and colonic inflammation. This method allows the researcher to modify key experimental variables, including both innate and adaptive immune cell populations, to answer biologically relevant questions relating to disease pathogenesis. Additionally, this method provides precise initiation of disease onset and a well-characterized experimental time course permitting the kinetic study of clinical features of disease progression in mice. Intestinal inflammation induced by this method shares many features with human IBD, including chronic large and small bowel transmural inflammation, pathogenesis driven by cytokines such as TNF and IL-12, and systemic symptoms such as wasting. Thus, it is an ideal model system for studying the pathogenesis of human IBD.

As disclosed in a related PCT application filed on even date an agonistic anti-human VISTA antibody according to the invention (INX901) was tested and shown to be efficacious in this IBD model. Particularly this agonist antibody was demonstrated to suppress cytokine levels and to effectively prevent or inhibit (i) colitis related weight loss, (ii) weight loss associated with colitis progression, (iii) colon shortening, (iv) the recruitment of inflammatory infiltrates to the colon and (v) the development of colitis. Therefore, agonist VISTA antibodies according to the invention may be used in the treatment of IBD and related inflammatory and intestinal conditions.

4. Testing of Vista Agonist Antibodies According to the Invention in Lupus Animal Models.

Lupus is an autoimmune or inflammatory condition with symptoms including kidney inflammation, increased proteinuria, and splenomegaly. There are 4 types of lupus of which Systemic Lupus Erythematosus or ("SLE") is the most common form. This disease can be mild or severe and can affect major organ systems. Lupus is an autoimmune condition of unknown cause that may result in inflammation of the kidneys—called lupus nephritis—which can affect the body's ability to filter waste from the blood, and or if severe may result in kidney damage requiring dialysis or kidney transplant. Also SLE may result in an increase in blood pressure in the lungs—called pulmonary hypertension—which can cause difficulty breathing. Further SLE may cause Inflammation of the nervous system and brain which can cause memory problems, confusion, headaches, and strokes. Further SLE may result in inflammation in the brain's blood vessels which can cause high fevers, seizures, and behavioral changes. Also SLE may result in hardening of the arteries or coronary artery disease—the buildup of deposits on coronary artery walls—can lead to a heart attack.

As disclosed in a related PCT application filed on even date agonistic anti-human VISTA antibodies according to the invention (INX903, INX901, INX901-A and INX901-B) and anti-murine VISTA antibodies were tested and shown to be efficacious in different lupus models including the MRL/lpr lupus model, the NZBWF-1 lupus model and the B6D2F model. The B6D2F model is a murine model wherein SLE is induced by the transfer of human VISTA knock-in DDE1 CD8 depleted splenocytes (donor) into a B6D2F1 host (recipient) In this model, donor CD4 T cell polyclonal activation drives cognate host B cell activation, expansion, and their production of autoantibodies leading to renal disease. Lupus-like features of B6 CD8 depleted transferred to B6D2F1 model include: (1) Immune complex glomerulonephritis; (2) anti-nuclear abs; (3) anti-dsDNA abs; and (4) anti-RBC abs (Coombs positivity). Additionally, this model meets sex-based differences in renal disease severity.

In 3 different lupus models agonistic anti-human and murine VISTA antibodies were demonstrated to be efficacious and to reduce the incidence of lupus disease development, disease progression, reduce proteinuria levels, inhibit nephritis and kidney damage, reduce T cell activation and accumulation, reduce B cell activation and accumulation, and to inhibit autoantibody production. Particularly, INX903, INX901, INX901-A and INX901-B were shown to (i) reduce T cell proliferation and activation, (ii) reduce cognate B cell activation (MHCII expression) and accumulation, reduce splenomegaly, reduce anti-dsDNA IgG autoantibody production and to reduce type I interferon signature. Also these immunosuppressive effects were not impacted by whether the human IgG2 constant region of the antibody was in the A or B form. Therefore, agonist VISTA antibodies according to the invention may be used in the treatment of lupus and related inflammatory and autoimmune conditions.

5. Testing of Vista Agonist Antibodies in a Psoriasis Animal Model Imiquimod (IMQD) Induced Psoriasis Model The ability of anti-VISTA antibodies to treat psoriasis was evaluated using the Imiquimod (IMQD) induced Psoriasis Model. Imiquimod (IMQD) is a commercially available cream containing TLR7/8 agonists that is widely used for dermatological conditions such as viral infections and melanoma. Application of IMQD to the skin over multiple days results in thickening of the epidermis via proliferation of the keratinocytes. Additionally, an immunological infiltration into the dermis layer occurs, with populations of both T cells and myeloid cells. Recurrent administration of IMQD creates a skin lesion similar to what is observed in patients with Psoriasis. IL-17 and IL-23 are thought to be the major cytokines involved in the immune response to IMQD.

As disclosed in a related PCT application filed on even date an agonistic anti-VISTA antibody was tested and shown to be efficacious in this psoriasis model. Particularly, this antibody reduced the number of $CD3^+$ T cells infiltrating Imiquimod treated skin. Based on the observed results VISTA agonist antibodies may be used in the treatment or prevention of psoriasis and other T cell mediated autoimmune or inflammatory skin conditions.

6. Testing of Vista Agonist Antibodies in Arthritis Animal Model

The immunosuppressive effects of anti-VISTA antibodies to treat arthritis may be tested in different animal models. As disclosed in a related PCT application filed on even date agonistic anti-murine and anti-human VISTA antibodies were tested and shown to be efficacious in a well-accepted arthritis model, i.e., the Collagen induced arthritis or CIA Model. INX800, INX901, INX902 and INX903 as well as a hamster anti-murine anti-VISTA antibodies were all tested in this arthritis model. Disease development was assessed by measuring inflammation swelling in the affected joints over time. Clinical scoring was accomplished by awarding a score of 1 for each swollen digit, a score of 5 for a swollen footpad and a score of 5 for a swollen wrist or ankle (Charles River Labs scoring system), which added together give a maximal score of 60 for each animal.

As shown in this PCT application each of these antibodies decreased the arthritis disease and INX901 and INX902 significantly decreased disease scope. Based on these results anti-human VISTA agonist antibodies may be used in the treatment or prevention of rheumatoid arthritis and other inflammatory or autoimmune conditions.

Figure 11:
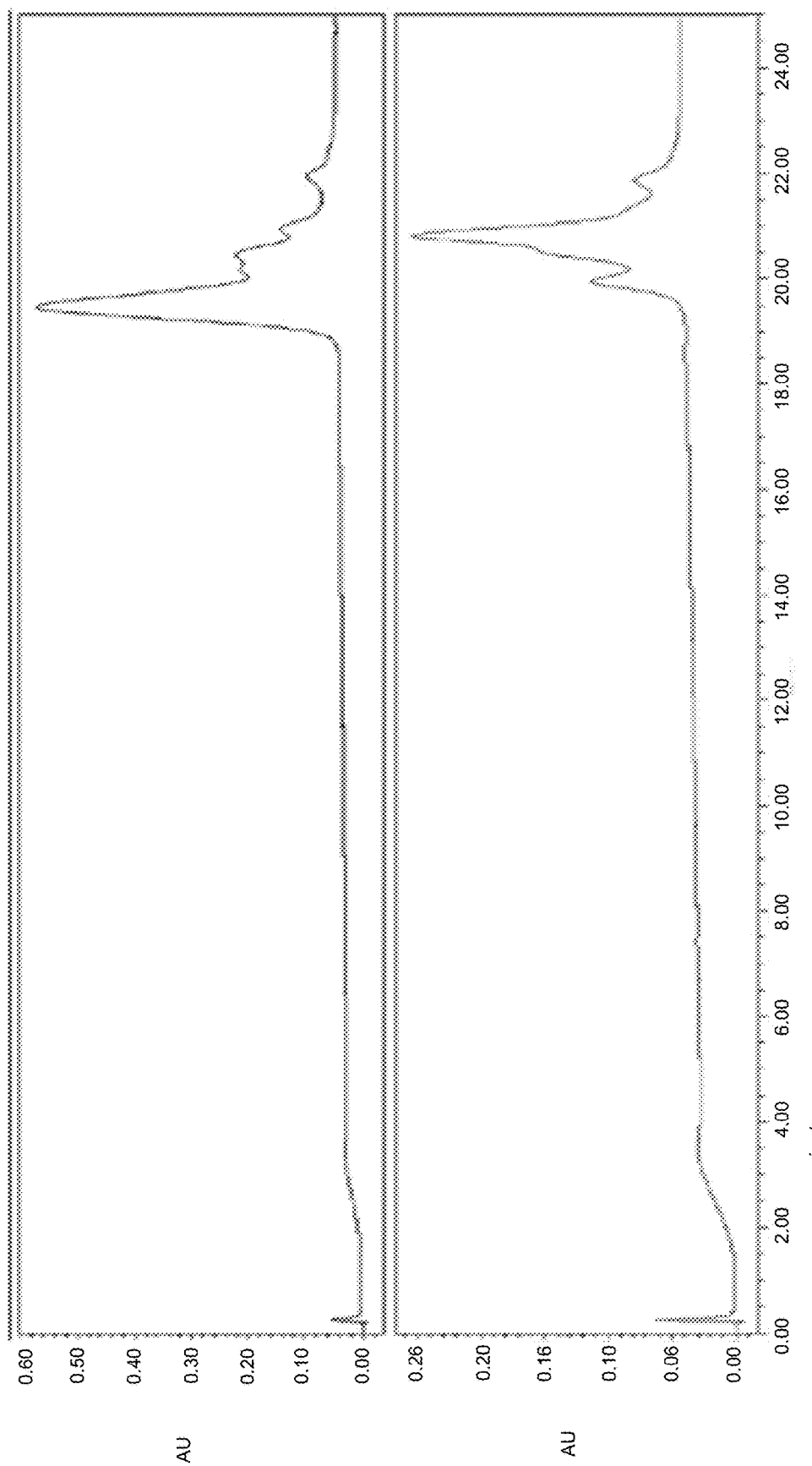
FIG. 11: shows chemical enrichment of IgG2 A or B isoforms. (Black line, top) Chromatogram shows a dominant left-most peak defining the B-form. (Red line, bottom) Chromatogram shows a dominant right peak defining the A-form.

Example 14: Evaluation of the Role of the Human IgG2 Backbone on α-Human VISTA Antibody INX901 Agonist/Immune-Suppressive Activity in Different In Vitro and In Vivo Models Antibodies on a native human IgG2 backbone exist as a mixture of isoforms caused by disulfide bond shuffling among cysteines present in the heavy chain hinge, CH1, and light chain (Zhang, A., (2015), "Conformational difference in human IgG2 disulfide isoforms revealed by hydrogen/deuterium exchange mass spectrometry", *Biochemistry*, 54(10), 1956-1962; FIG. 10). These isoforms were assessed by RP-HPLC (FIG. 10), based on methods developed by Dillon et al., "Optimization of a reversed-phase high-performance liquid chromatography/mass spectrometry method for characterizing recombinant antibody heterogeneity and stability", J Chromatography A, 1120(1), 112-120. The optimized method used a shallower and higher organic mobile phase B content relative to that in Dillon (id). Separate A and B forms enriched from INX901 were prepared closely following the conditions reported in Dillon (id) but combined with a buffer exchange back into DPBS and an endotoxin removal procedure employed subsequent to the enrichment reactions (FIG. 11).

In the course of preparing these experiments it was observed that reversion of the A-enriched form occurs more quickly than expected, and at lower residual redox reagent concentrations than expected. Utilization of a fast-spin, size-exclusion based desalting procedure was therefore employed, which appeared to largely prevent this reversion. As shown in panel (A) in FIG. 10 disulfide shuffling leads to isoforms A and B, along with the transition for A/B (reproduced from Zhang, A. et al., 2015). (B) Isoforms are distinguishable by RP-HPLC (figure from Zhang, A. et al., 2015). (C) Observed RP-HPLC chromatogram for INX901.

The inventors optimized RP-HPLC Method for detecting IgG2 isoforms is described below. In FIG. 11: (Black line, top) the chromatogram shows a dominant left-most peak defining the B-form. (Red line, bottom) Chromatogram shows a dominant right peak defining the A-form.

Optimized RP-HPLC Methods for Isoform Detection
Mobile Phase A Preparation (0.1% v/v TFA in Water):
1. Measured 1.0 L Milli-Q water in a 1.0 L graduated cylinder
2. Added 1.0 mL of TFA to the 1 L of water using a 1 mL glass Hamilton syringe
3. Transferred the solution to a 1 L bottle, mixed well.
4. Expiry is 2 weeks after preparation Mobile Phase B Preparation (70% v/v IPA, 20% v/v ACN, 9.9% v/v Water, 0.1% v/v TFA):
1. Measured 700 mL IPA into a 1.0 L graduated cylinder
2. Measured 200 mL ACN into a 250 mL graduated cylinder and transferred to the 1.0 L graduated cylinder containing the 700 mL IPA
3. Added Milli-Q water to the 1.0 L graduated cylinder containing the 700 mL IPA and 200 mL ACN until the liquid reached to 1.0 L mark
4. Added 1.0 mL of TFA to the 1 L of water using a 1 mL glass Hamilton syringe
5. Transferred the solution to a 1 L bottle, mixed well.
6. Expiry is 2 weeks after preparation RP-HPLC Chromatography Conditions
1. Column A (large bore): Zorbax 300SB-C8, 51 μm, 2.1×150 mm, <<OR>>
2. Column B (narrow bore): Zorbax 300SB-C8, 3.5 μm, 1×50 mm
3. Mobile Phase A: 0.1% v/v TFA in water
4. Mobile Phase B: 70% v/v IPA, 20% v/v ACN, 9.9% v/v water, 0.1% v/v TFA
5. Flow rate: 0.5 mL/min for Column A or 0.25 mL/min for Column B
6. Column compartment: 75.0±1.0° C.
7. Detection: 214 nm
8. RP-HPLC mobile phase gradient (Table below)

| Time (min) | Mobile Phase B % |
| --- | --- |
| 0 | 15 |
| 2 | 26 |
| 34 | 36 |
| 35 | 75 |
| 36 | 15 |
| 40 | 15 |

INX901 Disulfide Isoform Enrichment Methods
B-Form Enrichment
1. Into endotoxin free non-pyrogenic tube, add:
   2.1 mL of INX901 (5.66 mg/mL)
   792.6 μL 1 M Tris pH 8.0
   495.4 μL endo-free water
   396.3 additional endo-free water
   237.8 μL of 100 mM Cysteine
   39.6 μL of 100 mM Cystamine
2. Finger vortex (lightly), then place capped at 2-8° C. for 24 hr
3. Soaked Pall microsep spin-concentrator in 0.3M NaOH 2 hr at RT, then rinsed 3× with 10×DPBS, then 3× with endo-free water. Air dried in BSC before use
4. Followed vendor's instructions for regenerating 0.5 mL endotoxin removal column, using the 0.2N NaOH/95% ethanol (2 hrs at RT) option for step 3; used 1×DPBS as final equilibration buffer
5. Concentrated ~4,020 μL of reaction (from Step 2) in a separate PALL microsep (as prepared above).
6. Concentrated at 2,500×G for 35 min to less 0.4 mL (≥10×) then re-diluted with 4 mL 1×DPBS, repeated 2 additional times
7. Concentrated at 2,500×G for 15 min to below 2 mL, then added back 1×DPBS to 2 mL
8. Added all 2 mL of buffer exchanged sample to the regenerated, spun dried, bottom capped endotoxin removal column, capped the top tightly, inverted, placed at room temp-inverted 3 more times every ~20 minutes, then spun out the sample into non-pyrogenic tube (1 min at 500×G, as per Vendor's instructions), placed at 2-8° C.

A-Form Enrichment
1. Into endotoxin free non-pyrogenic tube, add:
   1750 μL INX901 (6.2 mg/mL)
   370 μL endo-free water
   700 μL 1M Tris pH8.0
   435 μL 8M GdCl
   210 μL 0.1 M Cysteine HCl (made fresh from 1 M stock)
   35 μL 0.1 M Cystamine-2HCl (made fresh from 1 M stock) (Final volume 3500 μL)
2. Finger vortex (lightly), then place capped at 2-8° C. for 24 hr
3. Prepared #7-2 mL Zeba spin columns (Thermo P/N 89890) as per vendor's instructions, equilibrating into 1× Dulbecco's Phosphate Buffered Saline (DPBS).
4. Loaded 500 μL of the above reaction mixture onto each of the #7, and spun 2 minutes at 1000×G (also as per vendor's instructions), collecting into clean pyrogen free tubes.
5. Placed in de-pyrogenated PALL microsep, spun total of 1 hour, 10 minutes, concentrated to approximately 1.7 mL at approximately 5 mg/mL
6. Added all ~1.7 mL above to one 0.5 mL endotoxin removal spin column (Thermo P/N 88274) prepared as per Vendor's instructions (including overnight in 0.2 M NaOH at room tempo), equilibrated into 1×DPBS. Left at room temp approximately 1 hr, then placed at 4° C. for approximately another 1 hr, in both cases inverting the capped tube about every 15 minutes.
7. Recovered prep by spinning 500×G for 1 minute (also as per vendor's instructions).
8. Recovered volume: approximately 1.3 mL at 4.61 mg/mL (all concentrations based on the NanoDrop's built-in IgG extinction coefficient of 0.73)

IgG2 A- and B-Locked Variants
Specific substitutions to the amino acid sequence of IgG2 are capable of preventing disulfide shuffling, and depending on the mutation will result in a locked conformation that is either A-like or B-like (Martinez, et al., (2008). "Disulfide connectivity of human immunoglobulin G2 structural isoforms", *Biochemistry*, 47(28), 7496-7508; Allen, et al., (2009), "Interchain disulfide bonding in human IgG2 antibodies probed by site-directed mutagenesis", *Biochemistry*, 48(17), 3755-3766.

The inventors therefore designed INX901 and INX908 variants with either the C233S (A-locked) or C127S (B-locked) mutation (Eu numbering) to match the IgG2 variants used by White et al., (2015), "Conformation of the human immunoglobulin G2 hinge imparts superagonistic properties to immunostimulatory anticancer antibodies", *Cancer Cell*, 27(1), 138-148. Constant heavy chain sequences are listed below.

IgG2 C233S (A-locked)
(SEQ ID NO: 63)
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCSVECPPCPAPPVAGPSVFLFPPKPKDTLMISRTPEVTCVVVDVSHEDP

EVQFNWYVDGVEVHNAKTKPREEQFNSTFRVVSVLTVVHQDWLNGKEYKC

KVSNKGLPAPIEKTISKTKGQPREPQVYTLPPSREEMTKNQVSLTCLVKG

FYPSDIAVEWESNGQPENNYKTTPPMLDSDGSFFLYSKLTVDKSRWQQGN

VFSCSVMHEALHNHYTQKSLSLSPGK

IgG2 C127S (B-locked)
(SEQ ID NO: 64)
ASTKGPSVFPLAPSSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDP

EVQFNWYVDGVEVHNAKTKPREEQFNSTFRVVSVLTVVHQDWLNGKEYKC

KVSNKGLPAPIEKTISKTKGQPREPQVYTLPPSREEMTKNQVSLTCLVKG

FYPSDIAVEWESNGQPENNYKTTPPMLDSDGSFFLYSKLTVDKSRWQQGN

VFSCSVMHEALHNHYTQKSLSLSPGK

Silent Fc Variants

Figure 12:
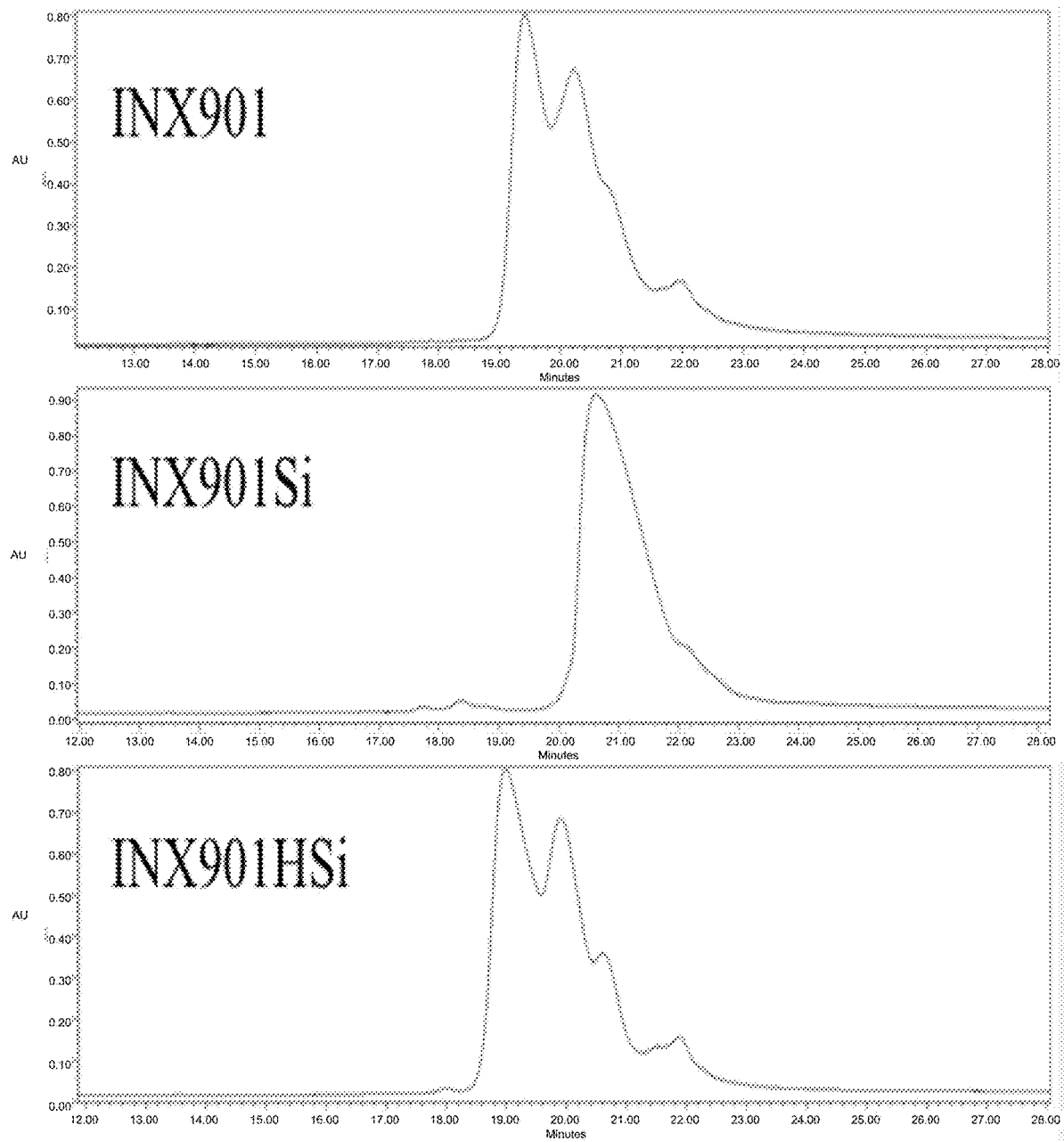
FIG. 12: compares INX901 Fc-silent variants with respect to disulfide shuffling. (Top) INX901 on an IgG2 backbone exhibits an expected mixture of A, A/B, and B isoforms. (Middle) INX901Si on a silent IgG1 backbone exists as a single isoform. (Bottom) INX901HSi possesses an IgG1 silent Fc region with a CH1/hinge from IgG2, which enables disulfide shuffling equivalent to native IgG2.

The inventors designed INX901 and INX908 variants with a silent Fc region by introducing the following point mutations on an IgG1 backbone: L234A/L235A/G237A/P238A/H268A/A330S/P331S (McCarthy et al., (2015) U.S. patent application Ser. No. 14/818,864. Washington, D.C.: U.S. In one type of variant (INX901Si and INX908Si), the CH1/hinge region of the heavy constant region is native IgG1, which does not support the disulfide shuffling of a native IgG2 (FIG. 12, middle). In a second type of variant (INX901HSi and INX908HSi), the CH1/hinge region is native IgG2, which does support disulfide shuffling (White, A. L. et al., 2015) (FIG. 12, bottom). Constant heavy chain sequences for both types of variants are listed below.

IgG1 with silent Fc (INX901Si and INX908Si)
(SEQ ID NO: 65)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPEAAGASSVFLFPPKPKDTLMISRTPEVTCVVVDVS

AEDPEVKFNWYVDGVEVHNAKTKPREEQYNSTYRVVSVLTVLHQDWLNGK

EYKCKVSNKALPSSIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK

IgG2 CH1/hinge + IgG1 silent Fc (INX901HSi and INX908HSi)
(SEQ ID NO: 66)
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCPAPEAAGASSVFLFPPKPKDTLMISRTPEVTCVVVDVSAED

PEVKFNWYVDGVEVHNAKTKPREEQYNSTYRVVSVLTVLHQDWLNGKEYK

CKVSNKALPSSIEKTISKAKGQPREPQVYTLPPSREEMTKNQVSLTCLVK

GFYPSDIAVEWESNGQPENNYKTTPPVLDSDGSFFLYSKLTVDKSRWQQG

NVFSCSVMHEALHNHYTQKSLSLSPGK

The experiments in FIG. 12 compare the immune properties of INX901 Fc-silent variants with respect to disulfide shuffling. (Top) INX901 on an IgG2 backbone exhibits an expected mixture of A, A/B, and B isoforms. (Middle) INX901Si on a silent IgG1 backbone exists as a single isoform. (Bottom) INX901HSi possesses an IgG1 silent Fc region with a CH1/hinge from IgG2, which enables disulfide shuffling equivalent to native IgG2. These results indicate that FcR binding appears to affect the agonist properties of the inventive antibodies.

Example 15: Function of INX901 and INX908 in Various Ig Backbones to Determine Requirement of Hinge and Fc Regions We conducted experiments to assess the functional requirements of the CH1/hinge and Fc regions of the heavy chain of the anti-human VISTA antibodies, INX901 and INX908. In their original state, both molecules are on native human IgG2 backbones, and are therefore mixtures of conformationally distinct isoforms resulting disulfide shuffling. The high cell density mixed lymphocyte reaction (MLR) was chosen for these studies as previous data indicates that this assay provides a robust read out of functionality for both INX901 and INX908. The following modifications of INX901 and/or INX908 were made to investigate whether specific isoforms are responsible for function: biochemical skewing to either the A or B isoform, genetic modifications to "lock" the conformation into the A or B form, and chimeric molecules where the Fc was silenced and the CH1/hinge region came from either IgG1, in which disulfide shuffling does not occur, or IgG2, which allows for native disulfide shuffling.

The results of the assay indicate that INX901 and INX908 retain function regardless of whether in the A form, B form, or the mixture of forms that characterizes a native IgG2. Additionally, both INX901 and INX908 require an active Fc region for functionality.

The MLR is a standard immunological assay that depends upon MHC class I and II mismatching to drive an allogeneic T cell response. Peripheral blood mononuclear cells are isolated from two mismatched individuals, incubated together and as a result of these mismatches, proliferation and cytokine production occurs. High cell density conditions (HCD), meaning cultures with $>1 \times 10^7$ cells/ml, have previously been reported to elucidate agonistic functions of antibodies in vitro. Our previous data indicates that both INX901 and INX908 can suppress the expression of TNFα under HCD conditions in the MLR.

The HCD MLR assay was used to assess the function of INX901 and INX908 following either genetic or biochemical modifications with respect to IgG2 disulfide isoforms and/or Fc silencing of each antibody. Prior to running the MLR, each antibody was confirmed to bind recombinant VISTA via ELISA. INX901 was sent to Elion, LLC (Louisville, Colo.) where it was modified by redox to either be predominantly A form (INX901 A skew) or B form (INX901 B skew). Skewing was confirmed by RP-HPLC as described in the prior example. (FIG. 11). Each antibody, as well as the parental INX901, was diluted in a dose response in the HCD MLR and cytokine production was measured by Luminex. Previous data has indicated that TNFα and/or IL-2 are robust readouts for antibody function of the parental INX901 antibody. In two separate MLRs, both TNFα and IL-2 were reduced by INX901 parental, INX901 A skew and INX901 B skew compared to the IgG2 control (FIG. 13).

Figure 13:
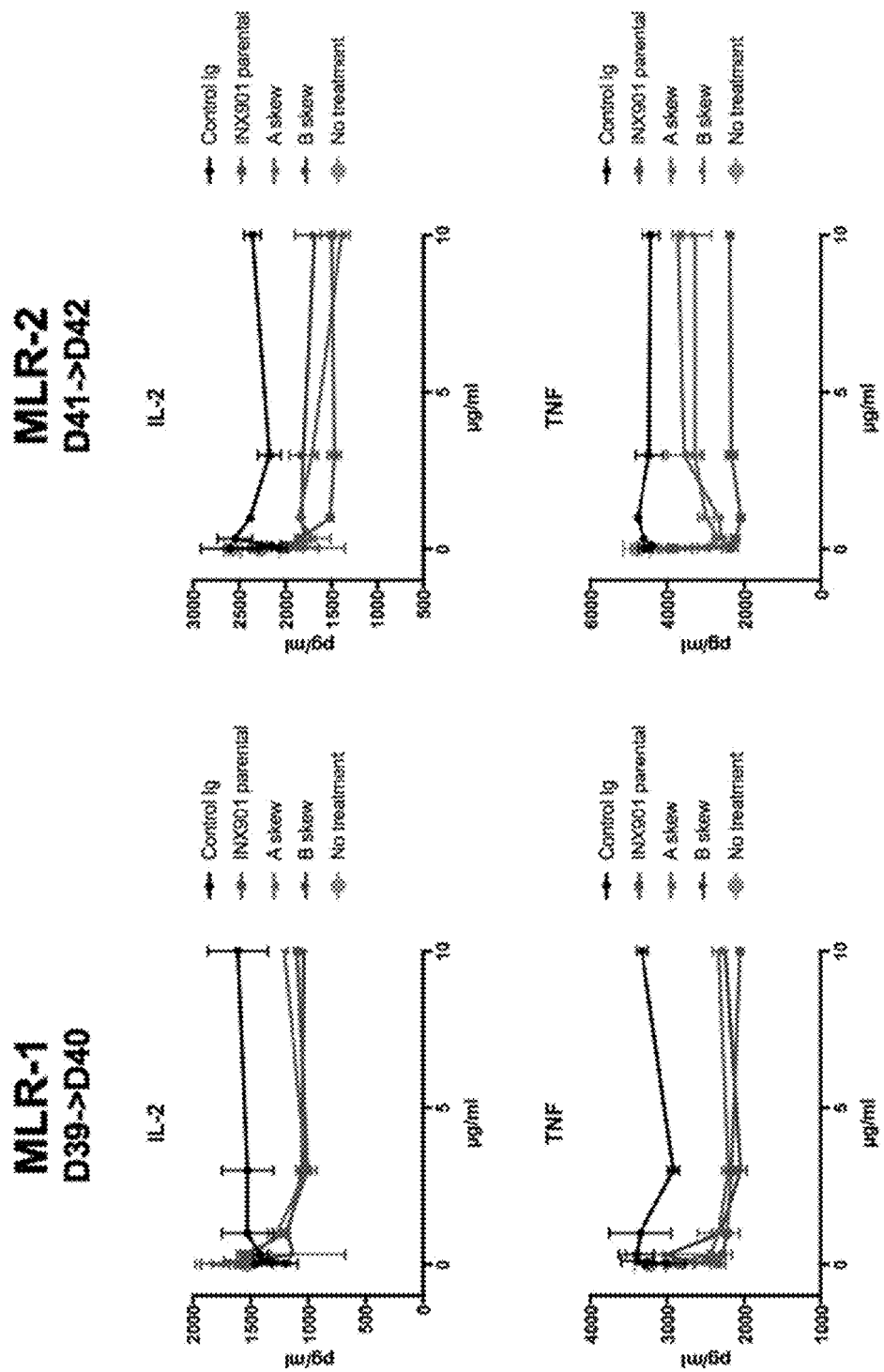
FIG. 13. Biochemically skewed INX901 forms can still reduce cytokine production in the MLR. Supernatants from two separate MLRs were analyzed for cytokine production at the 72-hour time point by Luminex analysis. INX901 parental, A skew and B skew all reduced the production of TNFα and IL-2 in a dose dependent fashion.
Figure 14:
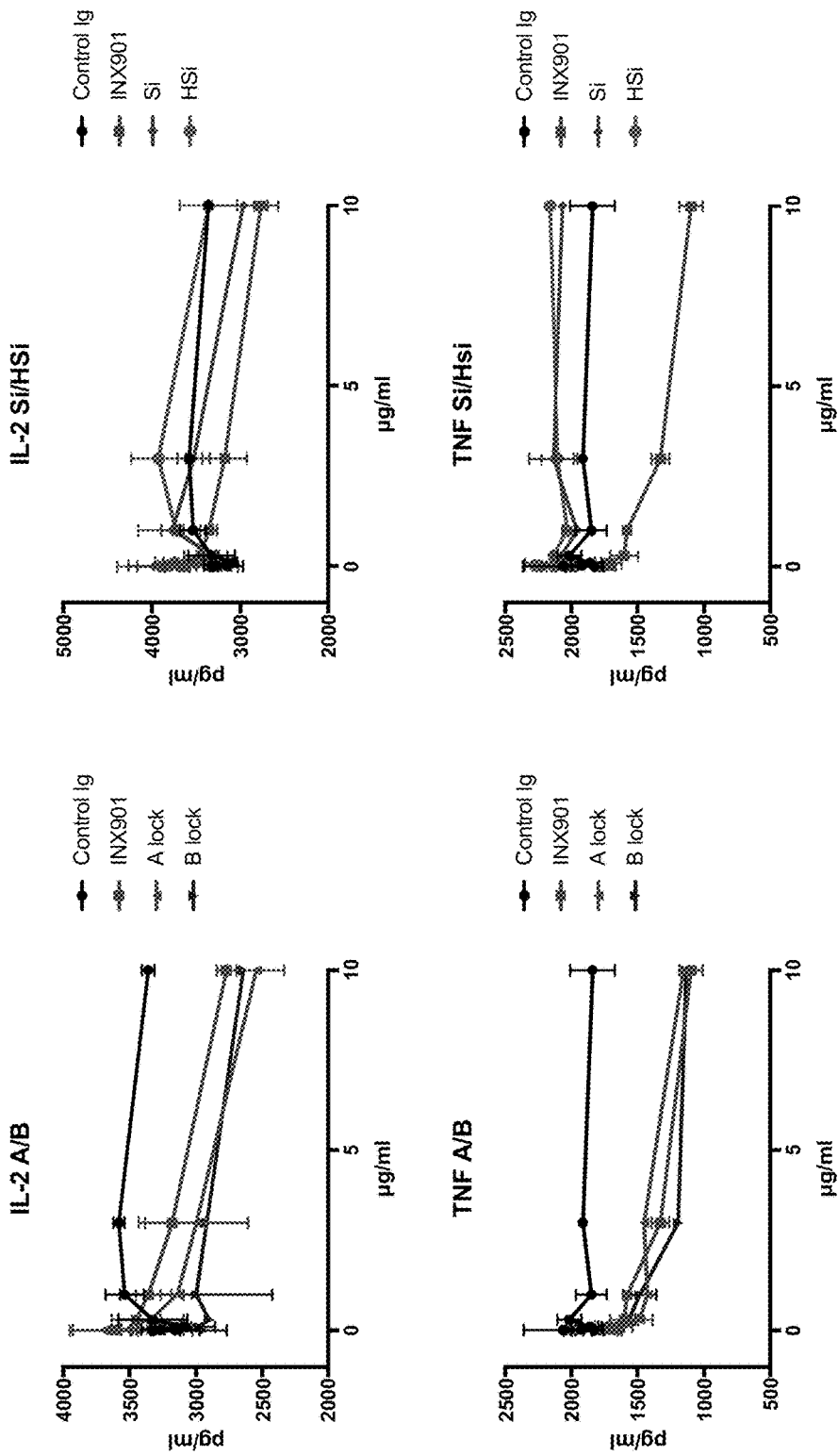
FIG. 14. Genetically locked INX901 forms can still reduce cytokine production in the MLR, but Fc silent variants cannot. Supernatants from each MLR were analyzed for cytokine production at the 72-hour time point by Luminex analysis. INX901 parental, A lock and B lock all reduced the production of TNFα and IL-2 in a dose dependent fashion. The Si and HSi variants, which contain mutations to silence the Fc domain, did not consistently suppress cytokine production.

To confirm the data from FIG. 13, additional variants of INX901 were made with mutations to generate locked variants in either the A form or the B form. Additionally, chimeric versions of INX901 were made with fully silent Fc regions to test the function of the Fc domain. INX901 Si is a fully silent IgG1 antibody. INX901 HSi has a fully silent IgG1 Fc, but also possesses an IgG2 CH1/hinge region that enables disulfide shuffling that is indistinguishable from a native IgG2. Prior to running the MLR, each antibody was confirmed to bind recombinant VISTA via ELISA. Confirming the data from the biochemical skewing, both the A lock and B locked versions of INX901 were able to reduce the production of both IL-2 and TNFα (FIG. 14). In contrast, both the Si and HSi versions of INX901 were unable to reduce production of IL-2 and TNFα (FIG. 14).

Figure 15:
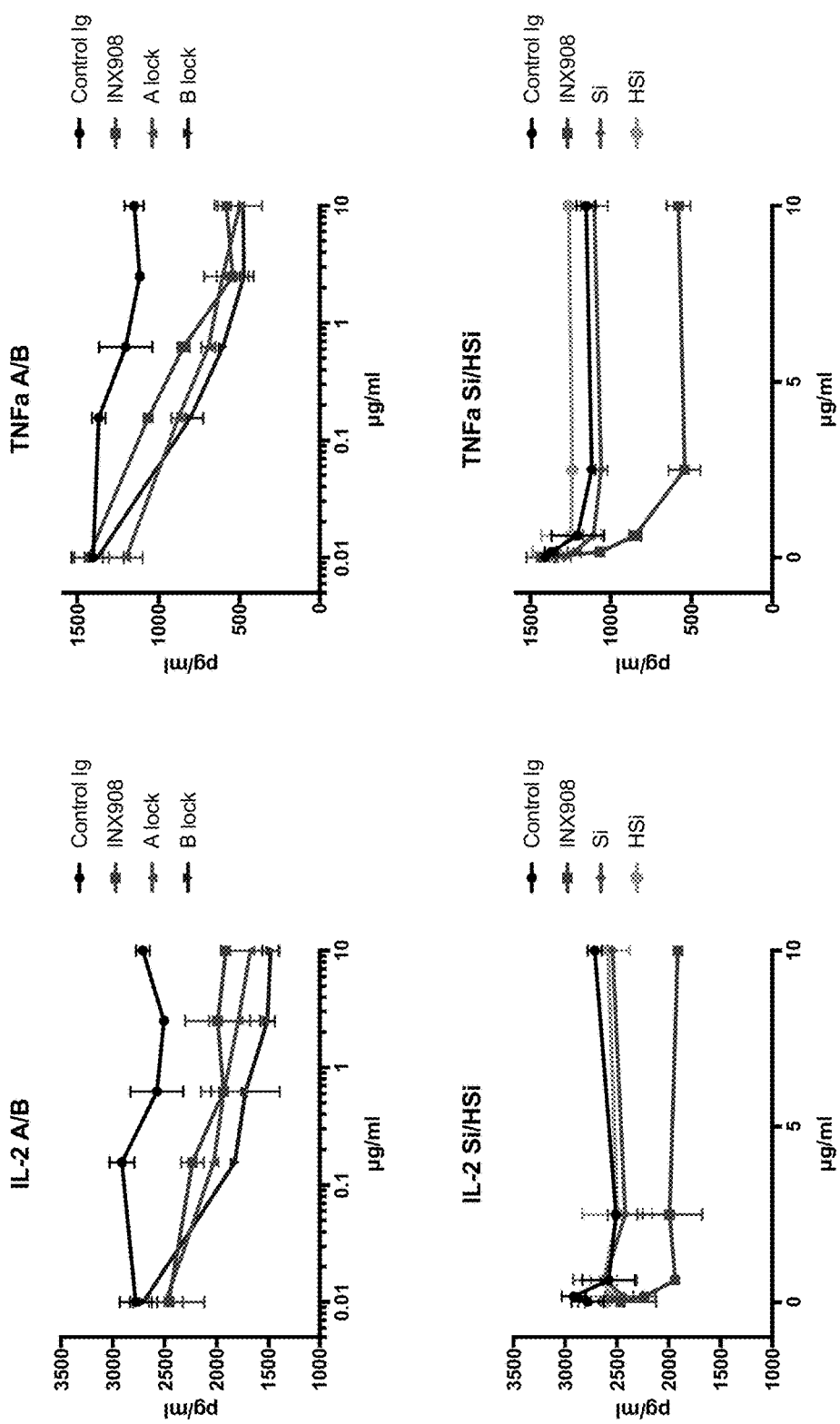
FIG. 15. Genetically locked INX908 forms can still reduce cytokine production in the MLR, but Fc silent variants cannot. Supernatants from each MLR were analyzed for cytokine production at the 72-hour time point by Luminex analysis. INX908 parental, A lock and B lock all reduced the production of TNFα and IL-2 in a dose dependent fashion. The Si and HSi variants, which contain mutations to silence the Fc domain, did not consistently suppress cytokine production.

To confirm the data from FIG. 14, identical mutations were made to the INX908 antibody to generate locked variants in either the A form or the B form. Additionally, chimeric versions of INX908 were made with fully silent Fc regions to test the function of the Fc domain. INX908 Si is a fully silent IgG1 antibody. INX908 HSi has a fully silent IgG1 Fc but contains the IgG2 CH1/hinge region. Prior to running the MLR, each antibody was confirmed to bind recombinant VISTA via ELISA. Confirming the data with the INX901 variants, both the A lock and B locked versions of INX908 were able to reduce the production of both IL-2 and TNFα (FIG. 15). In contrast, both the Si and HSi versions of INX908 were unable to reduce production of IL-2 and TNFα (FIG. 15).

Figure 16:
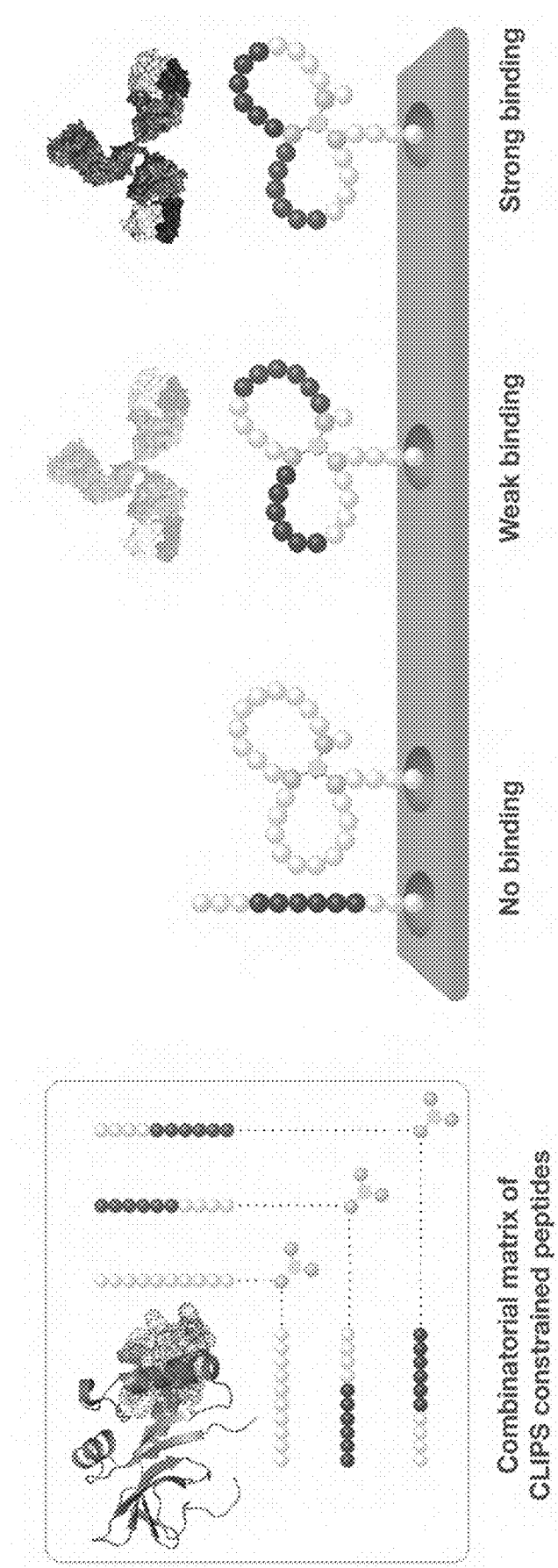
FIG. 16. This figure schematically describes the Pepscan® technology used to identify linear and discontinuous epitopes bound by agonist anti-human VISTA antibodies.

Example 15: Discontinuous Epitope Mapping of Agonist Antibodies Using PEPPSCAN Methods Pepscan uses peptide arrays to determine both linear and discontinuous epitopes. This methodology is an accepted method used by many researchers and companies to ascertain antibody epitopes. FIG. 16 schematically describes the Pepscan® technology used to identify linear and discontinuous epitopes bound by various agonist anti-human VISTA antibodies according to the invention.

The Principles of Clips Technology

CLIPS technology structurally fixes peptides into defined three-dimensional structures. This results in functional mimics of even the most complex binding sites. CLIPS technology is now routinely used to shape peptide libraries into single, double or triple looped structures as well as sheet- and helix-like folds. The CLIPS reaction takes place between bromo groups of the CLIPS scaffold and thiol sidechains of cysteines. The reaction is fast and specific under mild conditions. Using this elegant chemistry, native protein sequences are transformed into CLIPS constructs with a range of structures.

Combinatorial Clips Library Screening in Detail

CLIPS library screening starts with the conversion of the target protein into a library of up to 10,000 overlapping peptide constructs, using a combinatorial matrix design. On a solid carrier, a matrix of linear peptides is synthesized, which are subsequently shaped into spatially defined CLIPS constructs. Constructs representing both parts of the discontinuous epitope in the correct conformation bind the antibody with high affinity, which is detected and quantified. Constructs presenting the incomplete epitope bind the antibody with lower affinity, whereas constructs not containing the epitope do not bind at all. Affinity information is used in iterative screens to define the sequence and conformation of epitopes in detail. The results of this epitope analysis are summarized below.

Antibodies INX901, INX902, INX904, INX906, INX907, INX908

When tested under moderate stringency conditions antibodies INX901, INX902, INX904, INX906, INX907, INX908 strongly bound linear and conformational epitope mimics. Bound peptides contain core sequences $_{48}$NVTLTCRLLGPV$_{60}$ (SEQ ID NO:67), $_{79}$EVQTCSERRPIR$_{90}$ (SEQ ID NO:68), $_{123}$SDHHGNFS$_{130}$ (SEQ ID NO:69) and $_{153}$HHHSEH$_{158}$ (SEQ ID NO:70), where peptide stretch $_{79}$EVQTCSERRPIR$_{90}$ (SEQ ID NO:68) is the dominant part of the epitope.

Additional analysis of data recorded with linear epitope mimics allowed us to identify residues that are important for binding for INX 904, INX906, INX907 and INX908, as double Ala mutants on certain positions notably decreased signal intensities. In particular, replacement of residues CR within $_{48}$NVTLTCRLLGPV$_{60}$ (SEQ ID NO:71) affects binding of INX906, INX907 and INX908. Also the replacement of residues TC within $_{79}$EVQTCSERRPIR$_{90}$ (SEQ ID NO:68) notably affects binding of INX904 and INX907.

Antibody INX800

When tested under moderate stringency conditions antibody INX800 did not detectably bind linear and simple constrained epitope mimics, but showed detectable binding with discontinuous epitope mimics. Analysis of data obtained with discontinuous epitope mimics suggest that antibody INX800 recognizes a discontinuous epitope with core sequences $_{53}$TCRLLGPVDKG$_{63}$ (SEQ ID NO:72), 101HGGHQAA$_{107}$ (SEQ ID NO:73), $_{121}$SASDHHGNFS$_{130}$ (SEQ ID NO:74) and $_{153}$HHHSEHRVHGAM$_{164}$ (SEQ ID NO:75), where sequence $_{153}$HHHSEHRVHGAM$_{164}$ (SEQ ID NO:76) represents the dominant recognition site.

Antibodies INX803 AND INX804

When tested under high stringency conditions antibodies INX803 and INX804 did not bind any peptide present on the array. When tested under moderate stringency conditions both antibodies bound discontinuous epitope mimics. Cumulative analysis of binding profiles suggests that both antibodies similarly recognize peptide stretches $_{52}$LTCRLLGPV$_{60}$ (SEQ ID NO:77), $_{79}$EVQTCSERRPIR$_{90}$ (SEQ ID NO:78), $_{98}$HLHHGGHQAA$_{107}$ (SEQ ID NO:79), $_{123}$SDHHGNFS$_{130}$ (SEQ ID NO:80), $_{153}$HHHSEHRVHGAM$_{164}$ (SEQ ID NO:81), where region $_{52}$LTCRLLGPV$_{60}$ (SEQ ID NO:77) is the dominant recognition site.

Antibody INX900

When tested under high stringency conditions antibody INX900 very weakly bound linear epitope mimics with core sequence $_{79}$EVQTCSERRPIR$_{90}$ (SEQ ID NO:68). Notably higher binding was observed with discontinuous epitope mimics, which in addition to sequence $_{79}$EVQTCSERRPIR$_{90}$ (SEQ ID NO:68) contain core sequences $_{56}$LLGPVDKGHDVTFYK$_{70}$ (SEQ ID NO:82), $_{113}$LAQRHGLESASDHHG$_{127}$ (SEQ ID NO:83), $_{153}$HHHSEHRVHGAM$_{164}$ (SEQ ID NO:84).

Antibody INX903

When tested under high stringency conditions antibody INX903 did not bind linear epitope mimics, but weakly bound conformational epitope mimics. Analysis of recorded intensity profiles suggests that the antibody recognizes a discontinuous epitope composed of core sequences $_{79}$EVQTCSERR$_{87}$ (SEQ ID NO:85), $_{93}$TFQDLHLHHGGHQAA$_{107}$ (SEQ ID NO:86), $_{146}$CLVVEIRHHHSEH$_{158}$ (SEQ ID NO:87), where sequence $_{79}$EVQTCSERR$_{87}$ (SEQ ID NO:85) is the core of the epitope.

Antibody INX905

When tested under high stringency conditions antibody INX905 bound linear peptides with core sequence $_{79}$EVQTCSERRP$_{88}$ (SEQ ID NO:88). Data acquired with double Ala mutants indicate that motif RR within $_{79}$EVQTCSERRP$_{88}$ (SEQ ID NO:88) is critical for the recognition. Intensity profiles recorded with discontinuous epitope mimics suggest that addition of peptide sequences $_{53}$TCRLLGPVDKG$_{63}$ (SEQ ID NO:89), $_{123}$SDHHG$_{127}$ (SEQ ID NO:90) and $_{153}$HHHSEHRVHGAM$_{164}$ (SEQ ID NO:91) augments binding of the antibody. FIG. 17 shows that most agonist anti-human VISTA antibodies bind to the same core sequence. FIG. 18 also summarizes the epitope results. FIG. 19 shows the epitopes bound by exemplary agonist anti-human VISTA antibodies according to the invention and identifies important residues involved in binding.

REFERENCES CITED IN THIS APPLICATION

The following references and other references cited in this application are incorporated by reference in their entireties.

1 Dong, C., Juedes, A. E., Temann, U. A., Shresta, S., Allison, J. P., Ruddle, N. H. and Flavell, R. A., ICOS co-stimulatory receptor is essential for T-cell activation and function. *Nature* 2001. 409: 97-101.
2 Suh, W. K., Gajewska, B. U., Okada, H., Gronski, M. A., Bertram, E. M., Dawicki, W., Duncan, G. S., Bukczynski, J., Plyte, S., Elia, A., Wakeham, A., Itie, A., Chung, S., Da Costa, J., Arya, S., Horan, T., Campbell, P., Gaida, K., Ohashi, P. S., Watts, T. H., Yoshinaga, S. K., Bray, M. R., Jordana, M. and Mak, T. W., The B7 family member B7-H3 preferentially down-regulates T helper type 1-mediated immune responses. *Nat Immunol* 2003. 4: 899-906.
3 Borriello, F., Sethna, M. P., Boyd, S. D., Schweitzer, A. N., Tivol, E. A., Jacoby, D., Strom, T. B., Simpson, E. M., Freeman, G. J. and Sharpe, A. H., B7-1 and B7-2 have overlapping, critical roles in immunoglobulin class switching and germinal center formation. *Immunity* 1997. 6: 303-313.
4 Chambers, C. A., Sullivan, T. J. and Allison, J. P., Lymphoproliferation in CTLA-4-deficient mice is mediated by costimulation-dependent activation of CD4+ T cells. *Immunity* 1997. 7: 885-895.
5 Waterhouse, P., Penninger, J. M., Timms, E., Wakeham, A., Shahinian, A., Lee, K. P., Thompson, C. B., Griesser, H. and Mak, T. W., Lymphoproliferative disorders with early lethality in mice deficient in Ctla-4. *Science* 1995. 270: 985-988.
6 Tivol, E. A., Borriello, F., Schweitzer, A. N., Lynch, W. P., Bluestone, J. A. and Sharpe, A. H., Loss of CTLA-4 leads to massive lymphoproliferation and fatal multiorgan tissue destruction, revealing a critical negative regulatory role of CTLA-4. *Immunity* 1995. 3: 541-547.
7 Nishimura, H., Nose, M., Hiai, H., Minato, N. and Honjo, T., Development of lupus-like autoimmune diseases by disruption of the PD-1 gene encoding an ITIM motif-carrying immunoreceptor. *Immunity* 1999. 11: 141-151.
8 Keir, M. E., Liang, S. C., Guleria, I., Latchman, Y. E., Qipo, A., Albacker, L. A., Koulmanda, M., Freeman, G. J., Sayegh, M. H. and Sharpe, A. H., Tissue expression of PD-L1 mediates peripheral T cell tolerance. *J Exp Med* 2006. 203: 883-895.
9 Ortler, S., Leder, C., Mittelbronn, M., Zozulya, A. L., Knolle, P. A., Chen, L., Kroner, A. and Wiendl, H., B7-H1 restricts neuroantigen-specific T cell responses and confines inflammatory CNS damage: implications for the lesion pathogenesis of multiple sclerosis. *Eur J Immunol* 2008. 38: 1734-1744.
10 Zhu, G., Augustine, M. M., Azuma, T., Luo, L., Yao, S., Anand, S., Rietz, A. C., Huang, J., Xu, H., Flies, A. S., Flies, S. J., Tamada, K., Colonna, M., van Deursen, J. M. and Chen, L., B7-H4-deficient mice display augmented neutrophil-mediated innate immunity. *Blood* 2009. 113: 1759-1767.
11 Chen, Y., Wang, Q., Shi, B., Xu, P., Hu, Z., Bai, L. and Zhang, X., Development of a sandwich ELISA for evaluating soluble PD-L1 (CD274) in human sera of different ages as well as supernatants of PD-L1(+) cell lines. *Cytokine* 2011.
12 Greenwald, R. J., Freeman, G. J. and Sharpe, A. H., The B7 family revisited. *Annu Rev Immunol* 2005. 23: 515-548.
13 Zhu, Y., Yao, S., Iliopoulou, B. P., Han, X., Augustine, M. M., Xu, H., Phennicie, R. T., Flies, S. J., Broadwater, M., Ruff, W., Taube, J. M., Zheng, L., Luo, L., Zhu, G., Chen, J. and Chen, L., B7-H5 costimulates human T cells via CD28H. *Nat Commun* 2013. 4: 2043.
14 Brandt, C. S., Baratin, M., Yi, E. C., Kennedy, J., Gao, Z., Fox, B., Haldeman, B., Ostrander, C. D., Kaifu, T., Chabannon, C., Moretta, A., West, R., Xu, W., Vivier, E. and Levin, S. D., The B7 family member B7-H6 is a tumor cell ligand for the activating natural killer cell receptor NKp30 in humans. *J Exp Med* 2009. 206: 1495-1503.
15 Wang, L., Rubinstein, R., Lines, J. L., Wasiuk, A., Ahonen, C., Guo, Y., Lu, L. F., Gondek, D., Wang, Y., Fava, R. A., Fiser, A., Almo, S. and Noelle, R. J., VISTA, a novel mouse Ig superfamily ligand that negatively regulates T cell responses. *J Exp Med* 2011. 208: 577-592.
16 Lines, J. L., Sempere, L. F., Wang, L., Panttazi, E., Mak, J., O'Connell, S., Ceeraz, S., Suriawinata, A. A., Yan, S., Ernstoff, M. S. and Noelle, R. J., VISTA is an immune checkpoint regulator for human T cells. in revision (*Cancer Research*).
17 LeMercier, I., Lines, J. L., Sergent, P., Li, J., Noelle, R. J. and Wang, L., VISTA regulates the development of protective anti-tumor immunity. in revision (*Cancer Research*).
18 Wolchok, J. D., Kluger, H., Callahan, M. K., Postow, M. A., Rizvi, N. A., Lesokhin, A. M., Segal, N. H., Ariyan, C. E., Gordon, R. A., Reed, K., Burke, M. M., Caldwell, A., Kronenberg, S. A., Agunwamba, B. U., Zhang, X., Lowy, I., Inzunza, H. D., Feely, W., Horak, C. E., Hong, Q., Korman, A. J., Wigginton, J. M., Gupta, A. and Sznol, M., Nivolumab plus ipilimumab in advanced melanoma. *N Engl J Med* 2013. 369: 122-133.
19 Iliopoulos, D., Kavousanaki, M., Ioannou, M., Boumpas, D. and Verginis, P., The negative costimulatory molecule 19. PD-1 modulates the balance between immunity and tolerance via miR-21. *Eur J Immunol* 2011. 41: 1754-1763.
20. Ansari, M. J., Salama, A. D., Chitnis, T., Smith, R. N., Yagita, H., Akiba, H., Yamazaki, T., Azuma, M., Iwai, H., Khoury, S. J., Auchincloss, H., Jr. and Sayegh, M. H., The programmed death-1 (PD-1) pathway regulates autoimmune diabetes in nonobese diabetic (NOD) mice. *J Exp Med* 2003. 198: 63-69.
21. Bertsias, G. K., Nakou, M., Choulaki, C., Raptopoulou, A., Papadimitraki, E., Goulielmos, G., Kritikos, H., Sidiropoulos, P., Tzardi, M., Kardassis, D., Mamalaki, C. and Boumpas, D. T., Genetic, immunologic, and immunohistochemical analysis of the programmed death 1/programmed death ligand 1 pathway in human systemic lupus erythematosus. *Arthritis Rheum* 2009. 60: 207-218.
22. Prokunina, L., Castillejo-Lopez, C., Oberg, F., Gunnarsson, I., Berg, L., Magnusson, V., Brookes, A. J., Tentler, D., Kristjansdottir, H., Grondal, G., Bolstad, A. I., Svenungsson, E., Lundberg, I., Sturfelt, G., Jonssen, A., Truedsson, L., Lima, G., Alcocer-Varela, J., Jonsson, R., Gyllensten, U. B., Harley, J. B., Alarcon-Segovia, D., Steinsson, K. and Alarcon-Riquelme, M. E., A regulatory polymorphism in PDCD1 is associated with susceptibility to systemic lupus erythematosus in humans. *Nat Genet* 2002. 32: 666-669.
23. Ozkaynak, E., Wang, L., Goodearl, A., McDonald, K., Qin, S., O'Keefe, T., Duong, T., Smith, T., Gutierrez-Ramos, J. C., Rottman, J. B., Coyle, A. J. and Hancock, W. W., Programmed death-1 targeting can promote allograft survival. *J Immunol* 2002. 169: 6546-6553.
24. Watson, M. P., George, A. J. and Larkin, D. F., Differential effects of costimulatory pathway modulation on corneal allograft survival. *Invest Ophthalmol Vis Sci* 2006. 47: 3417-3422.
25. Podojil, J. R., Liu, L. N., Marshall, S. A., Chiang, M. Y., Goings, G. E., Chen, L., Langermann, S. and Miller, S. D., B7-H4Ig inhibits mouse and human T-cell function and treats EAE via IL-10/Treg-dependent mechanisms. *J Autoimmun* 2013. 44: 71-81.
26. Sica, G. L., Choi, I. H., Zhu, G., Tamada, K., Wang, S. D., Tamura, H., Chapoval, A. I., Flies, D. B., Bajorath, J. and Chen, L., B7-H4, a molecule of the B7 family, negatively regulates T cell immunity. *Immunity* 2003. 18: 849-861.
27. Wang, X., Hao, J., Metzger, D. L., Mui, A., Ao, Z., Verchere, C. B., Chen, L., Ou, D. and Warnock, G. L., B7-H4 induces donor-specific tolerance in mouse islet allografts. *Cell Transplant* 2012. 21: 99-111.
28. Yamaura, K., Watanabe, T., Boenisch, O., Yeung, M., Yang, S., Magee, C. N., Padera, R., Datta, S., Schatton, T., Kamimura, Y., Azuma, M. and Najafian, N., In vivo function of immune inhibitory molecule B7-H4 in alloimmune responses. *Am J Transplant* 2010. 10: 2355-2362.
29. Yi, K. H. and Chen, L., Fine tuning the immune response through B7-H3 and B7-H4. *Immunol Rev* 2009. 229: 145-151.
30. Wang, X., Hao, J., Metzger, D. L., Ao, Z., Chen, L., Ou, D., Verchere, C. B., Mui, A. and Warnock, G. L., B7-H4 Treatment of T Cells Inhibits ERK, JNK, p38, and AKT Activation. *PLoS One* 2012. 7: e28232.
31. Terawaki, S., Tanaka, Y., Nagakura, T., Hayashi, T., Shibayama, S., Muroi, K., Okazaki, T., Mikami, B., Garboczi, D. N., Honjo, T. and Minato, N., Specific and high-affinity binding of tetramerized PD-L1 extracellular domain to PD-1-expressing cells: possible application to enhance T cell function. *Int Immunol* 2007. 19: 881-890.
32. Sedy, J. R., Gavrieli, M., Potter, K. G., Hurchla, M. A., Lindsley, R. C., Hildner, K., Scheu, S., Pfeffer, K., Ware, C. F., Murphy, T. L. and Murphy, K. M., B and T lymphocyte attenuator regulates T cell activation through interaction with herpesvirus entry mediator. *Nat Immunol* 2005. 6: 90-98.
33. Parisi, S., Battista, M., Musto, A., Navarra, A., Tarantino, C. and Russo, T., A regulatory loop involving Dies1 and miR-125a controls BMP4 signaling in mouse embryonic stem cells. *FASEB J* 2012. 26: 3957-3968.
34. Youngnak, P., Kozono, Y., Kozono, H., Iwai, H., Otsuki, N., Jin, H., Omura, K., Yagita, H., Pardoll, D. M., Chen, L. and Azuma, M., Differential binding properties of B7-H1 and B7-DC to programmed death-1. *Biochem Biophys Res Commun* 2003. 307: 672-677.
35. Butte, M. J., Keir, M. E., Phamduy, T. B., Sharpe, A. H. and Freeman, G. J., Programmed death-1 ligand 1 interacts specifically with the b7-1 costimulatory molecule to inhibit T cell responses. *Immunity* 2007. 27: 111-122.
36. Sharpe, A. H. and Freeman, G. J., The B7-CD28 superfamily. *Nat Rev Immunol* 2002. 2: 116-126.
37. Bartel P. L. et al. (1993) Using the two-hybrid system to detect protein-protein interactions. In Cellular Interactions in Development: A Practical Approach, D. A. Hartley, Ed., Oxford University Press, Oxford; pp 153-179.
38. Béranger F. et al. (1997) Getting more from the two-hybrid system: N-terminal fusions to LexA are efficient and sensitive baits for two-hybrid studies. NAR 25: 2035-36.
39. Formstecher E. et al. (2005) Protein interaction mapping: a *Drosophila* case study. Genome Res. 15: 37684.
40. Fromont-Racine M., Rain J. C., and Legrain P. (1997) Toward a functional analysis of the yeast genome through exhaustive two-hybrid screens. Nat. Genet. 16: 277-82.
41. Rain J. C. et al. (2001) The protein-protein interaction map of *Helicobacter pylori*. Nature 409: 211-15.
42. Vojtek A. and Hollenberg S. M. (1995) Ras-Raf interaction: two-hybrid analysis. Methods Enzymol. 255: 33142.
43. Wojcik J., Boneca I. G., and Legrain P. (2002) Prediction, assessment and validation of protein interaction maps in bacteria. J. Mol. Biol. 323: 763-70.
44. Franklin E C, Kunkel H G. Immunologic Differences Between the 19 S and 7 S Components of Normal Human γ-Globulin. The Journal of Immunology. 1957; 78(1):11-8.
45. Roda G, Jharap B, Neeraj N, Colombel J-F. Loss of Response to Anti-TNFs: Definition, Epidemiology, and Management. Clin Trans Gastroenterol. 2016; 7:e135. doi: 10.1038/ctg.2015.63.
46. Greenwald R J, Freeman G J, Sharpe A H. The B7 family revisited. Annual review of immunology. 2005; 23:515-48. PubMed PMID: 15771580.
47. Lines J L, Pantazi E, Mak J, Sempere L F, Wang L, O'Connell S, Ceeraz S, Suriawinata A A, Yan S, Ernstoff M S, Noelle R. VISTA is an immune checkpoint molecule for human T cells. Cancer research. 2014; 74(7):1924-32. doi: 10.1158/0008-5472.CAN-13-1504. PubMed PMID: 24691993; PMCID: 3979527.
48. Le Mercier I, Chen W, Lines J L, Day M, Li J, Sergent P, Noelle R J, Wang L. VISTA Regulates the Development of Protective Antitumor Immunity. Cancer research. 2014; 74(7):1933-44. doi: 10.1158/0008-5472.CAN-13-1506. PubMed PMID: 24691994; PMCID: PMC4116689.
49. Flies D B, Han X, Higuchi T, Zheng L, Sun J, Ye J J, Chen L. Coinhibitory receptor PD-1H preferentially suppresses CD4(+) T cell-mediated immunity. The Journal of 50. Lines J L, Sempere L F, Broughton T, Wang L, Noelle R. VISTA Is a Novel Broad-Spectrum Negative Checkpoint Regulator for Cancer Immunotherapy. Cancer immunology research. 2014; 2(6):510-7. doi: 10.1158/2326-6066.CIR-14-0072. PubMed PMID: 24894088.

51. Wang L, Le Mercier I, Putra J, Chen W, Liu J, Schenk A D, Nowak E C, Suriawinata A A, Li J, Noelle R J. Disruption of the immune-checkpoint VISTA gene imparts a proinflammatory phenotype with predisposition to the development of autoimmunity. Proceedings of the National Academy of Sciences of the United States of America. 2014; 111(41):14846-51. doi: 10.1073/pnas.1407447111. PubMed PMID: 25267631; PMCID: 4205642.

52. Wang L, Rubinstein R, Lines J L, Wasiuk A, Ahonen C, Guo Y, Lu L F, Gondek D, Wang Y, Fava R A, Fiser A, Almo S, Noelle R J. VISTA, a novel mouse Ig superfamily ligand that negatively regulates T cell responses. The Journal of experimental medicine. 2011; 208(3):577-92. Epub 2011/03/09. doi: jem.20100619 [pii] 10.1084/jem.20100619. PubMed PMID: 21383057; PMCID: 3058578.

53. Flies D B, Han X, Higuchi T, Zheng L, Sun J, Ye J J, Chen L. Coinhibitory receptor PD-1H preferentially suppresses CD4(+) T cell-mediated immunity. The Journal of clinical investigation. 2014; 124(5):1966-75. doi: 10.1172/JCI74589. PubMed PMID: PMC4001557.

54. Yoon K W, Byun S, Kwon E, Hwang S Y, Chu K, Hiraki M, Jo S H, Weins A, Hakroush S, Cebulla A, Sykes D B, Greka A, Mundel P, Fisher D E, Mandinova A, Lee S W. Control of signaling-mediated clearance of apoptotic cells by the tumor suppressor p53. Science. 2015; 349(6247): 1261669. doi: 10.1126/science.1261669. PubMed PMID: 26228159.

55. Bettelli E, Pagany M, Weiner H L, Linington C, Sobel R A, Kuchroo V K. Myelin Oligodendrocyte Glycoprotein-specific T Cell Receptor Transgenic Mice Develop Spontaneous Autoimmune Optic Neuritis. The Journal of experimental medicine. 2003; 197(9):1073-81. doi: 10.1084/jem.20021603.

56. Ceeraz S, Sergent P, Plummer S, Schned A, Pechenick D, Burns C, Noelle R. VISTA deficiency accelerates the development of fatal murine lupus nephritis. Arthritis and Rheumatology. 2016; submitted.

57. Liu J, Yuan Y, Chen W, Putra J, Suriawinata A A, Schenk A D, Miller H E, Guleria I, Barth R J, Huang Y H, Wang L. Immune-checkpoint proteins VISTA and PD-1 nonredundantly regulate murine T-cell responses. Proceedings of the National Academy of Sciences of the United States of America. 2015; 112(21):6682-7. doi: 10.1073/pnas.1420370112. PubMed PMID: 25964334; PMCID: PMC4450438.

58. Flies D B, Higuchi T, Chen L. Mechanistic Assessment of PD-1H Coinhibitory Receptor-Induced T Cell Tolerance to Allogeneic Antigens. Journal of immunology. 2015; 194(11):5294-304. doi: 10.4049/jimmunol.1402648. PubMed PMID: 25917101; PMCID: PMC4433880.

59. DiLillo D J, Ravetch J V. Fc-Receptor Interactions Regulate Both Cytotoxic and Immunomodulatory Therapeutic Antibody Effector Functions. Cancer immunology research. 2015; 3(7):704-13. doi: 10.1158/2326-6066.cir-15-0120.

60. White A L, Chan H T, French R R, Willoughby J, Mockridge C I, Roghanian A, Penfold C A, Booth S G, Dodhy A, Polak M E, Potter E A, Ardern-Jones M R, Verbeek J S, Johnson P W, Al-Shamkhani A, Cragg M S, Beers S A, Glennie M J. Conformation of the human immunoglobulin G2 hinge imparts superagonistic properties to immunostimulatory anticancer antibodies. Cancer Cell. 2015; 27(1):138-48. doi: 10.1016/j.ccell.2014.11.001. PubMed PMID: 25500122; PMCID: PMC4297290.

61. Dubey A K, Handu S S, Dubey S, Sharma P, Sharma K K, Ahmed Q M. Belimumab: First targeted biological treatment for systemic lupus erythematosus. J Pharmacol Pharmacother. 2011; 2(4):317-9. doi: 10.4103/0976-500X.85930. PubMed PMID: 22025872; PMCID: PMC3198539.

62. Wallace D J, Hobbs K, Clowse M E, Petri M, Strand V, Pike M, Merrill J T, Leszczynski P, Neuwelt C M, Jeka S, Houssiau F, Keiserman M, Ordi-Ros J, Bongardt S, Kilgallen B, Galateanu C, Kalunian K, Furie R, Gordon C. Long-term safety and efficacy of epratuzumab in the treatment of moderate-to-severe systemic lupus erythematosus: results from an open-label extension study. Arthritis Care Res (Hoboken). 2015. doi: 10.1002/acr.22694. PubMed PMID: 26316325.

63. Van Wauwe J P, De Mey J R, Goossens J G. OKT3: a monoclonal anti-human T lymphocyte antibody with potent mitogenic properties. The Journal of Immunology. 1980; 124(6):2708-13.

64. Robertson J M, Jensen P E, Evavold B D. DO11.10 and OT-Ill T Cells Recognize a C-Terminal Ovalbumin 323-339 Epitope. The Journal of Immunology. 2000; 164(9): 4706-12. doi: 10.4049/jimmunol.164.9.4706.

65. Wang H-X, Liu M, Weng S-Y, Li J-J, Xie C, He H-L, Guan W, Yuan Y-S, Gao J. Immune mechanisms of Concanavalin A model of autoimmune hepatitis. World Journal of Gastroenterology: WJG. 2012; 18(2):119-25. doi: 10.3748/wjg.v18.i2.119. PubMed PMID: PMC3257438.

66. Weiner G J. Building better monoclonal antibody-based therapeutics. Nat Rev Cancer. 2015; 15(6):361-70. doi: 10.1038/nrc3930. PubMed PMID: 25998715; PMCID: PMC4491443.

67. Ravetch J V, Bolland S. IgG Fc receptors. Annual review of immunology. 2001; 19:275-90. doi: 10.1146/annurev.immunol.19.1.275. PubMed PMID: 11244038.

68. Li F, Smith P, Ravetch J V. Inhibitory Fcγ receptor is required for the maintenance of tolerance through distinct mechanisms( ). Journal of immunology (Baltimore, Md.: 1950). 2014; 192(7):3021-8. doi: 10.4049/jimmunol.1302934. PubMed PMID: PMC3967505.

69. Hinton P R, Johlfs M G, Xiong J M, Hanestad K, Ong K C, Bullock C, Keller S, Tang M T, Tso J Y, Vasquez M, Tsurushita N. Engineered human IgG antibodies with longer serum half-lives in primates. The Journal of biological chemistry. 2004; 279(8):6213-6. doi: 10.1074/jbc.C300470200. PubMed PMID: 14699147.

70. Vaccaro C, Zhou J, Ober R J, Ward E S. Engineering the Fc region of immunoglobulin G to modulate in vivo antibody levels. Nature biotechnology. 2005; 23(10): 1283-8. doi: 10.1038/nbt1143. PubMed PMID: 16186811.

71. Borrok M J, Wu Y, Beyaz N, Yu X-Q, Oganesyan V, Dall'Acqua W F, Tsui P. pH-dependent Binding Engineering Reveals an FcRn Affinity Threshold That Governs IgG Recycling. The Journal of biological chemistry. 2015; 290(7):4282-90. doi: 10.1074/jbc.M114.603712. PubMed PMID: PMC4326836.
72. Oyarzun P, Ellis J J, Gonzalez-Galarza F F, Jones A R, Middleton D, Boden M, Kobe B. A bioinformatics tool for epitope-based vaccine design that accounts for human ethnic diversity: Application to emerging infectious diseases. Vaccine. 2015; 33(10):1267-73. doi: http://dx.doi.org/10.1016/j.vaccine.2015.01.040.
73. Haskins K, Kubo R, White J, Pigeon M, Kappler J, Marrack P. The major histocompatibility complex-restricted antigen receptor on T cells. I. Isolation with a monoclonal antibody. The Journal of experimental medicine. 1983; 157(4):1149-69. Epub 1983/04/01. PubMed PMID: 6601175; PMCID: Pmc2186983.
74. Markees T G, Phillips N E, Noelle R J, Shultz L D, Mordes J P, Greiner D L, Rossini A A. Prolonged survival of mouse skin allografts in recipients treated with donor splenocytes and antibody to CD40 ligand. Transplantation. 1997; 64(2):329-35.
75. Ehst B D, Ingulli E, Jenkins M K. Development of a novel transgenic mouse for the study of interactions between CD4 and CD8 T cells during graft rejection. American journal of transplantation: official journal of the American Society of Transplantation and the American Society of Transplant Surgeons. 2003; 3(11):1355-62. PubMed PMID: 14525595.
76. Wu S, Jin L, Vence L, Radvanyi L G. Development and application of 'phosphoflow' as a tool for immunomonitoring. Expert Rev Vaccines. 2010; 9(6):631-43. doi: 10.1586/erv.10.59. PubMed PMID: 20518718; PMCID: PMC2933839.
77. Weissmuller S, Kronhart S, Kreuz D, Schnierle B, Kalinke U, Kirberg J, Hanschmann K M, Waibler Z. TGN1412 Induces Lymphopenia and Human Cytokine Release in a Humanized Mouse Model. PloS one. 2016; 11(3):e0149093. doi: 10.1371/journal.pone.0149093. PubMed PMID: 26959227; PMCID: PMC4784892.
78. Piccotti J R, Alvey J D, Reindel J F, Guzman R E. T-cell-dependent antibody response: assay development in cynomolgus monkeys. J Immunotoxicol. 2005; 2(4):191-6. doi: 10.1080/15476910500362838. PubMed PMID: 18958673.
79. Muller P Y, Brennan F R. Safety assessment and dose selection for first-in-human clinical trials with immunomodulatory monoclonal antibodies. Clin Pharmacol Ther. 2009; 85(3):247-58. doi: 10.1038/clpt.2008.273. PubMed PMID: 19177065

| SEQUENCE LISTING |
|---|
| SEQ ID NO: 1: *Homo sapiens* VISTA (Alternate names: B7-H5; B7H5; DD1alpha; GI24; PP2135; SISP1) AMINO ACID SEQUENCE<br>   1 mgvptaleag swrwgsllfa lflaaslgpv aafkvatpys lyvcpegqnv tltcrllgpv<br> 61 dkghdvtfyk twyrssrgev qtcserrpir nltfqdlhlh hgghqaants hdlaqrhgle<br>121 sasdhhgnfs itmrnltlld sglycclvve irhhhsehrv hgamelqvqt gkdapsncvv<br>181 ypsssqdsen itaaalatga civgilclpl illlvykqrq aasnrraqel vrmdsniqgi<br>241 enpgfeaspp aqgipeakvr hplsyvaqrq psesgrhlls epstplsppg pgdvffpsld<br>301 pvpdspnfev i<br><br>SEQ ID NO: 2: *Mus musculus* VISTA AMINO ACID SEQUENCE<br>   1 mgvpavpeas sprwgtllla iflaasrglv aafkvttpys lyvcpegqna tltcrilgpv<br> 61 skghdvtiyk twylssrgev qmckehrpir nftlqhlqhh gshlkanash dqpqkhglel<br>121 asdhhgnfsi tlrnvtprds glycclviel knhhpeqrfy gsmelqvqag kgsgstcmas<br>181 neqdsdsita aalatgaciv gilclplill lvykqrqvas hrraqelvrm dsntqgienp<br>241 gfettppfqg mpeaktrppl syvaqrqpse sgryllsdps tplsppgpgd vffpsldpvp<br>301 dspnseai<br><br>SEQ ID NO: 3: *Mus musculus* VISTA AMINO ACID SEQUENCE<br>   1 mgvpavpeas sprwgtllla iflaasrglv aafkvttpys lyvcpegqna tltcrilgpv<br> 61 skghdvtiyk twylssrgev qmckehrpir nftlqhlqhh gshlkanash dqpqkhglel<br>121 asdhhgnfsi tlrnvtprds glycclviel knhhpeqrfy gsmelqvqag kgsgstcmas<br>181 neqdsdsita aalatgaciv gilclplill lvykqrqvas hrraqelvrm dssntqgien<br>241 pgfettppfq gmpeaktrpp lsyvaqrqps esgryllsdp stplsppgpg dvffpsldpv<br>301 pdspnseai<br><br>SEQ ID NO: 4: *Homo sapiens* VISTA (Alternate names: B7-H5; B7H5; DD1alpha; GI24; PP2135; SISP1) NUCLEIC ACID SEQUENCE<br>   1 gggggcgggt gcctggagca cggcgctggg gccgcccgca gcgctcactc gctcgcactc<br> 61 agtcgcggga ggcttccccg cgccggccgc gtcccgcccg ctccccggca ccagaagttc<br>121 ctctgcgcgt ccgacggcga catgggcgtc cccacggccc tggaggccgg cagctggcgc<br>181 tggggatccc tgctcttcgc tctcttcctg gctgcgtccc taggtccggt ggcagccttc<br>241 aaggtcgcca cgccgtattc cctgtatgtc tgtcccgagg ggcagaacgt caccctcacc<br>301 tgcaggctct tgggccctgt ggacaaaggg cacgatgtga ccttctacaa gacgtggtac<br>361 cgcagctcga ggggcgaggt gcagacctgc tcagacgcc ggcccatccg caacctcacg<br>421 ttccaggacc ttcacctgca ccatggaggc caccaggctg ccaacaccag ccacgacctg<br>481 gctcagcgcc acgggctgga gtcggcctcc gaccaccatg gcaacttctc catcaccatg<br>541 cgcaacctga ccctgctgga tagcggcctc tactgctgcc tggtggtgga gatcaggcac<br>601 caccactcgg agcacagggt ccatggtgcc atggagctgc aggtgcagac aggcaaagat<br>661 gcaccatcca actgtgtggt gtacccatcc tcctcccagg atagtgaaaa catcacggct<br>721 gcagccctgg ctacgggtgc ctgcatcgta ggaatcctct gcctccccct catcctgctc<br>781 ctggtctaca agcaaaggca ggcagcctcc aaccgccgtg cccaggagct ggtgcggatg<br>841 gacagcaaca ttcaagggat tgaaaacccc ggctttgaag cctcaccacc tgcccagggg<br>901 ataccaggg ccaaagtcag gcacccctg tcctatgtgg cccagcggca gccttctgag<br>961 tctgggcggc atctgctttc ggagcccagc accccctgt ctcctccagg ccccggagac<br>1021 gtcttcttcc catccctgga ccctgtccct gactctccaa actttgaggt catctagccc<br>1081 agctggggga cagtgggctg ttgtggctgg gtctgggca ggtgcatttg agcagggct<br>1141 ggctctgtga gtggcctcct tggcctcggc cctggttccc tccctcctgc tctgggctca<br>1201 gatactgtga catcccagaa gcccagcccc tcaacccctc tggatgctac atggggatgc |

```
      1261 tggacggctc agccctgtt ccaaggattt tggggtgctg agattctccc ctagagacct
      1321 gaaattcacc agctacagat gccaaatgac ttacatctta agaagtctca gaacgtccag
      1381 cccttcagca gctctcgttc tgagacatga gccttgggat gtggcagcat cagtgggaca
      1441 agatggacac tgggccaccc tcccaggcac cagacacagg gcacggtgga gagacttctc
      1501 ccccgtggcc gccttggctc ccccgttttg cccgaggctg ctcttctgtc agacttcctc
      1561 tttgtaccac agtggctctg gggccaggcc tgcctgccca ctggccatcg ccaccttccc
      1621 cagctgcctc ctaccagcag tttctctgaa gatctgtcaa caggttaagt caatctgggg
      1681 cttccactgc ctgcattcca gtccccagag cttggtggtc ccgaaacggg aagtacatat
      1741 tggggcatgg tggcctccgt gagcaaatgg tgtcttgggc aatctgaggc caggacagat
      1801 gttgcccccac ccactggaga tggtgctgag ggaggtgggt ggggccttct gggaaggtga
      1861 gtggagaggg gcacctgccc cccgccctcc ccatccccta ctcccactgc tcagcgcggg
      1921 ccattgcaag ggtgccacac aatgtcttgt ccaccctggg acacttctga gtatgaagcg
      1981 ggatgctatt aaaaactaca tggggaaaca ggtgcaaacc ctggagatgg attgtaagag
      2041 ccagtttaaa tctgcactct gctgctcctc ccccacccccc accttccact ccatacaatc
      2101 tgggcctggt ggagtcttcg cttcagagcc attcggccag gtgcgggtga tgttcccatc
      2161 tcctgcttgt gggcatgccc tggctttgtt tttatacaca taggcaaggt gagtcctctg
      2221 tggaattgtg attgaaggat tttaaagcag gggaggagag taggggcat ctctgtacac
      2281 tctgggggta aaacagggaa ggcagtgcct gagcatgggg acaggtgagg tggggctggg
      2341 cagaccccct gtagcgttta gcaggatggg ggcccaggt actgtggaga catagtcca
      2401 gcctgggcat ttgtctccta gcagcctaca ctggcctgc tgagctgggc ctgggtgctg
      2461 aaagccagga tttggggcta ggcgggaaga tgttcgccca attgcttggg gggttggggg
      2521 gatggaaaag gggagcacct ctaggctgcc tggcagcagt gagccctggg cctgtggcta
      2581 cagccaggga accccacctg gacacatggc cctgcttcta agcccccag ttaggcccaa
      2641 aggaatggtc cactgagggc ctcctgctct gcctgggctg ggggggc tttgaggaga
      2701 gggtaaacat aggcccggag atggggctga cacctcgagt ggccagaata tgcccaaacc
      2761 ccggcttctc ccttgtccct aggcagaggg gggtccctc tttgttccc tctggtcacc
      2821 acaatgcttg atgccagctg ccataggaag agggtgctgg ctggccatgg tggcacacac
      2881 ctgtcctccc agcactttgc agggctgagg tggaaggacc gcttaagccc aggtgttcaa
      2941 ggctgctgtg agctgtgttc gagccactac actccagcct ggggacggag caaaactttg
      3001 cctcaaaaca aattttaaaa agaaagaaag aaggaaagag ggtatgtttt tcacaattca
      3061 tgggggcctg catggcagga gtggggacag acacctgct gttcctggag tcgaaggaca
      3121 agcccacagc ccagattccg gttctcccaa ctcaggaaga gcatgccctg ccctctgggg
      3181 aggctggcct ggccccagcc ctcagctgct gaccttgagg cagagacaac ttctaagaat
      3241 ttggctgcca gaccccaggc ctggctgctg ctgtgtggag agggaggcgg cccgcagcag
      3301 aacagccacc gcacttcctc ctcagcttcc tctggtgcgg ccctgccctc tcttctctgg
      3361 accctttac aactgaacgc atctgggctt cgtggtttcc tgttttcagc gaaatttact
      3421 ctgagctccc agttccatct tcatccatgg ccacaggccc tgcctacaac gcactaggga
      3481 cgtccctccc tgctgctgct ggggagggc aggctgctgg agccgcctc tgagttgccc
      3541 gggatggtag tgcctctgat gccagccctg gtggctgtgg gctggggtgc atgggagagc
      3601 tgggtgcgag aacatggcgc tccaggggg cggaggagc actagggct ggggcaggag
      3661 gctcctggag cgctggattc gtggcacagt ctgaggccct gagagggaaa tccatgcttt
      3721 taagaactaa ttcattgtta ggagatcaat caggaattag gggccatctt acctatctcc
      3781 tgacattcac agtttaatag agacttcctg cctttattcc ctcccaggga gaggctgaag
      3841 gaatggaatt gaaagcacca tttggagggt tttgctgaca cagcggggac tgctcagcac
      3901 tccctaaaaa cacaccatgg aggccactgg tgactgctgg aggccaggct ggccctgcct
      3961 ggggggagtcc gtggcgatgg gcgctgggt ggaggtgcag gagccccagg acctgctttt
      4021 caaaagactt ctgcctgacc agagctccca ctacatgcag tgcccaggg cagaggggct
      4081 gatacatggc cttttcagg gggtgctcct cgcggggtgg acttgggagt gtgcagtggg
      4141 acaggggct gcaggggtcc tgccaccacc gagcaccaac ttggccccctg gggtcctgcc
      4201 tcatgaatga ggccttcccc agggctggcc tgactgtgct gggggctggg ttaacgtttt
      4261 ctcagggaac cacaatgcac gaaagaggaa ctgggttgc taaccaggat gctgggaaca
      4321 aaggcctctt gaagcccagc cacagcccag ctgagcatga ggcccagccc atagacggca
      4381 caggccacct ggcccattcc ctgggcattc cctgctttgc attgctgctt ctcttcaccc
      4441 catggaggct atgtcaccct aactatcctg gaatgtgttg agagggattc tgaatgatca
      4501 atatagcttg gtgagacagt gccgagatag atagccatgt ctgccttggg cacgggagag
      4561 ggaagtggca gcatgcatgc tgtttcttgg ccttttctgt tagaatactt ggtgctttcc
      4621 aacacacttt cacatgtgtt gtaacttgtt tgatccaccc ccttccctga aaatcctggg
      4681 aggttttatt gctgccattt aacacagagg gcaatagagg ttctgaaagg tctgtgtctt
      4741 gtcaaaacaa gtaaacggtg gaactacgac taaa
//
```

SEQ ID NO: 5: *Homo sapiens* VISTA (Alternate names: B7-H5; B7H5; DD1alpha; GI24; PP2135; SISP1) CODING NUCLEIC ACID SEQUENCE

```
         1 ctcgccgcgc tgagccgcct cgggacggag ccatgcggcg ctgggcctgg gccgcggtcg
        61 tggtccccct cgggccgcag ctcgtgctcc tcggggcgt cggggcccgg cgggaggcac
       121 agaggacgca gcagctggc cagcgcgcag atcccccaa cgccaccgcc agcgcgtcct
       181 cccgcgaggg gctgcccgag gccccccaag catcccaggc ctcaggacct gagttctccg
       241 acgccacat gacatggctg aactttgtcc ggcggccgga cgacggcgcc ttaaggaagc
       301 ggtgcggaag caggacaag aagccgcggg atctcttcgg tcccccagga cctccaggtg
       361 cagaagtgac cgcggagact ctgcttcacg agtttcagga gctgctgaaa gaggccacgg
       421 agcgccggtt ctcagggctt ctggaccgc tgctgcccca ggggcgggc ctgcggctgg
       481 tgggcgaggc ctttcactgc ggctgcaag gtcccgcgg ggtggacaag cggacgctgg
       541 tggagctgca tggtttccag gctcctgctg cccaaggtgc cttcctgcga ggtccggtc
       601 tgagctggc ctcgggtcgg ttcacgccc ccgtgtccgg catcttccag ttctctgcca
       661 gtctgcacgt ggaccacagt gagctgcagg gcaaggccg gctgcgggcc cgggacgtgg
       721 tgtgtgttct catctgtatt gagtccctgt gccagcgcca cagtgcctg gaggccgtct
       781 caggcctgga gagcaacagc agggtcttca cgctacaggt gcagggctg ctgcagctgc
```

```
     841 aggctggaca gtacgcttct gtgtttgtgg acaatggctc cggggccgtc ctcaccatcc
     901 aggcgggctc cagcttctcc gggctgctcc tgggcacgtg agggcgccca gggggctgg
     961 cgaggagctg ccgccggatc ccggggaccc tcctactgat gcccgtggtc accacaataa
    1021 agagccctcc accctcaaaa aaaaaaaaaa aaaaa
//

SEQ ID NO: 6: Mus musculus VISTA CODING NUCLEIC ACID SEQUENCE
       1 ctcgccgcgc tgagccgcct cgggacggag ccatgcgcg ctgggcctgg gccgcggtcg
      61 tggtccccct cgggccgcag ctcgtgctcc tcggggggcgt cggggccgg cggaggcac
     121 agaggacgca gcagcctggc cagcgcgcag atcccccaa cgccaccgcc agcgcgtcct
     181 cccgcgaggg gctgcccgag gcccccaagc catcccaggc ctcaggacct gagttctccg
     241 acgcccacat gacatggctg aactttgtcc ggcggccgga cgacggccgga ttaaggaagc
     301 ggtgcggaag cagggacaag aagccgcggg atctcttcgg tcccccagga cctccaggtg
     361 cagaagtgac cgcggagact ctgcttcacg agtttcagga gctgctgaaa gaggccacgg
     421 agcgccggtt ctcagggctt ctggaccgc tgctgcccca ggggcgggc ctgcggctgg
     481 tgggcgaggc cttcactgc cggctgcagg gtccccgccg ggtggacaag cggacgctgg
     541 tggagctgca tggtttccag gctcctgctg cccaaggtgc cttcctgcga ggctccggtc
     601 tgagcctggc ctcgggtcgg ttcacggccc ccgtgtccgg catcttccag ttctctgcca
     661 gtctgcacgt ggaccacagt gagctgcagg gcaaggcccg gctgcgggcc cgggacgtgg
     721 tgtgtgttct catctgtatt gagtccctgt gccagcgcca cacgtgcctg gaggccgtct
     781 caggcctgga gagcaacagc agggtcttca cgctacaggt gcaggggctg ctgcagctgc
     841 aggctggaca gtacgcttct gtgtttgtgg acaatggctc cggggccgtc ctcaccatcc
     901 aggcgggctc cagcttctcc gggctgctcc tgggcacgtg agggcgccca gggggctgg
     961 cgaggagctg ccgccggatc ccggggaccc tcctactgat gcccgtggtc accacaataa
    1021 agagccctcc accctcaaaa aaaaaaaaaa aaaaa
//
```

The invention claimed is:

1. An agonistic antibody comprising an antigen binding region that specifically binds to human V-domain Ig Suppressor of T cell Activation (human VISTA), wherein (i) the antibody or antibody fragment agonizes or promotes the effect of VISTA on T cell immunity, wherein said antibody is selected from the following:
   (i) one comprising a heavy chain comprising the $V_H$ CDRs of SEQ ID NO:200, 201 and 202 and comprising a light chain comprising the $V_L$ CDRs of SEQ ID NO:203, 204 and 205;
   (ii) one comprising a heavy chain comprising the $V_H$ CDRs of SEQ ID NO:380, 381 and 382 and comprising a light chain comprising the $V_L$ CDRs of SEQ ID NO:383, 384 and 385;
   (iii) one comprising a heavy chain comprising the $V_H$ CDRs of SEQ ID NO:470, 471 and 472 and comprising a light chain comprising the $V_L$ CDRs of SEQ ID NO:473, 474 and 475;
   (iv) one comprising a heavy chain comprising the $V_H$ CDRs of SEQ ID NO:500, 501 and 502 and the VL CDR polypeptides of SEQ ID NO:503, 504 and 505;
and wherein the antibody of any of (i) to (iv) comprises a human IgG2 constant or Fc region.

2. The agonist antibody of claim 1, wherein the human IgG2 constant or Fc region binds to Fc gamma receptors including human CD32A.

3. The agonist antibody claim 1 which is chimeric, human or humanized.

4. The antibody or antibody fragment of claim 1 which:
   for embodiment (i) the antibody comprises the VH polypeptide of SEQ ID NO:206 and the VL polypeptide of SEQ ID NO:208;
   for embodiment (ii) the antibody comprises the VH polypeptide of SEQ ID NO:386 and the VL polypeptide of SEQ ID NO:388;
   for embodiment (iii) the antibody comprises the VH polypeptide of SEQ ID NO:476 and the VL polypeptide of SEQ ID NO:478; or
   for embodiment (iv) the antibody comprises the VH polypeptide of SEQ ID NO:506 and the VL polypeptide of SEQ ID NO:508.

5. The antibody of claim 1, which comprises a human IgG2 constant domain wherein at least one cysteine residue is deleted or changed to another amino acid.

6. A pharmaceutical or diagnostic composition comprising at least one agonistic antibody according to claim 1.

7. A pharmaceutical comprising at least agonistic antibody according to claim 2.

8. A pharmaceutical comprising at least agonistic antibody according to claim 3.

9. A pharmaceutical comprising at least agonistic antibody according to claim 4.

10. A pharmaceutical comprising at least agonistic antibody according to claim 5.

11. The agonistic antibody of claim 1, which is one comprising a heavy chain comprising the $V_H$ CDRs of SEQ ID NO:200, 201 and 202 and comprising a light chain comprising the $V_L$ CDRs of SEQ ID NO:203, 204 and 205.

12. The agonistic antibody of claim 1, which is one comprising a heavy chain comprising the $V_H$ CDRs of SEQ ID NO:380, 381 and 382 and comprising a light chain comprising the $V_L$ CDRs of SEQ ID NO:383, 384 and 385.

13. The agonistic antibody of claim 1, which is one comprising a heavy chain comprising the $V_H$ CDRs of SEQ ID NO:470, 471 and 472 and comprising a light chain comprising the $V_L$ CDRs of SEQ ID NO:473, 474 and 475.

14. The agonistic antibody of claim 1, which is one comprising a heavy chain comprising the $V_H$ CDRs of SEQ ID NO:500, 501 and 502 and the VL CDR polypeptides of SEQ ID NO:503, 504 and 505.

15. A pharmaceutical comprising at least agonistic antibody according to claim 11.

16. A pharmaceutical comprising at least agonistic antibody according to claim 12.

17. A pharmaceutical comprising at least agonistic antibody according to claim 13.

18. A pharmaceutical comprising at least agonistic antibody according to claim 14.

19. An antibody or antibody fragment comprising an antigen binding region that specifically binds to human V-domain Ig Suppressor of T cell Activation (human VISTA), wherein said antibody or antibody fragment is selected from the following:
   (i) one comprising a heavy chain comprising the $V_H$ CDRs of SEQ ID NO:200, 201 and 202 and comprising a light chain comprising the $V_L$ CDRs of SEQ ID NO:203, 204 and 205;
   (ii) one comprising a heavy chain comprising the $V_H$ CDRs of SEQ ID NO:380, 381 and 382 and comprising a light chain comprising the $V_L$ CDRs of SEQ ID NO:383, 384 and 385;
   (iii) one comprising a heavy chain comprising the $V_H$ CDRs of SEQ ID NO:470, 471 and 472 and comprising a light chain comprising the $V_L$ CDRs of SEQ ID NO:473, 474 and 475;
   (iv) one comprising a heavy chain comprising the $V_H$ CDRs of SEQ ID NO:500, 501 and 502 and the VL CDR polypeptides of SEQ ID NO:503, 504 and 505.

20. The antibody or antibody fragment of any of embodiments (i) to (iv) recited in claim 19, which comprises a human IgG1, IgG3 or IgG4 constant or Fc region.

21. The antibody or antibody fragment of claim 20, wherein said a human IgG1, IgG3 or IgG4 constant or Fc region comprises a modification which impairs FcR or complement binding.

22. The antibody or antibody fragment of claim 19 which:
   for embodiment (i) the antibody comprises the VH polypeptide of SEQ ID NO:206 and the VL polypeptide of SEQ ID NO:208;
   for embodiment (ii) the antibody comprises the VH polypeptide of SEQ ID NO:386 and the VL polypeptide of SEQ ID NO:388;
   for embodiment (iii) the antibody comprises the VH polypeptide of SEQ ID NO:476 and the VL polypeptide of SEQ ID NO:478; or
   for embodiment (iv) the antibody comprises the VH polypeptide of SEQ ID NO:506 and the VL polypeptide of SEQ ID NO:508.

23. The antibody or antibody fragment of any of embodiments (i) to (iv) recited in claim 22, which comprises a human IgG1, IgG3 or IgG4 constant or Fc region.

24. The antibody or antibody fragment of claim 23, wherein said a human IgG1, IgG3 or IgG4 constant or Fc region comprises a modification which impairs FcR or complement binding.

* * * * *

SEQUENCE LISTING

<160> NUMBER OF SEQ ID NOS: 819

<210> SEQ ID NO 1
<211> LENGTH: 311
<212> TYPE: PRT
<213> ORGANISM: Homo sapiens

<400> SEQUENCE: 1

Met Gly Val Pro Thr Ala Leu Glu Ala Gly Ser Trp Arg Trp Gly Ser
1               5                   10                  15

Leu Leu Phe Ala Leu Phe Leu Ala Ala Ser Leu Gly Pro Val Ala Ala
            20                  25                  30

Phe Lys Val Ala Thr Pro Tyr Ser Leu Tyr Val Cys Pro Glu Gly Gln
        35                  40                  45

Asn Val Thr Leu Thr Cys Arg Leu Leu Gly Pro Val Asp Lys Gly His
    50                  55                  60

Asp Val Thr Phe Tyr Lys Thr Trp Tyr Arg Ser Arg Gly Glu Val
65                  70                  75                  80

Gln Thr Cys Ser Glu Arg Arg Pro Ile Arg Asn Leu Thr Phe Gln Asp
                85                  90                  95

Leu His Leu His His Gly Gly His Gln Ala Ala Asn Thr Ser His Asp
            100                 105                 110

Leu Ala Gln Arg His Gly Leu Glu Ser Ala Ser Asp His His Gly Asn
        115                 120                 125

Phe Ser Ile Thr Met Arg Asn Leu Thr Leu Leu Asp Ser Gly Leu Tyr
    130                 135                 140

Cys Cys Leu Val Val Glu Ile Arg His His Ser Glu His Arg Val
145                 150                 155                 160

His Gly Ala Met Glu Leu Gln Val Gln Thr Gly Lys Asp Ala Pro Ser
                165                 170                 175

Asn Cys Val Val Tyr Pro Ser Ser Ser Gln Asp Ser Glu Asn Ile Thr
            180                 185                 190

```
Ala Ala Ala Leu Ala Thr Gly Ala Cys Ile Val Gly Ile Leu Cys Leu
            195                 200                 205

Pro Leu Ile Leu Leu Val Tyr Lys Gln Arg Gln Ala Ala Ser Asn
210                 215                 220

Arg Arg Ala Gln Glu Leu Val Arg Met Asp Ser Asn Ile Gln Gly Ile
225                 230                 235                 240

Glu Asn Pro Gly Phe Glu Ala Ser Pro Pro Ala Gln Gly Ile Pro Glu
                245                 250                 255

Ala Lys Val Arg His Pro Leu Ser Tyr Val Ala Gln Arg Gln Pro Ser
            260                 265                 270

Glu Ser Gly Arg His Leu Leu Ser Glu Pro Ser Thr Pro Leu Ser Pro
            275                 280                 285

Pro Gly Pro Gly Asp Val Phe Phe Pro Ser Leu Asp Pro Val Pro Asp
            290                 295                 300

Ser Pro Asn Phe Glu Val Ile
305                 310

<210> SEQ ID NO 2
<211> LENGTH: 308
<212> TYPE: PRT
<213> ORGANISM: Mus musculus

<400> SEQUENCE: 2

Met Gly Val Pro Ala Val Pro Glu Ala Ser Ser Pro Arg Trp Gly Thr
1               5                   10                  15

Leu Leu Leu Ala Ile Phe Leu Ala Ala Ser Arg Gly Leu Val Ala Ala
                20                  25                  30

Phe Lys Val Thr Thr Pro Tyr Ser Leu Tyr Val Cys Pro Glu Gly Gln
                35                  40                  45

Asn Ala Thr Leu Thr Cys Arg Ile Leu Gly Pro Val Ser Lys Gly His
50                  55                  60

Asp Val Thr Ile Tyr Lys Thr Trp Tyr Leu Ser Ser Arg Gly Glu Val
65                  70                  75                  80

Gln Met Cys Lys Glu His Arg Pro Ile Arg Asn Phe Thr Leu Gln His
                85                  90                  95

Leu Gln His His Gly Ser His Leu Lys Ala Asn Ala Ser His Asp Gln
                100                 105                 110

Pro Gln Lys His Gly Leu Glu Leu Ala Ser Asp His Gly Asn Phe
            115                 120                 125

Ser Ile Thr Leu Arg Asn Val Thr Pro Arg Asp Ser Gly Leu Tyr Cys
130                 135                 140

Cys Leu Val Ile Glu Leu Lys Asn His His Pro Glu Gln Arg Phe Tyr
145                 150                 155                 160

Gly Ser Met Glu Leu Gln Val Gln Ala Gly Lys Gly Ser Gly Ser Thr
                165                 170                 175

Cys Met Ala Ser Asn Glu Gln Asp Ser Asp Ser Ile Thr Ala Ala Ala
            180                 185                 190

Leu Ala Thr Gly Ala Cys Ile Val Gly Ile Leu Cys Leu Pro Leu Ile
            195                 200                 205

Leu Leu Leu Val Tyr Lys Gln Arg Gln Val Ala Ser His Arg Arg Ala
            210                 215                 220

Gln Glu Leu Val Arg Met Asp Ser Asn Thr Gln Gly Ile Glu Asn Pro
225                 230                 235                 240

Gly Phe Glu Thr Thr Pro Pro Phe Gln Gly Met Pro Glu Ala Lys Thr
```

```
                        245                 250                 255
Arg Pro Leu Ser Tyr Val Ala Gln Arg Gln Pro Ser Glu Ser Gly
            260                 265                 270

Arg Tyr Leu Leu Ser Asp Pro Thr Pro Leu Ser Pro Gly Pro
    275                 280                 285

Gly Asp Val Phe Phe Pro Ser Leu Asp Pro Val Pro Asp Ser Pro Asn
290                 295                 300

Ser Glu Ala Ile
305

<210> SEQ ID NO 3
<211> LENGTH: 309
<212> TYPE: PRT
<213> ORGANISM: Mus musculus

<400> SEQUENCE: 3

Met Gly Val Pro Ala Val Pro Glu Ala Ser Ser Pro Arg Trp Gly Thr
1               5                   10                  15

Leu Leu Leu Ala Ile Phe Leu Ala Ala Ser Arg Gly Leu Val Ala Ala
            20                  25                  30

Phe Lys Val Thr Thr Pro Tyr Ser Leu Tyr Val Cys Pro Glu Gly Gln
        35                  40                  45

Asn Ala Thr Leu Thr Cys Arg Ile Leu Gly Pro Val Ser Lys Gly His
    50                  55                  60

Asp Val Thr Ile Tyr Lys Thr Trp Tyr Leu Ser Ser Arg Gly Glu Val
65                  70                  75                  80

Gln Met Cys Lys Glu His Arg Pro Ile Arg Asn Phe Thr Leu Gln His
                85                  90                  95

Leu Gln His His Gly Ser His Leu Lys Ala Asn Ala Ser His Asp Gln
            100                 105                 110

Pro Gln Lys His Gly Leu Glu Leu Ala Ser Asp His His Gly Asn Phe
        115                 120                 125

Ser Ile Thr Leu Arg Asn Val Thr Pro Arg Asp Ser Gly Leu Tyr Cys
    130                 135                 140

Cys Leu Val Ile Glu Leu Lys Asn His His Pro Glu Gln Arg Phe Tyr
145                 150                 155                 160

Gly Ser Met Glu Leu Gln Val Gln Ala Gly Lys Gly Ser Gly Ser Thr
                165                 170                 175

Cys Met Ala Ser Asn Glu Gln Asp Ser Asp Ser Ile Thr Ala Ala Ala
            180                 185                 190

Leu Ala Thr Gly Ala Cys Ile Val Gly Ile Leu Cys Leu Pro Leu Ile
        195                 200                 205

Leu Leu Leu Val Tyr Lys Gln Arg Gln Val Ala Ser His Arg Arg Ala
    210                 215                 220

Gln Glu Leu Val Arg Met Asp Ser Ser Asn Thr Gln Gly Ile Glu Asn
225                 230                 235                 240

Pro Gly Phe Glu Thr Thr Pro Pro Phe Gln Gly Met Pro Glu Ala Lys
                245                 250                 255

Thr Arg Pro Pro Leu Ser Tyr Val Ala Gln Arg Gln Pro Ser Glu Ser
            260                 265                 270

Gly Arg Tyr Leu Leu Ser Asp Pro Ser Thr Pro Leu Ser Pro Pro Gly
        275                 280                 285

Pro Gly Asp Val Phe Phe Pro Ser Leu Asp Pro Val Pro Asp Ser Pro
    290                 295                 300
```

Asn Ser Glu Ala Ile
305

<210> SEQ ID NO 4
<211> LENGTH: 4774
<212> TYPE: DNA
<213> ORGANISM: Homo sapiens

<400> SEQUENCE: 4

| | |
|---|---:|
| gggggcgggt gcctggagca cggcgctggg gccgcccgca gcgctcactc gctcgcactc | 60 |
| agtcgcggga ggcttccccg cgccggccgc gtcccgcccg ctccccggca ccagaagttc | 120 |
| ctctgcgcgt ccgacggcga catgggcgtc cccacggccc tggaggccgg cagctggcgc | 180 |
| tggggatccc tgctcttcgc tctcttcctg gctgcgtccc taggtccggt ggcagccttc | 240 |
| aaggtcgcca cgccgtattc cctgtatgtc tgtcccgagg ggcagaacgt caccctcacc | 300 |
| tgcaggctct gggccctgt ggacaaaggg cacgatgtga ccttctacaa gacgtggtac | 360 |
| cgcagctcga ggggcgaggt gcagacctgc tcagagcgcc ggcccatccg caacctcacg | 420 |
| ttccaggacc ttcacctgca ccatggaggc caccaggctg ccaacaccag ccacgacctg | 480 |
| gctcagcgcc acgggctgga gtcggcctcc gaccaccatg gcaacttctc catcaccatg | 540 |
| cgcaacctga ccctgctgga tagcggcctc tactgctgcc tggtggtgga gatcaggcac | 600 |
| caccactcgg agcacagggt ccatggtgcc atggagctgc aggtgcagac aggcaaagat | 660 |
| gcaccatcca actgtgtggt gtacccatcc tcctcccagg atagtgaaaa catcacggct | 720 |
| gcagccctgg ctacgggtgc ctgcatcgta ggaatcctct gcctcccct catcctgctc | 780 |
| ctggtctaca gcaaaggca ggcagcctcc aaccgccgtg cccaggagct ggtgcggatg | 840 |
| gacagcaaca ttcaagggat tgaaaacccc ggctttgaag cctcaccacc tgcccagggg | 900 |
| atacccgagg ccaaagtcag gcaccccctg tcctatgtgg cccagcggca gccttctgag | 960 |
| tctgggcggc atctgctttc ggagcccagc accccctgt ctcctccagg ccccggagac | 1020 |
| gtcttcttcc catccctgga ccctgtccct gactctccaa actttgaggt catctagccc | 1080 |
| agctgggga cagtgggctg ttgtggctgg gtctggggca ggtgcatttg agccagggct | 1140 |
| ggctctgtga gtggcctcct tggcctcggc cctggttccc tccctcctgc tctgggctca | 1200 |
| gatactgtga catcccagaa gcccagcccc tcaacccctc tggatgctac atggggatgc | 1260 |
| tggacggctc agccctgtt ccaaggattt tggggtgctg agattctccc ctagagacct | 1320 |
| gaaattcacc agctacagat gccaaatgac ttacatctta agaagtctca gaacgtccag | 1380 |
| cccttcagca gctctcgttc tgagacatga gccttgggat gtggcagcat cagtgggaca | 1440 |
| agatggacac tgggccaccc tcccaggcac cagacacagg gcacggtgga gagacttctc | 1500 |
| ccccgtggcc gccttggctc cccgttttg ccgaggctg ctcttctgtc agacttcctc | 1560 |
| tttgtaccac agtggctctg ggccaggcc tgcctgccca ctggccatcg ccaccttccc | 1620 |
| cagctgcctc ctaccagcag tttctctgaa gatctgtcaa caggttaagt caatctgggg | 1680 |
| cttccactgc ctgcattcca gtccccagag cttggtggtc ccgaaacggg aagtacatat | 1740 |
| tggggcatgg tggcctccgt gagcaaatgg tgtcttgggc aatctgaggc caggacagat | 1800 |
| gttgccccac ccactggaga tggtgctgag ggaggtgggt ggggccttct gggaaggtga | 1860 |
| gtggagaggg gcacctgccc ccgcccctcc ccatccccta ctcccactgc tcagcgcggg | 1920 |
| ccattgcaag ggtgccacac aatgtcttgt ccacccctggg acacttctga gtatgaagcg | 1980 |
| ggatgctatt aaaaactaca tggggaaaca ggtgcaaacc ctggagatgg attgtaagag | 2040 |

```
ccagtttaaa tctgcactct gctgctcctc ccccacccccc accttccact ccatacaatc    2100
tgggcctggt ggagtcttcg cttcagagcc attcggccag gtgcgggtga tgttcccatc    2160
tcctgcttgt gggcatgccc tggctttgtt tttatacaca taggcaaggt gagtcctctg    2220
tggaattgtg attgaaggat tttaaagcag gggaggagag taggggggcat ctctgtacac    2280 tctggggggta aaacagggaa ggcagtgcct gagcatgggg acaggtgagg tggggctggg    2340 cagacccccct gtagcgttta gcaggatggg ggccccaggt actgtggaga gcatagtcca    2400
gcctgggcat ttgtctccta gcagcctaca ctggctctgc tgagctgggc ctgggtgctg    2460
aaagccagga tttggggcta ggcgggaaga tgttcgccca attgcttggg gggttggggg    2520
gatggaaaag gggagcacct ctaggctgcc tggcagcagt gagccctggg cctgtggcta    2580
cagccaggga accccacctg gacacatggc cctgcttcta agcccccag ttaggcccaa    2640 aggaatggtc cactgagggc ctcctgctct gcctgggctg ggcaggggc tttgaggaga    2700 gggtaaacat aggcccggag atggggctga cacctcgagt ggccagaata tgcccaaacc    2760
ccggcttctc ccttgtccct aggcagaggg gggtcccttc ttttgttccc tctggtcacc    2820
acaatgcttg atgccagctg ccataggaag agggtgctgg ctggccatgg tggcacacac    2880
ctgtcctccc agcactttgc agggctgagg tggaaggacc gcttaagccc aggtgttcaa    2940
ggctgctgtg agctgtgttc gagccactac actccagcct ggggacggag caaaactttg    3000
cctcaaaaca aattttaaaa agaaagaaag aaggaaagag ggtatgtttt tcacaattca    3060
tgggggcctg catggcagga gtggggacag gacacctgct gttcctggag tcgaaggaca    3120
agcccacagc ccagattccg gttctcccaa ctcaggaaga gcatgccctg ccctctgggg    3180
aggctggcct ggccccagcc ctcagctgct gaccttgagg cagagacaac ttctaagaat    3240
ttggctgcca gaccccaggc ctggctgctg ctgtgtggag agggaggcgg cccgcagcag    3300
aacagccacc gcacttcctc ctcagcttcc tctggtgcgg ccctgccctc tcttctctgg    3360
acccttttac aactgaacgc atctgggctt cgtggtttcc tgttttcagc gaaatttact    3420
ctgagctccc agttccatct tcatccatgg ccacaggccc tgcctacaac gcactaggga    3480
cgtccctccc tgctgctgct ggggaggggc aggctgctgg agccgccctc tgagttgccc    3540
gggatggtag tgcctctgat gccagccctg gtggctgtgg gctgggtgc atgggagagc    3600 tgggtgcgag aacatggcgc ctccagggg cgggaggagc actaggggct ggggcaggag    3660
gctcctggag cgctggattc gtggcacagt ctgaggccct gagagggaaa tccatgcttt    3720
taagaactaa ttcattgtta ggagatcaat caggaattag gggccatctt acctatctcc    3780
tgacattcac agtttaatag agacttcctg cctttattcc ctcccaggga gaggctgaag    3840
gaatggaatt gaaagcacca tttggagggt tttgctgaca cagcgggac tgctcagcac    3900 tccctaaaaa cacaccatgg aggccactgg tgactgctgg tgggcaggct ggccctgcct    3960 ggggggagtcc gtggcgatgg gcgctggggt ggaggtgcag gagccccagg acctgctttt    4020
caaaagactt ctgcctgacc agagctccca ctacatgcag tggcccaggg cagagggggct    4080 gatacatggc cttttcagg gggtgctcct cgcggggtgg acttgggagt gtgcagtggg    4140
acagggggct gcaggggtcc tgccaccacc gagcaccaac ttggcccctg ggtcctgcc    4200 tcatgaatga ggccttcccc agggctggcc tgactgtgct gggggctggg ttaacgtttt    4260 ctcaggggaac cacaatgcac gaaagaggaa ctgggggttgc taaccaggat gctgggaaca    4320
aaggcctctt gaagcccagc cacagcccag ctgagcatga ggcccagccc atagacggca    4380
caggccacct ggcccattcc ctgggcattc cctgctttgc attgctgctt ctcttcaccc    4440
```

```
catggaggct atgtcaccct aactatcctg gaatgtgttg agagggattc tgaatgatca    4500
atatagcttg gtgagacagt gccgagatag atagccatgt ctgccttggg cacgggagag    4560
ggaagtggca gcatgcatgc tgtttcttgg ccttttctgt tagaatactt ggtgctttcc    4620
aacacacttt cacatgtgtt gtaacttgtt tgatccaccc ccttccctga aaatcctggg    4680
aggttttatt gctgccattt aacacagagg gcaatagagg ttctgaaagg tctgtgtctt    4740
gtcaaaacaa gtaaacggtg gaactacgac taaa                                4774

<210> SEQ ID NO 5
<211> LENGTH: 1055
<212> TYPE: DNA
<213> ORGANISM: Homo sapiens

<400> SEQUENCE: 5
ctcgccgcgc tgagccgcct cgggacggag ccatgcggcg ctgggcctgg gccgcggtcg      60
tggtccccct cgggccgcag ctcgtgctcc tcggggcgt cggggcccgg cgggaggcac     120
agaggacgca gcagcctggc cagcgcgcag atccccccaa cgccaccgcc agcgcgtcct    180
cccgcgaggg gctgcccgag gcccccaagc catcccaggc ctcaggacct gagttctccg    240
acgcccacat gacatggctg aactttgtcc ggcggccgga cgacggcgcc ttaaggaagc    300
ggtgcggaag cagggacaag aagccgcggg atctcttcgg tccccagga cctccaggtg     360 cagaagtgac cgcggagact ctgcttcacg agtttcagga gctgctgaaa gaggccacgg    420
agcgccggtt ctcagggctt ctggaccgc tgctgcccca gggggcgggc ctgcggctgg     480
tgggcgaggc cttcactgc cggctgcagg gtccccgccg ggtggacaag cggacgctgg      540
tggagctgca tggtttccag gctcctgctg cccaaggtgc cttcctgcga ggctccggtc    600
tgagcctggc ctcgggtcgg ttcacggccc ccgtgtccgg catcttccag ttctctgcca    660
gtctgcacgt ggaccacagt gagctgcagg gcaaggcccg gctgcgggcc cgggacgtgg    720
tgtgtgttct catctgtatt gagtccctgt gccagcgcca cacgtgcctg gaggccgtct    780
caggcctgga gagcaacagc agggtcttca cgctacaggt gcaggggctg ctgcagctgc    840
aggctggaca gtacgcttct gtgtttgtgg acaatggctc cggggccgtc ctcaccatcc    900
aggcgggctc cagcttctcc gggctgctcc tgggcacgtg agggcgccca gggggctgg      960 cgaggagctg ccgccggatc ccggggaccc tcctactgat gcccgtggtc accacaataa   1020
agagccctcc accctcaaaa aaaaaaaaa aaaaa                                1055

<210> SEQ ID NO 6
<211> LENGTH: 1055
<212> TYPE: DNA
<213> ORGANISM: Mus musculus

<400> SEQUENCE: 6
ctcgccgcgc tgagccgcct cgggacggag ccatgcggcg ctgggcctgg gccgcggtcg      60
tggtccccct cgggccgcag ctcgtgctcc tcggggcgt cggggcccgg cgggaggcac     120
agaggacgca gcagcctggc cagcgcgcag atccccccaa cgccaccgcc agcgcgtcct    180
cccgcgaggg gctgcccgag gcccccaagc catcccaggc ctcaggacct gagttctccg    240
acgcccacat gacatggctg aactttgtcc ggcggccgga cgacggcgcc ttaaggaagc    300
ggtgcggaag cagggacaag aagccgcggg atctcttcgg tccccagga cctccaggtg     360 cagaagtgac cgcggagact ctgcttcacg agtttcagga gctgctgaaa gaggccacgg    420
```

```
agcgccggtt ctcagggctt ctggacccgc tgctgcccca gggggcgggc ctgcggctgg    480
tgggcgaggc ctttcactgc cggctgcagg gtccccgccg ggtggacaag cggacgctgg    540
tggagctgca tggtttccag gctcctgctg cccaaggtgc cttcctgcga ggctccggtc    600
tgagcctggc ctcgggtcgg ttcacggccc ccgtgtccgg catcttccag ttctctgcca    660
gtctgcacgt ggaccacagt gagctgcagg gcaaggcccg gctgcgggcc cgggacgtgg    720
tgtgtgttct catctgtatt gagtcccctgt gccagcgcca cacgtgcctg gaggccgtct    780
caggcctgga gagcaacagc agggtcttca cgctacaggt gcaggggctg ctgcagctgc    840
aggctggaca gtacgcttct gtgtttgtgg acaatggctc cggggccgtc ctcaccatcc    900
aggcgggctc cagcttctcc gggctgctcc tgggcacgtg agggcgccca gggggggctgg    960 cgaggagctg ccgccggatc ccggggaccc tcctactgat gcccgtggtc accacaataa    1020
agagccctcc accctcaaaa aaaaaaaaaa aaaaa    1055
```

<210> SEQ ID NO 7
<211> LENGTH: 15
<212> TYPE: PRT
<213> ORGANISM: Homo sapiens

<400> SEQUENCE: 7

Phe Lys Val Ala Thr Pro Tyr Ser Leu Tyr Val Cys Pro Glu Gly
1               5                   10                  15

<210> SEQ ID NO 8
<211> LENGTH: 15
<212> TYPE: PRT
<213> ORGANISM: Homo sapiens

<400> SEQUENCE: 8

Ala Thr Pro Tyr Ser Leu Tyr Val Cys Pro Glu Gly Gln Asn Val
1               5                   10                  15

<210> SEQ ID NO 9
<211> LENGTH: 15
<212> TYPE: PRT
<213> ORGANISM: Homo sapiens

<400> SEQUENCE: 9

Tyr Ser Leu Tyr Val Cys Pro Glu Gly Gln Asn Val Thr Leu Thr
1               5                   10                  15

<210> SEQ ID NO 10
<211> LENGTH: 15
<212> TYPE: PRT
<213> ORGANISM: Homo sapiens

<400> SEQUENCE: 10

Tyr Val Cys Pro Glu Gly Gln Asn Val Thr Leu Thr Cys Arg Leu
1               5                   10                  15

<210> SEQ ID NO 11
<211> LENGTH: 15
<212> TYPE: PRT
<213> ORGANISM: Homo sapiens

<400> SEQUENCE: 11

Pro Glu Gly Gln Asn Val Thr Leu Thr Cys Arg Leu Leu Gly Pro
1               5                   10                  15

<210> SEQ ID NO 12

```
<211> LENGTH: 15
<212> TYPE: PRT
<213> ORGANISM: Homo sapiens

<400> SEQUENCE: 12

Gln Asn Val Thr Leu Thr Cys Arg Leu Leu Gly Pro Val Asp Lys
1               5                   10                  15

<210> SEQ ID NO 13
<211> LENGTH: 15
<212> TYPE: PRT
<213> ORGANISM: Homo sapiens

<400> SEQUENCE: 13

Thr Leu Thr Cys Arg Leu Leu Gly Pro Val Asp Lys Gly His Asp
1               5                   10                  15

<210> SEQ ID NO 14
<211> LENGTH: 15
<212> TYPE: PRT
<213> ORGANISM: Homo sapiens

<400> SEQUENCE: 14

Cys Arg Leu Leu Gly Pro Val Asp Lys Gly His Asp Val Thr Phe
1               5                   10                  15

<210> SEQ ID NO 15
<211> LENGTH: 15
<212> TYPE: PRT
<213> ORGANISM: Homo sapiens

<400> SEQUENCE: 15

Leu Gly Pro Val Asp Lys Gly His Asp Val Thr Phe Tyr Lys Thr
1               5                   10                  15

<210> SEQ ID NO 16
<211> LENGTH: 15
<212> TYPE: PRT
<213> ORGANISM: Homo sapiens

<400> SEQUENCE: 16

Val Asp Lys Gly His Asp Val Thr Phe Tyr Lys Thr Trp Tyr Arg
1               5                   10                  15

<210> SEQ ID NO 17
<211> LENGTH: 15
<212> TYPE: PRT
<213> ORGANISM: Homo sapiens

<400> SEQUENCE: 17

Gly His Asp Val Thr Phe Tyr Lys Thr Trp Tyr Arg Ser Ser Arg
1               5                   10                  15

<210> SEQ ID NO 18
<211> LENGTH: 15
<212> TYPE: PRT
<213> ORGANISM: Homo sapiens

<400> SEQUENCE: 18

Val Thr Phe Tyr Lys Thr Trp Tyr Arg Ser Ser Arg Gly Glu Val
1               5                   10                  15

<210> SEQ ID NO 19
<211> LENGTH: 15
<212> TYPE: PRT
```

```
<213> ORGANISM: Homo sapiens

<400> SEQUENCE: 19

Tyr Lys Thr Trp Tyr Arg Ser Ser Arg Gly Glu Val Gln Thr Cys
1               5                   10                  15

<210> SEQ ID NO 20
<211> LENGTH: 15
<212> TYPE: PRT
<213> ORGANISM: Homo sapiens

<400> SEQUENCE: 20

Trp Tyr Arg Ser Ser Arg Gly Glu Val Gln Thr Cys Ser Glu Arg
1               5                   10                  15

<210> SEQ ID NO 21
<211> LENGTH: 15
<212> TYPE: PRT
<213> ORGANISM: Homo sapiens

<400> SEQUENCE: 21

Ser Ser Arg Gly Glu Val Gln Thr Cys Ser Glu Arg Arg Pro Ile
1               5                   10                  15

<210> SEQ ID NO 22
<211> LENGTH: 15
<212> TYPE: PRT
<213> ORGANISM: Homo sapiens

<400> SEQUENCE: 22

Gly Glu Val Gln Thr Cys Ser Glu Arg Arg Pro Ile Arg Asn Leu
1               5                   10                  15

<210> SEQ ID NO 23
<211> LENGTH: 15
<212> TYPE: PRT
<213> ORGANISM: Homo sapiens

<400> SEQUENCE: 23

Gln Thr Cys Ser Glu Arg Arg Pro Ile Arg Asn Leu Thr Phe Gln
1               5                   10                  15

<210> SEQ ID NO 24
<211> LENGTH: 15
<212> TYPE: PRT
<213> ORGANISM: Homo sapiens

<400> SEQUENCE: 24

Ser Glu Arg Arg Pro Ile Arg Asn Leu Thr Phe Gln Asp Leu His
1               5                   10                  15

<210> SEQ ID NO 25
<211> LENGTH: 15
<212> TYPE: PRT
<213> ORGANISM: Homo sapiens

<400> SEQUENCE: 25

Arg Pro Ile Arg Asn Leu Thr Phe Gln Asp Leu His Leu His His
1               5                   10                  15

<210> SEQ ID NO 26
<211> LENGTH: 15
<212> TYPE: PRT
<213> ORGANISM: Homo sapiens
```

-continued

<400> SEQUENCE: 26

Arg Asn Leu Thr Phe Gln Asp Leu His Leu His His Gly Gly His
1               5                   10                  15

<210> SEQ ID NO 27
<211> LENGTH: 15
<212> TYPE: PRT
<213> ORGANISM: Homo sapiens

<400> SEQUENCE: 27

Thr Phe Gln Asp Leu His Leu His His Gly Gly His Gln Ala Ala
1               5                   10                  15

<210> SEQ ID NO 28
<211> LENGTH: 15
<212> TYPE: PRT
<213> ORGANISM: Homo sapiens

<400> SEQUENCE: 28

Asp Leu His Leu His His Gly Gly His Gln Ala Ala Asn Thr Ser
1               5                   10                  15

<210> SEQ ID NO 29
<211> LENGTH: 15
<212> TYPE: PRT
<213> ORGANISM: Homo sapiens

<400> SEQUENCE: 29

Leu His His Gly Gly His Gln Ala Ala Asn Thr Ser His Asp Leu
1               5                   10                  15

<210> SEQ ID NO 30
<211> LENGTH: 15
<212> TYPE: PRT
<213> ORGANISM: Homo sapiens

<400> SEQUENCE: 30

Gly Gly His Gln Ala Ala Asn Thr Ser His Asp Leu Ala Gln Arg
1               5                   10                  15

<210> SEQ ID NO 31
<211> LENGTH: 15
<212> TYPE: PRT
<213> ORGANISM: Homo sapiens

<400> SEQUENCE: 31

Gln Ala Ala Asn Thr Ser His Asp Leu Ala Gln Arg His Gly Leu
1               5                   10                  15

<210> SEQ ID NO 32
<211> LENGTH: 15
<212> TYPE: PRT
<213> ORGANISM: Homo sapiens

<400> SEQUENCE: 32

Asn Thr Ser His Asp Leu Ala Gln Arg His Gly Leu Glu Ser Ala
1               5                   10                  15

<210> SEQ ID NO 33
<211> LENGTH: 15
<212> TYPE: PRT
<213> ORGANISM: Homo sapiens

<400> SEQUENCE: 33

His Asp Leu Ala Gln Arg His Gly Leu Glu Ser Ala Ser Asp His
1               5                   10                  15

<210> SEQ ID NO 34
<211> LENGTH: 15
<212> TYPE: PRT
<213> ORGANISM: Homo sapiens

<400> SEQUENCE: 34

Ala Gln Arg His Gly Leu Glu Ser Ala Ser Asp His His Gly Asn
1               5                   10                  15

<210> SEQ ID NO 35
<211> LENGTH: 15
<212> TYPE: PRT
<213> ORGANISM: Homo sapiens

<400> SEQUENCE: 35

His Gly Leu Glu Ser Ala Ser Asp His His Gly Asn Phe Ser Ile
1               5                   10                  15

<210> SEQ ID NO 36
<211> LENGTH: 15
<212> TYPE: PRT
<213> ORGANISM: Homo sapiens

<400> SEQUENCE: 36

Glu Ser Ala Ser Asp His His Gly Asn Phe Ser Ile Thr Met Arg
1               5                   10                  15

<210> SEQ ID NO 37
<211> LENGTH: 15
<212> TYPE: PRT
<213> ORGANISM: Homo sapiens

<400> SEQUENCE: 37

Ser Asp His His Gly Asn Phe Ser Ile Thr Met Arg Asn Leu Thr
1               5                   10                  15

<210> SEQ ID NO 38
<211> LENGTH: 15
<212> TYPE: PRT
<213> ORGANISM: Homo sapiens

<400> SEQUENCE: 38

His Gly Asn Phe Ser Ile Thr Met Arg Asn Leu Thr Leu Leu Asp
1               5                   10                  15

<210> SEQ ID NO 39
<211> LENGTH: 15
<212> TYPE: PRT
<213> ORGANISM: Homo sapiens

<400> SEQUENCE: 39

Phe Ser Ile Thr Met Arg Asn Leu Thr Leu Leu Asp Ser Gly Leu
1               5                   10                  15

<210> SEQ ID NO 40
<211> LENGTH: 15
<212> TYPE: PRT
<213> ORGANISM: Homo sapiens

<400> SEQUENCE: 40

Thr Met Arg Asn Leu Thr Leu Leu Asp Ser Gly Leu Tyr Cys Cys
1               5                   10                  15

<210> SEQ ID NO 41
<211> LENGTH: 15
<212> TYPE: PRT
<213> ORGANISM: Homo sapiens

<400> SEQUENCE: 41

Asn Leu Thr Leu Leu Asp Ser Gly Leu Tyr Cys Cys Leu Val Val
1               5                   10                  15

<210> SEQ ID NO 42
<211> LENGTH: 15
<212> TYPE: PRT
<213> ORGANISM: Homo sapiens

<400> SEQUENCE: 42

Leu Leu Asp Ser Gly Leu Tyr Cys Cys Leu Val Val Glu Ile Arg
1               5                   10                  15

<210> SEQ ID NO 43
<211> LENGTH: 15
<212> TYPE: PRT
<213> ORGANISM: Homo sapiens

<400> SEQUENCE: 43

Ser Gly Leu Tyr Cys Cys Leu Val Val Glu Ile Arg His His His
1               5                   10                  15

<210> SEQ ID NO 44
<211> LENGTH: 15
<212> TYPE: PRT
<213> ORGANISM: Homo sapiens

<400> SEQUENCE: 44

Tyr Cys Cys Leu Val Val Glu Ile Arg His His Ser Glu His
1               5                   10                  15

<210> SEQ ID NO 45
<211> LENGTH: 15
<212> TYPE: PRT
<213> ORGANISM: Homo sapiens

<400> SEQUENCE: 45

Leu Val Val Glu Ile Arg His His His Ser Glu His Arg Val His
1               5                   10                  15

<210> SEQ ID NO 46
<211> LENGTH: 15
<212> TYPE: PRT
<213> ORGANISM: Homo sapiens

<400> SEQUENCE: 46

Glu Ile Arg His His His Ser Glu His Arg Val His Gly Ala Met
1               5                   10                  15

<210> SEQ ID NO 47
<211> LENGTH: 15
<212> TYPE: PRT
<213> ORGANISM: Homo sapiens

<400> SEQUENCE: 47

His His His Ser Glu His Arg Val His Gly Ala Met Glu Leu Gln
1               5                   10                  15

```
<210> SEQ ID NO 48
<211> LENGTH: 15
<212> TYPE: PRT
<213> ORGANISM: Homo sapiens

<400> SEQUENCE: 48

Ser Glu His Arg Val His Gly Ala Met Glu Leu Gln Val Gln Thr
1               5                   10                  15

<210> SEQ ID NO 49
<211> LENGTH: 15
<212> TYPE: PRT
<213> ORGANISM: Homo sapiens

<400> SEQUENCE: 49

Arg Val His Gly Ala Met Glu Leu Gln Val Gln Thr Gly Lys Asp
1               5                   10                  15

<210> SEQ ID NO 50
<211> LENGTH: 15
<212> TYPE: PRT
<213> ORGANISM: Homo sapiens

<400> SEQUENCE: 50

Gly Ala Met Glu Leu Gln Val Gln Thr Gly Lys Asp Ala Pro Ser
1               5                   10                  15

<210> SEQ ID NO 51
<211> LENGTH: 15
<212> TYPE: PRT
<213> ORGANISM: Homo sapiens

<400> SEQUENCE: 51

Glu Leu Gln Val Gln Thr Gly Lys Asp Ala Pro Ser Asn Cys Val
1               5                   10                  15

<210> SEQ ID NO 52
<211> LENGTH: 15
<212> TYPE: PRT
<213> ORGANISM: Homo sapiens

<400> SEQUENCE: 52

Val Gln Thr Gly Lys Asp Ala Pro Ser Asn Cys Val Val Tyr Pro
1               5                   10                  15

<210> SEQ ID NO 53
<211> LENGTH: 15
<212> TYPE: PRT
<213> ORGANISM: Homo sapiens

<400> SEQUENCE: 53

Gly Lys Asp Ala Pro Ser Asn Cys Val Val Tyr Pro Ser Ser Ser
1               5                   10                  15

<210> SEQ ID NO 54
<211> LENGTH: 15
<212> TYPE: PRT
<213> ORGANISM: Homo sapiens

<400> SEQUENCE: 54

Ala Pro Ser Asn Cys Val Val Tyr Pro Ser Ser Ser Gln Asp Ser
1               5                   10                  15

<210> SEQ ID NO 55
<211> LENGTH: 15
```

-continued

```
<212> TYPE: PRT
<213> ORGANISM: Homo sapiens

<400> SEQUENCE: 55

Asn Cys Val Val Tyr Pro Ser Ser Gln Asp Ser Glu Asn Ile
1               5                   10                  15

<210> SEQ ID NO 56
<211> LENGTH: 15
<212> TYPE: PRT
<213> ORGANISM: Homo sapiens

<400> SEQUENCE: 56

Val Tyr Pro Ser Ser Gln Asp Ser Glu Asn Ile Thr Ala Ala
1               5                   10                  15

<210> SEQ ID NO 57
<211> LENGTH: 114
<212> TYPE: PRT
<213> ORGANISM: Artificial Sequence
<220> FEATURE:
<223> OTHER INFORMATION: IE8 VH Polypeptide

<400> SEQUENCE: 57

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
                20                  25                  30

Trp Met Ser Trp Val Arg Gln Ala Pro Gly Lys Gly Leu Glu Trp Ile
            35                  40                  45

Gly Glu Val Tyr Pro Asp Ser Ser Thr Ile Asn Tyr Thr Pro Ser Leu
        50                  55                  60

Lys Asp Lys Phe Ile Ile Ser Arg Asp Asn Ala Lys Asn Thr Leu Tyr
65                  70                  75                  80

Leu Gln Met Ile Lys Val Arg Ser Glu Asp Thr Ala Leu Tyr Tyr Cys
                85                  90                  95

Ala Arg Gly Arg Gly Asp Tyr Trp Gly Gln Gly Thr Ser Val Thr Val
            100                 105                 110

Ser Ser

<210> SEQ ID NO 58
<211> LENGTH: 108
<212> TYPE: PRT
<213> ORGANISM: Artificial Sequence
<220> FEATURE:
<223> OTHER INFORMATION: IE8 VL Polypeptide

<400> SEQUENCE: 58

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
                20                  25                  30

Leu Ser Trp Tyr His Gln Lys Gln Gly Lys Ser Pro Gln Leu Leu Val
            35                  40                  45

Tyr Asn Ala Lys Thr Leu Ala Asp Gly Val Pro Ser Arg Phe Ser Gly
        50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln Asn Phe Trp Ser Thr Pro Phe
                85                  90                  95
```

```
Thr Phe Gly Ser Gly Thr Lys Leu Glu Ile Lys Arg
            100                 105
```

<210> SEQ ID NO 59
<211> LENGTH: 9
<212> TYPE: PRT
<213> ORGANISM: Homo sapiens

<400> SEQUENCE: 59

```
Asn Leu Thr Leu Leu Asp Ser Gly Leu
1               5
```

<210> SEQ ID NO 60
<211> LENGTH: 11
<212> TYPE: PRT
<213> ORGANISM: Homo sapiens

<400> SEQUENCE: 60

```
Val Gln Thr Gly Lys Asp Ala Pro Ser Asn Cys
1               5                   10
```

<210> SEQ ID NO 61
<211> LENGTH: 10
<212> TYPE: PRT
<213> ORGANISM: Homo sapiens

<400> SEQUENCE: 61

```
Pro Val Asp Lys Gly His Asp Val Thr Phe
1               5                   10
```

<210> SEQ ID NO 62
<211> LENGTH: 12
<212> TYPE: PRT
<213> ORGANISM: Homo sapiens

<400> SEQUENCE: 62

```
Arg Arg Pro Ile Arg Asp Leu Thr Phe Gln Asp Leu
1               5                   10
```

<210> SEQ ID NO 63
<211> LENGTH: 326
<212> TYPE: PRT
<213> ORGANISM: Artificial Sequence
<220> FEATURE:
<223> OTHER INFORMATION: IgG2 C233S (A-locked)

<400> SEQUENCE: 63

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Ser Val Glu Cys Pro Pro Cys Pro Ala Pro
            100                 105                 110
```

```
Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 64
<211> LENGTH: 326
<212> TYPE: PRT
<213> ORGANISM: Artificial Sequence
<220> FEATURE:
<223> OTHER INFORMATION: IgG2 C127S (B-blocked)

<400> SEQUENCE: 64

Ala Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140
```

```
Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
            165                 170                 175

Ser Thr Phe Arg Val Val Ser Val Leu Thr Val Val His Gln Asp Trp
        180                 185                 190

Leu Asn Gly Lys Glu Tyr Lys Cys Lys Val Ser Asn Lys Gly Leu Pro
    195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
        260                 265                 270

Thr Pro Pro Met Leu Asp Ser Asp Gly Ser Phe Phe Leu Tyr Ser Lys
    275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 65
<211> LENGTH: 330
<212> TYPE: PRT
<213> ORGANISM: Artificial Sequence
<220> FEATURE:
<223> OTHER INFORMATION: IgG1 with silent Fc (INX901Si and INX908Si)

<400> SEQUENCE: 65

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
        100                 105                 110

Pro Ala Pro Glu Ala Ala Gly Ala Ser Ser Val Phe Leu Phe Pro Pro
    115                 120                 125

Lys Pro Lys Asp Thr Leu Met Ile Ser Arg Thr Pro Glu Val Thr Cys
130                 135                 140

Val Val Val Asp Val Ser Ala Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175
```

```
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ser Ser Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 66
<211> LENGTH: 327
<212> TYPE: PRT
<213> ORGANISM: Artificial Sequence
<220> FEATURE:
<223> OTHER INFORMATION: IgG2 CH1/hinge and IgG1 silent Fc (INX901HSi
      and INX908HSi)

<400> SEQUENCE: 66

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Glu Ala Ala Gly Ala Ser Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Ala Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205
```

```
Pro Ser Ser Ile Glu Lys Thr Ile Ser Lys Ala Lys Gly Gln Pro Arg
    210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 67
<211> LENGTH: 12
<212> TYPE: PRT
<213> ORGANISM: Homo sapiens

<400> SEQUENCE: 67

Asn Val Thr Leu Thr Cys Arg Leu Leu Gly Pro Val
1               5                   10

<210> SEQ ID NO 68
<211> LENGTH: 12
<212> TYPE: PRT
<213> ORGANISM: Homo sapiens

<400> SEQUENCE: 68

Glu Val Gln Thr Cys Ser Glu Arg Arg Pro Ile Arg
1               5                   10

<210> SEQ ID NO 69
<211> LENGTH: 8
<212> TYPE: PRT
<213> ORGANISM: Homo sapiens

<400> SEQUENCE: 69

Ser Asp His His Gly Asn Phe Ser
1               5

<210> SEQ ID NO 70
<211> LENGTH: 6
<212> TYPE: PRT
<213> ORGANISM: Homo sapiens

<400> SEQUENCE: 70

His His His Ser Glu His
1               5

<210> SEQ ID NO 71
<211> LENGTH: 12
<212> TYPE: PRT
<213> ORGANISM: Homo sapiens

<400> SEQUENCE: 71

Asn Val Thr Leu Thr Cys Arg Leu Leu Gly Pro Val
1               5                   10
```

```
<210> SEQ ID NO 72
<211> LENGTH: 11
<212> TYPE: PRT
<213> ORGANISM: Homo sapiens

<400> SEQUENCE: 72

Thr Cys Arg Leu Leu Gly Pro Val Asp Lys Gly
1               5                   10

<210> SEQ ID NO 73
<211> LENGTH: 7
<212> TYPE: PRT
<213> ORGANISM: Homo sapiens

<400> SEQUENCE: 73

His Gly Gly His Gln Ala Ala
1               5

<210> SEQ ID NO 74
<211> LENGTH: 10
<212> TYPE: PRT
<213> ORGANISM: Homo sapiens

<400> SEQUENCE: 74

Ser Ala Ser Asp His His Gly Asn Phe Ser
1               5                   10

<210> SEQ ID NO 75
<211> LENGTH: 12
<212> TYPE: PRT
<213> ORGANISM: Homo sapiens

<400> SEQUENCE: 75

His His His Ser Glu His Arg Val His Gly Ala Met
1               5                   10

<210> SEQ ID NO 76
<211> LENGTH: 12
<212> TYPE: PRT
<213> ORGANISM: Homo sapiens

<400> SEQUENCE: 76

His His His Ser Glu His Arg Val His Gly Ala Met
1               5                   10

<210> SEQ ID NO 77
<211> LENGTH: 9
<212> TYPE: PRT
<213> ORGANISM: Homo sapiens

<400> SEQUENCE: 77

Leu Thr Cys Arg Leu Leu Gly Pro Val
1               5

<210> SEQ ID NO 78
<211> LENGTH: 12
<212> TYPE: PRT
<213> ORGANISM: Homo sapiens

<400> SEQUENCE: 78

Glu Val Gln Thr Cys Ser Glu Arg Arg Pro Ile Arg
1               5                   10
```

```
<210> SEQ ID NO 79
<211> LENGTH: 10
<212> TYPE: PRT
<213> ORGANISM: Homo sapiens

<400> SEQUENCE: 79

His Leu His His Gly Gly His Gln Ala Ala
1               5                   10

<210> SEQ ID NO 80
<211> LENGTH: 8
<212> TYPE: PRT
<213> ORGANISM: Homo sapiens

<400> SEQUENCE: 80

Ser Asp His His Gly Asn Phe Ser
1               5

<210> SEQ ID NO 81
<211> LENGTH: 12
<212> TYPE: PRT
<213> ORGANISM: Homo sapiens

<400> SEQUENCE: 81

His His His Ser Glu His Arg Val His Gly Ala Met
1               5                   10

<210> SEQ ID NO 82
<211> LENGTH: 15
<212> TYPE: PRT
<213> ORGANISM: Homo sapiens

<400> SEQUENCE: 82

Leu Leu Gly Pro Val Asp Lys Gly His Asp Val Thr Phe Tyr Lys
1               5                   10                  15

<210> SEQ ID NO 83
<211> LENGTH: 15
<212> TYPE: PRT
<213> ORGANISM: Homo sapiens

<400> SEQUENCE: 83

Leu Ala Gln Arg His Gly Leu Glu Ser Ala Ser Asp His His Gly
1               5                   10                  15

<210> SEQ ID NO 84
<211> LENGTH: 12
<212> TYPE: PRT
<213> ORGANISM: Homo sapiens

<400> SEQUENCE: 84

His His His Ser Glu His Arg Val His Gly Ala Met
1               5                   10

<210> SEQ ID NO 85
<211> LENGTH: 9
<212> TYPE: PRT
<213> ORGANISM: Homo sapiens

<400> SEQUENCE: 85

Glu Val Gln Thr Cys Ser Glu Arg Arg
1               5

<210> SEQ ID NO 86
<211> LENGTH: 15
```

```
<212> TYPE: PRT
<213> ORGANISM: Homo sapiens

<400> SEQUENCE: 86

Thr Phe Gln Asp Leu His Leu His His Gly Gly His Gln Ala Ala
1               5                   10                  15

<210> SEQ ID NO 87
<211> LENGTH: 13
<212> TYPE: PRT
<213> ORGANISM: Homo sapiens

<400> SEQUENCE: 87

Cys Leu Val Val Glu Ile Arg His His His Ser Glu His
1               5                   10

<210> SEQ ID NO 88
<211> LENGTH: 10
<212> TYPE: PRT
<213> ORGANISM: Homo sapiens

<400> SEQUENCE: 88

Glu Val Gln Thr Cys Ser Glu Arg Arg Pro
1               5                   10

<210> SEQ ID NO 89
<211> LENGTH: 11
<212> TYPE: PRT
<213> ORGANISM: Homo sapiens

<400> SEQUENCE: 89

Thr Cys Arg Leu Leu Gly Pro Val Asp Lys Gly
1               5                   10

<210> SEQ ID NO 90
<211> LENGTH: 5
<212> TYPE: PRT
<213> ORGANISM: Homo sapiens

<400> SEQUENCE: 90

Ser Asp His His Gly
1               5

<210> SEQ ID NO 91
<211> LENGTH: 12
<212> TYPE: PRT
<213> ORGANISM: Homo sapiens

<400> SEQUENCE: 91

His His His Ser Glu His Arg Val His Gly Ala Met
1               5                   10

<210> SEQ ID NO 92

<400> SEQUENCE: 92

000

<210> SEQ ID NO 93

<400> SEQUENCE: 93

000

<210> SEQ ID NO 94
```

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100
<211> LENGTH: 8
<212> TYPE: PRT
<213> ORGANISM: Mus musculus

<400> SEQUENCE: 100

Gly Tyr Thr Leu Thr Asp Tyr Asn
1               5

<210> SEQ ID NO 101
<211> LENGTH: 8
<212> TYPE: PRT
<213> ORGANISM: Mus musculus

<400> SEQUENCE: 101

Ile Asn Leu Asn Tyr Ala Ile Thr
1               5

<210> SEQ ID NO 102
<211> LENGTH: 14
<212> TYPE: PRT
<213> ORGANISM: Mus musculus

<400> SEQUENCE: 102

Ala Arg Gly Gly Tyr Arg Tyr Thr Tyr Tyr Ala Met Asp Tyr
1               5                   10

<210> SEQ ID NO 103
<211> LENGTH: 6
<212> TYPE: PRT
<213> ORGANISM: Mus musculus -continued

```
<400> SEQUENCE: 103

Glu Asn Ile Tyr Ser Asn
1               5

<210> SEQ ID NO 104
<211> LENGTH: 3
<212> TYPE: PRT
<213> ORGANISM: Mus musculus

<400> SEQUENCE: 104

Ala Ala Thr
1

<210> SEQ ID NO 105
<211> LENGTH: 9
<212> TYPE: PRT
<213> ORGANISM: Mus musculus

<400> SEQUENCE: 105

Gln His Phe Trp Gly Thr Pro Arg Thr
1               5

<210> SEQ ID NO 106
<211> LENGTH: 121
<212> TYPE: PRT
<213> ORGANISM: Mus musculus

<400> SEQUENCE: 106

Glu Val Gln Leu Gln Gln Phe Gly Ala Glu Leu Val Lys Pro Gly Ala
1               5                   10                  15

Ser Val Lys Ile Ser Cys Lys Ala Ser Gly Tyr Thr Leu Thr Asp Tyr
                20                  25                  30

Asn Met Asp Trp Val Lys Gln Ser His Gly Lys Ser Leu Glu Trp Ile
            35                  40                  45

Gly His Ile Asn Leu Asn Tyr Ala Ile Thr Thr Tyr Asn Gln Lys Phe
        50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Gly Gly Tyr Arg Tyr Tyr Tyr Ala Met Asp Tyr Trp Gly
                100                 105                 110

Gln Gly Thr Ser Val Thr Val Ser Ser
            115                 120

<210> SEQ ID NO 107
<211> LENGTH: 222
<212> TYPE: PRT
<213> ORGANISM: Mus musculus

<400> SEQUENCE: 107

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
                20                  25                  30

Phe Pro Glu Pro Val Thr Val Thr Trp Asn Ser Gly Ser Leu Ser Ser
            35                  40                  45

Gly Val His Thr Phe Pro Ala Val Leu Gln Ser Asp Leu Tyr Thr Leu
        50                  55                  60
```

Ser Ser Ser Val Thr Val Pro Ser Ser Thr Trp Pro Ser Glu Thr Val
65                  70                  75                  80

Thr Cys Asn Val Ala His Pro Ala Ser Ser Thr Lys Val Asp Lys Lys
            85                  90                  95

Ile Val Pro Arg Asp Cys Gly Cys Lys Pro Cys Ile Cys Thr Val Pro
        100                 105                 110

Glu Val Ser Ser Val Phe Ile Phe Pro Pro Lys Pro Lys Asp Val Leu
    115                 120                 125

Thr Ile Thr Leu Thr Pro Lys Val Thr Cys Val Val Asp Ile Ser
130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
                180                 185                 190

Gly Lys Glu Phe Lys Cys Arg Val Asn Ser Ala Ala Phe Pro Ala Pro
            195                 200                 205

Ile Glu Lys Thr Ile Ser Lys Thr Lys Leu Asn Pro Lys Ser
210                 215                 220

<210> SEQ ID NO 108
<211> LENGTH: 107
<212> TYPE: PRT
<213> ORGANISM: Mus musculus

<400> SEQUENCE: 108

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Tyr Ser Asn
            20                  25                  30

Leu Ala Trp Tyr Gln Gln Lys Gln Gly Lys Ser Pro Gln Leu Leu Val
        35                  40                  45

Tyr Ala Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Arg
            85                  90                  95

Thr Phe Gly Gly Gly Thr Lys Leu Glu Ile Lys
            100                 105

<210> SEQ ID NO 109
<211> LENGTH: 107
<212> TYPE: PRT
<213> ORGANISM: Mus musculus

<400> SEQUENCE: 109

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

-continued

```
Thr Tyr Ser Met Ser Ser Thr Leu Thr Leu Thr Lys Asp Glu Tyr Glu
 65                  70                  75                  80

Arg His Asn Ser Tyr Thr Cys Glu Ala Thr His Lys Thr Ser Thr Ser
                 85                  90                  95

Pro Ile Val Lys Ser Phe Asn Arg Asn Glu Cys
            100                 105

<210> SEQ ID NO 110
<211> LENGTH: 8
<212> TYPE: PRT
<213> ORGANISM: Homo sapiens

<400> SEQUENCE: 110

Gly Tyr Thr Leu Thr Asp Tyr Asn
1               5

<210> SEQ ID NO 111
<211> LENGTH: 8
<212> TYPE: PRT
<213> ORGANISM: Homo sapiens

<400> SEQUENCE: 111

Ile Asn Leu Asn Tyr Ala Ile Thr
1               5

<210> SEQ ID NO 112
<211> LENGTH: 14
<212> TYPE: PRT
<213> ORGANISM: Homo sapiens

<400> SEQUENCE: 112

Ala Arg Gly Gly Tyr Arg Tyr Thr Tyr Tyr Ala Met Asp Tyr
1               5                   10

<210> SEQ ID NO 113
<211> LENGTH: 6
<212> TYPE: PRT
<213> ORGANISM: Homo sapiens

<400> SEQUENCE: 113

Glu Asn Ile Tyr Ser Asn
1               5

<210> SEQ ID NO 114
<211> LENGTH: 3
<212> TYPE: PRT
<213> ORGANISM: Homo sapiens

<400> SEQUENCE: 114

Ala Ala Thr
1

<210> SEQ ID NO 115
<211> LENGTH: 9
<212> TYPE: PRT
<213> ORGANISM: Homo sapiens

<400> SEQUENCE: 115

Gln His Phe Trp Gly Thr Pro Arg Thr
1               5

<210> SEQ ID NO 116
<211> LENGTH: 121
<212> TYPE: PRT
```

<213> ORGANISM: Homo sapiens

<400> SEQUENCE: 116

Glu Val Gln Leu Gln Gln Phe Gly Ala Glu Leu Val Lys Pro Gly Ala
1               5                   10                  15

Ser Val Lys Ile Ser Cys Lys Ala Ser Gly Tyr Thr Leu Thr Asp Tyr
            20                  25                  30

Asn Met Asp Trp Val Lys Gln Ser His Gly Lys Ser Leu Glu Trp Ile
        35                  40                  45

Gly His Ile Asn Leu Asn Tyr Ala Ile Thr Thr Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Gly Gly Tyr Arg Tyr Thr Tyr Tyr Ala Met Asp Tyr Trp Gly
            100                 105                 110

Gln Gly Thr Ser Val Thr Val Ser Ser
            115                 120

<210> SEQ ID NO 117
<211> LENGTH: 326
<212> TYPE: PRT
<213> ORGANISM: Homo sapiens

<400> SEQUENCE: 117

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn

```
                225                 230                 235                 240
        Gln Val Ser Leu Thr Cys Leu Val Lys Gly Phe Tyr Pro Ser Asp Ile
                            245                 250                 255

Ala Val Glu Trp Glu Ser Asn Gly Gln Pro Glu Asn Asn Tyr Lys Thr
                        260                 265                 270

Thr Pro Pro Met Leu Asp Ser Asp Gly Ser Phe Phe Leu Tyr Ser Lys
                        275                 280                 285

Leu Thr Val Asp Lys Ser Arg Trp Gln Gln Gly Asn Val Phe Ser Cys
                290                 295                 300

Ser Val Met His Glu Ala Leu His Asn His Tyr Thr Gln Lys Ser Leu
        305                 310                 315                 320

Ser Leu Ser Pro Gly Lys
                            325

<210> SEQ ID NO 118
<211> LENGTH: 107
<212> TYPE: PRT
<213> ORGANISM: Homo sapiens

<400> SEQUENCE: 118

Asp Ile Gln Met Thr Gln Ser Pro Ala Ser Leu Ser Val Ser Val Gly
        1               5                   10                  15

Glu Thr Val Thr Ile Thr Cys Arg Ala Ser Glu Asn Ile Tyr Ser Asn
                    20                  25                  30

Leu Ala Trp Tyr Gln Gln Lys Gln Gly Lys Ser Pro Gln Leu Leu Val
                35                  40                  45

Tyr Ala Ala Thr Asn Leu Ala Asp Gly Val Pro Ser Arg Phe Ser Gly
            50                  55                  60

Ser Gly Ser Gly Thr Gln Tyr Ser Leu Lys Ile Asn Ser Leu Gln Ser
        65                  70                  75                  80

Glu Asp Phe Gly Ser Tyr Tyr Cys Gln His Phe Trp Gly Thr Pro Arg
                        85                  90                  95

Thr Phe Gly Gly Gly Thr Lys Leu Glu Ile Lys
                    100                 105

<210> SEQ ID NO 119
<211> LENGTH: 107
<212> TYPE: PRT
<213> ORGANISM: Homo sapiens

<400> SEQUENCE: 119

Arg Thr Val Ala Ala Pro Ser Val Phe Ile Phe Pro Pro Ser Asp Glu
        1               5                   10                  15

Gln Leu Lys Ser Gly Thr Ala Ser Val Val Cys Leu Leu Asn Asn Phe
                    20                  25                  30

Tyr Pro Arg Glu Ala Lys Val Gln Trp Lys Val Asp Asn Ala Leu Gln
                35                  40                  45

Ser Gly Asn Ser Gln Glu Ser Val Thr Glu Gln Asp Ser Lys Asp Ser
            50                  55                  60

Thr Tyr Ser Leu Ser Ser Thr Leu Thr Leu Ser Lys Ala Asp Tyr Glu
        65                  70                  75                  80

Lys His Lys Val Tyr Ala Cys Glu Val Thr His Gln Gly Leu Ser Ser
                        85                  90                  95

Pro Val Thr Lys Ser Phe Asn Arg Gly Glu Cys
                    100                 105
```

-continued

```
<210> SEQ ID NO 120
<211> LENGTH: 8
<212> TYPE: PRT
<213> ORGANISM: Mus musculus

<400> SEQUENCE: 120

Gly Tyr Ser Phe Thr Gly Tyr Thr
1               5

<210> SEQ ID NO 121
<211> LENGTH: 8
<212> TYPE: PRT
<213> ORGANISM: Mus musculus

<400> SEQUENCE: 121

Ile Asn Pro Tyr Asn Gly Gly Ile
1               5

<210> SEQ ID NO 122
<211> LENGTH: 13
<212> TYPE: PRT
<213> ORGANISM: Mus musculus

<400> SEQUENCE: 122

Ala Arg Arg Thr Leu Leu Arg Pro Tyr Phe Phe Asp Tyr
1               5                   10

<210> SEQ ID NO 123
<211> LENGTH: 10
<212> TYPE: PRT
<213> ORGANISM: Mus musculus

<400> SEQUENCE: 123

Gln Ser Val Ser Thr Ser Thr Phe Ser Tyr
1               5                   10

<210> SEQ ID NO 124
<211> LENGTH: 3
<212> TYPE: PRT
<213> ORGANISM: Mus musculus

<400> SEQUENCE: 124

Tyr Ala Ser
1

<210> SEQ ID NO 125
<211> LENGTH: 9
<212> TYPE: PRT
<213> ORGANISM: Mus musculus

<400> SEQUENCE: 125

Gln His Ser Trp Glu Ile Pro Tyr Thr
1               5

<210> SEQ ID NO 126
<211> LENGTH: 120
<212> TYPE: PRT
<213> ORGANISM: Mus musculus

<400> SEQUENCE: 126

Glu Val Gln Leu Gln Gln Ser Gly Pro Glu Leu Val Lys Pro Gly Thr
1               5                   10                  15

Ser Met Lys Ile Ser Cys Lys Ala Ser Gly Tyr Ser Phe Thr Gly Tyr
            20                  25                  30
```

```
Thr Met Asn Trp Val Arg Gln Ser His Gly Lys Asn Leu Glu Trp Ile
        35                  40                  45

Gly Leu Ile Asn Pro Tyr Asn Gly Gly Ile Asn Tyr Asn Gln Lys Phe
    50                  55                  60

Lys Ala Arg Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Arg Thr Leu Leu Arg Pro Tyr Phe Phe Asp Tyr Trp Gly Gln
            100                 105                 110

Gly Thr Thr Leu Thr Val Ser Ser
        115                 120
```

<210> SEQ ID NO 127
<211> LENGTH: 120
<212> TYPE: PRT
<213> ORGANISM: Mus musculus

<400> SEQUENCE: 127

```
Glu Val Gln Leu Gln Gln Ser Gly Pro Glu Leu Val Lys Pro Gly Thr
1               5                   10                  15

Ser Met Lys Ile Ser Cys Lys Ala Ser Gly Tyr Ser Phe Thr Gly Tyr
            20                  25                  30

Thr Met Asn Trp Val Arg Gln Ser His Gly Lys Asn Leu Glu Trp Ile
        35                  40                  45

Gly Leu Ile Asn Pro Tyr Asn Gly Gly Ile Asn Tyr Asn Gln Lys Phe
    50                  55                  60

Lys Ala Arg Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Arg Thr Leu Leu Arg Pro Tyr Phe Phe Asp Tyr Trp Gly Gln
            100                 105                 110

Gly Thr Thr Leu Thr Val Ser Ser
        115                 120
```

<210> SEQ ID NO 128
<211> LENGTH: 111
<212> TYPE: PRT
<213> ORGANISM: Mus musculus

<400> SEQUENCE: 128

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Thr Phe Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Tyr Thr Phe Gly Gly Gly Thr Lys Leu Glu Ile Lys
            100                 105                 110
```

-continued

```
<210> SEQ ID NO 129
<211> LENGTH: 111
<212> TYPE: PRT
<213> ORGANISM: Mus musculus

<400> SEQUENCE: 129

Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Thr Phe Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Tyr Thr Phe Gly Gly Gly Thr Lys Leu Glu Ile Lys
            100                 105                 110

<210> SEQ ID NO 130
<211> LENGTH: 8
<212> TYPE: PRT
<213> ORGANISM: Homo sapiens

<400> SEQUENCE: 130

Gly Tyr Ser Phe Thr Gly Tyr Thr
1               5

<210> SEQ ID NO 131
<211> LENGTH: 8
<212> TYPE: PRT
<213> ORGANISM: Homo sapiens

<400> SEQUENCE: 131

Ile Asn Pro Tyr Asn Gly Gly Ile
1               5

<210> SEQ ID NO 132
<211> LENGTH: 13
<212> TYPE: PRT
<213> ORGANISM: Homo sapiens

<400> SEQUENCE: 132

Ala Arg Arg Thr Leu Leu Arg Pro Tyr Phe Phe Asp Tyr
1               5                   10

<210> SEQ ID NO 133
<211> LENGTH: 10
<212> TYPE: PRT
<213> ORGANISM: Homo sapiens

<400> SEQUENCE: 133

Gln Ser Val Ser Thr Ser Thr Phe Ser Tyr
1               5                   10

<210> SEQ ID NO 134
<211> LENGTH: 3
<212> TYPE: PRT
<213> ORGANISM: Homo sapiens
```

```
<400> SEQUENCE: 134

Tyr Ala Ser
1

<210> SEQ ID NO 135
<211> LENGTH: 9
<212> TYPE: PRT
<213> ORGANISM: Homo sapiens

<400> SEQUENCE: 135

Gln His Ser Trp Glu Ile Pro Tyr Thr
1               5

<210> SEQ ID NO 136
<211> LENGTH: 120
<212> TYPE: PRT
<213> ORGANISM: Homo sapiens

<400> SEQUENCE: 136

Glu Val Gln Leu Gln Gln Ser Gly Pro Glu Leu Val Lys Pro Gly Thr
1               5                   10                  15

Ser Met Lys Ile Ser Cys Lys Ala Ser Gly Tyr Ser Phe Thr Gly Tyr
            20                  25                  30

Thr Met Asn Trp Val Arg Gln Ser His Gly Lys Asn Leu Glu Trp Ile
        35                  40                  45

Gly Leu Ile Asn Pro Tyr Asn Gly Gly Ile Asn Tyr Asn Gln Lys Phe
    50                  55                  60

Lys Ala Arg Ala Thr Leu Thr Val Asp Lys Ser Ser Ser Thr Ala Tyr
65                  70                  75                  80

Met Glu Leu Leu Ser Leu Thr Ser Glu Asp Ser Ala Val Tyr Tyr Cys
                85                  90                  95

Ala Arg Arg Thr Leu Leu Arg Pro Tyr Phe Phe Asp Tyr Trp Gly Gln
            100                 105                 110

Gly Thr Thr Leu Thr Val Ser Ser
        115                 120

<210> SEQ ID NO 137
<211> LENGTH: 326
<212> TYPE: PRT
<213> ORGANISM: Homo sapiens

<400> SEQUENCE: 137

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125
```

```
Thr Leu Met Ile Ser Arg Thr Pro Glu Val Thr Cys Val Val Asp
    130                 135                 140
Val Ser His Glu Asp Pro Glu Val Gln Phe Asn Trp Tyr Val Asp Gly
145                 150                 155                 160
Val Glu Val His Asn Ala Lys Thr Lys Pro Arg Glu Glu Gln Phe Asn
                165                 170                 175
Ser Thr Phe Arg Val Val Ser Val Leu Thr Val Val His Gln Asp Trp
            180                 185                 190
Leu Asn Gly Lys Glu Tyr Lys Cys Lys Val Ser Asn Lys Gly Leu Pro
        195                 200                 205
Ala Pro Ile Glu Lys Thr Ile Ser Lys Thr Lys Gly Gln Pro Arg Glu
    210                 215                 220
Pro Gln Val Tyr Thr Leu Pro Pro Ser Arg Glu Glu Met Thr Lys Asn
225                 230                 235                 240
Gln Val Ser Leu Thr Cys Leu Val Lys Gly Phe Tyr Pro Ser Asp Ile
                245                 250                 255
Ala Val Glu Trp Glu Ser Asn Gly Gln Pro Glu Asn Asn Tyr Lys Thr
            260                 265                 270
Thr Pro Pro Met Leu Asp Ser Asp Gly Ser Phe Phe Leu Tyr Ser Lys
        275                 280                 285
Leu Thr Val Asp Lys Ser Arg Trp Gln Gln Gly Asn Val Phe Ser Cys
    290                 295                 300
Ser Val Met His Glu Ala Leu His Asn His Tyr Thr Gln Lys Ser Leu
305                 310                 315                 320
Ser Leu Ser Pro Gly Lys
                325

<210> SEQ ID NO 138
<211> LENGTH: 111
<212> TYPE: PRT
<213> ORGANISM: Homo sapiens

<400> SEQUENCE: 138

Asp Ile Val Leu Thr Gln Ser Pro Ala Ser Leu Ala Val Ser Leu Gly
1               5                   10                  15
Gln Arg Ala Thr Ile Ser Cys Arg Ala Ser Gln Ser Val Ser Thr Ser
            20                  25                  30
Thr Phe Ser Tyr Met His Trp Tyr Gln Gln Lys Pro Gly Gln Pro Pro
        35                  40                  45
Lys Leu Leu Ile Lys Tyr Ala Ser Asn Leu Glu Ser Gly Val Pro Ala
    50                  55                  60
Arg Phe Ser Gly Ser Gly Ser Gly Thr Asp Phe Thr Leu Asn Ile His
65                  70                  75                  80
Pro Val Glu Glu Glu Asp Thr Ala Thr Tyr Tyr Cys Gln His Ser Trp
                85                  90                  95
Glu Ile Pro Tyr Thr Phe Gly Gly Gly Thr Lys Leu Glu Ile Lys
            100                 105                 110

<210> SEQ ID NO 139
<211> LENGTH: 107
<212> TYPE: PRT
<213> ORGANISM: Homo sapiens

<400> SEQUENCE: 139

Arg Thr Val Ala Ala Pro Ser Val Phe Ile Phe Pro Pro Ser Asp Glu
1               5                   10                  15
```

-continued

```
Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 140
<211> LENGTH: 8
<212> TYPE: PRT
<213> ORGANISM: Mus musculus

<400> SEQUENCE: 140

Gly Phe Asp Phe Ser Arg Tyr Trp
1               5

<210> SEQ ID NO 141
<211> LENGTH: 8
<212> TYPE: PRT
<213> ORGANISM: Mus musculus

<400> SEQUENCE: 141

Val Tyr Pro Asp Ser Ser Thr Ile
1               5

<210> SEQ ID NO 142
<211> LENGTH: 7
<212> TYPE: PRT
<213> ORGANISM: Mus musculus

<400> SEQUENCE: 142

Ala Arg Gly Arg Gly Asp Tyr
1               5

<210> SEQ ID NO 143
<211> LENGTH: 6
<212> TYPE: PRT
<213> ORGANISM: Mus musculus

<400> SEQUENCE: 143

Gly Asn Ile His Asn Tyr
1               5

<210> SEQ ID NO 144
<211> LENGTH: 3
<212> TYPE: PRT
<213> ORGANISM: Mus musculus

<400> SEQUENCE: 144

Asn Ala Lys
1

<210> SEQ ID NO 145
<211> LENGTH: 9
<212> TYPE: PRT
<213> ORGANISM: Mus musculus
```

<400> SEQUENCE: 145

Gln Asn Phe Trp Ser Thr Pro Phe Thr
1               5

<210> SEQ ID NO 146
<211> LENGTH: 114
<212> TYPE: PRT
<213> ORGANISM: Mus musculus

<400> SEQUENCE: 146

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
                20                  25                  30

Trp Met Ser Trp Val Arg Gln Ala Pro Gly Lys Gly Leu Glu Trp Ile
            35                  40                  45

Gly Glu Val Tyr Pro Asp Ser Ser Thr Ile Asn Tyr Thr Pro Ser Leu
        50                  55                  60

Lys Asp Lys Phe Ile Ile Ser Arg Asp Asn Ala Lys Asn Thr Leu Tyr
65                  70                  75                  80

Leu Gln Met Ile Lys Val Arg Ser Glu Asp Thr Ala Leu Tyr Tyr Cys
                85                  90                  95

Ala Arg Gly Arg Gly Asp Tyr Trp Gly Gln Gly Thr Ser Val Thr Val
            100                 105                 110

Ser Ser

<210> SEQ ID NO 147
<211> LENGTH: 326
<212> TYPE: PRT
<213> ORGANISM: Mus musculus

<400> SEQUENCE: 147

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp

```
                180                 185                 190
Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 148
<211> LENGTH: 107
<212> TYPE: PRT
<213> ORGANISM: Mus musculus

<400> SEQUENCE: 148

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ser Trp Tyr His Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln Asn Phe Trp Ser Thr Pro Phe
                85                  90                  95

Thr Phe Gly Ser Gly Thr Lys Leu Glu Ile Lys
            100                 105

<210> SEQ ID NO 149
<211> LENGTH: 107
<212> TYPE: PRT
<213> ORGANISM: Mus musculus

<400> SEQUENCE: 149

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
```

```
                65                  70                  75                  80
Lys His Lys Val Tyr Ala Cys Glu Val Thr His Gln Gly Leu Ser Ser
                    85                  90                  95
Pro Val Thr Lys Ser Phe Asn Arg Gly Glu Cys
                100                 105
```

<210> SEQ ID NO 150
<211> LENGTH: 8
<212> TYPE: PRT
<213> ORGANISM: Homo sapiens

<400> SEQUENCE: 150

```
Gly Phe Asp Phe Ser Arg Tyr Trp
1               5
```

<210> SEQ ID NO 151
<211> LENGTH: 8
<212> TYPE: PRT
<213> ORGANISM: Homo sapiens

<400> SEQUENCE: 151

```
Val Tyr Pro Asp Ser Ser Thr Ile
1               5
```

<210> SEQ ID NO 152
<211> LENGTH: 7
<212> TYPE: PRT
<213> ORGANISM: Homo sapiens

<400> SEQUENCE: 152

```
Ala Arg Gly Arg Gly Asp Tyr
1               5
```

<210> SEQ ID NO 153
<211> LENGTH: 6
<212> TYPE: PRT
<213> ORGANISM: Homo sapiens

<400> SEQUENCE: 153

```
Gly Asn Ile His Asn Tyr
1               5
```

<210> SEQ ID NO 154
<211> LENGTH: 3
<212> TYPE: PRT
<213> ORGANISM: Homo sapiens

<400> SEQUENCE: 154

```
Asn Ala Lys
1
```

<210> SEQ ID NO 155
<211> LENGTH: 9
<212> TYPE: PRT
<213> ORGANISM: Homo sapiens

<400> SEQUENCE: 155

```
Gln Asn Phe Trp Ser Thr Pro Phe Thr
1               5
```

<210> SEQ ID NO 156
<211> LENGTH: 114
<212> TYPE: PRT
<213> ORGANISM: Homo sapiens

<400> SEQUENCE: 156

| Glu | Val | Lys | Leu | Leu | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Lys | Leu | Ser | Cys | Ala | Ala | Ser | Gly | Phe | Asp | Phe | Ser | Arg | Tyr |
|---|---|---|---|---|---|---|---|---|---|---|---|---|---|---|---|
| | | | 20 | | | | | 25 | | | | | 30 | | |

| Trp | Met | Ser | Trp | Val | Arg | Gln | Ala | Pro | Gly | Lys | Gly | Leu | Glu | Trp | Ile |
|---|---|---|---|---|---|---|---|---|---|---|---|---|---|---|---|
| | | 35 | | | | | 40 | | | | | 45 | | | |

| Gly | Glu | Val | Tyr | Pro | Asp | Ser | Ser | Thr | Ile | Asn | Tyr | Thr | Pro | Ser | Leu |
|---|---|---|---|---|---|---|---|---|---|---|---|---|---|---|---|
| 50 | | | | | 55 | | | | | 60 | | | | | |

| Lys | Asp | Lys | Phe | Ile | Ile | Ser | Arg | Asp | Asn | Ala | Lys | Asn | Thr | Leu | Tyr |
|---|---|---|---|---|---|---|---|---|---|---|---|---|---|---|---|
| 65 | | | | 70 | | | | | 75 | | | | | 80 | |

| Leu | Gln | Met | Ile | Lys | Val | Arg | Ser | Glu | Asp | Thr | Ala | Leu | Tyr | Tyr | Cys |
|---|---|---|---|---|---|---|---|---|---|---|---|---|---|---|---|
| | | | | 85 | | | | | 90 | | | | | 95 | |

| Ala | Arg | Gly | Arg | Gly | Asp | Tyr | Trp | Gly | Gln | Gly | Thr | Ser | Val | Thr | Val |
|---|---|---|---|---|---|---|---|---|---|---|---|---|---|---|---|
| | | | 100 | | | | | 105 | | | | | 110 | | |

Ser Ser

<210> SEQ ID NO 157
<211> LENGTH: 326
<212> TYPE: PRT
<213> ORGANISM: Homo sapiens

<400> SEQUENCE: 157

| Ala | Ser | Thr | Lys | Gly | Pro | Ser | Val | Phe | Pro | Leu | Ala | Pro | Cys | Ser | Arg |
|---|---|---|---|---|---|---|---|---|---|---|---|---|---|---|---|
| 1 | | | | 5 | | | | | 10 | | | | | 15 | |

| Ser | Thr | Ser | Glu | Ser | Thr | Ala | Ala | Leu | Gly | Cys | Leu | Val | Lys | Asp | Tyr |
|---|---|---|---|---|---|---|---|---|---|---|---|---|---|---|---|
| | | | 20 | | | | | 25 | | | | | 30 | | |

| Phe | Pro | Glu | Pro | Val | Thr | Val | Ser | Trp | Asn | Ser | Gly | Ala | Leu | Thr | Ser |
|---|---|---|---|---|---|---|---|---|---|---|---|---|---|---|---|
| | | 35 | | | | | 40 | | | | | 45 | | | |

| Gly | Val | His | Thr | Phe | Pro | Ala | Val | Leu | Gln | Ser | Ser | Gly | Leu | Tyr | Ser |
|---|---|---|---|---|---|---|---|---|---|---|---|---|---|---|---|
| 50 | | | | | 55 | | | | | 60 | | | | | |

| Leu | Ser | Ser | Val | Val | Thr | Val | Pro | Ser | Ser | Asn | Phe | Gly | Thr | Gln | Thr |
|---|---|---|---|---|---|---|---|---|---|---|---|---|---|---|---|
| 65 | | | | 70 | | | | | 75 | | | | | 80 | |

| Tyr | Thr | Cys | Asn | Val | Asp | His | Lys | Pro | Ser | Asn | Thr | Lys | Val | Asp | Lys |
|---|---|---|---|---|---|---|---|---|---|---|---|---|---|---|---|
| | | | | 85 | | | | | 90 | | | | | 95 | |

| Thr | Val | Glu | Arg | Lys | Cys | Cys | Val | Glu | Cys | Pro | Pro | Cys | Pro | Ala | Pro |
|---|---|---|---|---|---|---|---|---|---|---|---|---|---|---|---|
| | | | 100 | | | | | 105 | | | | | 110 | | |

| Pro | Val | Ala | Gly | Pro | Ser | Val | Phe | Leu | Phe | Pro | Pro | Lys | Pro | Lys | Asp |
|---|---|---|---|---|---|---|---|---|---|---|---|---|---|---|---|
| | | 115 | | | | | 120 | | | | | 125 | | | |

| Thr | Leu | Met | Ile | Ser | Arg | Thr | Pro | Glu | Val | Thr | Cys | Val | Val | Val | Asp |
|---|---|---|---|---|---|---|---|---|---|---|---|---|---|---|---|
| 130 | | | | | 135 | | | | | 140 | | | | | |

| Val | Ser | His | Glu | Asp | Pro | Glu | Val | Gln | Phe | Asn | Trp | Tyr | Val | Asp | Gly |
|---|---|---|---|---|---|---|---|---|---|---|---|---|---|---|---|
| 145 | | | | 150 | | | | | 155 | | | | | 160 | |

| Val | Glu | Val | His | Asn | Ala | Lys | Thr | Lys | Pro | Arg | Glu | Glu | Gln | Phe | Asn |
|---|---|---|---|---|---|---|---|---|---|---|---|---|---|---|---|
| | | | | 165 | | | | | 170 | | | | | 175 | |

| Ser | Thr | Phe | Arg | Val | Val | Ser | Val | Leu | Thr | Val | Val | His | Gln | Asp | Trp |
|---|---|---|---|---|---|---|---|---|---|---|---|---|---|---|---|
| | | | 180 | | | | | 185 | | | | | 190 | | |

| Leu | Asn | Gly | Lys | Glu | Tyr | Lys | Cys | Lys | Val | Ser | Asn | Lys | Gly | Leu | Pro |
|---|---|---|---|---|---|---|---|---|---|---|---|---|---|---|---|
| | | 195 | | | | | 200 | | | | | 205 | | | |

| Ala | Pro | Ile | Glu | Lys | Thr | Ile | Ser | Lys | Thr | Lys | Gly | Gln | Pro | Arg | Glu |
|---|---|---|---|---|---|---|---|---|---|---|---|---|---|---|---|
| 210 | | | | | 215 | | | | | 220 | | | | | |

| Pro | Gln | Val | Tyr | Thr | Leu | Pro | Pro | Ser | Arg | Glu | Glu | Met | Thr | Lys | Asn |
|---|---|---|---|---|---|---|---|---|---|---|---|---|---|---|---|
| 225 | | | | 230 | | | | | 235 | | | | | 240 | |

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 158
<211> LENGTH: 107
<212> TYPE: PRT
<213> ORGANISM: Homo sapiens

<400> SEQUENCE: 158

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ser Trp Tyr His Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln Asn Phe Trp Ser Thr Pro Phe
                85                  90                  95

Thr Phe Gly Ser Gly Thr Lys Leu Glu Ile Lys
            100                 105

<210> SEQ ID NO 159
<211> LENGTH: 107
<212> TYPE: PRT
<213> ORGANISM: Homo sapiens

<400> SEQUENCE: 159

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 160
<211> LENGTH: 8

```
<212> TYPE: PRT
<213> ORGANISM: Homo sapiens

<400> SEQUENCE: 160

Gly Phe Asp Phe Ser Arg Tyr Trp
1               5

<210> SEQ ID NO 161
<211> LENGTH: 8
<212> TYPE: PRT
<213> ORGANISM: Homo sapiens

<400> SEQUENCE: 161

Val Tyr Pro Asp Ser Ser Thr Ile
1               5

<210> SEQ ID NO 162
<211> LENGTH: 7
<212> TYPE: PRT
<213> ORGANISM: Homo sapiens

<400> SEQUENCE: 162

Ala Arg Gly Arg Gly Asp Tyr
1               5

<210> SEQ ID NO 163
<211> LENGTH: 6
<212> TYPE: PRT
<213> ORGANISM: Homo sapiens

<400> SEQUENCE: 163

Gly Asn Ile His Asn Tyr
1               5

<210> SEQ ID NO 164
<211> LENGTH: 3
<212> TYPE: PRT
<213> ORGANISM: Homo sapiens

<400> SEQUENCE: 164

Asn Ala Lys
1

<210> SEQ ID NO 165
<211> LENGTH: 9
<212> TYPE: PRT
<213> ORGANISM: Homo sapiens

<400> SEQUENCE: 165

Gln Asn Phe Trp Ser Thr Pro Phe Thr
1               5

<210> SEQ ID NO 166
<211> LENGTH: 114
<212> TYPE: PRT
<213> ORGANISM: Homo sapiens

<400> SEQUENCE: 166

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45
```

```
Gly Glu Val Tyr Pro Asp Ser Ser Thr Ile Asn Tyr Thr Pro Ser Leu
             50                  55                  60

Lys Asp Lys Phe Ile Ile Ser Arg Asp Asn Ala Lys Asn Thr Leu Tyr
 65                  70                  75                  80

Leu Gln Met Ile Lys Val Arg Ser Glu Asp Thr Ala Leu Tyr Tyr Cys
                 85                  90                  95

Ala Arg Gly Arg Gly Asp Tyr Trp Gly Gln Gly Thr Ser Val Thr Val
                100                 105                 110

Ser Ser

<210> SEQ ID NO 167
<211> LENGTH: 326
<212> TYPE: PRT
<213> ORGANISM: Homo sapiens

<400> SEQUENCE: 167

Ala Ser Thr Lys Gly Pro Ser Val Phe Pro Leu Ala Pro Ser Ser Arg
 1               5                  10                  15

Ser Thr Ser Glu Ser Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300
```

Ser Val Met His Glu Ala Leu His Asn His Tyr Thr Gln Lys Ser Leu
305                 310                 315                 320

Ser Leu Ser Pro Gly Lys
                325

<210> SEQ ID NO 168
<211> LENGTH: 107
<212> TYPE: PRT
<213> ORGANISM: Homo sapiens

<400> SEQUENCE: 168

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ser Trp Tyr His Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln Asn Phe Trp Ser Thr Pro Phe
                85                  90                  95

Thr Phe Gly Ser Gly Thr Lys Leu Glu Ile Lys
            100                 105

<210> SEQ ID NO 169
<211> LENGTH: 107
<212> TYPE: PRT
<213> ORGANISM: Homo sapiens

<400> SEQUENCE: 169

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 170
<211> LENGTH: 8
<212> TYPE: PRT
<213> ORGANISM: Homo sapiens

<400> SEQUENCE: 170

Gly Tyr Ser Phe Thr Ser Tyr Trp
1               5

<210> SEQ ID NO 171
<211> LENGTH: 8

```
<212> TYPE: PRT
<213> ORGANISM: Homo sapiens

<400> SEQUENCE: 171

Ile Tyr Pro Gly Asp Ser Asp Thr
1               5

<210> SEQ ID NO 172
<211> LENGTH: 16
<212> TYPE: PRT
<213> ORGANISM: Homo sapiens

<400> SEQUENCE: 172

Ala Arg Asp Val Ser Ser Phe Tyr Gly Tyr Ser Pro Met Phe Asp Tyr
1               5                   10                  15

<210> SEQ ID NO 173
<211> LENGTH: 6
<212> TYPE: PRT
<213> ORGANISM: Homo sapiens

<400> SEQUENCE: 173

Gln Ser Val Ser Ser Tyr
1               5

<210> SEQ ID NO 174
<211> LENGTH: 3
<212> TYPE: PRT
<213> ORGANISM: Homo sapiens

<400> SEQUENCE: 174

Asp Ala Ser
1

<210> SEQ ID NO 175
<211> LENGTH: 9
<212> TYPE: PRT
<213> ORGANISM: Homo sapiens

<400> SEQUENCE: 175

Gln Gln Arg Ser Asn Trp Pro Leu Thr
1               5

<210> SEQ ID NO 176
<211> LENGTH: 123
<212> TYPE: PRT
<213> ORGANISM: Homo sapiens

<400> SEQUENCE: 176

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Val Ser Ser Phe Tyr Gly Tyr Ser Pro Met Phe Asp Tyr
```

100                 105                 110
Trp Gly Gln Gly Thr Leu Val Thr Val Ser Ser
            115                 120

<210> SEQ ID NO 177
<211> LENGTH: 330
<212> TYPE: PRT
<213> ORGANISM: Homo sapiens

<400> SEQUENCE: 177

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 178
<211> LENGTH: 107

<212> TYPE: PRT
<213> ORGANISM: Homo sapiens

<400> SEQUENCE: 178

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gln Gly Thr Lys Val Glu Ile Lys
            100                 105

<210> SEQ ID NO 179
<211> LENGTH: 107
<212> TYPE: PRT
<213> ORGANISM: Homo sapiens

<400> SEQUENCE: 179

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 180
<211> LENGTH: 8
<212> TYPE: PRT
<213> ORGANISM: Homo sapiens

<400> SEQUENCE: 180

Gly Tyr Ser Phe Thr Ser Tyr Trp
1               5

<210> SEQ ID NO 181
<211> LENGTH: 8
<212> TYPE: PRT
<213> ORGANISM: Homo sapiens

<400> SEQUENCE: 181

Ile Tyr Pro Gly Asp Ser Asp Thr
1               5

<210> SEQ ID NO 182

```
<211> LENGTH: 16
<212> TYPE: PRT
<213> ORGANISM: Homo sapiens

<400> SEQUENCE: 182

Ala Arg Asp Ala His Ser Phe Tyr Gly Tyr Ser Ala Leu Leu Asp Tyr
1               5                   10                  15

<210> SEQ ID NO 183
<211> LENGTH: 7
<212> TYPE: PRT
<213> ORGANISM: Homo sapiens

<400> SEQUENCE: 183

Gln Ser Val Ser Ser Ser Tyr
1               5

<210> SEQ ID NO 184
<211> LENGTH: 3
<212> TYPE: PRT
<213> ORGANISM: Homo sapiens

<400> SEQUENCE: 184

Gly Ala Ser
1

<210> SEQ ID NO 185
<211> LENGTH: 9
<212> TYPE: PRT
<213> ORGANISM: Homo sapiens

<400> SEQUENCE: 185

Gln Gln Tyr Gly Ser Ser Pro Leu Thr
1               5

<210> SEQ ID NO 186
<211> LENGTH: 123
<212> TYPE: PRT
<213> ORGANISM: Homo sapiens

<400> SEQUENCE: 186

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Ala His Ser Phe Tyr Gly Tyr Ser Ala Leu Leu Asp Tyr
                100                 105                 110

Trp Gly Gln Gly Thr Leu Val Thr Val Ser Ser
            115                 120

<210> SEQ ID NO 187
<211> LENGTH: 330
<212> TYPE: PRT
<213> ORGANISM: Homo sapiens
```

<400> SEQUENCE: 187

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 188
<211> LENGTH: 108
<212> TYPE: PRT
<213> ORGANISM: Homo sapiens

<400> SEQUENCE: 188

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
                35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys
            100                 105

<210> SEQ ID NO 189
<211> LENGTH: 107
<212> TYPE: PRT
<213> ORGANISM: Homo sapiens

<400> SEQUENCE: 189

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 190
<211> LENGTH: 8
<212> TYPE: PRT
<213> ORGANISM: Homo sapiens

<400> SEQUENCE: 190

Gly Tyr Ser Phe Thr Ser Tyr Trp
1               5

<210> SEQ ID NO 191
<211> LENGTH: 8
<212> TYPE: PRT
<213> ORGANISM: Homo sapiens

<400> SEQUENCE: 191

Ile Tyr Pro Gly Asp Ser Asp Thr
1               5

<210> SEQ ID NO 192
<211> LENGTH: 16
<212> TYPE: PRT
<213> ORGANISM: Homo sapiens

<400> SEQUENCE: 192

Ala Arg Asp Ser Tyr Ser Phe Tyr Gly His Thr Pro Val Leu Asp Tyr
1               5                   10                  15

```
<210> SEQ ID NO 193
<211> LENGTH: 7
<212> TYPE: PRT
<213> ORGANISM: Homo sapiens

<400> SEQUENCE: 193

Gln Ser Val Ser Ser Ser Tyr
1               5

<210> SEQ ID NO 194
<211> LENGTH: 3
<212> TYPE: PRT
<213> ORGANISM: Homo sapiens

<400> SEQUENCE: 194

Gly Ala Ser
1

<210> SEQ ID NO 195
<211> LENGTH: 9
<212> TYPE: PRT
<213> ORGANISM: Homo sapiens

<400> SEQUENCE: 195

Gln Gln Tyr Gly Ser Ser Pro Leu Thr
1               5

<210> SEQ ID NO 196
<211> LENGTH: 123
<212> TYPE: PRT
<213> ORGANISM: Homo sapiens

<400> SEQUENCE: 196

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Ser Tyr Ser Phe Tyr Gly His Thr Pro Val Leu Asp Tyr
            100                 105                 110

Trp Gly Gln Gly Thr Leu Val Thr Val Ser Ser
        115                 120

<210> SEQ ID NO 197
<211> LENGTH: 330
<212> TYPE: PRT
<213> ORGANISM: Homo sapiens

<400> SEQUENCE: 197

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
```

```
        35                  40                  45
Gly Val His Thr Phe Pro Ala Val Leu Gln Ser Ser Gly Leu Tyr Ser
 50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                 85                  90                  95
Lys Val Glu Pro Lys Ser Cys Asp Lys Thr His Thr Cys Pro Pro Cys
                100                 105                 110
Pro Ala Pro Glu Leu Leu Gly Gly Pro Ser Val Phe Leu Phe Pro Pro
                115                 120                 125
Lys Pro Lys Asp Thr Leu Met Ile Ser Arg Thr Pro Glu Val Thr Cys
            130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
                180                 185                 190
His Gln Asp Trp Leu Asn Gly Lys Glu Tyr Lys Cys Lys Val Ser Asn
            195                 200                 205
Lys Ala Leu Pro Ala Pro Ile Glu Lys Thr Ile Ser Lys Ala Lys Gly
210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 198
<211> LENGTH: 108
<212> TYPE: PRT
<213> ORGANISM: Homo sapiens

<400> SEQUENCE: 198

Glu Ile Val Leu Thr Gln Ser Pro Gly Thr Leu Ser Leu Ser Pro Gly
1               5                   10                  15
Glu Arg Ala Thr Leu Ser Cys Arg Ala Ser Gln Ser Val Ser Ser Ser
            20                  25                  30
Tyr Leu Ala Trp Tyr Gln Gln Lys Pro Gly Gln Ala Pro Arg Leu Leu
        35                  40                  45
Ile Tyr Gly Ala Ser Ser Arg Ala Thr Gly Ile Pro Asp Arg Phe Ser
    50                  55                  60
Gly Ser Gly Ser Gly Thr Asp Phe Thr Leu Thr Ile Ser Arg Leu Glu
65                  70                  75                  80
```

```
Pro Glu Asp Phe Ala Val Tyr Tyr Cys Gln Gln Tyr Gly Ser Ser Pro
            85                  90                  95

Leu Thr Phe Gly Gln Gly Thr Lys Val Glu Ile Lys
        100                 105
```

<210> SEQ ID NO 199
<211> LENGTH: 107
<212> TYPE: PRT
<213> ORGANISM: Homo sapiens

<400> SEQUENCE: 199

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 200
<211> LENGTH: 8
<212> TYPE: PRT
<213> ORGANISM: Homo sapiens

<400> SEQUENCE: 200

```
Gly Tyr Ser Phe Thr Ser Tyr Trp
1               5
```

<210> SEQ ID NO 201
<211> LENGTH: 8
<212> TYPE: PRT
<213> ORGANISM: Homo sapiens

<400> SEQUENCE: 201

```
Ile Tyr Pro Gly Asp Ser Asp Thr
1               5
```

<210> SEQ ID NO 202
<211> LENGTH: 14
<212> TYPE: PRT
<213> ORGANISM: Homo sapiens

<400> SEQUENCE: 202

```
Ala Arg Asp Asp Ala Leu Tyr Gly Gly Tyr Tyr Leu Asp Tyr
1               5                   10
```

<210> SEQ ID NO 203
<211> LENGTH: 12
<212> TYPE: PRT
<213> ORGANISM: Homo sapiens

<400> SEQUENCE: 203

```
Gln Ser Val Leu Tyr Ser Ser Asn Asn Lys Asn Tyr
1               5                   10
```

<210> SEQ ID NO 204
<211> LENGTH: 3
<212> TYPE: PRT
<213> ORGANISM: Homo sapiens

<400> SEQUENCE: 204

Trp Ala Ser
1

<210> SEQ ID NO 205
<211> LENGTH: 9
<212> TYPE: PRT
<213> ORGANISM: Homo sapiens

<400> SEQUENCE: 205

Gln Gln Tyr Tyr Ser Thr Pro Leu Thr
1               5

<210> SEQ ID NO 206
<211> LENGTH: 121
<212> TYPE: PRT
<213> ORGANISM: Homo sapiens

<400> SEQUENCE: 206

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Asp Ala Leu Tyr Gly Gly Tyr Tyr Leu Asp Tyr Trp Gly
                100                 105                 110

Gln Gly Thr Leu Val Thr Val Ser Ser
            115                 120

<210> SEQ ID NO 207
<211> LENGTH: 330
<212> TYPE: PRT
<213> ORGANISM: Homo sapiens

<400> SEQUENCE: 207

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

```
Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 208
<211> LENGTH: 113
<212> TYPE: PRT
<213> ORGANISM: Homo sapiens

<400> SEQUENCE: 208

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gln Gly Thr Lys Val Glu Ile
            100                 105                 110

Lys

<210> SEQ ID NO 209
```

```
<211> LENGTH: 107
<212> TYPE: PRT
<213> ORGANISM: Homo sapiens

<400> SEQUENCE: 209

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65              70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 210
<211> LENGTH: 8
<212> TYPE: PRT
<213> ORGANISM: Homo sapiens

<400> SEQUENCE: 210

Gly Tyr Ser Phe Thr Ser Tyr Trp
1               5

<210> SEQ ID NO 211
<211> LENGTH: 8
<212> TYPE: PRT
<213> ORGANISM: Homo sapiens

<400> SEQUENCE: 211

Ile Tyr Pro Gly Asp Ser Asp Thr
1               5

<210> SEQ ID NO 212
<211> LENGTH: 16
<212> TYPE: PRT
<213> ORGANISM: Homo sapiens

<400> SEQUENCE: 212

Ala Arg Asp Ala Asn Ser Phe Tyr Ser Ala Ser Ile Phe Asp Tyr
1               5                   10                  15

<210> SEQ ID NO 213
<211> LENGTH: 12
<212> TYPE: PRT
<213> ORGANISM: Homo sapiens

<400> SEQUENCE: 213

Gln Ser Val Leu Tyr Ser Ser Asn Asn Lys Asn Tyr
1               5                   10

<210> SEQ ID NO 214
<211> LENGTH: 3
<212> TYPE: PRT
<213> ORGANISM: Homo sapiens

<400> SEQUENCE: 214
```

Trp Ala Ser
1

<210> SEQ ID NO 215
<211> LENGTH: 9
<212> TYPE: PRT
<213> ORGANISM: Homo sapiens

<400> SEQUENCE: 215

Gln Gln Tyr Tyr Ser Thr Pro Leu Thr
1               5

<210> SEQ ID NO 216
<211> LENGTH: 123
<212> TYPE: PRT
<213> ORGANISM: Homo sapiens

<400> SEQUENCE: 216

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
                20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Ala Asn Ser Phe Tyr Ser Ala Ala Ser Ile Phe Asp Tyr
            100                 105                 110

Trp Gly Gln Gly Thr Leu Val Thr Val Ser Ser
        115                 120

<210> SEQ ID NO 217
<211> LENGTH: 330
<212> TYPE: PRT
<213> ORGANISM: Homo sapiens

<400> SEQUENCE: 217

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
    115                 120                 125

Lys Pro Lys Asp Thr Leu Met Ile Ser Arg Thr Pro Glu Val Thr Cys

```
                    130                 135                 140
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 218
<211> LENGTH: 113
<212> TYPE: PRT
<213> ORGANISM: Homo sapiens

<400> SEQUENCE: 218

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gln Gly Thr Lys Val Glu Ile
            100                 105                 110

Lys

<210> SEQ ID NO 219
<211> LENGTH: 107
<212> TYPE: PRT
<213> ORGANISM: Homo sapiens

<400> SEQUENCE: 219

Arg Thr Val Ala Ala Pro Ser Val Phe Ile Phe Pro Pro Ser Asp Glu
1               5                   10                  15
```

```
Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 220
<211> LENGTH: 8
<212> TYPE: PRT
<213> ORGANISM: Homo sapiens

<400> SEQUENCE: 220

```
Gly Gly Thr Phe Ser Ser Tyr Ala
1               5
```

<210> SEQ ID NO 221
<211> LENGTH: 8
<212> TYPE: PRT
<213> ORGANISM: Homo sapiens

<400> SEQUENCE: 221

```
Ile Ile Pro Ile Phe Gly Thr Ala
1               5
```

<210> SEQ ID NO 222
<211> LENGTH: 13
<212> TYPE: PRT
<213> ORGANISM: Homo sapiens

<400> SEQUENCE: 222

```
Ala Arg Ser Ser Tyr Gly Trp Ser Tyr Glu Phe Asp Tyr
1               5                   10
```

<210> SEQ ID NO 223
<211> LENGTH: 6
<212> TYPE: PRT
<213> ORGANISM: Homo sapiens

<400> SEQUENCE: 223

```
Gln Ser Ile Ala Thr Asn
1               5
```

<210> SEQ ID NO 224
<211> LENGTH: 3
<212> TYPE: PRT
<213> ORGANISM: Homo sapiens

<400> SEQUENCE: 224

```
Ala Ala Ser
1
```

<210> SEQ ID NO 225
<211> LENGTH: 9
<212> TYPE: PRT
<213> ORGANISM: Homo sapiens

<400> SEQUENCE: 225

Gln Gln Asn Asp Asp Arg Pro Ile Thr
1               5

<210> SEQ ID NO 226
<211> LENGTH: 120
<212> TYPE: PRT
<213> ORGANISM: Homo sapiens

<400> SEQUENCE: 226

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Tyr Gly Trp Ser Tyr Glu Phe Asp Tyr Trp Gly Gln
            100                 105                 110

Gly Thr Leu Val Thr Val Ser Ser
        115                 120

<210> SEQ ID NO 227
<211> LENGTH: 330
<212> TYPE: PRT
<213> ORGANISM: Homo sapiens

<400> SEQUENCE: 227

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

```
Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 228
<211> LENGTH: 107
<212> TYPE: PRT
<213> ORGANISM: Homo sapiens

<400> SEQUENCE: 228

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ala Thr Asn
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Asp Asp Arg Pro Ile
                85                  90                  95

Thr Phe Gly Gln Gly Thr Lys Val Glu Ile Lys
            100                 105

<210> SEQ ID NO 229
<211> LENGTH: 107
<212> TYPE: PRT
<213> ORGANISM: Homo sapiens

<400> SEQUENCE: 229

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60
```

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 230
<211> LENGTH: 8
<212> TYPE: PRT
<213> ORGANISM: Homo sapiens

<400> SEQUENCE: 230

Gly Gly Thr Phe Ser Ser Tyr Ala
1               5

<210> SEQ ID NO 231
<211> LENGTH: 8
<212> TYPE: PRT
<213> ORGANISM: Homo sapiens

<400> SEQUENCE: 231

Ile Ile Pro Ile Phe Gly Thr Ala
1               5

<210> SEQ ID NO 232
<211> LENGTH: 13
<212> TYPE: PRT
<213> ORGANISM: Homo sapiens

<400> SEQUENCE: 232

Ala Arg Ser Ser Tyr Gly Trp Ser Tyr Glu Phe Asp Tyr
1               5                   10

<210> SEQ ID NO 233
<211> LENGTH: 6
<212> TYPE: PRT
<213> ORGANISM: Homo sapiens

<400> SEQUENCE: 233

Gln Ser Ile Arg Thr Asp
1               5

<210> SEQ ID NO 234
<211> LENGTH: 3
<212> TYPE: PRT
<213> ORGANISM: Homo sapiens

<400> SEQUENCE: 234

Ser Ala Ser
1

<210> SEQ ID NO 235
<211> LENGTH: 9
<212> TYPE: PRT
<213> ORGANISM: Homo sapiens

<400> SEQUENCE: 235

Gln Gln Asn Glu Arg Thr Pro Ile Thr
1               5

<210> SEQ ID NO 236
<211> LENGTH: 120
<212> TYPE: PRT

<213> ORGANISM: Homo sapiens

<400> SEQUENCE: 236

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Tyr Gly Trp Ser Tyr Glu Phe Asp Tyr Trp Gly Gln
            100                 105                 110

Gly Thr Leu Val Thr Val Ser Ser
            115                 120

<210> SEQ ID NO 237
<211> LENGTH: 330
<212> TYPE: PRT
<213> ORGANISM: Homo sapiens

<400> SEQUENCE: 237

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu

```
                225                 230                 235                 240
Leu Thr Lys Asn Gln Val Ser Leu Thr Cys Leu Val Lys Gly Phe Tyr
                    245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 238
<211> LENGTH: 107
<212> TYPE: PRT
<213> ORGANISM: Homo sapiens

<400> SEQUENCE: 238

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Thr Asp
            20                  25                  30

Leu Asn Trp Tyr Gln Gln Lys Pro Gly Lys Ala Pro Lys Leu Leu Ile
        35                  40                  45

Tyr Ser Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Glu Arg Thr Pro Ile
                85                  90                  95

Thr Phe Gly Gln Gly Thr Lys Val Glu Ile Lys
            100                 105

<210> SEQ ID NO 239
<211> LENGTH: 107
<212> TYPE: PRT
<213> ORGANISM: Homo sapiens

<400> SEQUENCE: 239

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

```
<210> SEQ ID NO 240
<211> LENGTH: 8
<212> TYPE: PRT
<213> ORGANISM: Homo sapiens

<400> SEQUENCE: 240

Gly Gly Thr Phe Ser Ser Tyr Ala
1               5

<210> SEQ ID NO 241
<211> LENGTH: 8
<212> TYPE: PRT
<213> ORGANISM: Homo sapiens

<400> SEQUENCE: 241

Ile Ile Pro Ile Phe Gly Thr Ala
1               5

<210> SEQ ID NO 242
<211> LENGTH: 13
<212> TYPE: PRT
<213> ORGANISM: Homo sapiens

<400> SEQUENCE: 242

Ala Arg Ser Ser Tyr Gly Trp Ser Tyr Glu Phe Asp Tyr
1               5                   10

<210> SEQ ID NO 243
<211> LENGTH: 6
<212> TYPE: PRT
<213> ORGANISM: Homo sapiens

<400> SEQUENCE: 243

Gln Ser Ile Asn Asn Asp
1               5

<210> SEQ ID NO 244
<211> LENGTH: 3
<212> TYPE: PRT
<213> ORGANISM: Homo sapiens

<400> SEQUENCE: 244

Ala Ala Ser
1

<210> SEQ ID NO 245
<211> LENGTH: 9
<212> TYPE: PRT
<213> ORGANISM: Homo sapiens

<400> SEQUENCE: 245

Gln Gln Asn Arg Ala Thr Pro Ile Thr
1               5

<210> SEQ ID NO 246
<211> LENGTH: 120
<212> TYPE: PRT
<213> ORGANISM: Homo sapiens

<400> SEQUENCE: 246

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30
```

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
 50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Tyr Gly Trp Ser Tyr Glu Phe Asp Tyr Trp Gly Gln
            100                 105                 110

Gly Thr Leu Val Thr Val Ser Ser
        115                 120

<210> SEQ ID NO 247
<211> LENGTH: 330
<212> TYPE: PRT
<213> ORGANISM: Homo sapiens

<400> SEQUENCE: 247

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

```
Leu Tyr Ser Lys Leu Thr Val Asp Lys Ser Arg Trp Gln Gln Gly Asn
        290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
            325                 330

<210> SEQ ID NO 248
<211> LENGTH: 107
<212> TYPE: PRT
<213> ORGANISM: Homo sapiens

<400> SEQUENCE: 248

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Asn Asn Asp
            20                  25                  30
Leu Asn Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Asn Arg Ala Thr Pro Ile
                85                  90                  95
Thr Phe Gly Gln Gly Thr Lys Val Glu Ile Lys
            100                 105

<210> SEQ ID NO 249
<211> LENGTH: 107
<212> TYPE: PRT
<213> ORGANISM: Homo sapiens

<400> SEQUENCE: 249

Arg Thr Val Ala Ala Pro Ser Val Phe Ile Phe Pro Pro Ser Asp Glu
1               5                   10                  15
Gln Leu Lys Ser Gly Thr Ala Ser Val Val Cys Leu Leu Asn Asn Phe
            20                  25                  30
Tyr Pro Arg Glu Ala Lys Val Gln Trp Lys Val Asp Asn Ala Leu Gln
        35                  40                  45
Ser Gly Asn Ser Gln Glu Ser Val Thr Glu Gln Asp Ser Lys Asp Ser
50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
                85                  90                  95
Pro Val Thr Lys Ser Phe Asn Arg Gly Glu Cys
            100                 105

<210> SEQ ID NO 250
<211> LENGTH: 8
<212> TYPE: PRT
<213> ORGANISM: Homo sapiens

<400> SEQUENCE: 250

Gly Gly Thr Phe Ser Ser Tyr Ala
1               5
```

<210> SEQ ID NO 251
<211> LENGTH: 8
<212> TYPE: PRT
<213> ORGANISM: Homo sapiens

<400> SEQUENCE: 251

Ile Ile Pro Ile Phe Gly Thr Ala
1               5

<210> SEQ ID NO 252
<211> LENGTH: 13
<212> TYPE: PRT
<213> ORGANISM: Homo sapiens

<400> SEQUENCE: 252

Ala Arg Asn Thr Phe Gly Trp Ser Gly Glu Leu Asp Tyr
1               5                   10

<210> SEQ ID NO 253
<211> LENGTH: 6
<212> TYPE: PRT
<213> ORGANISM: Homo sapiens

<400> SEQUENCE: 253

Gln Ser Ile Ser Asn Arg
1               5

<210> SEQ ID NO 254
<211> LENGTH: 3
<212> TYPE: PRT
<213> ORGANISM: Homo sapiens

<400> SEQUENCE: 254

Ser Ala Ser
1

<210> SEQ ID NO 255
<211> LENGTH: 9
<212> TYPE: PRT
<213> ORGANISM: Homo sapiens

<400> SEQUENCE: 255

Gln Gln Asn His Asp Asn Pro Ile Thr
1               5

<210> SEQ ID NO 256
<211> LENGTH: 120
<212> TYPE: PRT
<213> ORGANISM: Homo sapiens

<400> SEQUENCE: 256

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys

```
            85                  90                  95
Ala Arg Asn Thr Phe Gly Trp Ser Gly Glu Leu Asp Tyr Trp Gly Gln
                100                 105                 110

Gly Thr Leu Val Thr Val Ser Ser
            115                 120

<210> SEQ ID NO 257
<211> LENGTH: 330
<212> TYPE: PRT
<213> ORGANISM: Homo sapiens

<400> SEQUENCE: 257

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 258
<211> LENGTH: 107
<212> TYPE: PRT
<213> ORGANISM: Homo sapiens

<400> SEQUENCE: 258

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Asn Arg
            20                  25                  30
Leu Asn Trp Tyr Gln Gln Lys Pro Gly Lys Ala Pro Lys Leu Leu Ile
        35                  40                  45
Tyr Ser Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Asn His Asp Asn Pro Ile
                85                  90                  95
Thr Phe Gly Gln Gly Thr Lys Val Glu Ile Lys
            100                 105
```

<210> SEQ ID NO 259
<211> LENGTH: 107
<212> TYPE: PRT
<213> ORGANISM: Homo sapiens

<400> SEQUENCE: 259

```
Arg Thr Val Ala Ala Pro Ser Val Phe Ile Phe Pro Pro Ser Asp Glu
1               5                   10                  15
Gln Leu Lys Ser Gly Thr Ala Ser Val Val Cys Leu Leu Asn Asn Phe
            20                  25                  30
Tyr Pro Arg Glu Ala Lys Val Gln Trp Lys Val Asp Asn Ala Leu Gln
        35                  40                  45
Ser Gly Asn Ser Gln Glu Ser Val Thr Glu Gln Asp Ser Lys Asp Ser
    50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
                85                  90                  95
Pro Val Thr Lys Ser Phe Asn Arg Gly Glu Cys
            100                 105
```

<210> SEQ ID NO 260
<211> LENGTH: 8
<212> TYPE: PRT
<213> ORGANISM: Homo sapiens

<400> SEQUENCE: 260

```
Gly Gly Thr Phe Ser Ser Tyr Ala
1               5
```

<210> SEQ ID NO 261
<211> LENGTH: 8
<212> TYPE: PRT
<213> ORGANISM: Homo sapiens

<400> SEQUENCE: 261

```
Ile Ile Pro Ile Phe Gly Thr Ala
1               5
```

<210> SEQ ID NO 262
<211> LENGTH: 13
<212> TYPE: PRT
<213> ORGANISM: Homo sapiens

<400> SEQUENCE: 262

Ala Arg Ser Ser Tyr Gly Trp Ser Tyr Glu Phe Asp Tyr
1               5                   10

<210> SEQ ID NO 263
<211> LENGTH: 6
<212> TYPE: PRT
<213> ORGANISM: Homo sapiens

<400> SEQUENCE: 263

Gln Ser Ile Ala Thr Tyr
1               5

<210> SEQ ID NO 264
<211> LENGTH: 3
<212> TYPE: PRT
<213> ORGANISM: Homo sapiens

<400> SEQUENCE: 264

Ala Ala Ser
1

<210> SEQ ID NO 265
<211> LENGTH: 9
<212> TYPE: PRT
<213> ORGANISM: Homo sapiens

<400> SEQUENCE: 265

Gln Gln Asn His Asn Arg Pro Ile Thr
1               5

<210> SEQ ID NO 266
<211> LENGTH: 120
<212> TYPE: PRT
<213> ORGANISM: Homo sapiens

<400> SEQUENCE: 266

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Tyr Gly Trp Ser Tyr Glu Phe Asp Tyr Trp Gly Gln
                100                 105                 110

Gly Thr Leu Val Thr Val Ser Ser
        115                 120

<210> SEQ ID NO 267

<211> LENGTH: 330
<212> TYPE: PRT
<213> ORGANISM: Homo sapiens

<400> SEQUENCE: 267

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 268
<211> LENGTH: 107
<212> TYPE: PRT
<213> ORGANISM: Homo sapiens

<400> SEQUENCE: 268

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gln Ser Ile Ala Thr Tyr
            20                  25                  30

Leu Asn Trp Tyr Gln Gln Lys Pro Gly Lys Ala Pro Lys Leu Leu Ile
        35                  40                  45

Tyr Ala Ala Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn His Asn Arg Pro Ile
                85                  90                  95

Thr Phe Gly Gln Gly Thr Lys Val Glu Ile Lys
            100                 105
```

<210> SEQ ID NO 269
<211> LENGTH: 107
<212> TYPE: PRT
<213> ORGANISM: Homo sapiens

<400> SEQUENCE: 269

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 270
<211> LENGTH: 8
<212> TYPE: PRT
<213> ORGANISM: Homo sapiens

<400> SEQUENCE: 270

```
Gly Gly Thr Phe Ser Ser Tyr Ala
1               5
```

<210> SEQ ID NO 271
<211> LENGTH: 8
<212> TYPE: PRT
<213> ORGANISM: Homo sapiens

<400> SEQUENCE: 271

```
Ile Ile Pro Ile Phe Gly Thr Ala
1               5
```

<210> SEQ ID NO 272
<211> LENGTH: 13
<212> TYPE: PRT
<213> ORGANISM: Homo sapiens

<400> SEQUENCE: 272

```
Ala Arg His Ser Ile Gly Trp Val Ala Glu Leu Asp Tyr
```

1               5                    10

<210> SEQ ID NO 273
<211> LENGTH: 6
<212> TYPE: PRT
<213> ORGANISM: Homo sapiens

<400> SEQUENCE: 273

Gln Ser Ile Asn Thr Asp
1               5

<210> SEQ ID NO 274
<211> LENGTH: 3
<212> TYPE: PRT
<213> ORGANISM: Homo sapiens

<400> SEQUENCE: 274

Ala Ala Ser
1

<210> SEQ ID NO 275
<211> LENGTH: 9
<212> TYPE: PRT
<213> ORGANISM: Homo sapiens

<400> SEQUENCE: 275

Gln Gln Gly Ala Ser Asp Pro Ile Thr
1               5

<210> SEQ ID NO 276
<211> LENGTH: 120
<212> TYPE: PRT
<213> ORGANISM: Homo sapiens

<400> SEQUENCE: 276

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Ser Ile Gly Trp Val Ala Glu Leu Asp Tyr Trp Gly Gln
            100                 105                 110

Gly Thr Leu Val Thr Val Ser Ser
        115                 120

<210> SEQ ID NO 277
<211> LENGTH: 330
<212> TYPE: PRT
<213> ORGANISM: Homo sapiens

<400> SEQUENCE: 277

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr

```
            20                  25                  30
Phe Pro Glu Pro Val Thr Val Ser Trp Asn Ser Gly Ala Leu Thr Ser
         35                  40                  45
Gly Val His Thr Phe Pro Ala Val Leu Gln Ser Ser Gly Leu Tyr Ser
     50                  55                  60
Leu Ser Ser Val Val Thr Val Pro Ser Ser Ser Leu Gly Thr Gln Thr
 65                  70                  75                  80
Tyr Ile Cys Asn Val Asn His Lys Pro Ser Asn Thr Lys Val Asp Lys
                 85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 278
<211> LENGTH: 107
<212> TYPE: PRT
<213> ORGANISM: Homo sapiens

<400> SEQUENCE: 278

Asp Ile Gln Met Thr Gln Ser Pro Ser Ser Leu Ser Ala Ser Val Gly
  1               5                  10                  15
Asp Arg Val Thr Ile Thr Cys Arg Ala Ser Gln Ser Ile Asn Thr Asp
             20                  25                  30
Leu Asn Trp Tyr Gln Gln Lys Pro Gly Lys Ala Pro Lys Leu Leu Ile
         35                  40                  45
Tyr Ala Ala Ser Ser Leu Gln Ser Gly Val Pro Ser Arg Phe Ser Gly
     50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ala Ser Asp Pro Ile
                85                  90                  95

Thr Phe Gly Gln Gly Thr Lys Val Glu Ile Lys
            100                 105

<210> SEQ ID NO 279
<211> LENGTH: 107
<212> TYPE: PRT
<213> ORGANISM: Homo sapiens

<400> SEQUENCE: 279

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 280
<211> LENGTH: 8
<212> TYPE: PRT
<213> ORGANISM: Homo sapiens

<400> SEQUENCE: 280

Gly Gly Thr Phe Ser Ser Tyr Ala
1               5

<210> SEQ ID NO 281
<211> LENGTH: 8
<212> TYPE: PRT
<213> ORGANISM: Homo sapiens

<400> SEQUENCE: 281

Ile Ile Pro Ile Phe Gly Thr Ala
1               5

<210> SEQ ID NO 282
<211> LENGTH: 13
<212> TYPE: PRT
<213> ORGANISM: Homo sapiens

<400> SEQUENCE: 282

Ala Arg Ser Ser Tyr Gly Trp Ser Tyr Glu Phe Asp Tyr
1               5                   10

<210> SEQ ID NO 283
<211> LENGTH: 6
<212> TYPE: PRT
<213> ORGANISM: Homo sapiens

<400> SEQUENCE: 283

```
Gln Ser Ile Asn Thr Asp
1               5
```

<210> SEQ ID NO 284
<211> LENGTH: 3
<212> TYPE: PRT
<213> ORGANISM: Homo sapiens

<400> SEQUENCE: 284

```
Ala Ala Ser
1
```

<210> SEQ ID NO 285
<211> LENGTH: 9
<212> TYPE: PRT
<213> ORGANISM: Homo sapiens

<400> SEQUENCE: 285

```
Gln Gln Asn Arg Gly Ser Pro Ile Thr
1               5
```

<210> SEQ ID NO 286
<211> LENGTH: 120
<212> TYPE: PRT
<213> ORGANISM: Homo sapiens

<400> SEQUENCE: 286

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Tyr Gly Trp Ser Tyr Glu Phe Asp Tyr Trp Gly Gln
            100                 105                 110

Gly Thr Leu Val Thr Val Ser Ser
        115                 120
```

<210> SEQ ID NO 287
<211> LENGTH: 330
<212> TYPE: PRT
<213> ORGANISM: Homo sapiens

<400> SEQUENCE: 287

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80
```

```
Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 288
<211> LENGTH: 107
<212> TYPE: PRT
<213> ORGANISM: Homo sapiens

<400> SEQUENCE: 288

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Thr Asp
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Arg Gly Ser Pro Ile
                85                  90                  95

Thr Phe Gly Gln Gly Thr Lys Val Glu Ile Lys
            100                 105
```

```
<210> SEQ ID NO 289
<211> LENGTH: 107
<212> TYPE: PRT
<213> ORGANISM: Homo sapiens

<400> SEQUENCE: 289

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 290
<211> LENGTH: 8
<212> TYPE: PRT
<213> ORGANISM: Homo sapiens

<400> SEQUENCE: 290

Gly Gly Thr Phe Ser Ser Tyr Ala
1               5

<210> SEQ ID NO 291
<211> LENGTH: 8
<212> TYPE: PRT
<213> ORGANISM: Homo sapiens

<400> SEQUENCE: 291

Ile Ile Pro Ile Phe Gly Thr Ala
1               5

<210> SEQ ID NO 292
<211> LENGTH: 13
<212> TYPE: PRT
<213> ORGANISM: Homo sapiens

<400> SEQUENCE: 292

Ala Arg His Ser Ile Gly Trp Val Ala Glu Leu Asp Tyr
1               5                   10

<210> SEQ ID NO 293
<211> LENGTH: 6
<212> TYPE: PRT
<213> ORGANISM: Homo sapiens

<400> SEQUENCE: 293

Gln Ser Ile Ala Thr Asp
1               5

<210> SEQ ID NO 294
<211> LENGTH: 3
<212> TYPE: PRT
<213> ORGANISM: Homo sapiens

<400> SEQUENCE: 294
```

Ala Ala Ser
1

<210> SEQ ID NO 295
<211> LENGTH: 9
<212> TYPE: PRT
<213> ORGANISM: Homo sapiens

<400> SEQUENCE: 295

Gln Gln Ala His Trp Tyr Pro Leu Thr
1               5

<210> SEQ ID NO 296
<211> LENGTH: 120
<212> TYPE: PRT
<213> ORGANISM: Homo sapiens

<400> SEQUENCE: 296

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Ser Ile Gly Trp Val Ala Glu Leu Asp Tyr Trp Gly Gln
            100                 105                 110

Gly Thr Leu Val Thr Val Ser Ser
        115                 120

<210> SEQ ID NO 297
<211> LENGTH: 330
<212> TYPE: PRT
<213> ORGANISM: Homo sapiens

<400> SEQUENCE: 297

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

-continued

Lys Pro Lys Asp Thr Leu Met Ile Ser Arg Thr Pro Glu Val Thr Cys
        130                 135                 140

Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 298
<211> LENGTH: 107
<212> TYPE: PRT
<213> ORGANISM: Homo sapiens

<400> SEQUENCE: 298

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ala Thr Asp
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala His Trp Tyr Pro Leu
                85                  90                  95

Thr Phe Gly Gln Gly Thr Lys Val Glu Ile Lys
            100                 105

<210> SEQ ID NO 299
<211> LENGTH: 107
<212> TYPE: PRT
<213> ORGANISM: Homo sapiens

<400> SEQUENCE: 299

Arg Thr Val Ala Ala Pro Ser Val Phe Ile Phe Pro Pro Ser Asp Glu
1               5                   10                  15

```
Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
     50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105
```

<210> SEQ ID NO 300
<211> LENGTH: 8
<212> TYPE: PRT
<213> ORGANISM: Homo sapiens

<400> SEQUENCE: 300

```
Gly Gly Thr Phe Ser Ser Tyr Ala
 1               5
```

<210> SEQ ID NO 301
<211> LENGTH: 8
<212> TYPE: PRT
<213> ORGANISM: Homo sapiens

<400> SEQUENCE: 301

```
Ile Ile Pro Ile Phe Gly Thr Ala
 1               5
```

<210> SEQ ID NO 302
<211> LENGTH: 13
<212> TYPE: PRT
<213> ORGANISM: Homo sapiens

<400> SEQUENCE: 302

```
Ala Arg His Ser Ile Gly Trp Val Ala Glu Leu Asp Tyr
 1               5                  10
```

<210> SEQ ID NO 303
<211> LENGTH: 6
<212> TYPE: PRT
<213> ORGANISM: Homo sapiens

<400> SEQUENCE: 303

```
Gln Ser Ile Ala Thr Ser
 1               5
```

<210> SEQ ID NO 304
<211> LENGTH: 3
<212> TYPE: PRT
<213> ORGANISM: Homo sapiens

<400> SEQUENCE: 304

```
Tyr Ala Ser
 1
```

<210> SEQ ID NO 305
<211> LENGTH: 9
<212> TYPE: PRT
<213> ORGANISM: Homo sapiens

<400> SEQUENCE: 305

Gln Gln Gly Ala Tyr Tyr Pro Leu Thr
1               5

<210> SEQ ID NO 306
<211> LENGTH: 120
<212> TYPE: PRT
<213> ORGANISM: Homo sapiens

<400> SEQUENCE: 306

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Ser Ile Gly Trp Val Ala Glu Leu Asp Tyr Trp Gly Gln
            100                 105                 110

Gly Thr Leu Val Thr Val Ser Ser
        115                 120

<210> SEQ ID NO 307
<211> LENGTH: 330
<212> TYPE: PRT
<213> ORGANISM: Homo sapiens

<400> SEQUENCE: 307

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu

```
                180               185               190
His Gln Asp Trp Leu Asn Gly Lys Glu Tyr Lys Cys Lys Val Ser Asn
            195               200               205

Lys Ala Leu Pro Ala Pro Ile Glu Lys Thr Ile Ser Lys Ala Lys Gly
        210               215               220

Gln Pro Arg Glu Pro Gln Val Tyr Thr Leu Pro Pro Ser Arg Asp Glu
225               230               235               240

Leu Thr Lys Asn Gln Val Ser Leu Thr Cys Leu Val Lys Gly Phe Tyr
                245               250               255

Pro Ser Asp Ile Ala Val Glu Trp Glu Ser Asn Gly Gln Pro Glu Asn
            260               265               270

Asn Tyr Lys Thr Thr Pro Pro Val Leu Asp Ser Asp Gly Ser Phe Phe
        275               280               285

Leu Tyr Ser Lys Leu Thr Val Asp Lys Ser Arg Trp Gln Gln Gly Asn
    290               295               300

Val Phe Ser Cys Ser Val Met His Glu Ala Leu His Asn His Tyr Thr
305               310               315               320

Gln Lys Ser Leu Ser Leu Ser Pro Gly Lys
                325               330

<210> SEQ ID NO 308
<211> LENGTH: 107
<212> TYPE: PRT
<213> ORGANISM: Homo sapiens

<400> SEQUENCE: 308

Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Ser Ile Ala Thr Ser
            20                  25                  30

Leu Asn Trp Tyr Gln Gln Lys Pro Gly Lys Ala Pro Lys Leu Leu Ile
        35                  40                  45

Tyr Tyr Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Ala Tyr Tyr Pro Leu
                85                  90                  95

Thr Phe Gly Gln Gly Thr Lys Val Glu Ile Lys
            100                 105

<210> SEQ ID NO 309
<211> LENGTH: 107
<212> TYPE: PRT
<213> ORGANISM: Homo sapiens

<400> SEQUENCE: 309

Arg Thr Val Ala Ala Pro Ser Val Phe Ile Phe Pro Pro Ser Asp Glu
1               5                  10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
```

65                  70                  75                  80
Lys His Lys Val Tyr Ala Cys Glu Val Thr His Gln Gly Leu Ser Ser
                    85                  90                  95
Pro Val Thr Lys Ser Phe Asn Arg Gly Glu Cys
                100                 105

<210> SEQ ID NO 310
<211> LENGTH: 8
<212> TYPE: PRT
<213> ORGANISM: Homo sapiens

<400> SEQUENCE: 310

Gly Gly Thr Phe Ser Ser Tyr Ala
1               5

<210> SEQ ID NO 311
<211> LENGTH: 8
<212> TYPE: PRT
<213> ORGANISM: Homo sapiens

<400> SEQUENCE: 311

Ile Ile Pro Ile Phe Gly Thr Ala
1               5

<210> SEQ ID NO 312
<211> LENGTH: 13
<212> TYPE: PRT
<213> ORGANISM: Homo sapiens

<400> SEQUENCE: 312

Ala Arg Ser Ser Tyr Gly Trp Ser Tyr Glu Phe Asp Tyr
1               5                   10

<210> SEQ ID NO 313
<211> LENGTH: 6
<212> TYPE: PRT
<213> ORGANISM: Homo sapiens

<400> SEQUENCE: 313

Gln Ser Ile Arg Thr Tyr
1               5

<210> SEQ ID NO 314
<211> LENGTH: 3
<212> TYPE: PRT
<213> ORGANISM: Homo sapiens

<400> SEQUENCE: 314

Ala Ala Ser
1

<210> SEQ ID NO 315
<211> LENGTH: 9
<212> TYPE: PRT
<213> ORGANISM: Homo sapiens

<400> SEQUENCE: 315

Gln Gln Ala Tyr Ser Asn Pro Ile Thr
1               5

<210> SEQ ID NO 316
<211> LENGTH: 120
<212> TYPE: PRT
<213> ORGANISM: Homo sapiens

<400> SEQUENCE: 316

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Tyr Gly Trp Ser Tyr Glu Phe Asp Tyr Trp Gly Gln
            100                 105                 110

Gly Thr Leu Val Thr Val Ser Ser
        115                 120

<210> SEQ ID NO 317
<211> LENGTH: 330
<212> TYPE: PRT
<213> ORGANISM: Homo sapiens

<400> SEQUENCE: 317

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

```
Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 318
<211> LENGTH: 107
<212> TYPE: PRT
<213> ORGANISM: Homo sapiens

<400> SEQUENCE: 318

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Thr Tyr
            20                  25                  30

Leu Asn Trp Tyr Gln Gln Lys Pro Gly Lys Ala Pro Lys Leu Leu Ile
        35                  40                  45

Tyr Ala Ala Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Ser Asn Pro Ile
                85                  90                  95

Thr Phe Gly Gln Gly Thr Lys Val Glu Ile Lys
            100                 105

<210> SEQ ID NO 319
<211> LENGTH: 107
<212> TYPE: PRT
<213> ORGANISM: Homo sapiens

<400> SEQUENCE: 319

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 320
```

```
<211> LENGTH: 8
<212> TYPE: PRT
<213> ORGANISM: Homo sapiens

<400> SEQUENCE: 320

Gly Gly Thr Phe Ser Ser Tyr Ala
1               5

<210> SEQ ID NO 321
<211> LENGTH: 8
<212> TYPE: PRT
<213> ORGANISM: Homo sapiens

<400> SEQUENCE: 321

Ile Ile Pro Ile Phe Gly Thr Ala
1               5

<210> SEQ ID NO 322
<211> LENGTH: 13
<212> TYPE: PRT
<213> ORGANISM: Homo sapiens

<400> SEQUENCE: 322

Ala Arg Ser Ser Tyr Gly Trp Ser Tyr Glu Phe Asp Tyr
1               5                  10

<210> SEQ ID NO 323
<211> LENGTH: 6
<212> TYPE: PRT
<213> ORGANISM: Homo sapiens

<400> SEQUENCE: 323

Gln Ser Ile Asn Thr Asn
1               5

<210> SEQ ID NO 324
<211> LENGTH: 3
<212> TYPE: PRT
<213> ORGANISM: Homo sapiens

<400> SEQUENCE: 324

Ala Ala Ser
1

<210> SEQ ID NO 325
<211> LENGTH: 9
<212> TYPE: PRT
<213> ORGANISM: Homo sapiens

<400> SEQUENCE: 325

Gln Gln Ala Arg Asp Thr Pro Ile Thr
1               5

<210> SEQ ID NO 326
<211> LENGTH: 120
<212> TYPE: PRT
<213> ORGANISM: Homo sapiens

<400> SEQUENCE: 326

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
```

```
            35                  40                  45
Gly Gly Ile Ile Pro Ile Phe Gly Thr Ala Asn Tyr Ala Gln Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ser Tyr Gly Trp Ser Tyr Glu Phe Asp Tyr Trp Gly Gln
                100                 105                 110

Gly Thr Leu Val Thr Val Ser Ser
                115                 120

<210> SEQ ID NO 327
<211> LENGTH: 330
<212> TYPE: PRT
<213> ORGANISM: Homo sapiens

<400> SEQUENCE: 327

Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
            290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
            325                 330
```

<210> SEQ ID NO 328
<211> LENGTH: 107
<212> TYPE: PRT
<213> ORGANISM: Homo sapiens

<400> SEQUENCE: 328

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Asn Thr Asn
            20                  25                  30
Leu Asn Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ala Arg Asp Thr Pro Ile
                85                  90                  95
Thr Phe Gly Gln Gly Thr Lys Val Glu Ile Lys
            100                 105
```

<210> SEQ ID NO 329
<211> LENGTH: 107
<212> TYPE: PRT
<213> ORGANISM: Homo sapiens

<400> SEQUENCE: 329

```
Arg Thr Val Ala Ala Pro Ser Val Phe Ile Phe Pro Pro Ser Asp Glu
1               5                   10                  15
Gln Leu Lys Ser Gly Thr Ala Ser Val Val Cys Leu Leu Asn Asn Phe
            20                  25                  30
Tyr Pro Arg Glu Ala Lys Val Gln Trp Lys Val Asp Asn Ala Leu Gln
        35                  40                  45
Ser Gly Asn Ser Gln Glu Ser Val Thr Glu Gln Asp Ser Lys Asp Ser
50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
                85                  90                  95
Pro Val Thr Lys Ser Phe Asn Arg Gly Glu Cys
            100                 105
```

<210> SEQ ID NO 330
<211> LENGTH: 8
<212> TYPE: PRT
<213> ORGANISM: Homo sapiens

<400> SEQUENCE: 330

```
Gly Tyr Thr Phe Pro Ser His Thr
1               5
```

```
<210> SEQ ID NO 331
<211> LENGTH: 8
<212> TYPE: PRT
<213> ORGANISM: Homo sapiens

<400> SEQUENCE: 331

Ile Tyr Pro Phe Ile Asp Ser Thr
1               5

<210> SEQ ID NO 332
<211> LENGTH: 11
<212> TYPE: PRT
<213> ORGANISM: Homo sapiens

<400> SEQUENCE: 332

Ala Arg Gly Ile Arg Gly Tyr Thr Met Asp Tyr
1               5                   10

<210> SEQ ID NO 333
<211> LENGTH: 10
<212> TYPE: PRT
<213> ORGANISM: Homo sapiens

<400> SEQUENCE: 333

Glu Ser Val Asp Asn Tyr Gly Leu Ser Phe
1               5                   10

<210> SEQ ID NO 334
<211> LENGTH: 3
<212> TYPE: PRT
<213> ORGANISM: Homo sapiens

<400> SEQUENCE: 334

Gly Ala Ser
1

<210> SEQ ID NO 335
<211> LENGTH: 9
<212> TYPE: PRT
<213> ORGANISM: Homo sapiens

<400> SEQUENCE: 335

Gln Gln Ser Lys Glu Val Pro Tyr Thr
1               5

<210> SEQ ID NO 336
<211> LENGTH: 118
<212> TYPE: PRT
<213> ORGANISM: Homo sapiens

<400> SEQUENCE: 336

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Pro Ser His
                20                  25                  30

Thr Ile His Trp Val Arg Gln Ala Pro Gly Gln Arg Leu Glu Trp Met
            35                  40                  45

Gly Ser Ile Tyr Pro Phe Ile Asp Ser Thr Ile Tyr Asn Gln Lys Phe
        50                  55                  60

Lys Asp Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95
```

```
Ala Arg Gly Ile Arg Gly Tyr Thr Met Asp Tyr Trp Gly Gln Gly Thr
            100                 105                 110

Leu Val Thr Val Ser Ser
        115

<210> SEQ ID NO 337
<211> LENGTH: 330
<212> TYPE: PRT
<213> ORGANISM: Homo sapiens

<400> SEQUENCE: 337

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

-continued

```
<210> SEQ ID NO 338
<211> LENGTH: 111
<212> TYPE: PRT
<213> ORGANISM: Homo sapiens

<400> SEQUENCE: 338

Asp Val Val Met Thr Gln Ser Pro Leu Ser Leu Pro Val Thr Leu Gly
1               5                   10                  15

Gln Pro Ala Ser Ile Ser Cys Arg Ala Ser Glu Ser Val Asp Asn Tyr
            20                  25                  30

Gly Leu Ser Phe Met Asn Trp Phe Gln Gln Arg Pro Gly Gln Ser Pro
        35                  40                  45

Arg Arg Leu Ile Tyr Gly Ala Ser Asn Gln Gly Ser Gly Val Pro Asp
50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Ser Lys
                85                  90                  95

Glu Val Pro Tyr Thr Phe Gly Gln Gly Thr Lys Leu Glu Ile Lys
            100                 105                 110

<210> SEQ ID NO 339
<211> LENGTH: 107
<212> TYPE: PRT
<213> ORGANISM: Homo sapiens

<400> SEQUENCE: 339

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 340
<211> LENGTH: 8
<212> TYPE: PRT
<213> ORGANISM: Homo sapiens

<400> SEQUENCE: 340

Gly Tyr Thr Phe Thr Asn Tyr Gly
1               5

<210> SEQ ID NO 341
<211> LENGTH: 8
<212> TYPE: PRT
<213> ORGANISM: Homo sapiens

<400> SEQUENCE: 341

Ile Asn Pro Tyr Thr Gly Glu Pro
1               5
```

<210> SEQ ID NO 342
<211> LENGTH: 12
<212> TYPE: PRT
<213> ORGANISM: Homo sapiens

<400> SEQUENCE: 342

Ala Arg Glu Gly Tyr Gly Asn Tyr Ile Phe Pro Tyr
1               5                   10

<210> SEQ ID NO 343
<211> LENGTH: 10
<212> TYPE: PRT
<213> ORGANISM: Homo sapiens

<400> SEQUENCE: 343

Glu Ser Val Asp Thr Tyr Ala Asn Ser Leu
1               5                   10

<210> SEQ ID NO 344
<211> LENGTH: 3
<212> TYPE: PRT
<213> ORGANISM: Homo sapiens

<400> SEQUENCE: 344

Arg Ala Ser
1

<210> SEQ ID NO 345
<211> LENGTH: 9
<212> TYPE: PRT
<213> ORGANISM: Homo sapiens

<400> SEQUENCE: 345

Gln Gln Thr Asn Glu Asp Pro Arg Thr
1               5

<210> SEQ ID NO 346
<211> LENGTH: 119
<212> TYPE: PRT
<213> ORGANISM: Homo sapiens

<400> SEQUENCE: 346

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Leu Asn Trp Val Arg Gln Ala Pro Gly Gln Gly Leu Glu Trp Met
            35                  40                  45

Gly Trp Ile Asn Pro Tyr Thr Gly Glu Pro Thr Tyr Ala Asp Asp Phe
        50                  55                  60

Lys Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg Glu Gly Tyr Gly Asn Tyr Ile Phe Pro Tyr Trp Gly Gln Gly
                100                 105                 110

Thr Leu Val Thr Val Ser Ser
            115

<210> SEQ ID NO 347
<211> LENGTH: 330

<212> TYPE: PRT
<213> ORGANISM: Homo sapiens

<400> SEQUENCE: 347

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 348
<211> LENGTH: 111
<212> TYPE: PRT
<213> ORGANISM: Homo sapiens

<400> SEQUENCE: 348

```
Asp Ile Val Met Thr Gln Thr Pro Leu Ser Leu Ser Val Thr Pro Gly
1               5                   10                  15
```

Gln Pro Ala Ser Ile Ser Cys Arg Ala Ser Glu Ser Val Asp Thr Tyr
                20                  25                  30

Ala Asn Ser Leu Met His Trp Tyr Leu Gln Lys Pro Gly Gln Pro Pro
            35                  40                  45

Gln Leu Leu Ile Tyr Arg Ala Ser Asn Leu Glu Ser Gly Val Pro Asp
50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Thr Asn
                85                  90                  95

Glu Asp Pro Arg Thr Phe Gly Gln Gly Thr Lys Leu Glu Ile Lys
            100                 105                 110

<210> SEQ ID NO 349
<211> LENGTH: 107
<212> TYPE: PRT
<213> ORGANISM: Homo sapiens

<400> SEQUENCE: 349

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 350
<211> LENGTH: 8
<212> TYPE: PRT
<213> ORGANISM: Homo sapiens

<400> SEQUENCE: 350

Gly Phe Thr Phe Ser Ser Tyr Thr
1               5

<210> SEQ ID NO 351
<211> LENGTH: 8
<212> TYPE: PRT
<213> ORGANISM: Homo sapiens

<400> SEQUENCE: 351

Ile Ser Asn Ser Gly Ser Tyr Thr
1               5

<210> SEQ ID NO 352
<211> LENGTH: 11
<212> TYPE: PRT
<213> ORGANISM: Homo sapiens

<400> SEQUENCE: 352

Ala Arg Asp Thr Val Leu Ser Pro Phe Asp Tyr
1               5                   10

-continued

<210> SEQ ID NO 353
<211> LENGTH: 5
<212> TYPE: PRT
<213> ORGANISM: Homo sapiens

<400> SEQUENCE: 353

Ser Ser Ile Ser Tyr
1               5

<210> SEQ ID NO 354
<211> LENGTH: 3
<212> TYPE: PRT
<213> ORGANISM: Homo sapiens

<400> SEQUENCE: 354

Asp Thr Ser
1

<210> SEQ ID NO 355
<211> LENGTH: 7
<212> TYPE: PRT
<213> ORGANISM: Homo sapiens

<400> SEQUENCE: 355

His Gln Arg Ser Ser Phe Thr
1               5

<210> SEQ ID NO 356
<211> LENGTH: 118
<212> TYPE: PRT
<213> ORGANISM: Homo sapiens

<400> SEQUENCE: 356

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ala Thr Ile Ser Asn Ser Gly Ser Tyr Thr Tyr Tyr Leu Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Thr Val Leu Ser Pro Phe Asp Tyr Trp Gly Gln Gly Thr
            100                 105                 110

Thr Val Thr Val Ser Ser
            115

<210> SEQ ID NO 357
<211> LENGTH: 330
<212> TYPE: PRT
<213> ORGANISM: Homo sapiens

<400> SEQUENCE: 357

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 358
<211> LENGTH: 104
<212> TYPE: PRT
<213> ORGANISM: Homo sapiens

<400> SEQUENCE: 358

Glu Ile Val Leu Thr Gln Ser Pro Asp Phe Gln Ser Val Thr Pro Lys
1               5                   10                  15

Glu Lys Val Thr Ile Thr Cys Ser Ala Thr Ser Ser Ile Ser Tyr Met
            20                  25                  30

His Trp Tyr Gln Gln Lys Pro Asp Gln Ser Pro Lys Leu Leu Ile Lys
            35                  40                  45

Asp Thr Ser Glu Leu Ala Ser Gly Val Pro Ser Arg Phe Ser Gly Ser
 50                  55                  60

Gly Ser Gly Thr Asp Phe Thr Leu Thr Ile Asn Ser Leu Glu Ala Glu 65                  70                  75                  80
Asp Ala Ala Thr Tyr Tyr Cys His Gln Arg Ser Ser Phe Thr Phe Gly
                    85                  90                  95
Gln Gly Thr Lys Leu Glu Ile Lys
                100

<210> SEQ ID NO 359
<211> LENGTH: 107
<212> TYPE: PRT
<213> ORGANISM: Homo sapiens

<400> SEQUENCE: 359

Arg Thr Val Ala Ala Pro Ser Val Phe Ile Phe Pro Pro Ser Asp Glu
1               5                   10                  15
Gln Leu Lys Ser Gly Thr Ala Ser Val Val Cys Leu Leu Asn Asn Phe
            20                  25                  30
Tyr Pro Arg Glu Ala Lys Val Gln Trp Lys Val Asp Asn Ala Leu Gln
        35                  40                  45
Ser Gly Asn Ser Gln Glu Ser Val Thr Glu Gln Asp Ser Lys Asp Ser
    50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
                85                  90                  95
Pro Val Thr Lys Ser Phe Asn Arg Gly Glu Cys
                100                 105

<210> SEQ ID NO 360
<211> LENGTH: 8
<212> TYPE: PRT
<213> ORGANISM: Homo sapiens

<400> SEQUENCE: 360

Gly Gly Thr Phe Ser Asn Tyr Trp
1               5

<210> SEQ ID NO 361
<211> LENGTH: 8
<212> TYPE: PRT
<213> ORGANISM: Homo sapiens

<400> SEQUENCE: 361

Ile Tyr Pro Gly Gly Gly Phe Thr
1               5

<210> SEQ ID NO 362
<211> LENGTH: 14
<212> TYPE: PRT
<213> ORGANISM: Homo sapiens

<400> SEQUENCE: 362

Ala Arg Tyr Tyr Arg Ser Asp Glu Asp Tyr Ser Met Asp Phe
1               5                   10

<210> SEQ ID NO 363
<211> LENGTH: 11
<212> TYPE: PRT
<213> ORGANISM: Homo sapiens

<400> SEQUENCE: 363

Gln Ser Leu Leu Tyr Ser Asn Gly Lys Thr Tyr

```
1               5                   10
```

<210> SEQ ID NO 364
<211> LENGTH: 3
<212> TYPE: PRT
<213> ORGANISM: Homo sapiens

<400> SEQUENCE: 364

Leu Val Ser
1

<210> SEQ ID NO 365
<211> LENGTH: 9
<212> TYPE: PRT
<213> ORGANISM: Homo sapiens

<400> SEQUENCE: 365

Val Gln Ala Thr His Phe Pro Gln Thr
1               5

<210> SEQ ID NO 366
<211> LENGTH: 121
<212> TYPE: PRT
<213> ORGANISM: Homo sapiens

<400> SEQUENCE: 366

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Asn Tyr
            20                  25                  30

Trp Ile Gly Trp Val Arg Gln Ala Pro Gly Gln Gly Leu Glu Trp Met
        35                  40                  45

Gly Glu Ile Tyr Pro Gly Gly Phe Thr His Tyr Asn Glu Lys Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Arg Ser Asp Glu Asp Tyr Ser Met Asp Phe Trp Gly
            100                 105                 110

Gln Gly Thr Leu Val Thr Val Ser Ser
        115                 120

<210> SEQ ID NO 367
<211> LENGTH: 330
<212> TYPE: PRT
<213> ORGANISM: Homo sapiens

<400> SEQUENCE: 367

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

```
Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 368
<211> LENGTH: 112
<212> TYPE: PRT
<213> ORGANISM: Homo sapiens

<400> SEQUENCE: 368

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Phe Gln Gln Arg Pro Gly Gln Ser
        35                  40                  45

Pro Arg Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Ala
                85                  90                  95

Thr His Phe Pro Gln Thr Phe Gly Gln Gly Thr Lys Leu Glu Ile Lys
            100                 105                 110

<210> SEQ ID NO 369
```

-continued

```
<211> LENGTH: 107
<212> TYPE: PRT
<213> ORGANISM: Homo sapiens

<400> SEQUENCE: 369

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 370
<211> LENGTH: 8
<212> TYPE: PRT
<213> ORGANISM: Homo sapiens

<400> SEQUENCE: 370

Gly Tyr Thr Phe Thr His Tyr Thr
1               5

<210> SEQ ID NO 371
<211> LENGTH: 8
<212> TYPE: PRT
<213> ORGANISM: Homo sapiens

<400> SEQUENCE: 371

Ile Ile Pro Ser Ser Gly Tyr Ser
1               5

<210> SEQ ID NO 372
<211> LENGTH: 16
<212> TYPE: PRT
<213> ORGANISM: Homo sapiens

<400> SEQUENCE: 372

Ala Arg Gly Ala Tyr Asp Asp Tyr Asp Tyr Tyr Ala Met Asp Tyr
1               5                   10                  15

<210> SEQ ID NO 373
<211> LENGTH: 11
<212> TYPE: PRT
<213> ORGANISM: Homo sapiens

<400> SEQUENCE: 373

Gln Thr Ile Val His Ser Asn Gly Asn Thr Tyr
1               5                   10

<210> SEQ ID NO 374
<211> LENGTH: 3
<212> TYPE: PRT
<213> ORGANISM: Homo sapiens

<400> SEQUENCE: 374
```

Lys Val Ser
1

<210> SEQ ID NO 375
<211> LENGTH: 9
<212> TYPE: PRT
<213> ORGANISM: Homo sapiens

<400> SEQUENCE: 375

Phe Gln Ala Ser His Val Pro Trp Thr
1               5

<210> SEQ ID NO 376
<211> LENGTH: 123
<212> TYPE: PRT
<213> ORGANISM: Homo sapiens

<400> SEQUENCE: 376

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr His Tyr
            20                  25                  30

Thr Ile His Trp Val Arg Gln Ala Pro Gly Gln Gly Leu Glu Trp Met
        35                  40                  45

Gly Tyr Ile Ile Pro Ser Ser Gly Tyr Ser Glu Tyr Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Ala Tyr Asp Asp Tyr Tyr Asp Tyr Tyr Ala Met Asp Tyr
            100                 105                 110

Trp Gly Gln Gly Thr Leu Val Thr Val Ser Ser
        115                 120

<210> SEQ ID NO 377
<211> LENGTH: 330
<212> TYPE: PRT
<213> ORGANISM: Homo sapiens

<400> SEQUENCE: 377

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys

```
            130                 135                 140
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 378
<211> LENGTH: 112
<212> TYPE: PRT
<213> ORGANISM: Homo sapiens

<400> SEQUENCE: 378

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Thr Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Ser His Val Pro Trp Thr Phe Gly Gln Gly Thr Lys Leu Glu Ile Lys
            100                 105                 110

<210> SEQ ID NO 379
<211> LENGTH: 107
<212> TYPE: PRT
<213> ORGANISM: Homo sapiens

<400> SEQUENCE: 379

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
```

```
            20                  25                  30
Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 380
<211> LENGTH: 8
<212> TYPE: PRT
<213> ORGANISM: Homo sapiens

<400> SEQUENCE: 380

Gly Tyr Asn Ile Lys Asp Thr Tyr
1               5

<210> SEQ ID NO 381
<211> LENGTH: 8
<212> TYPE: PRT
<213> ORGANISM: Homo sapiens

<400> SEQUENCE: 381

Ile Asp Pro Thr His Gly Tyr Val
1               5

<210> SEQ ID NO 382
<211> LENGTH: 13
<212> TYPE: PRT
<213> ORGANISM: Homo sapiens

<400> SEQUENCE: 382

Ala Arg Asp Arg Phe Asp Pro Tyr Trp Phe Leu Asp Val
1               5                   10

<210> SEQ ID NO 383
<211> LENGTH: 10
<212> TYPE: PRT
<213> ORGANISM: Homo sapiens

<400> SEQUENCE: 383

Glu Ser Val Glu Tyr Tyr Gly Thr Ser Leu
1               5                   10

<210> SEQ ID NO 384
<211> LENGTH: 3
<212> TYPE: PRT
<213> ORGANISM: Homo sapiens

<400> SEQUENCE: 384

Asp Ala Phe
1

<210> SEQ ID NO 385
<211> LENGTH: 9
<212> TYPE: PRT
<213> ORGANISM: Homo sapiens

<400> SEQUENCE: 385
```

Gln Gln Ser Arg Lys Val Pro Trp Thr
1               5

<210> SEQ ID NO 386
<211> LENGTH: 120
<212> TYPE: PRT
<213> ORGANISM: Homo sapiens

<400> SEQUENCE: 386

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Asn Ile Lys Asp Thr
            20                  25                  30

Tyr Met His Trp Val Arg Gln Ala Pro Gly Gln Gly Leu Glu Trp Met
        35                  40                  45

Gly Arg Ile Asp Pro Thr His Gly Tyr Val Ile Tyr Asp Pro Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Arg Phe Asp Pro Tyr Trp Phe Leu Asp Val Trp Gly Gln
            100                 105                 110

Gly Thr Leu Val Thr Val Ser Ser
        115                 120

<210> SEQ ID NO 387
<211> LENGTH: 330
<212> TYPE: PRT
<213> ORGANISM: Homo sapiens

<400> SEQUENCE: 387

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

```
His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 388
<211> LENGTH: 111
<212> TYPE: PRT
<213> ORGANISM: Homo sapiens

<400> SEQUENCE: 388

```
Asp Ile Val Met Thr Gln Thr Pro Leu Ser Leu Ser Val Thr Pro Gly
1               5                   10                  15

Gln Pro Ala Ser Ile Ser Cys Arg Ala Ser Glu Ser Val Glu Tyr Tyr
            20                  25                  30

Gly Thr Ser Leu Met Gln Trp Tyr Leu Gln Lys Pro Gly Gln Ser Pro
        35                  40                  45

Gln Leu Leu Ile Tyr Asp Ala Phe Asn Val Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Ser Arg
                85                  90                  95

Lys Val Pro Trp Thr Phe Gly Gln Gly Thr Lys Leu Glu Ile Lys
            100                 105                 110
```

<210> SEQ ID NO 389
<211> LENGTH: 107
<212> TYPE: PRT
<213> ORGANISM: Homo sapiens

<400> SEQUENCE: 389

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80
```

```
Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 390
<211> LENGTH: 9
<212> TYPE: PRT
<213> ORGANISM: Homo sapiens

<400> SEQUENCE: 390

Gly Tyr Ser Ile Ala Ser Asp Tyr Val
1               5

<210> SEQ ID NO 391
<211> LENGTH: 7
<212> TYPE: PRT
<213> ORGANISM: Homo sapiens

<400> SEQUENCE: 391

Ile Ser Tyr Ser Gly Ser Thr
1               5

<210> SEQ ID NO 392
<211> LENGTH: 17
<212> TYPE: PRT
<213> ORGANISM: Homo sapiens

<400> SEQUENCE: 392

Ala Arg Ile Thr Thr Val Val Pro Thr Gly Ser Tyr Tyr Gly Val Asp
1               5                   10                  15

Phe

<210> SEQ ID NO 393
<211> LENGTH: 5
<212> TYPE: PRT
<213> ORGANISM: Homo sapiens

<400> SEQUENCE: 393

Ser Ser Val Asn Phe
1               5

<210> SEQ ID NO 394
<211> LENGTH: 3
<212> TYPE: PRT
<213> ORGANISM: Homo sapiens

<400> SEQUENCE: 394

Asp Thr Ser
1

<210> SEQ ID NO 395
<211> LENGTH: 9
<212> TYPE: PRT
<213> ORGANISM: Homo sapiens

<400> SEQUENCE: 395

Gln Gln Trp Ser Asn Tyr Pro Phe Thr
1               5

<210> SEQ ID NO 396
<211> LENGTH: 124
<212> TYPE: PRT
```

<213> ORGANISM: Homo sapiens

<400> SEQUENCE: 396

```
Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Ala Ser Asp
            20                  25                  30

Tyr Val Trp Asn Trp Ile Arg Gln Pro Pro Gly Lys Gly Leu Glu Trp
        35                  40                  45

Ile Gly Tyr Ile Ser Tyr Ser Gly Ser Thr Ser Asn Asn Pro Ser Leu
    50                  55                  60

Asn Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ile Thr Thr Val Val Pro Thr Gly Ser Tyr Tyr Gly Val Asp
            100                 105                 110

Phe Trp Gly Gln Gly Thr Thr Val Thr Val Ser Ser
        115                 120
```

<210> SEQ ID NO 397
<211> LENGTH: 330
<212> TYPE: PRT
<213> ORGANISM: Homo sapiens

<400> SEQUENCE: 397

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
```

```
                225                 230                 235                 240
Leu Thr Lys Asn Gln Val Ser Leu Thr Cys Leu Val Lys Gly Phe Tyr
                    245                 250                 255

Pro Ser Asp Ile Ala Val Glu Trp Glu Ser Asn Gly Gln Pro Glu Asn
                    260                 265                 270

Asn Tyr Lys Thr Thr Pro Pro Val Leu Asp Ser Asp Gly Ser Phe Phe
                    275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                    325                 330

<210> SEQ ID NO 398
<211> LENGTH: 106
<212> TYPE: PRT
<213> ORGANISM: Homo sapiens

<400> SEQUENCE: 398

Glu Ile Val Leu Thr Gln Ser Pro Asp Phe Gln Ser Val Thr Pro Lys
1               5                   10                  15

Glu Lys Val Thr Ile Thr Cys Ser Gly Ser Ser Ser Val Asn Phe Met
                    20                  25                  30

Tyr Trp Tyr Gln Gln Lys Pro Asp Gln Ser Pro Lys Leu Leu Ile Lys
                35                  40                  45

Asp Thr Ser Asn Leu Ala Ser Gly Val Pro Ser Arg Phe Ser Gly Ser
            50                  55                  60

Gly Ser Gly Thr Asp Phe Thr Leu Thr Ile Asn Ser Leu Glu Ala Glu
65                  70                  75                  80

Asp Ala Ala Thr Tyr Tyr Cys Gln Gln Trp Ser Asn Tyr Pro Phe Thr
                    85                  90                  95

Phe Gly Gln Gly Thr Lys Leu Glu Ile Lys
                100                 105

<210> SEQ ID NO 399
<211> LENGTH: 107
<212> TYPE: PRT
<213> ORGANISM: Homo sapiens

<400> SEQUENCE: 399

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                    20                  25                  30

Tyr Pro Arg Glu Ala Lys Val Gln Trp Lys Val Asp Asn Ala Leu Gln
                35                  40                  45

Ser Gly Asn Ser Gln Glu Ser Val Thr Glu Gln Asp Ser Lys Asp Ser
            50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                    85                  90                  95

Pro Val Thr Lys Ser Phe Asn Arg Gly Glu Cys
                100                 105
```

```
<210> SEQ ID NO 400
<211> LENGTH: 8
<212> TYPE: PRT
<213> ORGANISM: Homo sapiens

<400> SEQUENCE: 400

Gly Tyr Thr Phe Thr Ser Tyr Trp
1               5

<210> SEQ ID NO 401
<211> LENGTH: 8
<212> TYPE: PRT
<213> ORGANISM: Homo sapiens

<400> SEQUENCE: 401

Ile Ile Pro Asn Thr Leu His Thr
1               5

<210> SEQ ID NO 402
<211> LENGTH: 13
<212> TYPE: PRT
<213> ORGANISM: Homo sapiens

<400> SEQUENCE: 402

Ala Arg Leu Asp Gly Asp Tyr Asp Tyr Ala Leu Asp Tyr
1               5                   10

<210> SEQ ID NO 403
<211> LENGTH: 10
<212> TYPE: PRT
<213> ORGANISM: Homo sapiens

<400> SEQUENCE: 403

Glu Ser Val Glu Tyr Tyr Gly Thr Ser Phe
1               5                   10

<210> SEQ ID NO 404
<211> LENGTH: 3
<212> TYPE: PRT
<213> ORGANISM: Homo sapiens

<400> SEQUENCE: 404

Thr Ala Ser
1

<210> SEQ ID NO 405
<211> LENGTH: 9
<212> TYPE: PRT
<213> ORGANISM: Homo sapiens

<400> SEQUENCE: 405

Gln Gln Ser Arg Lys Val Pro Tyr Thr
1               5

<210> SEQ ID NO 406
<211> LENGTH: 120
<212> TYPE: PRT
<213> ORGANISM: Homo sapiens

<400> SEQUENCE: 406

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30
```

```
Trp Leu His Trp Val Arg Gln Ala Pro Gly Gln Gly Leu Glu Trp Met
             35                  40                  45

Gly Tyr Ile Ile Pro Asn Thr Leu His Thr Asp Tyr Asn Gln Lys Phe
 50                  55                  60

Lys Asp Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
             85                  90                  95

Ala Arg Leu Asp Gly Asp Tyr Asp Tyr Ala Leu Asp Tyr Trp Gly Gln
            100                 105                 110

Gly Thr Leu Val Thr Val Ser Ser
            115                 120

<210> SEQ ID NO 407
<211> LENGTH: 330
<212> TYPE: PRT
<213> ORGANISM: Homo sapiens

<400> SEQUENCE: 407

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
             85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285
```

```
Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 408
<211> LENGTH: 111
<212> TYPE: PRT
<213> ORGANISM: Homo sapiens

<400> SEQUENCE: 408

Asp Ile Val Met Thr Gln Thr Pro Leu Ser Leu Ser Val Thr Pro Gly
1               5                   10                  15

Gln Pro Ala Ser Ile Ser Cys Arg Ala Ser Glu Ser Val Glu Tyr Tyr
            20                  25                  30

Gly Thr Ser Phe Met Gln Trp Tyr Leu Gln Lys Pro Gly Gln Pro Pro
        35                  40                  45

Gln Leu Leu Ile Tyr Thr Ala Ser Asn Val Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Ser Arg
                85                  90                  95

Lys Val Pro Tyr Thr Phe Gly Gln Gly Thr Lys Leu Glu Ile Lys
            100                 105                 110

<210> SEQ ID NO 409
<211> LENGTH: 107
<212> TYPE: PRT
<213> ORGANISM: Homo sapiens

<400> SEQUENCE: 409

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 410
<211> LENGTH: 8
<212> TYPE: PRT
<213> ORGANISM: Homo sapiens

<400> SEQUENCE: 410

Gly Phe Thr Phe Ser Thr Tyr Ala
1               5
```

<210> SEQ ID NO 411
<211> LENGTH: 8
<212> TYPE: PRT
<213> ORGANISM: Homo sapiens

<400> SEQUENCE: 411

Ile Ser Ser Gly Gly Ser Asp Thr
1               5

<210> SEQ ID NO 412
<211> LENGTH: 14
<212> TYPE: PRT
<213> ORGANISM: Homo sapiens

<400> SEQUENCE: 412

Ala Arg Pro Thr Tyr Tyr Gly Ile Phe Ser Tyr Phe Asp Tyr
1               5                   10

<210> SEQ ID NO 413
<211> LENGTH: 5
<212> TYPE: PRT
<213> ORGANISM: Homo sapiens

<400> SEQUENCE: 413

Ser Ser Val Ser Tyr
1               5

<210> SEQ ID NO 414
<211> LENGTH: 3
<212> TYPE: PRT
<213> ORGANISM: Homo sapiens

<400> SEQUENCE: 414

Ser Thr Ser
1

<210> SEQ ID NO 415
<211> LENGTH: 8
<212> TYPE: PRT
<213> ORGANISM: Homo sapiens

<400> SEQUENCE: 415

His Gln Trp Arg Thr Tyr Pro Thr
1               5

<210> SEQ ID NO 416
<211> LENGTH: 121
<212> TYPE: PRT
<213> ORGANISM: Homo sapiens

<400> SEQUENCE: 416

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45

Ala Thr Ile Ser Ser Gly Gly Ser Asp Thr Tyr Tyr Pro Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys

```
            85                  90                  95
Ala Arg Pro Thr Tyr Tyr Gly Ile Phe Ser Tyr Phe Asp Tyr Trp Gly
            100                 105                 110

Gln Gly Thr Leu Val Thr Val Ser Ser
            115                 120

<210> SEQ ID NO 417
<211> LENGTH: 330
<212> TYPE: PRT
<213> ORGANISM: Homo sapiens

<400> SEQUENCE: 417

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 418
<211> LENGTH: 105
<212> TYPE: PRT
<213> ORGANISM: Homo sapiens

<400> SEQUENCE: 418

Asp Ile Gln Leu Thr Gln Ser Pro Ser Phe Leu Ser Ala Ser Val Gly
1               5                   10                  15

Asp Arg Val Thr Ile Thr Cys Ser Ala Ser Ser Val Ser Tyr Met
            20                  25                  30

His Trp Tyr Gln Gln Lys Pro Gly Lys Ala Pro Lys Leu Leu Ile Tyr
                35                  40                  45

Ser Thr Ser Asn Leu Ala Ser Gly Val Pro Ser Arg Phe Ser Gly Ser
        50                  55                  60

Gly Ser Gly Thr Glu Phe Thr Leu Thr Ile Ser Ser Leu Gln Pro Glu
65                  70                  75                  80

Asp Phe Ala Thr Tyr Tyr Cys His Gln Trp Arg Thr Tyr Pro Thr Phe
                85                  90                  95

Gly Gln Gly Thr Lys Leu Glu Ile Lys
            100                 105

<210> SEQ ID NO 419
<211> LENGTH: 107
<212> TYPE: PRT
<213> ORGANISM: Homo sapiens

<400> SEQUENCE: 419

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
                35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 420
<211> LENGTH: 8
<212> TYPE: PRT
<213> ORGANISM: Homo sapiens

<400> SEQUENCE: 420

Gly Phe Ser Leu Thr Asn Tyr Gly
1               5

<210> SEQ ID NO 421
<211> LENGTH: 7
<212> TYPE: PRT
<213> ORGANISM: Homo sapiens

<400> SEQUENCE: 421

Ile Trp Arg Gly Gly Asn Thr
1               5

<210> SEQ ID NO 422
<211> LENGTH: 11
<212> TYPE: PRT
<213> ORGANISM: Homo sapiens

<400> SEQUENCE: 422

Ala Arg Ser Met Val Ser Tyr Thr Val Asp Tyr
1               5                   10

<210> SEQ ID NO 423
<211> LENGTH: 5
<212> TYPE: PRT
<213> ORGANISM: Homo sapiens

<400> SEQUENCE: 423

Ser Ser Val Ser Tyr
1               5

<210> SEQ ID NO 424
<211> LENGTH: 3
<212> TYPE: PRT
<213> ORGANISM: Homo sapiens

<400> SEQUENCE: 424

Asp Thr Ser
1

<210> SEQ ID NO 425
<211> LENGTH: 9
<212> TYPE: PRT
<213> ORGANISM: Homo sapiens

<400> SEQUENCE: 425

Gln Gln Trp Ser Ser Tyr Pro Pro Thr
1               5

<210> SEQ ID NO 426
<211> LENGTH: 117
<212> TYPE: PRT
<213> ORGANISM: Homo sapiens

<400> SEQUENCE: 426

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Gly Val His Trp Ile Arg Gln Pro Pro Gly Lys Gly Leu Glu Trp Ile
        35                  40                  45

Gly Val Ile Trp Arg Gly Gly Asn Thr Asp Tyr Asn Ala Ala Phe Met
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ser Met Val Ser Tyr Thr Val Asp Tyr Trp Gly Gln Gly Thr Leu
            100                 105                 110

Val Thr Val Ser Ser
        115

<210> SEQ ID NO 427

```
<211> LENGTH: 330
<212> TYPE: PRT
<213> ORGANISM: Homo sapiens

<400> SEQUENCE: 427

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 428
<211> LENGTH: 106
<212> TYPE: PRT
<213> ORGANISM: Homo sapiens

<400> SEQUENCE: 428

Glu Ile Val Leu Thr Gln Ser Pro Asp Phe Gln Ser Val Thr Pro Lys
1               5                   10                  15
```

Glu Lys Val Thr Ile Thr Cys Ser Ala Ser Ser Val Ser Tyr Met
            20                  25                  30

His Trp Tyr Gln Gln Lys Pro Asp Gln Ser Pro Lys Leu Leu Ile Lys
            35                  40                  45

Asp Thr Ser Asn Leu Ala Ser Gly Val Pro Ser Arg Phe Ser Gly Ser
50                  55                  60

Gly Ser Gly Thr Asp Phe Thr Leu Thr Ile Asn Ser Leu Glu Ala Glu
65                  70                  75                  80

Asp Ala Ala Thr Tyr Tyr Cys Gln Gln Trp Ser Ser Tyr Pro Pro Thr
                85                  90                  95

Phe Gly Gln Gly Thr Lys Leu Glu Ile Lys
            100                 105

<210> SEQ ID NO 429
<211> LENGTH: 107
<212> TYPE: PRT
<213> ORGANISM: Homo sapiens

<400> SEQUENCE: 429

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 430
<211> LENGTH: 8
<212> TYPE: PRT
<213> ORGANISM: Homo sapiens

<400> SEQUENCE: 430

Gly Tyr Thr Phe Thr Asp Tyr Trp
1               5

<210> SEQ ID NO 431
<211> LENGTH: 8
<212> TYPE: PRT
<213> ORGANISM: Homo sapiens

<400> SEQUENCE: 431

Ile Glu Thr Ser Leu Asn Tyr Pro
1               5

<210> SEQ ID NO 432
<211> LENGTH: 13
<212> TYPE: PRT
<213> ORGANISM: Homo sapiens

<400> SEQUENCE: 432

Ala Arg Trp Gly Ile Tyr Gly Asn Pro Trp Phe Ala Tyr

```
<210> SEQ ID NO 433
<211> LENGTH: 10
<212> TYPE: PRT
<213> ORGANISM: Homo sapiens

<400> SEQUENCE: 433

Glu Ser Val Asp Ser Tyr Val Asn Ser Phe
1               5                   10

<210> SEQ ID NO 434
<211> LENGTH: 3
<212> TYPE: PRT
<213> ORGANISM: Homo sapiens

<400> SEQUENCE: 434

Arg Ala Ser
1

<210> SEQ ID NO 435
<211> LENGTH: 9
<212> TYPE: PRT
<213> ORGANISM: Homo sapiens

<400> SEQUENCE: 435

Gln Gln Ser Asn Glu Asp Pro Tyr Thr
1               5

<210> SEQ ID NO 436
<211> LENGTH: 120
<212> TYPE: PRT
<213> ORGANISM: Homo sapiens

<400> SEQUENCE: 436

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Trp Met His Trp Val Arg Gln Ala Pro Gly Gln Gly Leu Glu Trp Met
            35                  40                  45

Gly Ala Ile Glu Thr Ser Leu Asn Tyr Pro Ser Tyr Asn Gln Lys Phe
        50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Trp Gly Ile Tyr Gly Asn Pro Trp Phe Ala Tyr Trp Gly Arg
            100                 105                 110

Gly Thr Leu Val Thr Val Ser Ser
        115                 120

<210> SEQ ID NO 437
<211> LENGTH: 330
<212> TYPE: PRT
<213> ORGANISM: Homo sapiens

<400> SEQUENCE: 437

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
```

```
                    20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
             50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 438
<211> LENGTH: 111
<212> TYPE: PRT
<213> ORGANISM: Homo sapiens

<400> SEQUENCE: 438

Asp Ile Val Met Thr Gln Thr Pro Leu Ser Leu Ser Val Thr Pro Gly
 1               5                  10                  15

Gln Pro Ala Ser Ile Ser Cys Arg Ala Ser Glu Ser Val Asp Ser Tyr
            20                  25                  30

Val Asn Ser Phe Val His Trp Tyr Leu Gln Lys Pro Gly Gln Pro Pro
        35                  40                  45

Gln Leu Leu Ile Tyr Arg Ala Ser Asn Leu Glu Ser Gly Val Pro Asp
    50                  55                  60
```

-continued

```
Arg Phe Ser Gly Ser Gly Ser Gly Thr Asp Phe Thr Leu Lys Ile Ser
 65                  70                  75                  80

Arg Val Glu Ala Glu Asp Val Gly Val Tyr Tyr Cys Gln Gln Ser Asn
                 85                  90                  95

Glu Asp Pro Tyr Thr Phe Gly Gln Gly Thr Lys Leu Glu Ile Lys
            100                 105                 110

<210> SEQ ID NO 439
<211> LENGTH: 107
<212> TYPE: PRT
<213> ORGANISM: Homo sapiens

<400> SEQUENCE: 439

Arg Thr Val Ala Ala Pro Ser Val Phe Ile Phe Pro Pro Ser Asp Glu
  1               5                  10                  15

Gln Leu Lys Ser Gly Thr Ala Ser Val Val Cys Leu Leu Asn Asn Phe
                 20                  25                  30

Tyr Pro Arg Glu Ala Lys Val Gln Trp Lys Val Asp Asn Ala Leu Gln
             35                  40                  45

Ser Gly Asn Ser Gln Glu Ser Val Thr Glu Gln Asp Ser Lys Asp Ser
         50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 440
<211> LENGTH: 8
<212> TYPE: PRT
<213> ORGANISM: Homo sapiens

<400> SEQUENCE: 440

Gly Tyr Thr Phe Thr Asn Tyr Gly
 1               5

<210> SEQ ID NO 441
<211> LENGTH: 8
<212> TYPE: PRT
<213> ORGANISM: Homo sapiens

<400> SEQUENCE: 441

Ile Asn Thr Tyr Thr Gly Glu Ser
 1               5

<210> SEQ ID NO 442
<211> LENGTH: 12
<212> TYPE: PRT
<213> ORGANISM: Homo sapiens

<400> SEQUENCE: 442

Ala Arg Asp Tyr Tyr Gly Ile Tyr Val Ser Ala Tyr
 1               5                  10

<210> SEQ ID NO 443
<211> LENGTH: 10
<212> TYPE: PRT
<213> ORGANISM: Homo sapiens

<400> SEQUENCE: 443
```

Glu Ser Val Asp Asn Tyr Ala Asn Ser Phe
1               5                   10

<210> SEQ ID NO 444
<211> LENGTH: 3
<212> TYPE: PRT
<213> ORGANISM: Homo sapiens

<400> SEQUENCE: 444

Arg Ala Ser
1

<210> SEQ ID NO 445
<211> LENGTH: 9
<212> TYPE: PRT
<213> ORGANISM: Homo sapiens

<400> SEQUENCE: 445

Gln Gln Ser His Glu Asp Pro Tyr Thr
1               5

<210> SEQ ID NO 446
<211> LENGTH: 119
<212> TYPE: PRT
<213> ORGANISM: Homo sapiens

<400> SEQUENCE: 446

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Thr Trp Val Arg Gln Ala Pro Gly Gln Gly Leu Glu Trp Met
            35                  40                  45

Gly Trp Ile Asn Thr Tyr Thr Gly Glu Ser Thr Tyr Ala Asp Asp Phe
        50                  55                  60

Lys Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg Asp Tyr Tyr Gly Ile Tyr Val Ser Ala Tyr Trp Gly Gln Gly
                100                 105                 110

Thr Leu Val Thr Val Ser Ser
            115

<210> SEQ ID NO 447
<211> LENGTH: 330
<212> TYPE: PRT
<213> ORGANISM: Homo sapiens

<400> SEQUENCE: 447

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

-continued

```
Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 448
<211> LENGTH: 111
<212> TYPE: PRT
<213> ORGANISM: Homo sapiens

<400> SEQUENCE: 448

Asp Ile Val Met Thr Gln Thr Pro Leu Ser Leu Ser Val Thr Pro Gly
1               5                   10                  15

Gln Pro Ala Ser Ile Ser Cys Arg Ala Ser Glu Ser Val Asp Asn Tyr
            20                  25                  30

Ala Asn Ser Phe Met His Trp Tyr Leu Gln Lys Pro Gly Gln Ser Pro
        35                  40                  45

Gln Leu Leu Ile Tyr Arg Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Ser His
                85                  90                  95

Glu Asp Pro Tyr Thr Phe Gly Gln Gly Thr Lys Leu Glu Ile Lys
            100                 105                 110
```

```
<210> SEQ ID NO 449
<211> LENGTH: 107
<212> TYPE: PRT
<213> ORGANISM: Homo sapiens

<400> SEQUENCE: 449

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 450
<211> LENGTH: 8
<212> TYPE: PRT
<213> ORGANISM: Homo sapiens

<400> SEQUENCE: 450

Gly Tyr Thr Phe Thr Ser His Trp
1               5

<210> SEQ ID NO 451
<211> LENGTH: 8
<212> TYPE: PRT
<213> ORGANISM: Homo sapiens

<400> SEQUENCE: 451

Ile Asn Pro Arg Asp Gly Arg Thr
1               5

<210> SEQ ID NO 452
<211> LENGTH: 16
<212> TYPE: PRT
<213> ORGANISM: Homo sapiens

<400> SEQUENCE: 452

Ala Arg Gly Asp Phe His Tyr Gly Asp Tyr Phe Trp Tyr Phe Asp Val
1               5                   10                  15

<210> SEQ ID NO 453
<211> LENGTH: 6
<212> TYPE: PRT
<213> ORGANISM: Homo sapiens

<400> SEQUENCE: 453

Gln Asn Val His Gly Ala
1               5

<210> SEQ ID NO 454
<211> LENGTH: 3
<212> TYPE: PRT
<213> ORGANISM: Homo sapiens

<400> SEQUENCE: 454
```

Met Ala Ser
1

<210> SEQ ID NO 455
<211> LENGTH: 8
<212> TYPE: PRT
<213> ORGANISM: Homo sapiens

<400> SEQUENCE: 455

Leu Gln His Trp Asn Tyr Leu Thr
1               5

<210> SEQ ID NO 456
<211> LENGTH: 123
<212> TYPE: PRT
<213> ORGANISM: Homo sapiens

<400> SEQUENCE: 456

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser His
            20                  25                  30

Trp Met His Trp Val Arg Gln Ala Pro Gly Gln Gly Leu Glu Trp Met
        35                  40                  45

Gly Glu Ile Asn Pro Arg Asp Gly Arg Thr Asn Tyr Asn Glu Lys Phe
    50                  55                  60

Lys Thr Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Asp Phe His Tyr Gly Asp Tyr Phe Trp Tyr Phe Asp Val
            100                 105                 110

Trp Gly Gln Gly Thr Leu Val Thr Val Ser Ser
        115                 120

<210> SEQ ID NO 457
<211> LENGTH: 330
<212> TYPE: PRT
<213> ORGANISM: Homo sapiens

<400> SEQUENCE: 457

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 458
<211> LENGTH: 106
<212> TYPE: PRT
<213> ORGANISM: Homo sapiens

<400> SEQUENCE: 458

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val His Gly Ala
            20                  25                  30

Val Ala Trp Tyr Gln Gln Lys Pro Gly Lys Val Pro Lys Leu Leu Ile
        35                  40                  45

Tyr Met Ala Ser Asn Arg Pro Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Leu Gln His Trp Asn Tyr Leu Thr
                85                  90                  95

Phe Gly Gln Gly Thr Lys Leu Glu Ile Lys
            100                 105

<210> SEQ ID NO 459
<211> LENGTH: 107
<212> TYPE: PRT
<213> ORGANISM: Homo sapiens

<400> SEQUENCE: 459

Arg Thr Val Ala Ala Pro Ser Val Phe Ile Phe Pro Pro Ser Asp Glu
1               5                   10                  15

-continued

```
Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 460
<211> LENGTH: 8
<212> TYPE: PRT
<213> ORGANISM: Homo sapiens

<400> SEQUENCE: 460

```
Gly Tyr Thr Phe Thr His Tyr Trp
1               5
```

<210> SEQ ID NO 461
<211> LENGTH: 8
<212> TYPE: PRT
<213> ORGANISM: Homo sapiens

<400> SEQUENCE: 461

```
Ile Tyr Pro Gly Asp Gly Asp Thr
1               5
```

<210> SEQ ID NO 462
<211> LENGTH: 10
<212> TYPE: PRT
<213> ORGANISM: Homo sapiens

<400> SEQUENCE: 462

```
Ala Arg Arg Asp Tyr Asp Tyr Gly Asp Tyr
1               5                   10
```

<210> SEQ ID NO 463
<211> LENGTH: 5
<212> TYPE: PRT
<213> ORGANISM: Homo sapiens

<400> SEQUENCE: 463

```
Ser Ser Val Ser His
1               5
```

<210> SEQ ID NO 464
<211> LENGTH: 3
<212> TYPE: PRT
<213> ORGANISM: Homo sapiens

<400> SEQUENCE: 464

```
Leu Thr Ser
1
```

<210> SEQ ID NO 465
<211> LENGTH: 9
<212> TYPE: PRT
<213> ORGANISM: Homo sapiens -continued

```
<400> SEQUENCE: 465

Gln Gln Tyr Gln Thr Tyr Pro Pro Thr
1               5

<210> SEQ ID NO 466
<211> LENGTH: 117
<212> TYPE: PRT
<213> ORGANISM: Homo sapiens

<400> SEQUENCE: 466

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr His Tyr
                20                  25                  30

Trp Ile Gln Trp Val Arg Gln Ala Pro Gly Gln Gly Leu Glu Trp Met
            35                  40                  45

Gly Ala Ile Tyr Pro Gly Asp Gly Asp Thr Arg Tyr Thr Gln Lys Phe
        50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Asp Tyr Asp Tyr Gly Asp Tyr Trp Gly Gln Gly Thr Thr
            100                 105                 110

Val Thr Val Ser Ser
        115

<210> SEQ ID NO 467
<211> LENGTH: 330
<212> TYPE: PRT
<213> ORGANISM: Homo sapiens

<400> SEQUENCE: 467

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
```

```
                180                 185                 190
His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 468
<211> LENGTH: 106
<212> TYPE: PRT
<213> ORGANISM: Homo sapiens

<400> SEQUENCE: 468

Glu Ile Val Leu Thr Gln Ser Pro Asp Phe Gln Ser Val Thr Pro Lys
1               5                   10                  15

Glu Lys Val Thr Ile Thr Cys Ser Ala Ser Ser Ser Val Ser His Met
            20                  25                  30

Tyr Trp Tyr Gln Gln Lys Pro Asp Gln Ser Pro Lys Leu Leu Ile Lys
        35                  40                  45

Leu Thr Ser Asn Leu Ala Ser Gly Val Pro Ser Arg Phe Ser Gly Ser
    50                  55                  60

Gly Ser Gly Thr Asp Phe Thr Leu Thr Ile Asn Ser Leu Glu Ala Glu
65                  70                  75                  80

Asp Ala Ala Thr Tyr Tyr Cys Gln Gln Tyr Gln Thr Tyr Pro Pro Thr
                85                  90                  95

Phe Gly Gln Gly Thr Arg Leu Glu Ile Lys
            100                 105

<210> SEQ ID NO 469
<211> LENGTH: 107
<212> TYPE: PRT
<213> ORGANISM: Homo sapiens

<400> SEQUENCE: 469

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
```

```
              65                  70                  75                  80
Lys His Lys Val Tyr Ala Cys Glu Val Thr His Gln Gly Leu Ser Ser
                    85                  90                  95

Pro Val Thr Lys Ser Phe Asn Arg Gly Glu Cys
                100                 105
```

<210> SEQ ID NO 470
<211> LENGTH: 9
<212> TYPE: PRT
<213> ORGANISM: Homo sapiens

<400> SEQUENCE: 470

```
Gly Phe Ser Ile Thr Ser Asp Phe Ala
1               5
```

<210> SEQ ID NO 471
<211> LENGTH: 7
<212> TYPE: PRT
<213> ORGANISM: Homo sapiens

<400> SEQUENCE: 471

```
Ile Thr Tyr Ser Gly Phe Thr
1               5
```

<210> SEQ ID NO 472
<211> LENGTH: 14
<212> TYPE: PRT
<213> ORGANISM: Homo sapiens

<400> SEQUENCE: 472

```
Ala Arg Gln Glu Tyr Gly Asn Tyr Val Trp Tyr Phe Asp Val
1               5                   10
```

<210> SEQ ID NO 473
<211> LENGTH: 10
<212> TYPE: PRT
<213> ORGANISM: Homo sapiens

<400> SEQUENCE: 473

```
Glu Ser Val Glu Tyr Tyr Gly Thr Ser Leu
1               5                   10
```

<210> SEQ ID NO 474
<211> LENGTH: 3
<212> TYPE: PRT
<213> ORGANISM: Homo sapiens

<400> SEQUENCE: 474

```
Ala Ala Ser
1
```

<210> SEQ ID NO 475
<211> LENGTH: 9
<212> TYPE: PRT
<213> ORGANISM: Homo sapiens

<400> SEQUENCE: 475

```
Gln Gln Ser Arg Lys Val Pro Trp Thr
1               5
```

<210> SEQ ID NO 476
<211> LENGTH: 121
<212> TYPE: PRT
<213> ORGANISM: Homo sapiens

<400> SEQUENCE: 476

Gln Val Gln Leu Gln Glu Ser Gly Pro Gly Leu Val Lys Pro Ser Glu
1               5                   10                  15

Thr Leu Ser Leu Thr Cys Ala Val Ser Gly Phe Ser Ile Thr Ser Asp
            20                  25                  30

Phe Ala Trp Asn Trp Ile Arg Gln Pro Pro Gly Lys Gly Leu Glu Trp
        35                  40                  45

Ile Gly Tyr Ile Thr Tyr Ser Gly Phe Thr Asn Tyr Asn Pro Ser Leu
    50                  55                  60

Glu Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gln Glu Tyr Gly Asn Tyr Val Trp Tyr Phe Asp Val Trp Gly
            100                 105                 110

Gln Gly Thr Leu Val Thr Val Ser Ser
        115                 120

<210> SEQ ID NO 477
<211> LENGTH: 330
<212> TYPE: PRT
<213> ORGANISM: Homo sapiens

<400> SEQUENCE: 477

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

```
Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 478
<211> LENGTH: 111
<212> TYPE: PRT
<213> ORGANISM: Homo sapiens

<400> SEQUENCE: 478

```
Asp Ile Val Met Thr Gln Thr Pro Leu Ser Leu Ser Val Thr Pro Gly
1               5                   10                  15

Gln Pro Ala Ser Ile Ser Cys Arg Ala Ser Glu Ser Val Glu Tyr Tyr
            20                  25                  30

Gly Thr Ser Leu Leu Gln Trp Tyr Leu Gln Lys Pro Gly Gln Pro Pro
        35                  40                  45

Gln Leu Leu Ile Tyr Ala Ala Ser Asn Val Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Ser Arg
                85                  90                  95

Lys Val Pro Trp Thr Phe Gly Gln Gly Thr Lys Leu Glu Ile Lys
            100                 105                 110
```

<210> SEQ ID NO 479
<211> LENGTH: 107
<212> TYPE: PRT
<213> ORGANISM: Homo sapiens

<400> SEQUENCE: 479

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 480

```
<211> LENGTH: 9
<212> TYPE: PRT
<213> ORGANISM: Homo sapiens

<400> SEQUENCE: 480

Gly Tyr Ser Ile Thr Ser Gly Tyr Phe
1               5

<210> SEQ ID NO 481
<211> LENGTH: 7
<212> TYPE: PRT
<213> ORGANISM: Homo sapiens

<400> SEQUENCE: 481

Met Gly Tyr Asp Gly Arg Ile
1               5

<210> SEQ ID NO 482
<211> LENGTH: 14
<212> TYPE: PRT
<213> ORGANISM: Homo sapiens

<400> SEQUENCE: 482

Ala Arg Glu Gly Asp Tyr Tyr Gly Ser Gly Phe Ala Tyr Trp
1               5                   10

<210> SEQ ID NO 483
<211> LENGTH: 6
<212> TYPE: PRT
<213> ORGANISM: Homo sapiens

<400> SEQUENCE: 483

Gln Asn Val Asn Thr Asn
1               5

<210> SEQ ID NO 484
<211> LENGTH: 3
<212> TYPE: PRT
<213> ORGANISM: Homo sapiens

<400> SEQUENCE: 484

Ser Ala Ser
1

<210> SEQ ID NO 485
<211> LENGTH: 120
<212> TYPE: PRT
<213> ORGANISM: Homo sapiens

<400> SEQUENCE: 485

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Thr Ser Gly
            20                  25                  30

Tyr Phe Trp Asn Trp Ile Arg Gln Pro Pro Gly Lys Gly Leu Glu Trp
        35                  40                  45

Ile Gly Tyr Met Gly Tyr Asp Gly Arg Ile Phe Tyr Ser Pro Ser Leu
    50                  55                  60

Lys Asn Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95
```

```
Ala Arg Glu Gly Asp Tyr Tyr Gly Ser Gly Phe Ala Tyr Trp Gly Gln
            100                 105                 110

Gly Thr Leu Val Thr Val Ser Ser
        115                 120

<210> SEQ ID NO 486
<211> LENGTH: 120
<212> TYPE: PRT
<213> ORGANISM: Homo sapiens

<400> SEQUENCE: 486

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Thr Ser Gly
            20                  25                  30

Tyr Phe Trp Asn Trp Ile Arg Gln Pro Pro Gly Lys Gly Leu Glu Trp
        35                  40                  45

Ile Gly Tyr Met Gly Tyr Asp Gly Arg Ile Phe Tyr Ser Pro Ser Leu
    50                  55                  60

Lys Asn Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Gly Asp Tyr Tyr Gly Ser Gly Phe Ala Tyr Trp Gly Gln
            100                 105                 110

Gly Thr Leu Val Thr Val Ser Ser
        115                 120

<210> SEQ ID NO 487
<211> LENGTH: 330
<212> TYPE: PRT
<213> ORGANISM: Homo sapiens

<400> SEQUENCE: 487

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175
```

```
Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 488
<211> LENGTH: 107
<212> TYPE: PRT
<213> ORGANISM: Homo sapiens

<400> SEQUENCE: 488

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Asn Thr Asn
            20                  25                  30

Leu Ala Trp Tyr Gln Gln Lys Pro Gly Lys Val Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Asn Asn Tyr Pro Leu
                85                  90                  95

Thr Phe Gly Gln Gly Thr Lys Leu Glu Ile Lys
            100                 105

<210> SEQ ID NO 489
<211> LENGTH: 107
<212> TYPE: PRT
<213> ORGANISM: Homo sapiens

<400> SEQUENCE: 489

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60
```

-continued

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
            85                  90                  95

Pro Val Thr Lys Ser Phe Asn Arg Gly Glu Cys
        100                 105

<210> SEQ ID NO 490
<211> LENGTH: 8
<212> TYPE: PRT
<213> ORGANISM: Homo sapiens

<400> SEQUENCE: 490

Gly Tyr Thr Phe Thr Ser Tyr Trp
1               5

<210> SEQ ID NO 491
<211> LENGTH: 8
<212> TYPE: PRT
<213> ORGANISM: Homo sapiens

<400> SEQUENCE: 491

Ile Asn Pro Ser Asn Gly Leu Thr
1               5

<210> SEQ ID NO 492
<211> LENGTH: 15
<212> TYPE: PRT
<213> ORGANISM: Homo sapiens

<400> SEQUENCE: 492

Ala Arg Ser Tyr Asp Tyr Asp Gly Asp Tyr Tyr Ala Met Asp Tyr
1               5                   10                  15

<210> SEQ ID NO 493
<211> LENGTH: 11
<212> TYPE: PRT
<213> ORGANISM: Homo sapiens

<400> SEQUENCE: 493

Gln Ser Ile Val His Ser Asn Gly Asn Thr Tyr
1               5                   10

<210> SEQ ID NO 494
<211> LENGTH: 3
<212> TYPE: PRT
<213> ORGANISM: Homo sapiens

<400> SEQUENCE: 494

Lys Val Ser
1

<210> SEQ ID NO 495
<211> LENGTH: 9
<212> TYPE: PRT
<213> ORGANISM: Homo sapiens

<400> SEQUENCE: 495

Phe Gln Ala Ser His Val Pro Trp Thr
1               5

<210> SEQ ID NO 496
<211> LENGTH: 122
<212> TYPE: PRT

<213> ORGANISM: Homo sapiens

<400> SEQUENCE: 496

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile His Trp Val Arg Gln Ala Pro Gly Gln Gly Leu Glu Trp Met
        35                  40                  45

Gly Glu Ile Asn Pro Ser Asn Gly Leu Thr Asn Tyr Asn Glu Lys Phe
    50                  55                  60

Arg Asn Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Tyr Asp Tyr Asp Gly Asp Tyr Tyr Ala Met Asp Tyr Trp
            100                 105                 110

Gly Gln Gly Thr Leu Val Thr Val Ser Ser
        115                 120

<210> SEQ ID NO 497
<211> LENGTH: 330
<212> TYPE: PRT
<213> ORGANISM: Homo sapiens

<400> SEQUENCE: 497

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu

```
                225                 230                 235                 240
Leu Thr Lys Asn Gln Val Ser Leu Thr Cys Leu Val Lys Gly Phe Tyr
                    245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 498
<211> LENGTH: 112
<212> TYPE: PRT
<213> ORGANISM: Homo sapiens

<400> SEQUENCE: 498

Asp Ile Val Met Thr Gln Ser Pro Leu Ser Leu Pro Val Thr Pro Gly
1               5                   10                  15

Glu Pro Ala Ser Ile Ser Cys Arg Ser Thr Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Ala
                85                  90                  95

Ser His Val Pro Trp Thr Phe Gly Gln Gly Thr Lys Leu Glu Ile Lys
            100                 105                 110

<210> SEQ ID NO 499
<211> LENGTH: 107
<212> TYPE: PRT
<213> ORGANISM: Homo sapiens

<400> SEQUENCE: 499

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

```
<210> SEQ ID NO 500
<211> LENGTH: 8
<212> TYPE: PRT
<213> ORGANISM: Homo sapiens

<400> SEQUENCE: 500

Gly Tyr Pro Phe Thr Gly Tyr Phe
1               5

<210> SEQ ID NO 501
<211> LENGTH: 8
<212> TYPE: PRT
<213> ORGANISM: Homo sapiens

<400> SEQUENCE: 501

Ile Asn Pro Tyr Asn Gly Gly Thr
1               5

<210> SEQ ID NO 502
<211> LENGTH: 12
<212> TYPE: PRT
<213> ORGANISM: Homo sapiens

<400> SEQUENCE: 502

Ala Arg Trp Thr Phe Asp Gly Leu Phe Met Asp Tyr
1               5                   10

<210> SEQ ID NO 503
<211> LENGTH: 10
<212> TYPE: PRT
<213> ORGANISM: Homo sapiens

<400> SEQUENCE: 503

Glu Asn Val Asp Lys Tyr Gly Ile Ser Phe
1               5                   10

<210> SEQ ID NO 504
<211> LENGTH: 3
<212> TYPE: PRT
<213> ORGANISM: Homo sapiens

<400> SEQUENCE: 504

Ala Thr Ser
1

<210> SEQ ID NO 505
<211> LENGTH: 9
<212> TYPE: PRT
<213> ORGANISM: Homo sapiens

<400> SEQUENCE: 505

Gln Gln Ser Lys Glu Asp Pro Tyr Thr
1               5

<210> SEQ ID NO 506
<211> LENGTH: 119
<212> TYPE: PRT
<213> ORGANISM: Homo sapiens

<400> SEQUENCE: 506

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Pro Phe Thr Gly Tyr
            20                  25                  30
```

```
Phe Met His Trp Val Arg Gln Ala Pro Gly Gln Gly Leu Glu Trp Met
         35                  40                  45

Gly Arg Ile Asn Pro Tyr Asn Gly Gly Thr Val Tyr Asn Gln Asn Phe
 50                  55                  60

Asn Asp Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Trp Thr Phe Asp Gly Leu Phe Met Asp Tyr Trp Gly Gln Gly
             100                 105                 110

Thr Thr Val Thr Val Ser Ser
             115
```

<210> SEQ ID NO 507
<211> LENGTH: 330
<212> TYPE: PRT
<213> ORGANISM: Homo sapiens

<400> SEQUENCE: 507

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
             100                 105                 110

Pro Ala Pro Glu Leu Leu Gly Gly Pro Ser Val Phe Leu Phe Pro Pro
         115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
            290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 508
<211> LENGTH: 111
<212> TYPE: PRT
<213> ORGANISM: Homo sapiens

<400> SEQUENCE: 508

Asp Val Val Met Thr Gln Ser Pro Leu Ser Leu Pro Val Thr Leu Gly
1               5                   10                  15
Gln Pro Ala Ser Ile Ser Cys Arg Ala Ser Glu Asn Val Asp Lys Tyr
            20                  25                  30
Gly Ile Ser Phe Met Asn Trp Phe Gln Gln Arg Pro Gly Gln Ser Pro
        35                  40                  45
Arg Arg Leu Ile Tyr Ala Thr Ser Asn Gln Gly Ser Gly Val Pro Asp
50                  55                  60
Arg Phe Ser Gly Ser Gly Ser Gly Thr Asp Phe Thr Leu Lys Ile Ser
65                  70                  75                  80
Arg Val Glu Ala Glu Asp Val Gly Val Tyr Tyr Cys Gln Gln Ser Lys
                85                  90                  95
Glu Asp Pro Tyr Thr Phe Gly Gln Gly Thr Lys Leu Glu Ile Lys
            100                 105                 110

<210> SEQ ID NO 509
<211> LENGTH: 107
<212> TYPE: PRT
<213> ORGANISM: Homo sapiens

<400> SEQUENCE: 509

Arg Thr Val Ala Ala Pro Ser Val Phe Ile Phe Pro Pro Ser Asp Glu
1               5                   10                  15
Gln Leu Lys Ser Gly Thr Ala Ser Val Val Cys Leu Leu Asn Asn Phe
            20                  25                  30
Tyr Pro Arg Glu Ala Lys Val Gln Trp Lys Val Asp Asn Ala Leu Gln
        35                  40                  45
Ser Gly Asn Ser Gln Glu Ser Val Thr Glu Gln Asp Ser Lys Asp Ser
50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
                85                  90                  95
Pro Val Thr Lys Ser Phe Asn Arg Gly Glu Cys
            100                 105

<210> SEQ ID NO 510
<211> LENGTH: 8
<212> TYPE: PRT
<213> ORGANISM: Homo sapiens

<400> SEQUENCE: 510

Asp Tyr Ile Phe Ser Ser Tyr Trp
1               5
```

```
<210> SEQ ID NO 511
<211> LENGTH: 8
<212> TYPE: PRT
<213> ORGANISM: Homo sapiens

<400> SEQUENCE: 511

Ile Phe Pro Gly Ser Gly Gly Thr
1               5

<210> SEQ ID NO 512
<211> LENGTH: 15
<212> TYPE: PRT
<213> ORGANISM: Homo sapiens

<400> SEQUENCE: 512

Ala Arg Ala Ile Tyr Tyr Asp Tyr Asp Met Tyr Tyr Phe Asp Ser
1               5                   10                  15

<210> SEQ ID NO 513
<211> LENGTH: 6
<212> TYPE: PRT
<213> ORGANISM: Homo sapiens

<400> SEQUENCE: 513

Gln Asp Ile Ser Ser Tyr
1               5

<210> SEQ ID NO 514
<211> LENGTH: 3
<212> TYPE: PRT
<213> ORGANISM: Homo sapiens

<400> SEQUENCE: 514

Tyr Thr Ser
1

<210> SEQ ID NO 515
<211> LENGTH: 9
<212> TYPE: PRT
<213> ORGANISM: Homo sapiens

<400> SEQUENCE: 515

Gln His Val Asn Thr Leu Pro Trp Thr
1               5

<210> SEQ ID NO 516
<211> LENGTH: 122
<212> TYPE: PRT
<213> ORGANISM: Homo sapiens

<400> SEQUENCE: 516

Gln Val Gln Leu Val Gln Ser Gly Ala Glu Val Lys Lys Pro Gly Ala
1               5                   10                  15

Ser Val Lys Val Ser Cys Lys Ala Ser Asp Tyr Ile Phe Ser Ser Tyr
                20                  25                  30

Trp Ile Gln Trp Val Arg Gln Ala Pro Gly Gln Gly Leu Glu Trp Met
            35                  40                  45

Gly Glu Ile Phe Pro Gly Ser Gly Gly Thr Asn Tyr Asn Glu Lys Phe
        50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
```

```
                        85                  90                  95
Ala Arg Ala Ile Tyr Tyr Asp Tyr Asp Met Tyr Tyr Phe Asp Ser Trp
                    100                 105                 110

Gly Gln Gly Thr Thr Val Thr Val Ser Ser
                115                 120

<210> SEQ ID NO 517
<211> LENGTH: 330
<212> TYPE: PRT
<213> ORGANISM: Homo sapiens

<400> SEQUENCE: 517

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 518
<211> LENGTH: 107
<212> TYPE: PRT
<213> ORGANISM: Homo sapiens

<400> SEQUENCE: 518

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Val Pro Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln His Val Asn Thr Leu Pro Trp
                85                  90                  95

Thr Phe Gly Gln Gly Thr Lys Leu Glu Ile Lys
            100                 105
```

<210> SEQ ID NO 519
<211> LENGTH: 107
<212> TYPE: PRT
<213> ORGANISM: Homo sapiens

<400> SEQUENCE: 519

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 520
<211> LENGTH: 8
<212> TYPE: PRT
<213> ORGANISM: Homo sapiens

<400> SEQUENCE: 520

```
Gly Tyr Thr Phe Thr Asp Tyr Thr
1               5
```

<210> SEQ ID NO 521
<211> LENGTH: 8
<212> TYPE: PRT
<213> ORGANISM: Homo sapiens

<400> SEQUENCE: 521

```
Ile Asn Pro Tyr Asn Gly Gly Thr
1               5
```

<210> SEQ ID NO 522
<211> LENGTH: 13
<212> TYPE: PRT
<213> ORGANISM: Homo sapiens

<400> SEQUENCE: 522

Ala Arg His Tyr Gly Asn Tyr Asn Trp Tyr Phe Asp Val
1               5                   10

<210> SEQ ID NO 523
<211> LENGTH: 6
<212> TYPE: PRT
<213> ORGANISM: Homo sapiens

<400> SEQUENCE: 523

Gln Tyr Val Asn Thr Ala
1               5

<210> SEQ ID NO 524
<211> LENGTH: 3
<212> TYPE: PRT
<213> ORGANISM: Homo sapiens

<400> SEQUENCE: 524

Ser Ala Ser
1

<210> SEQ ID NO 525
<211> LENGTH: 9
<212> TYPE: PRT
<213> ORGANISM: Homo sapiens

<400> SEQUENCE: 525

Gln Gln His Phe Thr Thr Pro Ile Thr
1               5

<210> SEQ ID NO 526
<211> LENGTH: 120
<212> TYPE: PRT
<213> ORGANISM: Homo sapiens

<400> SEQUENCE: 526

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Thr Met Asn Trp Val Arg Gln Ala Pro Gly Gln Arg Leu Glu Trp Met
        35                  40                  45

Gly Leu Ile Asn Pro Tyr Asn Gly Gly Thr Thr Tyr Asn Gln Lys Phe
    50                  55                  60

Lys Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Tyr Gly Asn Tyr Asn Trp Tyr Phe Asp Val Trp Gly Gln
            100                 105                 110

Gly Thr Thr Val Thr Val Ser Ser
        115                 120

<210> SEQ ID NO 527

```
<211> LENGTH: 330
<212> TYPE: PRT
<213> ORGANISM: Homo sapiens

<400> SEQUENCE: 527

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 528
<211> LENGTH: 107
<212> TYPE: PRT
<213> ORGANISM: Homo sapiens

<400> SEQUENCE: 528

Asp Ile Gln Leu Thr Gln Ser Pro Ser Phe Leu Ser Ala Ser Val Gly
1               5                   10                  15
```

```
Asp Arg Val Thr Ile Thr Cys Lys Ala Ser Gln Tyr Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln His Phe Thr Thr Pro Ile
                85                  90                  95

Thr Phe Gly Gln Gly Thr Lys Leu Glu Ile Lys
            100                 105
```

<210> SEQ ID NO 529
<211> LENGTH: 107
<212> TYPE: PRT
<213> ORGANISM: Homo sapiens

<400> SEQUENCE: 529

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 530
<211> LENGTH: 8
<212> TYPE: PRT
<213> ORGANISM: Homo sapiens

<400> SEQUENCE: 530

```
Gly Tyr Thr Phe Thr Asn Tyr Gly
1               5
```

<210> SEQ ID NO 531
<211> LENGTH: 8
<212> TYPE: PRT
<213> ORGANISM: Homo sapiens

<400> SEQUENCE: 531

```
Ile Asn Thr Tyr Thr Gly Glu Pro
1               5
```

<210> SEQ ID NO 532
<211> LENGTH: 10
<212> TYPE: PRT
<213> ORGANISM: Homo sapiens

<400> SEQUENCE: 532

```
Ala Arg Asn Tyr Gly Asn Tyr Val Ala Tyr
```

<210> SEQ ID NO 533
<211> LENGTH: 6
<212> TYPE: PRT
<213> ORGANISM: Homo sapiens

<400> SEQUENCE: 533

Gln Asp Ile Asn Ser Tyr
1               5

<210> SEQ ID NO 534
<211> LENGTH: 3
<212> TYPE: PRT
<213> ORGANISM: Homo sapiens

<400> SEQUENCE: 534

Arg Ala Asn
1

<210> SEQ ID NO 535
<211> LENGTH: 9
<212> TYPE: PRT
<213> ORGANISM: Homo sapiens

<400> SEQUENCE: 535

Leu Gln Tyr Asp Glu Phe Pro Leu Thr
1               5

<210> SEQ ID NO 536
<211> LENGTH: 117
<212> TYPE: PRT
<213> ORGANISM: Homo sapiens

<400> SEQUENCE: 536

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Arg Gln Ala Pro Gly Gln Gly Leu Glu Trp Met
            35                  40                  45

Gly Trp Ile Asn Thr Tyr Thr Gly Glu Pro Thr Tyr Ala Asp Asp Phe
    50                  55                  60

Lys Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg Asn Tyr Gly Asn Tyr Val Ala Tyr Trp Gly Gln Gly Thr Thr
            100                 105                 110

Val Thr Val Ser Ser
        115

<210> SEQ ID NO 537
<211> LENGTH: 330
<212> TYPE: PRT
<213> ORGANISM: Homo sapiens

<400> SEQUENCE: 537

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr

```
            20                  25                  30
Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 538
<211> LENGTH: 107
<212> TYPE: PRT
<213> ORGANISM: Homo sapiens

<400> SEQUENCE: 538

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Ser Leu Ile
        35                  40                  45

Tyr Arg Ala Asn Arg Leu Val Asp Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Tyr Asp Glu Phe Pro Leu
                 85                  90                  95

Thr Phe Gly Gln Gly Thr Arg Leu Glu Ile Lys
            100                 105
```

<210> SEQ ID NO 539
<211> LENGTH: 107
<212> TYPE: PRT
<213> ORGANISM: Homo sapiens

<400> SEQUENCE: 539

```
Arg Thr Val Ala Ala Pro Ser Val Phe Ile Phe Pro Pro Ser Asp Glu
  1               5                  10                  15

Gln Leu Lys Ser Gly Thr Ala Ser Val Val Cys Leu Leu Asn Asn Phe
                 20                  25                  30

Tyr Pro Arg Glu Ala Lys Val Gln Trp Lys Val Asp Asn Ala Leu Gln
             35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105
```

<210> SEQ ID NO 540
<211> LENGTH: 8
<212> TYPE: PRT
<213> ORGANISM: Homo sapiens

<400> SEQUENCE: 540

```
Gly Tyr Thr Phe Ser Asn Tyr Trp
  1               5
```

<210> SEQ ID NO 541
<211> LENGTH: 8
<212> TYPE: PRT
<213> ORGANISM: Homo sapiens

<400> SEQUENCE: 541

```
Ile Leu Pro Gly Ser Gly Asn Val
  1               5
```

<210> SEQ ID NO 542
<211> LENGTH: 16
<212> TYPE: PRT
<213> ORGANISM: Homo sapiens

<400> SEQUENCE: 542

```
Ala Thr Pro Pro His Tyr Tyr Gly Tyr Asp Tyr Tyr Asp Val Asn Tyr
  1               5                  10                  15
```

<210> SEQ ID NO 543
<211> LENGTH: 11
<212> TYPE: PRT
<213> ORGANISM: Homo sapiens

<400> SEQUENCE: 543

```
Gln Ser Leu Leu Asp Ser Asp Gly Lys Thr Tyr
1               5                   10
```

<210> SEQ ID NO 544
<211> LENGTH: 3
<212> TYPE: PRT
<213> ORGANISM: Homo sapiens

<400> SEQUENCE: 544

```
Leu Val Ser
1
```

<210> SEQ ID NO 545
<211> LENGTH: 9
<212> TYPE: PRT
<213> ORGANISM: Homo sapiens

<400> SEQUENCE: 545

```
Trp Gln Gly Thr His Phe Pro Gln Thr
1               5
```

<210> SEQ ID NO 546
<211> LENGTH: 123
<212> TYPE: PRT
<213> ORGANISM: Homo sapiens

<400> SEQUENCE: 546

```
Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Ser Asn Tyr
            20                  25                  30

Trp Ile Glu Trp Val Gln Gln Ala Pro Gly Lys Gly Leu Glu Trp Met
        35                  40                  45

Gly Glu Ile Leu Pro Gly Ser Gly Asn Val His Tyr Asn Glu Lys Phe
    50                  55                  60

Lys Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Pro Pro His Tyr Tyr Gly Tyr Asp Tyr Tyr Asp Val Asn Tyr
            100                 105                 110

Trp Gly Gln Gly Thr Leu Val Thr Val Ser Ser
        115                 120
```

<210> SEQ ID NO 547
<211> LENGTH: 330
<212> TYPE: PRT
<213> ORGANISM: Homo sapiens

<400> SEQUENCE: 547

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80
```

Tyr Ile Cys Asn Val Asn His Lys Pro Ser Asn Thr Lys Val Asp Lys
              85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 548
<211> LENGTH: 112
<212> TYPE: PRT
<213> ORGANISM: Homo sapiens

<400> SEQUENCE: 548

Asp Val Val Met Thr Gln Ser Pro Leu Ser Leu Pro Val Thr Leu Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Arg Arg Leu Ile Tyr Leu Val Ser Glu Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Gln Thr Phe Gly Gln Gly Thr Lys Leu Glu Ile Lys
            100                 105                 110

```
<210> SEQ ID NO 549
<211> LENGTH: 107
<212> TYPE: PRT
<213> ORGANISM: Homo sapiens

<400> SEQUENCE: 549

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 550
<211> LENGTH: 8
<212> TYPE: PRT
<213> ORGANISM: Homo sapiens

<400> SEQUENCE: 550

Gly Tyr Val Phe Ser Arg Ser Trp
1               5

<210> SEQ ID NO 551
<211> LENGTH: 8
<212> TYPE: PRT
<213> ORGANISM: Homo sapiens

<400> SEQUENCE: 551

Ile Tyr Pro Gly Asp Gly Asp Thr
1               5

<210> SEQ ID NO 552
<211> LENGTH: 6
<212> TYPE: PRT
<213> ORGANISM: Homo sapiens

<400> SEQUENCE: 552

Ala Ala Arg Trp Phe Leu
1               5

<210> SEQ ID NO 553
<211> LENGTH: 12
<212> TYPE: PRT
<213> ORGANISM: Homo sapiens

<400> SEQUENCE: 553

Gln Ser Leu Leu Asn Ser Gly Asp Gln Lys Ser Tyr
1               5                   10

<210> SEQ ID NO 554
<211> LENGTH: 3
<212> TYPE: PRT
<213> ORGANISM: Homo sapiens

<400> SEQUENCE: 554
```

```
Gly Ala Ser
1

<210> SEQ ID NO 555
<211> LENGTH: 9
<212> TYPE: PRT
<213> ORGANISM: Homo sapiens

<400> SEQUENCE: 555

Gln Asn Asp His Ser Tyr Pro Leu Thr
1               5

<210> SEQ ID NO 556
<211> LENGTH: 113
<212> TYPE: PRT
<213> ORGANISM: Homo sapiens

<400> SEQUENCE: 556

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Val Phe Ser Arg Ser
                20                  25                  30

Trp Ile Asn Trp Val Arg Gln Ala Pro Gly Gln Gly Leu Glu Trp Met
            35                  40                  45

Gly Arg Ile Tyr Pro Gly Asp Gly Asp Thr Asn Tyr Asn Gly Lys Phe
        50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Trp Phe Leu Trp Gly Gln Gly Thr Leu Val Thr Val Ser
            100                 105                 110

Ser

<210> SEQ ID NO 557
<211> LENGTH: 330
<212> TYPE: PRT
<213> ORGANISM: Homo sapiens

<400> SEQUENCE: 557

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
```

-continued

```
                130                 135                 140
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 558
<211> LENGTH: 113
<212> TYPE: PRT
<213> ORGANISM: Homo sapiens

<400> SEQUENCE: 558

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Asp Gln Lys Ser Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp His Ser Tyr Pro Leu Thr Phe Gly Gln Gly Thr Lys Leu Glu Ile
            100                 105                 110

Lys

<210> SEQ ID NO 559
<211> LENGTH: 107
<212> TYPE: PRT
<213> ORGANISM: Homo sapiens

<400> SEQUENCE: 559

Arg Thr Val Ala Ala Pro Ser Val Phe Ile Phe Pro Pro Ser Asp Glu
1               5                   10                  15
```

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
                35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 560
<211> LENGTH: 8
<212> TYPE: PRT
<213> ORGANISM: Homo sapiens

<400> SEQUENCE: 560

Gly Phe Thr Phe Ser Ser Tyr Ala
1               5

<210> SEQ ID NO 561
<211> LENGTH: 8
<212> TYPE: PRT
<213> ORGANISM: Homo sapiens

<400> SEQUENCE: 561

Ile Ser Ser Gly Gly Ser His Thr
1               5

<210> SEQ ID NO 562
<211> LENGTH: 11
<212> TYPE: PRT
<213> ORGANISM: Homo sapiens

<400> SEQUENCE: 562

Ala Arg Arg Gly Asn Leu Tyr Asp Gly Pro Tyr
1               5                   10

<210> SEQ ID NO 563
<211> LENGTH: 5
<212> TYPE: PRT
<213> ORGANISM: Homo sapiens

<400> SEQUENCE: 563

Ser Ser Val Ser His
1               5

<210> SEQ ID NO 564
<211> LENGTH: 3
<212> TYPE: PRT
<213> ORGANISM: Homo sapiens

<400> SEQUENCE: 564

Asp Thr Ser
1

<210> SEQ ID NO 565
<211> LENGTH: 9
<212> TYPE: PRT
<213> ORGANISM: Homo sapiens

<400> SEQUENCE: 565

Gln Gln Trp Asn Phe Tyr Pro Phe Thr
1               5

<210> SEQ ID NO 566
<211> LENGTH: 118
<212> TYPE: PRT
<213> ORGANISM: Homo sapiens

<400> SEQUENCE: 566

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Glu Ile Ser Ser Gly Gly Ser His Thr Tyr Tyr Pro Asp Thr Val
    50                  55                  60

Thr Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Arg Gly Asn Leu Tyr Asp Gly Pro Tyr Trp Gly Gln Gly Thr
            100                 105                 110

Leu Val Thr Val Ser Ser
        115

<210> SEQ ID NO 567
<211> LENGTH: 330
<212> TYPE: PRT
<213> ORGANISM: Homo sapiens

<400> SEQUENCE: 567

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

```
Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 568
<211> LENGTH: 106
<212> TYPE: PRT
<213> ORGANISM: Homo sapiens

<400> SEQUENCE: 568

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Val Ser His Met
            20                  25                  30

Tyr Trp Tyr Gln Gln Lys Pro Gly Gln Ala Pro Arg Leu Leu Ile Tyr
            35                  40                  45

Asp Thr Ser Lys Leu Ala Ser Gly Ile Pro Ala Arg Phe Ser Gly Ser
        50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Trp Asn Phe Tyr Pro Phe Thr
                85                  90                  95

Phe Gly Gln Gly Thr Lys Leu Glu Ile Lys
            100                 105

<210> SEQ ID NO 569
<211> LENGTH: 107
<212> TYPE: PRT
<213> ORGANISM: Homo sapiens

<400> SEQUENCE: 569

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60
```

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 570
<211> LENGTH: 8
<212> TYPE: PRT
<213> ORGANISM: Homo sapiens

<400> SEQUENCE: 570

Gly Tyr Thr Phe Thr Asp Tyr Val
1               5

<210> SEQ ID NO 571
<211> LENGTH: 8
<212> TYPE: PRT
<213> ORGANISM: Homo sapiens

<400> SEQUENCE: 571

Ile Tyr Pro Gly Ser Gly Asn Thr
1               5

<210> SEQ ID NO 572
<211> LENGTH: 10
<212> TYPE: PRT
<213> ORGANISM: Homo sapiens

<400> SEQUENCE: 572

Ala Arg Val Leu Val Ser Val Met Asp Tyr
1               5                   10

<210> SEQ ID NO 573
<211> LENGTH: 5
<212> TYPE: PRT
<213> ORGANISM: Homo sapiens

<400> SEQUENCE: 573

Ser Ser Ile Asn Tyr
1               5

<210> SEQ ID NO 574
<211> LENGTH: 3
<212> TYPE: PRT
<213> ORGANISM: Homo sapiens

<400> SEQUENCE: 574

Asp Thr Ser
1

<210> SEQ ID NO 575
<211> LENGTH: 9
<212> TYPE: PRT
<213> ORGANISM: Homo sapiens

<400> SEQUENCE: 575

His Gln Arg Ser Ser Tyr Pro Trp Thr
1               5

<210> SEQ ID NO 576
<211> LENGTH: 117
<212> TYPE: PRT

<213> ORGANISM: Homo sapiens

<400> SEQUENCE: 576

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Val Ile Ser Trp Val Arg Gln Ala Pro Gly Gln Gly Leu Glu Trp Met
        35                  40                  45

Gly Glu Ile Tyr Pro Gly Ser Gly Asn Thr Tyr Tyr Glu Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Val Leu Val Ser Val Met Asp Tyr Trp Gly Gln Gly Thr Leu
            100                 105                 110

Val Thr Val Ser Ser
            115

<210> SEQ ID NO 577
<211> LENGTH: 330
<212> TYPE: PRT
<213> ORGANISM: Homo sapiens

<400> SEQUENCE: 577

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu

```
                225                 230                 235                 240
Leu Thr Lys Asn Gln Val Ser Leu Thr Cys Leu Val Lys Gly Phe Tyr
                    245                 250                 255

Pro Ser Asp Ile Ala Val Glu Trp Glu Ser Asn Gly Gln Pro Glu Asn
                    260                 265                 270

Asn Tyr Lys Thr Thr Pro Pro Val Leu Asp Ser Asp Gly Ser Phe Phe
                    275                 280                 285

Leu Tyr Ser Lys Leu Thr Val Asp Lys Ser Arg Trp Gln Gln Gly Asn
                    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                    325                 330

<210> SEQ ID NO 578
<211> LENGTH: 106
<212> TYPE: PRT
<213> ORGANISM: Homo sapiens

<400> SEQUENCE: 578

Glu Ile Val Leu Thr Gln Ser Pro Asp Phe Gln Ser Val Thr Pro Lys
1               5                   10                  15

Glu Lys Val Thr Ile Thr Cys Ser Ala Ser Ser Ser Ile Asn Tyr Ile
                20                  25                  30

Thr Trp Tyr Gln Gln Lys Pro Asp Gln Ser Pro Lys Leu Leu Ile Lys
            35                  40                  45

Asp Thr Ser Lys Leu Ala Ser Gly Val Pro Ser Arg Phe Ser Gly Ser
        50                  55                  60

Gly Ser Gly Thr Asp Phe Thr Leu Thr Ile Asn Ser Leu Glu Ala Glu
65                  70                  75                  80

Asp Ala Ala Thr Tyr Tyr Cys His Gln Arg Ser Ser Tyr Pro Trp Thr
                85                  90                  95

Phe Gly Gln Gly Thr Arg Leu Glu Ile Lys
                100                 105

<210> SEQ ID NO 579
<211> LENGTH: 107
<212> TYPE: PRT
<213> ORGANISM: Homo sapiens

<400> SEQUENCE: 579

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
                20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
        50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105
```

```
<210> SEQ ID NO 580
<211> LENGTH: 8
<212> TYPE: PRT
<213> ORGANISM: Homo sapiens

<400> SEQUENCE: 580

Gly Tyr Ile Phe Thr Asp Tyr Asn
1               5

<210> SEQ ID NO 581
<211> LENGTH: 8
<212> TYPE: PRT
<213> ORGANISM: Homo sapiens

<400> SEQUENCE: 581

Ile Asn Pro Lys Tyr Asp Ser Thr
1               5

<210> SEQ ID NO 582
<211> LENGTH: 10
<212> TYPE: PRT
<213> ORGANISM: Homo sapiens

<400> SEQUENCE: 582

Ala Ala Asp Gly Ser Ser Ala Met Asp Tyr
1               5                   10

<210> SEQ ID NO 583
<211> LENGTH: 12
<212> TYPE: PRT
<213> ORGANISM: Homo sapiens

<400> SEQUENCE: 583

Gln Ser Leu Leu Asn Ser Gly His Gln Lys Asn Tyr
1               5                   10

<210> SEQ ID NO 584
<211> LENGTH: 3
<212> TYPE: PRT
<213> ORGANISM: Homo sapiens

<400> SEQUENCE: 584

Gly Ala Ser
1

<210> SEQ ID NO 585
<211> LENGTH: 9
<212> TYPE: PRT
<213> ORGANISM: Homo sapiens

<400> SEQUENCE: 585

Gln Asn Asp His Arg Tyr Pro Leu Thr
1               5

<210> SEQ ID NO 586
<211> LENGTH: 117
<212> TYPE: PRT
<213> ORGANISM: Homo sapiens

<400> SEQUENCE: 586

Gln Met Gln Leu Val Gln Ser Gly Pro Glu Val Lys Lys Pro Gly Thr
1               5                   10                  15

Ser Val Lys Val Ser Cys Lys Ala Ser Gly Tyr Ile Phe Thr Asp Tyr
            20                  25                  30
```

```
Asn Ile Asp Trp Val Arg Gln Ala Arg Gly Gln Arg Leu Glu Trp Ile
            35                  40                  45
Gly Asp Ile Asn Pro Lys Tyr Asp Ser Thr Arg Tyr Asn Gln Lys Phe
 50                  55                  60
Lys Gly Arg Val Thr Ile Thr Arg Asp Met Ser Thr Ser Thr Ala Tyr
 65                  70                  75                  80
Met Glu Leu Ser Ser Leu Arg Ser Glu Asp Thr Ala Val Tyr Tyr Cys
                85                  90                  95
Ala Ala Asp Gly Ser Ser Ala Met Asp Tyr Trp Gly Gln Gly Thr Thr
                100                 105                 110
Val Thr Val Ser Ser
        115

<210> SEQ ID NO 587
<211> LENGTH: 330
<212> TYPE: PRT
<213> ORGANISM: Homo sapiens

<400> SEQUENCE: 587

Ala Ser Thr Lys Gly Pro Ser Val Phe Pro Leu Ala Pro Ser Ser Lys
 1               5                  10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
 50                  55                  60
Leu Ser Ser Val Val Thr Val Pro Ser Ser Ser Leu Gly Thr Gln Thr
 65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
                100                 105                 110
Pro Ala Pro Glu Leu Leu Gly Gly Pro Ser Val Phe Leu Phe Pro Pro
            115                 120                 125
Lys Pro Lys Asp Thr Leu Met Ile Ser Arg Thr Pro Glu Val Thr Cys
130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
                180                 185                 190
His Gln Asp Trp Leu Asn Gly Lys Glu Tyr Lys Cys Lys Val Ser Asn
            195                 200                 205
Lys Ala Leu Pro Ala Pro Ile Glu Lys Thr Ile Ser Lys Ala Lys Gly
210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
                260                 265                 270
Asn Tyr Lys Thr Thr Pro Pro Val Leu Asp Ser Asp Gly Ser Phe Phe
            275                 280                 285
```

```
Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 588
<211> LENGTH: 113
<212> TYPE: PRT
<213> ORGANISM: Homo sapiens

<400> SEQUENCE: 588

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly His Gln Lys Asn Tyr Leu Ala Trp Tyr Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp His Arg Tyr Pro Leu Thr Phe Gly Gln Gly Thr Lys Leu Glu Ile
            100                 105                 110

Lys

<210> SEQ ID NO 589
<211> LENGTH: 107
<212> TYPE: PRT
<213> ORGANISM: Homo sapiens

<400> SEQUENCE: 589

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 590
<211> LENGTH: 8
<212> TYPE: PRT
<213> ORGANISM: Homo sapiens

<400> SEQUENCE: 590

Gly Phe Asn Ile Lys Asp Tyr Tyr
```

-continued

<210> SEQ ID NO 591
<211> LENGTH: 8
<212> TYPE: PRT
<213> ORGANISM: Homo sapiens

<400> SEQUENCE: 591

Ile Asp Pro Glu Asn Gly Asn Thr
1               5

<210> SEQ ID NO 592
<211> LENGTH: 10
<212> TYPE: PRT
<213> ORGANISM: Homo sapiens

<400> SEQUENCE: 592

Ala Arg Asp Tyr Gly Tyr Phe Asp Tyr Trp
1               5                   10

<210> SEQ ID NO 593
<211> LENGTH: 5
<212> TYPE: PRT
<213> ORGANISM: Homo sapiens

<400> SEQUENCE: 593

Ser Ser Val Ile Tyr
1               5

<210> SEQ ID NO 594
<211> LENGTH: 3
<212> TYPE: PRT
<213> ORGANISM: Homo sapiens

<400> SEQUENCE: 594

Ser Thr Ser
1

<210> SEQ ID NO 595
<211> LENGTH: 9
<212> TYPE: PRT
<213> ORGANISM: Homo sapiens

<400> SEQUENCE: 595

Gln Gln Arg Ser Ser Tyr Pro His Thr
1               5

<210> SEQ ID NO 596
<211> LENGTH: 116
<212> TYPE: PRT
<213> ORGANISM: Homo sapiens

<400> SEQUENCE: 596

Gln Val Gln Leu Val Gln Ser Gly Ala Glu Val Lys Lys Pro Gly Ser
1               5                   10                  15

Ser Val Lys Val Ser Cys Lys Ala Ser Gly Phe Asn Ile Lys Asp Tyr
            20                  25                  30

Tyr Ile His Trp Val Arg Gln Ala Pro Gly Gln Gly Leu Glu Trp Met
        35                  40                  45

Gly Trp Ile Asp Pro Glu Asn Gly Asn Thr Ile Tyr Asp Pro Lys Phe
    50                  55                  60

Gln Gly Arg Val Thr Ile Thr Ala Asp Glu Ser Thr Ser Thr Ala Tyr
65                  70                  75                  80

```
Met Glu Leu Ser Ser Leu Arg Ser Glu Asp Thr Ala Val Tyr Tyr Cys
                85                  90                  95

Ala Arg Asp Tyr Gly Tyr Phe Asp Tyr Trp Gly Gln Gly Thr Leu Val
            100                 105                 110

Thr Val Ser Ser
        115

<210> SEQ ID NO 597
<211> LENGTH: 330
<212> TYPE: PRT
<213> ORGANISM: Homo sapiens

<400> SEQUENCE: 597

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 598
<211> LENGTH: 106
<212> TYPE: PRT
<213> ORGANISM: Homo sapiens

<400> SEQUENCE: 598

Asp Val Val Met Thr Gln Ser Pro Ala Phe Leu Ser Val Thr Pro Gly
1               5                   10                  15

Glu Lys Val Thr Ile Thr Cys Ser Ala Gly Ser Ser Val Ile Tyr Met
            20                  25                  30

Tyr Trp Tyr Gln Gln Lys Pro Asp Gln Ala Pro Lys Leu Leu Ile Lys
        35                  40                  45

Ser Thr Ser Asn Leu Ala Ser Gly Val Pro Ser Arg Phe Ser Gly Ser
    50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln Arg Ser Ser Tyr Pro His Thr
                85                  90                  95

Phe Gly Gln Gly Thr Lys Leu Glu Ile Lys
            100                 105

<210> SEQ ID NO 599
<211> LENGTH: 107
<212> TYPE: PRT
<213> ORGANISM: Homo sapiens

<400> SEQUENCE: 599

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 600
<211> LENGTH: 8
<212> TYPE: PRT
<213> ORGANISM: Homo sapiens

<400> SEQUENCE: 600

Gly Tyr Thr Phe Thr Asp Tyr Trp
1               5

<210> SEQ ID NO 601
<211> LENGTH: 8
<212> TYPE: PRT
<213> ORGANISM: Homo sapiens

<400> SEQUENCE: 601

Ile Tyr Pro Ser His Ser Tyr Thr
1               5

<210> SEQ ID NO 602
<211> LENGTH: 14
<212> TYPE: PRT
<213> ORGANISM: Homo sapiens

<400> SEQUENCE: 602

Ala Arg Gly Gly Tyr Arg Tyr Pro Tyr Tyr Ala Met Asp Tyr
1               5                   10

<210> SEQ ID NO 603
<211> LENGTH: 6
<212> TYPE: PRT
<213> ORGANISM: Homo sapiens

<400> SEQUENCE: 603

Glu Asn Ile Tyr Gly Ala
1               5

<210> SEQ ID NO 604
<211> LENGTH: 3
<212> TYPE: PRT
<213> ORGANISM: Homo sapiens

<400> SEQUENCE: 604

Gly Ala Thr
1

<210> SEQ ID NO 605
<211> LENGTH: 9
<212> TYPE: PRT
<213> ORGANISM: Homo sapiens

<400> SEQUENCE: 605

Gln Asn Val Leu Ser Thr Pro Tyr Thr
1               5

<210> SEQ ID NO 606
<211> LENGTH: 121
<212> TYPE: PRT
<213> ORGANISM: Homo sapiens

<400> SEQUENCE: 606

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Trp Ile Asn Trp Val Arg Gln Ala Pro Gly Gln Gly Leu Glu Trp Met
            35                  40                  45

Gly Asn Ile Tyr Pro Ser His Ser Tyr Thr Asn Tyr Asn Gln Glu Phe
        50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Arg Tyr Pro Tyr Tyr Ala Met Asp Tyr Trp Gly
                100                 105                 110

Gln Gly Thr Thr Val Thr Val Ser Ser
            115                 120

<210> SEQ ID NO 607
<211> LENGTH: 330
<212> TYPE: PRT
<213> ORGANISM: Homo sapiens

<400> SEQUENCE: 607

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 608
<211> LENGTH: 107
<212> TYPE: PRT
<213> ORGANISM: Homo sapiens

<400> SEQUENCE: 608

```
Ala Ile Gln Leu Thr Gln Ser Pro Ser Ser Leu Ser Ala Ser Val Gly
1               5                   10                  15

Asp Arg Val Thr Ile Thr Cys Gly Ala Ser Glu Asn Ile Tyr Gly Ala
            20                  25                  30

Leu Asn Trp Tyr Gln Gln Lys Pro Gly Lys Ala Pro Lys Leu Leu Ile
            35                  40                  45

Tyr Gly Ala Thr Asn Leu Ala Asp Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Val Leu Ser Thr Pro Tyr
                85                  90                  95

Thr Phe Gly Gln Gly Thr Lys Leu Glu Ile Lys
            100                 105
```

<210> SEQ ID NO 609
<211> LENGTH: 107
<212> TYPE: PRT
<213> ORGANISM: Homo sapiens

<400> SEQUENCE: 609

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 610
<211> LENGTH: 8
<212> TYPE: PRT
<213> ORGANISM: Homo sapiens

<400> SEQUENCE: 610

```
Gly Tyr Thr Phe Thr Asn Tyr Trp
1               5
```

<210> SEQ ID NO 611
<211> LENGTH: 8
<212> TYPE: PRT
<213> ORGANISM: Homo sapiens

<400> SEQUENCE: 611

```
Ile Asn Pro Ser Ser Gly Tyr Thr
1               5
```

<210> SEQ ID NO 612
<211> LENGTH: 11
<212> TYPE: PRT
<213> ORGANISM: Homo sapiens

<400> SEQUENCE: 612

```
Ala Arg Asp Gly Gly Ser Val Leu Phe Gly Tyr
1               5                   10
```

<210> SEQ ID NO 613
<211> LENGTH: 12
<212> TYPE: PRT
<213> ORGANISM: Homo sapiens

<400> SEQUENCE: 613

```
Gln Ser Leu Leu Asn Ser Gly Ile Arg Lys Asn Tyr
1               5                   10
```

<210> SEQ ID NO 614
<211> LENGTH: 3
<212> TYPE: PRT
<213> ORGANISM: Homo sapiens

<400> SEQUENCE: 614

```
Ser Ala Ser
1
```

<210> SEQ ID NO 615
<211> LENGTH: 8
<212> TYPE: PRT
<213> ORGANISM: Homo sapiens

<400> SEQUENCE: 615

```
Lys Gln Ser Tyr Asn Leu Tyr Thr
1               5
```

<210> SEQ ID NO 616
<211> LENGTH: 118
<212> TYPE: PRT
<213> ORGANISM: Homo sapiens

<400> SEQUENCE: 616

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Tyr Ile Asn Pro Ser Ser Gly Tyr Thr Glu Tyr Asn Gln Lys Phe
    50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Gly Gly Ser Val Leu Phe Gly Tyr Trp Gly Gln Gly Thr
                100                 105                 110

Thr Val Thr Val Ser Ser
            115
```

<210> SEQ ID NO 617
<211> LENGTH: 330
<212> TYPE: PRT
<213> ORGANISM: Homo sapiens

<400> SEQUENCE: 617

```
Ala Ser Thr Lys Gly Pro Ser Val Phe Pro Leu Ala Pro Ser Ser Lys
1               5                   10                  15
```

```
Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 618
<211> LENGTH: 112
<212> TYPE: PRT
<213> ORGANISM: Homo sapiens

<400> SEQUENCE: 618

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
            20                  25                  30

Gly Ile Arg Lys Asn Tyr Leu Ala Trp Tyr Gln Gln Lys Pro Gly Gln
        35                  40                  45

Pro Pro Lys Leu Leu Ile Tyr Ser Ala Ser Thr Arg Glu Ser Gly Val
```

```
            50                  55                  60
Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Lys Gln
                 85                  90                  95

Ser Tyr Asn Leu Tyr Thr Phe Gly Gln Gly Thr Lys Leu Glu Ile Lys
                100                 105                 110
```

<210> SEQ ID NO 619
<211> LENGTH: 107
<212> TYPE: PRT
<213> ORGANISM: Homo sapiens

<400> SEQUENCE: 619

```
Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
                 20                  25                  30

Tyr Pro Arg Glu Ala Lys Val Gln Trp Lys Val Asp Asn Ala Leu Gln
             35                  40                  45

Ser Gly Asn Ser Gln Glu Ser Val Thr Glu Gln Asp Ser Lys Asp Ser
         50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
                100                 105
```

<210> SEQ ID NO 620
<211> LENGTH: 9
<212> TYPE: PRT
<213> ORGANISM: Homo sapiens

<400> SEQUENCE: 620

```
Ala Tyr Ser Ile Thr Ser Asp Tyr Ala
 1               5
```

<210> SEQ ID NO 621
<211> LENGTH: 7
<212> TYPE: PRT
<213> ORGANISM: Homo sapiens

<400> SEQUENCE: 621

```
Ile Thr Tyr Ser Gly Ser Thr
 1               5
```

<210> SEQ ID NO 622
<211> LENGTH: 6
<212> TYPE: PRT
<213> ORGANISM: Homo sapiens

<400> SEQUENCE: 622

```
Ala Arg Ser Phe Gly Tyr
 1               5
```

<210> SEQ ID NO 623
<211> LENGTH: 6
<212> TYPE: PRT
<213> ORGANISM: Homo sapiens

```
<400> SEQUENCE: 623

Gln Ser Ile Gly Thr Ser
1               5

<210> SEQ ID NO 624
<211> LENGTH: 3
<212> TYPE: PRT
<213> ORGANISM: Homo sapiens

<400> SEQUENCE: 624

Tyr Ala Ser
1

<210> SEQ ID NO 625
<211> LENGTH: 7
<212> TYPE: PRT
<213> ORGANISM: Homo sapiens

<400> SEQUENCE: 625

Gln Gln Ile Asn Ser Trp Pro
1               5

<210> SEQ ID NO 626
<211> LENGTH: 113
<212> TYPE: PRT
<213> ORGANISM: Homo sapiens

<400> SEQUENCE: 626

Gln Val Gln Leu Gln Glu Ser Gly Pro Gly Leu Val Lys Pro Ser Glu
1               5                   10                  15

Thr Leu Ser Leu Thr Cys Ala Val Ser Ala Tyr Ser Ile Thr Ser Asp
            20                  25                  30

Tyr Ala Trp Asn Trp Ile Arg Gln Pro Pro Gly Lys Gly Leu Glu Trp
        35                  40                  45

Ile Gly Tyr Ile Thr Tyr Ser Gly Ser Thr Arg Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Phe Gly Tyr Trp Gly Gln Gly Thr Thr Val Thr Val Ser
            100                 105                 110

Ser

<210> SEQ ID NO 627
<211> LENGTH: 330
<212> TYPE: PRT
<213> ORGANISM: Homo sapiens

<400> SEQUENCE: 627

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
```

```
                65                  70                  75                  80
Tyr Ile Cys Asn Val Asn His Lys Pro Ser Asn Thr Lys Val Asp Lys
                    85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 628
<211> LENGTH: 107
<212> TYPE: PRT
<213> ORGANISM: Homo sapiens

<400> SEQUENCE: 628

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Ile Gly Thr Ser
                20                  25                  30

Ile His Trp Tyr Gln Gln Lys Pro Gly Gln Ala Pro Arg Leu Leu Ile
                35                  40                  45

Tyr Tyr Ala Ser Glu Ser Ile Ser Gly Ile Pro Ala Arg Phe Ser Gly
            50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Ile Asn Ser Trp Pro Thr
                85                  90                  95

Thr Phe Gly Gln Gly Thr Lys Leu Glu Ile Lys
                100                 105
```

<210> SEQ ID NO 629
<211> LENGTH: 107
<212> TYPE: PRT
<213> ORGANISM: Homo sapiens

<400> SEQUENCE: 629

```
Arg Thr Val Ala Ala Pro Ser Val Phe Ile Phe Pro Pro Ser Asp Glu
 1               5                  10                  15

Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
     50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105
```

<210> SEQ ID NO 630
<211> LENGTH: 8
<212> TYPE: PRT
<213> ORGANISM: Homo sapiens

<400> SEQUENCE: 630

```
Gly Phe Asn Ile Lys Asp Tyr Tyr
 1               5
```

<210> SEQ ID NO 631
<211> LENGTH: 8
<212> TYPE: PRT
<213> ORGANISM: Homo sapiens

<400> SEQUENCE: 631

```
Ile Asp Pro Glu Asn Gly Asp Thr
 1               5
```

<210> SEQ ID NO 632
<211> LENGTH: 10
<212> TYPE: PRT
<213> ORGANISM: Homo sapiens

<400> SEQUENCE: 632

```
Ala Arg Asp Met Gly Ser Ser Tyr Val Tyr
 1               5                  10
```

<210> SEQ ID NO 633
<211> LENGTH: 5
<212> TYPE: PRT
<213> ORGANISM: Homo sapiens

<400> SEQUENCE: 633

```
Ser Ser Val Ile Tyr
 1               5
```

<210> SEQ ID NO 634
<211> LENGTH: 3
<212> TYPE: PRT
<213> ORGANISM: Homo sapiens

```
<400> SEQUENCE: 634

Ser Thr Ser
1

<210> SEQ ID NO 635
<211> LENGTH: 9
<212> TYPE: PRT
<213> ORGANISM: Homo sapiens

<400> SEQUENCE: 635

Gln Gln Arg Ser Ser Tyr Pro Phe Thr
1               5

<210> SEQ ID NO 636
<211> LENGTH: 117
<212> TYPE: PRT
<213> ORGANISM: Homo sapiens

<400> SEQUENCE: 636

Gln Val Gln Leu Val Gln Ser Gly Ala Glu Val Lys Lys Pro Gly Ala
1               5                   10                  15

Ser Val Lys Val Ser Cys Lys Ala Ser Gly Phe Asn Ile Lys Asp Tyr
            20                  25                  30

Tyr Met His Trp Val Arg Gln Ala Pro Gly Gln Gly Leu Glu Trp Met
        35                  40                  45

Gly Trp Ile Asp Pro Glu Asn Gly Asp Thr Glu Tyr Ala Pro Lys Phe
    50                  55                  60

Gln Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Asp Met Gly Ser Ser Tyr Val Tyr Trp Gly Arg Gly Thr Leu
            100                 105                 110

Val Thr Val Ser Ser
        115

<210> SEQ ID NO 637
<211> LENGTH: 330
<212> TYPE: PRT
<213> ORGANISM: Homo sapiens

<400> SEQUENCE: 637

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125
```

```
Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 638
<211> LENGTH: 106
<212> TYPE: PRT
<213> ORGANISM: Homo sapiens

<400> SEQUENCE: 638

Asp Val Val Met Thr Gln Ser Pro Ala Phe Leu Ser Val Thr Pro Gly
1               5                   10                  15

Glu Lys Val Thr Ile Thr Cys Ser Ala Ser Ser Ser Val Ile Tyr Met
            20                  25                  30

His Trp Tyr Gln Gln Lys Pro Asp Gln Ala Pro Lys Leu Leu Ile Lys
        35                  40                  45

Ser Thr Ser Asn Leu Ala Ser Gly Val Pro Ser Arg Phe Ser Gly Ser
    50                  55                  60

Gly Ser Gly Thr Asp Phe Thr Phe Thr Ile Ser Ser Leu Glu Ala Glu
65                  70                  75                  80

Asp Ala Ala Thr Tyr Tyr Cys Gln Gln Arg Ser Ser Tyr Pro Phe Thr
                85                  90                  95

Phe Gly Gln Gly Thr Lys Leu Glu Ile Lys
            100                 105

<210> SEQ ID NO 639
<211> LENGTH: 107
<212> TYPE: PRT
<213> ORGANISM: Homo sapiens

<400> SEQUENCE: 639

Arg Thr Val Ala Ala Pro Ser Val Phe Ile Phe Pro Pro Ser Asp Glu
1               5                   10                  15
```

```
Gln Leu Lys Ser Gly Thr Ala Ser Val Cys Leu Leu Asn Asn Phe
             20                  25                  30

Tyr Pro Arg Glu Ala Lys Val Gln Trp Lys Val Asp Asn Ala Leu Gln
             35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 640
<211> LENGTH: 10
<212> TYPE: PRT
<213> ORGANISM: Homo sapiens

<400> SEQUENCE: 640

Gly Phe Ser Leu Ser Thr Ser Gly Met Gly
1               5                   10

<210> SEQ ID NO 641
<211> LENGTH: 7
<212> TYPE: PRT
<213> ORGANISM: Homo sapiens

<400> SEQUENCE: 641

Ile Tyr Trp Asp Asp Asp Lys
1               5

<210> SEQ ID NO 642
<211> LENGTH: 13
<212> TYPE: PRT
<213> ORGANISM: Homo sapiens

<400> SEQUENCE: 642

Ala Arg Arg Pro Asp Tyr Phe Gly Ser Ser Tyr Val Asp
1               5                   10

<210> SEQ ID NO 643
<211> LENGTH: 10
<212> TYPE: PRT
<213> ORGANISM: Homo sapiens

<400> SEQUENCE: 643

Glu Ser Val Asp Thr Tyr Gly Asn Ser Phe
1               5                   10

<210> SEQ ID NO 644
<211> LENGTH: 3
<212> TYPE: PRT
<213> ORGANISM: Homo sapiens

<400> SEQUENCE: 644

Leu Ala Ser
1

<210> SEQ ID NO 645
<211> LENGTH: 9
<212> TYPE: PRT
<213> ORGANISM: Homo sapiens
```

<400> SEQUENCE: 645

Gln Gln Asn Asn Glu Asp Pro Trp Thr
1               5

<210> SEQ ID NO 646
<211> LENGTH: 121
<212> TYPE: PRT
<213> ORGANISM: Homo sapiens

<400> SEQUENCE: 646

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Arg Pro Asp Tyr Phe Gly Ser Ser Tyr Val Asp Trp Gly
            100                 105                 110

Gln Gly Thr Thr Val Thr Val Ser Ser
        115                 120

<210> SEQ ID NO 647
<211> LENGTH: 330
<212> TYPE: PRT
<213> ORGANISM: Homo sapiens

<400> SEQUENCE: 647

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

```
Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 648
<211> LENGTH: 111
<212> TYPE: PRT
<213> ORGANISM: Homo sapiens

<400> SEQUENCE: 648

Asp Ile Val Met Thr Gln Thr Pro Leu Ser Leu Ser Val Thr Pro Gly
1               5                   10                  15

Gln Pro Ala Ser Ile Ser Cys Arg Ala Ser Glu Ser Val Asp Thr Tyr
            20                  25                  30

Gly Asn Ser Phe Met His Trp Tyr Leu Gln Lys Pro Gly Gln Pro Pro
        35                  40                  45

Gln Leu Leu Ile Tyr Leu Ala Ser Asn Leu Asp Phe Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Asn Asn
                85                  90                  95

Glu Asp Pro Trp Thr Phe Gly Gln Gly Thr Lys Leu Glu Ile Lys
            100                 105                 110

<210> SEQ ID NO 649
<211> LENGTH: 107
<212> TYPE: PRT
<213> ORGANISM: Homo sapiens

<400> SEQUENCE: 649

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60
```

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 650
<211> LENGTH: 9
<212> TYPE: PRT
<213> ORGANISM: Homo sapiens

<400> SEQUENCE: 650

Gly Tyr Ser Ile Thr Ser Asp Tyr Ala
1               5

<210> SEQ ID NO 651
<211> LENGTH: 7
<212> TYPE: PRT
<213> ORGANISM: Homo sapiens

<400> SEQUENCE: 651

Ile Thr Tyr Ser Gly Ser Thr
1               5

<210> SEQ ID NO 652
<211> LENGTH: 14
<212> TYPE: PRT
<213> ORGANISM: Homo sapiens

<400> SEQUENCE: 652

Ala Arg Ser His Tyr Gly Ser Thr Tyr Trp Tyr Phe Asp Val
1               5                   10

<210> SEQ ID NO 653
<211> LENGTH: 10
<212> TYPE: PRT
<213> ORGANISM: Homo sapiens

<400> SEQUENCE: 653

Glu Ser Val Glu Tyr Tyr Gly Thr Ser Leu
1               5                   10

<210> SEQ ID NO 654
<211> LENGTH: 3
<212> TYPE: PRT
<213> ORGANISM: Homo sapiens

<400> SEQUENCE: 654

Ala Ala Ser
1

<210> SEQ ID NO 655
<211> LENGTH: 9
<212> TYPE: PRT
<213> ORGANISM: Homo sapiens

<400> SEQUENCE: 655

Gln Gln Thr Arg Lys Val Pro Trp Thr
1               5

<210> SEQ ID NO 656
<211> LENGTH: 121
<212> TYPE: PRT

<213> ORGANISM: Homo sapiens

<400> SEQUENCE: 656

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Thr Ser Asp
            20                  25                  30

Tyr Ala Trp Asn Trp Ile Arg Gln Pro Pro Gly Lys Gly Leu Glu Trp
        35                  40                  45

Ile Gly Phe Ile Thr Tyr Ser Gly Ser Thr Asn Tyr Asn Pro Ser Leu
    50                  55                  60

Lys Ser Arg Val Thr Ile Ser Val Asp Thr Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser His Tyr Gly Ser Thr Tyr Trp Tyr Phe Asp Val Trp Gly
            100                 105                 110

Gln Gly Thr Thr Val Thr Val Ser Ser
            115                 120

<210> SEQ ID NO 657
<211> LENGTH: 330
<212> TYPE: PRT
<213> ORGANISM: Homo sapiens

<400> SEQUENCE: 657

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu

```
            225                 230                 235                 240
Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 658
<211> LENGTH: 111
<212> TYPE: PRT
<213> ORGANISM: Homo sapiens

<400> SEQUENCE: 658

Asp Ile Val Met Thr Gln Thr Pro Leu Ser Leu Ser Val Thr Pro Gly
1               5                   10                  15

Gln Pro Ala Ser Ile Ser Cys Arg Ala Ser Glu Ser Val Glu Tyr Tyr
            20                  25                  30

Gly Thr Ser Leu Met Gln Trp Tyr Leu Gln Lys Pro Gly Gln Ser Pro
        35                  40                  45

Gln Leu Leu Ile Tyr Ala Ala Ser Asn Val Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Thr Arg
                85                  90                  95

Lys Val Pro Trp Thr Phe Gly Gln Gly Thr Arg Leu Glu Ile Lys
            100                 105                 110

<210> SEQ ID NO 659
<211> LENGTH: 107
<212> TYPE: PRT
<213> ORGANISM: Homo sapiens

<400> SEQUENCE: 659

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

```
<210> SEQ ID NO 660
<211> LENGTH: 8
<212> TYPE: PRT
<213> ORGANISM: Homo sapiens

<400> SEQUENCE: 660

Gly Tyr Thr Phe Thr Ser Tyr Asp
1               5

<210> SEQ ID NO 661
<211> LENGTH: 8
<212> TYPE: PRT
<213> ORGANISM: Homo sapiens

<400> SEQUENCE: 661

Ile Tyr Pro Gly Asp Gly Tyr Thr
1               5

<210> SEQ ID NO 662
<211> LENGTH: 12
<212> TYPE: PRT
<213> ORGANISM: Homo sapiens

<400> SEQUENCE: 662

Ala Arg Trp Gly Tyr Gly Ser Tyr Ala Met Asp Tyr
1               5                   10

<210> SEQ ID NO 663
<211> LENGTH: 11
<212> TYPE: PRT
<213> ORGANISM: Homo sapiens

<400> SEQUENCE: 663

Gln Ser Leu Val His Ser Asn Gly Asn Thr Tyr
1               5                   10

<210> SEQ ID NO 664
<211> LENGTH: 3
<212> TYPE: PRT
<213> ORGANISM: Homo sapiens

<400> SEQUENCE: 664

Lys Val Ser
1

<210> SEQ ID NO 665
<211> LENGTH: 9
<212> TYPE: PRT
<213> ORGANISM: Homo sapiens

<400> SEQUENCE: 665

Ser Gln Ser Thr His Val Pro Pro Thr
1               5

<210> SEQ ID NO 666
<211> LENGTH: 119
<212> TYPE: PRT
<213> ORGANISM: Homo sapiens

<400> SEQUENCE: 666

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30
```

-continued

```
Asp Ile Asn Trp Val Arg Gln Ala Pro Gly Gln Gly Leu Glu Trp Met
            35                  40                  45

Gly Trp Ile Tyr Pro Gly Asp Gly Tyr Thr Glu Tyr Asn Glu Lys Phe
 50                  55                  60

Arg Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Trp Gly Tyr Gly Ser Tyr Ala Met Asp Tyr Trp Gly Gln Gly
                100                 105                 110

Thr Leu Val Thr Val Ser Ser
            115
```

<210> SEQ ID NO 667
<211> LENGTH: 330
<212> TYPE: PRT
<213> ORGANISM: Homo sapiens

<400> SEQUENCE: 667

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 668
<211> LENGTH: 112
<212> TYPE: PRT
<213> ORGANISM: Homo sapiens

<400> SEQUENCE: 668

Asp Ile Val Met Thr Gln Ser Pro Leu Ser Leu Pro Val Thr Pro Gly
1               5                   10                  15
Glu Pro Ala Ser Ile Ser Cys Arg Ser Ser Gln Ser Leu Val His Ser
                20                  25                  30
Asn Gly Asn Thr Tyr Leu His Trp Tyr Leu Gln Lys Pro Gly Gln Ser
            35                  40                  45
Pro Gln Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Ser Gln Ser
                85                  90                  95
Thr His Val Pro Pro Thr Phe Gly Gln Gly Thr Lys Leu Glu Ile Lys
                100                 105                 110

<210> SEQ ID NO 669
<211> LENGTH: 107
<212> TYPE: PRT
<213> ORGANISM: Homo sapiens

<400> SEQUENCE: 669

Arg Thr Val Ala Ala Pro Ser Val Phe Ile Phe Pro Pro Ser Asp Glu
1               5                   10                  15
Gln Leu Lys Ser Gly Thr Ala Ser Val Val Cys Leu Leu Asn Asn Phe
                20                  25                  30
Tyr Pro Arg Glu Ala Lys Val Gln Trp Lys Val Asp Asn Ala Leu Gln
            35                  40                  45
Ser Gly Asn Ser Gln Glu Ser Val Thr Glu Gln Asp Ser Lys Asp Ser
    50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
                85                  90                  95
Pro Val Thr Lys Ser Phe Asn Arg Gly Glu Cys
                100                 105

<210> SEQ ID NO 670
<211> LENGTH: 8
<212> TYPE: PRT
<213> ORGANISM: Homo sapiens

<400> SEQUENCE: 670

Gly Tyr Thr Phe Thr Ser Tyr Trp
1               5
```

<210> SEQ ID NO 671
<211> LENGTH: 8
<212> TYPE: PRT
<213> ORGANISM: Homo sapiens

<400> SEQUENCE: 671

Ile Asn Pro Ser Thr Gly Tyr Pro
1               5

<210> SEQ ID NO 672
<211> LENGTH: 15
<212> TYPE: PRT
<213> ORGANISM: Homo sapiens

<400> SEQUENCE: 672

Ala Arg Ser Tyr Tyr Asp Tyr Asp Gly Gly Ala Trp Phe Ala Tyr
1               5                   10                  15

<210> SEQ ID NO 673
<211> LENGTH: 10
<212> TYPE: PRT
<213> ORGANISM: Homo sapiens

<400> SEQUENCE: 673

Glu Ser Val Glu Tyr Tyr Gly Thr Ser Leu
1               5                   10

<210> SEQ ID NO 674
<211> LENGTH: 3
<212> TYPE: PRT
<213> ORGANISM: Homo sapiens

<400> SEQUENCE: 674

Ala Ala Ser
1

<210> SEQ ID NO 675
<211> LENGTH: 9
<212> TYPE: PRT
<213> ORGANISM: Homo sapiens

<400> SEQUENCE: 675

Gln Gln Ser Arg Lys Val Pro Ser Thr
1               5

<210> SEQ ID NO 676
<211> LENGTH: 122
<212> TYPE: PRT
<213> ORGANISM: Homo sapiens

<400> SEQUENCE: 676

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Met His Trp Val Arg Gln Ala Pro Gly Gln Gly Leu Glu Trp Met
            35                  40                  45

Gly Tyr Ile Asn Pro Ser Thr Gly Tyr Pro Gly Tyr Asn Gln Lys Phe
        50                  55                  60

Lys Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys

```
                    85                  90                  95
Ala Arg Ser Tyr Tyr Asp Tyr Asp Gly Gly Ala Trp Phe Ala Tyr Trp
                100                 105                 110

Gly Gln Gly Thr Thr Val Thr Val Ser Ser
                115                 120

<210> SEQ ID NO 677
<211> LENGTH: 330
<212> TYPE: PRT
<213> ORGANISM: Homo sapiens

<400> SEQUENCE: 677

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 678
<211> LENGTH: 111
<212> TYPE: PRT
<213> ORGANISM: Homo sapiens

<400> SEQUENCE: 678

Asp Ile Val Met Thr Gln Thr Pro Leu Ser Leu Ser Val Thr Pro Gly
1               5                   10                  15

Gln Pro Ala Ser Ile Ser Cys Arg Ala Ser Glu Ser Val Glu Tyr Tyr
            20                  25                  30

Gly Thr Ser Leu Met Gln Trp Tyr Leu Gln Lys Pro Gly Gln Pro Pro
        35                  40                  45

Gln Leu Leu Ile Tyr Ala Ala Ser Asn Val Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Ser Arg
                85                  90                  95

Lys Val Pro Ser Thr Phe Gly Gln Gly Thr Lys Leu Glu Ile Lys
            100                 105                 110

<210> SEQ ID NO 679
<211> LENGTH: 107
<212> TYPE: PRT
<213> ORGANISM: Homo sapiens

<400> SEQUENCE: 679

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 680
<211> LENGTH: 8
<212> TYPE: PRT
<213> ORGANISM: Homo sapiens

<400> SEQUENCE: 680

Gly Tyr Thr Phe Thr Asp Tyr Ala
1               5

<210> SEQ ID NO 681
<211> LENGTH: 8
<212> TYPE: PRT
<213> ORGANISM: Homo sapiens

<400> SEQUENCE: 681

Ile Asp Thr Tyr Tyr Gly Asn Thr
1               5

<210> SEQ ID NO 682
<211> LENGTH: 10
<212> TYPE: PRT
<213> ORGANISM: Homo sapiens

<400> SEQUENCE: 682

Ala Arg Gly Gly Gly Asp Ala Leu Asp Tyr
1               5                   10

<210> SEQ ID NO 683
<211> LENGTH: 6
<212> TYPE: PRT
<213> ORGANISM: Homo sapiens

<400> SEQUENCE: 683

Gln Ser Val Ser Asn Asp
1               5

<210> SEQ ID NO 684
<211> LENGTH: 3
<212> TYPE: PRT
<213> ORGANISM: Homo sapiens

<400> SEQUENCE: 684

Tyr Ala Ser
1

<210> SEQ ID NO 685
<211> LENGTH: 9
<212> TYPE: PRT
<213> ORGANISM: Homo sapiens

<400> SEQUENCE: 685

Gln Gln Gly Tyr Thr Ser Leu Arg Thr
1               5

<210> SEQ ID NO 686
<211> LENGTH: 117
<212> TYPE: PRT
<213> ORGANISM: Homo sapiens

<400> SEQUENCE: 686

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ala Met His Trp Val Arg Gln Ala Pro Gly Gln Gly Leu Glu Trp Met
        35                  40                  45

Gly Val Ile Asp Thr Tyr Tyr Gly Asn Thr Asn Tyr Asn Gln Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Arg Gly Gly Gly Asp Ala Leu Asp Tyr Trp Gly Gln Gly Thr Thr
            100                 105                 110

Val Thr Val Ser Ser
        115

<210> SEQ ID NO 687

```
<211> LENGTH: 330
<212> TYPE: PRT
<213> ORGANISM: Homo sapiens

<400> SEQUENCE: 687

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 688
<211> LENGTH: 107
<212> TYPE: PRT
<213> ORGANISM: Homo sapiens

<400> SEQUENCE: 688

Asp Ile Gln Met Thr Gln Ser Pro Ser Ser Leu Ser Ala Ser Val Gly
1               5                   10                  15
```

```
Asp Arg Val Thr Ile Thr Cys Lys Ala Ser Gln Ser Val Ser Asn Asp
            20                  25                  30

Val Val Trp Tyr Gln Gln Lys Pro Gly Lys Ala Pro Lys Leu Leu Ile
        35                  40                  45

Tyr Tyr Ala Ser Asn Arg Tyr Ile Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Gly Tyr Thr Ser Leu Arg
                85                  90                  95

Thr Phe Gly Gln Gly Thr Lys Leu Glu Ile Lys
            100                 105

<210> SEQ ID NO 689
<211> LENGTH: 107
<212> TYPE: PRT
<213> ORGANISM: Homo sapiens

<400> SEQUENCE: 689

Arg Thr Val Ala Ala Pro Ser Val Phe Ile Phe Pro Pro Ser Asp Glu
 1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 690
<211> LENGTH: 9
<212> TYPE: PRT
<213> ORGANISM: Homo sapiens

<400> SEQUENCE: 690

Gly Tyr Ser Ile Thr Ser Gly Tyr Ser
 1               5

<210> SEQ ID NO 691
<211> LENGTH: 7
<212> TYPE: PRT
<213> ORGANISM: Homo sapiens

<400> SEQUENCE: 691

Ile His Tyr Ile Gly Ile Thr
 1               5

<210> SEQ ID NO 692
<211> LENGTH: 13
<212> TYPE: PRT
<213> ORGANISM: Homo sapiens

<400> SEQUENCE: 692

Ala Arg Glu Asp Tyr Asp Tyr Asp Gly Val Phe Ala Tyr
```

<210> SEQ ID NO 693
<211> LENGTH: 6
<212> TYPE: PRT
<213> ORGANISM: Homo sapiens

<400> SEQUENCE: 693

Gln Ser Ile Ser Asn Asn
1               5

<210> SEQ ID NO 694
<211> LENGTH: 3
<212> TYPE: PRT
<213> ORGANISM: Homo sapiens

<400> SEQUENCE: 694

Tyr Ala Ser
1

<210> SEQ ID NO 695
<211> LENGTH: 9
<212> TYPE: PRT
<213> ORGANISM: Homo sapiens

<400> SEQUENCE: 695

Gln Gln Ser Asn Ser Trp Pro His Thr
1               5

<210> SEQ ID NO 696
<211> LENGTH: 120
<212> TYPE: PRT
<213> ORGANISM: Homo sapiens

<400> SEQUENCE: 696

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Thr Ser Gly
            20                  25                  30

Tyr Ser Trp His Trp Ile Arg Gln Pro Pro Gly Lys Gly Leu Glu Trp
        35                  40                  45

Ile Gly Tyr Ile His Tyr Ile Gly Ile Thr Asn Asn Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Asp Tyr Asp Tyr Asp Gly Val Phe Ala Tyr Trp Gly Gln
            100                 105                 110

Gly Thr Leu Val Thr Val Ser Ser
        115                 120

<210> SEQ ID NO 697
<211> LENGTH: 330
<212> TYPE: PRT
<213> ORGANISM: Homo sapiens

<400> SEQUENCE: 697

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr

```
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 698
<211> LENGTH: 107
<212> TYPE: PRT
<213> ORGANISM: Homo sapiens

<400> SEQUENCE: 698

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Ile Ser Asn Asn
             20                  25                  30

Leu His Trp Tyr Gln Gln Lys Pro Gly Gln Ala Pro Arg Leu Leu Ile
         35                  40                  45

Tyr Tyr Ala Ser Gln Ser Ile Ser Gly Ile Pro Ala Arg Phe Ser Gly
     50                  55                  60
```

-continued

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Ser Asn Ser Trp Pro His
                85                  90                  95

Thr Phe Gly Gln Gly Thr Lys Leu Glu Ile Lys
            100                 105

<210> SEQ ID NO 699
<211> LENGTH: 107
<212> TYPE: PRT
<213> ORGANISM: Homo sapiens

<400> SEQUENCE: 699

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 700
<211> LENGTH: 8
<212> TYPE: PRT
<213> ORGANISM: Homo sapiens

<400> SEQUENCE: 700

Gly Phe Ser Leu Thr Asn Tyr Asp
1               5

<210> SEQ ID NO 701
<211> LENGTH: 7
<212> TYPE: PRT
<213> ORGANISM: Homo sapiens

<400> SEQUENCE: 701

Ile Trp Thr Gly Gly Gly Thr
1               5

<210> SEQ ID NO 702
<211> LENGTH: 10
<212> TYPE: PRT
<213> ORGANISM: Homo sapiens

<400> SEQUENCE: 702

Ala Arg Glu Gly Leu Leu Leu Pro Leu Tyr
1               5                   10

<210> SEQ ID NO 703
<211> LENGTH: 6
<212> TYPE: PRT
<213> ORGANISM: Homo sapiens

<400> SEQUENCE: 703

```
Gln Asn Val Gly Thr Asn
1               5
```

<210> SEQ ID NO 704
<211> LENGTH: 3
<212> TYPE: PRT
<213> ORGANISM: Homo sapiens

<400> SEQUENCE: 704

```
Ser Ala Ser
1
```

<210> SEQ ID NO 705
<211> LENGTH: 9
<212> TYPE: PRT
<213> ORGANISM: Homo sapiens

<400> SEQUENCE: 705

```
Gln Gln Tyr Asn Ser Tyr Pro Leu Thr
1               5
```

<210> SEQ ID NO 706
<211> LENGTH: 116
<212> TYPE: PRT
<213> ORGANISM: Homo sapiens

<400> SEQUENCE: 706

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Asn Tyr
            20                  25                  30

Asp Ile Ser Trp Ile Arg Gln Pro Pro Gly Lys Gly Leu Glu Trp Ile
        35                  40                  45

Gly Val Ile Trp Thr Gly Gly Thr Asn Tyr Asn Ser Ala Phe Met
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Gly Leu Leu Leu Pro Leu Tyr Trp Gly Gln Gly Thr Leu Val
            100                 105                 110

Thr Val Ser Ser
            115
```

<210> SEQ ID NO 707
<211> LENGTH: 330
<212> TYPE: PRT
<213> ORGANISM: Homo sapiens

<400> SEQUENCE: 707

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80
```

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 708
<211> LENGTH: 107
<212> TYPE: PRT
<213> ORGANISM: Homo sapiens

<400> SEQUENCE: 708

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Tyr Gln Gln Lys Pro Gly Lys Val Pro Lys Leu Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Asn Ser Tyr Pro Leu
                85                  90                  95

Thr Phe Gly Gln Gly Thr Lys Leu Glu Ile Lys
            100                 105

```
<210> SEQ ID NO 709
<211> LENGTH: 107
<212> TYPE: PRT
<213> ORGANISM: Homo sapiens

<400> SEQUENCE: 709

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 710
<211> LENGTH: 8
<212> TYPE: PRT
<213> ORGANISM: Homo sapiens

<400> SEQUENCE: 710

Gly Tyr Thr Phe Thr Asn Phe Gly
1               5

<210> SEQ ID NO 711
<211> LENGTH: 8
<212> TYPE: PRT
<213> ORGANISM: Homo sapiens

<400> SEQUENCE: 711

Ile Asn Thr Tyr Thr Gly Glu Pro
1               5

<210> SEQ ID NO 712
<211> LENGTH: 15
<212> TYPE: PRT
<213> ORGANISM: Homo sapiens

<400> SEQUENCE: 712

Ala Arg Gly Ala Tyr Tyr Tyr Gly Ser Arg Val Trp Phe Ala Tyr
1               5                   10                  15

<210> SEQ ID NO 713
<211> LENGTH: 11
<212> TYPE: PRT
<213> ORGANISM: Homo sapiens

<400> SEQUENCE: 713

Gln Asn Leu Val His Ser Asn Gly Asn Thr Tyr
1               5                   10

<210> SEQ ID NO 714
<211> LENGTH: 3
<212> TYPE: PRT
<213> ORGANISM: Homo sapiens

<400> SEQUENCE: 714
```

Lys Val Ser
1

<210> SEQ ID NO 715
<211> LENGTH: 9
<212> TYPE: PRT
<213> ORGANISM: Homo sapiens

<400> SEQUENCE: 715

Ser Gln Ser Ser His Val Pro Tyr Thr
1               5

<210> SEQ ID NO 716
<211> LENGTH: 122
<212> TYPE: PRT
<213> ORGANISM: Homo sapiens

<400> SEQUENCE: 716

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Phe
                20                  25                  30

Gly Met Asn Trp Val Arg Gln Ala Pro Gly Gln Gly Leu Glu Trp Met
            35                  40                  45

Gly Trp Ile Asn Thr Tyr Thr Gly Glu Pro Thr Tyr Ala Asp Asp Phe
        50                  55                  60

Lys Gly Arg Phe Val Phe Ser Leu Asp Thr Ser Val Ser Thr Ala Tyr
65                  70                  75                  80

Leu Gln Ile Cys Ser Leu Lys Ala Glu Asp Thr Ala Val Tyr Tyr Cys
                85                  90                  95

Ala Arg Gly Ala Tyr Tyr Tyr Gly Ser Arg Val Trp Phe Ala Tyr Trp
            100                 105                 110

Gly Gln Gly Thr Leu Val Thr Val Ser Ser
        115                 120

<210> SEQ ID NO 717
<211> LENGTH: 330
<212> TYPE: PRT
<213> ORGANISM: Homo sapiens

<400> SEQUENCE: 717

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
            130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 718
<211> LENGTH: 112
<212> TYPE: PRT
<213> ORGANISM: Homo sapiens

<400> SEQUENCE: 718

Asp Ile Val Met Thr Gln Ser Pro Leu Ser Leu Pro Val Thr Pro Gly
1               5                   10                  15

Glu Pro Ala Ser Ile Ser Cys Thr Ser Ser Gln Asn Leu Val His Ser
                20                  25                  30

Asn Gly Asn Thr Tyr Leu His Trp Tyr Leu Gln Lys Pro Gly Gln Ser
            35                  40                  45

Pro Gln Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Ser His Val Pro Tyr Thr Phe Gly Gln Gly Thr Lys Leu Glu Ile Lys
            100                 105                 110

<210> SEQ ID NO 719
<211> LENGTH: 107
<212> TYPE: PRT
<213> ORGANISM: Homo sapiens

<400> SEQUENCE: 719

Arg Thr Val Ala Ala Pro Ser Val Phe Ile Phe Pro Pro Ser Asp Glu
1               5                   10                  15

-continued

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 720
<211> LENGTH: 8
<212> TYPE: PRT
<213> ORGANISM: Homo sapiens

<400> SEQUENCE: 720

Gly Phe Ser Leu Thr Ser Ser Gly
1               5

<210> SEQ ID NO 721
<211> LENGTH: 7
<212> TYPE: PRT
<213> ORGANISM: Homo sapiens

<400> SEQUENCE: 721

Ile Trp Ser Gly Gly Asn Thr
1               5

<210> SEQ ID NO 722
<211> LENGTH: 13
<212> TYPE: PRT
<213> ORGANISM: Homo sapiens

<400> SEQUENCE: 722

Ala Arg Glu Asp Tyr Asp Tyr Asp Trp Tyr Phe Asp Val
1               5                   10

<210> SEQ ID NO 723
<211> LENGTH: 10
<212> TYPE: PRT
<213> ORGANISM: Homo sapiens

<400> SEQUENCE: 723

Glu Ser Val Glu Tyr Tyr Gly Thr Ser Leu
1               5                   10

<210> SEQ ID NO 724
<211> LENGTH: 3
<212> TYPE: PRT
<213> ORGANISM: Homo sapiens

<400> SEQUENCE: 724

Ala Ala Ser
1

<210> SEQ ID NO 725
<211> LENGTH: 9
<212> TYPE: PRT
<213> ORGANISM: Homo sapiens

<400> SEQUENCE: 725

Gln Gln Ser Arg Lys Val Pro Trp Thr
1               5

<210> SEQ ID NO 726
<211> LENGTH: 119
<212> TYPE: PRT
<213> ORGANISM: Homo sapiens

<400> SEQUENCE: 726

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Ser
            20                  25                  30

Gly Val His Trp Ile Arg Gln Pro Pro Gly Lys Gly Leu Glu Trp Ile
        35                  40                  45

Gly Val Ile Trp Ser Gly Gly Asn Thr Asp Tyr Asn Ala Ala Phe Ile
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Asp Tyr Asp Tyr Asp Trp Tyr Phe Asp Val Trp Gly Gln Gly
            100                 105                 110

Thr Thr Val Thr Val Ser Ser
        115

<210> SEQ ID NO 727
<211> LENGTH: 330
<212> TYPE: PRT
<213> ORGANISM: Homo sapiens

<400> SEQUENCE: 727

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu

-continued

```
                180                 185                 190
His Gln Asp Trp Leu Asn Gly Lys Glu Tyr Lys Cys Lys Val Ser Asn
                    195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 728
<211> LENGTH: 111
<212> TYPE: PRT
<213> ORGANISM: Homo sapiens

<400> SEQUENCE: 728

```
Asp Ile Val Met Thr Gln Thr Pro Leu Ser Leu Ser Val Thr Pro Gly
1               5                   10                  15

Gln Pro Ala Ser Ile Ser Cys Arg Ala Ser Glu Ser Val Glu Tyr Tyr
            20                  25                  30

Gly Thr Ser Leu Met Gln Trp Tyr Leu Gln Lys Pro Gly Gln Pro Pro
        35                  40                  45

Gln Leu Leu Ile Tyr Ala Ala Ser Asn Val Lys Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Ser Arg
                85                  90                  95

Lys Val Pro Trp Thr Phe Gly Gln Gly Thr Lys Leu Glu Ile Lys
            100                 105                 110
```

<210> SEQ ID NO 729
<211> LENGTH: 107
<212> TYPE: PRT
<213> ORGANISM: Homo sapiens

<400> SEQUENCE: 729

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
```

65                  70                  75                  80
Lys His Lys Val Tyr Ala Cys Glu Val Thr His Gln Gly Leu Ser Ser
                    85                  90                  95

Pro Val Thr Lys Ser Phe Asn Arg Gly Glu Cys
                100                 105

<210> SEQ ID NO 730
<211> LENGTH: 8
<212> TYPE: PRT
<213> ORGANISM: Homo sapiens

<400> SEQUENCE: 730

Gly Tyr Thr Phe Ala Asn Phe Trp
1               5

<210> SEQ ID NO 731
<211> LENGTH: 8
<212> TYPE: PRT
<213> ORGANISM: Homo sapiens

<400> SEQUENCE: 731

Ile Phe Pro Gly Asn Ser Asp Thr
1               5

<210> SEQ ID NO 732
<211> LENGTH: 12
<212> TYPE: PRT
<213> ORGANISM: Homo sapiens

<400> SEQUENCE: 732

Ala Arg Glu Leu Thr Gly Thr Tyr Tyr Phe Asp Tyr
1               5                   10

<210> SEQ ID NO 733
<211> LENGTH: 5
<212> TYPE: PRT
<213> ORGANISM: Homo sapiens

<400> SEQUENCE: 733

Ser Ser Val Ser Tyr
1               5

<210> SEQ ID NO 734
<211> LENGTH: 3
<212> TYPE: PRT
<213> ORGANISM: Homo sapiens

<400> SEQUENCE: 734

Ser Ser Ser
1

<210> SEQ ID NO 735
<211> LENGTH: 8
<212> TYPE: PRT
<213> ORGANISM: Homo sapiens

<400> SEQUENCE: 735

His Gln Trp Ser Gly His Phe Thr
1               5

<210> SEQ ID NO 736
<211> LENGTH: 119
<212> TYPE: PRT
<213> ORGANISM: Homo sapiens

<400> SEQUENCE: 736

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Asn Phe
            20                  25                  30

Trp Met His Trp Val Arg Gln Ala Pro Gly Gln Gly Leu Glu Trp Met
        35                  40                  45

Gly Ala Ile Phe Pro Gly Asn Ser Asp Thr Gly Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Leu Thr Gly Thr Tyr Tyr Phe Asp Tyr Trp Gly Gln Gly
            100                 105                 110

Thr Leu Val Thr Val Ser Ser
        115

<210> SEQ ID NO 737
<211> LENGTH: 330
<212> TYPE: PRT
<213> ORGANISM: Homo sapiens

<400> SEQUENCE: 737

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

```
Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 738
<211> LENGTH: 105
<212> TYPE: PRT
<213> ORGANISM: Homo sapiens

<400> SEQUENCE: 738

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Tyr Gln Gln Lys Pro Gly Gln Ala Pro Arg Leu Leu Ile Tyr
        35                  40                  45

Ser Ser Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys His Gln Trp Ser Gly His Phe Thr Phe
                85                  90                  95

Gly Gln Gly Thr Lys Leu Glu Ile Lys
            100                 105

<210> SEQ ID NO 739
<211> LENGTH: 107
<212> TYPE: PRT
<213> ORGANISM: Homo sapiens

<400> SEQUENCE: 739

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 740
```

```
<211> LENGTH: 8
<212> TYPE: PRT
<213> ORGANISM: Homo sapiens

<400> SEQUENCE: 740

Gly Tyr Thr Phe Ala Asn Tyr Leu
1               5

<210> SEQ ID NO 741
<211> LENGTH: 8
<212> TYPE: PRT
<213> ORGANISM: Homo sapiens

<400> SEQUENCE: 741

Ile Tyr Pro Gly Gly Gly Phe Ile
1               5

<210> SEQ ID NO 742
<211> LENGTH: 13
<212> TYPE: PRT
<213> ORGANISM: Homo sapiens

<400> SEQUENCE: 742

Ala Arg Arg Phe Asp Tyr Gly Gly Tyr Phe Phe Asp Tyr
1               5                   10

<210> SEQ ID NO 743
<211> LENGTH: 11
<212> TYPE: PRT
<213> ORGANISM: Homo sapiens

<400> SEQUENCE: 743

Gln Ser Ile Val His Ser Asn Gly Asn Ile Tyr
1               5                   10

<210> SEQ ID NO 744
<211> LENGTH: 3
<212> TYPE: PRT
<213> ORGANISM: Homo sapiens

<400> SEQUENCE: 744

Lys Val Ser
1

<210> SEQ ID NO 745
<211> LENGTH: 9
<212> TYPE: PRT
<213> ORGANISM: Homo sapiens

<400> SEQUENCE: 745

Phe Gln Gly Ser His Val Pro Trp Thr
1               5

<210> SEQ ID NO 746
<211> LENGTH: 120
<212> TYPE: PRT
<213> ORGANISM: Homo sapiens

<400> SEQUENCE: 746

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Asn Tyr
            20                  25                  30

Leu Ile Gly Trp Val Arg Gln Ala Pro Gly Gln Arg Leu Glu Trp Met
```

```
                    35                  40                  45
Gly Asp Ile Tyr Pro Gly Gly Phe Ile Ser Tyr Asn Glu Lys Phe
 50                  55                  60

Lys Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Arg Phe Asp Tyr Gly Tyr Phe Phe Asp Tyr Trp Gly Gln
                100                 105                 110

Gly Thr Leu Val Thr Val Ser Ser
                115                 120
```

<210> SEQ ID NO 747
<211> LENGTH: 330
<212> TYPE: PRT
<213> ORGANISM: Homo sapiens

<400> SEQUENCE: 747

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
        290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330
```

<210> SEQ ID NO 748
<211> LENGTH: 112
<212> TYPE: PRT
<213> ORGANISM: Homo sapiens

<400> SEQUENCE: 748

```
Asp Ile Val Met Thr Gln Ser Pro Leu Ser Leu Pro Val Thr Pro Gly
1               5                   10                  15
Glu Pro Ala Ser Ile Ser Cys Arg Ser Ser Gln Ser Ile Val His Ser
            20                  25                  30
Asn Gly Asn Ile Tyr Leu Glu Trp Tyr Leu Gln Lys Pro Gly Gln Ser
        35                  40                  45
Pro Gln Leu Leu Ile Tyr Lys Val Ser Asn Arg Phe Ser Gly Val Pro
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Val Gly Val Tyr Tyr Cys Phe Gln Gly
                85                  90                  95
Ser His Val Pro Trp Thr Phe Gly Gln Gly Thr Lys Leu Glu Ile Lys
            100                 105                 110
```

<210> SEQ ID NO 749
<211> LENGTH: 107
<212> TYPE: PRT
<213> ORGANISM: Homo sapiens

<400> SEQUENCE: 749

```
Arg Thr Val Ala Ala Pro Ser Val Phe Ile Phe Pro Pro Ser Asp Glu
1               5                   10                  15
Gln Leu Lys Ser Gly Thr Ala Ser Val Val Cys Leu Leu Asn Asn Phe
            20                  25                  30
Tyr Pro Arg Glu Ala Lys Val Gln Trp Lys Val Asp Asn Ala Leu Gln
        35                  40                  45
Ser Gly Asn Ser Gln Glu Ser Val Thr Glu Gln Asp Ser Lys Asp Ser
    50                  55                  60
Thr Tyr Ser Leu Ser Ser Thr Leu Thr Leu Ser Lys Ala Asp Tyr Glu
65                  70                  75                  80
Lys His Lys Val Tyr Ala Cys Glu Val Thr His Gln Gly Leu Ser Ser
                85                  90                  95
Pro Val Thr Lys Ser Phe Asn Arg Gly Glu Cys
            100                 105
```

<210> SEQ ID NO 750
<211> LENGTH: 8
<212> TYPE: PRT
<213> ORGANISM: Homo sapiens

<400> SEQUENCE: 750

```
Gly Phe Ser Ile Thr Asn Tyr Asp
1               5
```

```
<210> SEQ ID NO 751
<211> LENGTH: 7
<212> TYPE: PRT
<213> ORGANISM: Homo sapiens

<400> SEQUENCE: 751

Ile Trp Thr Gly Gly Gly Thr
1               5

<210> SEQ ID NO 752
<211> LENGTH: 12
<212> TYPE: PRT
<213> ORGANISM: Homo sapiens

<400> SEQUENCE: 752

Ala Arg Asp Arg Ser Pro Tyr Phe Gly Tyr Asp Tyr
1               5                   10

<210> SEQ ID NO 753
<211> LENGTH: 11
<212> TYPE: PRT
<213> ORGANISM: Homo sapiens

<400> SEQUENCE: 753

Gln Ser Leu Val His Ser Asn Gly Asn Thr Tyr
1               5                   10

<210> SEQ ID NO 754
<211> LENGTH: 3
<212> TYPE: PRT
<213> ORGANISM: Homo sapiens

<400> SEQUENCE: 754

Lys Val Ser
1

<210> SEQ ID NO 755
<211> LENGTH: 9
<212> TYPE: PRT
<213> ORGANISM: Homo sapiens

<400> SEQUENCE: 755

Ser Gln Ser Thr His Val Pro Trp Thr
1               5

<210> SEQ ID NO 756
<211> LENGTH: 118
<212> TYPE: PRT
<213> ORGANISM: Homo sapiens

<400> SEQUENCE: 756

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Ile Thr Asn Tyr
            20                  25                  30

Asp Ile Ser Trp Ile Arg Gln Pro Pro Gly Lys Gly Leu Glu Trp Ile
        35                  40                  45

Gly Val Ile Trp Thr Gly Gly Gly Thr Asn Tyr Asn Ser Ala Phe Met
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95
```

```
Arg Asp Arg Ser Pro Tyr Phe Gly Tyr Asp Tyr Trp Gly Gln Gly Thr
                100                 105                 110

Thr Val Thr Val Ser Ser
        115

<210> SEQ ID NO 757
<211> LENGTH: 330
<212> TYPE: PRT
<213> ORGANISM: Homo sapiens

<400> SEQUENCE: 757

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 758
<211> LENGTH: 112
<212> TYPE: PRT
<213> ORGANISM: Homo sapiens

<400> SEQUENCE: 758

Asp Ile Val Met Thr Gln Thr Pro Leu Ser Leu Ser Val Thr Pro Gly
1               5                   10                  15

Gln Pro Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gln Gly Thr Lys Leu Glu Ile Lys
            100                 105                 110

<210> SEQ ID NO 759
<211> LENGTH: 107
<212> TYPE: PRT
<213> ORGANISM: Homo sapiens

<400> SEQUENCE: 759

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 760
<211> LENGTH: 9
<212> TYPE: PRT
<213> ORGANISM: Homo sapiens

<400> SEQUENCE: 760

Gly Tyr Ser Ile Thr Ser Asp Tyr Ala
1               5

<210> SEQ ID NO 761
<211> LENGTH: 7
<212> TYPE: PRT
<213> ORGANISM: Homo sapiens

<400> SEQUENCE: 761

Met Met Tyr Ser Gly Ser Ala
1               5

<210> SEQ ID NO 762
<211> LENGTH: 12
<212> TYPE: PRT
<213> ORGANISM: Homo sapiens

<400> SEQUENCE: 762

Ala Arg Phe Asp His Tyr Tyr Gly Arg Phe Asp Tyr
1               5                   10

<210> SEQ ID NO 763
<211> LENGTH: 5
<212> TYPE: PRT
<213> ORGANISM: Homo sapiens

<400> SEQUENCE: 763

Ser Ser Val Ser Tyr
1               5

<210> SEQ ID NO 764
<211> LENGTH: 3
<212> TYPE: PRT
<213> ORGANISM: Homo sapiens

<400> SEQUENCE: 764

Glu Ile Ser
1

<210> SEQ ID NO 765
<211> LENGTH: 9
<212> TYPE: PRT
<213> ORGANISM: Homo sapiens

<400> SEQUENCE: 765

Gln Gln Trp Asn Tyr Pro Leu Phe Thr
1               5

<210> SEQ ID NO 766
<211> LENGTH: 119
<212> TYPE: PRT
<213> ORGANISM: Homo sapiens

<400> SEQUENCE: 766

Gln Val Gln Leu Gln Glu Ser Gly Pro Gly Leu Val Lys Pro Ser Glu
1               5                   10                  15

Thr Leu Ser Leu Thr Cys Ala Val Ser Gly Tyr Ser Ile Thr Ser Asp
            20                  25                  30

Tyr Ala Trp Thr Trp Ile Arg Gln Pro Pro Gly Lys Gly Leu Glu Trp
        35                  40                  45

Ile Gly Tyr Met Met Tyr Ser Gly Ser Ala Ser Tyr Asn Pro Ser Leu
    50                  55                  60

Lys Gly Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Phe Asp His Tyr Tyr Gly Arg Phe Asp Tyr Trp Gly Gln Gly
            100                 105                 110

Thr Thr Val Thr Val Ser Ser
        115

<210> SEQ ID NO 767
<211> LENGTH: 330

```
<212> TYPE: PRT
<213> ORGANISM: Homo sapiens

<400> SEQUENCE: 767

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 768
<211> LENGTH: 106
<212> TYPE: PRT
<213> ORGANISM: Homo sapiens

<400> SEQUENCE: 768

Ala Ile Gln Leu Thr Gln Ser Pro Ser Ser Leu Ser Ala Ser Val Gly
1               5                   10                  15
```

-continued

Asp Arg Val Thr Ile Thr Cys Ser Ala Ser Ser Val Ser Tyr Ile
            20                  25                  30

His Trp Tyr Gln Gln Lys Pro Gly Lys Ala Pro Lys Leu Leu Ile Tyr
        35                  40                  45

Glu Ile Ser Lys Leu Ala Ser Gly Val Pro Ser Arg Phe Ser Gly Ser
 50                  55                  60

Gly Ser Gly Thr Asp Phe Thr Leu Thr Ile Ser Ser Leu Gln Pro Glu
 65                  70                  75                  80

Asp Phe Ala Thr Tyr Tyr Cys Gln Gln Trp Asn Tyr Pro Leu Phe Thr
                85                  90                  95

Phe Gly Gln Gly Thr Lys Leu Glu Ile Lys
            100                 105

<210> SEQ ID NO 769
<211> LENGTH: 107
<212> TYPE: PRT
<213> ORGANISM: Homo sapiens

<400> SEQUENCE: 769

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
 50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 770
<211> LENGTH: 8
<212> TYPE: PRT
<213> ORGANISM: Homo sapiens

<400> SEQUENCE: 770

Gly Phe Thr Phe Arg Asn Tyr Gly
1               5

<210> SEQ ID NO 771
<211> LENGTH: 8
<212> TYPE: PRT
<213> ORGANISM: Homo sapiens

<400> SEQUENCE: 771

Ile Ile Ser Gly Gly Ser Tyr Thr
1               5

<210> SEQ ID NO 772
<211> LENGTH: 15
<212> TYPE: PRT
<213> ORGANISM: Homo sapiens

<400> SEQUENCE: 772

Ala Arg Ile Tyr Asp His Asp Gly Asp Tyr Tyr Ala Met Asp Tyr
1               5                   10                  15

<210> SEQ ID NO 773
<211> LENGTH: 11
<212> TYPE: PRT
<213> ORGANISM: Homo sapiens

<400> SEQUENCE: 773

Gln Ser Ile Val His Ser Asn Gly Asn Thr Tyr
1               5                   10

<210> SEQ ID NO 774
<211> LENGTH: 3
<212> TYPE: PRT
<213> ORGANISM: Homo sapiens

<400> SEQUENCE: 774

Lys Val Ser
1

<210> SEQ ID NO 775
<211> LENGTH: 9
<212> TYPE: PRT
<213> ORGANISM: Homo sapiens

<400> SEQUENCE: 775

Phe Gln Gly Ser His Val Pro Trp Thr
1               5

<210> SEQ ID NO 776
<211> LENGTH: 122
<212> TYPE: PRT
<213> ORGANISM: Homo sapiens

<400> SEQUENCE: 776

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Asn Tyr
            20                  25                  30

Gly Met Ser Trp Val Arg Gln Ala Pro Gly Lys Gly Leu Glu Trp Val
        35                  40                  45

Ala Ser Ile Ile Ser Gly Gly Ser Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ile Tyr Asp His Asp Gly Asp Tyr Tyr Ala Met Asp Tyr Trp
            100                 105                 110

Gly Gln Gly Thr Thr Val Thr Val Ser Ser
        115                 120

<210> SEQ ID NO 777
<211> LENGTH: 330
<212> TYPE: PRT
<213> ORGANISM: Homo sapiens

<400> SEQUENCE: 777

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 778
<211> LENGTH: 112
<212> TYPE: PRT
<213> ORGANISM: Homo sapiens

<400> SEQUENCE: 778

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile

```
               65                  70                  75                  80
Ser Arg Val Glu Ala Glu Asp Val Gly Val Tyr Tyr Cys Phe Gln Gly
                    85                  90                  95

Ser His Val Pro Trp Thr Phe Gly Gln Gly Thr Lys Leu Glu Ile Lys
            100                 105                 110

<210> SEQ ID NO 779
<211> LENGTH: 107
<212> TYPE: PRT
<213> ORGANISM: Homo sapiens

<400> SEQUENCE: 779

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 780
<211> LENGTH: 8
<212> TYPE: PRT
<213> ORGANISM: Homo sapiens

<400> SEQUENCE: 780

Gly Tyr Thr Phe Thr Ser Tyr Asp
1               5

<210> SEQ ID NO 781
<211> LENGTH: 8
<212> TYPE: PRT
<213> ORGANISM: Homo sapiens

<400> SEQUENCE: 781

Ile Tyr Pro Gly Asp Gly Ser Thr
1               5

<210> SEQ ID NO 782
<211> LENGTH: 10
<212> TYPE: PRT
<213> ORGANISM: Homo sapiens

<400> SEQUENCE: 782

Ala Arg Glu Gly Ile Thr Pro Phe Ala Tyr
1               5                   10

<210> SEQ ID NO 783
<211> LENGTH: 6
<212> TYPE: PRT
<213> ORGANISM: Homo sapiens

<400> SEQUENCE: 783

Lys Ser Ile Ser Lys Tyr
```

-continued

```
1               5

<210> SEQ ID NO 784
<211> LENGTH: 3
<212> TYPE: PRT
<213> ORGANISM: Homo sapiens

<400> SEQUENCE: 784

Ser Gly Ser
1

<210> SEQ ID NO 785
<211> LENGTH: 9
<212> TYPE: PRT
<213> ORGANISM: Homo sapiens

<400> SEQUENCE: 785

Gln Gln His Asn Glu Tyr Pro Trp Thr
1               5

<210> SEQ ID NO 786
<211> LENGTH: 117
<212> TYPE: PRT
<213> ORGANISM: Homo sapiens

<400> SEQUENCE: 786

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Pro Gly Gln Gly Leu Glu Trp Met
        35                  40                  45

Gly Arg Ile Tyr Pro Gly Asp Gly Ser Thr Lys Tyr Asn Glu Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Ile Thr Pro Phe Ala Tyr Trp Gly Gln Gly Thr Thr
            100                 105                 110

Val Thr Val Ser Ser
        115

<210> SEQ ID NO 787
<211> LENGTH: 330
<212> TYPE: PRT
<213> ORGANISM: Homo sapiens

<400> SEQUENCE: 787

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80
```

```
Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 788
<211> LENGTH: 107
<212> TYPE: PRT
<213> ORGANISM: Homo sapiens

<400> SEQUENCE: 788

Ala Ile Gln Leu Thr Gln Ser Pro Ser Ser Leu Ser Ala Ser Val Gly
1               5                   10                  15

Asp Arg Val Thr Ile Thr Cys Arg Ala Ser Lys Ser Ile Ser Lys Tyr
            20                  25                  30

Leu Ala Trp Tyr Gln Gln Lys Pro Gly Lys Ala Pro Lys Leu Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Asn Glu Tyr Pro Trp
                85                  90                  95

Thr Phe Gly Gln Gly Thr Lys Leu Glu Ile Lys
            100                 105

<210> SEQ ID NO 789
```

```
<211> LENGTH: 107
<212> TYPE: PRT
<213> ORGANISM: Homo sapiens

<400> SEQUENCE: 789
```

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65              70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

```
<210> SEQ ID NO 790
<211> LENGTH: 8
<212> TYPE: PRT
<213> ORGANISM: Homo sapiens

<400> SEQUENCE: 790
```

Gly Gly Thr Phe Ser Ser Tyr Ala
1               5

```
<210> SEQ ID NO 791
<211> LENGTH: 8
<212> TYPE: PRT
<213> ORGANISM: Homo sapiens

<400> SEQUENCE: 791
```

Ile Ile Pro Ile Phe Gly Thr Ala
1               5

```
<210> SEQ ID NO 792
<211> LENGTH: 13
<212> TYPE: PRT
<213> ORGANISM: Homo sapiens

<400> SEQUENCE: 792
```

Ala Arg Ser Ser Tyr Gly Trp Ser Tyr Glu Phe Asp Tyr
1               5                   10

```
<210> SEQ ID NO 793
<211> LENGTH: 6
<212> TYPE: PRT
<213> ORGANISM: Homo sapiens

<400> SEQUENCE: 793
```

Gln Ser Ile Ser Ser Tyr
1               5

```
<210> SEQ ID NO 794
<211> LENGTH: 3
<212> TYPE: PRT
<213> ORGANISM: Homo sapiens

<400> SEQUENCE: 794
```

-continued

Ala Ala Ser
1

<210> SEQ ID NO 795
<211> LENGTH: 9
<212> TYPE: PRT
<213> ORGANISM: Homo sapiens

<400> SEQUENCE: 795

Gln Gln Ser Tyr Ser Thr Pro Leu Thr
1               5

<210> SEQ ID NO 796
<211> LENGTH: 120
<212> TYPE: PRT
<213> ORGANISM: Homo sapiens

<400> SEQUENCE: 796

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Tyr Gly Trp Ser Tyr Glu Phe Asp Tyr Trp Gly Gln
            100                 105                 110

Gly Thr Leu Val Thr Val Ser Ser
        115                 120

<210> SEQ ID NO 797
<211> LENGTH: 330
<212> TYPE: PRT
<213> ORGANISM: Homo sapiens

<400> SEQUENCE: 797

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys

```
                130             135             140
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 798
<211> LENGTH: 107
<212> TYPE: PRT
<213> ORGANISM: Homo sapiens

<400> SEQUENCE: 798

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
            100                 105

<210> SEQ ID NO 799
<211> LENGTH: 107
<212> TYPE: PRT
<213> ORGANISM: Homo sapiens

<400> SEQUENCE: 799

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
```

```
                 20                  25                  30
Tyr Pro Arg Glu Ala Lys Val Gln Trp Lys Val Asp Asn Ala Leu Gln
             35                  40                  45

Ser Gly Asn Ser Gln Glu Ser Val Thr Glu Gln Asp Ser Lys Asp Ser
         50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105
```

<210> SEQ ID NO 800
<211> LENGTH: 8
<212> TYPE: PRT
<213> ORGANISM: Homo sapiens

<400> SEQUENCE: 800

```
Gly Gly Thr Phe Ser Ser Tyr Ala
1               5
```

<210> SEQ ID NO 801
<211> LENGTH: 8
<212> TYPE: PRT
<213> ORGANISM: Homo sapiens

<400> SEQUENCE: 801

```
Ile Ile Pro Ile Phe Gly Thr Ala
1               5
```

<210> SEQ ID NO 802
<211> LENGTH: 13
<212> TYPE: PRT
<213> ORGANISM: Homo sapiens

<400> SEQUENCE: 802

```
Ala Arg Ser Thr Val Gly Trp Ser Tyr Glu Phe Asp Tyr
1               5                   10
```

<210> SEQ ID NO 803
<211> LENGTH: 6
<212> TYPE: PRT
<213> ORGANISM: Homo sapiens

<400> SEQUENCE: 803

```
Gln Ser Ile Ser Ser Tyr
1               5
```

<210> SEQ ID NO 804
<211> LENGTH: 3
<212> TYPE: PRT
<213> ORGANISM: Homo sapiens

<400> SEQUENCE: 804

```
Ala Ala Ser
1
```

<210> SEQ ID NO 805
<211> LENGTH: 9
<212> TYPE: PRT
<213> ORGANISM: Homo sapiens

<400> SEQUENCE: 805

Gln Gln Ser Tyr Ser Thr Pro Leu Thr
1               5

<210> SEQ ID NO 806
<211> LENGTH: 120
<212> TYPE: PRT
<213> ORGANISM: Homo sapiens

<400> SEQUENCE: 806

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Val Gly Trp Ser Tyr Glu Phe Asp Tyr Trp Gly Gln
            100                 105                 110

Gly Thr Leu Val Thr Val Ser Ser
        115                 120

<210> SEQ ID NO 807
<211> LENGTH: 330
<212> TYPE: PRT
<213> ORGANISM: Homo sapiens

<400> SEQUENCE: 807

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
             195                 200                 205

Lys Ala Leu Pro Ala Pro Ile Glu Lys Thr Ile Ser Lys Ala Lys Gly
         210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
             245                 250                 255

Pro Ser Asp Ile Ala Val Glu Trp Glu Ser Asn Gly Gln Pro Glu Asn
         260                 265                 270

Asn Tyr Lys Thr Thr Pro Pro Val Leu Asp Ser Asp Gly Ser Phe Phe
             275                 280                 285

Leu Tyr Ser Lys Leu Thr Val Asp Lys Ser Arg Trp Gln Gln Gly Asn
         290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
             325                 330

<210> SEQ ID NO 808
<211> LENGTH: 107
<212> TYPE: PRT
<213> ORGANISM: Homo sapiens

<400> SEQUENCE: 808

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
            100                 105

<210> SEQ ID NO 809
<211> LENGTH: 107
<212> TYPE: PRT
<213> ORGANISM: Homo sapiens

<400> SEQUENCE: 809

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
            85                  90                  95

Pro Val Thr Lys Ser Phe Asn Arg Gly Glu Cys
            100                 105

<210> SEQ ID NO 810
<211> LENGTH: 8
<212> TYPE: PRT
<213> ORGANISM: Homo sapiens

<400> SEQUENCE: 810

Gly Gly Thr Phe Ser Ser Tyr Ala
1               5

<210> SEQ ID NO 811
<211> LENGTH: 8
<212> TYPE: PRT
<213> ORGANISM: Homo sapiens

<400> SEQUENCE: 811

Ile Ile Pro Ile Phe Gly Thr Ala
1               5

<210> SEQ ID NO 812
<211> LENGTH: 13
<212> TYPE: PRT
<213> ORGANISM: Homo sapiens

<400> SEQUENCE: 812

Ala Arg His Val Leu Gly Trp Val Leu Glu Leu Asp Tyr
1               5                   10

<210> SEQ ID NO 813
<211> LENGTH: 6
<212> TYPE: PRT
<213> ORGANISM: Homo sapiens

<400> SEQUENCE: 813

Gln Ser Ile Ser Ser Tyr
1               5

<210> SEQ ID NO 814
<211> LENGTH: 3
<212> TYPE: PRT
<213> ORGANISM: Homo sapiens

<400> SEQUENCE: 814

Ala Ala Ser
1

<210> SEQ ID NO 815
<211> LENGTH: 9
<212> TYPE: PRT
<213> ORGANISM: Homo sapiens

<400> SEQUENCE: 815

Gln Gln Ser Tyr Ser Thr Pro Leu Thr
1               5

<210> SEQ ID NO 816
<211> LENGTH: 120
<212> TYPE: PRT
<213> ORGANISM: Homo sapiens

<400> SEQUENCE: 816

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Val Leu Gly Trp Val Leu Glu Leu Asp Tyr Trp Gly Gln
            100                 105                 110

Gly Thr Leu Val Thr Val Ser Ser
        115                 120

<210> SEQ ID NO 817
<211> LENGTH: 330
<212> TYPE: PRT
<213> ORGANISM: Homo sapiens

<400> SEQUENCE: 817

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 818
<211> LENGTH: 107
<212> TYPE: PRT
<213> ORGANISM: Homo sapiens

<400> SEQUENCE: 818

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gln Gly Thr Lys Val Glu Ile Lys
            100                 105

<210> SEQ ID NO 819
<211> LENGTH: 107
<212> TYPE: PRT
<213> ORGANISM: Homo sapiens

<400> SEQUENCE: 819

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105